(12) United States Patent
Sekiguchi et al.

(10) Patent No.: US 8,030,499 B2
(45) Date of Patent: Oct. 4, 2011

(54) 1,3-DIHYDRO-2H-INDOLE-2-ONE COMPOUND AND PYRROLIDINE-2-ONE COMPOUND FUSED WITH AROMATIC HETEROCYCLE

(75) Inventors: Yoshinori Sekiguchi, Tokyo (JP); Takeshi Kuwada, Tokyo (JP); Masato Hayashi, Tokyo (JP); Dai Nozawa, Tokyo (JP); Yuri Amada, Tokyo (JP); Tsuyoshi Shibata, Tokyo (JP); Shuji Yamamoto, Tokyo (JP); Hiroshi Ohta, Tokyo (JP); Taketoshi Okubo, Tokyo (JP); Takeshi Koami, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 895 days.

(21) Appl. No.: 11/883,236

(22) PCT Filed: Jan. 30, 2006

(86) PCT No.: PCT/JP2006/301913
§ 371 (c)(1),
(2), (4) Date: Jul. 26, 2007

(87) PCT Pub. No.: WO2006/080574
PCT Pub. Date: Aug. 3, 2006

(65) Prior Publication Data
US 2008/0318923 A1 Dec. 25, 2008

(30) Foreign Application Priority Data

Jan. 28, 2005 (JP) ................................. 2005-021010

(51) Int. Cl.
*C07D 209/04* (2006.01)
*A61K 31/404* (2006.01)
(52) U.S. Cl. ....................................... 548/466; 514/414
(58) Field of Classification Search .................. 548/466; 514/414
See application file for complete search history.

(56) References Cited

U.S. PATENT DOCUMENTS

| 7,528,124 B2 * | 5/2009 | Kumagai et al. ............... 514/183 |
| 2003/0114683 A1 * | 6/2003 | Roux et al. ..................... 548/486 |
| 2005/0070718 A1 * | 3/2005 | Lubisch et al. ............... 548/181 |

FOREIGN PATENT DOCUMENTS

| JP | 6-507182 A | 8/1994 |
| JP | 8-507092 A | 7/1996 |
| JP | 2003-523351 A | 8/2003 |
| JP | 2003-523354 A | 8/2003 |
| JP | 2003-525287 A | 8/2003 |
| JP | 2004-502654 A | 1/2004 |
| JP | 2004-536131 A | 12/2004 |
| WO | WO 93/15051 A1 | 8/1993 |
| WO | WO 95/18105 A1 | 7/1995 |
| WO | WO 01/55130 A2 | 8/2001 |
| WO | WO 01/55134 A2 | 8/2001 |
| WO | WO 01/64668 A2 | 9/2001 |
| WO | WO 01/98295 A1 | 12/2001 |
| WO | WO 03/008407 A2 | 1/2003 |
| WO | WO 2006/005609 A2 | 1/2006 |

OTHER PUBLICATIONS

Crombie et al. (Bioorg & Med. Chem. Lett., v. 20 (2010), p. 3742-45).*
Kubinyi (3D QSAR in Drug Design: Ligand-Protein Interactions and Molecular Similarity, vol. 2-3, Springer, 1998, 800 pages), TOC and pp. 243-244 provided.*
Patani et al. (Chem. Rev., 1996, vol. 96, No. 8, p. 3147-3176).*

* cited by examiner

*Primary Examiner* — Robert Havlin
(74) *Attorney, Agent, or Firm* — Sughrue Mion, PLLC

(57) ABSTRACT

It is intended to provide a drug which is efficacious against pathological conditions relating to arginine-vasopressin V1b receptor. More particularly speaking, it is intended to provide a drug which has a therapeutic or preventive effect on depression, anxiety, Alzheimer's disease, Parkinson's disease, Huntington's chorea, eating disorders, hypertension, digestive diseases, drug addiction, epilepsy, brain infarction, brain ischemia, brain edema, head injury, inflammation, immune diseases, alopecia and so on. As the results of intensive studies, a novel 1,3-dihydro-2H-indol-2-one compound and a pyrrolidin-2-one compound fused with a heteroaromatic ring, which are highly selective antagonists of arginine-vasopressin V1b receptor, have high metabolic stabilities and show favorable brain penetration and high plasma concentrations, are found, thereby achieving the above objective.

9 Claims, No Drawings

1,3-DIHYDRO-2H-INDOLE-2-ONE COMPOUND AND PYRROLIDINE-2-ONE COMPOUND FUSED WITH AROMATIC HETEROCYCLE

BACKGROUND ART

Arginine-vasopressin (AVP) is a peptide consisting of 9 amino acids which is synthesized predominantly in the hypothalamus, and is deeply involved as a posterior pituitary hormone in the regulation of blood plasma osmotic pressure, blood pressure and amount of body fluid.

To date, three subtypes of AVP receptor have been cloned, V1a, V1b and V2 receptors, and all are known to be seven times membrane receptors. The V2 receptor is coupled to Gs to increase the amount of cAMP. The V1a receptor is coupled to Gq/11 to enhance PI response and increase intracellular Ca. The V1a receptor is expressed in brain, liver, adrenal gland, vascular smooth muscle and the like, and is involved in vasoconstriction action. On the other hand, like V1a receptor, the V1b receptor is also coupled to the Gq/11 to enhance PI response (Non-patent Reference 1/Non-patent Reference 2). The V1b receptor is present mostly in the pituitary gland (expressed in 90% or more of ACTH secreting cells of the anterior lobe), and is postulated to participate in the ACTH secretion from the anterior pituitary gland by AVP. The V1b receptor is also present in a broad region of the brain other than the pituitary gland, and is present in large amounts in limbic systems such as hippocampus, amygdala and entorhinal cortex, and the cerebral cortices, olfactory bulb, raphe nuclei which are origion of serotonin nervous (Non-patent Reference 3/Non-patent Reference 4).

Recently, a relationship between the V1b receptor and depression and anxiety disorders has been suggested, and on the usefulness of a V1b receptor antagonist have been investigated. In V1b receptor KO mouse, aggressive behavior was shown to decrease (Non-patent Reference 5). In addition, an increase in time spent in the open arm (anxiolytic-like effect) by injection of a V1b receptor antagonist in the septal region was reported in an elevated plus-maze test (Non-patent Reference 6). Recently, a V1b receptor specific antagonist was discovered, which is a 1,3-dihydro-2H-indol-2-one compound that can be administered peripherally (Patent References 1 to 7). In addition, antidepressant and anxiolytic effects of 1,3-dihydro-2H-indol-2-one compound, have been reported in a variety of animal models (Non-patent Reference 7/Non-patent Reference 8). The compound disclosed in Patent Reference 1 is a compound that has a high affinity ($1 \times 10^{-9}$ mol/L to $4 \times 10^{-9}$ mol/L) for and acts selectively on the V1b receptor, and this compound antagonizes AVP, AVP+ CRF or restraint stress-induced ACTH increase.

In addition, compound with a fluorine atom-substituted alkoxy group introduced on the benzene sulfonyl moiety linked at position 1 of 1,3-dihydro-2H-indol-2-one, compound with three substituents introduced on the benzene sulfonyl moiety, and pyrrolidin-2-one compound fused with a heteroaromatic ring an the like are not disclosed in Patent References 1 to 7.

Reference List

Non-patent Reference 1: Sugimoto T, Kawashima Q J. Biol. Chem., 269, 27088-27092, 1994.
Non-patent Reference 2: Lolait S, Brownstein M, PNAS, 92, 6783-6787, 1995.
Non-patent Reference 3: Vaccari C, Ostrowski N, Endocrinology, 139, 5015-5033, 1998.
Non-patent Reference 4: Hernando F, Burbach J, Endocrinology, 142, 1659-1668, 2001.
Non-patent Reference 5: Wersinger S R, Toung W S, Mol, Psychiatry, 7, 975-984, 2002.
Non-patent Reference 6: Liebsch G, Engelmann M, Neurosci, Lett. 217, 101-104, 1996.
Non-patent Reference 7: Gal C S, Le Fur Q 300, 1122-1130, 2002.
Non-patent Reference 8: Griebel G. Soubrie P, 99, 6370a-6375, 2002.
Patent Reference 1: PCT Publication No. WO01/55130
Patent Reference 2: PCT Publication No. WO01/55134
Patent Reference 3: PCT Publication No. WO01/64668
Patent Reference 4: PCT Publication No. WO01/98295
Patent Reference 5: PCT Publication No. WO03/008407
Patent Reference 6: PCT Publication No. WO2004/009585
Patent Reference 7: PCT Publication No. WO2005/030755

DISCLOSURE OF THE INVENTION

An object of the present invention is to provide a novel compound that may be used in various applications. An object of the present invention is to provide a drug that is effective on diseases related to the arginine-vasopressin V1b receptor. Explaining more specifically, an object of the present invention is to provide a drug having a therapeutic effect or a prophylactic effect against depression, anxiety, Alzheimer's disease, Parkinson's disease, Huntington's chorea, eating disorders, hypertension, digestive diseases, drug addiction, epilepsy, brain infarction, brain ischemia, brain edema, head injury, inflammation, immune diseases, alopecia and the like.

As a result of earnest studies, the present inventors discovered a novel 1,3-dihydro-2H-indol-2-one compound and pyrrolidin-2-one compound fused with a heteroaromatic ring that highly selectively antagonize the arginine-vasopressin V1b receptor, excel in metabolic stability, demonstrate satisfactory brain penetrability and high plasma concentration, and completed the present invention.

That is to say, the present invention provides the following invention.

[1] A 1,3-dihydro-2H-indol-2-one compound or a pyrrolidin-2-one compound fused with a heteroaromatic ring Formula (1)

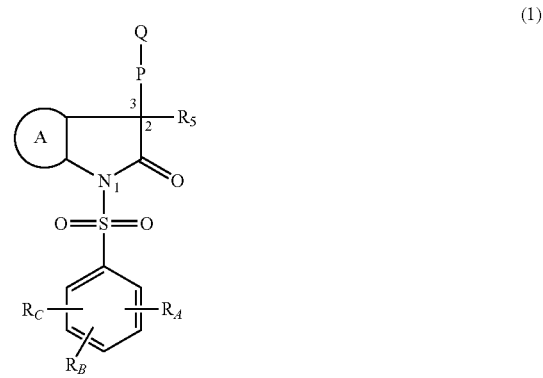

(1)

(in the formula, the A ring represents an aryl group having 6 to 14 carbon atoms or a heteroaromatic ring group, the A ring may be optionally substituted by 1 to 4 groups from $R_1$, $R_2$, $R_3$ and $R_4$ defined below, either $R_1$, $R_2$, $R_3$ and $R_4$ independently represents a group selected from a hydrogen atom, a halogen atom, a carboxyl group, a hydroxyl group, an amino group, a nitro group, a cyano group, an alkyl group having 1 to 5 carbon atoms, an alkyl group having 1 to 5 carbon atom substituted by 1 to 5 groups selected from the Substituent A group described below, an alkenyl group having 2 to 5 carbon atoms, an alkynyl group having 2 to 5 carbon atoms, a cycloalkyl group having 3 to 8 carbon atoms, an alkoxy group having 1 to 5 carbon atoms, an alkoxy group having 1 to 5 carbon atoms substituted by halogen atoms, an aryloxy group having 6 to 14 carbon atoms, a mono-alkyl amino group, a di-alkyl amino group, a mono-aryl amino group, a di-aryl amino group, a carbamoyl group, a mono-alkyl aminocarbonyl group, a di-alkyl aminocarbonyl group, a mono-aryl aminocarbonyl group, a di-aryl aminocarbonyl group, a mercapto group, an alkyl thio group having 1 to 5 carbon atoms, an alkyl sulfinyl group having 1 to 5 carbon atoms, an alkyl sulfonyl group having 1 to 5 carbon atoms, an aryl group having 6 to 14 carbon atoms, an aryl group having 6 to 14 carbon atoms substituted by 1 to 5 groups selected from the Substituent B group described below, heterocyclic group or a heterocyclic group substituted by 1 to 5 groups selected from the Substituent C group described below, or, any one set of $R_1$ and $R_2$, $R_2$ and $R_3$ or $R_3$ and $R_4$ together represents an alkylene group having 3 to 6 carbon atoms, an alkylene dioxy group having 1 to 3 carbon atoms, an alkylene dioxy group having 1 to 3 carbon atoms substituted by halogen atoms, a group represented by the formula —$(CH_2)_m$—O— or a group represented by the formula —$(CH_2)_m$—$NR^o$—, m represents an integer from 2 to 4, $R^0$ represents a hydrogen atom, an alkyl group having 1 to 5 carbon atoms, an aralkyl group having 7 to 19 carbon atoms, an alkylcarbonyl group having 1 to 5 carbon atoms, an arylcarbonyl group having 6 to 14 carbon atoms, an alkoxy carbonyl group having 1 to 5 carbon atoms or an aralkyl oxy carbonyl group having 7 to 19 carbon atoms;

P represents a single bond or an alkylene group having 1 to 5 carbon atoms;

Q represents an aryl group having 6 to 14 carbon atoms, an aryl group having 6 to 14 carbon atoms substituted by 1 to 5 groups selected from the Substituent D group described below, a heteroaromatic ring group, a heteroaromatic ring group substituted by 1 to 5 groups selected from the Substituent E group described below, or a group represented by Formula (2)

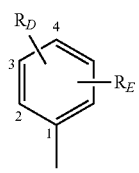

(2)

(in the formula, $R_D$ and $R_E$ are at substitution sites position 2 and position 3 or position 3 and position 4, $R_D$ and $R_E$ together represent an alkylene group having 3 to 6 carbon atoms, an alkylene dioxy group having 1 to 3 carbon atoms, an alkylene dioxy group having 1 to 3 carbon atoms substituted by halogen atoms, a group represented by the formula —$(CH_2)_m$—O—, a group represented by the formula —$(CH_2)_m$—$NR^{o'}$—, a group represented by the formula —$(CH_2)_m$—S—, a group represented by the formula —O—$(CH_2)_m$—$NR^{o'}$—, a group represented by the formula O—$(CH_2)_m$—S—, a group represented by the formula —$NR^{o'}$—$(CH_2)_m$—S— or a group represented by the formula —S—$(CH_2)_{m'}$—S—, m' represents an integer from 2 to 4, $R^{o'}$ represents a hydrogen atom, an alkyl group having 1 to 5 carbon atoms, an aralkyl group having 7 to 19 carbon atoms, an alkylcarbonyl group having 1 to 5 carbon atoms, an arylcarbonyl group having 6 to 14 carbon atoms, an alkoxy carbonyl group having 1 to 5 carbon atoms or an aralkyl oxy carbonyl group having 7 to 19 carbon atoms);

$R_5$ either represents a group represented by Formula (3)

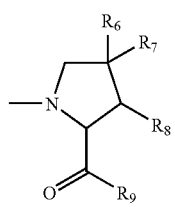

(3)

(in the formula, either $R_6$ represents a hydrogen atom, a halogen atom or a group represented by the formula —$OR_{10}$, $R_7$ represents a hydrogen atom, a halogen atom, a group represented by the formula —$SR_{10}$ or a group represented by the formula —$NR_{10}R_{11}$, and $R_8$ represents a hydrogen atom, a halogen atom or a hydroxyl group (with the proviso that (I) when $R_6$ represents a hydrogen atom and $R_7$ represents a halogen atom, a group represented by the formula —$SR_{10}$ or a group represented by the formula —$NR_{10}R_{11}$, $R_8$ represents a hydrogen atom, (II) when $R_6$ and $R_7$ represent a hydrogen atom, $R_5$ represents a hydroxyl group or a halogen atom, (III) when $R_6$ represents a halogen atom and $R_7$ represents a halogen atom, $R_8$ represents a hydrogen atom, (IV) when $R_6$ represents a group represented by the formula —$OR_{10}$ and $R_7$ represents a hydrogen atom, $R_8$ represents a hydrogen atom or a hydroxyl group), or $R_6$ and $R_7$ together represent an oxo group, $R_9$ represents a group represented by the formula —$OR_{12}$, a group represented by the formula —$SR_{13}$ or a group represented by the formula —$NR_{14}R_{15}$, $R_{10}$ represents a hydrogen atom, an alkyl group having 1 to 5 carbon atoms, an alkyl group having 1 to 5 carbon atoms substituted by 1 to 5 groups selected from the Substituent G group described below, an alkenyl group having 2 to 5 carbon atoms, an alkylcarbonyl group having 1 to 5 carbon atoms, an alkoxy carbonyl group having 1 to 5 carbon atoms, a mono-alkyl aminocarbonyl group, a di-alkyl aminocarbonyl group, a mono-aryl aminocarbonyl group, a mono-alkyl amino thio carbonyl group or a mono-aryl amino thio carbonyl group, $R_{11}$, represents a hydrogen atom or an alkyl group having 1 to 5 carbon atoms, $R_{12}$ represents a hydrogen atom, an alkyl group having 1 to 5 carbon atoms, an alkyl group having 1 to 5 carbon atoms substituted by 1 to 5 groups selected from the Substituent H group described below, a cycloalkyl group having 3 to 8 carbon atoms, an aryl group having 6 to 14 carbon atoms, an aralkyl group having 7 to 19 carbon atoms or a heterocyclic group, $R_{13}$ represents a hydrogen atom, an alkyl group having 1 to 5 carbon atoms or a cycloalkyl group having 3 to 8 carbon atoms, $R_{14}$ represents a hydrogen atom, an alkyl group having 1 to 5 carbon atoms, an alkyl group having 1 to 5 carbon atoms substituted by 1 to 5 groups selected from the Substituent I group described below, a cycloalkyl group having 3 to 8 carbon atoms, an aryl group having 6 to 14 carbon atoms, a heterocyclic group, an alkyl sulfonyl group having 1 to 5 carbon atoms, a group represented by the formula —OR$_{16}$ or a group represented by the formula —NR$_{17}$R$_{18}$, R$_{15}$ either represents an alkyl group having 1 to 5 carbon atoms substituted by a hydroxyl group, a hydrogen atom, an alkyl group having 1 to 5 carbon atoms or a cycloalkyl group having 3 to 8 carbon atoms, or R$_{14}$ and R$_{15}$ together with an adjacent nitrogen atom represent a nitrogen-containing heterocyclic group, a nitrogen-containing heterocyclic group substituted by an alkyl group having 1 to 5 carbon atoms, a nitrogen-containing heterocyclic group substituted by a di-alkyl amino group, a nitrogen-containing heterocyclic group substituted by an alkoxy carbonyl amino group having 1 to 5 carbon atoms, a nitrogen-containing heterocyclic group substituted by a heterocyclic group or a nitrogen-containing heterocyclic group substituted by an amino group, R$_{16}$ represents a hydrogen atom, an alkyl group having 1 to 5 carbon atoms, a cycloalkyl group having 3 to 8 carbon atoms, an aryl group having 6 to 14 carbon atoms, a heterocyclic group, an alkylcarbonyl group having 1 to 5 carbon atoms, a cycloalkylcarbonyl group having 3 to 8 carbon atoms, an arylcarbonyl group having 6 to 14 carbon atoms or a group represented by the formula —(CO)-(heterocycle), R$_{17}$ represents a hydrogen atom, an alkyl group having 1 to 5 carbon atoms, a cycloalkyl group having 3 to 8 carbon atoms, an aryl group having 6 to 14 carbon atoms, a heterocyclic group, an alkylcarbonyl group having 1 to 5 carbon atoms, a cycloalkylcarbonyl group having 3 to 8 carbon atoms, an arylcarbonyl group having 6 to 14 carbon atoms or a group represented by the formula —(CO)-(heterocycle), R$_{18}$ either represents a hydrogen atom or an alkyl group having 1 to 5 carbon atoms, or R$_{17}$ and R$_{18}$ together with an adjacent nitrogen atom represent a nitrogen-containing heterocyclic group), a group represented by Formula (4)

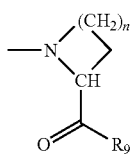

(4)

(in the formula, n represents an integer from 1 to 3, and R$_9$ has the same meaning as above), a group represented by Formula (5)

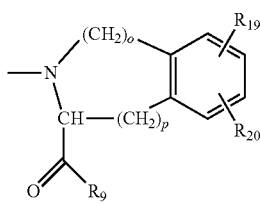

(5)

(in the formula, o and p independently represent an integer from 0 to 2, the sum of o and p represents 1 or 2, R$_{19}$ represents a hydrogen atom, a hydroxyl group, a halogen atom, an alkyl group having 1 to 5 carbon atoms, an alkoxy group having 1 to 5 carbon atoms, an amino group, a mono-alkyl amino group, a di-alkyl amino group or an alkoxy carbonyl amino group having 1 to 5 carbon atoms, R$_{20}$ represents a hydrogen atom, a halogen atom, an alkyl group having 1 to 5 carbon atoms or an alkoxy group having 1 to 5 carbon atoms, R$_9$ has the same meaning as above), a group represented by Formula (6)

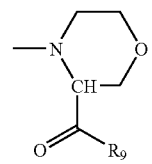

(6)

(in the formula, R$_9$ has the same meaning as above), a group represented by Formula (7)

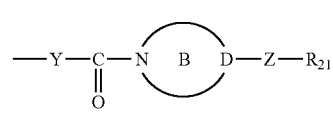

(7)

(in the formula, Y represents a methylene group, an oxygen atom, a group represented by the formula —NH—, a group represented by the formula —O—CH$_2$—, a group represented by the formula —NH—CH$_2$— or a group represented by the formula —NH—CH$_2$—CH$_2$—, Z represents a group represented by the formula —(CH$_2$)$_q$—, a carbonyl group, a group represented by the formula —(CO)—(CH$_2$)$_q$—, a group represented by the formula —(CO)—NH—, a group represented by the formula —(CS)—NH— or a single bond, q represents an integer from 1 to 5, B ring represents 5 to 9-membered nitrogen-containing heterocyclic group (N in the B ring represents a nitrogen atom), D in the B ring represents a carbon atom or a nitrogen atom, R$_{21}$ represents an aryl group having 6 to 14 carbon atoms, an aryl group having 6 to 14 carbon atoms substituted by 1 to 5 groups selected from the Substituent L group described below, a heterocyclic group or a heterocyclic group substituted by 1 to 5 groups selected from the Substituent M group described below), a group represented by Formula (8)

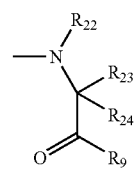

(8)

(in the formula, R$_{22}$ represents a hydrogen atom, an alkyl group having 1 to 5 carbon atoms, an alkyl group having 1 to 5 carbon atoms substituted by 1 to 5 groups selected from the Substituent G group described below, an alkenyl group having 2 to 5 carbon atoms, a cycloalkyl group having 3 to 8 carbon atoms, an aryl group having 6 to 14 carbon atoms or a heterocyclic group, R$_{23}$ represents a hydrogen atom, an alkyl group having 1 to 5 carbon atoms, an alkyl group having 1 to 5 carbon atoms substituted by 1 to 5 groups selected from the Substituent N group described below, an alkenyl group having 2 to 5 carbon atoms, a cycloalkyl group having 3 to 8 carbon atoms, an aryl group having 6 to 14 carbon atoms or a heterocyclic group, $R_{24}$ either represents a hydrogen atom, a halogen atom, an alkyl group having 1 to 5 carbon atoms, an alkyl group having 1 to 5 carbon atoms substituted by halogen atoms, an alkenyl group having 2 to 5 carbon atoms, an alkyl group having 1 to 5 carbon atoms substituted by hydroxyl groups, an aryl group having 6 to 14 carbon atoms or a cycloalkyl group having 3 to 8 carbon atoms (with the proviso that as a preferred combination of $R_{23}$ and $R_{24}$, either (I) $R_{23}$ represents a hydrogen atom, and $R_{24}$ represents a hydrogen atom, (II) $R_{23}$ represents an alkyl group having 1 to 5 carbon atoms or an alkyl group having 1 to 5 carbon atoms substituted by 1 to 5 groups selected from the Substituent N group described below, and $R_{24}$ represents a hydrogen atom, a halogen atom, an alkyl group having 1 to 5 carbon atoms, an alkyl group having 1 to 5 carbon atoms substituted by halogen atoms or an alkyl group having 1 to 5 carbon atoms substituted by a hydroxyl group, (III) $R_{23}$ represents an aryl group having 6 to 14 carbon atoms, and $R_{24}$ represents a hydrogen atom, an alkyl group having 1 to 5 carbon atoms, an aryl group having 6 to 14 carbon atoms or a cycloalkyl group having 3 to 8 carbon atoms, (IV) $R_{23}$ represents an alkenyl group having 2 to 5 carbon atoms, and $R_{24}$ represents a hydrogen atom, an alkyl group having 1 to 5 carbon atoms or an alkenyl group having 2 to 5 carbon atoms, or (V) $R_{23}$ represents a cycloalkyl group having 3 to 8 carbon atoms, and $R_{24}$ represents a hydrogen atom or an alkyl group having 1 to 5 carbon atoms), or $R_{23}$ and $R_{24}$ together with an adjacent carbon atom represent a cycloalkyl group having 3 to 8 carbon atoms, and $R_9$ has the same meaning as above), a group represented by Formula (9)

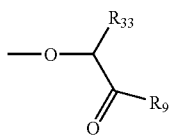

(9)

(in the formula, $R_{33}$ represents a hydrogen atom, an alkyl group having 1 to 5 carbon atoms, an alkyl group having 1 to 5 carbon atoms substituted by 1 to 5 groups selected from the Substituent O group described below, a cycloalkyl group having 3 to 8 carbon atoms, an aryl group having 6 to 14 carbon atoms or a heterocyclic group, and $R_9$ has the same meaning as above), or represents a group represented by Formula (10)

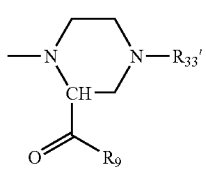

(10)

(in the formula, $R_{33'}$ represents a hydrogen atom, an alkyl group having 1 to 5 carbon atoms, an alkyl group having 1 to 5 carbon atoms substituted by 1 to 5 groups selected from the Substituent P group described below, a cycloalkyl group having 3 to 8 carbon atoms, an alkoxy carbonyl group having 1 to 5 carbon atoms, an aryl group having 6 to 14 carbon atoms or a heterocyclic group, and $R_9$ has the same meaning as above);

(i) when the A ring represents an aryl group having 6 to 14 carbon atoms and Q represents an aryl group having 6 to 14 carbon atoms, an aryl group having 6 to 14 carbon atoms substituted by 1 to 5 groups selected from the Substituent D group described below, or, among the groups represented by the above-mentioned Formula (2), a group wherein $R_D$ and $R_E$ together form an alkylene dioxy group having 1 to 3 carbon atoms, either (i-1) $R_A$ represents a hydrogen atom, a halogen atom, a nitro group, an amino group, a hydroxy amino group or an alkyl group having 1 to 5 carbon atoms, $R_B$ represents an alkoxy group having 1 to 5 carbon atoms, and $R_W$ represents a hydrogen atom, (i-2) $R_A$ represents an alkoxy group having 1 to 5 carbon atoms, and $R_B$ and $R_C$ independently represent an alkoxy group having 1 to 5 carbon atoms, (i-3) $R_A$ represents an alkyl thio group having 1 to 5 carbon atoms, $R_B$ represents an alkyl thio group having 1 to 5 carbon atoms or an alkoxy group having 1 to 5 carbon atoms, and $R_C$ represents a hydrogen atom, or (i-4) $R_A$ represents an alkoxy group having 1 to 5 carbon atoms substituted by fluorine atoms, $R_B$ represents a hydrogen atom, a halogen atom, an alkoxy group having 1 to 5 carbon atoms, an alkoxy group having 1 to 5 carbon atoms substituted by fluorine atoms, an alkyl thio group having 1 to 5 carbon atoms, an alkyl sulfinyl group having 1 to 5 carbon atoms or an alkyl sulfonyl group having 1 to 5 carbon atoms, and $R_C$ represents a hydrogen atom or an alkoxy group having 1 to 5 carbon atoms, (ii) when the A ring represents a heteroaromatic ring group and Q represents an aryl group having 6 to 14 carbon atoms, an aryl group having 6 to 14 carbon atoms substituted by 1 to 5 groups selected from the Substituent D group described below, a group represented by the above-mentioned Formula (2), a heteroaromatic ring group or a heteroaromatic ring group substituted by 1 to 5 groups selected from the Substituent E group described below, $R_A$, $R_B$ and $R_C$ independently represent a group selected from a hydrogen atom, a halogen atom, a nitro group, an amino group, a hydroxy amino group, an alkyl group having 1 to 5 carbon atoms, an alkoxy group having 1 to 5 carbon atoms, an alkyl thio group having 1 to 5 carbon atoms, an alkyl sulfinyl group having 1 to 5 carbon atoms, an alkyl sulfonyl group having 1 to 5 carbon atoms or an alkoxy group having 1 to 5 carbon atoms substituted by fluorine atoms, (iii) when the A ring represents an aryl group having 6 to 14 carbon atoms and Q represents a group represented by the above-mentioned Formula (2), a heteroaromatic ring group or a heteroaromatic ring group substituted by 1 to 5 groups selected from the Substituent E group described below, (iii-1) $R_A$ represents an alkoxy group having 1 to 5 carbon atoms or a trifluoromethoxy group, $R_B$ represents an alkoxy group having 1 to 5 carbon atoms, and $R_C$ represents an alkoxy group having 1 to 5 carbon atoms, or, (iii-2) $R_A$ represents an alkoxy group having 1 to 5 carbon atoms substituted by 1 to 2 fluorine atoms or an alkoxy group having 2 to 5 carbon atoms substituted by 3 to 5 fluorine atoms, $R_B$ represents an alkoxy group having 1 to 5 carbon atoms, and $R_C$ represents a hydrogen atom;

the Substituent A group represents a halogen atom, a hydroxyl group, an alkoxy group having 1 to 5 carbon atoms, an aryloxy group having 6 to 14 carbon atoms, an alkylcarbonyl oxy group having 1 to 5 carbon atoms, an arylcarbonyl oxy group having 6 to 14 carbon atoms, a cyano group, a mono-alkyl amino group, a di-alkyl amino group, a mono-alkyl aminocarbonyl group, a di-alkyl aminocarbonyl group, a di-aryl aminocarbonyl group, an aryl group having 6 to 14 carbon atoms and a heterocyclic group, the Substituent B group represents a halogen atom, a nitro group, an amino group, a hydroxyl group, a carboxyl group, a cyano group, an alkyl group having 1 to 5 carbon atoms, an alkyl group having 1 to 5 carbon atoms substituted by halogen atoms, an alkoxy group having 1 to 5 carbon atoms, an alkoxy group having 1 to 5 carbon atoms substituted by halogen atoms, an alkoxy carbonyl group having 1 to 5 carbon atoms, a mono-alkyl amino group, a di-alkyl amino group, an alkylcarbonyl amino group having 1 to 5 carbon atoms, a di-alkyl aminocarbonyl group, a carbamoyl group and an alkyl thio group having 1 to 5 carbon atoms, the Substituent C group represents an alkyl group having 1 to 5 carbon atoms, an alkoxy group having 1 to 5 carbon atoms, a cyano group, a carboxyl group, an alkoxy carbonyl group having 1 to 5 carbon atoms and an alkyl thio group having 1 to 5 carbon atoms, the Substituent D group represents a halogen atom, a hydroxyl group, an amino group, a nitro group, a cyano group, a formyl group, an alkyl group having 1 to 5 carbon atoms, an alkyl group having 1 to 5 carbon atoms substituted by 1 to 5 groups selected from the Substituent F group described below, an alkenyl group having 2 to 5 carbon atoms, an alkynyl group having 2 to 5 carbon atoms, an alkoxy group having 1 to 5 carbon atoms, an alkoxy group having 1 to 5 carbon atoms substituted by halogen atoms, an alkylcarbonyl group having 1 to 5 carbon atoms, an aryloxy group having 6 to 14 carbon atoms, a mono-alkyl amino group, a di-alkyl amino group, a mono-aryl amino group, a di-aryl amino group, a mercapto group, an alkyl thio group having 1 to 5 carbon atoms, an aryl group having 6 to 14 carbon atoms, a heterocyclic group, and a heterocyclic group substituted by an alkyl group having 1 to 5 carbon atoms, the Substituent E group represents an alkyl group having 1 to 5 carbon atoms, a mono-alkyl amino group, a di-alkyl amino group, and an alkoxy group having 1 to 5 carbon atoms, the Substituent F group represents a halogen atom, a hydroxyl group, a formyl group, an alkoxy group having 1 to 5 carbon atoms, a mono-alkyl amino group, a di-alkyl amino group, a mono-cycloalkyl amino group, an alkyl cycloalkyl amino group, a cyano group, an aryl group having 6 to 14 carbon atoms, a heterocyclic group, a heterocyclic group substituted by an alkyl group having 1 to 5 carbon atoms, and a heterocyclic group substituted by an alkoxy carbonyl group having 1 to 5 carbon atoms, the Substituent G group represents a halogen atom, a cyano group, an amino group, a hydroxyl group, a carboxyl group, a carbamoyl group, an alkoxy carbonyl group having 1 to 5 carbon atoms, a mono-alkyl aminocarbonyl group, a di-alkyl aminocarbonyl group, a mono-aryl aminocarbonyl group, a di-aryl aminocarbonyl group, a group represented by the formula —(CO)-(heterocycle), an alkoxy group having 1 to 5 carbon atoms, an alkylcarbonyl oxy group having 1 to 5 carbon atoms, an aralkyl oxy group having 7 to 19 carbon atoms, an aryloxy group having 6 to 14 carbon atoms, a group represented by the formula —O-(heterocycle), an alkoxy carbonyl group having 1 to 5 carbon atoms, a mono-alkyl amino group, a di-alkyl amino group, a mono-aryl amino group, a di-aryl amino group, an alkylcarbonyl amino group having 1 to 5 carbon atoms, an aralkylcarbonyl amino group having 7 to 19 carbon atoms, a group represented by the formula —NH—(C═O)-(heterocycle), an aryl sulfonyl amino group having 6 to 14 carbon atoms, an aryl sulfonyl amino group having 6 to 14 carbon atoms substituted by an alkyl group having 1 to 5 carbon atoms, an aryl sulfonyl amino group having 6 to 14 carbon atoms substituted by a nitro group, an alkyl thio group having 1 to 5 carbon atoms, an aralkyl thio group having 7 to 19 carbon atoms, an aryl thio group having 6 to 14 carbon atoms, an aryl thio group having 6 to 14 carbon atoms substituted by halogen atoms, an aryl thio group having 6 to 14 carbon atoms substituted by an alkyl group having 1 to 5 carbon atoms, a group represented by the formula —S-(heterocycle), an aryl sulfonyl group having 6 to 14 carbon atoms, an aryl sulfonyl group having 6 to 14 carbon atoms substituted by an alkyl group having 1 to 5 carbon atoms, a cycloalkyl group having 3 to 8 carbon atoms, a cycloalkenyl group having 3 to 8 carbon atoms, an aryl group having 6 to 14 carbon atoms, an aryl group having 6 to 14 carbon atoms substituted by 1 to 5 groups selected from the Substituent J group described below, a heterocyclic group, and a heterocyclic group substituted by 1 to 5 groups selected from the Substituent K group described below, the Substituent H group represents a halogen atom, a cyano group, an amino group, a hydroxyl group, an alkoxy group having 1 to 5 carbon atoms, a mono-alkyl amino group, a di-alkyl amino group, a mono-alkyl aminocarbonyl group, a di-alkyl aminocarbonyl group, an alkoxy carbonyl group having 1 to 5 carbon atoms, a carbamoyl group, a mercapto group, an alkyl thio group having 1 to 5 carbon atoms, a cycloalkyl group having 3 to 8 carbon atoms, a cycloalkenyl group having 3 to 8 carbon atoms, and a heterocyclic group, the Substituent I group represents a halogen atom, a cyano group, an amino group, a hydroxyl group, an alkoxy group having 1 to 5 carbon atoms, a mono-alkyl amino group, a di-alkyl amino group, a mono-alkyl aminocarbonyl group, a di-alkyl aminocarbonyl group, an alkoxy carbonyl group having 1 to 5 carbon atoms, a mercapto group, an alkyl thio group having 1 to 5 carbon atoms, a cycloalkyl group having 3 to 8 carbon atoms, and a heterocyclic group, the Substituent J group represents a cyano group, a halogen atom, an alkyl group having 1 to 5 carbon atoms, an alkyl group having 1 to 5 carbon atoms substituted by halogen atoms, an alkoxy group having 1 to 5 carbon atoms, a nitro group, and an alkoxy carbonyl group having 1 to 5 carbon atoms, the Substituent K group represents an alkyl group having 1 to 5 carbon atoms, an alkoxy group having 1 to 5 carbon atoms, an aralkyl oxy group having 7 to 19 carbon atoms, an aryl group having 6 to 14 carbon atoms, and an aryl group having 6 to 14 carbon atoms substituted by an alkoxy group having 1 to 5 carbon atoms, the Substituent L group represents a halogen atom, a cyano group, a nitro group, an amino group, an alkyl group having 1 to 5 carbon atoms, an alkyl group having 1 to 5 carbon atoms substituted by halogen atoms, an alkoxy group having 1 to 5 carbon atoms, an alkoxy group having 1 to 5 carbon atoms substituted by halogen atoms, an alkylcarbonyl oxy group having 1 to 5 carbon atoms, an alkylcarbonyl amino group having 1 to 5 carbon atoms, a di-alkyl amino group, an alkyl thio group having 1 to 5 carbon atoms, an aryl group having 6 to 14 carbon atoms, an aryloxy group having 6 to 14 carbon atoms, an aryl thio group having 6 to 14 carbon atoms, and a heterocyclic group, the Substituent M group represents a halogen atom, and an alkyl group having 1 to 5 carbon atoms, the Substituent N group represents a hydroxyl group, a halogen atom, an amino group, a carboxyl group, a mercapto group, an alkoxy group having 1 to 5 carbon atoms, an alkoxy carbonyl group having 1 to 5 carbon atoms, an aralkyl oxy carbonyl group having 7 to 19 carbon atoms, an aryl oxy carbonyl group having 6 to 14 carbon atoms, a group represented by the formula —(CO)—O-(heterocycle), an alkylcarbonyl oxy group having 1 to 5 carbon atoms, an arylcarbonyl oxy group having 6 to 14 carbon atoms, a group represented by the formula —O—(CO)-(heterocycle), a mono-alkyl amino group, a di-alkyl amino group, a mono-aryl amino group, an alkylcarbonyl amino group having 1 to 5 carbon atoms, an aralkylcarbonyl amino group having 7 to 19 carbon atoms, an arylcarbonyl amino group having 6 to 14 carbon atoms, a group represented by the formula —NH—(CO)-(heterocycle), an alkyl sulfonyl amino group having 1 to 5 carbon atoms, an aryl sulfonyl amino group having 6 to 14 carbon atoms, an aryl sulfonyl amino group having 6 to 14 carbon atoms substituted by an alkyl group having 1 to 5 carbon atoms, a group represented by the formula —NH—SO$_2$— (heterocycle), an alkyl thio group having 1 to 5 carbon atoms, an aralkyl thio group having 7 to 19 carbon atoms, an aryl thio group having 6 to 14 carbon atoms, a group represented by the formula —S-(heterocycle), an alkyl sulfinyl group having 1 to 5 carbon atoms, an alkyl sulfonyl group having 1 to 5 carbon atoms, an alkoxy carbonyl amino group having 1 to 5 carbon atoms, a aralkyl oxy carbonyl amino group having 7 to 19 carbon atoms, an aryl oxy carbonyl amino group having 6 to 14 carbon atoms, a group represented by the formula —(CO)—NR$_{14}$R$_{15}$ (in the formula, R$_{14}$ and R$_{15}$ have the same meaning as in the above description), a group represented by the formula —NR$_{28}$—(C=NR$_{27}$)—NR$_{25}$R$_{26}$ (in the formula, R$_{25}$ represents a hydrogen atom, an alkyl group having 1 to 5 carbon atoms, an alkenyl group having 2 to 5 carbon atoms, an amino group, a hydroxyl group or a nitro group, R$_{26}$, R$_{27}$ and R$_{28}$ independently represent a hydrogen atom or an alkyl group having 1 to 5 carbon atoms), a cycloalkyl group having 3 to 8 carbon atoms, an aryl group having 6 to 14 carbon atoms, an aryl group having 6 to 14 carbon atoms substituted by hydroxyl groups, an aryl group having 6 to 14 carbon atoms substituted by an alkoxy group having 1 to 5 carbon atoms, an aryl group having 6 to 14 carbon atoms substituted by an aralkyl oxy group having 7 to 19 carbon atoms, a heterocyclic group, and a heterocyclic group substituted by an alkoxy carbonyl group having 1 to 5 carbon atoms, the Substituent O group represents an amino group, a hydroxyl group, an alkoxy group having 1 to 5 carbon atoms, an alkylcarbonyl oxy group having 1 to 5 carbon atoms, an alkoxy carbonyl group having 1 to 5 carbon atoms, an aryl group having 6 to 14 carbon atoms, an aryl group having 6 to 14 carbon atoms substituted by hydroxyl groups, an aryl group having 6 to 14 carbon atoms substituted by an alkoxy group having 1 to 5 carbon atoms, an aryl group having 6 to 14 carbon atoms substituted by an aralkyl oxy group having 7 to 19 carbon atoms, an aralkyl oxy carbonyl amino group having 7 to 19 carbon atoms, a group represented by the formula —(CO)—NR$_{14}$R$_{15}$ (in the formula, R$_{14}$ and R$_{15}$ have the same meaning as in the above description), and a group represented by the formula —NR$_{32}$—(C=NR$_{31}$)—NR$_{29}$R$_{30}$ (in the formula, R$_{29}$, R$_{30}$, R$_{31}$, and R$_{32}$ independently represent a hydrogen atom or an alkyl group having 1 to 5 carbon atoms), and the Substituent P group represents a halogen atom, a hydroxyl group, an alkoxy group having 1 to 5 carbon atoms, an alkylcarbonyl oxy group having 1 to 5 carbon atoms, an alkoxy carbonyl group having 1 to 5 carbon atoms, an aralkyl oxy carbonyl group having 7 to 19 carbon atoms, an aryl group having 6 to 14 carbon atoms, and a heterocyclic group), or pharmaceutically acceptable salts thereof

[2] The pyrrolidin-2-one compound fused with a heteroaromatic ring as recited in [1] described above, wherein the A ring represents a heteroaromatic ring group optionally substituted by 1 to 4 groups selected from R$_1$, R$_2$, R$_3$ and R$_4$, R$_A$, R$_B$ and R$_C$ independently represent a group selected from a hydrogen atom, a halogen atom, a nitro group, an amino group, a hydroxy amino group, an alkyl group having 1 to 5 carbon atoms, an alkoxy group having 1 to 5 carbon atoms, an alkyl thio group having 1 to 5 carbon atoms, an alkyl sulfinyl group having 1 to 5 carbon atoms, an alkyl sulfonyl group having 1 to 5 carbon atoms or an alkoxy group having 1 to 5 carbon atoms substituted by fluorine atoms (with the proviso that at least one among R$_A$, R$_B$ and R$_C$ represents an alkoxy group having 1 to 5 carbon atoms substituted by fluorine atoms), or a pharmaceutically acceptable salt thereof.

[3]. The pyrrolidin-2-one compound fused with a heteroaromatic ring as recited in [2] described above, wherein the A ring represents a pyridine ring optionally substituted by 1 to 3 groups selected from R$_1$, R$_2$ and R$_3$, R$_1$, R$_2$ and R$_3$ either independently represent a hydrogen atom, a halogen atom, a carboxyl group, a hydroxyl group, an amino group, a nitro group, a cyano group, an alkyl group having 1 to 5 carbon atoms, an alkyl group having 1 to 5 carbon atoms substituted by 1 to 5 groups selected from the Substituent A group, an alkenyl group having 2 to 5 carbon atoms, an alkynyl group having 2 to 5 carbon atoms, a cycloalkyl group having 3 to 8 carbon atoms, an alkoxy group having 1 to 5 carbon atoms, an alkoxy group having 1 to 5 carbon atoms substituted by halogen atoms, an aryloxy group having 6 to 14 carbon atoms, a mono-alkyl amino group, a di-alkyl amino group, a mono-aryl amino group, a di-aryl amino group, a carbamoyl group, a mono-alkyl aminocarbonyl group, a di-alkyl aminocarbonyl group, a mono-aryl aminocarbonyl group, a di-aryl aminocarbonyl group, a mercapto group, an alkyl thio group having 1 to 5 carbon atoms, an alkyl sulfinyl group having 1 to 5 carbon atoms, an alkyl sulfonyl group having 1 to 5 carbon atoms, an aryl group having 6 to 14 carbon atoms, an aryl group having 6 to 14 carbon atoms substituted by 1 to 5 groups selected from the Substituent B group, a heterocyclic group or a heterocyclic group substituted by 1 to 5 groups selected from the Substituent C group, or any one combination of R$_1$ and R$_2$ or R$_2$ and R$_3$ together represents an alkylene group having 3 to 6 carbon atoms, an alkylene dioxy group having 1 to 3 carbon atoms, an alkylene dioxy group having 1 to 3 carbon atoms substituted by halogen atoms, a group represented by the formula —(CH$_2$)$_m$—O— (in the formula, m have the same meaning as in the above description) or a group represented by the formula —(CH$_2$)$_m$—NR$^o$— (in the formula, m and R$^o$ have the same meaning as in the above description), or a pharmaceutically acceptable salt thereof

[4]. The pyrrolidin-2-one compound fused with a heteroaromatic ring as recited in [3] described above, wherein R$_1$, R$_2$ and R$_3$ independently represent a hydrogen atom or a halogen atom, Q represents an aryl group having 6 to 14 carbon atoms or an aryl group having 6 to 14 carbon atoms substituted by 1 to 5 groups selected from "a hydrogen atom, an alkyl group having 1 to 5 carbon atoms or an alkoxy group having 1 to 5 carbon atoms", R$_5$ represents Formula (3) (herein, R$_6$ represents a hydroxyl group, R$_7$ represents a hydrogen atom, R$_8$ represents a hydrogen atom, and R$_9$ represents a di-alkyl amino group), R$_A$ and R$_B$ independently represent an alkoxy group having 1 to 5 carbon atoms or an alkoxy group having 1 to 5 carbon atoms substituted by fluorine atoms (with the proviso that at least one among them represents an alkoxy group having 1 to 5 carbon atoms substituted by fluorine atoms), $R_C$ represents a hydrogen atom, or a pharmaceutically acceptable salt thereof.

[5] The 1,3-dihydro-2H-indol-2-one compound as recited in [1] described above, wherein the A ring represents a benzene ring optionally substituted by 1 to 4 groups from $R_1$, $R_2$, $R_3$ and $R_4$, Q represents an aryl group having 6 to 14 carbon atoms, an aryl group having 6 to 14 carbon atoms substituted by 1 to 5 groups selected from the Substituent D group, or, among the groups represented by the above-mentioned Formula (2), a group wherein $R_D$ and $R_E$ together form an alkylene dioxy group having 1 to 3 carbon atoms, $R_A$, $R_B$ and $R_C$ independently represent a group selected from a hydrogen atom, a halogen atom, a nitro group, an amino group, a hydroxy amino group, an alkyl group having 1 to 5 carbon atoms, an alkoxy group having 1 to 5 carbon atoms, an alkyl thio group having 1 to 5 carbon atoms, an alkyl sulfinyl group having 1 to 5 carbon atoms, an alkyl sulfonyl group having 1 to 5 carbon atoms or an alkoxy group having 1 to 5 carbon atoms substituted by fluorine atoms (with the proviso that at least one among $R_A$, $R_B$ and $R_C$ represents an alkoxy group having 1 to 5 carbon atoms substituted by fluorine atoms), or a pharmaceutically acceptable salt thereof.

[6] The 1,3-dihydro-2H-indol-2-one compound as recited in [5] described above, wherein $R_5$ represents Formula (3), or a pharmaceutically acceptable salt thereof.

[7] The 1,3-dihydro-2H-indol-2-one compound as recited in [6] described above, wherein $R_1$, $R_2$, $R_3$ and $R_4$ independently represent a hydrogen atom, a carboxyl group, a halogen atom, an amino group, a nitro group, a cyano group, an alkyl group having 1 to 5 carbon atoms, an alkyl group having 1 to 5 carbon atoms substituted by 1 to 5 halogen atoms, an alkoxy group having 1 to 5 carbon atoms, an alkoxy group having 1 to 5 carbon atoms substituted by halogen atoms, a carbamoyl group or a heterocyclic group, P represents a single bond or an alkylene group having 1 to 5 carbon atoms, Q represents an aryl group having 6 to 14 carbon atoms, an aryl group having 6 to 14 carbon atoms substituted by 1 to 5 groups selected from the following substituents D' group or among the groups represented by the above-mentioned Formula (2), a group wherein $R_D$ and $R_E$ together form an alkylene dioxy group having 1 to 3 carbon atoms, $R_5$ represents Formula (3) (herein, $R_6$ represents a hydrogen atom, a halogen atom or a group represented by the formula —$OR_{10}$, when $R_6$ represents a hydrogen atom, $R_7$ represents a halogen atom, $R_8$ represents a hydrogen atom, when $R_6$ and $R_7$ represent a hydrogen atom, $R_9$ represents a hydroxyl group or a halogen atom, when $R_6$ represents a halogen atom, $R_7$ represents a halogen atom and $R_8$ represents a hydrogen atom, when $R_6$ represents a group represented by the formula —$OR_{10}$, $R_7$ represents a hydrogen atom and $R_9$ represents a hydrogen atom or a hydroxyl group, or, $R_6$ and $R_7$ together represent an oxo group, $R_9$ represents a group represented by the formula —$OR_{12}$ (in the formula, $R_{12}$ represents a hydrogen atom, an alkyl group having 1 to 5 carbon atoms or an aralkyl group having 7 to 19 carbon atoms) or a group represented by the formula —$NR_{14}R_{15}$, $R_{10}$ represents a hydrogen atom, an alkyl group having 1 to 5 carbon atoms, an alkylcarbonyl group having 1 to 5 carbon atoms, an alkyl group having 1 to 5 carbon atoms substituted by 1 to 5 groups selected from "a cyano group, a hydroxyl group, a carboxyl group, a carbamoyl group, an alkoxy carbonyl group having 1 to 5 carbon atoms, a di-alkyl amino group, a heterocyclic group or a heterocyclic group substituted by an alkyl group having 1 to 5 carbon atoms" or an alkenyl group having 2 to 5 carbon atoms, either $R_{14}$ represents a hydrogen atom, an alkyl group having 1 to 5 carbon atoms or an alkyl group having 1 to 5 carbon atoms substituted by 1 to 5 groups selected from "a hydroxyl group or di-alkyl amino group", and $R_{15}$ represents a hydrogen atom, an alkyl group having 1 to 5 carbon atoms or an alkyl group having 1 to 5 carbon atoms substituted by a hydroxyl group, or $R_{14}$ and $R_{15}$ together with an adjacent nitrogen atom represent a nitrogen-containing heterocyclic group, a nitrogen-containing heterocyclic group substituted by an alkyl group having 1 to 5 carbon atoms, a nitrogen-containing heterocyclic group substituted by a di-alkyl amino group, a nitrogen-containing heterocyclic group substituted by an alkoxy carbonyl amino group having 1 to 5 carbon atoms or a nitrogen-containing heterocyclic group substituted by an amino group, the Substituent D' group represents "a halogen atom, a cyano group, a formyl group, an alkyl group having 1 to 5 carbon atoms, an alkyl group having 1 to 5 carbon atoms substituted by 1 to 5 groups selected from the following substituents F' group, an alkenyl group having 2 to 5 carbon atoms, an alkoxy group having 1 to 5 carbon atoms, an alkoxy group having 1 to 5 carbon atoms substituted by halogen atoms, an alkylcarbonyl group having 1 to 5 carbon atoms, a di-alkyl amino group, an alkyl thio group having 1 to 5 carbon atoms, an aryl group having 6 to 14 carbon atoms, a 2-, 3- or 4-pyridyl group, a 1-, 2- or 3-pyrrolidinyl group, a 1-, 2-, 3- or 4-piperidyl group, a 1- or 2-piperazinyl group or a 2-, 3- or 4-morpholinyl group", the Substituent F' group represents "a hydroxyl group, a formyl group, a mono-alkyl amino group, a di-alkyl amino group, a mono-cycloalkyl amino group, an alkyl cycloalkyl amino group, a cyano group, an aryl group having 6 to 14 carbon atoms, a 1-, 2- or 3-pyrrolidinyl group, a 1-, 2-, 3- or 4-piperidyl group, a 1- or 2-piperazinyl group, a 2-, 3- or 4-morpholinyl group, a 1H-tetrazol-5-yl group, a heterocyclic group substituted by an alkyl group having 1 to 5 carbon atoms, and a heterocyclic group substituted by an alkoxy carbonyl group having 1 to 5 carbon atoms", or a pharmaceutically acceptable salt thereof.

[8] The 1,3-dihydro-2H-indol-2-one compound as recited in [7] described above, wherein $R_1$, $R_2$, $R_3$ and $R_4$ independently represent a hydrogen atom, a halogen atom, an amino group, a nitro group, a cyano group, an alkyl group having 1 to 5 carbon atoms, an alkoxy group having 1 to 5 carbon atoms substituted by halogen atoms or a carbamoyl group, P represents a single bond, Q represents an aryl group having 6 to 14 carbon atoms substituted by 1 to 5 groups selected from the following substituents D" group, or, among the groups represented by the above-mentioned Formula (2), a group wherein $R_D$ and $R_E$ together form an alkylene dioxy group having 1 to 3 carbon atoms, $R_{10}$ represents a hydrogen atom, an alkyl group having 1 to 5 carbon atoms, an alkylcarbonyl group having 1 to 5 carbon atoms or an alkyl group having 1 to 5 carbon atoms substituted by 1 to 5 groups selected from "a cyano group, a hydroxyl group, a carboxyl group, a carbamoyl group, a di-alkyl amino group, a heterocyclic group or a heterocyclic group substituted by an alkyl group having 1 to 5 carbon atoms" or an alkenyl group having 2 to 5 carbon atoms, either $R_{15}$ represents a hydrogen atom or an alkyl group having 1 to 5 carbon atoms, or $R_{15}$ together with a nitrogen atom adjacent to $R_{14}$ represent a nitrogen-containing heterocyclic group, the substituent D" group represents "a halogen atom, a cyano group, a formyl group, an alkyl group having 1 to 5 carbon atoms, an alkyl group having 1 to 5 carbon atoms substituted by 1 to 5 groups selected from the following substituents F" group, an alkenyl group having 2 to 5 carbon atoms, an alkoxy group having 1 to 5 carbon atoms, an alkoxy group having 1 to 5 carbon atoms substituted by halogen atoms, an alkylcarbonyl group having 1 to 5 carbon atoms, a di-alkyl amino group, an alkyl thio group having 1 to 5 carbon atoms, an aryl group having 6 to 14 carbon atoms, a 4-pyridyl group, a 1-piperidyl group or a 4-morpholinyl group", the substituent F" group represents "a hydroxyl group, a mono-alkyl amino group, a di-alkyl amino group, a mono-cycloalkyl amino group, an alkyl cycloalkyl amino group, a cyano group, an aryl group having 6 to 14 carbon atoms, a 1-pyrrolidinyl group, a 1-piperidyl group, a 1-piperazinyl group, a 4-morpholinyl group, a 1H-tetrazol-5-yl group, a heterocyclic group substituted by an alkyl group having 1 to 5 carbon atoms, and a heterocyclic group substituted by an alkoxy carbonyl group having 1 to 5 carbon atoms", or a pharmaceutically acceptable salt thereof

[9] The 1,3-dihydro-2H-indol-2-one compound as recited in [5] described above, wherein $R_5$ represents Formula (4), or a pharmaceutically acceptable salt thereof.

[10] The 1,3-dihydro-2H-indol-2-one compound as recited in [9] described above, wherein $R_1$, $R_2$, $R_3$ and $R_4$ independently represent a hydrogen atom, a halogen atom or an alkyl group having 1 to 5 carbon atoms, P represents a single bond, Q represents an aryl group having 6 to 14 carbon atoms, an aryl group having 6 to 14 carbon atoms substituted by 1 to 5 groups selected from the group consisting of "an alkyl group having 1 to 5 carbon atoms or an alkoxy group having 1 to 5 carbon atoms", $R_9$ represents a hydroxyl group, an alkoxy group having 1 to 5 carbon atoms, a di-alkyl amino group or 4-(4-pyridinyl) piperazin-1-yl group, or a pharmaceutically acceptable salt thereof.

[11] The 1,3-dihydro-2H-indol-2-one compound as recited in [5] described above, wherein $R_5$ represents Formula (5), or a pharmaceutically acceptable salt thereof.

[12] The 1,3-dihydro-2H-indol-2-one compound as recited in [11], wherein $R_1$, $R_2$, $R_3$ and $R_4$ independently represent a hydrogen atom or a halogen atom, P represents a single bond, Q represents an aryl group having 6 to 14 carbon atoms substituted by an alkoxy group having 1 to 5 carbon atoms, $R_{19}$ and $R_{20}$ respectively represent a hydrogen atom, $R_9$ represents a di-alkyl amino group, $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[13] The 1,3-dihydro-2H-indol-2-one compound as recited in [5] described above, wherein $R_5$ represents Formula (6), or a pharmaceutically acceptable salt thereof.

[14] The 1,3-dihydro-2H-indol-2-one compound as recited in [13] described above, wherein $R_1$, $R_2$, $R_3$ and $R_4$ independently represent a hydrogen atom or a halogen atom, P represents a single bond, Q represents an aryl group having 6 to 14 carbon atoms substituted by an alkoxy group having 1 to 5 carbon atoms, $R_9$ represents a di-alkyl amino group, $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[15] The 1,3-dihydro-2H-indol-2-one compound as recited in [5] described above, wherein $R_5$ represents Formula (7), or a pharmaceutically acceptable salt thereof.

[16]. The 1,3-dihydro-2H-indol-2-one derivative as recited in [15] described above, wherein $R_1$, $R_2$, $R_3$ and $R_4$ independently represent a hydrogen atom or a halogen atom, P represents a single bond, Q represents an aryl group having 6 to 14 carbon atoms substituted by an alkoxy group having 1 to 5 carbon atoms, Z represents a single bond, the B ring represents a 6-membered nitrogen-containing heterocyclic group, D in the B ring represents a nitrogen atom, $R_{21}$ represents a heterocyclic group, $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[17] The 1,3-dihydro-2H-indol-2-one compound as recited in [5] described above, wherein $R_5$ represents Formula (8), or a pharmaceutically acceptable salt thereof.

[18] The 1,3-dihydro-2H-indol-2-one compound as recited in [17] described above, wherein $R_1$, $R_2$, $R_3$ and $R_4$ independently represent a hydrogen atom or a halogen atom, P represents a single bond, Q represents an aryl group having 6 to 14 carbon atoms substituted by an alkoxy group having 1 to 5 carbon atoms, $R_{22}$ represents a hydrogen atom, an alkyl group having 1 to 5 carbon atoms, an alkyl group having 1 to 5 carbon atoms substituted by 1 to 5 groups selected from "an oxo group, a hydroxyl group, an aryl group having 6 to 14 carbon atoms or a heterocyclic group", $R_{23}$ represents a hydrogen atom, an alkyl group having 1 to 5 carbon atoms, an alkyl group having 1 to 5 carbon atoms substituted by 1 to 5 groups selected from "a hydroxyl group, an amino group, an alkyl thio group having 1 to 5 carbon atoms, an alkoxy carbonyl amino group having 1 to 5 carbon atoms, a carbamoyl group, a di-alkyl aminocarbonyl group, an aryl group having 6 to 14 carbon atoms, an aryl group having 6 to 14 carbon atoms substituted by hydroxyl groups, an aryl group having 6 to 14 carbon atoms substituted by an aralkyl oxy group having 7 to 19 carbon atoms, a heterocyclic group or a heterocyclic group substituted by an alkoxy carbonyl group having 1 to 5 carbon atoms", a cycloalkyl group having 3 to 8 carbon atoms or an aryl group having 6 to 14 carbon atoms, $R_{24}$ represents a hydrogen atom or an alkyl group having 1 to 5 carbon atoms, or $R_{23}$ and $R_{24}$ together with an adjacent carbon atom represent a cycloalkyl group having 3 to 8 carbon atoms, $R_9$ represents a hydroxyl group, an alkoxy group having 1 to 5 carbon atoms or a group represented by the formula —$NR_{14}R_{15}$ (herein, $R_{14}$ represents an alkyl group having 1 to 5 carbon atoms or an alkoxy group having 1 to 5 carbon atoms, and $R_{15}$ represents an alkyl group having 1 to 5 carbon atoms), $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[19] The 1,3-dihydro-2H-indol-2-one compound as recited in [5] described above, wherein $R_5$ represents Formula (9), or a pharmaceutically acceptable salt thereof.

[20] The 1,3-dihydro-2H-indol-2-one compound as recited in [19] described above, wherein $R_1$, $R_2$, $R_3$ and $R_4$ independently represent a hydrogen atom or a halogen atom, P represents a single bond, Q represents an aryl group having 6 to 14 carbon atoms substituted by an alkoxy group having 1 to 5 carbon atoms, $R_{33}$ represents an alkyl group having 1 to 5 carbon atoms, $R_9$ represents an alkoxy group having 1 to 5 carbon atoms or di-alkyl amino group, $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[21] The 1,3-dihydro-2H-indol-2-one compound as recited in [5] described above, wherein $R_5$ represents Formula (10), or a pharmaceutically acceptable salt thereof.

[22] The 1,3-dihydro-2H-indol-2-one compound as recited in [21] described above, wherein $R_1$, $R_2$, $R_3$ and $R_4$ independently represent a hydrogen atom or a halogen atom, P represents a single bond, Q represents an aryl group having 6 to 14 carbon atoms substituted by 1 to 5 groups selected from "an alkyl group having 1 to 5 carbon atoms or an alkoxy group having 1 to 5 carbon atoms", $R_{33'}$ represents a hydrogen atom, an alkyl group having 1 to 5 carbon atoms, an alkoxy carbonyl group having 1 to 5 carbon atoms or a heterocyclic group, $R_9$ represents a di-alkyl amino group, $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[23] The 1,3-dihydro-2H-indol-2-one compound as recited in [1] described above, wherein the A ring represents a benzene ring optionally substituted by 1 to 4 groups from $R_1$, $R_2$, $R_3$ and $R_4$, Q either represents a heteroaromatic ring group, a heteroaromatic ring group substituted by 1 to 5 groups selected from the Substituent E group described below, or a group represented by Formula (2) (herein, $R_D$ and $R_E$ are at substitution sites position 2 and position 3 or position 3 and position 4, $R_D$ and $R_E$ together represent a group represented by the formula —$(CH_2)_m$—O—, a group represented by the formula —$(CH_2)_m$—$NR^o$—, a group represented by the formula —$(CH_2)_m$—S—, a group represented by the formula —O—$(CH_2)_m$—$NR^o$—, a group represented by the formula —O—$(CH_2)_m$—S—, a group represented by the formula —$NR^o$—$(CH_2)_m$—S—, or a group represented by the formula —S—$(CH_2)_m$—S—, m and $R^o$ have the same meaning as above), when $R_A$ represents an alkoxy group having 1 to 5 carbon atoms, an alkoxy group having 1 to 5 carbon atoms substituted by 1 to 2 fluorine atoms, a trifluoromethoxy group or an alkoxy group having 2 to 5 carbon atoms substituted by 3 to 5 fluorine atoms, $R_B$ represents an alkoxy group having 1 to 5 carbon atoms, when $R_A$ represents an alkoxy group having 1 to 5 carbon atoms or trifluoromethoxy group, $R_C$ represents an alkoxy group having 1 to 5 carbon atoms, when $R_A$ represents an alkoxy group having 1 to 5 carbon atoms substituted by 1 to 2 fluorine atoms or an alkoxy group having 2 to 5 carbon atoms substituted by 3 to 5 fluorine atoms, $R_C$ represents a hydrogen atom or a pharmaceutically acceptable salt thereof.

[24] The 1,3-dihydro-2H-indol-2-one compound as recited in [23] described above, wherein $R_5$ represents Formula (3), or a pharmaceutically acceptable salt thereof.

[25] The 1,3-dihydro-2H-indol-2-one compound as recited in [24] described above, wherein $R_1$, $R_2$, $R_3$ and $R_4$ independently represent a hydrogen atom or a halogen atom, P represents a single bond, Q represents a heteroaromatic ring group substituted by 1 to 5 groups selected from "an alkyl group having 1 to 5 carbon atoms or an alkoxy group having 1 to 5 carbon atoms", $R_6$ represents a hydroxyl group, $R_7$ and $R_8$ respectively represent a hydrogen atom, and $R_9$ represents a di-alkyl amino group, or a pharmaceutically acceptable salt thereof.

[26] The 1,3-dihydro-2H-indol-2-one compound as recited in any one from [5] to [8] described above, wherein $R_A$ represents an alkoxy group having 1 to 5 carbon atoms substituted by fluorine atoms, $R_B$ represents an alkoxy group having 1 to 5 carbon atoms, and $R_C$ represents a hydrogen atom, or a pharmaceutically acceptable salt thereof.

[27] A mixture of any one species or two or more species selected from the following compound group, or pharmaceutically acceptable salts thereof.

(4R)-1-(5-chloro-3-(2-methoxyphenyl)-1-{[2-methoxy-4-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), methyl (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-hydroxy-L-prolinate (levorotatory isomer), 1-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl-L-prolinamide (levorotatory isomer), (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer), (4R)-1-(5-chloro-3-(2-methoxyphenyl)-1-{[2-methoxy-4-(trifluoromethoxy)phenyl]sulfonyl}-2-oxo-2,3-dihydro-1H-indol-3-yl)-4-fluoro-N,N-dimethyl-L-prolinamide, 3-[(2S)-2-(azetidin-1-ylcarbonyl)-4-fluoropyrrolidin-1-yl]-5-chloro-3-(2-methoxyphenyl)-1-{[4-methoxy-2-(trifluoromethoxy)phenyl]sulfonyl}-1,3-dihydro-2H-indol-2-one (levorotatory isomer), (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer), 1-(5-chloro-3-(2-methoxyphenyl)-1-{[4-methoxy-2-(trifluoromethoxy)phenyl]sulfonyl}-2-oxo-2,3-dihydro-1H-indol-3-yl)-4,4-difluoro-N,N-dimethyl-L-prolinamide (levorotatory isomer), methyl (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-L-prolinate (diastereoisomer mixture), (3S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-3-hydroxy-N,N-dimethyl-L-prolinamide (levorotatory isomer), 1-(5-chloro-3-(2-methoxyphenyl)-1-{[4-methoxy-2-(trifluoromethoxy)phenyl]sulfonyl}-2-oxo-2,3-dihydro-1H-indol-3-yl)-3-fluoro-N,N-dimethyl-L-prolinamide (levorotatory isomer), 1-(5-chloro-3-(2-methoxyphenyl)-1-{[4-methoxy-2-(trifluoromethoxy)phenyl]sulfonyl}-2-oxo-2,3-dihydro-1H-indol-3-yl)-3,4-dihydroxy-N,N-dimethyl-L-prolinamide (diastereoisomer mixture), (4R)-4-fluoro-1-[3-(2-methoxyphenyl)-1-{[4-methoxy-2-(trifluoromethoxy)phenyl]sulfonyl}-2-oxo-5-(trifluoromethoxy)-2,3-dihydro-1H-indol-3-yl]-N,N-dimethyl-L-prolinamide (levorotatory isomer), (4R)-1-(4,5-dichloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer), (4R)-1-(3-(1,3-benzodioxol-4-yl)-5-chloro-1-{[4-methoxy-2-(trifluoromethoxy)phenyl]sulfonyl }-2-oxo-2,3-dihydro-1H-indol-3-yl)-4-fluoro-N,N-dimethyl-L-prolinamide (levorotatory isomer), (4R)-4-fluoro-1-(3-(2-methoxyphenyl)-1-{[4-methoxy-2-(trifluoromethoxy)phenyl]sulfonyl}-5-methyl-2-oxo-2,3-dihydro-1H-indol-3-yl)-N,N-dimethyl-L-prolinamide (levorotatory isomer), (4R)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer), (2S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer), (2S)-1-(5-chloro-3-(2-methoxyphenyl)-1-{[2-methoxy-4-(trifluoromethoxy)phenyl]sulfonyl}-2-oxo-2,3-dihydro-1H-indol-3-yl)-N,N-dimethylpiperidine-2-carboxamide (levorotatory isomer), (2S)-1-(5-chloro-1-{[4-methoxy-2-(trifluoromethoxy)phenyl]sulfonyl}-2-oxo-3-phenyl-2,3-dihydro-1H-indol-3-yl)-N,N-dimethylpiperidine-2-carboxamide (levorotatory isomer), (2S)-1-(5-chloro-1-{[4-methoxy-2-(trifluoromethoxy)phenyl]sulfonyl}-2-oxo-3-pyridin-2-yl-2,3-dihydro-1H-indol-3-yl)-N,N-dimethylpiperidine-2-carboxamide (levorotatory isomer), (3S)-2-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl-1,2,3,4-tetrahydroisoquinoline-3-carboxamide (levorotatory isomer), (2S)-5'-chloro-3'-(2-methoxyphenyl)-1-{[4-methoxy-2-(trifluoromethoxy)phenyl]sulfonyl}-N, N-dimethyl-2'-oxo-2, 2',3,3'-tetrahydro-1'H-1,3'-biindole-2-carboxamide (levorotatory isomer), (3S)-4-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethylmorpholine-3-carboxamide (levorotatory isomer), 5-chloro-3-(2-methoxyphenyl)-1-{[4-methoxy-2-(trifluoromethoxy)phenyl]sulfonyl}-3-[2-oxo-2-(4-pyridin-4-ylpiperazin-1-yl)ethyl]-1,3-dihydro-2H-indol-2-one (levorotatory isomer), 5-chloro-3-(2-methoxyphenyl)-1-{[4-methoxy-2-(trifluoromethoxy)phenyl]sulfonyl}-3-{2-oxo-2-[4-(1,3-thiazol-2-yl)piperazin-1-yl]ethyl}-1,3-dihydro-2H-indol-2-one, 5-chloro-3-(2-methoxyphenyl)-1-{[4-methoxy-2-(trifluoromethoxy)phenyl]sulfonyl}-3-[2-oxo-2-(4-pyridin-3-ylpiperazin-1-yl)ethyl]-1,3-dihydro-2H-indol-2-one, 5-chloro-3-(2-methoxyphenyl)-1-{[4-methoxy-2-(trifluoromethoxy)phenyl]sulfonyl}-3-[2-oxo-2-(4-pyridazin-3-ylpiperazin-1-yl)ethyl]-1,3-dihydro-2H-indol-2-one, 5-chloro-3-(2-methoxyphenyl)-1-{[2-methoxy-4-(trifluoromethoxy)phenyl]sulfonyl}-3-[2-oxo-2-(4-pyridin-4-ylpiperazin-1-yl)ethyl]-1,3-dihydro-2H-indol-2-one, 5-chloro-3-(2-methoxyphenyl)-1-{[4-methoxy-2-(trifluoromethoxy)phenyl]sulfonyl}-3-[2-oxo-2-(4-pyridin-4-ylpiperazin-1-yl)ethoxy]-1,3-dihydro-2H-indol-2-one, N-(5-chloro-3-(2-methoxyphenyl)-1-{[4-methoxy-2-(trifluoromethoxy)phenyl]sulfonyl}-2-oxo-2,3-dihydro-1H-indol-3-yl)-4-pyridin-4-ylpiperazine-1-carboxamide, 5-chloro-3-(2-methoxyphenyl)-1-{[4-methoxy-2-(trifluoromethoxy)phenyl]sulfonyl}-2-oxo-2,3-dihydro-1H-indol-3-yl4-pyridin-4-ylpiperazine-1-carboxylate, 5-chloro-3-(2-methoxyphenyl)-1-{[4-methoxy-2-(trifluoromethoxy)phenyl]sulfonyl}-3-{[2-oxo-2-(4-pyridin-4-ylpiperazin-1-yl)ethyl]amino}-1,3-dihydro-2H-indol-2-one, 5-chloro-3-(2-methoxyphenyl)-1-{[4-methoxy-2-(trifluoromethoxy)phenyl]sulfonyl}-3-{[3-oxo-3-(4-pyridin-4-ylpiperazin-1-yl) propyl]amino}-1,3-dihydro-2H-indol-2-one, (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,4-trimethylpentanamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer), ((2S,3S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,3-trimethylpentanamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-phenylpropanamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-4-(methylthio)butanamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N1,N1-dimethylpentanediamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,N',N'-tetramethylpentanediamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(methyl)amino]-N,N-dimethylpropanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(1,3-thiazol-4-yl)propanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylbutanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(1H-imidazol-4-yl)-N,N-dimethylpropanamide (levorotatory isomer), tert-butyl [(5S)-5-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-6-(dimethylamino)-6-oxohexyl]carbamate (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(2-hydroxyethyl)amino]-N,N-dimethylpropanamide (levorotatory isomer), methyl
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)oxy]propanoate (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)oxy]-N,N-dimethylpropanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,3-trimethylbutanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(4-pyridinyl)propanamide (levorotatory isomer),
(2S)-2-[(5-chloro-3-(2-methoxyphenyl)-1-{[4-methoxy-2-(trifluoromethoxy)phenyl]sulfonyl)}-2-oxo-2,3-dihydro-1H-indol-3-yl)amino]-N,N-dimethyl-3-(2-pyridinyl)propanamide (levorotatory isomer),
(2S)-2-[(5-chloro-3-(2-methoxyphenyl)-1-({[4-methoxy-2-(trifluoromethoxy)phenyl]sulfonyl}-2-oxo-2,3-dihydro-1H-indol-3-yl)amino]-N,N-dimethyl-3-(3-pyridinyl)propanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(4-hydroxyphenyl)-N,N-dimethylpropanamide (levorotatory isomer),
(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-2-phenylacetamide (levorotatory isomer),
(4R)-1-(3-(1,3-benzodioxol-4-yl)-5-chloro-1-{[4-methoxy-2-(trifluoromethoxy)phenyl]sulfon yl}-2-oxo-2,3-dihydro-1H-indol-3-yl)-4-hydroxy-N,N-dimethyl-L-prolinamide (levorotatory isomer),
(4R)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(2S)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer),
(4R)-1-(3-(1,3-benzodioxol-4-yl)-5-iodo-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(3-(1,3-benzodioxol-4-yl)-5-bromo-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(3-(1,3-benzodioxol-4-yl)-5-fluoro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(3-(1,3-benzodioxol-4-yl)-1-{[4-methoxy-2-(trifluoromethoxy)phenyl]sulfonyl}-5-nitro-2-oxo-2,3-dihydro-1H-indol-3-yl)-4-hydroxy-N,N-dimethyl-L-prolinamide (levorotatory isomer),
(4R)-1-(3-(1,3-benzodioxol-4-yl)-6-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(2S)-1-(3-(4-methoxyphenyl)-1-{[4-methoxy-2-(trifluoromethoxy)phenyl]sulfonyl}-5-methyl-2-oxo-2,3-dihydro-1H-indol-3-yl)-N,N-dimethylpiperidine-2-carboxamide (levorotatory isomer),
(4R)-1-(5-chloro-3-(5-chloro-2-methoxyphenyl)-1-{[4-methoxy-2-(trifluoromethoxy)phenyl]sulfonyl}-4-methyl-2-oxo-2,3-dihydro-1H-indol-3-yl)-4-hydroxy-N,N-dimethyl-L-prolinamide (levorotatory isomer),
4R)-1-(4,5-dichloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-[5-chloro-1-{[4-methoxy-2-(trifluoromethoxy)phenyl]sulfonyl}-3-(2-methylphenyl)-2-oxo-2,3-dihydro-1H-indol-3-yl]-4-hydroxy-N,N-dimethyl-L-prolinamide (levorotatory isomer),
(4R)-1-(5-chloro-3-(2,4-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(5-chloro-3-(2-ethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(5-chloro-3-(2,5-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-[5-chloro-1-{[4-methoxy-2-(trifluoromethoxy)phenyl]sulfonyl}-2-oxo-3-(2-vinylphenyl)-2,3-dihydro-1H-indol-3-yl]-4-hydroxy-N,N-dimethyl-L-prolinamide (levorotatory isomer),
(4R)-1-[5-bromo-1-{[4-methoxy-2-(trifluoromethoxy)phenyl]sulfonyl}-3-(2-methylphenyl)-2-oxo-2,3-dihydro-1H-indol-3-yl]-4-hydroxy-N,N-dimethyl-L-prolinamide (levorotatory isomer),
(4R)-4-hydroxy-1-[5-iodo-1-{[4-methoxy-2-(trifluoromethoxy)phenyl]sulfonyl}-3-(2-methylphenyl)-2-oxo-2,3-dihydro-1H-indol-3-yl]-N,N-dimethyl-L-prolinamide (levorotatory isomer), (4R)-1-(3-(1,3-benzodioxol-4-yl)-1-{[4-methoxy-2-(trifluoromethoxy)phenyl]sulfonyl}-5-methyl-2-oxo-2,3-dihydro-1H-indol-3-yl)-4-hydroxy-N,N-dimethyl-L-prolinamide (levorotatory isomer), (4R)-1-(3-(1,3-benzodioxol-4-yl)-5-cyano-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), 1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N,4-trimethylpiperazine-2-carboxamide, 1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-pyridin-4-ylpiperazine-2-carboxamide, (2S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)piperidine-2-carboxylic acid (levorotatory isomer), (2S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer), (2S)-1-(5-chloro-3-(2,5-dimethoxyphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-pyrrolo[2,3-b]pyridin-3-yl)-4-hydroxy-N,N-dimethyl-L-prolinamide (levorotatory isomer), (4R)-1-(5-bromo-3-(2-methoxy-5-methylphenyl)-1-{[4-methoxy-2-(trifluoromethoxy)phenyl]sulfonyl}-2-oxo-2,3-dihydro-1H-pyrrolo[2,3-b]pyridin-3-yl)-4-hydroxy-N,N-dimethyl-L-prolinamide (levorotatory isomer), (4R)-1-[5-bromo-1-[(2,4-dimethoxyphenyl)sulfonyl]-3-(2-methoxy-5-methylphenyl)-2-oxo-2,3-dihydro-1H-pyrrolo[2,3-b]pyridin-3-yl]-4-hydroxy-N,N-dimethyl-L-prolinamide (levorotatory isomer), (4R)-1-(5-bromo-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-iodo-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-cyano-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), 3-{(2S,4R)-2-[(dimethylamino)carbonyl]-4-hydroxypyrrolidin-1-yl}-3-(2-methoxy-5-methylphenyl)-1-{[4-methoxy-2-(trifluoromethoxy)phenyl]sulfonyl}-2-oxo indoline-5-carboxamide (levorotatory isomer), (4R)-4-hydroxy-1-(3-(2-methoxy-5-methylphenyl)-1-{[4-methoxy-2-(trifluoromethoxy)phenyl]sulfonyl}-5-nitro-2-oxo-2,3-dihydro-1H-indol-3-yl)-N,N-dimethyl-L-prolinamide (levorotatory isomer), (4R)-1-(5-amino-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer), Methyl (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-L-prolinate (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer), (3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl acetate (levorotatory isomer), (3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl propionate (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(3-hydroxypropoxy)-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[3-(dimethylamino)propoxy]-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2-hydroxyethoxy)-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[2-(dimethylamino)ethoxy]-N,N-dimethyl-L-prolinamide (levorotatory isomer), (4R)-4-(3-amino-3-oxopropoxy)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(cyanomethoxy)-N,N-dimethyl-L-prolinamide (levorotatory isomer), (4R)-4-(2-amino-2-oxoethoxy)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-L-prolinamide (levorotatory isomer), ({(3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl}oxy)acetic acid (levorotatory isomer), (4R)-4-(allyloxy)-1-[5-chloro-3-(2-methoxy-5-methylphenyl)-2-oxo-2,3-dihydro-1H-indol-3-yl]-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2,3-dihydroxypropoxy)-N,N-dimethyl-L-prolinamide, (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[3-(diethylamino)propoxy]-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2, 3-dihydro-1H-indol-3-yl)-4-{3-[ethyl(methyl)amino]propoxy}-N,N-dimethyl-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-(3-piperidin-1-ylpropoxy)-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl4-[3-(4-methylpiperazin-1-yl)propoxy]-L-prolinamide (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-(3-morpholin-4-ylpropoxy)-L-prolinamide (levorotatory isomer), 1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-oxo-L-prolinamide (levorotatory isomer), 5-chloro-3-{(2S,4R)-4-hydroxy-2-[(4-methylpiperazin-1-yl)carbonyl]pyrrolidin-1-yl}-3-(2-methoxy-5-methylphenyl)-1-{[4-methoxy-2-(trifluoromethoxy)phenyl]sulfonyl}-1,3-dihydro-2H-indol-2-one (levorotatory isomer), (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-bis(2-hydroxyethyl)-L-prolinamide (levorotatory isomer), 3-[(2S,4R)-2-(azetidin-1-ylcarbonyl)-4-hydroxypyrrolidin-1-yl]-5-chloro-3-(2-methoxy-5-methylphenyl)-1-{[4-methoxy-2-(trifluoromethoxy)phenyl]sulfonyl}-1,3-dihydro-2H-indol-2-one (levorotatory isomer), (4R)-1-(5-chloro-3-(2-methoxy-5-methylphenyl)-2-oxo-1-{[2-(trifluoromethoxy)phenyl]sulfonyl}-2,3-dihydro-1H-indol-3-yl)-4-hydroxy-N,N-dimethyl-L-prolinamide (levorotatory isomer), (4R)-1-(5-chloro-3-(2-methoxy-5-methylphenyl)-2-oxo-1-{[4-(trifluoromethoxy)phenyl]sulfonyl}-2,3-dihydro-1H-indol-3-yl)-4-hydroxy-N,N-dimethyl-L-prolinamide (levorotatory isomer), (4R)-1-(5-chloro-3-(2-methoxy-5-methylpyridin-3-yl)-1-{[4-methoxy-2-(2,2,2-trifluoro ethoxy)phenyl]sulfonyl}-2-oxo-2,3-dihydro-1H-indol-3-yl)-4-hydroxy-N,N-dimethyl-L-prolinamide (levorotatory isomer), (4R)-1-[5-chloro-1-{[2-(difluoromethoxy)-4-methoxyphenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer), (4R)-1-(5-chloro-3-(2-methoxy-5-methylphenyl)-1-{[4-methoxy-2-(2,2,2-trifluoro ethoxy)phenyl]sulfonyl}-2-oxo-2,3-dihydro-1H-indol-3-yl)-4-hydroxy-N,N-dimethyl-L-prolinamide (levorotatory isomer), (4R)-1-{5-chloro-3-(2-methoxy-5-methylpyridin-3-yl)-2-oxo-1-[(2,3,4-trimethoxyphenyl)sulfonyl]-2,3-dihydro-1H-indol-3-yl}-4-hydroxy-N,N-dimethyl-L-prolinamide (levorotatory isomer), (4R)-1-{5-chloro-3-(2-methoxy-5-methylphenyl)-2-oxo-1-[(2,3,4-trimethoxyphenyl)sulfonyl]-2,3-dihydro-1H-indol-3-yl}-4-hydroxy-N,N-dimethyl-L-prolinamide (levorotatory isomer), (4R)-1-(5-chloro-3-(2-methoxy-5-methylphenyl)-1-{[4-(methylthio)-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-[5-chloro-1-{[3,4-dimethoxy-2-(trifluoromethoxy)phenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer), (4R)-1-[5-chloro-1-{[3,4-dimethoxy-2-(trifluoromethoxy)phenyl]sulfonyl}-3-(2-methoxy-5-m ethylphenyl)-2-oxo-2,3-dihydro-1H-indol-3-yl]-4-hydroxy-N,N-dimethyl-L-prolinamide (levorotatory isomer), (4R)-1-{5-chloro-3-(2-methoxy-5-methylphenyl)-1-[(2-methoxy-4-nitrophenyl)sulfonyl]-2-oxo-2,3-dihydro-1H-indol-3-yl}-4-hydroxy-N,N-dimethyl-L-prolinamide (levorotatory isomer), (4R)-1-{5-chloro-3-(2-methoxy-5-methylphenyl)-1-[(4-methoxy-2-nitrophenyl)sulfonyl]-2-oxo-2,3-dihydro-1H-indol-3-yl}-4-hydroxy-N,N-dimethyl-L-prolinamide (levorotatory isomer), (4R)-1-[5-chloro-1-{[4-(hydroxyamino)-2-methoxyphenyl]sulfonyl}-3-(2-methoxy-5-methylphenyl)-2-oxo-2,3-dihydro-1H-indol-3-yl]-4-hydroxy-N,N-dimethyl-L-prolinamide (levorotatory isomer), (4R)-1-[1-[(4-amino-2-methoxyphenyl)sulfonyl]-5-chloro-3-(2-methoxy-5-methylphenyl)-2-oxo-2,3-dihydro-1H-indol-3-yl]-4-hydroxy-N,N-dimethyl-L-prolinamide (levorotatory isomer), (4R)-1-{5-chloro-3-(2-methoxy-5-methylphenyl)-1-[(2-methoxy-4-methylphenyl)sulfonyl]-2-oxo-2,3-dihydro-1H-indol-3-yl}-4-hydroxy-N,N-dimethyl-L-prolinamide (levorotatory isomer), (4R)-1-(5-chloro-3-[5-(dimethylamino)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-(2-methoxy-5-morpholin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxy-5-pyridin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxy-5-piperidin-1-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

(4R)-1-(5-chloro-3-[4-(dimethylamino)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{5-[(dimethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-(5-formyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(morpholin-4-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(piperidin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-[2-methoxy-5-(pyrrolidin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-{2-methoxy-5-[(4-methylpiperazin-1-yl)methyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), tert-butyl 4-[3-(5-chloro-3-{(2S,4R)-2-[(dimethylamino)carbonyl]-4-hydroxypyrrolidin-1-yl}-1-{[4-methoxy-2-(trifluoromethoxy)phenyl]sulfonyl}-2-oxo-2,3-dihydro-1H-indol-3-yl)-4-methoxybenzyl]piperazine-1-carboxylate (4R)-1-(5-chloro-3-[2-methoxy-5-(piperazin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-[5-(hydroxymethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-{5-[(diethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-{[ethyl(methyl)amino]methyl}-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{2-methoxy-5-[(methylamino)methyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{5-[(cyclopropylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-{[cyclopropyl(methyl)amino]methyl}-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[5-(1-hydroxyethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide, (4R)-1-(3-(5-acetyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[5-(1-hydroxy-1-methylethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-[5-chloro-1-{[4-methoxy-2-(trifluoromethoxy)phenyl]sulfonyl}-3-(2-methoxy-5-vinyl phenyl)-2-oxo-2,3-dihydro-1H-indol-3-yl]-4-hydroxy-N,N-dimethyl-L-prolinamide (levorotatory isomer), (4R)-1-(5-chloro-3-(5-ethyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxy-5-propylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[5-(2-hydroxyethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[5-(2-hydroxyethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{5-[2-(dimethylamino)ethyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{5-[2-(dimethylamino)ethyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(2-morpholin-4-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{2-methoxy-5-[2-(4-methylpiperazin-1-yl)ethyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{5-[2-(diethylamino)ethyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(2-piperidin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(2-pyrrolidin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-{2-[ethyl(methyl)amino]ethyl}-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), tert-butyl 4-{2-[3-(5-chloro-3-{(2S,4R)-2-[(dimethylamino)carbonyl]-4-hydroxypyrrolidin-1-yl}-1-{[4-methoxy-2-(trifluoromethoxy)phenyl]sulfonyl}-2-oxo-2,3-dihydro-1H-indol-3-yl)-4-methoxyphenyl]ethyl}piperazine-1-carboxylate, (4R)-1-(5-chloro-3-[2-methoxy-5-(2-piperazin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-isopropyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(3-(5-tert-butyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(3-(5-sec-butyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-{5-chloro-1-{[4-methoxy-2-(trifluoromethoxy)phenyl]sulfonyl}-3-[2-(methylthio)phenyl]-2-oxo-2,3-dihydro-1H-indol-3-yl}-4-hydroxy-N,N-dimethyl-L-prolinamide (levorotatory isomer), (4R)-1-[5-chloro-1-{[4-methoxy-2-(trifluoromethoxy)phenyl]sulfonyl}-3-(1-naphthyl)-2-oxo-2,3-dihydro-1H-indol-3-yl]-4-hydroxy-N,N-dimethyl-L-prolinamide (levorotatory isomer), (4R)-1-(5-chloro-3-[5-(cyanomethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-cyano-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide, (4R)-1-(5-chloro-3-(2,6-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2,3-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-fluorophenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2,5-dimethylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(1H-tetrazol-5-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxy-3-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(4-methoxybiphenyl-3-yl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-fluoro-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(5-chloro-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{5-[hydroxy(phenyl)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide, (4R)-1-(3-(5-benzyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxy-4-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(2-methoxy-5-methyl)-1-{[4-methoxy-2-(trifluoromethoxy)phenyl]sulfonyl}-2-oxo-2,3-dihydro-1H-indol-3-yl)-4-methoxy-N,N-dimethyl-L-prolinamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(pyridin-2-ylmethyl)amino]-N,N-dimethylpropanamide (levorotatory isomer), (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N-methoxy-N-methylpropanamide (levorotatory isomer), 2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,2-trimethylpropanamide, (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-2-cyclohexyl-N,N-dimethylacetamide (levorotatory isomer), (2R)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (dextrorotatory isomer), (2S)-2-[benzyl(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer), N2-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl-L-lysinamide, (4R)-1-(5-chloro-3-[5-(2-cyanoethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-{2-methoxy-5-[2-(1H-tetrazol-5-yl)ethyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-pro linamide (levorotatory isomer), (4R)-1-(5-chloro-3-{5-[5-hydroxypent-2-en-1-yl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-pro linamide, (4R)-1-(5-chloro-3-[5-(5-hydroxypentyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-[2-methoxy-5-(5-piperidin-1-ylpentyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide, (4R)-1-(5-chloro-3-{5-[5-(dimethylamino)pentyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-pro linamide, (2S)-1-(3-(3-methoxyphenyl)-1-{[4-methoxy-2-(trifluoromethoxy)phenyl]sulfonyl}-5-methyl-2-oxo-2,3-dihydro-1H-indol-3-yl)-N,N-dimethylpiperidine-2-carboxamide (levorotatory isomer), (4R)-1-(3-(1,3-benzodioxol-5-yl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide, (4R)-1-(5-chloro-3-(4-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(5-chloro-3-(3-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), (4R)-1-(3-(1,3-benzodioxol-4-yl)-4-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), and (4R)-1-[3-(1,3-benzodioxol-4-yl)-1-{[4-methoxy-2-(trifluoromethoxy)phenyl]sulfonyl}-2-oxo-5-(trifluoromethoxy)-2,3-dihydro-1H-indol-3-yl]-4-hydroxy-N,N-dimethyl-L-prolinamide (levorotatory isomer)

[28] An arginine-vasopressin V1b receptor antagonist having as an active ingredient the 1,3-dihydro-2H-indol-2-one compound or a pyrrolidin-2-one compound fused with a heteroaromatic ring or pharmaceutically acceptable salts thereof as recited in any one from [1] to [27] described above.

[29] A drug which has a therapeutic or preventive effect on depression, anxiety, Alzheimer's disease, Parkinson's disease, Huntington's chorea, eating disorders, hypertension, digestive diseases, drug addiction, epilepsy, brain infarction, brain ischemia, brain edema, head injury, inflammation, immune diseases or alopecia, having as an active ingredient the 1,3-dihydro-2H-indol-2-one compound or the pyrrolidin-2-one compound fused with a heteroaromatic ring or pharmaceutically acceptable salts thereof as recited in any one from [1] to [27] described above.

[30] A benzene sulfonyl halide represented by Formula (13)

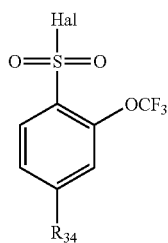

(13)

(in the formula, $R_{34}$ represents an alkoxy group having 1 to 5 carbon atoms, and Hal represents a halogen atom), or a pharmaceutically acceptable salt thereof.

In addition, the present invention also provides a medicinal composition containing the 1,3-dihydro-2H-indol-2-one compound, and the pyrrolidin-2-one compound fused with a heteroaromatic ring or pharmaceutically acceptable salts thereof described in any of the above and a pharmaceutically acceptable carrier or a pharmaceutically acceptable diluent, a medicinal composition containing a pharmaceutically acceptable carrier or a pharmaceutically acceptable diluent containing the 1,3-dihydro-2H-indol-2-one compound, and the pyrrolidin-2-one compound fused with a heteroaromatic ring or pharmaceutically acceptable salts thereof described in any of the above as an active ingredient in an effective dose, use of the 1,3-dihydro-2H-indol-2-one compound, and the pyrrolidin-2-one compound fused with a heteroaromatic ring or pharmaceutically acceptable salts thereof described in any of the above for preparing an agent, use of the 1,3-dihydro-2H-indol-2-one compound, and the pyrrolidin-2-one compound fused with a heteroaromatic ring or pharmaceutically acceptable salts thereof described in any of the above for preparing an arginine-vasopressin V1b receptor antagonist, use of the 1,3-dihydro-2H-indol-2-one compound, and the pyrrolidin-2-one compound fused with a heteroaromatic ring or pharmaceutically acceptable salts thereof described in any of the above for preparing a drug which has a therapeutic or preventive effect on depression, anxiety, Alzheimer's disease, Parkinson's disease, Huntington's chorea, eating disorders, hypertension, digestive diseases, drug addiction, epilepsy, brain infarction, brain ischemia, brain edema, head injury, inflammation, immune diseases or alopecia, use of the 1,3-dihydro-2H-indol-2-one compound, and the pyrrolidin-2-one compound fused with a heteroaromatic ring or pharmaceutically acceptable salts thereof described in any of the above for treating or preventing a disease related to the arginine-vasopressin V1b receptor, use of the 1,3-dihydro-2H-indol-2-one compound, and the pyrrolidin-2-one compound fused with a heteroaromatic ring or pharmaceutically acceptable salts thereof described in any of the above for treating or preventing depression, anxiety, Alzheimer's disease, Parkinson's disease, Huntington's chorea, eating disorders, hypertension, digestive diseases, drug addiction, epilepsy, brain infarction, brain ischemia, brain edema, head injury, inflammation, immune diseases or alopecia, a method using the 1,3-dihydro-2H-indol-2-one compound, and the pyrrolidin-2-one compound fused with a heteroaromatic ring or pharmaceutically acceptable salts thereof described in any of the above for treating or preventing a disease related to an arginine-vasopressin V1b receptor from human or other mammalian than human, a method using the 1,3-dihydro-2H-indol-2-one compound, and the pyrrolidin-2-one compound fused with a heteroaromatic ring or pharmaceutically acceptable salts thereof described in any of the above for treating or preventing depression, anxiety, Alzheimer's disease, Parkinson's disease, Huntington's chorea, eating disorders, hypertension, digestive diseases, drug addiction, epilepsy, brain infarction, brain ischemia, brain edema, head injury, inflammation, immune diseases or alopecia.

BEST MODE FOR CARRYING OUT THE INVENTION

Hereinafter, the present invention will be described in detail.

In the present specification, "halogen atom" means a fluorine atom, a chlorine atom, a bromine atom or an iodine atom.

"Alkyl group having 1 to 5 carbon atoms" means a linear chain or a branched chain of an alkyl group having 1 to 5 carbon atoms, and, for instance, methyl group, ethyl group, n-propyl group, isopropyl group, n-butyl group, isobutyl group, sec-butyl group, tert-butyl group, n-pentyl group, isopentyl group, neopentyl group, tert-pentyl group, and the like, can be cited.

"Alkyl group having 1 to 5 carbon atoms substituted by halogen atoms" means an alkyl group having 1 to 5 carbon atoms having 1 to 11 halogen atoms, and, for instance, chloromethyl group, difluoromethyl group, trichloromethyl group, trifluoromethyl group, 2-bromoethyl group, 2,2,2-trifluoroethyl group, pentafluoro ethyl group, 3,3,3-trifluoropropyl group, 4,4,4-trifluorobutyl group, 5,5,5-trifluoropentyl group, and the like, can be cited.

"Alkyl group substituted by a hydroxyl group" means a group having 1 to 2 hydroxyl groups substituted at any position on an alkyl group having 1 to 5 carbon atoms, and, for instance, 2-hydroxy ethyl group, 3-hydroxy propyl group, 4-hydroxy butyl group, 5-hydroxypentyl group, 2,3-dihydroxy propyl group, and the like, can be cited.

"Alkenyl group having 2 to 5 carbon atoms" means a group having one or more double bonds at any position of "an alkyl group having 2 to 5 carbon atoms" having two or more carbon atoms, and, for instance, vinyl group, allyl group, isopropenyl group, 2-methyl allyl group, 1-propenyl group, 2-methyl-1-propenyl group, 2-methyl-2-propenyl group, 1-butenyl group, 2-butenyl group, 3-butenyl group, 2-methyl-1-butenyl group, 3-methyl-2-butenyl group, 1-pentenyl group, 2-pentenyl group, 3-pentenyl group, 4-pentenyl group, and the like, can be cited.

"Alkynyl group having 2 to 5 carbon atoms" means a group having one or more triple bonds at any position of "an alkyl group having 2 to 5 carbon atoms" having two or more carbon atoms, and, for instance, ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, and the like, can be cited.

"Cycloalkyl group having 3 to 8 carbon atoms" means a cyclic aliphatic saturated hydrocarbon group having 3 to 8 carbons, and, for instance, cyclopropyl group, cyclobutyl group, cyclopentyl group, cyclohexyl group, cycloheptyl group, cyclooctyl group, and the like, can be cited.

"Alkylene group having 3 to 6 carbon atoms" means a divalent group that any hydrogen atom has been eliminated from an alkyl group having 3 to 6 carbon atoms or a cycloalkyl group having 3 to 6 carbon atoms, and, for instance, trimethylene group, tetramethylene group, penta methylene group, hexamethylene group, 1-methyl propylene group, 1,1-dimethyl propylene group, 1,1-dieth-ylethylene group, cyclopropylene group, cyclopropylene, 1,3-cyclobutylene, 1,3-cyclopentylene or 1,4-cyclohexylene, and the like, can be cited.

"Alkylene group having 1 to 5 carbon atoms" means a divalent group that any hydrogen atom has been eliminated from an alkyl group having 1 to 5 carbon atoms or a cycloalkyl group having 3 to 5 carbon atoms, for instance, a methylene group, ethylene group, trimethylene group, tetramethylene group, penta methylene, eth-ylethylene, methylethylene, prop-ylethylene cyclopropylene group, cyclopropylene, 1,3-cyclobutylene or 1,3-cyclopentylene, and the like, can be cited.

For "alkylene dioxy group having 1 to 3 carbon atoms", for instance, methylenedioxy group, ethylenedioxy group, trimethylenedioxy group, and the like, can be cited.

For "alkylene dioxy group having 1 to 3 carbon atoms substituted by halogen atoms", for instance, difluoromethylenedioxy group, tetrafluoro ethylenedioxy, hexafluoro trimethylenedioxy group, and the like, may be cited.

"Alkoxy group having 1 to 5 carbon atoms" means linear or branched alkoxy group having 1 to 5 carbon atoms, for instance, methoxy group, ethoxy group, n-propoxy group, isopropoxy group, n-butoxy group, isobutoxy group, sec-butoxy group, tert-butoxy group, n-pentoxy group, isopentoxy group, neopentoxy group, tert-pentoxy group, and the like, can be cited.

"Alkoxy group having 1 to 5 carbon atoms substituted by halogen atoms" means an alkoxy group having 1 to 5 carbon atoms having 1 to 11 halogen atoms, and, for instance, chloro methoxy group, fluoro methoxy group, difluoromethoxy group, trichloro methoxy group, a trifluoromethoxy group, 2-bromoethoxy group, 2,2,2-trifluoro ethoxy group, pentafluoro ethoxy group, 3,3,3-trifluoro propoxy group, 1,1,2,3,3,3-hexafluoro propoxy group, 4,4,4-trifluoro butoxy group, 5,5,5-trifluoro pentoxy group, and the like, can be cited.

"Alkoxy group having 1 to 5 carbon atoms substituted by fluorine atoms" means an alkoxy group having 1 to 5 carbon atoms having 1 to 11 fluorine atoms, and, for instance, fluoro methoxy group, a difluoromethoxy group, a trifluoromethoxy group, 2,2,2-trifluoro ethoxy group, pentafluoro ethoxy group, 3,3,3-trifluoro propoxy group, 1,1,2,3,3,3-hexafluoro propoxy group, 4,4,4-trifluoro butoxy group, 5,5,5-trifluoro pentoxy group, and the like, can be cited.

"Alkyl thio group having 1 to 5 carbon atoms" means a linear or branched alkyl thio group having 1 to 5 carbon atoms, and, for instance, methyl thio group, ethyl thio group, n-propyl thio group, isopropyl thio group, n-butyl thio group, isobutyl thio group, sec-butyl thio group, tert-butyl thio group, n-pentyl thio group, isopentyl thio group, neopentyl thio group, tert-pentyl thio group, and the like, can be cited.

"Alkoxy carbonyl group having 1 to 5 carbon atoms" means a carbonyl group conjugated with an alkoxy having 1 to 5 carbon atoms, and, for instance, methoxy carbonyl group, ethoxy carbonyl group, n-propoxy carbonyl group, isopropoxy carbonyl group, n-butoxy carbonyl group, isobutoxy carbonyl group, sec-butoxy carbonyl group, tert-butoxy carbonyl group, n-pentoxy carbonyl group, isopentoxy carbonyl group, neopentoxy carbonyl group, tert-pentoxy carbonyl group, and the like, can be cited.

"Alkoxy carbonyl amino group having 1 to 5 carbon atoms" means a carbonyl amino group conjugated with an alkoxy group having 1 to 5 carbon atoms, and, for instance, methoxy carbonyl amino group, ethoxy carbonyl amino group, n-propoxy carbonyl amino group, isopropoxy carbonyl amino group, n-butoxy carbonyl amino group, isobutoxy carbonyl amino group, sec-butoxy carbonyl amino group, tert-butoxy carbonyl amino group, n-pentoxy carbonyl amino group, isopentoxy carbonyl amino group, neopentoxy carbonyl amino group, tert-pentoxy carbonyl amino group, and the like, can be cited.

"Alkylcarbonyl group having 1 to 5 carbon atoms" means a carbonyl group conjugated with an alkyl group having 1 to 5 carbon atoms, and, for instance, acetyl group, propionyl group, n-butyryl group, isobutyryl group, 2-methyl butyryl group, n-valeryl group, isovaleryl group, and the like, can be cited.

"Alkylcarbonyl oxy group having 1 to 5 carbon atoms" means a carbonyl oxy group conjugated with an alkyl having 1 to 5 carbon atoms, and, for instance, acetoxy group, propionyl oxy group, isobutyryl oxy group, 2-methyl butyryl oxy group, n-valeryl oxy group, isovaleryl oxy group, and the like, can be cited.

"Alkylcarbonyl amino group having 1 to 5 carbon atoms" means a carbonyl amino group conjugated with an alkyl group having 1 to 5 carbon atoms, and, for instance, acetyl amino group, propionyl amino group, n-butyryl amino group, isobutyryl amino group, 2-methyl butyryl amino group, n-valeryl amino group, isovaleryl amino group, and the like, can be cited.

"Mono-alkyl amino group" means an amino group monosubstituted by an alkyl group having 1 to 5 carbon atoms, and, for instance, methyl amino group, ethyl amino group, n-propyl amino group, isopropyl amino group, n-butyl amino group, isobutyl amino group, sec-butyl amino group, n-pentyl amino group, isopentyl amino group, neopentyl amino group, tert-pentyl amino group, and the like, can be cited.

"Di-alkyl amino group" means an amino group di-substituted by identical or different alkyl groups having 1 to 5 carbon atoms, and, for instance, dimethyl amino group, diethyl amino group, ethylmethyl amino group, di-n-propyl amino group, and the like, can be cited.

"Cycloalkyl amino group" means an amino group monosubstituted by for instance a cycloalkyl group having 3 to 8 carbon atoms, and, for instance, cyclopropylamino group, cyclobutyl amino group, cyclopentyl amino group, cyclohexyl amino group, and the like, can be cited.

"Alkyl cycloalkyl amino group" means an amino group substituted by an alkyl group having 1 to 5 carbon atoms and a cycloalkyl group having 3 to 8 carbon atoms, and, for instance, cyclopropylmethyl amino group, cyclopropylethyl amino group, cyclobutylmethyl amino group, cyclobutylethyl amino group, cyclopentylmethyl amino group, cyclopentylethyl amino group, cyclohexylmethyl amino group, cyclohexylethyl amino group, and the like, can be cited.

"Mono-alkyl aminocarbonyl group" means an aminocarbonyl group mono-substituted by an alkyl group having 1 to 5 carbon atoms, and, for instance, methyl aminocarbonyl group, ethyl aminocarbonyl group, n-propyl aminocarbonyl group, isopropyl aminocarbonyl group, n-butyl aminocarbonyl group, isobutyl aminocarbonyl group, sec-butyl aminocarbonyl group, tert-butyl aminocarbonyl group, n-pentyl aminocarbonyl group, isopentyl aminocarbonyl group, neopentyl aminocarbonyl group, tert-pentyl aminocarbonyl group, and the like, can be cited.

"Di-alkyl aminocarbonyl group" means an aminocarbonyl group di-substituted by identical or different alkyl groups having 1 to 5 carbon atoms, and, for instance, dimethyl aminocarbonyl group, diethyl aminocarbonyl, methylethyl aminocarbonyl group, di-n-propyl aminocarbonyl, di-n-butyl aminocarbonyl group, and the like, can be cited.

For "alkyl sulfinyl group having 1 to 5 carbon atoms", for instance, methyl sulfinyl group, ethyl sulfinyl group, n-propyl sulfinyl group, isopropyl sulfinyl group, n-butyl sulfinyl group, isobutyl sulfinyl group, sec-butyl sulfinyl group, tert-butyl sulfinyl group, n-pentyl sulfinyl group, isopentyl sulfinyl group, neopentyl sulfinyl group, tert-pentyl sulfinyl group, and the like, can be cited.

For "alkyl sulfonyl group having 1 to 5 carbon atoms", for instance methyl sulfonyl group, ethyl sulfonyl group, n-propyl sulfonyl group, isopropyl sulfonyl group, n-butyl sulfonyl group, isobutyl sulfonyl group, sec-butyl sulfinyl group, tert-butyl sulfonyl group, n-pentyl sulfonyl group, isopentyl sulfonyl group, neopentyl sulfonyl group, tert-pentyl sulfonyl group, and the like, can be cited.

For "an alkyl sulfonyl amino group having 1 to 5 carbon atoms", for instance methyl sulfonyl amino group, ethyl sulfonyl amino group, n-propyl sulfonyl amino group, isopropyl sulfonyl amino group, n-butyl sulfonyl amino group, and the like, can be cited.

"Mono-alkyl aminothio carbonyl group" means an aminothio carbonyl group mono-substituted by an alkyl group having 1 to 5 carbon atoms, and, for instance, methyl aminothio carbonyl group, ethyl aminothio carbonyl group, n-propyl aminothio carbonyl group, n-butyl aminothio carbonyl group, tert-butyl aminothio carbonyl group, isobutyl aminothio carbonyl group, n-pentyl aminothio carbonyl group, isopentyl aminocarbonyl group, neopentyl aminocarbonyl group, tert-pentyl aminocarbonyl group, and the like, can be cited.

"Cycloalkylcarbonyl group having 3 to 8 carbon atoms" means a carbonyl group conjugated with a cycloalkyl having 3 to 8 carbon atoms, and, for instance, cyclobutylcarbonyl group, cyclopentylcarbonyl group, cyclohexylcarbonyl group, and the like, can be cited.

"Aryl having 6 to 14 carbon atoms" means a monocyclic or condensed polycyclic aromatic hydrocarbon having 6 to 14 carbon atoms. As concrete examples of "aryl having 6 to 14 carbon atoms", for instance, benzene can be cited for monocyclic aromatic hydrocarbon, and, for instance, indene, naphthalene, anthracene, phenanthrene, and the like, may be cited for condensed polycyclic aromatic hydrocarbon.

"Aryl group having 6 to 14 carbon atoms" means a monovalent group obtained by removing any hydrogen atom from the above-mentioned "aryl having 6 to 14 carbon atoms". Concretely, for instance, phenyl group, 1-naphthyl group, 2-naphthyl group, indenyl group, anthryl group, and the like, can be cited.

For "aryloxy group having 6 to 14 carbon atoms", for instance phenoxy group, 1-naphthoxy group, 2-naphthoxy group, indenyl oxy group, anthryl oxy group, and the like, can be cited.

For "aryl group having 6 to 14 carbon atoms substituted by a hydroxyl group", for instance, 2-hydroxyphenyl group, 3-hydroxyphenyl group, 4-hydroxyphenyl group, 5-hydroxy naphthyl group, and the like, can be cited.

For "aryl group having 6 to 14 carbon atoms substituted by an alkoxy group having 1 to 5 carbon atoms", for instance, 2-methoxyphenyl group, 3-methoxyphenyl group, 4-methoxyphenyl group, 5-methoxy naphthyl group, and the like, can be cited.

For "aryl group having 6 to 14 carbon atoms substituted by an aralkyl oxy group having 7 to 19 carbon atoms" for instance, 2-benzyl oxy phenyl group, 3-benzyl oxy phenyl group, 4-benzyl oxy phenyl group, 5-benzyl oxy naphthyl group, and the like, can be cited.

"Aryloxy carbonyl group having 6 to 14 carbon atoms" means a carbonyl group conjugated with an aryloxy having 6 to 14 carbon atoms, and, for instance, phenoxy carbonyl group, 1-naphthoxy carbonyl group, 2-naphthoxy carbonyl group, indenyl oxy carbonyl group, anthryl oxy carbonyl group, and the like, can be cited.

"Aryloxy carbonyl amino group having 6 to 14 carbon atoms" means an carbonyl amino group conjugated with an aryloxy group having 6 to 14 carbon atoms, and, phenoxy carbonyl amino group, 1-naphthoxy carbonyl amino group, 2-naphthoxy carbonyl amino group, indenyl oxy carbonyl amino group, anthryl oxy carbonyl amino group, and the like, can be cited.

"Arylcarbonyl group having 6 to 14 carbon atoms" means a carbonyl group conjugated with an aryl group having 6 to 14 carbon atoms, for instance, benzoyl group, 1-naphthoyl group, 2-naphthoyl group, 5-indenylcarbonyl group, 2-anthrylcarbonyl group, and the like, can be cited.

"A arylcarbonyl oxy group having 6 to 14 carbon atoms" means an aryl group having 6 to 14 carbon atoms conjugated with a carbonyl oxy group, and, for instance, benzoyl oxy group, 1-naphthoyl oxy group, 2-naphthoyl oxy group, and the like, can be cited.

"Arylcarbonyl amino group having 6 to 14 carbon atoms" represents an arylcarbonyl amino group having 6 to 14 carbon atoms, and for instance, benzoyl amino group, 1-naphthoyl amino group, 2-naphthoyl amino group, and the like, can be cited.

"Mono-aryl amino group" represents an amino group mono-substituted by an aryl group having 6 to 14 carbon atoms, and, for instance, phenyl amino group, 1-naphthyl amino group, 2-naphthyl amino group, and the like, can be cited.

"Di-aryl amino group" represents an amino group di-substituted by identical or different an aryl groups having 6 to 14 carbon atoms, and, for instance, diphenyl amino group, phenyl naphthyl amino group, and the like, can be cited.

"Mono-aryl aminocarbonyl group" represents an aminocarbonyl group mono-substituted by an aryl group having 6 to 14 carbon atoms, and, for instance, phenyl aminocarbonyl group, 1-naphthyl aminocarbonyl group, 2-naphthyl aminocarbonyl group, and the like, can be cited.

"Di-aryl aminocarbonyl group" represents an aminocarbonyl group di-substituted by an aryl group having 6 to 14 carbon atoms, and, for instance, diphenyl aminocarbonyl group, and the like, can be cited.

For "aryl thio group having 6 to 14 carbon atoms", for instance, phenyl thio group, 1-naphthyl thio group, 2-naphthyl thio group, indenyl thio group, anthryl thio group, and the like, can be cited.

For "aryl thio group having 6 to 14 carbon atoms substituted by halogen atoms", for instance, 3-chlorophenyl thio group, 2-bromophenyl thio group, 3-bromophenyl thio group, 4-bromophenyl thio group, 4-iodophenyl thio group, 2-fluorophenyl thio group, 3-fluorophenyl thio group, 2,4-difluorophenyl thio group, 2,5-difluorophenyl thio group, 3,4-difluorophenyl thio group, 3,5-difluorophenyl thio group, 4-fluorophenyl thio group, 4-chlorophenyl thio group, and the like, can be cited.

For "aryl thio group having 6 to 14 carbon atoms substituted by an alkyl group having 1 to 5 carbon atoms", for instance, 4-methylphenyl thio group, and the like, can be cited.

For "aryl sulfonyl group having 6 to 14 carbon atoms", for instance, phenyl sulfonyl group, 1-naphthyl sulfonyl group, 2-naphthyl sulfonyl group, and the like, can be cited.

For "aryl sulfonyl group having 6 to 14 carbon atoms substituted by an alkyl group having 1 to 5 carbon atoms", for instance, 4-methylphenyl sulfonyl group, and the like, can be cited.

"Mono-aryl aminothio carbonyl group" represents an aminothio carbonyl group mono-substituted by an aryl group having 6 to 14 carbon atoms, and, for instance, phenyl aminothio carbonyl group, 1-naphthyl aminothio carbonyl group, 2-naphthyl aminothio carbonyl group, and the like, can be cited.

For "aryl sulfonyl amino group having 6 to 14 carbon atoms", for instance phenyl sulfonyl amino group, naphthyl sulfonyl amino group, and the like, can be cited.

For "aryl sulfonyl amino group having 6 to 14 carbon atoms substituted by an alkyl group having 1 to 5 carbon atoms", for instance, 4-methylphenyl sulfonyl amino group, and the like, can be cited.

For "aryl sulfonyl amino group having 6 to 14 carbon atoms substituted by a nitro group", for instance, 4-nitrophenyl sulfonyl amino group, and the like, can be cited.

"Aralkyl group having 7 to 19 carbon atoms" represents a group comprising an alkyl group having 1 to 5 carbon atoms substituted by an aryl group having 6 to 14 carbon atoms, and, for instance, benzyl group, phenethyl group, 1-naphthylmethyl group, 2-naphthylmethyl group, and the like, can be cited.

"Aralkyl oxy group having 7 to 19 carbon atoms" represents a group comprising an alkoxy group having 1 to 5 carbon atoms substituted by an aryl group having 6 to 14 carbon atoms, and, for instance, benzyl oxy group, phenethyl oxy group, and the like, can be cited.

"Aralkyl oxy carbonyl group having 7 to 19 carbon atoms" represents a group comprising an alkoxy carbonyl group having 1 to 5 carbon atoms substituted by an aryl group having 6 to 14 carbon atoms, and, for instance, benzyl oxy carbonyl group, phenethyl oxy carbonyl group, and the like, can be cited.

"Aralkylcarbonyl amino group having 7 to 19 carbon atoms" represents a group comprising an alkylcarbonyl amino group having 1 to 5 carbon atoms substituted by an aryl group having 6 to 14 carbon atoms, and, for instance, benzylcarbonyl amino group, phenethylcarbonyl amino group, and the like, can be cited.

"Aralkyl thio group having 7 to 19 carbon atoms" represents a group comprising an alkyl thio group having 1 to 5 carbon atoms substituted by an aryl group having 6 to 14 carbon atoms, and, for instance, benzyl thio group, phenethyl thio group, and the like, can be cited.

"Aralkyl oxy carbonyl amino group having 7 to 19 carbon atoms" represents a group comprising an alkoxy carbonyl amino group having 1 to 5 carbon atoms substituted by an aryl group having 6 to 14 carbon atoms, and, benzyl oxy carbonyl amino group, phenethyl oxy carbonyl amino group, and the like, can be cited.

"Heterocycle" represents a monocyclic, a bicyclic or a tricyclic saturated or non-saturated heterocycle with 4 to 16-members per single ring, containing, in addition to carbon atoms, 1 to 4 heteroatoms selected from nitrogen atom, sulfur atom and oxygen atom, and, the heterocycle may ring-condense with each other or with a cycloalkyl aromatic hydrocarbon to form a bi- to tricyclic heterocycle. The ring atom sulfur or nitrogen may be oxidized to form an oxide or a dioxide. The heterocycles include saturated heterocycles, heteroaromatic cycles and partially saturated heterocycles thereof, condensation ring of an aromatic hydrocarbon and a saturated heterocycle, and in saturated heterocycles and partially saturated heterocycles, any carbon atom may be substituted by an oxo group. In addition, the "heterocycle" may be cross-linked, may form a spiro ring, or may include an acetal compound derived from an oxo group, such as, a 1,3-dioxolane ring.

"Heterocyclic group" represents a monovalent group obtained by removing any hydrogen atom from the above-mentioned "heterocycle".

For "monocyclic heterocycle", for instance, azetidine, oxetane, tetrahydrofuran, 1,3-dioxolane, tetrahydro-2H-pyran, pyrazolidine thiophene, furan, pyrrole, 2H-pyrrole, pyrazole, isooxazole, isothiazole, imidazole, oxazole, thiazole, pyridine, pyridazine, pyrimidine, pyrazine, pyrrolidine, pyrazolidine, imidazolidine, isooxazolidine, isothiazolidine, piperidine, piperazine, morpholine, thio morpholine, and the like, may be cited, for "bicyclic heterocycle", for instance, benzo[b]thiophene, benzo[b]furan, benzimidazole, benzoxazole, benzothiazole, benzo isothiazole, isoquinoline, quinoline, indole, isoindole, 1H-indazole, 4H-quinolizine, and the like, may be cited, and for "tricyclic heterocycle", for instance, carbazole, β-carboline, naphtho[2,3-b]thiophene, furazan, phenoxazine, and the like, may be cited.

For "heteroaromatic ring group", monovalent groups obtained by removing any hydrogen atom from these heteroaromatic rings, for instance thiophene, benzo[b]thiophene, benzo[b]furan, benzimidazole, benzoxazole, benzothiazole, benzo isothiazole, naphtho[2,3-b]thiophene, thianthrene, furan, isoindolizine, xanthrene, phenoxathiin, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphtyridine, quinoxaline, quinazoline, cinnoline, carbazole, β-carboline, phenathridine, acridine, phenazine, isothiazole, phenothiazine, isooxazole, furazan, phenoxazine, and the like, or condensation rings formed by condensing these rings with 1 or 2 aromatic hydrocarbons, and the like, may be cited. Among these, for instance 2-pyridyl group, 3-pyridyl group, a 4-pyridyl group, 2-quinolyl group, 3-quinolyl group, 4-quinolyl group, 5-quinolyl group, 8-quinolyl group, 1-isoquinolyl group, 3-isoquinolyl group, 4-isoquinolyl group, 5-isoquinolyl group, 1-indolyl group, 2-indolyl group, 3-indolyl group, 4-indolyl group, 5-indolyl group, 6-indolyl group, 7-indolyl group, 2-benzothiazolyl group, 2-benzo[b]

thienyl group, benzo[b]furanyl group, 2-thienyl group, 3-thienyl group, 2-furanyl group, 3-furanyl group, and the like, can be cited.

For "saturated heterocyclic group", monovalent groups obtained by removing any hydrogen atom from a "saturated heterocycle", such as, for instance, 1,3-dioxolane, tetrahydrofuran, tetrahydropyran, pentamethylene sulfide, azetidine, pyrrolidine, pyrazolidine, imidazolidine, isooxazolidine, isothiazolidine, piperidine, piperazine, morpholine, thio morpholine, oxacycloheptane, and the like, may be cited. Among these, 1,3-dioxolane-2-yl group, azetidin-1-yl group, azetidin-3-yl group, tetrahydrofuran-2-yl group, 1-, 2- or 3-pyrrolidinyl group, 1-, 2-, 3- or 4-piperidyl group, 2- or 4-imidazolidinyl group, 2-, 3- or 4-pyrazolidinyl group, 1- or 2-piperazinyl group, 2-, 3- or 4-morpholinyl group, and the like, can be cited.

For "partially saturated heterocycle", for instance, 2,3-dihydro benzofuran, indoline, isoindoline, chromane, isochromane, thio chromane, and the like, may be cited, and, as described above, in the present invention, "heterocyclic group" also includes monovalent groups obtained by removing any hydrogen atom from these compounds. Among these, for instance, 8-chromanyl group, 2,3-dihydro benzofuran-7-yl group, 2,3-dihydro benzofuran-4-yl group, and the like, can be cited.

For "condensation ring of an aromatic hydrocarbon and a saturated heterocycle", for instance, 1,2-benzodioxole, 2,3,4,5-tetrahydro-1-benzoxepin, and the like, may be cited, and "heterocyclic group" also includes monovalent groups obtained by removing any hydrogen atom from these compounds. Among these, for instance 1,3-benzodioxol-5-yl group, 1,3-benzodioxol-4-yl group, 2,3,4,5-tetrahydro-1-benzoxepin-9-yl group, and the like, can be cited.

"Nitrogen-containing heterocyclic group" represents heterocyclic group containing nitrogen, and, for instance, azetidin-1-yl group, pyrrolidin-1-yl group, piperidin-1-yl group, piperazin-1-yl group, morpholin-4-yl group, and the like, can be cited.

In addition, "heterocyclic group" also includes monovalent groups obtained by removing a hydrogen atom on a carbon atom from the heterocycle, known as carboxyl group equivalents, and groups substantially equally effective thereto. For instance, as such heterocycles, triazole, tetrazol, oxo-oxadiaxole, oxo thiadiazole, mercapto azole, isoxazole, isothiazole, hydroxy thiadiazole, hydroxy-γ-pyrone, and the like, can be cited.

"Heterocyclic group substituted by a nitrogen-containing heterocyclic group" means nitrogen-containing heterocyclic group in which one or a plurality of hydrogen atoms have been substituted by a heterocyclic group. Then, "heterocyclic group" and "nitrogen-containing heterocyclic group" are as described above.

For "B ring" in a group represented by Formula (7), for instance, piperazine, homo piperazine, piperazin-2-one or 2,3,6,7-tetrahydro-(1H)-1,4-diazepin-5(4H)-one, and the like, can be cited. In Formula (7), the B ring may be optionally substituted. As substituents on the B ring in Formula (7), oxo group, thioxo group, halogen atom, hydroxyl group or alkyl group having 1 to 5 carbon atoms may be cited.

"Group represented by the formula —(CO)-(heterocycle)" represents a carbonyl group substituted by a heterocyclic group, and, for instance, 2-pyridylcarbonyl group, 3-pyridylcarbonyl group, 4-pyridylcarbonyl group, quinoline-2-carbonyl group, 1-piperidylcarbonyl group, 1-piperazinylcarbonyl group, 1-pyrrolidinylcarbonyl group, 4-morpholinylcarbonyl group, and the like, can be cited.

"Group represented by the formula —O—(CO)-(heterocycle)" represents a carbonyl oxy group substituted by a heterocyclic group, and, for instance, 2-pyridylcarbonyl oxy group, 3-pyridylcarbonyl oxy group, 4-pyridylcarbonyl oxy, 1-piperidylcarbonyl oxy group, 1-piperazinylcarbonyl oxy group, 1-pyrrolidinylcarbonyl oxy group, 4-morpholinylcarbonyl oxy group, and the like, can be cited.

"Group represented by the formula —NH—(CO)-(heterocycle)" represents a carbonyl amino group substituted by a heterocyclic group, and, for instance, 2-pyridylcarbonyl amino group, 3-pyridylcarbonyl amino group, 4-pyridylcarbonyl amino group, 1-piperidylcarbonyl amino group, 1-piperazinylcarbonyl amino group, 1-pyrrolidinylcarbonyl amino group, 4-morpholinylcarbonyl amino group, and the like, can be cited.

"Group represented by the formula —O-(heterocycle)" represents an oxy group substituted by a heterocyclic group, and, for instance, 2-pyridyl oxy group, 3-pyridyl oxy group, 4-pyridyl oxy group, and the like, can be cited.

"Group represented by the formula —(CO)—O-(heterocycle)" represents an oxy carbonyl group substituted by a heterocyclic group, and, for instance, 2-pyridyl oxy carbonyl group, 3-pyridyl oxy carbonyl group, 4-pyridyl oxy carbonyl group, and the like, can be cited.

"Group represented by the formula —S-(heterocycle)" represents a thio group substituted by a heterocyclic group, and, for instance, 2-pyridyl thio group, 4-pyridyl thio group, and the like, can be cited.

"Group represented by the formula —NH—SO$_2$— (heterocycle)" represents a sulfonyl amino group a substituted by a heterocyclic group, and, for instance, 2-pyridine sulfonyl amino group, 3-pyridine sulfonyl amino group, 4-pyridine sulfonyl amino group, isoquinoline-5-sulfonyl amino group, and the like, can be cited.

"Heterocyclic group substituted by an alkoxy carbonyl group having 1 to 5 carbon atoms" represents a group comprising an alkoxy carbonyl group having 1 to 5 carbon atoms substituted on a nitrogen atom of a saturated heterocyclic group, and represent, for instance, 4-tert-butoxy carbonylpiperazin-1-yl group, and the like.

"Heterocyclic group substituted by an alkyl group having 1 to 5 carbon atoms" represents a heterocyclic group substituted by an alkyl group having 1 to 5 carbon atoms, and, for instance, 4-methylpiperazin-1-yl group, 4-ethylpiperazin-1-yl group, and the like, can be cited.

"Heterocyclic group substituted by a di-alkyl amino group" represents a group comprising a di-alkyl amino group having 1 to 5 carbon atoms substituted on any carbon atom of a heterocyclic group, and, for instance, 3-dimethylamino azetidin-1-yl group, and the like, can be cited.

"Heterocyclic group substituted by an amino group" represents a group comprising an amino group substituted on any carbon atom of a heterocyclic group, and, for instance, 3-amino azetidin-1-yl group, and the like, can be cited.

For "cycloalkenyl group having 3 to 8 carbon atoms", for instance, cyclopentenyl group, cyclohexenyl group, cycloheptenyl group, and the like, can be cited.

For "group represented by the formula —OR$_{10}$", for instance, hydroxyl group, methoxy group, ethoxy group, n-propoxy group, isopropoxy group, n-butoxy group, isobutoxy group, sec-butoxy group, tert-butoxy group, n-pentoxy group, acetoxy group, propionyl oxy group, isobutyryl oxy group, 2-methyl butyryl oxy group, n-valeryl oxy group, isovaleryl oxy group, benzyl oxy group, p-methoxy benzyl oxy group, 2-nitro benzyl oxy group, 3-nitro benzyl oxy group, 4-nitro benzyl oxy group, t-butoxy carbonyl oxy group, benzyl oxy carbonyl oxy group, 2-hydroxyethoxy group, 3-hydroxypropoxy group, 2-dimethylamino ethoxy group, 3-dimethylamino propoxy group, 2-cyano ethoxy group, 2-carbamoyl ethoxy group, 2-carboxy ethoxy group, cyano methoxy group, carbamoyl methoxy group, carboxy methoxy group, allyloxy group, 2,3-dihydroxypropoxy group, 3-diethylamino propoxy group, 3-methylethyl amino propoxy group, 3-piperidin-1-ylpropoxy group, 3-(4-methylpiperazin-1-yl)propoxy group, 3-morpholin-4-ylpropoxy group, and the like, can be cited. Groups represented by the formula —$OR_{10}$, preferably are hydroxyl group, methoxy group, 2-hydroxyethoxy group, 3-hydroxypropoxy group, 2-dimethylamino ethoxy group, 3-dimethylamino propoxy group, 2-cyano ethoxy group, 2-carbamoyl ethoxy group, 2-carboxy ethoxy group, cyano methoxy group, carbamoyl methoxy group, carboxy methoxy group, allyloxy group, 2,3-dihydroxypropoxy group, 3-diethylamino propoxy group, 3-methylethyl amino propoxy group, 3-piperidin-1-ylpropoxy group, 3-(4-methylpiperazin-1-yl)propoxy group and 3-morpholin-4-ylpropoxy group.

For "group represented by the formula —$SR_{10}$", for instance, methyl thio group, ethyl thio group, n-propyl thio group, isopropyl thio group, n-butyl thio group, isobutyl thio group, sec-butyl thio group, tert-butyl thio group, n-pentyl thio group, isopentyl thio group, neopentyl thio group, acethiothio group, propionyl thio group, isobutyryl thio group, 2-methyl butyryl thio group, n-valeryl thio group, isovaleryl thio group, benzyl thio group, p-methoxy benzyl thio group, 2-nitro benzyl thio group, 3-nitro benzyl thio group, 4-nitro benzyl thio group, t-butoxy carbonyl thio group, benzyl oxy carbonyl thio group, and the like, can be cited.

For "group represented by the formula —$NR_{10}R_{11}$", for instance, amino group, methyl amino group, ethyl amino group, n-propyl amino group, isopropyl amino group, n-butyl amino group, isobutyl amino group, sec-butyl amino group, n-pentyl amino group, dimethyl amino group, diethyl amino group, ethylmethyl amino group, acetyl amino group, n-propionyl amino group, n-butyryl amino group, isobutyryl amino group, 2-methyl butyryl amino group, n-valeryl amino group, isovaleryl amino group, benzylcarbonyl amino group, phenethylcarbonyl amino group, and the like, can be cited.

For "group represented by the formula —$OR_{12}$", for instance, hydroxyl group, methoxy group, ethoxy group, n-propoxy group, isopropoxy group, n-butoxy group, isobutoxy group, sec-butoxy group, tert-butoxy group, n-pentoxy group, isopentoxy, neopentoxy, tert-pentoxy group, benzyl oxy group, and the like, can be cited. Preferred is methoxy group.

For "group represented by the formula —$SR_{13}$", for instance, methyl thio group, ethyl thio group, and the like, can be cited.

For "group represented by the formula —$NR_{14}R_{15}$", for instance, amino group, methyl amino group, dimethyl amino group, ethyl amino group, azetidin-1-yl group, pyrrolidin-1-yl group, piperazin-1-yl group, methoxy amino group, pyrrolidin-1-yl amino group, morpholin-1-yl amino group, piperidin-1-yl amino group, 4-methylpiperazin-1-yl group, 2-dimethylamino ethylmethyl amino group, diethanol amino group, 3-tert-butoxy carbonyl amino azetidin-1-yl group, 3-amino azetidin-1-yl group, 3-dimethylamino-azetidin-1-yl group, 4-(4-pyridyl)piperazin-1-yl group, and the like, can be cited. Preferred are dimethyl amino group and azetidin-1-yl group.

For "group represented by the formula —(CO)—$NR_{14}R_{15}$", for instance, carbamoyl group, dimethyl aminocarbonyl group, ethyl aminocarbonyl group, azetidin-1-ylcarbonyl group, pyrrolidin-1-ylcarbonyl group, piperazin-1-ylcarbonyl group, methoxy aminocarbonyl group, 2-methyl hydrazino carbonyl group, 2-ethyl hydrazino carbonyl group, 2-n-propyl hydrazino carbonyl group, 2-isopropyl hydrazino carbonyl, 2-(2-hydroxy ethyl) hydrazino carbonyl group, pyrrolidin-1-yl aminocarbonyl group, morpholin-1-yl aminocarbonyl group, piperidin-1-yl aminocarbonyl group, and the like, can be cited.

For "group represented by the formula —$OR_{16}$", for instance, methoxy group, ethoxy group, n-propoxy group, isopropoxy group, n-butoxy group, isobutoxy group, sec-butoxy group, tert-butoxy group, n-pentoxy group, and the like, can be cited.

For "group represented by the formula —$NR_{17}R_{18}$", for instance, methyl amino group, dimethyl amino group, ethyl amino group, isopropyl amino group, 2-hydroxy ethyl amino group, pyrrolidin-1-yl group, morpholin-1-yl group, piperidin-1-yl group, and the like, can be cited.

For "group represented by the formula —$NR_{28}$—(C=$NR_{27}$)—$NR_{25}R_{26}$", for instance, a group represented by the formula —NH—(C=NH)—$NH_2$, a group represented by the formula —NH—(C=NH)—NH—$NO_2$, a group represented by the formula —NH—(C=N)—$NMe_2$, a group represented by the formula —NH—(C=NH)—NHEt, a group represented by the formula —NH—(C=NH)—NHOH, a group represented by the formula —NH—(C=NH)—NHEt, a group represented by the formula —NH—(C=NH)—$NEt_2$, a group represented by the formula —NH—(C=NH)—NH-n-propyl, a group represented by the formula —NH—(C=NMe)—NHMe, a group represented by the formula —NH—(C=NEt)—NHEt, a group represented by the formula —NH—(C=NH)—$NHCH_2CH=CH_2$, and the like, can be cited.

For "group represented by the formula —$NR_{32}$—(C=$NR_{31}$)—$NR_{29}R_{30}$", for instance, a group represented by the formula —NH—(C=NH)—$NH_2$, a group represented by the formula —NH—(C=NMe)—NHMe, and the like, can be cited.

For $R_A$, $R_B$ and $R_C$, which are substituents of the benzene sulfonyl group of the compound of the present invention, in order to antagonize highly selectively the arginine-vasopressin V1b receptor, preferably, $R_A$ is an alkoxy group having 1 to 5 carbon atoms substituted by fluorine atoms, $R_B$ is an alkoxy group having 1 to 5 carbon atoms, and $R_C$ is a hydrogen atom. Moreover, preferably, $R_A$ is substituted at position 2 of the benzene sulfonyl group, and $R_B$ is substituted at position 4. For the compound of the present invention, more preferable is one with a trifluoromethoxy group substituted at position 2 of the benzene sulfonyl group, and a methoxy group substituted at position 4, from the point of view of antagonizing highly selectively the arginine-vasopressin V1b receptor.

The compound of the present invention comprises all isomers unless indicated specifically. For instance, alkyl group, alkylene group and alkoxy group include those that are linear and those that are branched. In addition, isomers in double bond, ring and condensed ring (E isomer, Z isomer, cis isomer and trans isomer), isomers due to the presence of an asymmetric carbon and the like (R isomer, S isomer, α isomer, β isomer and enantiomer, diastereomer), optical isomers having optical rotation (D isomer, L isomer, d isomer, l isomer), polarity isomers by chromatographic separation (high polarity isomer, hypo polarity isomer), equilibrium compounds, mixtures thereof at any proportions, and racemic mixtures, are all included.

For the compound of the present invention, a levorotatory isomer is more desirable.

Among the vasopressin receptors (V1a, V1b and V2 receptors), the compound of the present invention highly selectively antagonizes the V1b receptor.

The compound of the present invention demonstrates satisfactory stability in metabolic stability studies using human liver microsomes.

The compound of the present invention sustains high plasma concentration longer and demonstrates higher brain penetrability in disposition studies by oral administration.

There is no particular limitation on "salt" as long as the salt is usable for the synthesis of the compound, and pharmaceutically acceptable salts may be cited; concretely, inorganic salts or organic salts may be cited. Note that, "salt" includes solvates such as hydrates, and not only anhydrides but also hydrate salts are included.

For "inorganic salts", for instance hydrochloride, hydrobromide, sulphates, hydrogen phosphate salts, nitrates, hydrogen sulfates, dihydrogen phosphates, and the like, can be cited.

For "organic salts", for instance, acetates, oxalates, lactates, tartrates, fumarates, maleates, succinates, trifluoroacetates, dichloroacetates, methane sulfonates, p-toluene sulfonates, naphthalene sulfonates, gluconates, benzene sulfonates, citrates, and the like, can be cited.

For "pharmaceutically acceptable salt thereof", salts of inorganic acids, for instance hydrochloric acid, hydrogen bromide, sulfuric acid and phosphoric acid, and salts of organic acids, such as, acetic acid, oxalic acid, lactic acid, tartaric acid, fumaric acid, maleic acid, succinic acid, trifluoroacetic acid, dichloroacetic acid, methanesulfonic acid, p-toluene sulfonic acid, naphthalene sulfonic acid, gluconic acid, benzene sulfonic acid and citric acid can be cited. Note that the compound of the present invention may also exist as various solvates. In addition, from the aspects of applicability as a medicinal drug, it may also be a hydrate.

The compound of the present invention also includes compounds in which one or more hydrogen atoms, carbon atoms, nitrogen atoms, oxygen atoms and sulfur atoms have been substituted by a radioactive isotope or a stable isotope. These labeled compounds are useful in, for instance, metabolism and pharmacokinetics studies, biological analysis as receptor ligands, and the like.

The compound of the present invention can be combined with one, or two or more pharmaceutically acceptable carriers, excipients or diluents, to yield a pharmacological formulation. The above-mentioned carriers, excipients and diluents include, for instance, water, lactose, dextrose, fructose, sucrose, sorbitol, mannitol, polyethylene glycol, propylene glycol, starch, gum, gelatin, alginate, calcium silicate, calcium phosphate, cellulose, water syrup, methyl cellulose, polyvinylpyrrolidone, alkyl parahydroxy benzosorbate, talc, magnesium stearate, stearic acid, glycerin, various oils such as sesame oil, olive oil and soybean oil, and the like.

In addition, additives such as expander, bonding agent, disintegration agent, pH adjuster, solubilizer, which are generally used, can be mixed to the above-mentioned carrier, excipient or diluent as necessary, and prepared as medicinal drug for peroral or non-peroral use, such as tablet, pill, encapsulated formulation, granule, powder, liquid, emulsion, suspension, ointment, injectable and adhesive skin patch, by regular formulation techniques. The compound of the present invention can be administered perorally or non-perorally atone time doses of 0.001 to 500 mg per adult patient, once daily or in multiple times. Note that this dose may be increased or decreased appropriately according to the type of illness to treat, patient's age, body weight, and symptoms, and the like.

The compound of the present invention can be prepared following, for instance, the methods described below.

The compound defined by the above-mentioned Formula (1) can be prepared by reacting, among the compounds of the present invention, the compound represented by Formula (14)

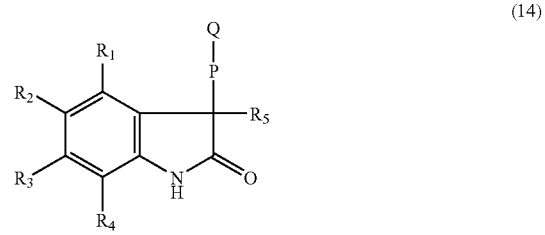

(14)

(in the formula, $R_1$, $R_2$, $R_3$, $R_4$, $R_5$, P and Q are respectively the same as described above) and the compound represented by Formula (15)

(15)

(in the formula, $R_A$, $R_B$ and $R_C$ are respectively the same as described above. Hal represents a halogen atom) in the presence of a base or a catalyst, then, as desired, converting the obtained compound into a salt with an inorganic acid, or an organic acid.

The reaction can be carried out in the presence of a base, for instance, metal hydride such as sodium hydride and the like, alkaline metal alkoxide such as potassium tert-butoxide, in an anhydrous solvent such as N,N-dimethylformamide, tetrahydrofuran and the like, or a mixed solvent thereof, under a temperature condition of −70° C. to +60° C. ("−70° C. or higher 60° C. or lower" idem hereinafter).

The compound of the present invention can be obtained by removal from the reaction system, then, purification by a general method, for instance, crystallization, chromatography, and the like.

The compound of the present invention can be obtained in free form, or by isolation as a salt by a general method. If the compound of the present invention is obtained in free form, salt formation can be carried out by treatment with an acid in an organic solvent. For instance, the free form can be dissolved, together with an acid, in ethers such as diethyl ether and the like, alcohols such as isopropyl alcohol and the like, acetone, dichloromethane, ethyl acetate, acetonitrile and the like, and the above-mentioned salt can be obtained by using a general method.

As acids used when forming a salt from a free form, for instance, hydrochloric acid, hydrogen bromide acid, sulfuric acid, phosphoric acid, acetic acid, oxalic acid, lactic acid, tartaric acid, fumaric acid, maleic acid, succinic acid, trifluoroacetic acid, dichloroacetic acid, methanesulfonic acid, p-toluene sulfonic acid, naphthalene sulfonic acid, benzene sulfonic acid, gluconic acid, citric acid, and the like, may be cited.

At the end of the reaction, the compound of the present invention sometimes is isolated as, for instance, hydrochloride, oxalate and the like; however, if necessary, the free form can be obtained by neutralization of the obtained salt using, for instance, a base such as sodium hydroxide, triethylamine, alkaline metal carbonate and alkaline metal hydrogen carbonate such as sodium carbonate and sodium bicarbonate and the like.

The compound defined by Formula (14) can be prepared by reacting the 3-halo-1,3-dihydro-2H-indol-2-one derivative represented by Formula (16)

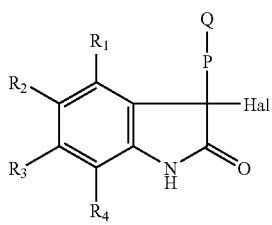

(16)

(in the formula, $R_1$, $R_2$, $R_3$, $R_4$, P and Q are respectively the same as described above. Hal represents a halogen atom) and the compound represented by Formula (17)

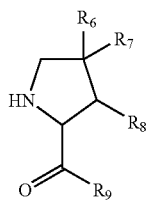

(17)

(in the formula, $R_6$, $R_7$, $R_8$, and $R_9$ are respectively the same as described above)

or a salt thereof or the compound represented by Formula (18)

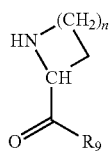

(18)

(in the formula, n and $R_9$ have the same meaning as above)

or a salt thereof or the compound represented by Formula (19)

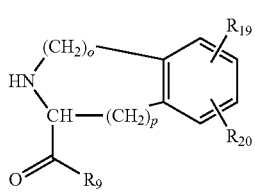

(19)

(in the formula, o, p, $R_9$, $R_{19}$ and $R_{20}$ are respectively the same as described above)

or a salt thereof or the compound represented by Formula (20)

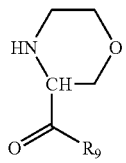

(20)

(in the formula, $R_9$ has the same meaning as above)

or a salt thereof or the compound represented by Formula (21)

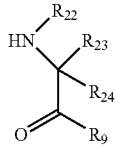

(21)

(in the formula, $R_9$, $R_{22}$, $R_{23}$ and $R_{24}$ are respectively the same as described above)

or a salt thereof or the compound represented by Formula (22)

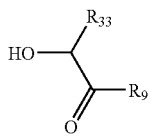

(22)

(in the formula, $R_9$ and $R_{33}$ are respectively the same as described above)

or a salt thereof or the compound represented by Formula (23)

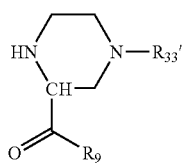

(23)

(in the formula, $R_9$ and $R_{33}$ are respectively the same as described above)

or a salt thereof in the presence of a base, for instance, diisopropylethylamine, triethylamine, sodium hydride and the like, in an inert solvent, for instance, chloroform, dichloromethane, tetrahydrofuran, and the like, or a mixed solvent thereof, under the temperature condition of room temperature to near the solvent boiling point.

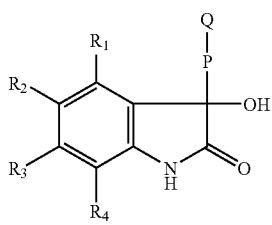

(24)

(in the formula, $R_1$, $R_2$, $R_3$, $R_4$, P and Q are respectively the same as described above) For the compound represented by Formula (16) can convert the compound represented by Formula (24) into the compound represented by Formula (16) (Hal=Cl) by action of, for instance, thionyl chloride, and the like, in the presence of a base, for instance, pyridine and the like, in an inert solvent, for instance, dichloromethane, chloroform and the like, under a temperature condition of 0° C. to room temperature.

As another manufacturing method of the compound represented by Formula (16), the compound represented by Formula (25)

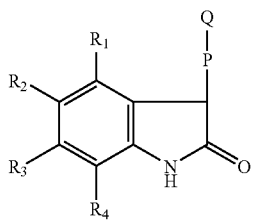

(25)

(in the formula, $R_1$, $R_2$, $R_3$, $R_4$, P and Q are respectively the same as described above)

can be converted into the compound represented by Formula (16) using a halogenation agent such as bromine, N-chloro succinimide and the like according to methods described in the references (Farm. Zh. (K-iev), 1976, 5, 30-33).

The compound represented by Formula (25) can be prepared according to methods described in, for instance, PCT Publication No. WO95/18105, PCT Publication No. WO01/74775, PCT Publication No. WO01/55130, PCT Publication No. WO01/55134, PCT Publication No. WO01/64668, PCT Publication No. WO01/98295, PCT Publication No. WO03/008407, J. Org. Chem., 33(4), 1640-1643 (1968) or Publication No. EP0747354, and the like.

In addition, for instance, the compound represented by Formula (24) can be obtained by hydrolysis of an intermediate obtained by action onto the 1H-indol-2,3-dione derivative represented by Formula (26)

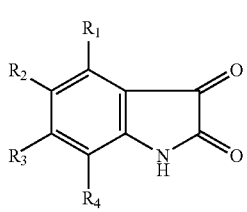

(26)

(in the formula, $R_1$, $R_2$, $R_3$ and $R_4$ are respectively the same as described above) of the organo-metallic reagent represented by Formula (27)

Q-P-M  (27)

(in the formula, P and Q are the same as in the above description. M represents a group represented by the formula —Mg—Hal or a group represented by the formula —Li. Hal represents a halogen atom).

These reactions can be carried out, for instance, in diethyl ether, tetrahydrofuran, n-hexane and the like, or a mixed solvent thereof, under a temperature condition between −70° C. to room temperature.

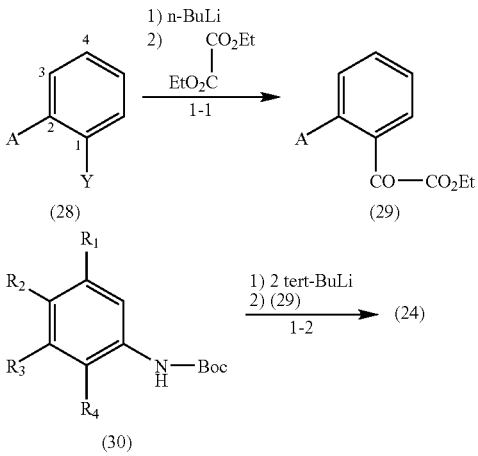

The compound represented by Formula (27) can be prepared by usual practice well-known to those skilled in the art.

In particular, among the compounds represented by Formula (24), for instance in a case where A ring represents a benzene ring, $R_2$ represents a trifluoromethyl group, P represents a single bond, Q represents a phenyl, and having a fluorine atom at position 2 as a substituent on Q (phenyl), or in a case wherein $R_2$ represents a chloro atom, $R_3$ represents a trifluoromethyl group, P represents a single bond, Q represents a phenyl, and having a trifluoromethoxy group at position 2 as a substituent on Q (phenyl), preparation is possible by the method described in Scheme 1.

(in Scheme 1, $R_1$, $R_2$, $R_3$ and $R_4$ are respectively the same as in the above description, and Boc represents a tert-butoxy carbonyl group)

In Step 1-1 of Scheme 1, the compound represented by Formula (28) is first lithiated by reacting with a lithiation reagent, for instance, n-butyl lithium and the like, in the presence of a base, for instance, N,N,N',N'-tetramethylethylenediamine and the like, or in a state with no base added, and reacts with diethyl oxalate to obtain the compound represented by Formula (29). The present reaction proceeds in an inert solvent, for instance, diethyl ether, tetrahydrofuran, hexane and the like, or in a mixed solvent thereof, under a temperature condition between −70° C. up to room temperature.

In Step 1-2, the desired compound represented by Formula (24) can be obtained by reacting with 2 equivalents of lithium derivative such as tert-butyl lithium and the like, and lithiating the compound represented by Formula (30), and reacting with the compound represented by Formula (29). The present reaction proceeds in an inert solvent, for instance, diethyl ether, tetrahydrofuran, pentane and the like, or in a mixed solvent thereof, under a temperature condition between −70° C. to room temperature.

The compound represented by Formula (28) is either commercially available, or can be prepared according to usual practice generally well-known to those skilled in the art.

The compound represented by Formula (30) can be prepared according to known methods described in Publication No. WO95/18105 or J. Org. Chem., 33, 1640-1643 (1968), and the like.

instance thionyl chloride or a chlorine additive equivalent thereto. In addition, the compound represented by Formula (24) can be obtained by oxidizing in air the compound represented by Formula (25), in the presence of a base, for instance, sodium hydride, dimethyl disulphide, and the like.

Among the compound represented by Formula (12), compounds where $R_5$ represents the above-mentioned Formula (3), Formula (4), Formula (5), Formula (6), Formula (8), Formula (9) and Formula (10) can also be prepared by the synthesis methods shown in Scheme 2.

Scheme 2

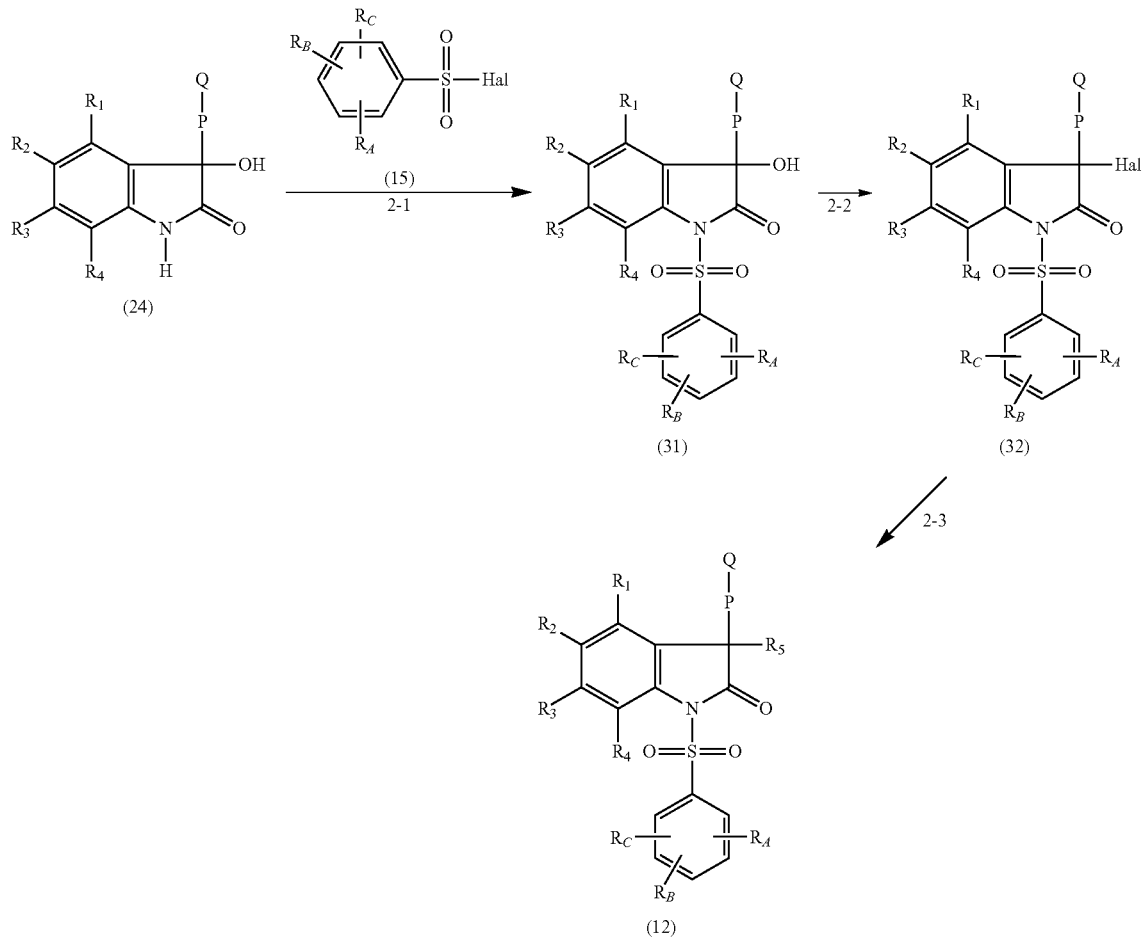

1H-indol-2,3-dione derivative (26) is either commercially available, or can be prepared according to methods described in the following references.

T. Helv. Chim. Acta, 2, 234 (1919), J. Prakt. Chim., 105, 137 (1922), Tetrahedron Letters, 1998, 39, 7679-7682. Tetrahedron Letters, 1994, 35, 7303-7306, J. Org. Chem., 1977, 42(8), 1344-1348, J. Org. Chem., 1952, 17, 149-156, Journal of American Chemical Society, 1946, 68, 2697-2703, Organic Synthesis, 1925, V, 71-74, Advances in Heterocyclic Chemistry, A. R. Katritzky and A. J. Boulton, Academic Press, New York, 1975, 18, 2-58.

Then, the obtained compound represented by Formula (24) can be converted into the corresponding 3-halogeno-1,3-dihydro indol-2-one compound (16) by reaction with for (in the formula, $R_1$, $R_2$, $R_3$, $R_4$, $R_B$, $R_C$, P and Q are the same as in the above description. $R_5$ is the same as the group defined in the above Formulae (3), (4), (5), (6), (8), (9) and (10). Hal represents a halogen atom)

The compound represented by Formula (31) can be obtained by reacting the compound represented by Formula (24) in the presence of a base or a catalyst and carrying out benzene sulfonylation on the nitrogen atom of the indoline (Step 2-1).

The reaction can be carried out in the presence of a base, for instance, metal hydride such as sodium hydride and the like, alkaline metal alkoxide such as potassium tert-butoxide and the like, in an anhydrous solvent, for instance, N,N-dimethyl formamide, tetrahydrofuran and the like, or a mixed solvent thereof, under a temperature condition of −70° C. to +60° C.

The compound represented by Formula (32) can be obtained by carrying out halogenation of the compound represented by Formula (31) in the same reaction conditions as when deriving the compound represented by Formula (16) from the compound represented by Formula (24) described above (Step 2-2).

The compound represented by Formula (12) ($R_5$ is the same as the group defined in the above Formulae (3), (4), (5), (6), (8), (9) and (10)) can be obtained by reacting the compound represented by Formula (32) in the presence of a base, for instance sodium bis-(trimethylsilyl) amide, potassium bis-(trimethylsilyl) amide, lithium bis-(trimethylsilyl) amide and the like, in an anhydrous solvent, for instance, N,N-dimethyl formamide and the like, under a temperature condition of −70° C. to +60° C. (Step 2-3).

In addition, the compound represented by Formula (12) ($R_5$ is the same as the group defined in the above Formulae (3), (4), (5), (6), (8), (9) and (10)) can be obtained by reacting the compound represented by Formula (32) in the presence of a catalyst, for instance, silver oxide and the like, in an anhydrous solvent, for instance, N,N-dimethyl formamide and the like, under a heating condition close to the boiling point of the solvent or under a heating condition of microwave irradiation (Step 2-3).

Among the compounds represented by Formula (15), when $R_A$ represents a trifluoromethoxy group and is at the position 2 of the benzene sulfonyl moiety, $R_B$ represents a methoxy group and is at position 4 of the benzene sulfonyl moiety, and $R_C$ represents a hydrogen atom, or, when $R_A$ represents a trifluoromethoxy group and is at position 4 of the benzene sulfonyl moiety, $R_B$ represents a methoxy group and is at position 2 of the benzene sulfonyl moiety and $R_C$ represents a hydrogen atom, a mixture of 2-methoxy-4-(trifluoromethoxy)benzene sulfonyl halide and 4-methoxy-2-(trifluoromethoxy)benzene sulfonyl halide can be prepared by the methods described in Recueil des Travaux Chimiques des Pays-Bas, 111, 215 (1992), that is to say, by neutralization with a base, for instance, potassium carbonate, sodium bicarbonate and the like, of 3-(trifluoromethoxy)anisole, after action of anhydrous sulfuric acid in a solvent, for instance, nitromethane and the like, and halogenation of the obtained salt.

The halogenation reaction proceeds in the presence of a halogenation agent, for instance, thionyl chloride, phosphorus oxy chloride, and the like, in the absence of solvent or in an inert solvent, for instance, halogenated hydrocarbon such as dichloromethane and the like, a solvent such as N,N-dimethyl formamide and the like, under a temperature condition between −10° C. to 200° C.

After halogenation, from the obtained mixture, 2-methoxy-4-(trifluoromethoxy)benzene sulfonyl halide and 4-methoxy-2-(trifluoromethoxy)benzene sulfonyl halide can be separated and purified by a purification technique, for instance, silica gel column chromatography. These compounds are novel, and constitute further subjects of the present invention. Such compounds can be also used effectively as intermediates when preparing the compound of the present invention.

3-(trifluoromethoxy) anisole is either commercially available, or can be prepared by reacting 3-(trifluoromethoxy) phenol with a methyl halide in the presence of a base, for instance, an alkaline metal salt such as potassium carbonate and the like, a metal hydride such as sodium hydride and the like, or an alkaline metal alkoxide such as potassium tert-butoxide and the like, in an anhydrous solvent, for instance, N,N-dimethyl formamide, tetrahydrofuran and the like, or a mixed solvent thereof, under a temperature condition of −70° C. to +60° C. In addition, it can also be prepared by reacting 3-(trifluoromethoxy)phenol with a diazo compound, for instance, diazo methane and the like, in a solvent, for instance, dichloromethane, chloroform, methanol, ethanol and the like, or a mixed solvent thereof. In addition, hydroxyl group alkylating reactions generally known to those skilled in the art can be used, such as methods using dimethyl sulfuric acid.

2-difluoromethoxy-4-benzene sulfonyl chloride can be obtained using commercially available 3-(difluoromethoxy) phenol, according to manufacturing methods for the above 2-methoxy-4-(trifluoromethoxy)benzene sulfonyl halide or 4-methoxy-2-(trifluoromethoxy)benzene sulfonyl halide.

2,4,6-trimethoxy benzene sulfonyl chloride can be obtained by well-known methods, for instance, by reacting commercially available 1,3,5-trimethoxy benzene with chlorosulfonic acid in a solvent, for instance, chloroform and the like.

3,4,6-trimethoxy benzene sulfonyl chloride and 2,3,4-trimethoxy benzene sulfonyl chloride can be obtained by subjecting 1,2,4-trimethoxy benzene or 1,2,3-trimethoxy benzene to general benzene sulfonylation and neutralization to obtain a salt, and subjecting the obtained salt to a halogenation reaction using, for instance thionyl chloride, phosphorus oxy chloride, and the like. 2-(2,2,2-trifluoro ethoxy)-4-methoxy benzene sulfonyl chloride can be obtained as a salt thereof by the treatment of 2-(2,2,2-trifluoro ethoxy)-4-methoxy benzene in a solvent, for instance, carbon tetrachloride and the like with a sulfonylation agent, for instance, trimethylsilyl sulfonyl chloride and the like, under ice cooling to room temperature conditions, and neutralization with a base, for instance, potassium carbonate, sodium hydroxide, potassium hydroxide and the like. The compound can be obtained by subjecting the obtained salt to the above halogenation reaction.

2-(2,2,2-trifluoro ethoxy)-4-methoxy benzene can be obtained by reacting commercially available 3-methoxy phenol in a solvent, for instance, N,N-dimethyl formamide and the like with commercially available 2-halogeno-1,1,1-trifluoroethane in the presence of a base, for instance cesium carbonate and the like, under room temperature to a temperature near the boiling point of the solvent.

2,5-bis(2,2,2-trifluoro ethoxy)benzene sulfonyl chloride, 2-(trifluoromethoxy)benzene sulfonyl chloride, 3-(trifluoromethoxy)benzene sulfonyl chloride, 4-(trifluoromethoxy) benzene sulfonyl chloride, 4-bromo-2-(trifluoromethoxy) benzene-1-sulfonyl chloride, 2-methoxy-4-methyl benzene sulfonyl chloride and 2-methoxy-4-nitrobenzene sulfonyl chloride are all commercially available.

A portion of the compounds represented by $R_6$ represents a hydroxyl group or a fluorine atom, $R_7$ and $R_8$ represent hydrogen atoms when $R_6$ represents a hydroxyl group, and $R_7$ represents a hydrogen atom or a fluorine atom and $R_8$ represents a hydrogen atom when $R_6$ represents a fluorine atom in Formula (17), can be prepared in general by the synthesis route shown in Scheme 3. Note that Pr represents a protecting group of nitrogen atom, for instance, a tert-butoxy carbonyl group such as benzyl oxy carbonyl group and the like.

Scheme 3

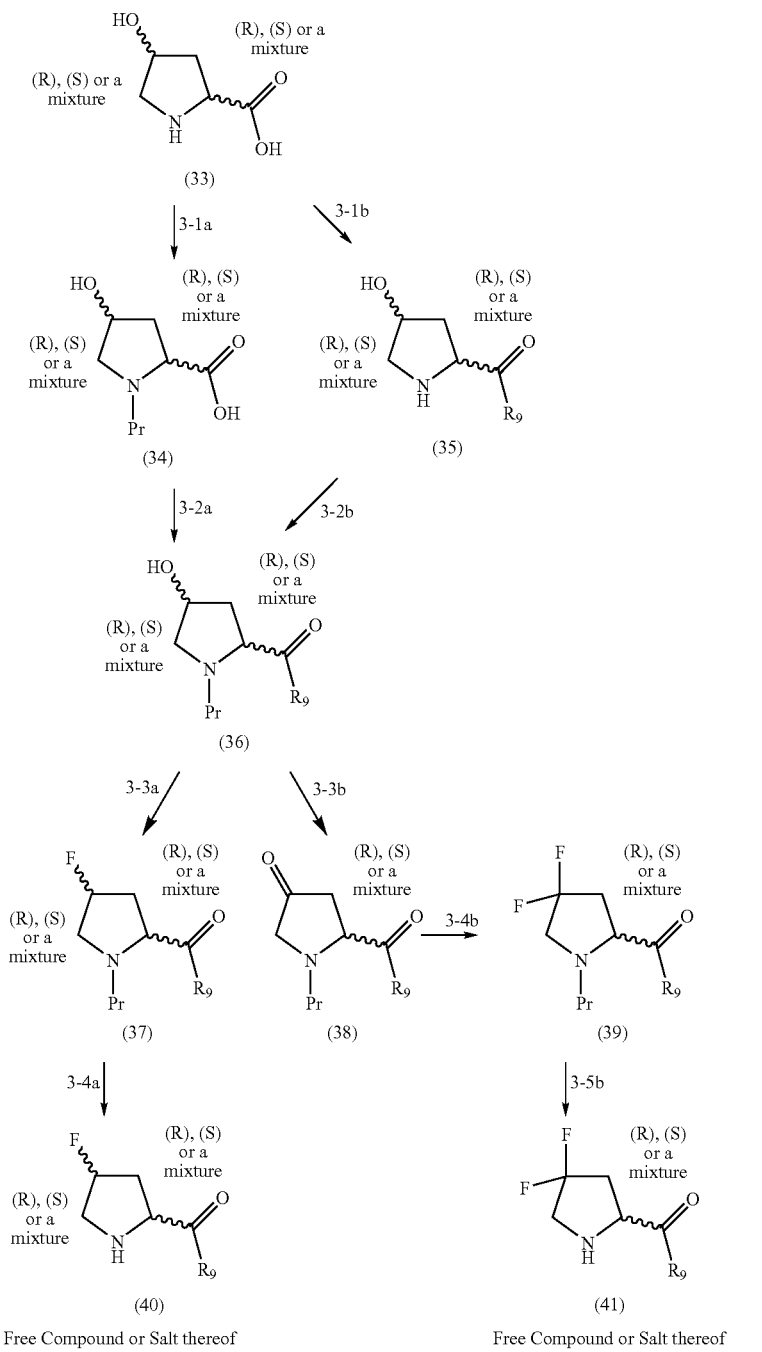

(in the formula, $R_9$ has the same meaning as in the above description. Pr represents a protecting group)

In Scheme 3, the compound represented by Formula (34) can be prepared by introduction of a protecting group according to a general method as the nitrogen atom in Formula (33): (4R)- or (4S)-4-hydroxy-L-proline or, (4R)- or (4S)-4-hydroxy-D-proline, in Step 3-1a. In the subsequent Step 3-2a, the compound represented by Formula (36) can be prepared by esterification, or amidation of the compound represented by Formula (34) according to general method. In addition, similarly, the compound represented by Formula (35) can be produced by esterification or amidation of the carboxylic acid of the compound represented by Formula (33) according to general methods in Step 3-1b, thereafter the compound represented by Formula (36) can be produced by introduction of a protecting group on the nitrogen atom of the obtained compound represented by Formula (35) according to general methods (Step 3-2b).

General amidation reactions include the following. For instance, methods using a dehydration condensation agent may be cited. As dehydration condensation agent, for instance, 1-ethyl-3-(3-dimethylamino propyl) carbodiimide/ hydrochloride, dicyclohexyl carbodiimide, diphenyl phosphonyl azide, carbonyl diimidazole, and the like, may be cited, and an activator can be used as necessary, for instance, 1-hydroxy benzo triazole, hydroxy succinimide and the like. As reaction solvent, for instance, dichloromethane, chloroform, 1,2-dichloro ethane, N,N-dimethyl formamide, tetrahydrofuran, dioxane, toluene, ethyl acetate and the like, or mixed solvent thereof may be cited. In so doing, base can be used to carry out the reaction, and as examples of base, organic amines, for instance, triethylamine, diisoprop-ylethyl amine and the like, organic salts such as sodium 2-ethyl hexanoate, potassium 2-ethyl hexanoate and the like, inorganic bases such as potassium carbonate, and the like, may be cited. The reaction can be carried out at −50° C. to near the boiling point of the solvent.

In addition amidation is possible using, for instance, mixed acid anhydride and the like obtained from carboxylic acid and carbonochloridic acid ester, pivaloyl chloride and the like. As solvents for these reactions solvents that do not participate in the reaction, for instance, tetrahydrofuran, dioxane, dichloromethane, chloroform, N,N-dimethyl formamide, toluene, ethyl acetate and the like, or mixed solvents thereof, may be cited. In so doing, a base can be used to carry out the reaction, and as examples of bases, organic amines such as triethylamine, diisoprop-ylethyl amine and the like, organic salts such as sodium 2-ethyl hexanoate, potassium 2-ethyl hexanoate and the like, inorganic bases such as potassium carbonate, and the like, may be cited. The reaction can be carried out under temperature conditions from −50° C. to near the boiling point of the solvent.

In addition, the following general esterification reaction of carboxylic acid exists. For instance, methyl esterification can be carried out by a diazo compound such as diazo methane and the like. In so doing, as solvent, solvents, for instance dichloromethane, chloroform, methanol, ethanol and the like, or mixed solvents thereof can be used. Furthermore, esterification can be carried out by deriving a carboxylic acid into an acid halide, and action of an alcohol compound. Acid halogenation can be carried out for instance by using thionyl chloride, bromide thionyl, phosphorus oxy chloride and the like. In so doing, the reaction can be carried out in solvents that do not participate in the reaction such as dichloromethane, chloroform, N,N-dimethyl formamide, toluene, tetrahydrofuran and the like, or mixed solvent thereof as solvent. Esterification can be carried out by action of alcohols, for instance, methanol, ethanol and the like, on the acid halide prepared in this way. In addition this reaction is achieved by adding alcohol to the acid halogenation reaction system, and can also be achieved by action of an alcohol on an isolated acid halide.

In addition, for instance, methods using a dehydration condensation agent may be cited. As dehydration condensation agent, for instance, 1-ethyl-3-(3-dimethylamino propyl) carbodiimide/hydrochloride, dicyclohexyl carbodiimide, diphenyl phosphonyl azide, carbonyl diimidazole, and the like, may be cited. As reaction solvents, for instance, dichloromethane, chloroform, 1,2-dichloro ethane, N,N-dimethyl formamide, tetrahydrofuran, dioxane, toluene, ethyl acetate and the like, or, mixed solvents thereof may be cited. In so doing, the reaction can be carried out using a base, and as examples of base, amines, for instance, triethylamine, diisoprop-ylethyl amine, 4-(dimethylamino) pyridine and the like, organic salts, for instance sodium 2-ethyl hexanoate, potassium 2-ethyl hexanoate and the like, and inorganic bases, for instance, potassium carbonate and the like may be cited. The reaction can be carried out under a temperature condition from −50° C. to near the boiling point of the solvent.

In addition, esterification is possible using, for instance, a mixed acid anhydride obtained from carboxylic acid and carbonochloridic acid ester, or di-tert-butyl dicarbonate and the like. As solvent of these reactions, solvents that do not participate in the reaction, for instance, tetrahydrofuran, dioxane, dichloromethane, chloroform, N,N-dimethyl formamide, toluene, ethyl acetate and the like, or mixed solvent thereof may be cited. In so doing, the reaction can be carried out using a base, and as examples of base, organic amines, for instance, triethylamine, diisoprop-ylethyl amine, 4-(dimethylamino) pyridine and the like, organic salts such as sodium 2-ethyl hexanoate, potassium 2-ethyl hexanoate and the like, and inorganic bases, for instance, potassium carbonate and the like, may be cited. The reaction can be carried out under temperature conditions from −50° C. to near the boiling point of the solvent.

In addition, esterification is possible, for instance, by the reaction of a carboxylic acid with a alkyl halide. As solvents of these reactions, solvents that do not participate in the reaction, for instance, tetrahydrofuran, dioxane, dichloromethane, chloroform, N,N-dimethyl formamide, dimethylsulfoxide, acetonitrile, toluene, ethyl acetate and the like, or mixed solvents thereof may be cited. In so doing, the reaction can be carried out using a base, and as examples of base, organic amines, for instance, triethylamine, diisoprop-ylethyl amine, 4-(dimethylamino) pyridine and the like, organic salts such as sodium 2-ethyl hexanoate, potassium 2-ethyl hexanoate and the like, and inorganic bases, for instance, potassium carbonate and the like may be cited. The reaction can be carried out under temperature conditions from −50° C. to near the boiling point of the solvent.

In any step for preparing the compound represented by Formula (3), (4), (5), (6), (7), (8), (9) and (10) or intermediates thereof, the necessity is considered, of protecting reactive or sensitive functional groups that are present in the molecules, such as amine, carboxylic acid and hydroxyl groups. In this regard, protection or deprotection can be carried out using protecting groups that are in common usage described in Protective Groups in Organic Chemistry by author J. F. W. McOmie, and in Protective Groups in Organic Synthesis by authors T. W. Greene and P. G. M. Wuts.

The protection of amino groups can be carried out using, for instance, di-tert-butyl dicarbonate, benzylchloro formate and the like, in the presence of an adequate base. As examples of base, for instance, amines such as triethylamine, diisopropylethyl amine and the like, or inorganic bases such as potassium carbonate and the like, and the like, may be cited. As solvents of these reactions solvents that do not participate in the reaction, for instance, tetrahydrofuran, dioxane, dichloromethane, chloroform, N,N-dimethyl formamide, toluene, ethyl acetate, tert-butyl alcohol, water and the like, or mixed solvent thereof may be cited. These reaction can be carried out at −50° C. to 50° C.

In addition, regarding protection of carboxylic acid, it is accomplished, for instance, by carrying out esterification. The esterification is according to the above methods.

The fluorination of a pyrrolidine ring allows to obtain, for instance, a 4-fluoro compound from a 4-hydroxy compound, and a 4,4-difluoro compound from a 4-keto compound.

In Scheme 3, as examples of mono fluorination in Step 3-3a, methods using, for instance, diethylamino sulfur trifluoride, dimethyl sulfur trifluoride, a mixture of 1,1,2,3,3,3-hexafluoro-1-(diethylamino) propane and 1,2,3,3,3-pentafluoro-1-(diethylamino)-2-propene, and the like, may be cited. When using a mixture of 1,1,2,3,3,3-hexafluoro-1-(diethylamino) propane and 1,2,3,3,3-pentafluoro-1-(diethylamino)-2-propene, the presence of, for instance, caesium fluoride, sodium fluoride, potassium fluoride and the like, mixed in the reaction system, gives satisfactory results. These reactions are accomplished using solvents that do not participate in the reaction, for instance, tetrahydrofuran, dioxane, dichloromethane, chloroform, 1,2-dichloro ethane, toluene and the like, or mixed solvents, starting the reaction at −78° C. to room temperature, and continuously carrying out the reaction at room temperature to 50° C. In addition, as example of mono fluorination methods may be cited, whereby, for instance, a hydroxyl group is converted into a leaving group and then converted into a fluoro group. As conversion into a leaving group, for instance, chlorination, bromination, iodization, methane sulfonylation, p-toluene sulfonylation, and the like, may be cited.

As examples of chlorination reaction, for instance, methods using carbon tetrachloride and triphenyl phosphine, methods using thionyl chloride and phosphorus oxy chloride, methods using p-toluene sulfonyl chloride and the like turning it into a leaving group, then substituting it with chloride lithium and the like, and the like, may be cited. These reactions can use solvents that do not participate in the reaction, for instance, tetrahydrofuran, dioxane, dichloromethane, chloroform, N,N-dimethyl formamide and the like, or mixed solvents thereof. These reaction can be carried out at −50° C. to 100° C.

As examples of bromination reaction methods using, for instance, carbon tetra bromide, triphenyl phosphine and the like may be cited. This reaction can be carried out in solvents that do not participate in the reaction, for instance, tetrahydrofuran, dioxane, dichloromethane, chloroform, N,N-dimethyl formamide and the like, or mixed solvents thereof, at −50° C. to 50° C.

As examples of iodization reaction, method using, for instance, iodide, triphenyl phosphine and imidazole, may be cited. This reaction use solvents that do not participate in the reaction, for instance tetrahydrofuran, dioxane, dichloromethane, chloroform, N,N-dimethyl formamide and the like, or mixed solvents thereof. These reaction can be carried out under temperature conditions from −50° C. to 100° C.

Methane sulfonylation and p-toluene sulfonylation can be carried out using respectively, for instance methane sulfonyl chloride, methanesulfonic acid anhydride, p-toluene sulfonyl chloride and the like. In so doing, an adequate base may be added. As examples of base to be added, organic amines, for instance, triethylamine, pyridine, diisoprop-ylethyl amine and the like, or inorganic bases, for instance, potassium carbonate and the like may be cited. In solvents that do not participate in the reaction, for instance, N,N-dimethyl formamide, tetrahydrofuran, dioxane, dichloromethane, chloroform, 1,2-dichloro ethane and the like, or mixed solvents thereof, as reaction solvents, the reaction can be carried out under temperature conditions from −50° C. to 50° C.

As methods for converting into a leaving group and then converting into a fluoro group, methods causing to react, for instance, tetrabutyl ammonium fluoride, caesium fluoride, potassium fluoride, sodium fluoride and the like may be cited. These reactions can be carried out in solvents that do not participate in the reaction, for instance tetrahydrofuran, dioxane, dichloromethane, chloroform, N,N-dimethyl formamide, water and the like, or mixed solvents thereof, under a temperature condition of −50° C. to 100° C.

In addition, difluorination can be carried out for instance after oxidizing hydroxyl group into ketone group.

The method of oxidation (Step 3-3b) can be carried out using a chromate, for instance, pyridinium chlorochromate pyridinium dichromate and the like. As reaction solvents, dichloromethane, chloroform, and the like, may be cited, and the reaction temperature can be carried out at 0° C. to near the boiling point of the solvent.

In addition, reaction is possible using, for instance, Dess-Martin Reagent (1,1,1-triacetoxy-1,1-dihydro-1,2-benziodo oxaol-3-(1H)-one) and the like. As reaction solvent, for instance, dichloromethane, chloroform, and the like, may be cited, and the reaction temperature can be carried out at 0° C. to 40° C.

In addition, as another example, the reaction is also possible using, for instance, IBX (1-hydroxy-1,2-benz iodoxol-3(1H)-one 1-oxide) and the like. The reaction can be carried out using as reaction solvent, for instance, dimethylsulfoxide and further diluting with a solvent that does not participate in the reaction, for instance, tetrahydrofuran, dichloromethane, chloroform and the like. The reaction temperature can be carried out at 0° C. to 40° C.

In regard to this oxidation reaction, other methods than those described above are not limited in particular, as long as the methods can oxidize an alcohol into a ketone. For instance, reactions by a dimethylsulfoxide and an activator (oxalyl chloride, N-chloro succinimide, dicyclohexyl carbodiimide, and the like), oxidation method using tetra-n-propyl ammonium perruthenate (VII) and N-methyl morpholine oxide, and the like, may be cited. A comprehensively overview of this oxidation reaction may be found in Richard C. Larock, Comprehensive Organic Transformation, WILEY-VCH, 1999, 604.

In addition, difluorination at Step 3-4b in Scheme 3, method using a fluorination agent for, instance, dimethyl sulfur trifluoride, [bis(2-methoxy ethyl)amino]sulfur trifluoride, may be cited. These reactions are accomplished by starting the reaction in a solvent that dos not participate in the reaction, for instance, tetrahydrofuran, dioxane, dichloromethane, chloroform, 1,2-dichloro ethane, toluene and the like, or mixed solvents thereof, at −78° C. to room temperature, and carrying out the reaction continuously from room temperature to near the boiling point of the solvent.

The protecting group of the nitrogen atom is removed by general methods (Steps 3-4a and 3-5b), allowing the compound represented by Formulae (40) and (41) or salts thereof to be prepared.

For instance, when the protection is achieved with a group that is removed by an acid, such as the tert-butyl oxy carbonyl group, the protective group can be removed by using an acid, for instance, hydrochloric acid, sulfuric acid, trifluoroacetic acid, p-toluene sulfonic acid, methanesulfonic acid and the like. In so doing, deprotection can be carried out by diluting or dissolving the acid in an organic solvent or water, and the reaction can be carried out under temperature conditions from −50° C. to 50° C. As organic solvent, for instance, ethanol, methanol, tetrahydrofuran, N,N-dimethyl formamide, dichloromethane, chloroform, 1,2-dichloro ethane and the like, or mixed solvent thereof may be cited.

Furthermore, in the case of a protecting group that is removed by hydrogenolysis, for instance, benzyl oxy carbonyl group and the like, deprotection can be by a hydrogenolysis reaction using a metal catalyst such as palladium and the like. As solvent, solvents that do not participate in the reaction, for instance, ethanol, methanol, tetrahydrofuran, ethyl acetate and the like, or mixed solvents thereof can be used. The reaction can be carried out at 0° C. to 100° C. In addition, hydrogen gas can also be used in this reaction, which can otherwise also be carried out using, for instance, a combination of formic acid-ammonium formate.

Furthermore, a compound with, for instance, a protecting group removed by a base, for instance, fluorenyl oxy carbonyl group and the like, can be deprotected using bases, for instance, diethyl amine, piperidine, ammonia, sodium hydroxide, potassium hydroxide and the like. These bases can be used alone or in combination, by diluting, dissolving or suspending in a solvent. In so doing, as solvent, for instance water, ethanol, methanol, tetrahydrofuran, N,N-dimethyl formamide, dichloromethane, chloroform, 1,2-dichloro ethane and the like, or mixed solvent thereof can be used. The reaction can be carried out under temperature conditions from 0° C. to near the boiling point of the solvent.

Furthermore, a compound with a group that is removed by a metal catalyst such as allyloxy carbonyl group and the like can be deprotected using as catalyst or reagent, for instance, tetrakis(triphenyl phosphine) palladium$^0$ and the like. In so doing, the reaction can be carried out in solvents that do not participate in the reaction, for instance, dichloromethane, chloroform, tetrahydrofuran and the like. The reaction can be carried out under temperature conditions from 0° C. to near the boiling point of the solvent.

(4R)- and (4S)-4-hydroxy-L-proline or, (4R)- and (4S)-4-hydroxy-D-proline are commercially available.

Among the compounds represented by Formula (17), (4R)-4-fluoro-N,N-dimethyl-L-prolinamide (47) can be prepared by the synthesis route shown in Scheme 4.

(in the formula, Pr has the same meaning as in the above description.)

The compounds represented by Formulae (42) and (44), that is (4R)—N-protection-4-hydroxy-L-proline (42) or (4S)—N-protection-4-hydroxy-L-proline (44) are used as synthetic raw materials for N,N-dimethyl amidation according to a general method for amide bond formation in Steps 4-1a and 4-1b, then, a mixture of fluorination agents, for instance, 1,1,2,3,3,3-hexafluoro-1-(diethylamino) propane and 1,2,3,3,3-pentafluoro-1-(diethylamino)-2-propene and the like is used to carry out fluorination in Steps 4-2a and 4-2b. In the present fluorination, a satisfactory result is provided when a metal fluoride, for instance, sodium fluoride, potassium fluoride, cesium fluoride and the like is present mixed in the reaction system. The present reaction is accomplished by starting the reaction a in solvent that does not participate in the reaction, for instance, tetrahydrofuran, dioxane, dichloromethane, chloroform, 1,2-dichloro ethane, toluene and the like, or a mixed solvent thereof, at −78° C. to room temperature and carrying out the reaction continuously at room temperature to near the boiling point of the solvent.

When mono-fluorination is carried out using a mixture of 1,1,2,3,3,3-hexafluoro-1-(diethylamino) propane and 1,2,3,3,3-pentafluoro-1-(diethylamino)-2-propene, even when the

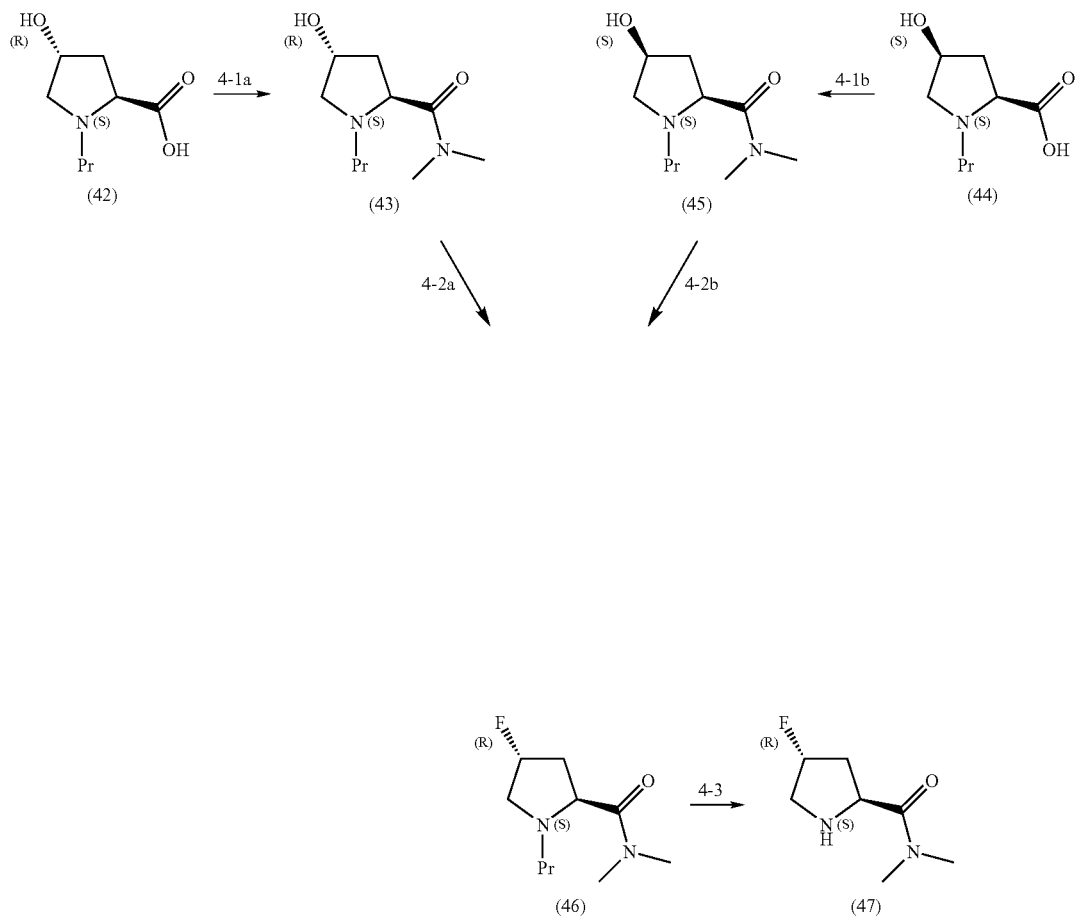

Free form or salt thereof configuration at position 4 of the synthetic raw materials compounds represented by Formulae (42) and (44) is either the (R) configuration or the (S) configuration, as a result, the 4-fluorinated compound (46) with the (4R) configuration can be obtained. The obtained compound represented by Formula (46) is deprotected by a general method, and the compound represented by Formula (47) or a salt thereof can be obtained.

In addition, when the carboxylic acid was protected by a group that can be removed by an acid such as another ester, for instance tert-butyl ester, the carboxylic acid can be deprotected using an acid such as hydrochloric acid, sulfuric acid, trifluoroacetic acid, p-toluene sulfonic acid, methanesulfonic acid and the like. In so doing, the deprotection can be carried out by diluting or dissolving the acid in an organic solvent or

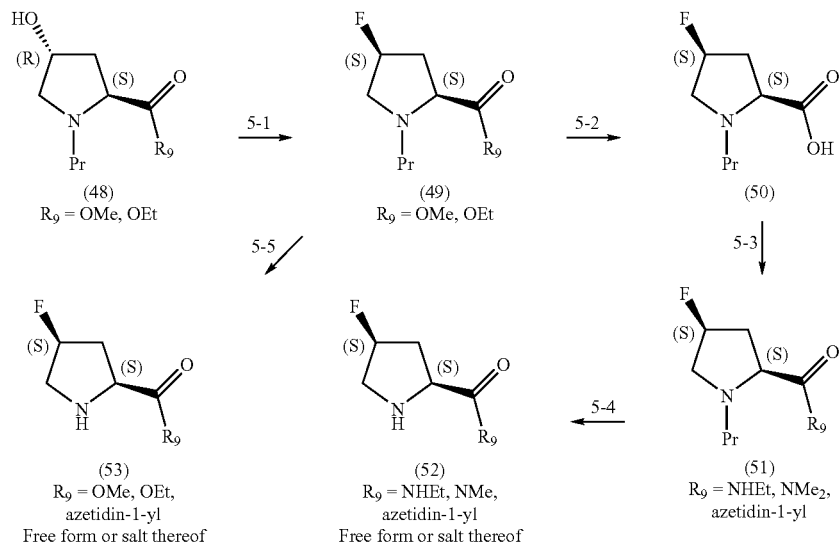

(in the formula, Pr has the same meaning as in the above description.)

Among the compounds represented by Formula (17), when $R_6$ represents a fluorine atom in the beta position, $R_7$ represents a hydrogen atom in the alpha position, $R_9$ represents a hydrogen atom, $R_9$ represents an alkoxy group having 1 to 5 carbon atoms, a dimethyl amino group, an ethyl amino group or an azetidin-1-yl group, the compound can be prepared by the synthesis route shown in Scheme 5. The methyl or ethyl (2S,4R)—N-protection-4-hydroxy-2-pyrrolidine carboxylate compound shown in Formula (47) is used as synthetic raw materials, and a fluorine in the (4S) configuration is introduced by a general fluorination of hydroxyl group (Step 5-1). The obtained compound represented by Formula (49) is deprotected by a general method (Step 5-5), and methyl or ethyl (4S)-4-fluoro-L-prolinate body (53) or a salt thereof can be obtained. On the other hand, the compound represented by Formula (49) can be hydrolyzed of an ester group according to a general method (Step 5-2), and a carboxylic acid compound (50) can be prepared. The obtained carboxylic acid compound (50) is amidated by a general method for peptide bond formation (Step 5-3), then, protecting group of the nitrogen atom is removed by a general method (Step 5-4), and a (4S)-4-fluoro-L-prolinamide compound (52) or a salt thereof can be prepared.

Hydrolysis of ester can be performed by using a base, for instance, metal hydroxide salt such as sodium hydroxide and the like, metal carbonate salt such as potassium carbonate and the like. As solvents for this reaction, for instance, alcohols such as methanol, ethanol and the like, solvents such as tetrahydrofuran, dioxane, N,N-dimethyl formamide water and the like, or mixed solvent thereof may be cited. The reaction can be carried out under temperature conditions of −20° C. to near the boiling point of the solvent.

water, and the reaction can be carried out under temperature conditions from −50° C. to 50° C. As organic solvents, solvents, for instance, ethanol, methanol, tetrahydrofuran, N,N-dimethyl formamide, dichloromethane, chloroform, 1,2-dichloro ethane and the like, or mixed solvent thereof may be cited.

Furthermore, when protection was by a group that is removed by hydrogenolysis, for instance, benzyl ester and the like, deprotection is possible by a hydrogenolysis reaction using a metal catalyst such as palladium and the like. As solvent, solvents that do not participate in the reaction, for instance, ethanol, methanol, tetrahydrofuran, ethyl acetate and the like or mixed solvents thereof can be used. The reaction can be carried out at 0° C. to 100° C. In addition, hydrogen gas can also be used in this reaction, and otherwise for instance a combination of formic acid-ammonium formate can be used to carry out the reaction.

Furthermore, when protection was by a group removed by a metal catalyst, for instance, allyl ester and the like, deprotection is possible by using a catalyst or a reagent, for instance, tetrakis (triphenyl phosphine) palladium⁰ and the like. In so doing, the reaction can be carried out in solvents that do not participate in the reaction, for instance, dichloromethane, chloroform, tetrahydrofuran and the like. The reaction can be carried out under temperature conditions of 0° C. to near the boiling point of the solvent.

Among the compounds represented by Formula (17), when $R_6$ and $R_7$ represent fluorine atoms, $R_8$ represents a hydrogen atom, $R_9$ represents an ethyl amino group, a dimethyl amino group or an azetidin-1-yl group, the compound can be prepared by the synthesis route shown in Scheme 6. Using the 4,4-difluoro-N-protection-2-pyrrolidine carboxylate compound among the compounds represented by Formula (39) described in Scheme 3, the synthetic raw materials is turned into carboxylic acid compound (54) by hydrolysis in Step 6-1. The obtained carboxylic acid compound (54), according to a general method for amide bond formation, allows the compound represented by Formula (55) to be prepared (Step 6-2). The protecting group of the nitrogen atom is removed by a general method (Step 6-3), and the compound represented by Formula (56) or a salt thereof can be prepared.

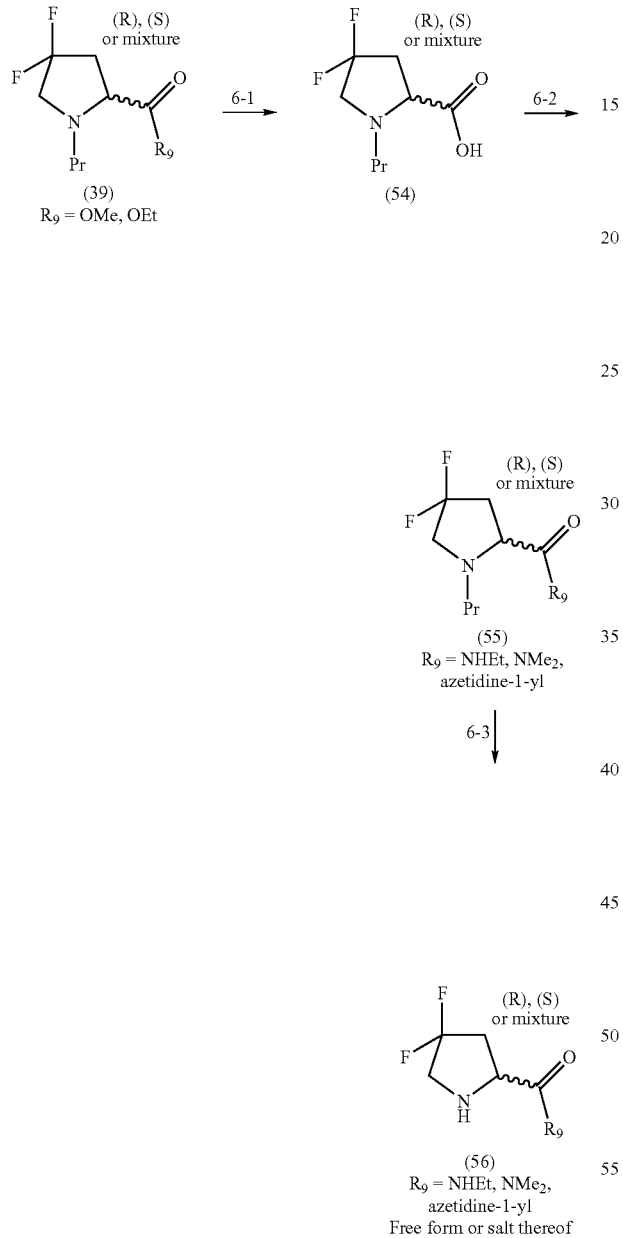

(in the formula, Pr has the same meaning as in the above description.)

The compounds represented by Formula (60), which are a portion of the compounds represented by Formula (17) ($R_6$ and $R_7$ represent a hydrogen atom, $R_8$ represents a hydroxyl group, $R_9$ has the same meaning as in the above description. Pr has the same meaning as in the above description.) can be obtained according to the method synthesis of Scheme 7.

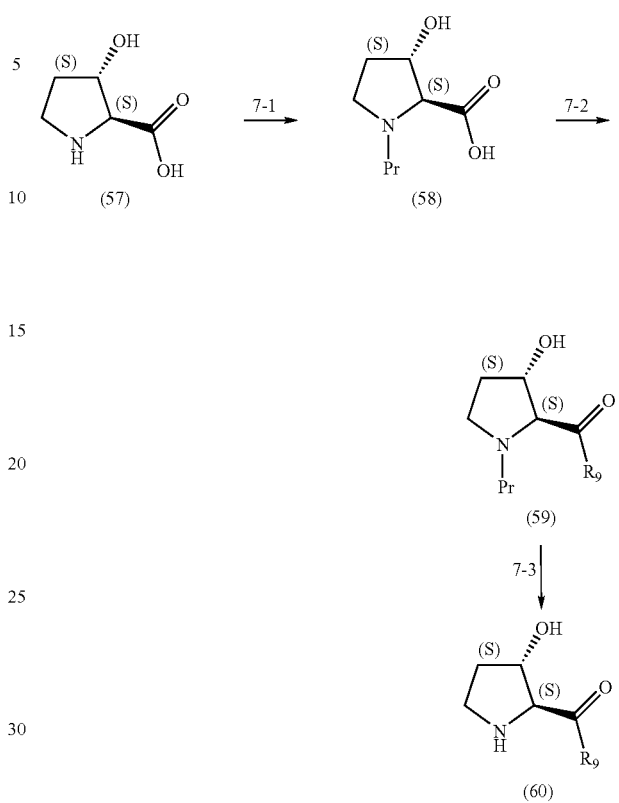

(in the formula, $R_9$ and Pr have the same meaning as in the above description.)

(3S)-3-hydroxy-L-proline (57) is commercially available, and the compound, by introducing a protecting group onto the nitrogen atom by a general method (Step 7-1), allows the compound represented by Formula (58) to be obtained. The compound represented by Formula (59) can be obtained by esterification or amidation of the compound represented by Formula (58) via a general method (Step 7-2), then, deprotected by a general method (Step 7-3), and free form of the compound represented by Formula (60) or a salt thereof can be obtained.

Compound (61), which is a portion of the compounds represented by Formula (17) ($R_6$ represents a hydroxyl group, $R_7$ represents a hydrogen atom, $R_8$ represents a hydroxyl group and $R_9$ represents a methoxy group) and, in particular N-tert-butoxy carbonyl protected compound, can be prepared according to methods described in Tetrahedron: Asymmetry, 9, 47 (1998), and other protected compounds can also be prepared according to the above reference. As shown in Scheme 8, a carboxylic acid compound (62) is obtained by a general hydrolysis reaction of the obtained compound represented by Formula (61) (Step 8-1), esterification or amidation is performed (Step 8-2), then, the compound is deprotected (Step 8-3), and the compound represented by Formula (64) or a salt thereof can be obtained.

In addition, by deprotecting the compound represented by Formula (61) (Step 8-4), 2-methyl-3,4-dihydroxy pyrrolidine-2-carboxylate (65) or a salt thereof can be obtained.

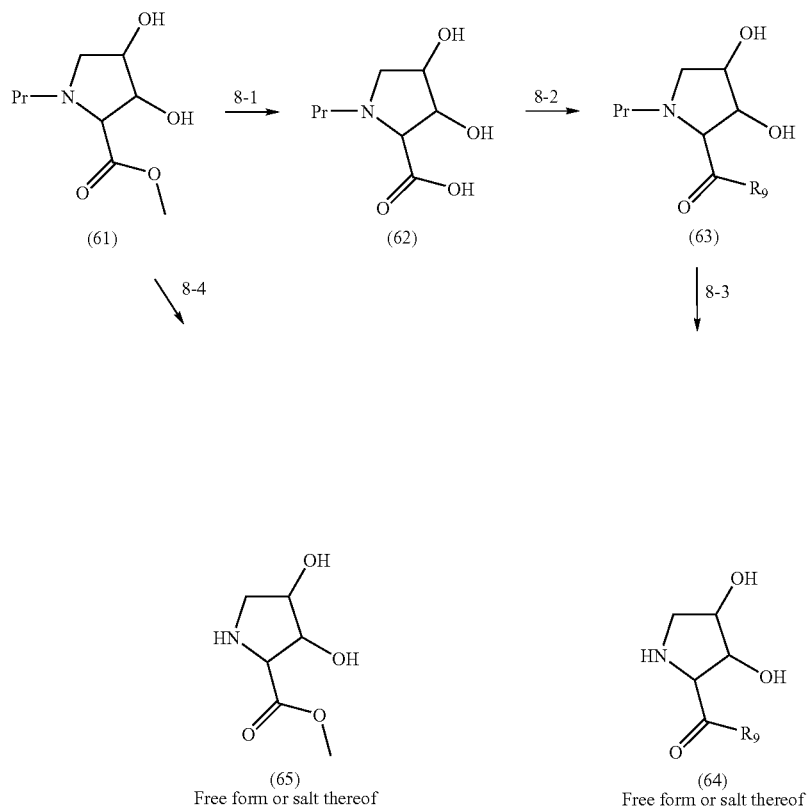

(in the formula, $R_9$ and Pr have the same meaning as in the above description.)

In addition, a portion of the compounds represented by Formula (12) ($R_1$, $R_2$, $R_3$, $R_4$, P, Q, $R_A$, $R_B$ and $R_C$ have the same meaning as in the above description. $R_5$ among the compounds represented by the above Formula (3), in cases where $R_6$, $R_7$ represents a hydrogen atom, $R_8$ represents a fluorine atom, and $R_9$ has the same meaning as in the above description) can be obtained as shown in Scheme 9 by fluorinating the hydroxyl group at position 3 of the pyrrolidine moiety by a general method.

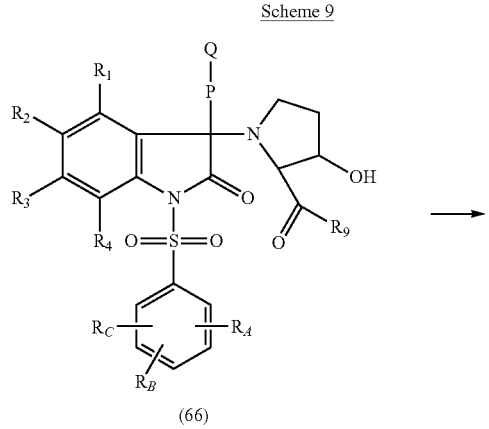

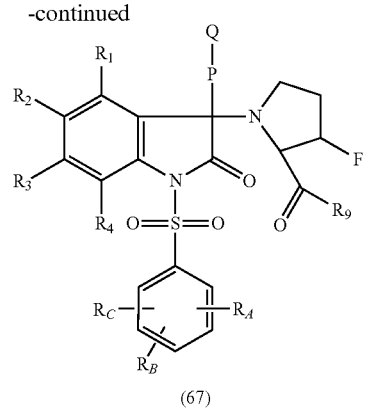

(in the formula, $R_1$, $R_2$, $R_3$, $R_4$, $R_9$, P, Q, $R_A$, $R_B$ and $R_C$ have the same meaning as above)

the compound represented by Formula (18) can be prepared by the synthesis method shown below in Scheme 10.

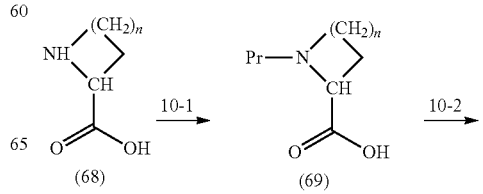

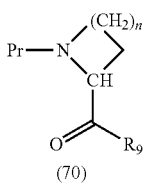

(70)

↓ 10-3

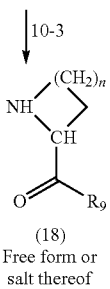

(18)
Free form or
salt thereof (in the formula, n, $R_9$ and Pr have the same meaning as in the above description.)

The compound represented by Formula (69) is either commercially available, or can be obtained by introducing an N-protecting group by a general method as the compound represented by Formula (68). By esterification or amidation of the compound represented by Formula (69) via a general method, the compound represented by Formula (70) is obtained, then, which is deprotected by a general method, and the free form of the compound represented by Formula (18) or a salt thereof can be obtained.

The compound represented by Formula (19) can be prepared by the synthesis method shown in the following Scheme 11.

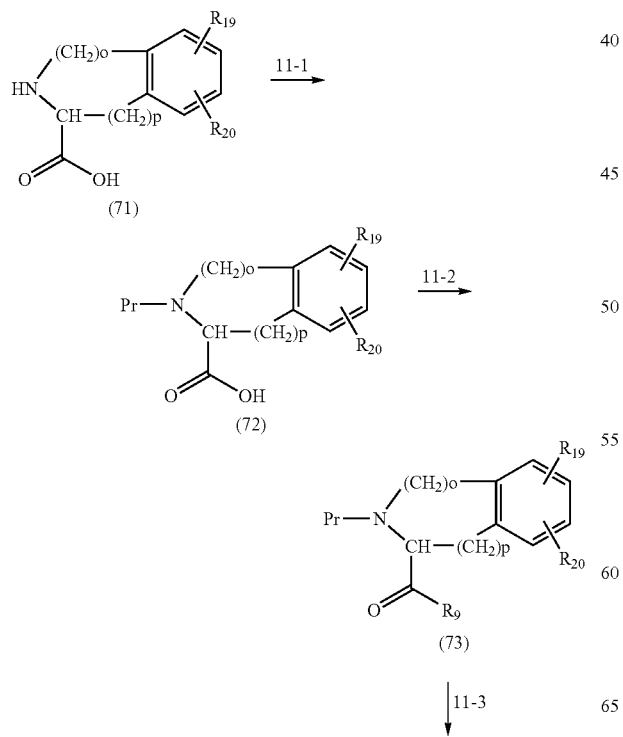

Scheme 11

(19)
Free form or
salt thereof (in the formula, o, p, $R_9$, $R_{19}$ $R_{20}$ and Pr are respectively the same as described above)

The compound represented by Formula (72) can be obtained by introducing a protecting group to the nitrogen atom of the compound represented by Formula (71) according to a general method, or, a portion of the compounds represented by Formula (72) is commercially available.

By esterification or amidation of the carboxylic acid of the compound represented by Formula (72) by a general method, the compound represented by Formula (73) can be obtained. The obtained compound represented by Formula (73) allows the compound represented by Formula (19), or a salt thereof, to be obtained by deprotection by general methods.

The compound represented by Formula (71) is either commercially available, or can be prepared by a known method. For instance, 2,3-dihydro-1H-indole-2-carboxylic acid can be prepared by methods described in J. Med. Chem., 26, 394 (1983); Agric. Biol. Chem., 51, 1833 (1987); J. Med. Chem., 26, 1267 (1983); Helv. Chim. Acta, 45, 638 (1962); Helv. Chim. Acta, 51, 1476 (1968). Isoindole-1-carboxylic acid can be prepared by methods described in J. Heterocyclic. Chem., 21, 1355(1984). 1,2,3,4-tetrahydroisoquinoline-3-carboxylic acid can be prepared by methods described in Synthesis, 11, 1157 (1992); Int. J. Peptide Protein Res., 43, 62(1994); Liebigs Ann./Recueil, 1997, 3, 533 (1997); J. Med. Chem., 31, 2092 (1998); J. Chem. Soc., 172 (1938); J. Chem. Soc., 1534 (1950); Synthesis, 1990, 550; Heterocycles, 34, 757 (1992); J. Med. Chem., 26, 1267 (1983). 1,2,3,4-tetrahydroquinoline-2-carboxylic acid can be prepared by methods described in J. Org. Chem., 55, 738 (1990); J. Med. Chem., 35, 1942 (1992). 1,2,3,4-tetrahydroisoquinoline-1-carboxylic acid can be prepared by methods described in J. Med. Chem., 34, 757 (1993); Synthesis, 550 (1990); Heterocycles, 34, 757 (1992); J. Med. Chem., 26, 1267 (1983).

The compound represented by Formula (20) can be prepared by the synthesis method shown in the following Scheme 12.

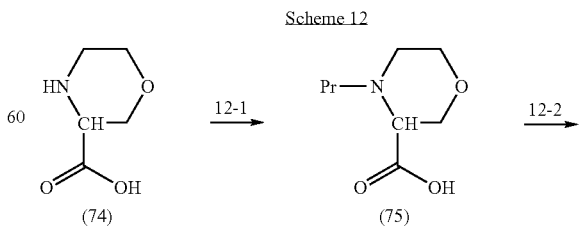

Scheme 12

-continued

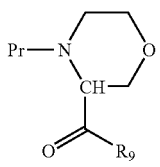

(76)

↓ 12-3

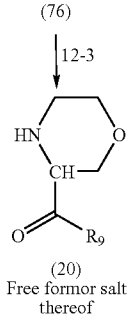

(20)
Free form or salt thereof (in the formula, $R_9$ and Pr have the same meaning as in the above description.)

The nitrogen atom of the compound represented by Formula (74), by introducing a protecting group by a general method, allows the compound represented by Formula (75) to be obtained, or, a portion of the compounds represented by Formula (75) is commercially available. By esterification or amidation of the carboxylic acid of the compound represented by Formula (75) by general methods, the compound represented by Formula (76) can be obtained. The obtained compound represented by Formula (76) allows the compound represented by Formula (20), or a salt thereof, to be obtained by deprotection by general methods.

In addition, among the compounds represented by Formula (76), in cases where $R_9$ represents an alkoxy group having 1 to 5 carbon atoms, derivation into a carboxylic acid by a general hydrolysis reaction, allows the compound represented by Formula (75) to be obtained.

The compound represented by Formula (74) can be prepared from serine, according to the methods described in J. Chem. Soc. Perkin Trans., I, 2577 (1985).

Among the above-mentioned compounds represented by Formula (12), when $R_5$ represents a substituent represented by the above Formula (7), the B ring represents a 5 to 9-membered nitrogen-containing heterocyclic group, Y represents a group represented by the formula —$CH_2$— or a group represented by the formula —$OCH_2$—, Z represents a single bond, D represents a carbon atom or a nitrogen atom and $R_2$, represents a heterocyclic group, preparation is possible by reacting in the presence of a base the compound represented by Formula (77) prepared beforehand with the compound represented by Formula (15) (Scheme 13).

Scheme 13

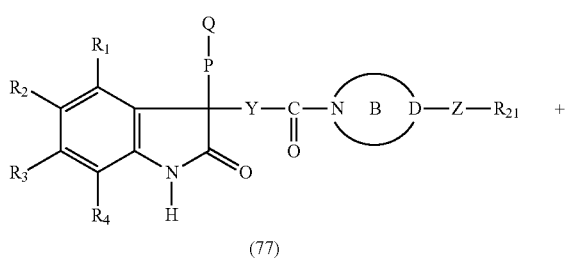

+

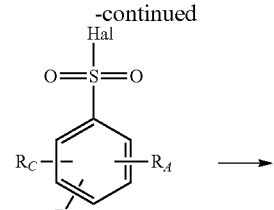

(15)

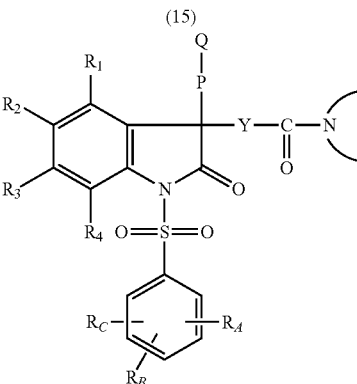

(78)

(in the formula, $R_1$, $R_2$, $R_3$, $R_4$, $R_A$, $R_B$, $R_C$, P and Q are the same as in the above description. In ring B, N represents a nitrogen atom, D represents a nitrogen atom or a carbon atom. Y represents a group represented by the formula —$CH_2$— or a group represented by the formula —$OCH_2$—, Z represents a single bond, Hal represents a halogen atom, B ring represents a 5 to 9-membered nitrogen-containing heterocyclic group, and $R_2$, represents a heterocyclic group)

The reaction of Scheme 13 can be carried out in the presence of a base, for instance, metal hydride such as sodium hydride and the like, alkaline metal alkoxide such as potassium tert-butoxide and the like, in an anhydrous solvent, for instance, N,N-dimethyl formamide, tetrahydrofuran and the like or a mixed solvent thereof, and under a temperature condition of $-70°$ C. to $+60°$ C.

The compound represented by Formula (77) (in the formula, $R_1$, $R_2$, $R_3$, $R_4$, P and Q are the same as in the above description. Y represents a group represented by the formula —$CH_2$— or a group represented by the formula —$OCH_2$—, Z represents a single bond, D represents a nitrogen atom, B ring represents a 5 to 9-membered nitrogen-containing heterocyclic group, and $R_2$, represents a heterocyclic group) can be prepared according to methods described in, for instance, Publication No. WO 03/008407.

Among the compounds represented by Formula (12), when $R_5$ represents a substituent represented by the above Formula (7), D represents a nitrogen atom, Y represents a group represented by the formula —O— or a group represented by the formula —N—, Z represents a single bond, and $R_{21}$ represents a heterocyclic group circumstance, the compound can be prepared by the synthesis method shown in Scheme 14.

First, by reacting the compound represented by Formula (79) with the compound represented by Formula (15) in the presence of a base, the compound represented by Formula (80) can be obtained. The present reaction can be carried out in the presence of a base, for instance, metal hydride such as sodium hydride and the like, alkaline metal alkoxide such as potassium tert-butoxide and the like, in an anhydrous solvent, for instance, N,N-dimethyl formamide tetrahydrofuran and the like or a mixed solvent thereof, and under a temperature condition of −70° C. to +60° C.

By carrying out carbonic acid ester or carbonic acid amidation to activate the hydroxyl group or the amino group of the obtained compound represented by Formula (80), and reacting the obtained compound represented by Formula (81) with the compound represented by Formula (82) prepared beforehand, the compound represented by Formula (78) can be obtained.

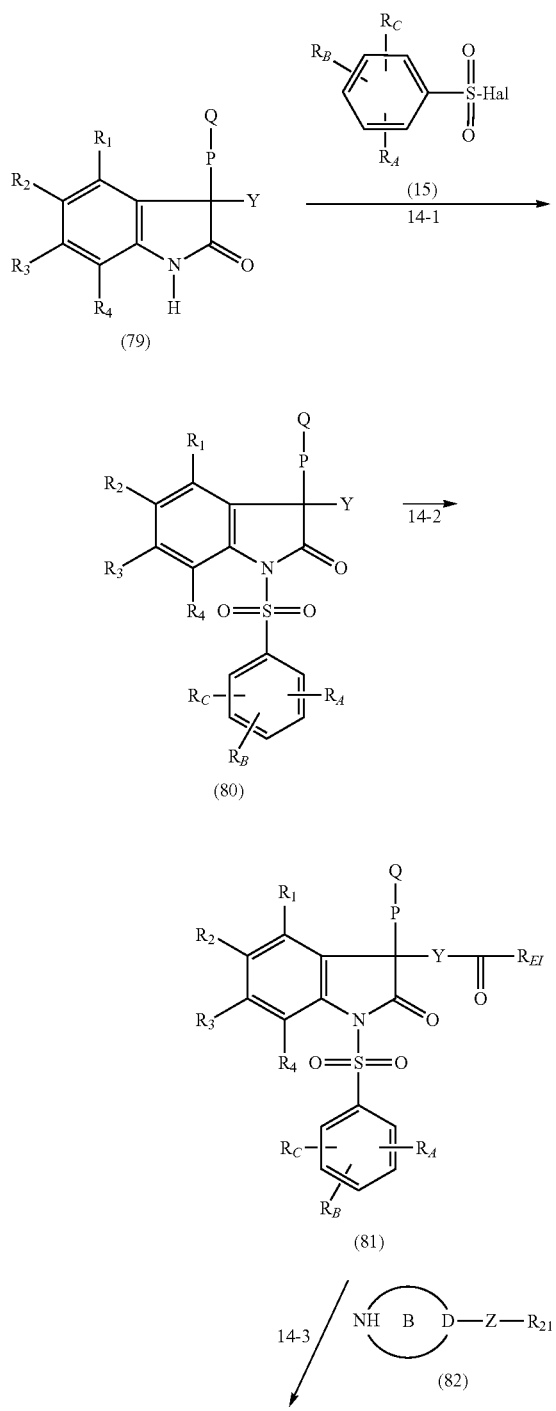

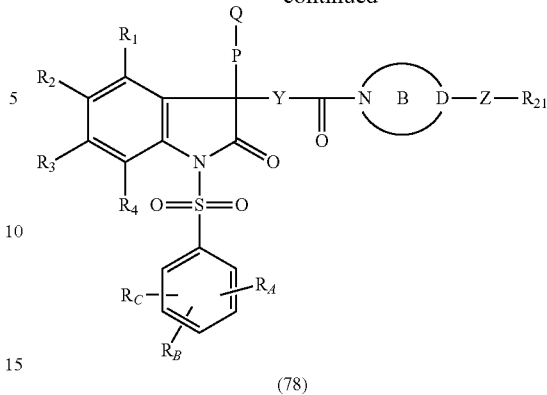

(in the formula, $R_1$, $R_2$, $R_3$, $R_4$, P and Q are the same as in the above description. N represents a nitrogen atom, D represents a nitrogen atom or a carbon atom, Y represents a group represented by the formula —OH or a group represented by the formula —O—, a group represented by the formula —NH$_2$ or a group represented by the formula —NH—, Z represents a single bond, Hal represents a halogen atom, B ring represents a 5 to 9-membered nitrogen-containing heterocyclic group, $R_{21}$ represents a heterocyclic group, and $R_{EI}$ represents a leaving group, for instance, phenyl oxy group and the like.)

Carbonic acid esterification and carbonic acid amidation of hydroxyl group and amino group are accomplished, for instance, by phenyloxy carbonation or phenyloxy carbamation, and the like.

Here, phenyloxy carbonation and phenyloxy carbamation are accomplished by reacting, for instance, chlorophenyl formate and the like, in the presence of a base, for instance, pyridine, diisopropylethyl amine, triethylamine and the like, in a solvent, for instance, tetrahydrofuran, chloroform and the like, under a temperature of 0° C. to 100° C.

In addition, the reaction of the compound represented by Formula (81) and the compound represented by Formula (82) is accomplished by continuously reacting in the presence of a base, for instance, an organic amine such as diisopropylethyl amine, triethylamine and the like, in a solvent, for instance, toluene, chloroform, N,N-dimethyl formamide and the like, at a temperature of 0° C. to near the boiling point of the solvent used.

The compound represented by Formula (79) (in the formula, $R_1$, $R_2$, $R_3$, $R_4$, P and Q are the same as in the above description. Y represents a racemic form or an optically active form ((+) isomer or (−) isomer) of an amino group or a hydroxyl group, Z represents a single bond, D represents a nitrogen atom, and $R_{21}$ represents a heterocyclic group) can be prepared according to methods described in, for instance, PCT Publication No. WO 03/008407.

Among the compounds represented by Formula (12), when $R_5$ represents a substituent represented by the above Formula (7), D represents a nitrogen atom, Y represents a group represented by the formula —NHCH$_2$— or a group represented by the formula —NHCH$_2$CH$_2$—, Z represents a single bond and $R_{21}$ represents a heterocyclic group, the compound can be prepared by the synthesis method shown in Scheme 15.

By reacting the compound represented by Formula (83) and the compound represented by Formula (15) in the presence of a base, the compound represented by Formula (84) can be obtained. A carboxylic acid compound (85) can be obtained by reacting the tert-butyl ester group of the obtained compound represented by Formula (84) with an acid, for instance, trifluoroacetic acid, hydrochloric acid, sulfuric acid and the like, and by condensing the compound represented by Formula (82) prepared beforehand, the compound represented by Formula (78) can be prepared.

Scheme 15

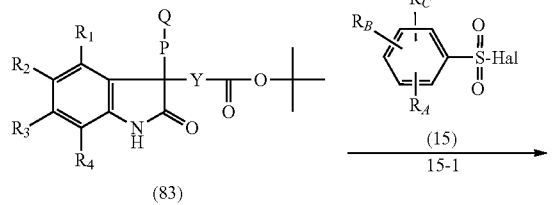

(83)

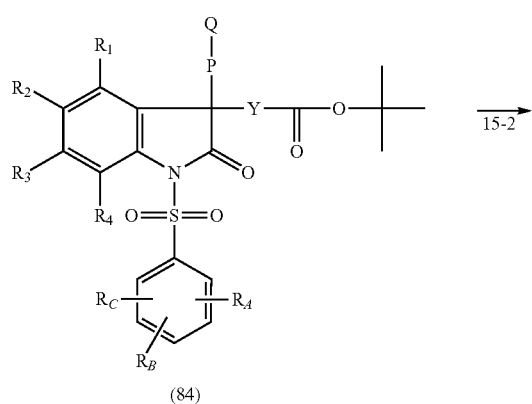

(84)

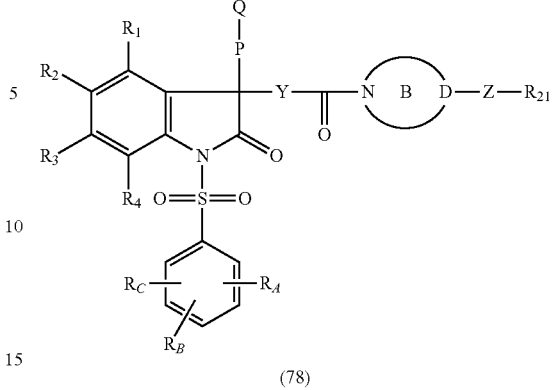

(78)

(in the formula, $R_1$, $R_2$, $R_3$, $R_4$, P and Q are the same as in the above description. N represents a nitrogen atom, D represents a nitrogen atom or a carbon atom, Y represents a group represented by the formula —NHCH$_2$— or a group represented by the formula —NHCH$_2$CH$_2$—, Z represents a single bond, Hal represents a halogen atom, B ring represents a 5 to 9-membered nitrogen-containing heterocyclic group, and $R_{21}$ represents a heterocyclic group)

Regarding condensation from the compound represented by Formula (85) to the compound represented by Formula (78), for instance, a method using a dehydration condensation agent may be cited. For the dehydration condensation agent, for instance, 1-ethyl-3-(3-dimethylamino propyl)carbodiimide/hydrochloride, dicyclohexyl carbodiimide, diphenyl phosphonyl azide, carbonyl diimidazole and the like, may be cited, and as necessary, an activator such as 1-hydroxy benzo triazole, hydroxy succinimide and the like can be used. As reaction solvent, for instance, dichloromethane, chloroform, 1,2-dichloro ethane, N,N-dimethyl formamide, tetrahydrofuran, dioxane, toluene, ethyl acetate and the like, or, mixed solvents thereof may be cited. In so doing, the reaction can be carried out using a base, and as examples of base, amines, for instance, triethylamine, diisopropylethyl amine, 4-(dimethylamino) pyridine and the like, organic salts such as sodium 2-ethyl hexanoate, potassium 2-ethyl hexanoate and the like, and inorganic bases such as potassium carbonate and the like may be cited. The reaction can be carried out under a temperature condition from −50° C. to near the boiling point of the solvent.

The compound represented by Formula (83) (in the formula, $R_1$, $R_2$, $R_3$, $R_4$, P and Q are the same as in the above description. Y represents a group represented by the formula —NHCH$_2$— or a group represented by the formula —NHCH$_2$CH$_2$—), can be prepared according to methods described in Publication No. WO 03/008407.

Among the compounds represented by Formula (82), compounds in which D represents a nitrogen atom, Z represents a single bond, and $R_{21}$ represents a heterocyclic group, are either commercially available, or can be synthesized by methods described in J. Org. Chem., 18, 1484 (1953), J. Med. Chem., 21(6), 536 (1978), Chem. Pharm. Bull., 39(9), 2288 (1991), Tetrahedron Letters, 39, 617 (1998). or Publication No. WO 97/28129.

Among the compounds represented by Formula (82), compounds in which D represents a carbon atom, Z represents a single bond, and $R_{21}$ represents a heterocyclic group substituted by nitrogen-containing heterocyclic group, in particular 4-piperidin-4-yl pyridine, can be prepared following the methods described in Tetrahedron Lett., 34 (33), 5287-5288 (1993).

(85)

(82)

Compounds in which $R_5$ represents an amino acid residue or the Formula (21)

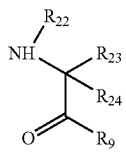
(21)

(in the formula, $R_9$, $R_{22}$, $R_{23}$ and $R_{24}$ has the same meaning as above)
or salts thereof, can be prepared from amino acids, or derivatives thereof, optionally protected by a protecting group commonly used generally in peptide synthesis (Scheme 16).

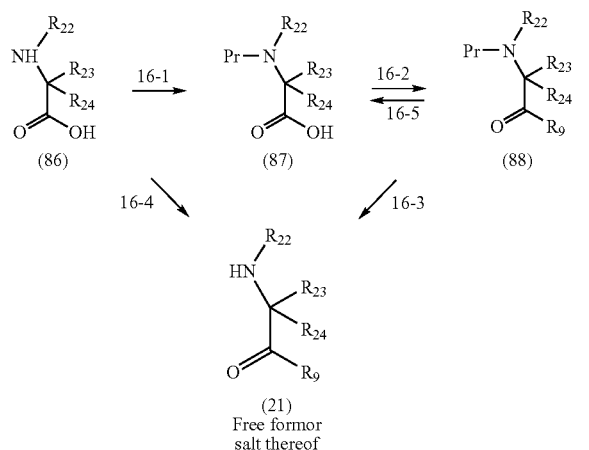

(in the formula, $R_9$, $R_{22}$, $R_{23}$, $R_{24}$ and Pr are respectively the same as described above)

In Scheme 16, at Step 16-1, the nitrogen atom of the compound represented by Formula (86), by introducing a protecting group according to a general method, allows the compound represented by Formula (87) to be prepared. In the subsequent Step 16-2, the compound represented by Formula (87), by esterification or amidation according to a general method, allows the compound represented by Formula (88) to be prepared. The protecting group of the nitrogen atom is removed by a general method (Step 16-3), and the compound represented by Formula (21) or a salt thereof can be prepared. In addition, meanwhile, the carboxyl group of the compound represented by Formula (86) also allows the compound represented by Formula (18) to be prepared directly, by esterification and amidation according to a general method as Step 16-4. In addition, when $R_9$ in the compound represented by Formula (88) represents for instance an alkoxy group having 1 to 5 carbon atoms and the like, the compound represented by Formula (87) can be prepared by subjecting $R_9$ to a general hydrolysis reaction (Step 16-5).

Regarding natural amino acids and protected forms thereof and a portion of non-natural amino acids and protected forms thereof, those that are commercially available are used; in addition, regarding amino acids that are not available commercially, they can be prepared by carrying out synthesis according to methods by Strecker et al. (Angewante Chemiche, 75, 27(1850)) or synthesis according to J. Pract. Chem., 141, 5(1934) by H. T. Bucherer et al., followed by hydrolysis.

α-amino cycloalkyl carboxylic acids can be prepared according to methods described in, J. W Tsang et al., J. Med. Chem., 27, 1663(1984).

R- and S-pentyl glycines can be prepared according to methods described in EP477049.

R- and S-hexyl glycines can be prepared according to methods described in Rudman et al., J. Am. Chem. Soc., 74, 551 (1952).

R- and S-cyclohexyl glycines can be prepared by catalytic reduction of R- and S-phenyl glycines.

α-amino cycloalkyl carboxylic acids having R- and S-configurations can also be prepared by stereospecific enzymatic degradation of the corresponding racemic N-acetylated derivatives according to methods described in J. Hill et al., J. Org. Chem., 30, 1321 (1965).

The compound represented by Formula (22)

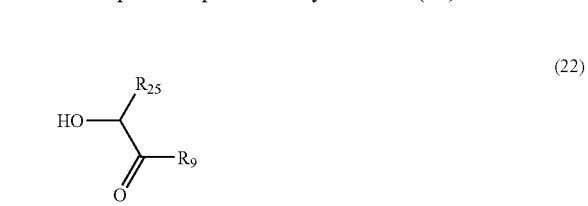
(22)

(in the formula, $R_9$ and $R_{25}$ has the same meaning as above) can be prepared according to the synthesis method shown in Scheme 17.

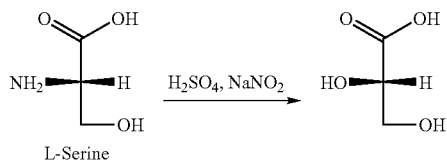

For instance, L-serine can be converted from amino group into hydroxyl group while retaining the steric arrangement by diazotization with sodium nitrite under acidic condition and hydrolysis (refer to Helvetica Chimica Acta, 68, 1863).

Under similar conditions as described above, for instance, the following compounds can be synthesized.

That is to say, S-leucic acid (from L-leucine; refer to Tetrahedron Letters, 26, 2187 (1975));
S-malic acid (from L-aspartic acid; refer to Synthetic Communication, 16(2), 183 (1986));
(2S)-2-hydroxy-3-cyclohexyl propionic acid (from (S)-2-amino-3-cyclohexyl propionic acid; refer to Tetrahedron Letters, 22, 45, 4533 (1981));
(2S)-2-hydroxy-3-phenyl propionic acid
(from L-phenylalanine; refer to EP0230379);
(S)-2-acetoxy-3-(4-benzylphenyl)propionic acid from (O-benzyl-L-tyrosine); refer to J. Org. Chem., 67, 4945 (2002));
(S)-hydroxy isovaleric acid (from L-valine; refer to Organic Process Research & Development, 6, 246 (2002); Organic Letters, 5, 16, 2821 (2003); J. Am. Chem. Soc., 123, 4469 (2001));
(S)-2,3-dimethyl-2-hydroxy butyric acid (from L-valine; refer to Organic Process Research & Development, 6, 246 (2002)); then (R)-2-hydroxy pent-4-ynoic acid (from D-propargylglycine; refer to J. Med. Chem., 46, 4572 (2003)) can be synthesized.

The compound represented by Formula (23) can be prepared by the synthesis method shown in the following Scheme 18.

Scheme 18

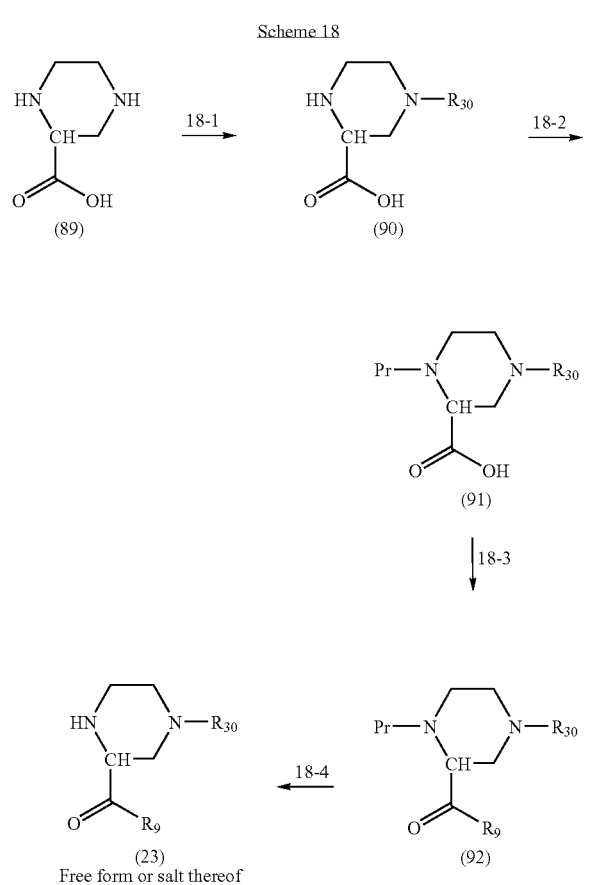

Scheme 19

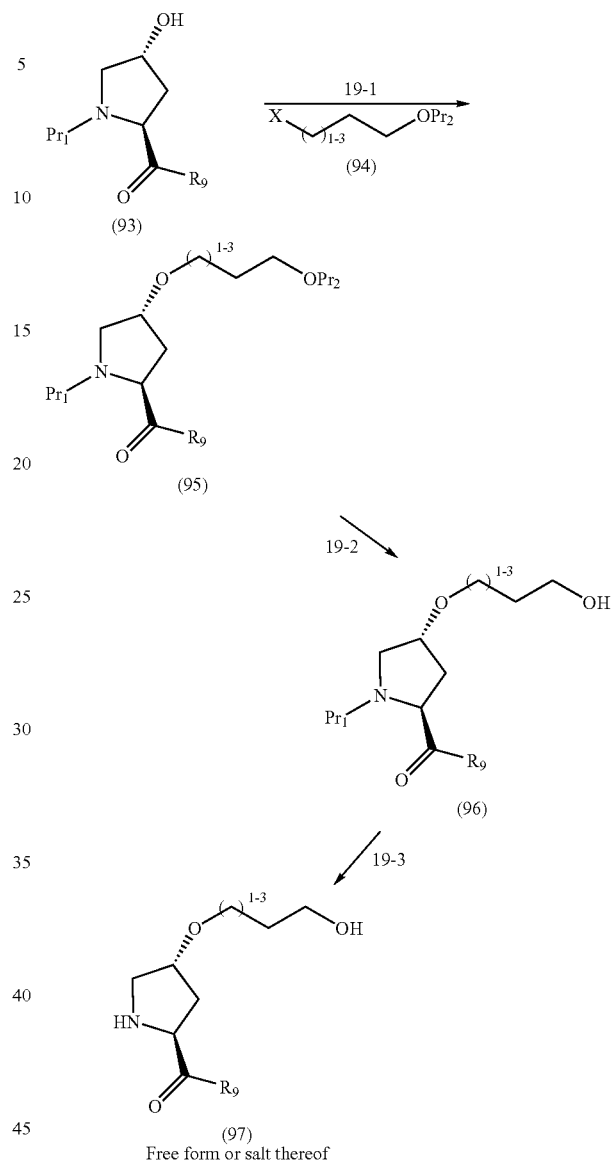

(in the formula, $R_9$ and $R_{30}$ have the same meaning as in the above description. Pr represents a protecting group)

The compound represented by Formula (89) (2-piperazine carboxylic acid) is either commercially available or can be prepared from 2-pyrazine carboxylic acid using methods described in Chimia., 13, 263 (1959) as well as in J. Med. Chem., 15, 291 (1972).

By introducing a substituent on the nitrogen atom of the compound represented by Formula (89) using methods described in Protective Group in Organic Synthesis (T. W. Greene, P. G. M. Wuts; $3^{rd}$ ed., 1999, John Wiley & sons, Inc.), the compounds represented by Formulae (90) and (91) can be obtained (Steps 18-1 and 18-2). In addition, the compound represented by Formula (92) can be obtained (Step 18-3) by esterification and amidation of the carboxylic acid of the compound represented by Formula (91) by a general method. The obtained compound represented by Formula (92), allows the compound represented by Formula (23), or a salt thereof, to be obtained by deprotection by general methods (Step 18-4).

When $R_6$ represents a hydroxy alkoxy group in the compound represented by Formula (17), the compound can be prepared by the synthesis method shown in the following Scheme 19.

(in the formula, $R_9$ has the same meaning as in the above description. $Pr_1$ and $Pr_2$ represent protecting groups, in addition, X represents a leaving group)

The compound represented by Formula (95) can be prepared by alkylating according to a general method using the compound represented by Formula (94) the hydroxyl group of the compound represented by Formula (93) (Step 19-1). The compound represented by Formula (96) can be obtained by deprotecting the protecting group of the hydroxyl group of the compound represented by Formula (95) by general methods (Step 19-2). The obtained compound represented by Formula (96) allows the compound represented by Formula (97), or a salt thereof, to be obtained by deprotection by general methods (Step 19-3). A portion of the compounds represented by Formula (94) is commercially available.

The following exist as leaving groups used in general alkylation reactions. For instance, halogens such as chlorine, bromine and iodide, sulfonate and the like may be cited. A base may be used in an alkylating reaction, and as bases to be used, for instance, organic amines such as triethylamine, diisopropylethyl amine, pyridine and the like, inorganic bases such as sodium carbonate, potassium carbonate, sodium bicarbonate, potassium hydrogen carbonate, sodium hydride, potassium hydride, sodium hydroxide potassium hydroxide and the like, metal alcoholates such as sodium methoxide, sodium ethoxide, potassium tert-butoxide and the like, metal amides such as sodium amide, lithium diisopropyl amide and the like may be cited. As reaction solvents used in alkylating reaction, for instance, ethers such as diethyl ether, tetrahydrofuran, 1,4-dioxane, 1,2-dimethoxy ethane and the like, hydrocarbons such as benzene, toluene, xylene and the like, amides such as N,N-dimethyl formamide, N-methylpyrrolidine N,N-dimethylacetamide and the like, dichloromethane, chloroform, 1,2-dichloro ethane, acetonitrile, dimethylsulfoxide, pyridine and the like, or, mixed solvents thereof, may be cited. In addition, for instance an activator such as potassium iodide or sodium iodide can be used as necessary. The reaction can be carried out from −80° C. to near the boiling point of the solvent.

When $R_6$ represents a hydroxyethoxy group in the compound represented by Formula (17), the compound can be prepared by the synthesis method shown in the following Scheme 20.

By alkylating the hydroxyl group of the compound represented by Formula (93) using the compound represented by Formula (98) by a similar method to Step 19-1, the compound represented by Formula (99) can be prepared (Step 20-1). By deprotecting the protecting group of the hydroxyl group of the compound represented by Formula (99) by a general method, the compound represented by Formula (102) can be obtained (Step 20-2).

In addition, the compound represented by Formula (102) can also be obtained by the following method. By alkylating the hydroxyl group of the compound represented by Formula (93) using the compound represented by Formula (100) by a similar method to Step 20-1, the compound represented by Formula (101) can be prepared (Step 20-3). By reducing the ester group of the compound represented by Formula (101) by a general method, the compound represented by Formula (102) can be obtained (Step 20-4). the obtained compound represented by Formula (102) by deprotection by a general method allows the compound represented by Formula (103) or a salt thereof to be obtained (Step 20-5). A portion of the compounds represented by Formula (98) and Formula (100) are commercially available.

Scheme 20

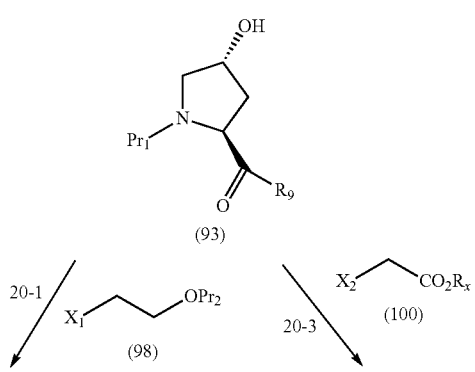

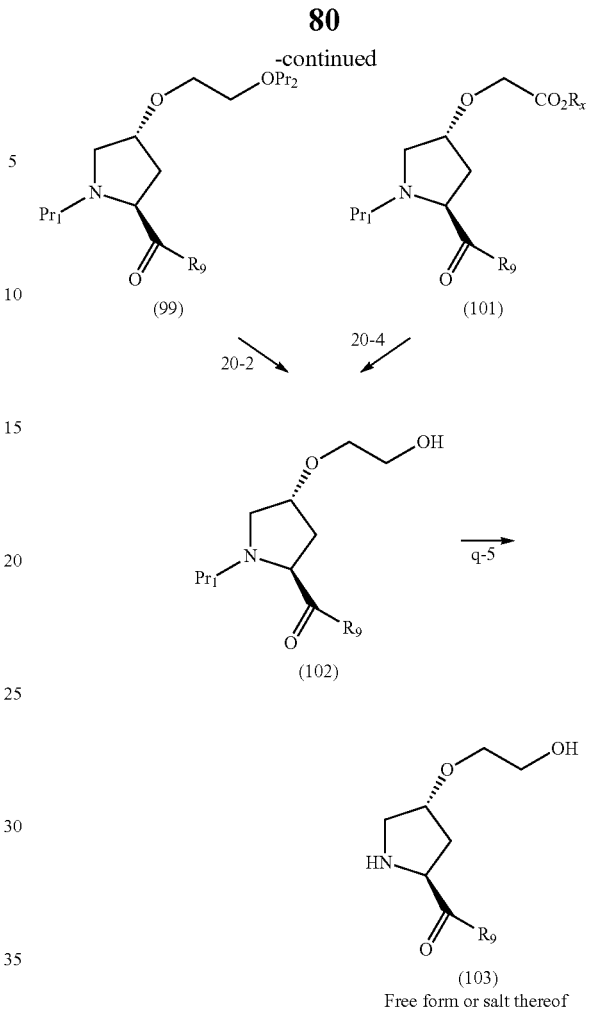

Free form or salt thereof (in the formula, $R_9$ has the same meaning as in the above description. $Pr_1$ and $Pr_2$ represent protecting groups, $R_X$ represents an alkyl group having 1 to 5 carbon atoms and $X_1$ and $X_2$ represent leaving groups)

The following exist as reagents used in general reduction reactions. For instance, lithium aluminum hydride, sodium aluminum hydride, sodium borohydride, lithium borohydride, calcium borohydride, potassium borohydride, diisobutyl aluminum hydride, sodium bis(2-methoxy ethoxy) aluminum hydride, zinc borohydride, sodium trimethoxy borohydride and the like may be cited. In addition, these reagents can have their reduction capabilities adjusted by combination with other reagents. For instance, lithium aluminum hydride, sodium borohydride and the like can be used in combination with aluminum trichloride, boron trifluoride and the like. As reaction solvents used in reduction reactions, for instance, alcohols such as methanol, ethanol, isopropyl alcohol, ethylene glycol and the like, ethers such as diethyl ether, tetrahydrofuran, 1,4-dioxane, 1,2-dimethoxy ethane and the like, hydrocarbons such as benzene, toluene and the like, dichloromethane, chloroform, 1,2-dichloro ethane, acetonitrile, dimethyl sulfoxide, pyridine, water and the like, or, mixed solvent thereof may be cited. The reaction can be carried out at −80° C. to near the boiling point of the solvent.

When $R_6$ represents a cyano alkoxy group in the compound represented by Formula (17), the compound can be prepared by the synthesis method shown in the following Scheme 21.

Scheme 21

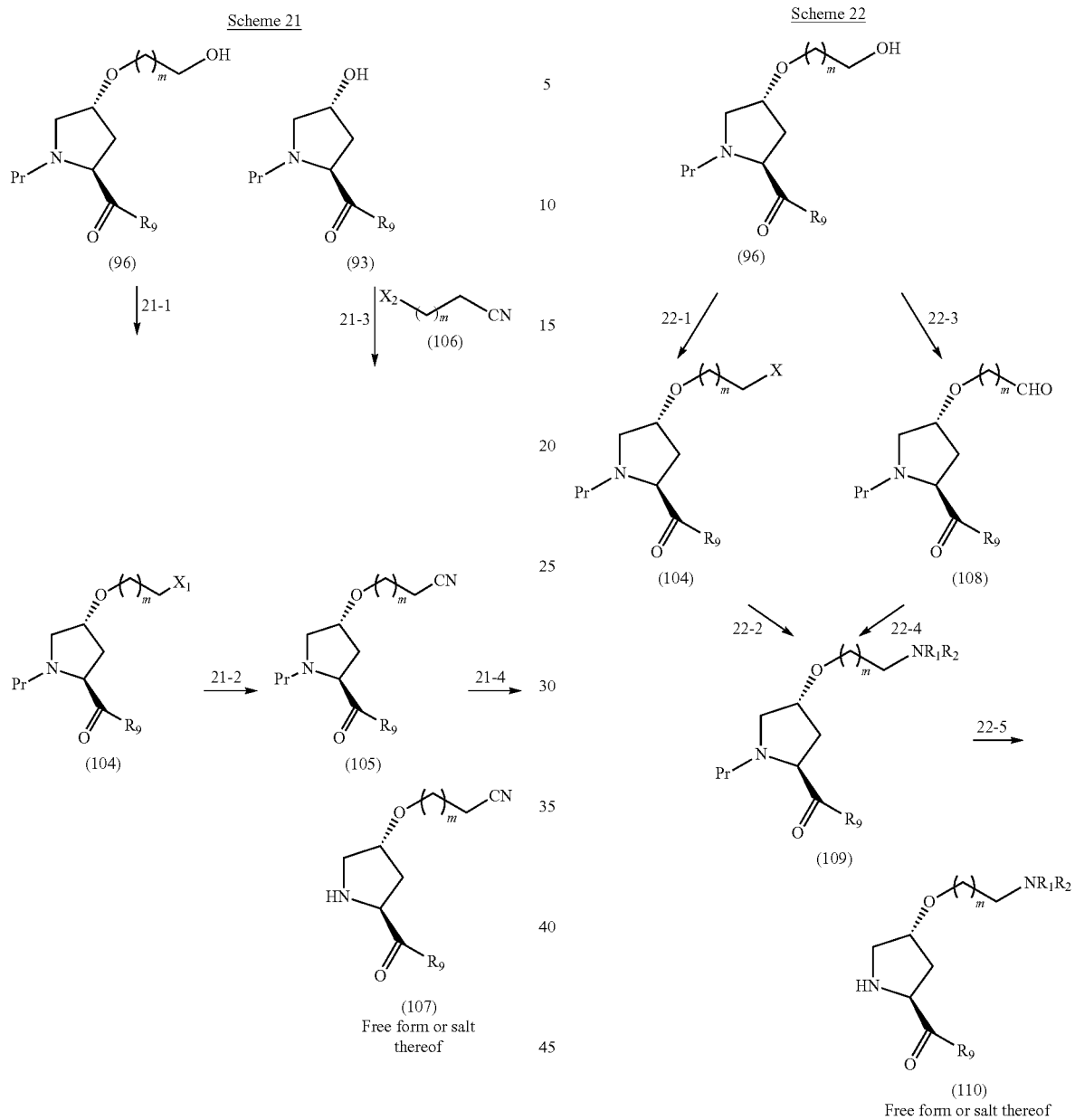

Scheme 22

(in the formula, $R_9$ have the same meaning as in the above description. m represents an integer from 1 to 4, Pr represents a protecting group and $X_1$ and $X_2$ represent leaving groups)

By converting the hydroxyl group of the compound represented by Formula (96) into a leaving group by a general method, the compound represented by Formula (104) can be obtained Step 21-1). By cyanating (Step 21-2) and deprotecting (Step 21-4) the obtained compound represented by Formula (104), the compound represented by Formula (107) or a salt thereof can be obtained.

In addition, by alkylation of the hydroxyl group of the compound represented by Formula (93) Step 21-3) using the compound represented by Formula (106) similarly to Scheme 19 (Step 19-1) and deprotection (Step 21-4), the compound represented by Formula (107) can be prepared.

(in the formula, $R_9$ have the same meaning as in the above description. m represents an integer from 1 to 4, Pr represents a protecting group and X represents a leaving group. $R_1$ and $R_2$ represent alkyl groups having 1 to 5 carbon atoms or $R_1$ and $R_2$ represent groups forming a heterocyclic group or groups forming a heterocyclic group substituted by an alkyl group having 1 to 5 carbon atoms, with an adjacent nitrogen atom)

The compound represented by Formula (110) can be obtained with the methods represented in the above Scheme 22. By converting the hydroxyl group of the compound represented by Formula (96) into a leaving group by a general method, the compound represented by Formula (104) can be obtained (Step 22-1). By aminating the obtained compound represented by Formula (104) by a general method, the compound represented by Formula (109) can be obtained (Step 22-2). In addition, by oxidizing the hydroxyl group of the compound represented by Formula (96) into a formyl group by a general method (Step 22-3) and subjecting the obtained formyl group to a reductive amination reaction (Step 22-4), the compound represented by Formula (109) can be obtained. The obtained compound represented by Formula (109) allows each of the compounds represented by Formula (110), or salts thereof, to be obtained by deprotection by a general method (Step 22-5).

represented by Formula (107) and the compound represented by Formula (16), the compound represented by Formula (111), by being subjected to a general cyano group hydrolysis reaction, allows the compound represented by Formula (112) and the compound represented by Formula (113) to be obtained. The present hydrolysis is accomplished under acidic hydrolysis, for instance, conditions using hydrochloric acid, sulfuric acid, hydrogen bromide acid and the like. As Scheme 23

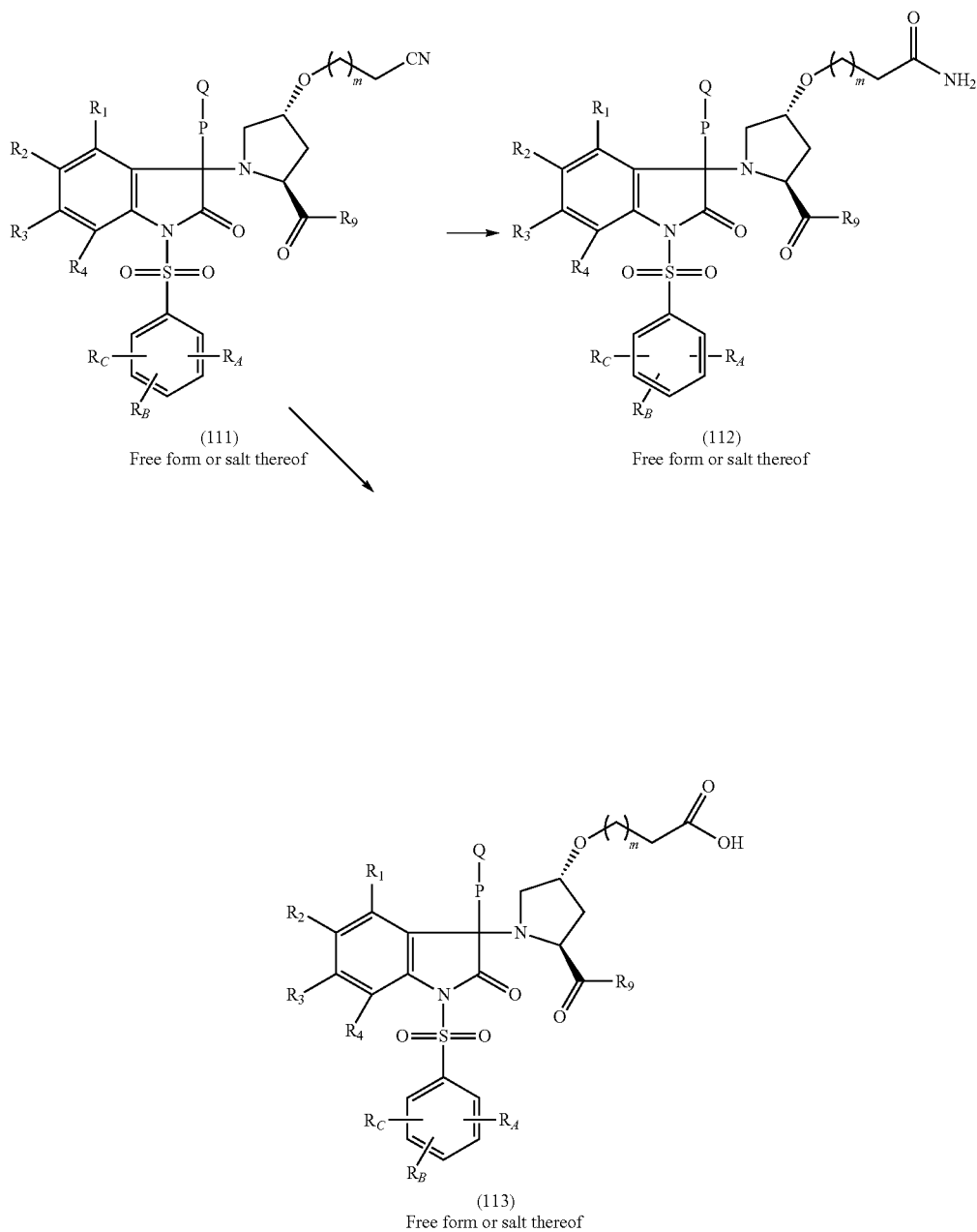

(in the formula, $R_1, R_2, R_3, R_4, R_9, P, Q, R_A, R_B$ and $R_C$ have the same meaning as in the above description.)

The compounds represented by Formulae (112) and (113) can be obtained with the methods represented in the above Scheme 23. Prepared by reacting the compound represented by Formula (15) with the reaction product of the compound solvents used in the present acidic hydrolysis reaction, for instance, solvents such as methanol, ethanol, dioxane, tetrahydrofuran, water and the like, or mixed solvents thereof may be cited. The present reaction proceeds at temperatures from −50° to near the boiling point of the solvent.

Scheme 24

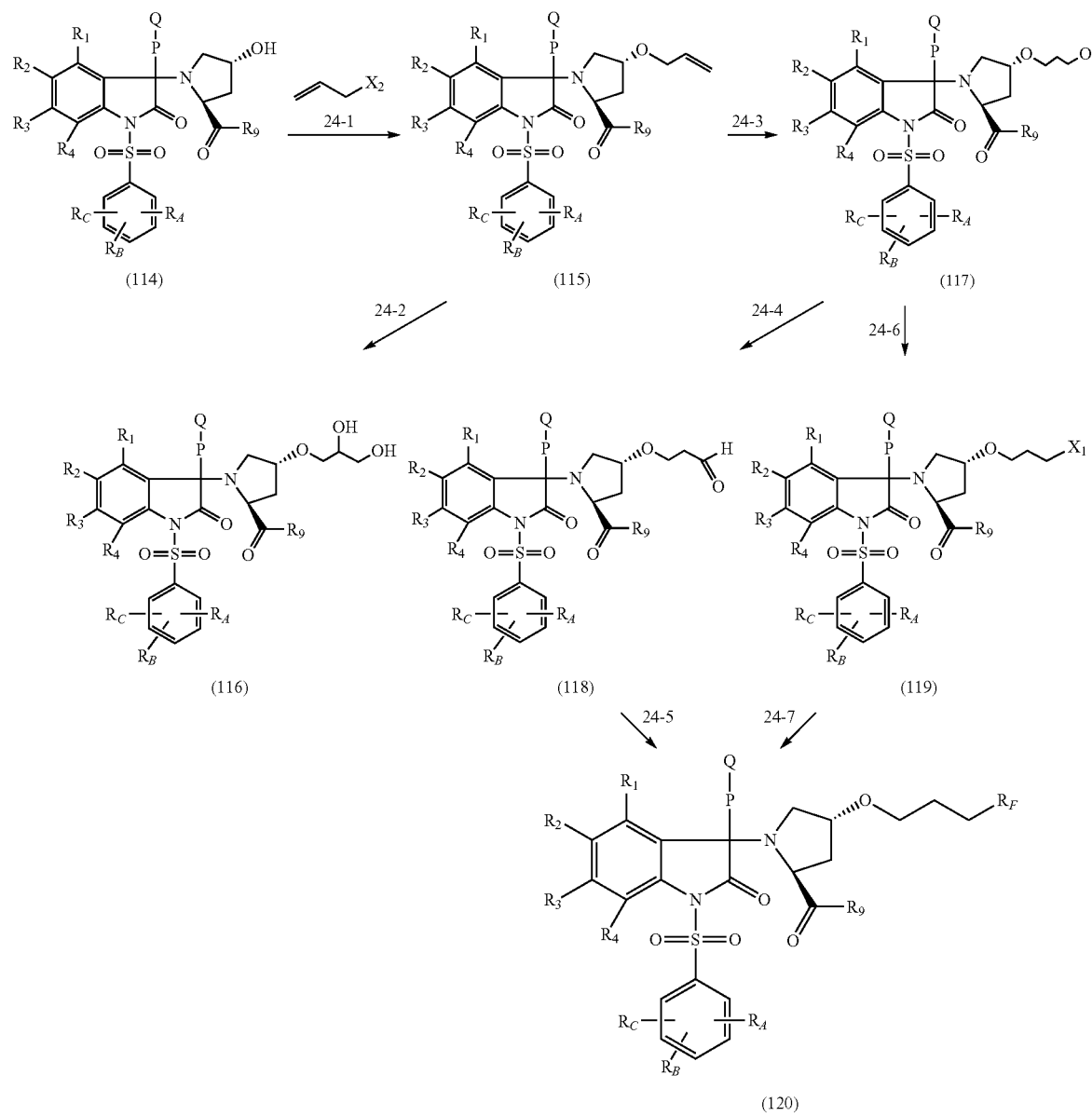

(in the formula, $R_1$, $R_2$, $R_3$, $R_4$, $R_9$, P, Q, $R_A$, $R_B$ and $R_C$ have the same meaning as in the above description. RF represents a mono-alkyl amine, a di-alkyl amine, a cycloalkyl amine or an alkyl-cycloalkyl amine. $X_1$ and $X_2$ represent leaving groups)

The compound represented by Formula (120) can be obtained with the methods represented in the above Scheme 24.

The compounds represented by Formula (114), which are a portion of the compounds represented by Formula (12), by reacting with an allyl halide under basic conditions to allylate the hydroxyl moiety, allow the compound represented by Formula (115) to be obtained (Step 24-1). The compound represented by Formula (116) can be obtained by dihydroxylation of an alkene group of the compound represented by Formula (115) using a peroxide such as hydrogen peroxide water and, for instance, with osmium tetraoxide and the like as a catalyst (Step 24-2). In addition, the compound represented by Formula (115) allows, by a general hydroboration, the compound represented by Formula (117) with a hydroxylated terminal alkylene moiety to be obtained (Step 24-3). The compound represented by Formula (117) allows, the compound represented by Formula (118) to be obtained (Step 24-4) by a general oxidation reaction from a hydroxyl group to a formyl group, and subsequently the compound represented by Formula (120) by subjecting the formyl group to a general reductive amination reaction (Step 24-5). On the other hand, the compound represented by Formula (117) allows the compound represented by Formula (120) to be obtained, by converting the hydroxyl group into a leaving group, for instance, halogen, methane sulfonyl oxy group, p-toluene sulfonyl oxy group and the like, then (Step 24-6), by action of a variety of amines (Step 24-7).

Scheme 25

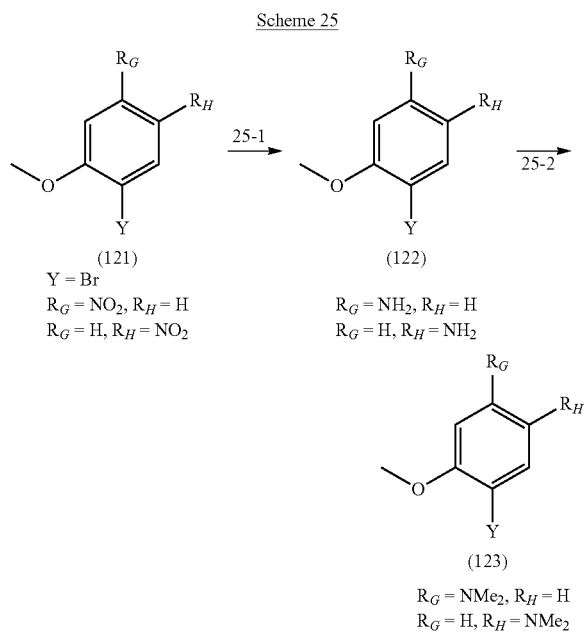

The compounds represented by Formula (123), which are a portion of source materials for the synthesis of the compound represented by Formula (27), can be prepared according to the synthesis methods shown by Scheme 24. In Step 25-1, the compound represented by Formula (121) allows, by being subjected to a general reduction reaction, the compound represented by Formula (122) to be obtained. The present reduction reaction proceeds in the presence of a metal, for instance, iron, zinc, tin and the like, in a solvent, for instance, acetic acid, hydrochloric acid, trifluoroacetic acid and the like, under a temperature condition between 0° C. to under a heating condition close to the boiling point of the solvent. In addition to the above description, this reduction reaction can be also conducted using hydrogen gas via palladium carbon and Raney nickel. In addition, a comprehensive overview of the present reduction reaction may be found in Richard C. Larock, Comprehensive Organic Transformation, WILEY-VCH, 1999, 821. The obtained compound represented by Formula (122), by being subjected to a reductive amination reaction, allows the compound represented by Formula (123) to be obtained. The present reductive amination reaction is accomplished by reacting with an aldehyde, for instance, formaldehyde and the like to generate an imine derivative and reducing with a reducing agent, for instance, sodium triacetoxy borohydride and the like. The present reaction proceeds in an inert solvent, for instance, methanol, ethanol, tetrahydrofuran, dichloromethane, chloroform and the like, or in a mixed solvent thereof, under a temperature condition between −70° C. to room temperature. In addition, in this reaction hydrogen gas can also be used with, for instance, palladium carbon and the like as catalyst, and the reaction can otherwise be also carried out using, for instance, borohydride, sodium borohydride, sodium cyano borohydride and the like, which are other boron reagents.

The compound represented by Formula (121) is either commercially available or can be prepared according to usual practice generally well-known to those skilled in the art.

Scheme 26

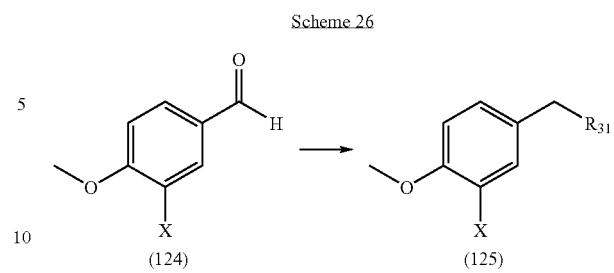

(in the formula, $R_3$, represents a mono-alkyl amino group, a di-alkyl amino group, an alkyl-cycloalkyl amino group and a heterocyclic group. X represents a halogen atom (preferably, chlorine, bromine, and iodide))

The compounds represented by Formula (125), which are a portion of source materials for the synthesis the compound represented by Formula (27), can be prepared according to the synthesis method shown by Scheme 26. The compound represented by Formula (124), by reacting with a secondary amine, for instance, dimethylamine, piperidine, pyrrolidine, piperazine and the like, and a primary amine to generate an imine derivative, and by being reduced by a reducing agent, for instance, sodium cyano borohydride and the like, allows the desired compound represented by Formula (125) to be obtained. The present reaction proceeds in a solvent, for instance, methanol, ethanol, tetrahydrofuran, dichloromethane, chloroform and the like, or in a mixed solvent thereof, under a temperature condition between −70° C. to room temperature. In addition, hydrogen gas can be used in this reaction with, for instance, palladium carbon or the like as catalyst, and the reaction can otherwise be also carried out using, for instance, borohydride, sodium borohydride, sodium triacetoxy borohydride and the like, which are other boron reagents.

The compound represented by Formula (124) is either commercially available, or can be prepared according to usual practice generally well-known to those skilled in the art.

Scheme 27

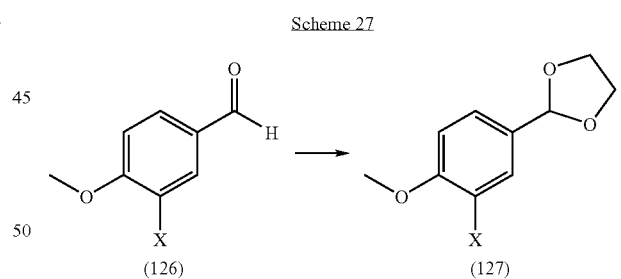

(in the formula, X represents a halogen atom (preferably, chlorine, bromine, and iodide))

The compounds represented by Formula (127), which are source materials for the synthesis of the compound represented by Formula (27), can be prepared according to the synthesis method shown in Scheme 25. The compound represented by Formula (126) can react with, for instance, ethylene glycol, methanol, ethanol and the like, under such acid catalysts as, for instance, p-toluene sulfonic acid, hydrochloric acid, acetic acid and the like to generate an acetal, a ketal and the like. The present reaction can use solvents, for instance, benzene, toluene, ethyl ortho-formate, chloroform and the like or proceeds in a mixed solvent thereof under a temperature condition between room temperature to under a heating condition close to the boiling point of the solvent. Regarding these protecting groups, they are described in Protective Groups in Organic Synthesis, by Authors T. W. Greene and P. G. M. Wuts.

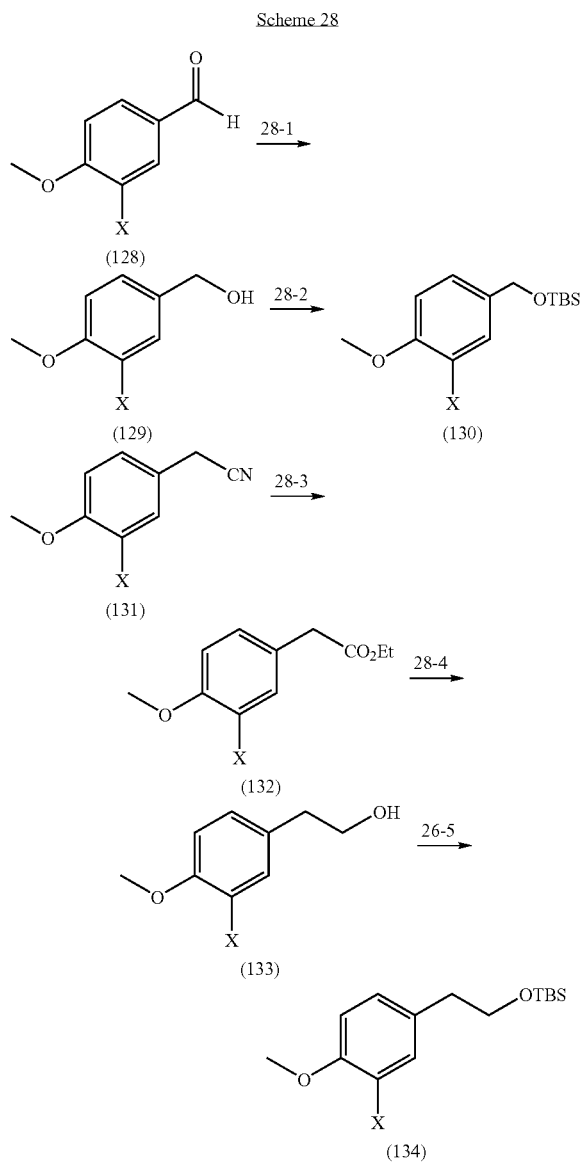

(in the formula, X represents a halogen atom (preferably, chlorine, bromine, and iodide))

The compounds represented by Formulae (130) and (134), which are a portion of synthetic raw materials for the synthesis of Formula (27), can be prepared according to the synthesis method shown in Scheme 28. The compound represented by Formula (128), by a reduction reaction, allows the compound represented by Formula (129) to be obtained. The present reduction reaction is accomplished using a reducing agent, for instance, sodium borohydride and the like, in a solvent, for instance, methanol, ethanol, isopropyl alcohol, chloroform, tetrahydrofuran and the like, or mixed solvent thereof, under a temperature condition between −78° C. to under a heating condition close to the boiling point of the solvent. In addition, as other examples, for instance, lithium aluminum hydride, diisobutyl aluminum hydride, lithium borohydride and the like, can be used. In regard to this oxidation reaction, other methods than those described above are not limited in particular, as long as the methods can reduce an ester into an alcohol. The oxygen atom of the obtained Formula (129) is protected by a general method, and allows the compound represented by Formula (130) to be prepared. As protecting groups for the oxygen atom, groups that are removed by an acid, for instance, tert-butyl dimethyl silyl group, trimethyl silyl group, triisopropyl silyl group, tert-butyl diphenyl silyl group and the like may be used, and when the present protecting groups are used, deprotection is possible using an acid, for instance, hydrochloric acid, sulfuric acid, trifluoroacetic acid, p-toluene sulfonic acid, methanesulfonic acid and the like. In addition, since these are groups that are removed by a fluorine atom, they can otherwise also be deprotected using, for instance, tetrabutyl ammonium fluoride, hydrogen fluoride and the like. Regarding these protecting groups, descriptions may be found in Protective Groups in Organic Synthesis, by authors T. W. Greene and P. G. M. Wuts.

In addition, as another method, the compound represented by Formula (131) can be converted into an ester using, for instance, hydrochloric acid, sulfuric acid, trifluoroacetic acid, p-toluene sulfonic acid, methanesulfonic acid and the like, in a solvent such as methanol, ethanol, isopropyl alcohol and the like, or a mixed solvent thereof, and under a temperature condition of 0° C. to near the boiling point of the solvent (Step 28-3).

In addition, the reduction reaction at Step 28-4 in Scheme 28 is accomplished by using, for instance, lithium aluminum hydride, sodium borohydride, lithium borohydride, lithium triethyl borohydride and the like, and reacting in, for instance, methanol, ethanol, isopropyl alcohol, tetrahydrofuran, chloroform, dichloromethane and the like, or a mixed solvent thereof, at 0° C. to under a heating condition close to the boiling point of the solvent. Regarding this reduction reaction, other methods than those described above are not limited in particular, as long as the methods can reduce a ketone into an alcohol. A comprehensive overview of the present reduction reaction may be found in, Comprehensive Organic Transformation, WILEY-VCH, 1999, 1114, by Richard C. Larock. As protecting groups for alcohol, groups that are removed by an acid or fluorine, for instance, tert-butyl dimethyl silyl group and the like, are used. Concepts regarding these protecting groups may be found in Protective Groups in Organic Synthesis, by authors T. W. Greene and P. G. M. Wuts (Step 28-5).

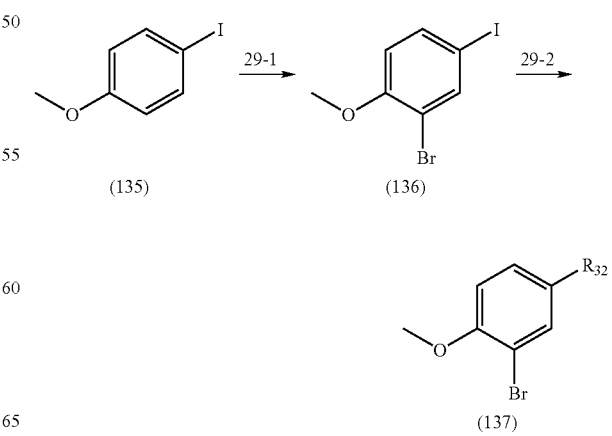

(in the formula, $R_{32}$ represents an aryl group having 6 to 14 carbon atoms, an aryl group having 6 to 14 carbon atoms substituted by the above-mentioned substituent group D, a heterocyclic group or a heterocyclic group substituted by above-mentioned substituent E group.)

The compounds represented by Formula (137), which are a portion of source materials for the synthesis of Formula (27) can be prepared according to the synthesis method shown in Hartwig, Angew. Chem. Int. Ed., Engl. 1998, 37, 2046-2067; Muci, A. R. Buchwald, S. L. Top. Curr. Chem. 2002, 219, 131; and J. P. Wolfe, H Tomori, J. P Sadighi, J. Yin, S. L. Buchwald, J. Org. Chem., 2000, 365, 1158-1174.

A comprehensive overview regarding Suzuki-Miyaura coupling may be found in Angew. Chem. Int. Ed. 2001, 40, 4544.

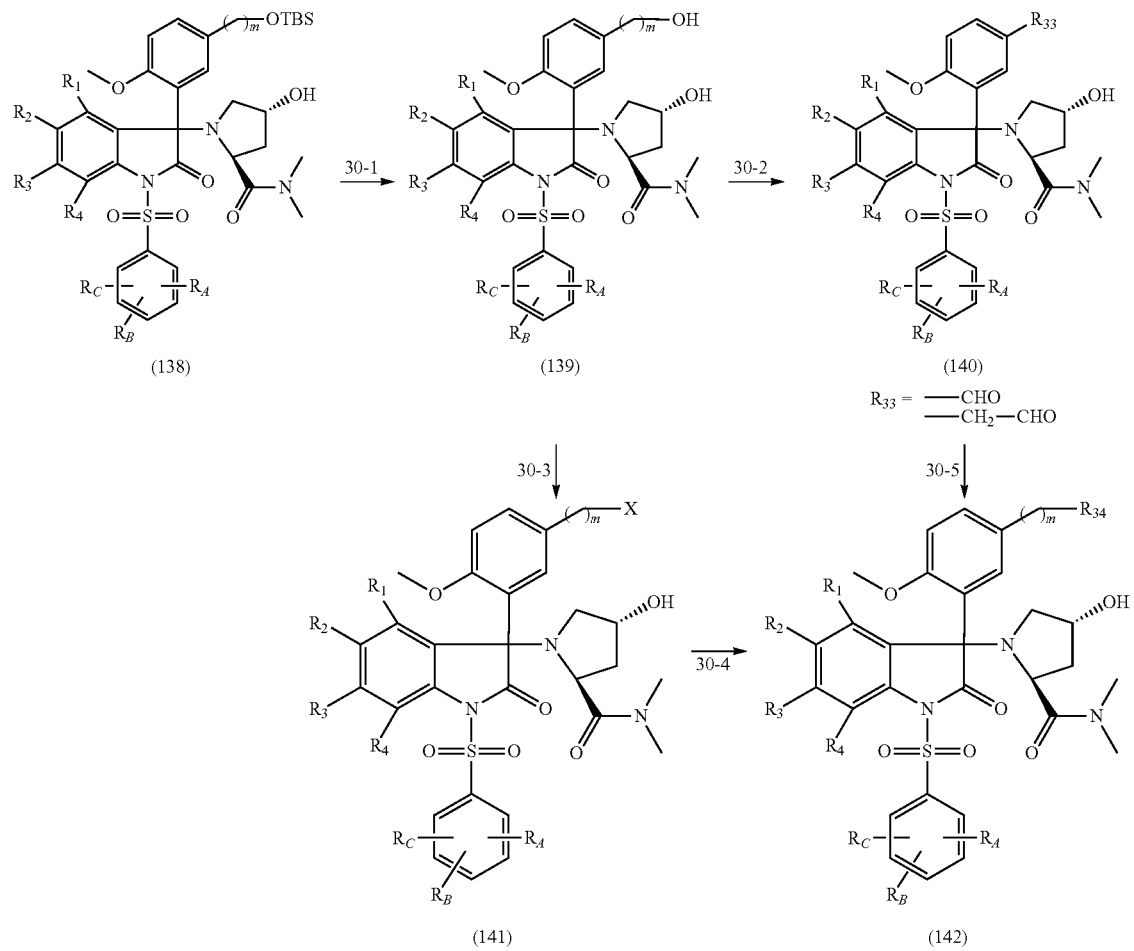

Scheme 28. The compound represented by Formula (136) can be obtained by reacting commercially available 4-iodoanisole with bromine in a solvent, for instance, acetic acid and the like. By reacting a heterocycle or a heterocycle substituted by the above-mentioned substituent E group on the obtained compound represented by Formula (136) under Buchwald-Hartwig amination conditions, the compound represented by Formula (137) can be obtained.

In addition, by reacting an aryl boronic acid derivative or a heterocyclic boronic acid derivative on the compound represented by Formula (136) under Suzuki-Miyaura coupling conditions, the compound represented by Formula (137) can be obtained.

A comprehensive overview regarding Buchwald-Hartwig amination may be found in A. S. Guram, R. A. Rennels, S. L. Buchwald, Angew. Chem., Int Ed. Engl. 1995, 34, 1348; J. Louie, J. F. Hartwig, Tetrahedron Lett. 1995, 36, 3609; J. F.

(in the formula, $R_1$, $R_2$, $R_3$, $R_4$, $R_9$, $R_A$, $R_B$ and $R_C$ have the same meaning as in the above description. m represents an integer from 1 to 5. $R_{34}$ represents a mono-alkyl amino group, a di-alkyl amino group, an alkyl cycloalkyl amino group or a heterocyclic group. X represents a leaving group)

Prepared by sequentially reacting the compound represented by Formula (17) and the compound represented by Formula (15) with the reaction product from the Grignard reagent, whish was derived from the compounds represented by Formula (130) and Formula (134), or a lithiation reagent, and the compound represented by Formula (26), the compound represented by Formula (138) is deprotected by a general method, allowing the compound represented by Formula (139) to be obtained (Step 30-1). By oxidizing the hydroxyl group of the obtained compound represented by Formula (139) to a formyl group by a general oxidation reaction, the compound represented by Formula (140) is obtained (Step 30-2), and the compound represented by Formula (142) can be obtained by a reductive amination reaction (Step 30-5). In addition, by converting the hydroxyl group the compound represented by Formula (139) into a leaving group (Step 30-3), then carrying out a substitution reaction with an amine, the compound represented by Formula (141) can be obtained (Step 30-4).

(in the formula, $R_1$, $R_2$, $R_3$, $R_4$, $R_9$, $R_A$, $R_B$ and $R_C$ have the same meaning as in the above description. $R_{35}$ represents a mono-alkyl amino group, a di-alkyl amino group, a mono-cycloalkyl amino group, alkyl-cycloalkyl amino group or a heterocyclic group)

Prepared by sequentially reacting the compound represented by Formula (17) and the compound represented by Formula (15) with the reaction product from the Grignard reagent, which was derived from the compound represented by Formula (127), or a lithiation reagent, and the compound represented by Formula (26), the compound represented by Formula (143) is deacetalized by a general method, allowing the compound represented by Formula (144) to be obtained (Step 31-1). The compound represented by Formula (145) can be obtained by subjecting the obtained compound represented by Formula (144) to a general reductive amination reaction (Step 31-2).

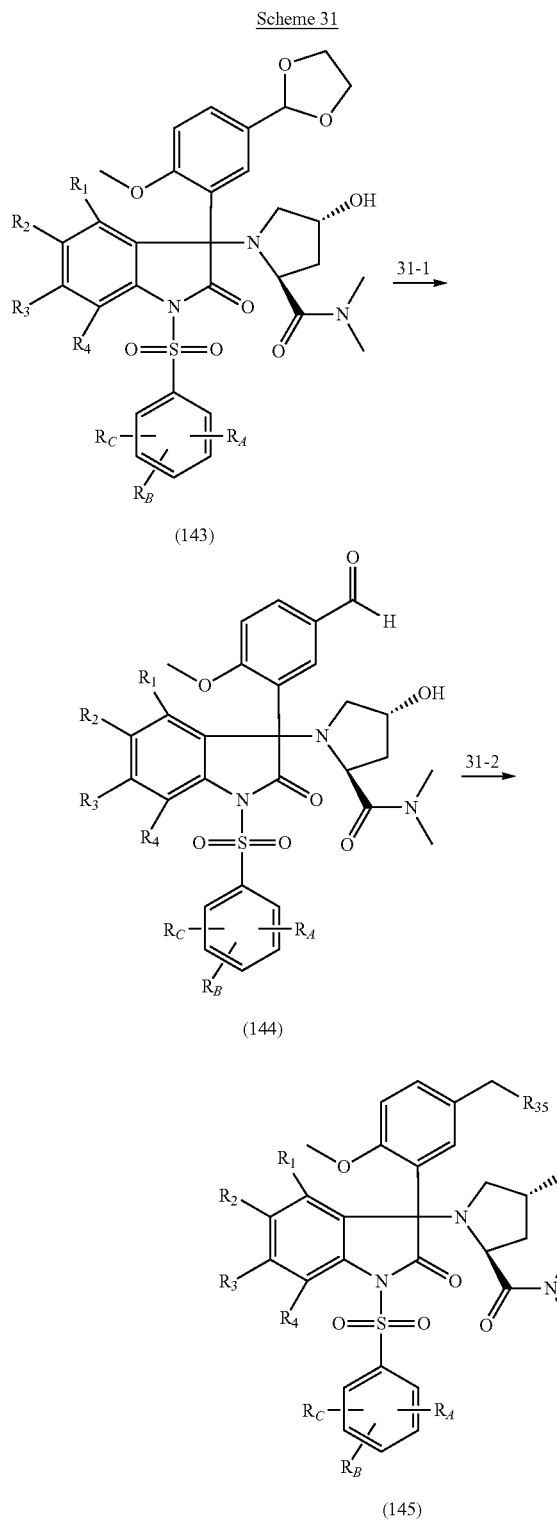

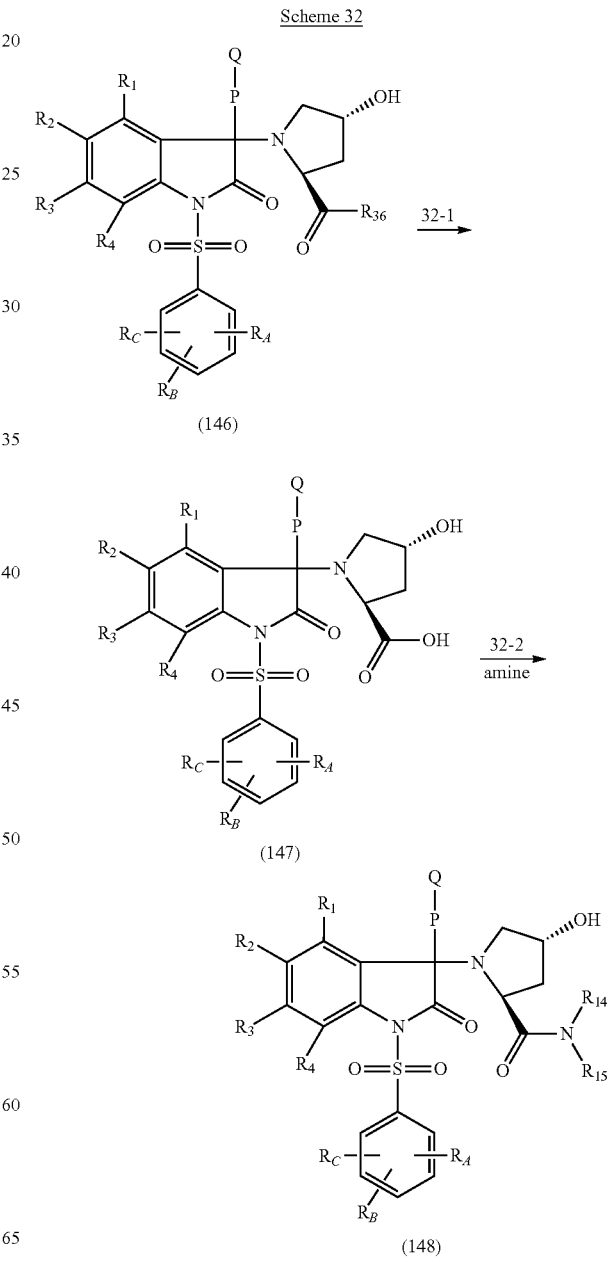

(in the formula, $R_1$, $R_2$, $R_3$, $R_4$, $R_9$, $R_{14}$, $R_{15}$, P, Q, $R_A$, $R_B$ and $R_C$ have the same meaning as in the above description. $R_{36}$ represents benzyl oxy group or p-methoxybenzyl oxy)

The compound represented by Formula (146) is deprotected by a general hydrogen addition reaction, allowing the compound represented by Formula (147) to be obtained. The obtained compound represented by Formula (147), by carrying out amidation with amines, using dehydration condensation agent, for instance 1-ethyl-3-(3-dimethylamino propyl) carbodiimide/hydrochloride, dicyclohexyl carbodiimide, diphenyl phosphonyl azide, carbonyl diimidazole and the like, as necessary and activator, for instance 1-hydroxy benzo triazole, hydroxy succinimide and the like, allows the compound represented by Formula (148) to be obtained). The compound represented by Formula (145) can be obtained by subjecting the obtained compound represented by Formula (144) to a general reductive amination reaction (Step 32-2).

Among the compounds represented by Formula (1), the compounds represented by Formula (152), in which the A ring represents a heteroaromatic ring group, can be prepared according to synthesis method shown in Scheme 33.

By reacting the compound represented by Formula (149) in the presence of a base or a catalyst, and carrying out benzene sulfonylation on the nitrogen atom of indoline, the compound represented by Formula (150) can be obtained (Step 33-1).

The reaction can be carried out in the presence of a base, for instance, metal hydride such as sodium hydride and the like, alkaline metal alkoxide such as tert-butoxy potassium and the like, in an anhydrous solvent, for instance, N,N-dimethyl formamide, tetrahydrofuran and the like, or mixed solvents thereof, under a temperature condition of −70° C. to +60° C.

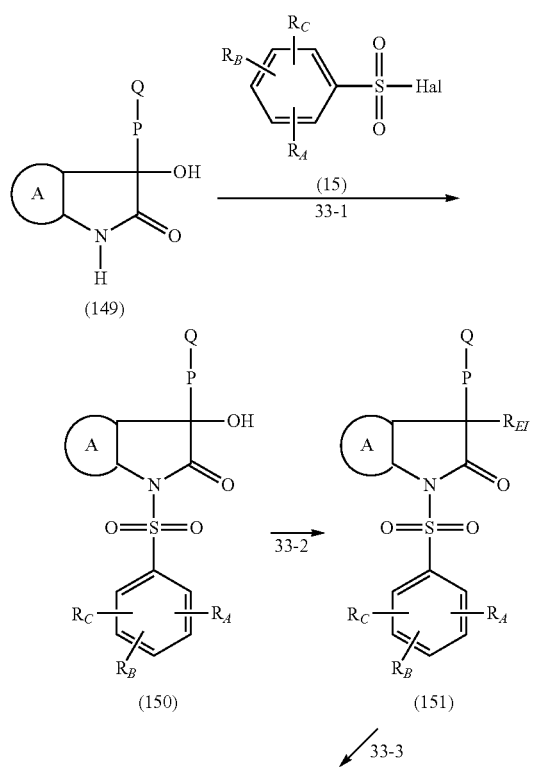

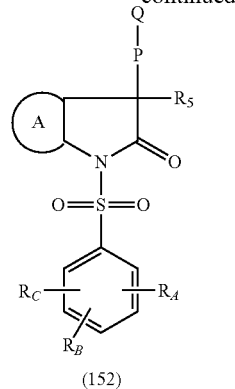

(in the formula, A, $R_5$, $R_A$, $R_B$ and $R_C$ are the same as in the above description. $R_5$ is the same as the group defined in the above Formulae (3), (4), (5), (6), (8), (9) and (10). Hal represents a halogen atom. $R_{EI}$ represents a leaving group such as, for instance, phenyl oxy group)

The compound represented by Formula (151) can be obtained by halogenating the compound represented by Formula (150) under similar reaction conditions as in the above case when deriving from the compound represented by Formula (24) to the compound represented by Formula (16) (Step 33-2).

By reacting the compound represented by Formula (33) in the presence of a base, for instance, triethylamine, di-isopropylethyl amine, sodium bis-(trimethylsilyl) amide, potassium bis-(trimethylsilyl) amide, lithium bis-(trimethylsilyl) amide and the like, in an anhydrous solvent, for instance, N,N-dimethyl formamide and the like, under a temperature condition of −70° C. to +60° C. reaction, the compound represented by Formula (152) ($R_5$ is the same as the group defined in the above Formulae (3), (4), (5), (6), (8), (9) and (10)) can be obtained (Step 33-3).

In addition, by reacting the compound represented by Formula (32) in the presence of a catalyst, for instance, silver oxide in an anhydrous solvent, for instance, N,N-dimethyl formamide and the like, under a heating condition close to the boiling point of the solvent or under a heating condition under microwave radiation, the compound represented by Formula (12) ($R_5$ is the same as the group defined in the above Formulae (3), (4), (5), (6), (8), (9) and (10)) can be obtained (Step 2-3).

In addition, for instance, the compound represented by Formula (149) can be obtained by action on the compound represented by Formula (153)

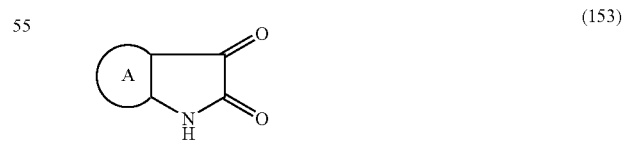

(in the formula, A represents a heteroaromatic ring group) of the organo-metallic reagent represented by Formula (27)

Q-P-M     (27)

(in the formula, P and Q are the same as in the above description. M represents a group represented by the formula —Mg—Hal or a group represented by the formula —Li. Hal represents a halogen atom), and hydrolysis of the obtained intermediate.

These reactions can be carried out in, for instance, diethyl ether, tetrahydrofuran, hexane and the like, or mixed solvents thereof, under temperature conditions between −70° C. to room temperature enforcement possible.

The compound represented by Formula (27) can be prepared by usual practice well-known to those skilled in the art.

In particular, among the compounds represented by Formula (153), 7-aza indoline can be prepared according to the synthesis method shown by Scheme 34.

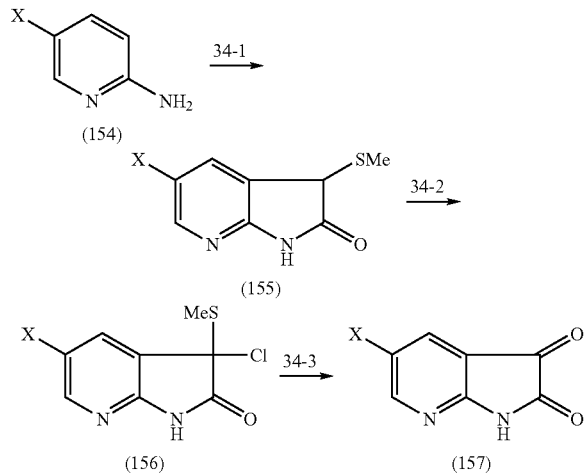

(in the formula, X represents a halogen atom)

Action of perchloric acid tert-butyl ester, methyl thio ethyl acetate, triethylamine on 5-halogeno-2-aminopyridine (154), for instance, in dichloromethane, chloroform, acetonitrile, tetrahydrofuran and the like, or mixed solvents thereof, under temperature conditions of −78° C. to 0° C., then, treatment by an acid, for instance, hydrochloric acid and the like, allows the cyclized compound represented by Formula (155) to be obtained (Step 34-1). Thereafter, halogenation of position 3 of azaindoline, using a halogenation agent, for instance, N-chloro succinimide and the like (Step 34-2), then action of a Lewis acid, for instance, boron trifluoride diethyletherate and mercury oxide in a tetrahydrofuran-water mix solvent, allows the desired 5-halogeno-7-azaisatin (157) to be prepared (Step 34-3).

The preparation method shown in Scheme 34 is an application of the preparation method for Oxindoles in J. Am. Chem. Soc., 5508 (1974), to the preparation of azaisatin.

7-azaisatin can also be prepared by methods describes in Heterocycles, Vol. 53, No. 5 (2000), Heterocycles, 1145 (2000), ARKIVOC, i, 67 (2001), Bioorg. & Med. Chem. Lett., 333 (1992), Bioorg. & Med. Chem. Lett., 195 (1994), J. Chem. Soc. Perkin Trans. I, 2009 (1989), Publication No. WO95/13807 or EP0556060.

4-azaisatin can be prepared by methods described in Publication No. WO95/13807, or EP0556060.

5-azaisatin can be prepared by methods described in J. Heterocycl. Chem., 34 (1997) 2, 441 or Publication No. WO95/13807.

6-azaisatin can be prepared by methods described in Publication No. WO95/13807.

Hereinafter, the present invention will be described in further detail by giving synthesis examples, examples and test example; however these do not limit the present invention, and in addition can be modified to the extent that they do not depart from the scope of the present invention.

Note that in the examples, silicagel 60, silicagel 60N is silica gel commercialized by Kanto Kagaku Co. Chromatorex NH is silica gel commercialized by Fuji Silysia LTD. In addition, progression of the reaction was followed up by thin layer chromatography (TLC) using 0.25 mm silicagel 60 $F_{254}$ plates (manufactured by Merck). The TLC plates were observed by UV (254 nm), or by coloration using a 20% sodium phosphomolybdate/EtOH solution. The compounds were named using ACD/NAME (Product Version: 7.0 or 8.05, ACD/LABS). $^1$H-NMR spectra had tetramethyl silane as internal standard, and the chemical shifts were reported by ppm. The melting points are non-corrected values.

In the present examples, the following terms and reagents were reported as follows.

MeOH (methanol), NaOH (sodium hydroxide), KOH (potassium hydroxide), $MgSO_4$ (anhydrous magnesium sulfate), $Na_2SO_4$ (anhydrous sodium sulfate), $NaHCO_3$ (sodium bicarbonate), $Na_2CO_3$ (sodium carbonate), $K_2CO_3$ (potassium carbonate), NaH (sodium hydride, 50-72% in oil), $NH_4Cl$ (ammonium chloride), Py (pyridine), THF (tetrahydrofuran), DMF (N,N-dimethylformamide), $Et_2O$ (diethylether), IPE (diisopropylether), EtOH (ethanol), $NH_4OH$ (28% aqueous ammonia), EtOAc (ethylacetate), MeCN (acetonitrile), $Et_3N$ (triethylamine), $CHCl_3$ (chloroform), TMEDA (N,N,N',N'-tetramethylethylenediamine), TBAF (tetra-n-butylammoniumfluoride), LAH (lithiumaluminumhydride), $NaBH_4$ (sodiumborohydride), TFA (trifluoroacetic acid), $HOBt/H_2O$ (1-hydroxybenzotriazole/1 hydrate), EDC/HCl [1-(3-dimethylaminopropyl)-3-ethylcarbodiimide/1 hydrochloride], $(Boc)_2O$ (di-tert-butyldicarbonate), TBSCl (t-butyldimethylchlorosilane), DMAP (4-dimethyl aminopyridine), IPA (isopropylalcohol), IBX (1-hydroxy-1,2-benz iodoxol-3(1H)-one 1-oxide)

Synthesis Example 1

Synthesis of 4-methoxy-2-(trifluoromethoxy)benzene sulfonyl chloride, 2-methoxy-4-(trifluoromethoxy)benzene sulfonyl chloride Step G1-1: Synthesis of 1-methoxy-3-(trifluoromethoxy)benzene To a suspension of 20.0 g of 3-(trifluoromethoxy)phenol and 23.3 g of $K_2CO_3$ (anhydrous) in DMF (100 ml) was added 23.9 g of iodine methane under ice cooling, then the reaction mixture was warmed to room temperature, and was stirred at room temperature for 13 hours. To the reaction solution was added EtOAc (100 ml) and purified water (150 ml), and the resulting mixture was stirred for 30 minutes. After liquid separation, the aqueous layer was extracted with EtOAc (50 ml×2), the combined organic layer was washed with purified water (100 ml×3) and with saturated brine (50 ml) and dried overover $MgSO_4$, then, the drying agent was separated by filtration, and the solvent was removed under reduced pressure to obtain 27.7 g of the title compound (crude form, yellow oil). The present compound was used in the next reaction without purification.

MS (CI pos.) m/z: 193 ([M+H]$^+$)

$^1$H-NMR (300 MHz, CDCl$_3$) δ (ppm); 3.81 (s, 3H), 6.73-6.87 (m, 3H), 7.25-7.32 (m, 1H)

Step G1-2: Synthesis of potassium 4-methoxy-2-(trifluoromethoxy)benzene sulfonate and potassium 2-methoxy-4-(trifluoromethoxy)benzene sulfonate (mixture)

Under a nitrogen atmosphere, to a solution of 27.0 g of compound obtained in Step G1-1 in nitromethane (270 ml) was added dropwise a solution of 9.86 g of anhydrous sulfuric acid in nitromethane (100 ml) over 3 minutes under ice cooling. After warming to room temperature, the reaction mixture was stirred for 3 days at room temperature. To the reaction solution was added water (100 ml) and CHCl$_3$ (50 ml), and the resulting mixture was stirred at room temperature for 30 minutes. After liquid separation, and the aqueous layer was washed with CHCl$_3$ (50 ml). The obtained aqueous layer was cooled with ice, neutralized with a 2 mol/L KOH aqueous solution (PH=9). The neutralized solution was dried under reduced pressure to obtain 32.9 g of the title compound (crude form, brown solid). The present compound was used in the next reaction without purification.

MS (ESI pos.) m/z: 333 ([M+Na]$^+$)
$^1$H-NMR (300 MHz, DMSO-d$_6$) δ (ppm); 3.78 & 3.79 (each-s, 3H), 6.72-6.95 (m, 3H), 7.75 (t, J=8.9 Hz, 1H)

Step G1-3: Synthesis of 4-methoxy-2-(trifluoromethoxy)benzene sulfonyl chloride and 2-methoxy-4-(trifluoromethoxy)benzene sulfonyl chloride Phosphorusoxychloride (100 ml) was added to 32.8 g of the compound obtained in Step G1-2, and the solution was stirred for 5.5 hours at an external temperature of 130° C. The reaction solution was cooled down, then, the reaction solution was poured over ice (1.5 L), and the solution was stirred for 1 hour. The precipitation was extracted with Et$_2$O (100 ml×3), the combined organic layer was washed with saturated brine (50 ml), then, dried over MgSO$_4$, the drying agent was separated by filtration, then, the solvent was evaporated under reduced pressure. The obtained residue was purified by column chromatography (silicagel 60; mobile phase: EtOAc/n-hexane=1/20 to 1/10; v/v) to obtain 17.8 g of 4-methoxy-2-(trifluoromethoxy)benzene sulfonyl chloride (pale yellow oil) and 8.28 g of 2-methoxy-4-(trifluoromethoxy)benzene sulfonyl chloride (pale yellow oil).

4-methoxy-2-(trifluoromethoxy)benzene sulfonyl chloride

MS (EI) m/z: 290 ([M]$^+$)
$^1$H-NMR (300 MHz, CDCl$_3$) δ (ppm); 3.94 (s, 3H), 6.92 (dd, J=9.0, 2.5 Hz, 1H), 6.95-6.99 (m, 1H), 8.03 (d, J=9.0 Hz, 1H)

2-methoxy-4-(trifluoromethoxy)benzene sulfonyl chloride

MS (EI) m/z: 290 ([M]$^+$)
$^1$H-NMR (300 MHz, CDCl$_3$) δ (ppm); 4.09 (s, 3H), 6.90-6.99 (m, 2H), 8.00-8.05 (m, 1H)

Example 1

Synthesis of (4R)-1-(5-chloro-3-(2-methoxyphenyl)-1-{[2-methoxy-4-(trifluoromethoxy)phenyl]sulfonyl}-2-oxo-2,3-dihydro-1H-indol-3-yl)-4-hydroxy-N,N-dimethyl-L-prolinamide (levorotatory isomer)

To a solution of 512 mg of (4R)-1-[5-chloro-3-(2-methoxyphenyl)-2-oxo-2,3-dihydro-1H-indol-3-yl]-4-hydroxy-N,N-dimethyl-L-prolinamide (levorotatory isomer), which is the compound described in Preparation 3.2 (Isomer B) of Brochure No. WO01/55130 in DMF (5 ml) was added 57.1 mg of NaH under ice cooling, and the solution was stirred for 30 minutes at the same temperature. A solution of 415 mg of 2-methoxy-4-(trifluoromethoxy)benzene sulfonyl chloride in DMF (3 ml) was added, then, the solution was stirred for 30 minutes at the same temperature. To the reaction solution was added an aqueous solution of 10% K$_2$CO$_3$, and the resulting mixture was stirred at room temperature for 1 hour. Water and EtOAc were added, liquid separation was performed, and the aqueous layer was extracted with EtOAc. The combined organic layer was washed with water and saturated brine, then, was dried over MgSO$_4$. The drying agent was separated by filtration, solvent was evaporated under reduced pressure. The obtained residue was purified by column chromatography (silicagel 60; mobile phase: n-hexane/EtOAc=1/2 to 1/2.5; v/v), to obtain 561 mg of the title compound (colorless amorphous).

[α]$_D$$^{21}$=−898° (c=0.217, CHCl$_3$)
MS (ESI pos.) m/z: 706 ([M+Na]$^+$)
$^1$H-NMR (300 MHz, CDCl$_3$) δ (ppm); 1.17-1.50 (m, 2H), 1.69-1.78 (m, 1H), 1.88-2.07 (m, 1H), 2.29 (s, 3H), 2.77 (s, 3H), 3.02-3.16 (m, 1H), 3.68 (s, 3H), 3.73 (s, 3H), 4.60-4.85 (m, 1H), 4.79 (d, J=8.9 Hz, 1H), 6.76-6.82 (m, 2H), 6.91-7.01 (m, 2H), 7.12 (d, J=2.2 Hz, 1H), 7.20-7.31 (m, 2H), 7.74 (d, J=7.6 Hz, 1H), 7.89 (d, J=8.9 Hz, 1H), 8.28 (d, J=8.9 Hz, 1H)

Example 2

Synthesis of (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

To a solution of 300 mg of (4R)-1-[5-chloro-3-(2-methoxyphenyl)-2-oxo-2,3-dihydro-1H-indol-3-yl]-4-hydroxy-N,N-dimethyl-L-prolinamide (levorotatory isomer), which is the compound described in Preparation 3.2 (Isomer B) of Brochure No. WO01/55130 in DMF (3 ml) was added 30.5 mg of NaH under ice cooling, and the solution was stirred for 30 minutes at the same temperature. After stirring, to the solution was added a solution of 222 mg of 2-methoxy-4-(trifluoromethoxy)benzene sulfonyl chloride in DMF (1 ml), then, the reaction solution was stirred for 30 minutes at the same temperature. To the reaction solution was added an aqueous solution of 10% K$_2$CO$_3$, and the resulting mixture was stirred at room temperature for 1 hour. Water and EtOAc were added, liquid separation was performed, and the aqueous layer was extracted with EtOAc. The combined organic layer was washed with water and with saturated brine, then, was dried over MgSO$_4$, the drying agent was separated by filtration, and the solvent was evaporated under reduced pressure. The obtained residue was purified by column chromatography (silicagel 60; mobile phase: EtOAc) to obtain 409 mg of the title compound (colorless amorphous).

[α]$_D$$^{21}$=−879° (c=0.211, CHCl$_3$)
MS (ESI pos.) m/z: 706 ([M+Na]$^+$)
$^1$H-NMR (300 MHz, CDCl$_3$) δ (ppm); 1.22-2.54 (m, 4H), 2.34 (s, 3H), 2.74 (s, 3H), 3.11-3.29 (m, 1H), 3.59 (s, 3H), 3.89 (s, 3H), 4.54-4.85 (m, 2H), 6.73-6.80 (m, 1H), 6.85-7.13

(m, 4H), 7.19-7.29 (m, 2H), 7.73-7.93 (m, 1H), 7.88 (d, J=8.9 Hz, 1H), 8.34 (d, J=9.0 Hz, 1H)

Example 3

Synthesis of (4R)-1-[1-{[2,5-bis (2,2,2-trifluoroethoxy)phenyl]sulfonyl}-5-chloro-3-(2-methoxyphenyl)-2-oxo-2,3-dihydro-1H-indol-3-yl]-4-hydroxy-N,N-dimethyl-L-prolinamide (levorotatory isomer)

With 100 mg of (4R)-1-[5-chloro-3-(2-methoxyphenyl)-2-oxo-2,3-dihydro-1H-indol-3-yl]-4-hydroxy-N,N-dimethyl-L-prolinamide (levorotatory isomer), which is the compound described in Preparation 3.2 (Isomer B) of the brochure Publication No. WO01/55130, and 89 mg of 2,5-bis (2,2,2-trifluoroethoxy)benzene sulfonyl chloride as starting materials, 119 mg of the title compound (colorless amorphous) was obtained by a similar method to Example 2.

$[\alpha]_D^{25}=-140°$ (c=0.206, CHCl$_3$)

MS (ESI pos.) m/z: 766 ([M+H]$^+$), 788 ([M+Na]$^+$), (ESI neg.) m/z: 764 ([M−H]$^−$)

$^1$H-NMR (300 MHz, CDCl$_3$) δ (ppm); 0.76-4.90 (m, 20H), 6.79 (dd, J=8.24, 1.09 Hz, 1H), 6.89-7.01 (m, 2H), 7.02-7.12 (m, 1H), 7.20-7.34 (m, 3H), 7.67-7.80 (m, 1H), 7.83-7.95 (m, 2H)

Example 4

Synthesis of Methyl (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-hydroxy-L-prolinate (levorotatory isomer)

Step 4-1: Synthesis of methyl (4R)-4-hydroxy-L-prolinate trifluoroacetate

To a solution of 2.00 g of 1-tert-butyl 2-methyl (2S,4R)-4-hydroxypyrrolidine-1,2-dicarboxylate in CHCl$_3$ (20 ml) was added TFA (10 ml) under ice cooling, the reaction mixture was warmed to room temperature, then was stirred for 3 hours at the same temperature. Thereafter, the reaction solution was concentrated under reduced pressure to obtain 3.82 g of the title compound (crude form, colorless oil). The present compound was used in the next reaction without purification.

MS (ESI pos.) m/z: 146 ([M+H]$^+$)

$^1$H-NMR (300 MHz, DMSO-d$_6$) δ (ppm); 2.05-2.29 (m, 2H), 3.04-3.16 (m, 1H), 3.27-3.41 (m, 1H), 3.77 & 3.78 (each-s, 3H), 4.40-4.67 (m, 2H), 9.06 (s, 1H), 9.98 (s, 1H)

Step 4-2: Synthesis of methyl (4R)-1-[5-chloro-3-(2-methoxyphenyl)-2-oxo-2,3-dihydro-1H-indol-3-yl]-4-hydroxy-L-prolinate (diastereoisomer mixture)

To a suspension of 2.28 g of 3,5-dichloro-3-(2-methoxyphenyl)-1,3-dihydro-2H-indol-2-one, which is the compound described in Preparation 1.1 of Brochure No. WO01/55130, and the compound obtained in Step 4-1 (8.15 mmol) in CHCl$_3$ (23 ml) was added dropwise 4.49 g of Et$_3$N over 2 minutes under ice cooling, then, the reaction mixture was stirred at room temperature for 13 hours. An aqueous solution of 5% K$_2$CO$_3$ was added to the reaction solution, and the resulting mixture was stirred for 15 minutes. liquid separation was performed, and the aqueous layer was extracted with CHCl$_3$ extraction. The combined organic layer was washed with saturated brine, then, dried over MgSO$_4$, the drying agent was separated by filtration, then, the solution was concentrated under reduced pressure. The obtained residue was purified by column chromatography (silicagel 60; mobile phase: EtOAc) to obtain 2.37 g of a diastereoisomer mixture of the title compound (colorless amorphous).

MS (ESI pos.) m/z: 439 ([M+Na]$^+$)

$^1$H-NMR (300 MHz, CDCl$_3$) δ (ppm); 1.51-4.61 (m, 13H), 6.65-7.33 (m, 6H), 7.86 & 8.09 (each-dd, J=7.8, 1.7 Hz, 1H), 8.30 & 8.53 (each-brs, 1H)

Step 4-3: Synthesis of methyl (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-hydroxy-L-prolinate (levorotatory isomer)

From 1.00 g of the compound obtained in Step 4-2 and 692 mg of 4-methoxy-2-(trifluoromethoxy)benzene sulfonyl chloride, respectively 770 mg (Isomer A: colorless amorphous) and 423 mg (Isomer B: colorless amorphous) of two species of diastereoisomers of the title compound were obtained by a similar procedure as Example 2.

Isomer A: $[\alpha]_D^{21}=-92°$ (c=0.189, CHCl$_3$)

MS (ESI pos.) m/z: 693 ([M+Na]$^+$), (ESI neg.) m/z: 669 ([M−H]$^−$)

$^1$H-NMR (300 MHz, CDCl$_3$) δ (ppm); 1.30-3.61 (m, 5H), 3.49 (s, 6H), 3.90 (s, 3H), 4.23-4.33 (m, 1H), 4.39-4.52 (m, 1H), 6.77 (d, J=8.2 Hz, 1H), 6.81-7.05 (m, 4H), 7.17-7.30 (m, 2H), 7.72-7.91 (m, 1H), 7.88 (d, J=8.9 Hz, 1H), 8.36 (d, J=9.0 Hz, 1H)

Isomer B: $[\alpha]_D^{21}=-298°$ (c=0.187, CHCl$_3$)

MS (ESI pos.) m/z: 693 ([M+Na]$^+$), (ESI neg.) m/z: 669 ([M−H]$^−$)

$^1$H-NMR (300 MHz, CDCl$_3$) δ (ppm); 1.70-1.92 (m, 2H), 3.30-3.52 (m, 3H), 3.39 (s, 3H), 3.65 (s, 3H), 3.90 (s, 3H), 4.09-4.15 (m, 1H), 6.80 (dd, J=8.2, 0.9 Hz, 1H), 6.85-6.93 (m, 3H), 7.05-7.13 (m, 1H), 7.23-7.32 (m, 2H), 7.94 (d, J=8.9 Hz, 1H), 7.99 (dd, J=7.8, 1.7 Hz, 1H), 8.26 (d, J=9.6 Hz, 1H)

Example 5

Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl-L-prolinamide (levorotatory isomer)

With 300 mg of 1-[5-chloro-3-(2-methoxyphenyl)-2-oxo-2,3-dihydro-1H-indol-3-yl]-N,N-dimethyl-L-prolinamid e (levorotatory isomer), which is the compound described in Preparation 3.1 of the brochure Publication No. WO01/98295, as starting materials, 452 mg of the title compound (colorless amorphous) was obtained by a similar method to Example 2.

$[\alpha]_D^{21}=-75.4°$ (c=0.208, CHCl$_3$)

MS (ESI pos.) m/z: 690 ([M+Na]$^+$)

$^1$H-NMR (300 MHz, CDCl$_3$) δ (ppm); 1.22-3.06 (m, 7H), 2.38 (s, 3H), 2.82 (s, 3H), 3.61 (s, 3H), 3.91 (s, 3H), 4.55-4.72 (m, 1H), 6.72-6.99 (m, 4H), 7.09-7.28 (m, 3H), 7.81 (dd, J=7.8, 1.4 Hz, 1H), 7.87 (d, J=8.9 Hz, 1H), 8.33 (d, J=9.0 Hz, 1H)

Example 6

Synthesis of (4R)-1-[1-{[4-bromo-2-(trifluoromethoxy)phenyl]sulfonyl}-5-chloro-3-(2-methoxyphenyl)-2-oxo-2,3-dihydro-1H-indol-3-yl]-4-fluoro-N,N-dimethyl-L-prolinamide (levorotatory isomer)

Step 6-1a: Synthesis of tert-butyl (2S,4R)-2-[(dimethylamino)carbonyl]-4-hydroxypyrrolidine-1-carboxylate To a solution of 25.1 g of (4R)-1-(tert-butoxy carbonyl)-4-hydroxy-L-proline in THF (250 ml) was added 24.9 g of HOBt/$H_2O$ and 24.9 g of EDC/HCl under ice cooling, and the reaction mixture was stirred for 15 minutes. To the reaction mixture was added dropwise 10.7 g of an aqueous solution of 50% dimethylamine over 10 minutes, then, the reaction mixture was stirred at room temperature for 15 hours. The solvent was evaporated under reduced pressure, then, an aqueous solution of saturated $NaHCO_3$ was added to the solution, and the resulting mixture was extracted with $CHCl_3$. After drying with $Na_2SO_4$, the drying agent was separated by filtration, and the solution was concentrated under reduced pressure. The residue was purified by column chromatography (silicagel 60N; mobile phase: $CHCl_3$/MeOH=20/1 to 9/1; v/v) to obtain 26.2 g of the title compound (colorless solid).

MS (ESI pos.) m/z: 281 ([M+Na]$^+$)
$^1$H-NMR (300 MHz, CDCl$_3$) δ (ppm); 1.40 & 1.45 (each-s, 9H), 1.95-2.36 (m, 3H), 2.97 & 2.98 (each-s, 3H), 3.08 & 3.13 (each-s, 3H), 3.41-3.62 (m, 1H), 3.63-3.76 (m, 1H), 4.46-4.60 (m, 1H), 4.69-4.87 (m, 1H)

Step 6-2a: Synthesis of tert-butyl (2S,4R)-2-[(dimethylamino)carbonyl]-4-fluoropyrrolidine-1-carboxylate To a suspension of 25.7 g of the compound obtained in Step 6-1a and 5.00 g of sodium fluoride in dichloromethane (260 ml) was added dropwise under ice cooling a mixture (approximately 3:1) of 1,1,2,3,3,3-hexafluoro-1-(diethylamino)propane and 26.6 g 1,2,3,3,3-pentafluoro-1-(diethylamino)-2-propene over 10 minutes, then, the solution was stirred at room temperature for 16 hours. To the reaction solution was added an aqueous solution of 5% $K_2CO_3$ under ice cooling, and the resulting mixture was stirred for 30 minutes at the same temperature. After liquid separation, obtained aqueous layer was extracted with $CHCl_3$, the combined organic layer was washed with saturated brine, dried over $MgSO_4$, then, the drying agent was separated by filtration, and the solvent was evaporated under reduced pressure. The obtained residue was subjected to column chromatography (silicagel 60; mobile phase: EtOAc/n-hexane=1/1 to 10/0; v/v) to obtain 12.2 g of the title compound (pale yellow solid).

MS (ESI pos.) m/z: 283 ([M+Na]$^+$)
$^1$H-NMR (300 MHz, CDCl$_3$) δ (ppm); 1.42 & 1.46 (each-s, 9H), 2.00-2.26 (m, 1H), 2.36-2.55 (m, 1H), 2.98 & 2.99 (each-s, 3H), 3.10 & 3.16 (each-s, 3H), 3.58-3.99 (m, 2H), 4.71-4.92 (m, 1H), 5.12-5.38 (m, 1H)

Step 6-1b: Synthesis of tert-butyl (2S,4S)-2-[(dimethylamino)carbonyl]-4-hydroxypyrrolidine-1-carboxylate With 10.0 g of (4S)-1-(tert-butoxy carbonyl)-4-hydroxy-L-proline as starting material, 8.66 g of the title compound (colorless solid) was obtained by a similar method to Step 6-1a.

MS (ESI pos.) m/z: 281 ([M+Na]$^+$)
$^1$H-NMR (300 MHz, CDCl$_3$) δ (ppm); 1.42 & 1.45 (each-s, 9H), 1.91-1.99 (m, 1H), 2.17-2.35 (m, 1H), 3.02 & 3.03 (each-s, 3H), 3.16 & 3.27 (each-s, 3H), 3.48-3.56 (m, 1H), 3.64-3.86 (m, 1H), 4.26-4.37 (m, 1H), 4.66-4.84 (m, 1H), 5.28-5.83 (m, 1H)

Step 6-2b: Synthesis of tert-butyl (2S,4R)-2-[(dimethylamino)carbonyl]-4-fluoropyrrolidine-1-carboxylate With 8.54 g of the compound obtained in Step 6-1b as starting material, 7.54 g of the title compound (pale yellow solid) was obtained by a similar method to Step 6-2a.

Step 6-3: Synthesis of (4R)-4-fluoro-N,N-dimethyl-L-prolinamide trifluoroacetate With 3.50 g of the compound obtained in Step 6-2b as starting material, 7.27 g of the title compound (crude form yellow oil) was obtained by a similar method to Step 4-1. The present compound was used in the next reaction without purification.

MS (ESI pos.) m/z: 161 ([M+H]$^+$)
$^1$H-NMR (300 MHz, DMSO-d$_6$) δ (ppm); 1.97-2.21 (m, 1H), 2.68-2.87 (m, 1H), 2.92 (s, 3H), 3.02 (s, 3H), 3.37-3.62 (m, 2H), 4.72-4.85 (m, 1H), 5.36-5.60 (m, 1H), 8.83 (brs, 1H), 9.99 (brs, 1H)

Step 6-4: Synthesis of (4R)-1-[5-chloro-3-(2-methoxyphenyl)-2-oxo-2,3-dihydro-1H-indol-3-yl]-4-fluoro-N,N-dimethyl-L-prolinamide ((levorotatory isomer, and dextrorotatory isomer))

With 3.78 g of 3,5-dichloro-3-(2-methoxyphenyl)-1,3-dihydro-2H-indol-2-one and the compound obtained in Step 6-3 (13.5 mmol) as starting materials, respectively 2.06 g (Isomer A: colorless powder) and 2.74 g (Isomer B: colorless powder) of two species of diastereoisomers of the title compound were obtained by a similar method to Step 4-2.

Isomer A: [α]$_D^{29}$=+129° (c=0.578, CHCl$_3$)
MS (ESI pos.) m/z: 454 ([M+Na]$^+$), (ESI neg.) m/z: 430 ([M−H]$^-$)
$^1$H-NMR (300 MHz, DMSO-d$_6$) δ (ppm); 1.65-1.94 (m, 1H), 2.17-2.35 (m, 1H), 2.42-2.85 (m, 6H), 3.22-3.56 (m, 1H), 3.47 (s, 3H), 3.75-3.97 (m, 2H), 5.05-5.31 (m, 1H), 6.50 (s, 1H), 6.82 (d, J=8.1 Hz, 1H), 6.92 (d, J=8.2 Hz, 1H), 7.07-7.21 (m, 2H), 7.29 (t, J=7.5 Hz, 1H), 8.05 (d, J=7.5 Hz, 1H), 10.52 (s, 1H)

Isomer B: [α]$_D^{28}$=−188° (c=0.219, CHCl$_3$)
MS (ESI pos.) m/z: 454 ([M+Na]$^+$), (ESI neg.) m/z: 430 ([M−H]$^-$)
$^1$H-NMR (300 MHz, DMSO-d$_6$) δ (ppm); 1.79-1.99 (m, 1H), 2.23-2.54 (m, 7H), 2.88-3.06 (m, 1H), 3.42-3.72 (m, 1H), 3.46 (s, 3H), 4.58-4.70 (m, 1H), 5.18-5.43 (m, 1H), 6.74 (d, J=8.2 Hz, 1H), 6.83 (d, J=2.2 Hz, 1H), 6.91 (dd, J=8.2, 1.09 Hz, 1H), 6.97-7.05 (m, 1H), 7.15-7.20 (m, 1H), 7.23-7.31 (m, 1H), 7.86 (dd, J=7.7, 1.5 Hz, 1H), 10.33 (s, 1H)

Step 6-5: Synthesis of (4R)-1-[1-{[4-bromo-2-(trifluoromethoxy)phenyl]sulfonyl}-5-chloro-3-(2-methoxyphenyl)-2-oxo-2,3-dihydro-1H-indol-3-yl]-4-fluoro-N,N-dimethyl-L-prolinamide (levorotatory isomer)

From 250 mg of the compound obtained in Step 6-4 (Isomer B) and 216 mg of 4-bromo-2-(trifluoromethoxy)benzene sulfonyl chloride, 370 mg of the title compound (colorless amorphous) was obtained in by a similar method to Example 2.

$[\alpha]_D^{21}$=145° (c=0.212, CHCl$_3$)

MS (ESI pos.) m/z: 756 ([M+Na−1]$^+$), 758 ([M+Na+1]$^+$)

$^1$H-NMR (300 MHz, CDCl$_3$) δ (ppm); 1.54-5.27 (m, 15H), 6.78 (d, J=8.2 Hz, 1H), 6.94-7.09 (m, 2H), 7.21-7.30 (m, 2H), 7.49-7.56 (m, 1H), 7.61 (dd, J=8.6, 1.9 Hz, 1H), 7.81-7.95 (m, 2H), 8.20-8.37 (m, 1H)

Example 7

Synthesis of (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

From 300 mg of the compound obtained in Step 6-4 (Isomer B) and 222 mg of 4-methoxy-2-(trifluoromethoxy)benzene sulfonyl chloride, 402 mg of the title compound (colorless amorphous) was obtained by a similar method to Example 2.

$[\alpha]_D^{21}$=−342° (c=0.202, CHCl$_3$)

MS (ESI pos.) m/z: 708 ([M+Na]$^+$), (ESI neg.) m/z: 684 ([M−H]$^-$)

$^1$H-NMR (300 MHz, CDCl$_3$) δ (ppm); 1.85-5.30 (m, 9H), 2.41 (s, 3H), 2.71 (s, 3H), 3.88 (s, 3H), 6.71-7.09 (m, 5H), 7.20-7.32 (m, 2H), 7.78-7.98 (m, 1H), 7.91 (d, J=8.9 Hz, 1H), 8.23-8.44 (m, 1H)

Example 7-2

Synthesis of (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

Step 7-2-1: Synthesis of (4R)-4-fluoro-N,N-dimethyl-L-prolinamide

To a solution of 5.00 g of compound obtained in Step 6-2a or 6-2b in CHCl$_3$ (50 ml) was added TFA (15 ml) and the reaction mixture was stirred at room temperature for 2 hours. The reaction solution was concentrated under reduced pressure, then to the obtained residue was added CHCl$_3$ under ice cooling and an aqueous solution of 5% K$_2$CO$_3$ was added until the aqueous layer became basic. Liquid separation was performed, and the aqueous layer was extracted with CHCl$_3$. The combined organic layer was washed with saturated brine, dried over MgSO$_4$, then, the drying agent was separated by filtration, and the solution was concentrated under reduced pressure. The obtained residue was purified by column chromatography (silicagel 60; mobile phase: CHCl$_3$/MeOH/NH$_4$OH=10/1/0.1; v/v/v) to obtain 3.10 g of the title compound (yellow oil).

MS (ESI pos.) m/z: 161 ([M+H]$^+$)

$^1$H-NMR (300 MHz, CDCl$_3$) δ (ppm); 1.79-2.02 (m, 1H), 2.04-2.67 (m, 1H), 2.26-2.42 (m, 1H), 2.99 (s, 3H), 3.06-3.25 (m, 1H), 3.07 (s, 3H), 3.37 (ddd, J=33.0, 13.3, 4.3 Hz, 1H), 4.17 (dd, J=9.2, 6.7 Hz, 1H), 5.16-5.39 (m, 1H)

Step 7-2-2: Synthesis of 5-chloro-3-hydroxy-3-(2-methoxyphenyl)-1-{[4-methoxy-2-(trifluoromethoxy)phenyl]sulfonyl}-1,3-dihydro-2H-indol-2-one Under nitrogen atmosphere, to a solution of 5.00 g of 5-chloro-3-hydroxy-3-(2-methoxyphenyl)-1,3-dihydro-2H-indol-2-one, which is the compound described in Preparation 1.1A of brochure Publication No. WO01/5513,0 in DMF (50 ml) was added 760 mg of NaH under ice cooling, then, the reaction mixture was warmed to room temperature and stirred for 30 minutes. To the stirred solution, under cooling at −20° C., was added dropwise a solution of 5.52 g of 4-methoxy-2-(trifluoromethoxy)benzene sulfonyl chloride in DMF (10 ml) over 3 minutes, then, the solution was stirred at the same temperature for 5 hours. After warming to 0° C., to the reaction solution was added CHCl$_3$ and an aqueous solution of 5% K$_2$CO$_3$, and the solution was stirred at room temperature for 30 minutes. The liquid separation of the stirred solution was performed, then the aqueous layer was extracted with CHCl$_3$, the combined organic layer was washed with saturated brine, dried over MgSO$_4$, then, the drying agent was separated by filtration, and was solvent under reduced pressure. The obtained residue was purified by column chromatography (silicagel 60; mobile phase: EtOAc/n-hexane=1/1; v/v) to obtain 4.55 g of the title compound (orange color solid).

MS (ESI pos.) m/z: 566 ([M+Na]$^+$)

$^1$H-NMR (300 MHz, CDCl$_3$) δ (ppm); 3.65 (s, 3H), 3.89 (s, 3H), 6.78-6.95 (m, 3H), 7.02-7.09 (m, 2H), 7.28-7.37 (m, 2H), 7.68 (dd, J=7.8, 1.7 Hz, 1H), 7.90 (d, J=8.7 Hz, 1H), 8.25 (d, J=9.0 Hz, 1H)

Step 7-2-3: Synthesis of 3,5-dichloro-3-(2-methoxyphenyl)-1-{[4-methoxy-2-(trifluoromethoxy)phenyl]sulfonyl}-1,3-dihydro-2H-indol-2-one To a solution of 3.00 g of compound obtained in Step 7-2-2 in CHCl$_3$ (30 ml) was added sequentially 654 mg of Py and 984 mg of thionyl chloride under ice cooling, and the reaction mixture was stirred for 2 hours at the same temperature. The reaction solution was concentrated under reduced pressure, and the obtained residue was purified by column chromatography (silicagel 60; mobile phase: EtOAc/n-hexane=1/4; v/v) to obtain 2.63 g of the title compound (orange color solid).

MS (ESI pos.) m/z: 562 ([M+H]$^+$), (ESI neg.) m/z: 560 ([M−H]$^-$)

$^1$H-NMR (300 MHz, CDCl$_3$) δ (ppm); 3.57 (s, 3H), 3.90 (s, 3H), 6.77-6.98 (m, 4H), 7.05-7.13 (m, 1H), 7.29-7.40 (m, 2H), 7.89-7.97 (m, 2H), 8.25 (d, J=8.9 Hz, 1H)

Step 7-2-4: Synthesis of (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

Under nitrogen atmospher, To a solution of 178 mg of compound obtained in Step 7-2-1 in DMF (1.8 ml) was added 170 mg sodium bis-(trimethylsilyl) amide (38% THF solution) under ice cooling, and the reaction mixture was stirred for 15 minutes at the same temperature. Thereafter a solution of 178 mg of compound obtained in Step 7-2-3 in THF (500 µL) was added, and the solution was stirred at the same temperature for one hour, and at room temperature for 15 hours. To the reaction solution was added EtOAc and an aqueous solution of 5% K$_2$CO$_3$, and was stirred for 10 minutes. Liquid separation was performed, and the aqueous layer was extracted with EtOAc. The combined organic layer was washed in water and saturated brine, dried over MgSO$_4$, then, the drying agent was separated by filtration, and the solvent was evaporated under reduced pressure. The obtained residue was subjected to column chromatography (silicagel 60; mobile phase: EtOAc/n-hexane=1/1; v/v) to obtain a brown oil (8 mg). Among the obtained brown oil, 2.0 mg was purified by thin layer chromatography (silicagel 60F$_{254}$; 1 mm thick; mobile phase: EtOAc/n-hexane=7/3; v/v) to obtain 0.13 mg of the title compound (yellow oil).

Example 7-3

Synthesis of (4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide To a solution of 57 mg of compound obtained in Example 7-2-1 in DMF (1.5 ml) was added 50 mg of the compound 3,5-dichloro-3-(2-methoxyphenyl)-1-{[4-methoxy-2-(trifluoromethoxy)phenyl]sulfonyl}-1,3-dihydro-2H-indol-2-one obtained in Example 7-2-3 and 41 mg of silver oxide, and the solution was stirred for 2 hours at 110° C. under microwave irradiation. The reaction solution was filtered, then, the solvent was evaporated from filtrate under reduced pressure. The residue was separated and purified by column chromatography (silicagel 60; mobile phase: MeOH/CHCl$_3$=1/9: v/v) to obtain 3.9 mg (Isomer A: colorless amorphous) and 1.7 mg (Isomer B: colorless amorphous) of each of the isomers of the title compound.

Example 8

Synthesis of (4R)-1-(5-chloro-3-(2-methoxyphenyl)-1-{[2-methoxy-4-(trifluoromethoxy)phenyl]sulfonyl}-2-oxo-2,3-dihydro-1H-indol-3-yl)-4-fluoro-N,N-dimethyl-L-prolinamide (levorotatory isomer)

With 500 mg of the compound obtained in Step 6-4 (Isomer B) and 404 mg of 2-methoxy-4-(trifluoromethoxy)benzene sulfonyl chloride as starting materials, 658 mg of the title compound (colorless amorphous) was obtained by a similar method to Example 1.

$[\alpha]_D^{21}$=−367° (c=0.212, CHCl$_3$)

MS (ESI pos.) m/z: 708 ([M+Na]$^+$), (ESI neg.) m/z: 684 ([M−H]$^-$)

$^1$H-NMR (300 MHz, CDCl$_3$) δ (ppm); 1.51-3.98 (m, 7H), 2.35 (s, 3H), 2.75 (s, 3H), 3.71 (s, 3H), 4.73-4.98 (m, 1H), 5.08-5.37 (m, 1H), 6.74-6.83 (m, 2H), 6.93-7.12 (m, 3H), 7.21-7.32 (m, 2H), 7.79 (d, J=7.3 Hz, 1H), 7.90 (d, J=8.9 Hz, 1H), 8.28 (d, J=8.7 Hz, 1H)

Example 9

Synthesis of (4R)-1-[1-{[2,5-bis (2,2,2-trifluoroethoxy)phenyl]sulfonyl}-5-chloro-3-(2-methoxyphenyl)-2-oxo-2,3-dihydro-1H-indol-3-yl]-4-fluoro-N,N-dimethyl-L-prolinamide (levorotatory isomer)

With 100 mg of the compound obtained in Step 6-4 and 91 mg of 2,5-bis (2,2,2-trifluoroethoxy)benzene sulfonyl chloride as starting material, 106 mg of the title compound (colorless amorphous) was obtained by a similar method to Example 2.

$[\alpha]_D^{22}$=149° (c=0.213, CHCl$_3$)

MS (ESI pos.) m/z: 768 ([M+H]$^+$), (ESI neg.) m/z: 766 ([M−H]$^-$)

$^1$H-NMR (300 MHz, CDCl$_3$) δ (ppm); 1.37-4.94 (m, 18H), 5.05-5.43 (m, 1H), 6.71-7.09 (m, 4H), 7.16-7.38 (m, 3H), 7.70-7.96 (m, 3H)

Example 10

Synthesis of 3-[(2S)-2-(azetidin-1-ylcarbonyl)-4-fluoropyrrolidin-1-yl]-5-chloro-3-(2-methoxyphenyl)-1-{[4-methoxy-2-(trifluoromethoxy)phenyl]sulfonyl}-1,3-dihydro-2H-indol-2-one (levorotatory isomer)

Step 10-1: Synthesis of tert-butyl (2S,4S)-2-(azetidin-1-ylcarbonyl)-4-hydroxypyrrolidine-1-carboxylate To a solution of 2.50 g of (4S)-1-(tert-butoxy carbonyl)-4-hydroxy-L-proline in DMF (25 ml) was added 2.19 g of HOBt/H$_2$O and 2.49 g of EDC/HCl under ice cooling, and the reaction mixture was stirred for 30 minutes. To the reaction mixture was added dropwise 1.23 g of trimethylene imine over 1 minute, then, the mixture was stirred at room temperature for 16 hours. To the reaction solution was added EtOAc and an aqueous solution of 5% K$_2$CO$_3$, and the resulting mixture was stirred for 30 minutes. Liquid separation of the stirred solution was performed, the aqueous layer was extracted with EtOAc, the combined organic layer was washed with water and with saturated brine, dried over MgSO$_4$, then, the drying agent was separated by filtration, and the solution was concentrated under reduced pressure. The residue was purified by column chromatography (silicagel 60; mobile phase: EtOAc) to obtain 2.81 g of the title compound (pale yellow solid).

MS (ESI pos.) m/z: 293 ([M+Na]$^+$)

$^1$H-NMR (300 MHz, CDCl$_3$) δ (ppm); 1.44-1.51 (m, 9H), 1.92-2.01 (m, 1H), 2.13-2.43 (m, 3H), 3.42-3.52 (m, 1H), 3.60-3.83 (m, 1H), 3.97-4.81 (m, 7H)

Step 10-2: Synthesis of tert-butyl (2S)-2-(azetidin-1-ylcarbonyl)-4-fluoropyrrolidine-1-carboxylate With 2.71 g of compound obtained at Step 10-1 as starting material, 2.30 g of the title compound (colorless oil) was obtained by a similar method to Step 6-2a.

MS (ESI pos.) m/z: 295 ([M+Na]$^+$)

$^1$H-NMR (300 MHz, CDCl$_3$) δ (ppm); 1.35-1.52 (m, 9H), 2.02-2.50 (m, 4H), 3.54-4.65 (m, 7H), 5.09-5.35 (m, 1H)

Step 10-3: Synthesis of (2S)-2-(azetidin-1-ylcarbonyl)-4-fluoropyrrolidine trifluoroacetate With 2.20 g of the compound obtained in Step 10-2 as starting material, 3.82 g of the title compound (crude form pale yellow oil) was obtained by a similar method to Step 4-1. The present compound was used in the next reaction without purification.

MS (ESI pos.) m/z: 173 ([M+H]$^+$)

$^1$H-NMR (300 MHz, DMSO-d$_6$) δ (ppm); 1.97-2.36 (m, 3H), 2.48-2.75 (m, 1H), 3.37-3.66 (m, 2H), 3.89-4.07 (m, 2H), 4.14-4.50 (m, 3H), 5.38-5.61 (m, 1H)

Step 10-4: Synthesis of 3-[(2S)-2-(azetidin-1-ylcarbonyl)-4-fluoropyrrolidin-1-yl]-5-chloro-3-(2-methoxyphenyl)-1,3-dihydro-2H-indol-2-one ((levorotatory isomer, and dextrorotatory isomer))

With 2.37 g of 3,5-dichloro-3-(2-methoxyphenyl)-1,3-dihydro-2H-indol-2-one and the compound obtained in Step 10-3 (3.82 g, crude form) as starting materials, respectively 874 mg (Isomer A: colorless solid) and 1.45 g (Isomer B:

colorless amorphous) of two species of diastereoisomers of the title compound were obtained by a similar method to Step 4-2.

Isomer A: $[\alpha]_D^{29}$=+168° (c=0.205, CHCl$_3$)
MS (ESI pos.) m/z: 444 ([M+H]$^+$), (ESI neg.) m/z: 442 ([M−H]$^-$)
$^1$H-NMR (300 MHz, DMSO-d$_6$) δ (ppm); 1.67-2.30 (m, 4H), 3.13-3.73 (m, 5H), 3.48 (s, 3H), 3.78-4.02 (m, 2H), 5.02-5.27 (m, 1H), 6.59 (d, J=2.2 Hz, 1H), 6.87 (d, J=8.2 Hz, 1H), 6.93 (dd, J=8.2, 1.1 Hz, 1H), 7.11 (dt, J=7.5, 1.2 Hz, 1H), 7.23-7.33 (m, 2H), 7.98 (dd, J=7.6, 1.7 Hz, 1H), 10.54 (s, 1H)

Isomer B: $[\alpha]_D^{28}$=−137° (c=0.223, CHCl$_3$)
MS (ESI pos.) m/z: 466 ([M+Na]$^+$), (ESI neg.) m/z: 442 ([M−H]$^-$)
$^1$H-NMR (300 MHz, DMSO-d$_6$) δ (ppm); 1.70-2.06 (m, 3H), 2.16-2.38 (m, 1H), 2.82-3.02 (m, 1H), 3.05-3.15 (m, 1H), 3.41-3.72 (m, 3H), 3.48 (s, 3H), 3.74-3.86 (m, 1H), 4.08-4.23 (m, 1H), 5.17-5.42 (m, 1H), 6.81-6.87 (m, 2H), 6.91-6.97 (m, 1H), 7.02-7.09 (m, 1H), 7.22-7.34 (m, 2H), 7.83 (dd, J=7.8, 1.7 Hz, 1H), 10.40 (s, 1H)

Step 10-5: Synthesis of 3-[(2S)-2-(azetidin-1-ylcarbonyl)-4-fluoropyrrolidin-1-yl]-5-chloro-3-(2-methoxyphenyl)-1-{[4-methoxy-2-(trifluoromethoxy)phenyl]sulfonyl}-1,3-dihydro-2H-indol-2-one (levorotatory isomer)

With 500 mg of the compound obtained in Step 10-4 (Isomer B) and 360 mg of 4-methoxy-2-(trifluoromethoxy)benzene sulfonyl chloride as starting materials, 642 mg of the title compound (colorless amorphous) was obtained by a similar method to Example 2.

$[\alpha]_D^{21}$=−320° (c=0.220, CHCl$_3$)
MS (ESI pos.) m/z: 720 ([M+Na]$^+$), (ESI neg.) m/z: 696 ([M−H]$^-$)
$^1$H-NMR (300 MHz, CDCl$_3$) δ (ppm); 1.44-4.57 (m, 14H), 3.88 (s, 3H), 4.98-5.27 (m, 1H), 6.76-6.88 (m, 2H), 6.91 (dd, J=9.0, 2.3 Hz, 1H), 6.99-7.15 (m, 2H), 7.22-7.35 (m, 2H), 7.87-7.98 (m, 2H), 8.22-8.39 (m, 1H)

Example 11

Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-N-ethyl-4-fluoro-L-prolinamide (levorotatory isomer)

Step 11-1: Synthesis of 1-benzyl 2-methyl (2S)-4-fluoropyrrolidine-1,2-dicarboxylate With 5.33 g of 1-benzyl 2-methyl (2S,4S)-4-hydroxypyrrolidine-1,2-dicarboxylate as starting material, 1.50 g of the title compound (colorless oil) was obtained by a similar method to Step 6-2a.

MS (ESI pos.) m/z: 304 ([M+Na]$^+$)
$^1$H-NMR (300 MHz, CDCl$_3$) δ (ppm); 2.00-2.26 (m, 1H), 2.37-2.71 (m, 1H), 3.48-3.80 (m, 4H), 3.83-4.09 (m, 1H), 4.46-4.59 (m, 1H), 5.00-5.52 (m, 3H), 7.26-7.44 (m, 5H)

Step 11-2: Synthesis of 1-[(benzyl oxy)carbonyl]-4-fluoro-L-proline

To a solution of 1.45 g of the compound obtained in Step 11-1 in MeOH (15 ml) was added an aqueous solution of 2 mol/L NaOH (3.6 ml) under ice cooling, and the reaction mixture was stirred at room temperature for 4 hours. MeOH was evaporated under reduced pressure, EtOAc was added, then, the resulting mixture was adjusted to pH=2 with 1 mol/L hydrochloric acid under ice cooling. Liquid separation of the PH-adjusted solution was performed, the aqueous layer was extracted with EtOAc, the combined organic layer was washed with saturated brine, dried over Na$_2$SO$_4$, then, the drying agent was separated by filtration, and the solvent was evaporated under reduced pressure to obtain 1.98 g of pale yellow oil. The obtained residue was subjected to column chromatography (silicagel 60; mobile phase: EtOAc) to obtain 1.46 g of the title compound (pale yellow oil).

MS (ESI pos.) m/z: 290 ([M+H]$^+$)
$^1$H-NMR (300 MHz, CDCl$_3$) δ (ppm); 2.21-2.47 (m, 1H), 2.55-2.79 (m, 1H), 3.51-3.76 (m, 1H), 3.91-4.15 (m, 1H), 4.41-4.65 (m, 1H), 5.08-5.36 (m, 3H), 6.89-7.47 (m, 6H)

Step 11-3: Synthesis of benzyl(2S)-2-[(ethyl amino)carbonyl]-4-fluoropyrrolidine-1-carboxylate With 3.02 g of the compound obtained in Step 11-2 and 1.16 g of an aqueous solution of 70% ethyl amine as starting material, 1.92 g of the title compound (colorless solid) was obtained by a similar method to Step 10-1.

MS (ESI pos.) m/z: 317 ([M+Na]$^+$)
$^1$H-NMR (300 MHz, CDCl$_3$) δ (ppm); 0.81%-1.30 (m, 3H), 2.12-2.76 (m, 2H), 3.01-3.69 (m, 3H), 3.92-4.52 (m, 2H), 4.97-5.35 (m, 3H), 5.62-6.80 (m, 1H), 7.23-7.45 (m, 5H)

Step 11-4: Synthesis of N-ethyl-4-fluoro-L-prolinamide

Under hydrogen atmosphere, a suspension of 1.80 g of the compound obtained in Step 11-3 and 360 mg of 10% palladium-carbon in MeOH (36 ml) was stirred at room temperature for 3 hours. From the stirred solution, insoluble matter was separated by filtration, the solution was concentrated under reduced pressure to obtain 1.07 g of the title compound. The present compound was used in the next reaction without purification.

MS (ESI pos.) m/z: 183 ([M+Na]$^+$)
$^1$H-NMR (300 MHz, CDCl$_3$) δ (ppm); 1.14 (t, J=7.2 Hz, 3H), 1.93-2.18 (m, 1H), 2.26-2.87 (m, 3H), 3.17-3.38 (m, 3H), 3.98 (q, J=8.6 Hz, 1H), 5.07-5.30 (m, 1H), 7.56 (s, 1H)

Step 11-5: Synthesis of 1-[5-chloro-3-(2-methoxyphenyl)-2-oxo-2,3-dihydro-1H-indol-3-yl]-N-ethyl-4-fluoro-L-prolinamide ((levorotatory isomer, and dextrorotatory isomer))

With 1.02 g of 3,5-dichloro-3-(2-methoxyphenyl)-1,3-dihydro-2H-indol-2-one and 530 mg of the compound obtained in Step 11-4 as starting materials, respectively 708 mg (Isomer A: colorless amorphous) and 501 mg (Isomer B: colorless amorphous) of two species of diastereoisomers of the title compound were obtained by a similar method to Step 4-2.

Isomer A: $[\alpha]_D^{25}$=−171° (c=0.200, CHCl$_3$)
MS (ESI pos.) m/z: 432 ([M+H]$^+$), 454 ([M+Na]$^+$), (ESI neg.) m/z: 430 ([M−H]$^-$)
$^1$H-NMR (300 MHz, DMSO-d$_6$) δ (ppm); 0.85 (t, J=7.2 Hz, 3H), 1.86-2.06 (m, 1H), 2.16-2.41 (m, 1H), 2.72-2.95 (m, 3H), 3.38-3.58 (m, 4H), 4.07 (dd, J=8.6, 4.5 Hz, 1H), 5.09-5.39 (m, 1H), 6.71-6.85 (m, 2H), 6.89-7.19 (m, 3H), 7.21-7.32 (m, 1H), 7.39 (s, 1H), 7.76 (dd, J=7.7, 1.6 Hz, 1H), 10.41 (s, 1H)

Isomer B: $[\alpha]_D^{25}$=+54° (c=0.224, CHCl$_3$)
MS (ESI pos.) m/z: 454 ([M+Na]$^+$), (ESI neg.) m/z: 430 ([M−H]$^-$)

¹H-NMR (300 MHz, DMSO-d₆) δ (ppm); 0.89-0.98 (t, J=7.0 Hz, 3H), 1.71-1.96 (m, 1H), 2.08-2.28 (m, 1H), 2.80-2.94 (m, 2H), 3.20-3.55 (m, 5H), 3.74-3.91 (m, 1H), 4.98-5.25 (m, 1H), 6.53 (d, J=2.2 Hz, 1H), 6.73 (d, J=8.2 Hz, 1H), 6.92 (dd, J=8.2, 1.0 Hz, 1H), 7.06-7.15 (m, 2H), 7.25-7.35 (m, 1H), 7.47-7.55 (m, 1H), 8.13 (dd, J=7.8, 1.7 Hz, 1H), 10.50 (s, 1H)

Step 11-6: Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-N-ethyl-4-fluoro-L-prolinamide (levorotatory isomer)

With 200 mg of the compound obtained in Step 11-5 (Isomer B) and 150 mg of 4-methoxy-2-(trifluoromethoxy)benzene sulfonyl chloride as starting materials, 179 mg of the title compound (colorless amorphous) was obtained by a similar method to Example 2.

$[α]_D^{25}$=−190° (c=0.206, CHCl₃)
MS (ESI pos.) m/z: 686 ([M+H]⁺), (ESI neg.) m/z: 684 ([M−H]⁻)
¹H-NMR (300 MHz, CDCl₃) δ (ppm); 0.85 (t, J=7.2 Hz, 3H), 2.11-2.34 (m, 2H), 2.66-2.95 (m, 3H), 3.23-3.59 (m, 4H), 3.88-4.05 (m, 4H), 4.94-5.22 (m, 1H), 6.00-6.12 (m, 1H), 6.77 (d, J=8.4 Hz, 1H), 6.85-7.09 (m, 4H), 7.20-7.32 (m, 2H), 7.72-7.80 (m, 1H), 7.89 (d, J=8.6 Hz, 1H), 8.28-8.35 (m, 1H)

Example 12

Synthesis of tert-butyl 1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-L-prolinate (levorotatory isomer)

Step 12-1: Synthesis of 1-benzyl 2-tert-butyl (2S)-4-fluoropyrrolidine-1,2-dicarboxylate A solution of 1.40 g of the compound obtained in Step 11-2, 4.57 g of (Boc)₂O and 192 mg of DMAP in tert-butyl alcohol (28 ml) was stirred at room temperature for 16 hours. The reaction solution was concentrated under reduced pressure, then, the obtained residue was purified by column chromatography (silicagel 60; mobile phase: EtOAc/n-hexane=1/4; v/v) to obtain 1.35 g of the title compound (colorless oil).

MS (ESI pos.) m/z: 346 ([M+Na]⁺)
¹H-NMR (300 MHz, CDCl₃) δ (ppm); 1.29-1.51 (m, 9H), 1.96-2.23 (m, 1H), 2.51-2.71 (m, 1H), 3.55-3.76 (m, 1H), 3.83-4.09 (m, 1H), 4.41 (q, J=8.3 Hz, 1H), 5.08-5.33 (m, 3H), 7.24-7.40 (m, 5H)

Step 12-2: Synthesis of tert-butyl 4-fluoro-L-prolinate

With 1.25 g of the compound obtained in Step 12-1 as starting material, 704 mg of the title compound (colorless oil) was obtained by a similar method to Step 11-4. The present compound was used in the next reaction without purification.

MS (ESI pos.) m/z: 190 ([M+H]⁺)
¹H-NMR (300 MHz, CDCl₃) δ (ppm); 1.47 (s, 9H), 1.86-2.18 (m, 2H), 2.31-2.49 (m, 1H), 3.10-3.29 (m, 2H), 3.90 (t, J=7.9 Hz, 1H), 5.10-5.34 (m, 1H)

Step 12-3: Synthesis of tert-butyl 1-[5-chloro-3-(2-methoxyphenyl)-2-oxo-2,3-dihydro-1H-indol-3-yl]-4-fluoro-L-prolinate ((levorotatory isomer, and dextrorotatory isomer))

With 1.06 g of 3,5-dichloro-3-(2-methoxyphenyl)-1,3-dihydro-2H-indol-2-one and 685 mg of the compound obtained in Step 12-2 as starting materials, respectively 678 mg (Isomer A: colorless solid) and 839 mg (Isomer B: colorless amorphous) of two species of diastereoisomers of the title compound were obtained by a similar method to Step 4-2.

Isomer A: $[α]_D^{29}$=+75.7° (c=0.228, CHCl₃)
MS (ESI pos.) m/z: 483 ([M+Na]⁺), (ESI neg.) m/z: 459 ([M−H]⁻)
¹H-NMR (300 MHz, CDCl₃) δ (ppm); 1.29 (s, 9H), 1.84-2.06 (m, 1H), 2.33-2.49 (m, 1H), 3.40-3.65 (m, 2H), 3.56 (s, 3H), 3.95-4.11 (m, 1H), 5.02-5.26 (m, 1H), 6.73-6.84 (m, 3H), 7.08-7.15 (m, 2H), 7.25-7.32 (m, 1H), 8.03 (s, 1H), 8.12 (dd, J=7.7, 1.8 Hz, 1H)

Isomer B: $[α]_D^{28}$=−169° (c=0.197, CHCl₃)
MS (ESI pos.) m/z: 483 ([M+Na]⁺), (ESI neg.) m/z: 459 ([M−H]⁻)
¹H-NMR (300 MHz, CDCl₃) δ (ppm); 1.29 (s, 9H), 1.95-2.19 (m, 1H), 2.42-2.65 (m, 1H), 3.17-3.39 (m, 1H), 3.49-3.70 (m, 1H), 3.58 (s, 3H), 4.10-4.23 (m, 1H), 5.14-5.39 (m, 1H), 6.72 (d, J=8.2 Hz, 1H), 6.81 (dd, J=8.2, 1.0 Hz, 1H), 6.92 (d, J=2.0 Hz, 1H), 7.01-7.09 (m, 1H), 7.14 (dd, J=8.2, 2.2 Hz, 1H), 7.23-7.39 (m, 2H), 7.91 (dd, J=7.7, 1.8 Hz, 1H)

Step 12-4: Synthesis of tert-butyl 1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-L-prolinate (levorotatory isomer)

From 500 mg of the compound obtained in Step 12-3 (Isomer A) and 139 mg of 4-methoxy-2-(trifluoromethoxy)benzene sulfonyl chloride, 264 mg of the title compound (colorless amorphous) was obtained by a similar method to Example 2.

$[α]_D^{28}$=−485° (c=0.224, CHCl₃)
MS (ESI pos.) m/z: 715 ([M+H]⁺)
¹H-NMR (300 MHz, CDCl₃) δ (ppm) 1.28 (s, 9H), 1.66-1.91 (m, 1H), 2.05-2.23 (m, 1H), 3.22-3.44 (m, 1H), 3.48 (dd, J=9.6, 7.4 Hz, 1H), 3.57 (s, 3H), 3.64-3.81 (m, 1H), 3.89 (s, 3H), 4.75-4.99 (m, 1H), 6.78 (dd, J=8.2, 1.0 Hz, 1H), 6.83-6.94 (m, 3H), 7.04-7.12 (m, 1H), 7.21-7.32 (m, 2H), 7.93 (d, J=8.7 Hz, 1H), 8.03 (dd, J=7.8, 1.7 Hz, 1H), 8.28 (d, J=8.9 Hz, 1H)

Example 13

Synthesis of (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-D-prolinamide (levorotatory isomer)

Step 13-1: Synthesis of tert-butyl (2R,4S)-2-[(dimethylamino)carbonyl]-4-hydroxypyrrolidine-1-carboxylate With 2.50 g of (4S)-1-(tert-butoxy carbonyl)-4-hydroxy-D-proline as starting material, 2.74 g of the title compound (pale yellow solid) was obtained by a similar method to Step 6-1a.

MS (ESI pos.) m/z: 281 ([M+Na]⁺)
¹H-NMR (300 MHz, CDCl₃) δ (ppm); 1.39-1.48 (m, 9H), 1.95 (d, J=13.8 Hz, 1H), 2.17-2.34 (m, 1H), 2.88-3.29 (m, 6H), 3.48-3.56 (m, 1H), 3.64-3.86 (m, 1H), 4.32 (q, J=4.8 Hz, 1H), 4.66-4.83 (m, 1H)

Step 13-2: Synthesis of tert-butyl (2R,4S)-2-[(dimethylamino)carbonyl]-4-fluoropyrrolidine-1-carboxylate With 2.64 g of the compound obtained at Step 13-1 as starting material, 2.17 g of the title compound (colorless solid) was obtained by a similar method to Step 6-2a.
MS (ESI pos.) m/z: 283 ([M+Na]$^+$)
$^1$H-NMR (300 MHz, CDCl$_3$) δ (ppm); 1.39-1.50 (m, 9H), 2.00-2.29 (m, 1H), 2.36-2.55 (m, 1H), 2.95-3.18 (m, 6H), 3.58-3.98 (m, 2H), 4.71-4.90 (m, 1H), 5.12-5.36 (m, 1H)

Step 13-3: Synthesis of (4S)-4-fluoro-N,N-dimethyl-D-prolinamide trifluoroacetate With 2.09 g of the compound obtained in Step 13-2 as starting material, 3.42 g of the title compound (crude form pale yellow oil) was obtained by a similar method to Step 4-1. The present compound was used in the next reaction without purification.
MS (ESI pos.) m/z: 161 ([M+H]$^+$)
$^1$H-NMR (300 MHz, DMSO-d$_6$) δ (ppm); 1.96-2.22 (m, 1H), 2.67-2.88 (m, 1H), 2.92 (s, 3H), 3.02 (s, 3H), 3.38-3.66 (m, 2H), 4.74-4.88 (m, 1H), 5.36-5.61 (m, 1H), 8.84 (s, 1H), 10.15 (s, 1H)

Step 13-4: Synthesis of (4S)-1-[5-chloro-3-(2-methoxyphenyl)-2-oxo-2,3-dihydro-1H-indol-3-yl]-4-fluoro-N,N-dimethyl-D-prolinamide ((levorotatory isomer, and dextrorotatory isomer))

With 2.36 g of 3,5-dichloro-3-(2-methoxyphenyl)-1,3-dihydro-2H-indol-2-one and 3.30 g of the compound obtained in Step 13-3 as starting materials, respectively 874 mg (Isomer A: colorless solid) and 1.80 g (Isomer B: colorless solid) of two species of diastereoisomers of the title compound were obtained by a similar method to Step 4-2.
Isomer A: [α]$_D^{29}$=-128° (c=0.227, CHCl$_3$)
MS (ESI pos.) m/z: 454 ([M+Na]$^+$), (ESI neg.) m/z: 430 ([M-H]$^-$)
$^1$H-NMR (300 MHz, DMSO-d$_6$) δ (ppm); 1.65-1.90 (m, 1H), 2.16-2.34 (m, 1H), 2.43-2.61 (m, 6H), 3.22-3.34 (m, 1H), 3.32 (s, 3H), 3.77-3.96 (m, 2H), 5.05-5.29 (m, 1H), 6.49 (d, J=2.3 Hz, 1H), 6.81 (d, J=8.2 Hz, 1H), 6.92 (dd, J=8.2, 0.9 Hz, 1H), 7.07-7.15 (m, 1H), 7.18 (dd, J=8.3, 2.3 Hz, 1H), 7.25-7.33 (m, 1H), 8.05 (dd, J=7.8, 1.7 Hz, 1H), 10.51 (s, 1H)
Isomer B: [α]$_D^{28}$=+188° (c=0.215, CHCl$_3$)
MS (ESI pos.) m/z: 454 ([M+Na]$^+$), (ESI neg.) m/z: 430 ([M-H]$^-$)
$^1$H-NMR (300 MHz, DMSO-d$_6$) δ (ppm); 1.79-2.00 (m, 1H), 2.21-2.77 (m, 7H), 2.86-3.08 (m, 1H), 3.38-3.85 (m, 1H), 3.46 (s, 3H), 4.57-4.69 (m, 1H), 5.18-5.43 (m, 1H), 6.74 (d, J=8.2 Hz, 1H), 6.83 (d, J=2.2 Hz, 1H), 6.89-6.94 (m, 1H), 6.97-7.06 (m, 1H), 7.14-7.20 (m, 1H), 7.23-7.31 (m, 1H), 7.86 (dd, J=7.7, 1.6 Hz, 1H), 10.32 (s, 1H)

Step 13-5: Synthesis of (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-D-prolinamide (levorotatory isomer)

With 200 mg of the compound obtained in Step 13-4 (Isomer A) and 148 mg of 4-methoxy-2-(trifluoromethoxy)benzene sulfonyl chloride as starting materials, 274 mg of the title compound (colorless amorphous) was obtained by a similar method to Example 2.
[α]$_D^{21}$=-75° (c=0.208, CHCl$_3$)
MS (ESI pos.) m/z: 708 ([M+Na]$^+$), (ESI neg.) m/z: 684 ([M-H]$^-$)
$^1$H-NMR (300 MHz, CDCl$_3$) δ (ppm); 1.22-3.06 (m, 7H), 2.38 (s, 3H), 2.82 (s, 3H), 3.61 (s, 3H), 3.91 (s, 3H), 4.55-4.72 (m, 1H), 6.72-6.99 (m, 4H), 7.09-7.28 (m, 3H), 7.81 (dd, J=7.8, 1.4 Hz, 1H), 7.87 (d, J=8.9 Hz, 1H), 8.33 (d, J=9.0 Hz, 1H)

Example 14

Synthesis of (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

Step 14-1: Synthesis of 1-tert-butyl 2-methyl (2S,4S)-4-fluoropyrrolidine-1,2-dicarboxylate With 30.0 g of 1-tert-butyl 2-methyl (2S,4R)-4-hydroxypyrrolidine-1,2-dicarboxylate as starting material, 34.6 g of the title compound (colorless oil) was obtained by a similar method to Step 6-2a.
MS (ESI pos.) m/z: 270 ([M+Na]$^+$)
$^1$H-NMR (200 MHz, DMSO-d$_6$) δ (ppm); 1.35 & 1.41 (each-s, 9H), 2.13-2.76 (m, 2H), 3.19-3.74 (m, 5H), 4.33-4.45 (m, 1H), 5.13-5.39 (m, 1H)

Step 14-2: Synthesis of (4S)-1-(tert-butoxy carbonyl)-4-fluoro-L-proline

To an aqueous solution of 2 mol/L NaOH (86 ml) was added dropwise under ice cooling a solution of 30.2 g of the compound obtained in Step 14-1 in MeOH (181 ml) under stirring over 60 minute, then the reaction mixture was stirred at room temperature for 16 hours. MeOH was evaporated under reduced pressure, to the solution was added toluene and stirred, then the aqueous layer was separated and the solution was stirred under ice cooling. To the solution was added dropwise 2 mol/L hydrochloric acid over 40 minutes, then extracted with EtOAc, the combined organic layer was washed with saturated brine, dried over Na$_2$SO$_4$, then, the drying agent was separated by filtration, and the solvent was evaporated under reduced pressure to obtain 25.1 g of a colorless solid. IPE (91 ml) was added, the suspension was stirred for 2 hours at room temperature, then, crystals were collected by filtration as 20.2 g of the title compound (colorless solid). The filtrate was concentrated under reduced pressure, IPE (9 ml) was added, stirred for 2 hours at room temperature, then, crystals were collected by filtration to 540 mg of the title compound (colorless solid).
MS (ESI neg.) m/z: 232 ([M-H]$^-$)
$^1$H-NMR (300 MHz, DMSO-d$_6$) δ (ppm); 1.36 & 1.41 (each-s, 9H) 2.13-2.63 (m, 2H), 3.29-3.71 (m, 2H), 4.28 (t, J=9.1 Hz, 1H), 5.13-5.39 (m, 1H) 12.55 (brs, 1H)

Step 14-3: Synthesis of tert-butyl (2S,4S)-2-[(dimethylamino)carbonyl]-4-fluoropyrrolidine-1-carboxylate With 19.9 g of the compound obtained in Step 14-2 as starting material, 20.5 g of the title compound (colorless solid) was obtained by a similar method to Step 6-1a.
MS (ESI pos.) m/z: 283 ([M+Na]$^+$)

¹H-NMR (300 MHz, DMSO-d₆) δ (ppm); 1.31 & 1.39 (each-s, 9H), 1.93-2.10 (m, 1H), 2.40-2.71 (m, 1H), 2.81 & 2.83 (each-s, 3H), 2.97 (s, 3H), 3.42-3.79 (m, 2H), 4.59-4.71 (m, 1H), 5.10-5.37 (m, 1H)

Step 14-4: Synthesis of (4S)-4-fluoro-N,N-dimethyl-L-prolinamide trifluoroacetate With 5.98 g of the compound obtained in Step 14-3 as starting material, 12.1 g of the title compound (crude form colorless oil) was obtained by a similar method to Step 4-1. The present compound was used in the next reaction without purification.

MS (ESI pos.) m/z: 161 ([M+H]⁺), 183 ([M+Na]⁺)
¹H-NMR (300 MHz, DMSO-d₆) δ (ppm); 2.12-2.30 (m, 1H), 2.68-3.02 (m, 1H), 2.93 (s, 3H), 2.98 (s, 3H), 3.27-3.53 (m, 1H), 3.59-3.77 (m, 1H), 4.67-4.81 (m, 1H), 5.32-5.55 (m, 1H), 8.83 (brs, 1H), 10.19 (brs, 1H)

Step 14-5: Synthesis of (4S)-1-[5-chloro-3-(2-methoxyphenyl)-2-oxo-2,3-dihydro-1H-indol-3-yl]-4-fluoro-N,N-dimethyl-L-prolinamide ((levorotatory isomer, and dextrorotatory isomer))

Under nitrogen atmosphere, to a solution of 6.44 g of 3,5-dichloro-3-(2-methoxyphenyl)-1,3-dihydro-2H-indol-2-one and the compound obtained in Step 14-4 (23.0 mmol crude form) in CHCl₃ was added 12.7 g of Et₃N under ice cooling, then, the reaction mixture was stirred for 24 hours at room temperature. While stirring, the reaction solution was poured into an aqueous solution of 5% K₂CO₃ and the resulting mixture was extracted with CHCl₃. The combined organic layer was washed with saturated brine, dried over MgSO₄, then, the drying agent was separated by filtration, the solvent was evaporated under reduced pressure to obtain 12.2 g of residue (brown solid). The obtained residue was suspended in a CHCl₃:MeOH=1:1 (v/v) mixed solvent and the insoluble matter was collected as the title compound by filtration (Isomer B; colorless powder; 3.64 g). The filtrate was concentrated, and the obtained residue was purified by column chromatography (first time: silicagel 60; mobile phase: EtOAc/n-hexane=1/3 to 10/0; v/v, second time: Chromatorex NH; mobile phase: CHCl₃/MeOH=13/1; v/v) to obtain the title compound (Isomer A; colorless powder; 340 mg).

Isomer A: $[\alpha]_D^{29}$=+32° (c=0.224, MeOH)
MS (ESI pos.) m/z: 454 ([M+Na]⁺), (ESI neg.) m/z: 430 ([M−H]⁻)
¹H-NMR (300 MHz, CDCl₃) δ (ppm); 2.03-2.24 (m, 1H), 2.60-2.95 (m, 1H), 2.70 (s, 3H), 3.23 (s, 3H), 3.42-3.84 (m, 3H), 3.58 (s, 3H), 5.01-5.28 (m, 1H), 6.75 (d, J=8.2 Hz, 1H), 6.79-6.91 (m, 2H), 7.07-7.20 (m, 2H), 7.23-7.33 (m, 1H), 8.00 (d, J=7.5 Hz, 1H), 9.54 (brs, 1H)

Isomer B: $[\alpha]_D^{28}$=−198° (c=0.733, DMF)
MS (ESI pos.) m/z: 454 ([M+Na]⁺), (ESI neg.) m/z: 430 ([M−H]⁻)
¹H-NMR (300 MHz, DMSO-d₆) δ (ppm); 1.67-1.84 (m, 1H), 2.20-3.55 (m, 3H), 2.56 (s, 3H), 2.57 (s, 3H), 3.48 (s, 3H), 4.49-4.58 (m, 1H), 5.12-5.40 (m, 1H), 6.77 (d, J=8.2 Hz, 1H), 6.81 (d, J=2.0 Hz, 1H), 6.93 (dd, J=8.2, 1.1 Hz, 1H), 6.97-7.05 (m, 1H), 7.18 (dd, J=8.3, 2.3 Hz, 1H), 7.23-7.31 (m, 1H), 7.60-7.70 (m, 1H), 10.44 (brs, 1H)

Step 14-6: Synthesis of (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

From 300 mg of the compound obtained in Step 14-5 (Isomer B) and 222 mg of 4-methoxy-2-(trifluoromethoxy) benzene sulfonyl chloride as starting materials, 420 mg of the title compound (colorless amorphous) was obtained by a similar method to Example 2.

$[\alpha]_D^{21}$=−809° (c=0.224, CHCl₃)
MS (ESI pos.) m/z: 685 ([M+Na]⁺)
¹H-NMR (300 MHz, CDCl₃) δ (ppm); 1.65-2.29 (m, 2H), 2.43-2.98 (m, 1H), 2.50 (s, 3H), 2.84 (s, 3H), 3.22-3.44 (m, 1H), 3.58 (s, 3H), 3.91 (s, 3H), 4.42-4.88 (m, 2H), 6.76 (d, J=8.1 Hz, 1H), 6.87-6.92 (m, 1H), 6.93-7.04 (m, 2H), 7.14 (brs, 1H), 7.21-7.30 (m, 2H), 7.80-7.98 (m, 1H), 7.87 (d, J=8.9 Hz, 1H), 8.32 (d, J=9.0 Hz, 1H)

Example 15

Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-4,4-difluoro-N,N-dimethyl-L-prolinamide (levorotatory isomer)

Step 15-1: Synthesis of 1-tert-butyl 2-methyl (2S)-4-oxo pyrrolidine-1,2-dicarboxylate A solution of 150 g of 1-tert-butyl 2-methyl (2S,4R)-4-hydroxypyrrolidine-1,2-dicarboxylate, 264 g of pyridinium chlorochromate and 75 g of celite in CHCl₃ (2 L) was stirred at room temperature. In midway, 100 g of pyridinium chlorochromate was added and the solution was stirred for a total of 7 days. The reaction solution was filtered with celite and the obtained filtrate was concentrated under reduced pressure to obtain 197 g of black oil. The obtained residue was purified by column chromatography (silicagel 60; mobile phase: EtOAc/n-hexane=2/1; v/v) to obtain 119 g of the title compound (yellow oil).

MS (ESI neg.) m/z: 242 ([M−H]⁻)
¹H-NMR (300 MHz, CDCl₃) δ (ppm); 1.30-1.50 (m, 9H), 2.59 (dd, J=18.9, 2.6 Hz, 1H), 2.84-3.05 (m, 1H), 3.77 (s, 3H), 3.86-4.03 (m, 2H), 4.67-4.92 (m, 1H)

Step 15-2: Synthesis of 1-tert-butyl 2-methyl (2S)-4,4-difluoropyrrolidine-1,2-dicarboxylate To a solution of 18.0 g of the compound obtained in Step 15-1 in CHCl₃ (150 ml) was added dropwise 36.0 g of [bis (2-methoxy ethyl)amino]sulfur trifluoride under ice cooling over 5 minutes, then, the reaction mixture was stirred at room temperature for 19 hours. The reaction solution was added dropwise to a saturated aqueous solution of K₂CO₃ over 10 minutes under ice cooling. After liquid separation, the aqueous layer was extracted, the combined organic layer was washed with saturated brine, dried over MgSO₄, then, the drying agent was separated by filtration, and the solvent was evaporated under reduced pressure. The obtained residue was purified by column chromatography (silicagel 60; mobile phase: EtOAc/n-hexane=1/4; v/v) to obtain 15.4 g of the title compound (yellow oil).

MS (ESI pos.) m/z: 288 ([M+Na]⁺)
¹H-NMR (300 MHz, CDCl₃) δ (ppm); 1.43 & 1.46 (each-s, 9H), 2.36-2.56 (m, 1H), 2.58-2.82 (m, 1H), 3.69-3.92 (m, 2H), 3.77 (s, 3H) 4.40-4.61 (m, 1H)

Step 15-3: Synthesis of 1-(tert-butoxy carbonyl)-4,4-difluoro-L-proline

With 15.2 g of the compound obtained in Step 15-2 as starting material, 12.6 g of the title compound (colorless crystal) was obtained by a similar method to Step 14-2.

MS (ESI neg.) m/z: 250 ([M−H]⁻)

¹H-NMR (300 MHz, DMSO-d₆) δ (ppm); 1.36 & 1.41 (each-s, 9H), 2.31-2.53 (m, 1H), 2.69-3.02 (m, 1H), 3.59-3.86 (m, 2H) 4.30-4.43 (m, 1H), 12.98 (brs, 1H)

Step 15-4: Synthesis of tert-butyl (2S)-2-[(dimethylamino)carbonyl]-4,4-difluoropyrrolidine-1-carboxylate With 4.00 g of the compound obtained in Step 15-3 as starting material, 4.02 g of the title compound (colorless solid) was obtained by a similar method to Step 6-1a.
MS (ESI pos.) m/z: 301 ([M+Na]⁺)
¹H-NMR (300 MHz, CDCl₃) δ (ppm); 1.41 & 1.46 (each-s, 9H), 2.28-2.48 (m, 1H), 2.55-2.73 (m, 1H), 2.99 & 3.00 (each-s, 3H), 3.06 & 3.10 (each-s, 3H), 3.75-4.02 (m, 2H), 4.68-4.91 (m, 1H)

Step 15-5: Synthesis of 4,4-difluoro-N,N-dimethyl-L-prolinamide trifluoroacetate With 3.85 g of the compound obtained in Step 15-4 as starting material, 8.02 g of the title compound (crude form pale yellow oil) was obtained by a similar method to Step 4-1. The present compound was used in the next reaction without purification.
MS (ESI pos.) m/z: 179 ([M+H]⁺)
¹H-NMR (300 MHz, DMSO-d₆) δ (ppm); 2.43-2.62 (m, 1H), 2.89-3.18 (m, 1H), 2.92 (s, 3H), 2.98 (s, 3H), 3.65-3.88 (m, 2H), 4.97 (t, J=8.7 Hz, 1H)

Step 15-6: Synthesis of 1-[5-(chloro-3-(2-methoxyphenyl)-2-oxo-2,3-dihydro-1H-indol-3-yl)-4,4-difluoro-N,N-dimethyl-L-prolinamide (levorotatory isomer, and dextrorotatory isomer) (levorotatory isomer, and dextrorotatory isomer)

With 3.88 g of 3,5-dichloro-3-(2-methoxyphenyl)-1,3-dihydro-2H-indol-2-one and the compound obtained in Step 15-5 (crude form) as starting materials, respectively 2.23 g (Isomer A: colorless powder) and 2.70 g (Isomer B: colorless powder) of two species of diastereoisomers of the title compound were obtained by a similar method to Step 4-2.
Isomer A: $[\alpha]_D^{29}$=+16° (c=0.425, CHCl₃)
MS (ESI pos.) m/z: 472 ([M+Na]⁺), (ESI neg.) m/z: 448 ([M−H]⁻)
¹H-NMR (300 MHz, DMSO-d₆) δ (ppm); 1.96-2.16 (m, 1H), 2.47-2.58 (m, 6H), 2.59-2.78 (m, 1H), 3.24-3.53 (m, 1H), 3.49 (s, 3H), 3.72-3.99 (m, 2H), 6.54 (d, J=2.2 Hz, 1H), 6.85 (d, J=8.2 Hz, 1H), 6.94 (dd, J=8.2, 0.9 Hz, 1H), 7.09-7.17 (m, 1H), 7.20 (dd, J=8.3, 2.3 Hz, 1H), 7.26-7.35 (m, 1H), 8.05 (dd, J=7.7, 1.6 Hz, 1H), 10.68 (s, 1H)
Isomer B: $[\alpha]_D^{28}$=−159° (c=0.296, CHCl₃)
MS (ESI pos.) m/z: 472 ([M+Na]⁺), (ESI neg.) m/z: 448 ([M−H]⁻)
¹H-NMR (300 MHz, DMSO-d₆) δ (ppm); 1.94-2.13 (m, 1H), 2.36-2.53 (m, 6H), 2.68-2.93 (m, 1H), 3.07-3.20 (m, 1H), 3.46 (s, 3H), 3.84-4.03 (m, 1H), 4.56-4.63 (m, 1H), 6.77 (d, J=8.2 Hz, 1H), 6.86 (d, J=2.2 Hz, 1H), 6.93 (dd, J=8.2, 1.1 Hz, 1H), 7.02-7.10 (m, 1H), 7.20 (dd, J=8.4, 2.2 Hz, 1H), 7.25-7.33 (m, 1H), 7.77 (dd, J=7.9, 1.8 Hz, 1H), 10.39 (s, 1H)

Step 15-7: Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-4,4-difluoro-N,N-dimethyl-L-prolinamide (levorotatory isomer)

With 300 mg of the compound obtained in Step 15-6 (Isomer B) and 213 mg of 4-methoxy-2-(trifluoromethoxy)benzene sulfonyl chloride as starting materials, 433 mg of the title compound (colorless amorphous) was obtained by a similar method to Example 2.
$[\alpha]_D^{21}$=−846° (c=0.213, CHCl₃)
MS (ESI pos.) m/z: 726 ([M+Na]⁺)
¹H-NMR (300 MHz, CDCl₃) δ (ppm); 2.01-5.03 (m, 8H), 2.44 (s, 3H), 2.72 (s, 3H), 3.90 (s, 3H), 6.77 (d, J=8.2 Hz, 1H), 6.85-7.12 (m, 4H), 7.22-7.34 (m, 2H), 7.84 (dd, J=7.9, 1.5 Hz, 1H), 7.91 (d, J=8.9 Hz, 1H), 8.24-8.44 (m, 1H)

Example 16

Synthesis of Methyl (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-L-prolinate (diastereoisomer mixture)

Step 16-1: Synthesis of methyl (4S)-4-fluoro-L-prolinate trifluoroacetate

With 1.5 g of the compound obtained in Step 14-1 as starting material, 2.56 g of the title compound (crude form yellow oil) was obtained by a similar method to Step 4-1. The present compound was used in the next reaction without purification.
MS (ESI pos.) m/z: 270 ([M+Na]⁺)
¹H-NMR (300 MHz, DMSO-d₆) δ (ppm); 2.23-2.76 (m, 2H), 3.20-3.87 (m, 2H), 3.78 (s, 3H), 4.69 (dd, J=10.1, 3.9 Hz, 1H), 5.32-5.64 (m, 1H).

Step 16-2: methyl (4S)-1-[5-chloro-3-(2-methoxyphenyl)-2-oxo-2,3-dihydro-1H-indol-3-yl]-4-fluoro-L-prolinate (diastereoisomer mixture) Synthesis of With 1.70 g of 3,5-dichloro-3-(2-methoxyphenyl)-1,3-dihydro-2H-indol-2-one and 1.03 g of the compound obtained in Step 16-1 as starting materials, 1.98 g of a diastereoisomer mixture of the title compound (pea green amorphous) was obtained by a similar method to Step 4-2.
MS (ESI pos.) m/z: 441 ([M+Na]⁺), (ESI neg.) m/z: 417 ([M−H]⁻)
¹H-NMR (300 MHz, CDCl₃) δ (ppm); 2.14-5.34 (m, 12H), 6.71-8.31 (m, 8H)

Step 16-3: Synthesis of methyl (4S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-fluoro-L-prolinate (diastereoisomer mixture)

With 400 mg of the diastereoisomer mixture obtained at Step 16-2 and 305 mg of 4-methoxy-2-(trifluoromethoxy) benzene sulfonyl chloride as starting materials, 516 mg of the title compound (yellow amorphous) was obtained by a similar method to Example 2.
MS (ESI pos.) m/z: 695 ([M+Na]⁺)
¹H-NMR (300 MHz, CDCl₃) δ (ppm); 1.71-2.20 (m, 2H), 2.47-5.05 (m, 13H), 6.75-7.32 (m, 7H), 7.84-8.35 (m, 3H)

Example 17

Synthesis of (3S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-3-hydroxy-N,N-dimethyl-L-prolinamide (levorotatory isomer)

Step 17-1: Synthesis of tert-butyl (2S,3S)-2-[(dimethylamino)carbonyl]-3-hydroxypyrrolidine-1-carboxylate With 5.85 g of (3S)-1-(tert-butoxy carbonyl)-3-hydroxy-L-proline as starting material, 4.05 g of the title compound (colorless solid) was obtained by a similar method to Step 6-1a.

MS (ESI pos.) m/z: 281 ([M+Na]$^+$)

$^1$H-NMR (300 MHz, CDCl$_3$) δ (ppm); 1.40 & 1.46 (each-s, 9H), 1.80-1.94 (m, 1H), 2.16-2.37 (m, 1H), 2.38 (dd, J=28.9, 5.1 Hz, 1H), 2.96 & 2.98 (each-s, 3H), 3.15 & 3.19 (each-s, 3H), 3.51-3.76 (m, 2H), 4.26-4.38 (m, 1H), 4.48-4.68 (m, 1H)

Step 17-2: Synthesis of (3S)-3-hydroxy-N,N-dimethyl-L-prolinamide trifluoroacetate With 3.90 g of the compound obtained in Step 17-1 as starting material, 9.23 g of the title compound (crude form pale yellow oil) was obtained by a similar method to Step 4-1. The present compound was used in the next reaction without purification.

MS (ESI pos.) m/z: 159 ([M+H]$^+$)

$^1$H-NMR (300 MHz, DMSO-d$_6$) δ (ppm); 1.74-1.95 (m, 2H), 2.91 (s, 3H), 3.08 (s, 3H), 3.22-3.64 (m, 2H), 4.35-4.47 (m, 2H), 8.42-8.59 (m, 1H), 9.60-9.78 (m, 1H)

Step 17-3: Synthesis of (3S)-1-[5-chloro-3-(2-methoxyphenyl)-2-oxo-2,3-dihydro-1H-indol-3-yl]-3-hydroxy-N,N-dimethyl-L-prolinamide (levorotatory isomer)

With 4.23 g of 3,5-dichloro-3-(2-methoxyphenyl)-1,3-dihydro-2H-indol-2-one and the compound obtained in Step 17-2 (crude form 15.1 mmol) as starting materials, respectively 2.75 g (Isomer A) and 2.28 g (Isomer B) of two species of diastereoisomers of the title compound were obtained by a similar method to Step 4-2.

Isomer A: [α]$_D^{21}$=−361° (c=0.217, CHCl$_3$)

MS (ESI pos.) m/z: 452 ([M+Na]$^+$), (ESI neg.) m/z: 428 ([M−H]$^-$)

$^1$H-NMR (300 MHz, DMSO-d$_6$) δ (ppm); 1.57-1.68 (m, 1H), 1.93 (d, J=4.5 Hz, 1H), 2.48-2.67 (m, 6H), 2.70-3.20 (m, 2H), 3.47 (s, 3H), 3.92 (m, 1H), 4.50 (m, 1H) 5.10 (brs, 1H), 6.69-6.79 (m, 2H), 6.92 (dd, J=8.2, 0.9 Hz, 1H), 6.95-7.04 (m, 1H), 7.15 (dd, J=8.3, 2.3 Hz, 1H), 7.23-7.31 (m, 1H), 7.87 (dd, J=7.5, 1.5 Hz, 1H), 10.37 (s, 1H)

Isomer B: [α]$_D^{21}$=−988° (c=0.214, CHCl$_3$)

MS (ESI pos.) m/z: 452 ([M+Na]$^+$), (ESI neg.) m/z: 428 ([M−H]$^-$)

$^1$H-NMR (300 MHz, DMSO-d$_6$) δ (ppm); 1.54-1.65 (m, 1H), 1.77-1.90 (m, 1H), 2.44 (s, 3H), 2.61 (s, 3H), 2.87-2.96 (m, 1H), 3.25-3.52 (m, 2H), 3.49 (s, 3H), 3.86-3.95 (m, 1H), 5.06-5.25 (brs, 1H), 6.44 (d, J=2.0 Hz, 1H), 6.81 (d, J=8.2 Hz, 1H), 6.92 (dd, J=8.1, 0.9 Hz, 1H), 7.05-7.13 (m, 1H), 7.18 (dd, J=8.3, 2.3 Hz, 1H), 7.23-7.31 (m, 1H), 8.11 (dd, J=7.7, 1.6 Hz, 1H), 10.51 (s, 1H)

Step 17-4: Synthesis of (3S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-3-hydroxy-N,N-dimethyl-L-prolinamide (levorotatory isomer)

With 800 mg of the compound obtained in Step 17-3 (Isomer A) and 592 mg of 4-methoxy-2-(trifluoromethoxy)benzene sulfonyl chloride as starting materials, 997 mg of the title compound (pale yellow amorphous) was obtained by a similar method to Example 2.

[α]$_D^{21}$=−893° (c=0.210, CHCl$_3$)

MS (ESI pos.) m/z: 706 ([M+Na]$^+$)

$^1$H-NMR (300 MHz, CDCl$_3$) δ (ppm); 1.32-3.98 (m, 6H), 2.40 (s, 3H), 2.84 (s, 3H), 3.70 (s, 3H), 3.90 (s, 3H), 4.55 (s, 1H), 6.75-7.00 (m, 4H), 7.18-7.30 (m, 3H), 7.77 (dd, J=7.9, 1.6 Hz, 1H), 7.92 (d, J=8.9 Hz, 1H), 8.30 (d, J=9.0 Hz, 1H)

Example 18

Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-3-fluoro-N,N-dimethyl-L-prolinamide (levorotatory isomer)

With 600 mg of the compound obtained in Step 17-4 as starting material, 283 mg of the title compound (pale yellow solid) was obtained by a similar method to Step 6-2a.

[α]$_D^{21}$=−928° (c=0.206, CHCl$_3$)

MS (ESI pos.) m/z: 708 ([M+Na]$^+$)

$^1$H-NMR (300 MHz, CDCl$_3$) δ (ppm); 1.59-1.89 (m, 1H), 2.12-2.58 (m, 5H), 2.69-2.98 (m, 1H), 2.74 (s, 3H), 3.57-3.74 (m, 3H), 3.85-3.93 (m, 3H), 4.57-5.03 (m, 2H), 6.73-7.13 (m, 5H), 7.21-7.32 (m, 2H), 7.75 (dd, J=7.8, 1.7 Hz, 1H), 7.93 (d, J=8.9 Hz, 1H), 8.30 (d, J=9.0 Hz, 1H)

Example 19

Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-3,4-dihydroxy-N,N-dimethyl-L-prolinamide (diastereoisomer mixture)

Step 19-1: Synthesis of 1-tert-butyl 2-methyl (2S,4S)-4-iodopyrrolidine-1,2-dicarboxylate Under nitrogen atmosphere, to a solution of 19.3 g of 1-tert-butyl 2-methyl (2S,4R)-4-hydroxypyrrolidine-1,2-dicarboxylate and 24.8 g of triphenyl phosphine in THF (275 ml) was added dropwise a solution of diethyl azodicarboxylate/40% toluene (41.1 ml) over 15 minutes under ice cooling. After stirring at the same temperature for 30 minutes, iodine methane (5.88 ml) was added dropwise to the solution over 3 minutes, thereafter, the reaction mixture was warmed to room temperature, and then was stirred for 36 hours. To the reaction solution was added EtOAc and an aqueous solution of 5% K$_2$CO$_3$ and the resulting mixture was stirred for 15 minutes. Liquid separation was performed and the obtained aqueous layer was extracted with EtOAc. The combined organic layer was washed with saturated brine, then, was concentrated under reduced pressure. The concentrated solution was purified by column chromatography (silicagel 60; mobile phase: EtOAc/n-hexane=3/7; v/v) to obtain 27.8 g of the title compound (orange color oil).

MS (ESI pos.) m/z: 378 ([M+Na]$^+$)

$^1$H-NMR (300 MHz, CDCl$_3$) δ (ppm); 1.32-1.57 (m, 9H), 2.21-4.53 (m, 9H)

Step 19-2: Synthesis of 1-tert-butyl 2-methyl (2S)-2,3-dihydro-1H-pyrrole-1,2-dicarboxylate and 1-tert-butyl 2-methyl (2S)-2,5-dihydro-1H-pyrrole-1,2-dicarboxylate To a solution of 27.3 g of the compound obtained in Step 19-1 in toluene (500 ml) was added 1,8-diaza bicyclo[5,4,0] undec-7-ene (DBU) (12.7 ml) and the reaction mixture was stirred for 10 hours at an external temperature of 85° C. After being to cool, the precipitation was separated by filtration and the solvent was evaporated under reduced pressure. The obtained residue was separated and purified by column chromatography (silicagel 60; mobile phase: EtOAc/n-hexane=1/10 to 1/5; v/v) to obtain 4.15 g of 1-tert-butyl 2-methyl (2S)-2,3-dihydro-1H-pyrrole-1,2-dicarboxylate (colorless oil) and 12.5 g of 1-tert-butyl 2-methyl (2S)-2,5-dihydro-1H-pyrrole-1,2-dicarboxylate (colorless oil).

1-tert-butyl 2-methyl (2S)-2,3-dihydro-1H-pyrrole-1,2-dicarboxylate

MS (ESI pos.) m/z: 250 ([M+Na]$^+$)
$^1$H-NMR (300 MHz, CDCl$_3$) δ (ppm); 1.44 & 1.49 (each-s, 9H), 2.56-2.76 (m, 1H), 2.96-3.17 (m, 1H), 3.76 (s, 3H), 4.50-4.72 (m, 1H), 4.86-5.03 (m, 1H), 6.44-6.69 (m, 1H)

1-tert-butyl 2-methyl (2S)-2,5-dihydro-1H-pyrrole-1,2-dicarboxylate

MS (ESI pos.) m/z: 250 ([M+Na]$^+$)
$^1$H-NMR (300 MHz, CDCl$_3$) δ (ppm); 1.43 & 1.48 (each s, 9H), 3.74 & 3.75 (each-s, 3H), 4.07-4.36 (m, 2H), 4.93-5.08 (m, 1H), 5.67-5.79 (m, 1H), 5.91-6.03 (m, 1H)

Step 19-3: Synthesis of 1-tert-butyl 2-methyl (2S,3R,4S)-3,4-dihydroxypyrrolidine-1,2-dicarboxylate, 1-tert-butyl 2-methyl (2S,3S,4R)-3,4-dihydroxypyrrolidine-1,2-dicarboxylate (mixture)

A solution of 10.0 g of 1-tert-butyl 2-methyl (2S)-2,5-dihydro-1H-pyrrole-1,2-dicarboxylate obtained at Step 19-2, 20.6 g of N-methyl morpholine and osumium tetroxide (4% aqueous solution, 5 ml) in a 1,4-dioxane (300 ml)-water (70 ml) mix was stirred at room temperature for 35 hours. To the reaction solution was added EtOAc and an aqueous solution of 10% sodium thiosulfate, and the reaction solution was stirred at room temperature for 30 minutes. Liquid separation was performed and the obtained aqueous layer was extracted with EtOAc. The combined organic layer was washed with μmol/L hydrochloric acid, with a saturated aqueous solution of NaHCO$_3$ and with a saturated brine, then, the solvent was evaporated under reduced pressure. The obtained residue was purified by column chromatography (silicagel 60; mobile phase: CHCl$_3$/MeOH/NH$_4$OH=10/1/0.1; v/v/v) to obtain 10.4 g of the title compound (colorless oil).
MS (ESI pos.) m/z: 228 ([M+H]$^+$), 250 ([M+Na]$^+$)
$^1$H-NMR (300 MHz, CDCl$_3$) δ (ppm); 1.36-1.49 (m, 9H), 2.70-2.92 (m, 1H), 3.06-3.24 (m, 1H), 3.40-3.85 (m, 5H), 4.12-4.51 (m, 3H)

Step 19-4: Synthesis of 1-(tert-butoxy carbonyl)-3,4-dihydroxy-L-proline

With 5.00 g of the mixture obtained at Step 19-3 as starting material, 4.32 g of the title compound (colorless crystal) was obtained by a similar method to Step 11-2.
MS (ESI pos.) m/z: 270 ([M+Na]$^+$)
$^1$H-NMR (300 MHz, DMSO-d$_6$) δ (ppm); 1.33 & 1.39 (each-s, 9H), 3.11-3.52 (m, 3H), 3.91-4.06 (m, 2H), 5.04 (s, 1H), 5.39 (s, 1H)

Step 19-5: Synthesis of tert-butyl (2S)-2-[(dimethylamino)carbonyl]-3,4-dihydroxypyrrolidine-1-carboxylate With 2.00 g of the compound obtained in Step 19-4 as starting material, 1.72 g of the title compound (colorless crystal) was obtained by a similar method to Step 6-1a.
MS (ESI pos.) m/z: 297 ([M+Na]$^+$)
$^1$H-NMR (300 MHz, CDCl$_3$) δ (ppm); 1.39 & 1.44 (each-s, 9H), 2.99 & 3.01 (each-s, 3H), 3.16 & 3.22 (each-s, 3H), 3.41-3.60 (m, 1H), 3.70-3.81 (m, 1H), 4.16-4.25 (m, 1H), 4.32-4.47 (m, 1H), 4.60 (dd, J=28.4, 4.1 Hz, 1H)

Step 19-6: Synthesis of 3,4-dihydroxy-N,N-dimethyl-L-prolinamide trifluoroacetate With 1.65 g of the compound obtained in Step 19-5 as the raw materials, 2.56 g of the title compound (crude form yellow oil) was obtained by a similar method to Step 4-1. The present compound was used in the next reaction without purification.
MS (ESI pos.) m/z: 175 ([M+H]$^+$)
$^1$H-NMR (300 MHz, DMSO-d$_6$) δ (ppm); 2.94 (s, 3H), 2.97-3.21 (m, 1H), 3.09 (s, 3H), 3.29-3.47 (m, 1H), 3.98-4.10 (m, 2H), 4.27-4.47 (m, 1H), 8.48 (brs, 1H), 9.77 (brs, 1H)

Step 19-7: Synthesis of 1-[5-chloro-3-(2-methoxyphenyl)-2-oxo-2,3-dihydro-1H-indol-3-yl]-3,4-dihydroxy-N,N-dimethyl-L-prolinamide (diastereoisomer mixture)

With 1.69 g of 3,5-dichloro-3-(2-methoxyphenyl)-1,3-dihydro-2H-indol-2-one and 19-6 of the compound obtained in Step (crude form 6.01 mmol) as starting material, 1.63 g of the title compound (diastereoisomers) (colorless solid) was obtained by a similar method to Step 4-2.
MS (ESI pos.) m/z: 468 ([M+Na]$^+$)
$^1$H-NMR (300 MHz, DMSO-d$_6$) δ (ppm); 2.25-5.10 (m, 14H), 3.47 & 3.47 (each-s, 3H), 6.39-8.16 (m, 7H), 10.27-10.56 (m, 1H)

Step 19-8: Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-3,4-dihydroxy-N,N-dimethyl-L-prolinamide (diastereoisomer mixture)

With 300 mg of the compound obtained in Step 19-7 and 215 mg of 4-methoxy-2-(trifluoromethoxy)benzene sulfonyl chloride as starting material, 248 mg of the title compound (colorless amorphous) was obtained by a similar method to Example 2.
MS (ESI pos.) m/z: 722 ([M+Na]$^+$)
$^1$H-NMR (300 MHz, CDCl$_3$) δ (ppm); 1.50-4.68 (m, 10H) 2.35 & 2.47 (each-s, 3H), 2.80 (s, 3H), 3.89 & 3.92 (each-s, 3H) 6.74-8.36 (m, 10H)

Example 20

Synthesis of (4R)-4-fluoro-1-[3-(2-methoxyphenyl)-1-{[4-methoxy-2-(trifluoromethoxy)phenyl]sulfonyl}-2-oxo-5-(trifluoromethoxy)-2,3-dihydro-1H-indol-3-yl]-N,N-dimethyl-L-prolinamide (levorotatory isomer)

Step 20-1: Synthesis of (4R)-4-fluoro-1-[3-(2-methoxyphenyl)-2-oxo-5-(trifluoromethoxy)-2,3-dihydro-1H-indol-3-yl]-N,N-dimethyl-L-prolinamide (levorotatory isomer and dextrorotatory isomer) (levorotatory isomer and dextrorotatory isomer)

With 2.24 g of 3-hydroxy-3-(2-methoxyphenyl)-5-(trifluoromethoxy)-1,3-dihydro-2H-indol-2-one and (4R)-4-fluoro-N,N-dimethyl-L-prolinamide trifluoroacetate (6.57 mmol) as starting material, respectively 761 mg (Isomer A: colorless amorphous) and 633 mg (Isomer B: colorless amorphous) of two species of diastereomers were obtained by a similar method to Step 4-2.

Isomer A: $[\alpha]_D^{25}$=+123° (c=0.291, CHCl$_3$)
MS (ESI pos.) m/z: 482 ([M+H]$^+$), 504 ([M+Na]$^+$), (ESI neg.) m/z: 480 ([M−H]$^-$)
$^1$H-NMR (300 MHz, DMSO-d$_6$) δ (ppm); 1.65-1.93 (m, 1H), 2.17-2.38 (m, 1H), 2.42-2.58 (m, 5H), 3.24-3.50 (m, 5H), 3.74-3.95 (m, 2H), 5.04-5.32 (m, 1H), 6.44 (d, J=1.71 Hz, 1H), 6.84-6.98 (m, 2H), 7.06-7.18 (m, 2H), 7.24-7.35 (m, 1H), 8.04 (dd, J=7.62, 1.71 Hz, 1H), 10.58 (s, 1H)
$^1$H-NMR (300 MHz, CDCl$_3$) δ (ppm); 1.85-2.35 (m, 2H), 2.53 (s, 3H), 2.66 (s, 3H), 3.49-3.73 (m, 4H), 4.03-4.21 (m, 2H), 5.05-5.32 (m, 1H), 6.75 (d, J=2.18 Hz, 1H), 6.80-6.87 (m, 2H), 6.97-7.05 (m, 1H), 7.08-7.17 (m, 1H), 7.25-7.32 (m, 1H), 8.23 (dd, J=7.77, 1.71 Hz, 1H), 9.43 (s, 1H)

Isomer B: $[\alpha]_D^{25}$=−172° (c=0.287, CHCl$_3$)
MS (ESI pos.) m/z: 504 ([M+Na]$^+$), (ESI neg.) m/z: 480 ([M−H]$^-$)
$^1$H-NMR (300 MHz, DMSO-d$_6$) δ (ppm); 1.82-2.02 (m, 1H), 2.26-2.56 (m, 7H), 2.84-3.09 (m, 1H), 3.41-3.73 (m, 4H), 4.54-4.64 (m, 1H), 5.31 (d, 1H), 6.75-6.86 (m, 2H), 6.92 (d, J=8.08 Hz, 1H), 7.00-7.05 (m, 1H), 7.11-7.20 (m, 1H), 7.23-7.32 (m, 1H), 7.88 (dd, J=7.69, 1.32 Hz, 1H), 10.39 (s, 1H)

Step 20-2: Synthesis of (4R)-4-fluoro-1-[3-(2-methoxyphenyl)-1-{[4-methoxy-2-(trifluoromethoxy)phenyl]sulfonyl}-2-oxo-5-(trifluoromethoxy)-2,3-dihydro-1H-indol-3-yl]-N,N-dimethyl-L-prolinamide (levorotatory isomer)

With 200 mg of the compound obtained in Step 20-1 (Isomer B) and 133 mg of 4-methoxy-2-(trifluoromethoxy)benzene sulfonyl chloride as starting material, 158 mg of the title compound (colorless amorphous) was obtained by a similar method to Example 2.

$[\alpha]_D^{27}$=−165° (c=0.218, CHCl$_3$)
MS (ESI pos.) m/z: 736 ([M+H]$^+$), 758 ([M+Na]$^+$), (ESI neg.) m/z: 734 ([M−H]$^-$)
$^1$H-NMR (300 MHz, CDCl$_3$) δ (ppm); 1.82-2.13 (m, 2H), 2.39 (s, 3H), 2.70 (s, 3H), 3.20-3.76 (m, 4H), 3.89 (s, 3H), 4.24-4.93 (m, 2H), 5.00-5.31 (m, 1H), 6.73-6.79 (m, 1H), 6.82-7.06 (m, 4H), 7.10-7.19 (m, 1H), 7.20-7.30 (m, 1H), 7.83-7.93 (m, 1H), 7.99 (d, J=9.0 Hz, 1H), 8.29-8.42 (m, 1H)

Example 21

Synthesis of (4R)-1-(4,5-dichloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer and dextrorotatory isomer) (levorotatory isomer and dextrorotatory isomer)

Step 21-1: Synthesis of 4,5-dichloro-3-hydroxy-3-(2-methoxy-5-methylphenyl)-1,3-dihydro-2H-indol-2-one Under nitrogen atmosphere, to a suspension of 0.36 g of magnesium in THF (10 ml) was added dropwise a solution of 3.02 g of 2-bromo-1-methoxy-4-methyl benzene in THF (10 ml). Thereafter, the solution was stirred under heat reflux for 30 minutes, then, allowed to come to room temperature.

Under nitrogen atmosphere, to a suspension of 0.31 g NaH in THF (40 ml), under ice bath conditions, was added 1.50 g of 4,5-dichloroisatin, which is the compound described in the specifications of U.S. Pat. No. 4,146,718, and the reaction mixture was stirred for 1 hour. Thereafter, a solution of bromo (2-methoxy-5-methylphenyl) magnesium in THF (20 ml) prepared beforehand was added dropwise over 20 minutes. The solution was stirred at the same temperature for 4 hours. Then a saturated aqueous solution of NH$_4$Cl was added, and the reaction mixture was stirred at room temperature for 30 minutes. Liquid separation was performed, the aqueous layer was extracted with EtOAc, the combined organic layer was washed with saturated brine, dried over Na$_2$SO$_4$, then, the drying agent was separated by filtration and the solvent was evaporated under reduced pressure. The obtained residue was washed by stirring in IPE and the solid was collected by filtration to obtain 1.23 g of the title compound (yellow solid).

MS (ESI pos.) m/z: 360 ([M+Na]$^+$), (ESI neg.) m/z: 336 ([M−H]$^-$)
$^1$H-NMR (200 MHz, DMSO-d$_6$) δ (ppm); 2.31 (s, 3H), 3.38 (s, 3H), 6.64-6.87 (m, 3H), 7.00-7.13 (m, 1H), 7.42 (d, J=8.35 Hz, 1H), 7.68 (d, J=2.20 Hz, 1H), 10.61 (s, 1H)

Step 21-2: Synthesis of (4R)-1-[4,5-dichloro-3-(2-methoxy-5-methylphenyl)-2-oxo-2,3-dihydro-1H-indol-3-yl]-4-fluoro-N,N-dimethyl-L-prolinamide (diastereoisomer mixture)

To a solution of 0.60 g of 4,5-dichloro-3-hydroxy-3-(2-methoxy-5-methylphenyl)-1,3-dihydro-2H-indol-2-one obtained at Step 21-1 and 0.30 g of Py in CHCl$_3$ (5 ml) was added salt thionyl (0.18 ml) under ice cooling, and the reaction mixture was stirred for 1 hour at the same temperature. A solution of 0.43 g of (4R)-4-fluoro-N,N-dimethyl-L-prolinamide in CHCl$_3$ (5 ml) was added, and Et$_3$N (20 ml) was added dropwise under ice cooling. The solution was stirred at room temperature for 88 hours. To the reaction solution was added an aqueous solution of 5% K$_2$CO$_3$, liquid separation was performed, and the aqueous layer was extracted with CHCl$_3$. The combined organic layer was washed with saturated brine, then dried over MgSO$_4$, the drying agent was separated by filtration, then, the solution was concentrated under reduced pressure. The obtained residue was purified by column chromatography (silicagel 60; mobile phase: EtOAc) to obtain 640 mg of the title compound (mixture of two species of diastereoisomers) (beige amorphous).

MS (ESI pos.) m/z: 480 ([M+H]$^+$), 502 ([M+Na]$^+$), (ESI neg.) m/z: 478 ([M−H]$^-$)

¹H-NMR (300 MHz, DMSO-d₆) δ (ppm); 1.69-4.69 (m, 17H), 5.04-5.50 (m, 1H), 6.71-6.84 (m, 2H), 7.01-7.13 (m, 1H), 7.35-7.47 (m, 1H), 7.63-7.83 (m, 1H), 10.47-10.78 (m, 1H)

Step 21-3: Synthesis of (4R)-1-(4,5-dichloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer and dextrorotatory isomer)

With 300 mg of the compound obtained in Example 21-2 as starting material, respectively 175 mg (Isomer A: colorless amorphous) and 151 mg (Isomer B: colorless amorphous) of two species of diastereoisomers, which are the title compounds, were obtained by a similar method to Example 2.

Isomer A: $[\alpha]_D^{27}$=−198° (c=0.197, CHCl₃)
MS (ESI pos.) m/z: 734 ([M+H]⁺), 756 ([M+Na]⁺)
¹H-NMR (300 MHz, CDCl₃) δ (ppm); 1.81-2.06 (m, 1H), 2.30 (s, 3H), 2.48-3.65 (m, 12H), 3.88 (s, 3H), 4.38-4.84 (m, 1H), 5.07-5.35 (m, 1H), 6.61 (d, J=8.4 Hz, 1H), 6.85-6.95 (m, 2H), 7.02 (dd, J=8.4, 2.3 Hz, 1H), 7.41 (d, J=8.9 Hz, 1H), 7.77-8.02 (m, 2H), 8.37 (d, J=8.9 Hz, 1H)

Isomer B: $[\alpha]_D^{25}$=+163° (c=0.218, CHCl₃)
MS (ESI pos.) m/z: 734 ([M+H]⁺), 756 ([M+Na]⁺), (ESI neg.) m/z: 732 ([M−H]⁻)
¹H-NMR (300 MHz, CDCl₃) δ (ppm); 1.75-2.81 (m, 11H), 3.38-3.93 (m, 8H), 4.13 (t, J=7.2 Hz, 1H), 4.87-5.18 (m, 1H), 6.64 (d, J=8.2 Hz, 1H), 6.83-7.13 (m, 3H), 7.47 (d, J=8.9 Hz, 1H), 7.78 (s, 1H), 7.98 (d, J=8.9 Hz, 1H), 8.28 (d, J=8.9 Hz, 1H)

Example 22

Synthesis of (4R)-1-(3-(1,3-benzodioxol-4-yl)-5-chloro-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer and dextrorotatory isomer)

Step 22-1: Synthesis of (4R)-1-[3-(1,3-benzodioxol-4-yl)-5-chloro-2-oxo-2,3-dihydro-1H-indol-3-yl]-4-fluoro-N,N-dimethyl-L-prolinamide From 1.06 g of 3-(1,3-benzodioxol-4-yl)-5-chloro-3-hydroxy-1,3-dihydro-2H-indol-2-one, which is the compound described in Preparation 1.7 of the brochure Publication No. WO01/064668, and (4R)-4-fluoro-N,N-dimethyl-L-prolinamide trifluoroacetate (3.53 mmol), 418 mg of the title compound (mixture of two species of diastereomers) (yellow amorphous) was obtained by a similar method to Step 21-2.

MS (ESI pos.) m/z: 446 ([M+H]⁺), 468 ([M+Na]⁺), (ESI neg.) m/z: 444 ([M−H]⁻)
¹H-NMR (200 MHz, DMSO-d₆) δ (ppm); 1.65-4.87 (m, 11H), 4.95-5.57 (m, 1H), 5.76-5.92 (m, 2H), 6.69-7.47 (m, 6H), 10.50-10.84 (m, 1H)

Step 22-2: Synthesis of (4R)-1-(3-(1,3-benzodioxol-4-yl)-5-chloro-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer and dextrorotatory isomer)

With 500 mg of the compound obtained in Step 22-1 as starting material, respectively 231 mg (Isomer A: colorless amorphous) and 228 mg (Isomer B: colorless amorphous) of two species of diastereoisomers, which are the title compounds, were obtained by a similar method to Example 2.

Isomer A: $[\alpha]_D^{25}$=−209° (c=0.185, CHCl₃)
MS (ESI pos.) m/z: 700 ([M+H]⁺), 722 ([M+Na]⁺), (ESI neg.) m/z: 698 ([M−H]⁻)
¹H-NMR (300 MHz, CDCl₃) δ (ppm); 1.92-2.46 (m, 2H), 2.48 (s, 3H), 2.71 (s, 3H), 3.03 (dd, J=20.8, 11.9 Hz, 1H), 3.60-3.80 (m, 1H), 3.90 (s, 3H), 4.64 (dd, J=8.6, 5.1 Hz, 1H), 5.08-5.55 (m, 3H), 6.66-6.98 (m, 4H), 7.24-7.33 (m, 3H), 7.93 (d, J=8.9 Hz, 1H), 8.40 (d, J=8.9 Hz, 1H)

Isomer B: $[\alpha]_D^{25}$=+134° (c=0.220, CHCl₃)
MS (ESI pos.) m/z: 700 ([M+H]⁺), 722 ([M+Na]⁺), (ESI neg.) m/z: 698 ([M−H]⁻)
¹H-NMR (300 MHz, CDCl₃) δ (ppm); 1.78-2.38 (m, 2H), 2.51 (s, 3H), 2.74 (s, 3H), 3.36-3.58 (m, 1H), 3.73-4.05 (m, 5H), 4.97-5.23 (m, 1H), 5.32-5.52 (m, 2H), 6.68-6.76 (m, 1H), 6.82-6.99 (m, 3H), 7.04 (d, J=2.0 Hz, 1H), 7.24-7.35 (m, 1H), 7.61 (d, J=8.1 Hz, 1H), 7.94 (d, J=8.7 Hz, 1H), 8.36 (dd, J=9.0, 0.62 Hz, 1H)

Example 23

Synthesis of (4R)-4-fluoro-1-(3-(2-methoxyphenyl)-1-{[4-methoxy-2-(trifluoromethoxy)phenyl]sulfonyl}-5-methyl-2-oxo-2,3-dihydro-1H-indol-3-yl)-N,N-dimethyl-L-prolinamide (levorotatory isomer and dextrorotatory isomer)

Step 23-1: Synthesis of (4R)-4-fluoro-1-[3-(2-methoxyphenyl)-5-methyl-2-oxo-2,3-dihydro-1H-indol-3-yl]-N,N-dimethyl-L-prolinamide (diastereo mixture)

From 1.78 g of 3-hydroxy-3-(2-methoxyphenyl)-5-methyl-1,3-dihydro-2H-indol-2-one, which is the compound described in Preparation 1.3 of the brochure Publication No. WO01/055130, and (4R)-4-fluoro-N,N-dimethyl-L-prolinamide trifluoroacetate (6.60 mmol), 1.30 g of the title compound (two species of diastereoisomers mixture) (colorless solid) was obtained by a similar method to Step 21-2.

MS (ESI pos.) m/z: 412 ([M+H]⁺), 434 ([M+Na]⁺), (ESI neg.) m/z: 410 ([M−H]⁻)
¹H-NMR (300 MHz, DMSO-d₆) δ (ppm); 1.52-4.76 (m, 17H), 5.01-5.48 (m, 1H), 6.32-7.33 (m, 5H), 7.19-7.30 (m, 1H), 7.82-8.12 (m, 1H), 9.99-10.28 (m, 1H)

Step 23-2: Synthesis of (4R)-4-fluoro-1-(3-(2-methoxyphenyl)-1-{[4-methoxy-2-(trifluoromethoxy)phenyl]sulfonyl}-5-methyl-2-oxo-2,3-dihydro-1H-indol-3-yl)-N,N-dimethyl-L-prolinamide (levorotatory isomer and dextrorotatory isomer)

With 500 mg of the compound obtained in Step 23-1 as starting material, respectively 208 mg (Isomer A: colorless amorphous) and 229 mg (Isomer B: colorless amorphous) of two species of diastereoisomers, which are the title compounds, were obtained by a similar method to Example 2.

Isomer A: $[\alpha]_D^{25}$=−182° (c=0.196, CHCl₃)
MS (ESI pos.) m/z: 666 ([M+H]⁺), 688 ([M+Na]⁺)
¹H-NMR (300 MHz, CDCl₃) δ (ppm); 1.85-2.09 (m, 2H), 2.14-4.07 (m, 17H), 4.58-5.36 (m, 2H), 6.71-7.12 (m, 6H), 7.18-7.29 (m, 1H), 7.75-8.01 (m, 2H), 8.20-8.46 (m, 1H)

Isomer B: $[\alpha]_D^{25}$=+78.0° (c=0.181, CHCl₃)
MS (ESI pos.) m/z: 666 ([M+H]⁺), 688 ([M+Na]⁺)
¹H-NMR (300 MHz, CDCl₃) δ (ppm); 1.65-2.23 (m, 5H), 2.37 (s, 3H), 2.70 (s, 3H), 3.28-4.04 (m, 9H), 4.83-5.11 (m, 1H), 6.65-6.81 (m, 2H), 6.83-6.98 (m, 2H), 7.04-7.16 (m, 2H), 7.19-7.33 (m, 1H), 7.87 (d, J=8.4 Hz, 1H), 8.23 (d, J=9.0 Hz, 1H), 8.34 (d, J=9.0 Hz, 1H)

Example 24

Synthesis of (4R)-1-(5-chloro-3-(5-chloro-2-methoxyphenyl)-1-{[4-methoxy-2-(trifluoromethoxy)phenyl]sulfonyl}-4-methyl-2-oxo-2,3-dihydro-1H-indol-3-yl)-4-fluoro-N,N-dimethyl-L-prolinamide (levorotatory isomer)

Step 24-1: Synthesis of 5-chloro-3-(5-chloro-2-methoxyphenyl)-3-hydroxy-4-methyl-1,3-dihydro-2H-indol-2-one With 4.75 g of 2-bromo-4-chloro-1-methoxy benzene and 1.96 g of 5-chloro-4-methyl isatin, which is the compound described in Example 136 of the brochure Publication No. WO03106435, as starting materials, 2.43 g of the title compound (yellow solid) was obtained by a similar method to Step 21-1.

MS (ESI neg.) m/z: 336 ([M−H]−)
$^1$H-NMR (300 MHz, DMSO-d$_6$) δ (ppm); 1.87 (s, 3H), 3.41 (s, 3H), 6.70 (dd, J=8.2, 0.4 Hz, 1H), 6.78 (s, 1H), 6.93 (d, J=8.7 Hz, 1H), 7.25 (dd, J=8.2, 0.4 Hz, 1H), 7.35 (dd, J=8.7, 2.8 Hz, 1H), 7.83 (d, J=2.8 Hz, 1H), 10.48 (s, 1H)

Step 24-2: Synthesis of (4R)-1-[5-chloro-3-(5-chloro-2-methoxyphenyl)-4-methyl-2-oxo-2,3-dihydro-1H-indol-3-yl]-4-fluoro-N,N-dimethyl-L-prolinamide (levorotatory isomer and dextrorotatory isomer)

From 1.19 g of the compound obtained in Step 24-1 and (4R)-4-fluoro-N,N-dimethyl-L-prolinamide trifluoroacetate (3.53 mmol), respectively 880 mg (Isomer A: orange color solid) and 465 mg (Isomer B: orange color solid) of two species of diastereoisomers of the title compound were obtained by a similar method to Step 21-2.

Isomer A: $[α]_D^{25}$=+205° (c=0.284, CHCl$_3$)
MS (ESI pos.) m/z: 480 ([M+H]+), 502 ([M+Na]+), (ESI neg.) m/z: 478 ([M−H]−)
$^1$H-NMR (300 MHz, DMSO-d$_6$) δ (ppm); 1.63-1.92 (m, 4H), 2.18-2.43 (m, 4H), 2.46-2.57 (m, 3H), 3.27-3.57 (m, 4H), 3.88-4.09 (m, 2H), 5.06-5.33 (m, 1H), 6.70 (d, J=8.2 Hz, 1H), 6.97 (d, J=8.8 Hz, 1H), 7.26 (d, J=8.2 Hz, 1H), 7.36 (dd, J=8.8, 2.8 Hz, 1H), 7.87 (d, J=2.8 Hz, 1H), 10.58 (s, 1H)

Isomer B: $[α]_D^{25}$=−156° (c=0.175, CHCl$_3$)
MS (ESI pos.) m/z: 480 ([M+H]+), 502 ([M+Na]+), (ESI neg.) m/z: 478 ([M−H]−)
$^1$H-NMR (300 MHz, DMSO-d$_6$) δ (ppm); 1.71-2.09 (m, 4H), 2.22-4.46 (m, 13H), 5.18-5.53 (m, 1H), 6.63 (d, J=8.2 Hz, 1H), 6.94 (d, J=8.7 Hz, 1H), 7.19-7.39 (m, 2H), 7.91 (d, J=2.3 Hz, 1H), 10.36 (s, 1H)

Step 24-3

Synthesis of (4R)-1-(5-chloro-3-(5-chloro-2-methoxyphenyl)-1-{[4-methoxy-2-(trifluoromethoxy)phenyl]sulfonyl}-4-methyl-2-oxo-2,3-dihydro-1H-indol-3-yl)-4-fluoro-N,N-dimethyl-L-prolinamide (levorotatory isomer)

With 100 mg of the compound obtained in Step 24-2 (Isomer B) and 70 mg of 4-methoxy-2-(trifluoromethoxy)benzene sulfonyl chloride as starting materials, 75 mg of the title compound (colorless amorphous) was obtained by a similar method to Example 2.

$[α]_D^{25}$=−203° (c=0.214, CHCl$_3$)
MS (ESI pos.) m/z: 734 ([M+H]+)
$^1$H-NMR (300 MHz, CDCl$_3$) δ (ppm); 0.80-3.72 (m, 17H), 3.90 (s, 3H), 5.06-5.36 (m, 1H), 6.63-6.76 (m, 1H), 6.82-6.98 (m, 2H), 7.15-7.40 (m, 2H), 7.78-7.98 (m, 2H), 8.25-8.43 (m, 1H)

Example 25

Synthesis of (4R)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

Step 25-1: Synthesis of 5-chloro-3-(2,3-dihydro-1-benzofuran-7-yl)-3-hydroxy-1,3-dihydro-2H-indol-2-one With 3.00 g of 7-bromo-2,3-dihydro-1-benzofuran and 1.10 g of 5-chloroisatin as starting material, 1.32 g of the title compound (white solid) was obtained by a similar method to Step 21-1.

MS (ESI pos.) m/z: 302 ([M+H]+), 324 ([M+Na]+), (ESI neg.) m/z: 300 ([M−H]−)
$^1$H-NMR (300 MHz, DMSO-d$_6$) δ (ppm); 2.96-3.13 (m, 2) 4.16-4.45 (m, 2H) 6.77-6.99 (m, 3H) 7.08-7.27 (m, 2H) 7.47-7.64 (m, 1H) 10.49 (s, 1H)

Step 25-2: Synthesis of (4R)-1-[5-chloro-3-(2,3-dihydro-1-benzofuran-7-yl)-2-oxo-2,3-dihydro-1H-indol-3-yl]-4-fluoro-N,N-dimethyl-L-prolinamide From 500 mg of the compound obtained in Step 25-1 and 319 mg of the compound obtained in Step 7-2-1, 449 mg of the title compound (colorless amorphous) was obtained by a similar method to Step 21-2.

MS (ESI pos.) m/z: 444 ([M+H]+), 466 ([M+Na]+), (ESI neg.) m/z: 442 ([M−H]−)
$^1$H-NMR (300 MHz, DMSO-d$_6$) δ (ppm); 1.76-2.02 (m, 1H) 2.25-2.57 (m, 1H) 2.78-3.13 (m, 3H) 3.24-3.38 (m, 6H) 3.50-3.72 (m, 1H) 4.18-4.45 (m, 2H) 4.59-4.78 (m, 1H) 5.14-5.46 (m, 1H) 6.70-6.92 (m, 2H) 7.00 (d, J=2.2 Hz, 1H) 7.09-7.26 (m, 2H) 7.57 (d, J=6.8 Hz, 1H) 10.45 (s, 1H)

Step 25-3: Synthesis of (4R)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

With 191 mg of the compound obtained in Step 25-2 and 150 mg of 4-methoxy-2-(trifluoromethoxy)benzene sulfonyl chloride as starting materials, 212 mg of the title compound (colorless amorphous) was obtained by a similar method to Example 2.

Isomer B: $[α]_D^{22}$=−166° (c=0.213, CHCl$_3$)
MS (ESI pos.) m/z: 698 ([M+H]+), (ESI neg.) m/z: 696 ([M−H]−)
$^1$H-NMR (300 MHz, CDCl$_3$) δ (ppm); 1.89-2.18 (m, 1H) 2.20-2.54 (m, 4H) 2.73 (s, 3H) 2.84-3.17 (m, 3H) 3.53-3.96 (m, 5H) 3.96-4.18 (m, 1H) 4.55-4.69 (m, 1H) 5.10-5.38 (m, 1H) 6.79-6.98 (m, 3H) 6.99-7.14 (m, 2H) 7.25 (dd, J=8.9, 2.3 Hz, 1H) 7.60 (d, J=7.2 Hz, 1H) 7.93 (d, J=8.9 Hz, 1H) 8.40 (d, J=8.9 Hz, 1H)

Example 26

Synthesis of (4R)-1-(3-(2,4-dimethoxyphenyl)-5,6-dimethoxy-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer and dextrorotatory isomer)

Step 26-1: Synthesis of 3-(2,4-dimethoxyphenyl)-3-hydroxy-5,6-dimethoxy-1,3-dihydro-2H-indol-2-one With 1.38 g of 5,6-dimethoxyisatin and 3.61 g of 2,4-dimethoxy bromobenzene as starting material, 1.37 g of the title compound (brown solid) was obtained by a similar method to Step 21-1.
MS (ESI pos.) m/z: 368 ([M+Na]$^+$)
$^1$H-NMR (300 MHz, DMSO-d$_6$) δ (ppm); 3.43 (s, 3H), 3.55 (s, 3H), 3.75 (s, 6H), 6.16 (s, 1H), 6.40 (s, 1H), 6.44 (d, J=2.3 Hz, 1H), 6.47 (s, 1H), 6.59 (dd, J=8.6, 2.3 Hz, 1H), 7.68 (d, J=8.6 Hz, 1H), 9.98 (s, 1H)

Step 26-2: Synthesis of (4R)-1-[3-(2,4-dimethoxyphenyl)-5,6-dimethoxy-2-oxo-2,3-dihydro-1H-indol-3-yl]-4-fluoro-N N-dimethyl-L-prolinamide (diastereoisomer mixture)

Under nitrogen atmosphere, to a solution of 700 mg of the compound obtained in Step 26-1 and 240 mg of Py in CHCl$_3$ (14 ml), at −78° C., was added 362 mg of thionyl chloride, and the reaction mixture was stirred for 30 minutes at the same temperature. Thereafter, to the solution was added dropwise a solution of 485 mg of the compound obtained in Step 7-2-1 and 2.05 g of Et$_3$N in CHCl$_3$ (5 ml) over 2 minutes, then, the reaction mixture was warmed to room temperature, and was stirred at room temperature for 15 hours. To the reaction solution was added EtOAc and an aqueous solution of 5% K$_2$CO$_3$, and the resulting mixture was stirred for 5 minutes. Liquid separation was performed, the aqueous layer was extracted with EtOAc, the combined organic layer was washed with saturated brine, dried over MgSO$_4$, then, the drying agent was separated by filtration, and the solution was concentrated under reduced pressure. The obtained residue was purified by column chromatography (silicagel 60N; mobile phase: EtOAc/acetone=1/1; v/v) to obtain 697 mg of a diastereoisomer mixture of the title compound (brown amorphous).
MS (ESI pos.) m/z: 510 ([M+Na]$^+$)
$^1$H-NMR (300 MHz, CDCl$_3$) δ (ppm); 1.82-5.47 (m, 24H), 6.35-6.67 (m, 4H), 7.44-8.15 (m, 2H)

Step 26-3: Synthesis of (4R)-1-(3-(2,4-dimethoxyphenyl)-5,6-dimethoxy-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer and dextrorotatory isomer)

With 200 mg of the compound obtained in Step 26-2 (diastereoisomer mixture), and 131 mg of 4-methoxy-2-(trifluoromethoxy)benzene sulfonyl chloride as starting materials, respectively 120 mg (Isomer A: red-brown amorphous) and 160 mg (Isomer B: red-brown amorphous) of two species of diastereoisomers of the title compound were obtained by a similar method to Example Isomer A: [α]$_D^{23}$=−118° (c=0.148, CHCl$_3$)
MS (ESI pos.) m/z: 764 ([M+Na]$^+$)
$^1$H-NMR (300 MHz, CDCl$_3$) δ (ppm); 1.68-4.09 (m, 25H), 4.72-5.41 (m, 2H), 6.27-8.45 (m, 8H)
Isomer B: [α]$_D^{23}$=+89° (c=0.110, CHCl$_3$)
MS (ESI pos.) m/z: 764 ([M+Na]$^+$)
$^1$H-NMR (300 MHz, CDCl$_3$) δ (ppm); 1.66-1.91 (m, 1H), 1.99-2.20 (m, 1H), 2.46 (s, 3H), 2.69 (s, 3H), 3.25-4.03 (m, 3H), 3.46 (s, 3H), 3.68 (s, 3H), 3.78 (s, 3H), 3.90 (s, 3H), 3.93 (s, 3H), 4.85-5.07 (m, 1H), 6.32 (d, J=2.5 Hz, 1H), 6.40 (s, 1H), 6.59 (dd, J=8.6, 2.4 Hz, 1H), 6.84-6.91 (m, 1H), 6.94 (dd, J=9.0, 2.3 Hz, 1H), 7.64 (s, 1H), 8.07 (d, J=8.6 Hz, 1H), 8.35 (d, J=9.0 Hz, 1H)

Example 27

Synthesis of (4R)-4-fluoro-1-[3-(2-fluorophenyl)-1-{[4-methoxy-2-(trifluoromethoxy)phenyl]sulfonyl}-2-oxo-5-(trifluoromethyl)-2,3-dihydro-1H-indol-3-yl]-N,N-dimethyl-L-prolinamide (levorotatory isomer and dextrorotatory isomer)

Step 27-1: Synthesis of 3-(2-fluorophenyl)-3-hydroxy-5-(trifluoromethyl)-1,3-dihydro-2H-indol-2-one To a solution of 2 g of tert-butyl[4-(trifluoromethyl)phenyl]carbamate in THF (15 ml) under cooling at −78° C. was added dropwise a solution of 1.0 mol/L sec-butyl lithium in cyclohexane (16.8 ml) and the reaction mixture was stirred for 1 hour. Thereafter, the solution was warmed to −40° C. and stirred under the same temperature condition for two hours. The solution was cooled again to −78° C., a solution of 2.23 g of ethyl (2-fluorophenyl)(oxo) acetate in THF (7.5 ml) was added dropwise, and the reaction mixture was stirred under the same temperature condition for two hours. Thereafter, the solution was warmed to room temperature and stirred for 12 hours. To the reaction solution was added a saturated aqueous solution of NH$_4$Cl and the resulting mixture was extracted with EtOAc. The organic layer was washed with saturated brine, dried over MgSO$_4$, then and the solvent was evaporated under reduced pressure. The residue was purified by column chromatography (silicagel 60; mobile phase: EtOAc/n-hexane=1/1; v/v) to obtain 389 mg of the title compound (colorless powder).
MS (ESI pos.) m/z: 334 ([M+Na]$^+$), (ESI neg.) m/z: 332 ([M−H]$^-$)
$^1$H-NMR (300 MHz, DMSO-d$_6$) δ (ppm); 7.01-7.13 (m, 2H), 7.18 (d, J=1.9 Hz, 1H), 7.29-7.45 (m, 2H), 7.59-7.68 (m, 1H), 7.88-8.02 (m, 1H), 10.95 (s, 1H)

Step 27-2: Synthesis of (4R)-4-fluoro-1-[3-(2-fluorophenyl)-2-oxo-5-(trifluoromethyl)-2,3-dihydro-1H-indol-3-yl]-N,N-dimethyl-L-prolinamide (diastereoisomer mixture)

From 389 mg of the compound obtained in Step 27-1 and 240 mg of the compound obtained in Step 7-2-1, 315 mg of a diastereoisomer mixture of the title compound (colorless amorphous) was obtained by a similar method to Step 21-2.
MS (ESI pos.) m/z: 454 ([M+H]$^+$, 476 ([M+Na]$^+$), (ESI neg.) m/z: 452 ([M−H]$^-$)
$^1$H-NMR (300 MHz, DMSO-d$_6$) δ (ppm); 1.75-4.65 (m, 11H), 5.12-5.41 (m, 1H), 6.89-8.15 (m, 7H), 10.88-11.10 (m, 1H)

Step 27-3: Synthesis of (4R)-4-fluoro-1-[3-(2-fluorophenyl)-1-{[4-methoxy-2-(trifluoromethoxy)phenyl]sulfonyl}-2-oxo-5-(trifluoromethyl)-2,3-dihydro-1H-indol-3-yl]-N,N-dimethyl-L-prolinamide (levorotatory isomer and dextrorotatory isomer)

With 120 mg of the compound obtained in Step 27-2 (diastereoisomer mixture) and 92 mg of 4-methoxy-2-(trifluoromethoxy)benzene sulfonyl chloride as starting material, respectively 78 mg (Isomer A: colorless solid) and 43 mg (Isomer B: colorless amorphous) of two species of diastereoisomers of the title compound were obtained by a similar method to Example 2.

Isomer A: $[\alpha]_D^{22}=-242°$ (c=0.203, CHCl$_3$)
MS (ESI pos.) m/z: 708 ([M+H]$^+$), 730 ([M+Na]$^+$)
$^1$H-NMR (300 MHz, CDCl$_3$) δ (ppm); 1.92-2.13 (m, 1H), 2.34-2.54 (m, 1H), 2.42 (s, 3H), 2.68 (s, 3H), 3.08-3.23 (m, 1H), 3.62-3.82 (m, 1H), 3.90 (s, 3H), 4.52 (dd, J=8.8, 4.9 Hz, 1H), 5.11-5.35 (m, 1H), 6.73-6.82 (m, 1H), 6.85-6.95 (m, 2H), 7.16-7.29 (m, 3H), 7.56-7.63 (m, 1H), 7.93-8.04 (m, 1H), 8.15 (d, J=8.7 Hz, 1H), 8.37 (d, J=8.9 Hz, 1H)

Isomer B: $[\alpha]_D^{22}=+162°$ (c=0.113, CHCl$_3$)
MS (ESI pos.) m/z: 708 ([M+H]$^+$), 730 ([M+Na]$^+$), (ESI neg.) m/z: 706 ([M−H]$^-$)
$^1$H-NMR (300 MHz, CDCl$_3$) δ (ppm); 1.76-2.00 (m, 1H), 2.19-2.36 (m, 1H), 2.45 (s, 3H), 2.63-2.69 (m, 3H), 3.34-3.56 (m, 1H), 3.74-3.94 (m, 1H), 3.92 (s, 3H), 3.99 (dd, J=9.3, 7.2 Hz, 1H), 4.98-5.20 (m, 1H), 6.77-6.90 (m, 2H), 6.93 (dd, J=9.0, 2.3 Hz, 1H), 7.15-7.20 (m, 1H), 7.22-7.32 (m, 2H), 7.56-7.64 (m, 1H), 8.16 (d, J=8.7 Hz, 1H), 8.26-8.37 (m, 2H)

Example 28

Synthesis of (4R)-1-(5-chloro-3-(2-isopropylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (dextrorotatory isomer)

Step 28-1: Synthesis of 5-chloro-3-hydroxy-3-(2-isopropylphenyl)-1,3-dihydro-2H-indol-2-one With 8.2 g of 1-bromo-2-isopropyl benzene and 3.0 g of 5-chloroisatin as starting materials, 4.9 g of the title compound (pale yellow amorphous) was obtained by a similar method to Step 21-1.

MS (ESI pos.) m/z: 302 ([M+H]$^+$), 324 ([M+Na]$^+$), (ESI neg.) m/z: 300 ([M−H]$^-$)
$^1$H-NMR (300 MHz, CDCl$_3$) δ (ppm); 0.71 (d, J=6.7 Hz, 3H), 1.13 (d, J=6.7 Hz, 3H), 2.31-2.66 (m, 1H), 3.94 (s, 1H), 6.73 (d, J=8.1 Hz, 1H), 7.00 (d, J=8.1 Hz, 1H), 7.16 (dd, J=8.4, 2.2 Hz, 1H), 7.21-7.46 (m, 1H), 7.87 (d, J=2.2 Hz, 1H), 8.79 (s, 1H)

Step 28-2: Synthesis of (4R)-1-[5-chloro-3-(2-isopropylphenyl)-2-oxo-2,3-dihydro-1H-indol-3-yl]-4-fluoro-N,N-dimethyl-L-prolinamide (levorotatory isomer and dextrorotatory isomer)

From 1.5 g of the compound obtained in Step 28-1 and the compound obtained in Step 7-2-1 (5.96 mmol), respectively 1.08 g (Isomer A: colorless amorphous) and 0.15 g (Isomer B: colorless amorphous) of two species of diastereoisomers of the title compound were obtained by a similar method to Step 21-2.

Isomer A: $[\alpha]_D^{28}=+110°$ (c=0.218, CHCl$_3$)
MS (ESI pos.) m/z: 444 ([M+H]$^+$), 466 ([M+Na]$^+$), (ESI neg.) m/z: 442 ([M−H]$^-$)
$^1$H-NMR (300 MHz, DMSO-d$_6$) δ (ppm); 0.45 (d, J=6.5 Hz, 3H), 1.08 (d, J=6.7 Hz, 3H), 2.18-2.42 (m, 2H), 2.46 (s, 3H), 2.57 (s, 3H), 3.18-3.51 (m, 1H), 3.62-3.95 (m, 2H), 5.09-5.27 (m, 1H), 6.47 (s, 1H), 6.91 (d, J=8.2 Hz, 1H), 7.10-7.49 (m, 4H), 8.11-8.60 (m, 1H), 10.87 (s, 1H)

Isomer B: $[\alpha]_D^{28}=-136°$ (c=0.215, CHCl$_3$)
MS (ESI pos.) m/z: 444 ([M+H]$^+$), 466 ([M+Na]$^+$), (ESI neg.) m/z: 442 ([M−H]$^-$)
$^1$H-NMR (300 MHz, DMSO-d$_6$) δ (ppm); 0.34-0.58 (m, 3H), 1.06 (d, J=6.5 Hz, 3H), 1.75-2.03 (m, 1H), 2.31-2.64 (m, 5H), 2.87-3.23 (m, 1H), 3.43-3.74 (m, 1H), 4.46-4.65 (m, 1H), 5.24-5.43 (m, 1H), 6.72-6.93 (m, 2H), 7.13-7.38 (m, 4H), 7.99 (s, 1H), 10.62 (s, 1H)

Step 28-3: Synthesis of (4R)-1-(5-chloro-3-(2-isopropylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

With 74 mg of the compound obtained in Step 28-2 (Isomer B) and 59 mg of 4-methoxy-2-(trifluoromethoxy)benzene sulfonyl chloride as starting materials, 58 mg of the title compound (colorless solid) was obtained by a similar method to Example 2.

$[\alpha]_D^{29}=-200°$ (c=0.129, CHCl$_3$)
MS (ESI pos.) m/z: 698 ([M+H]$^+$), 720 ([M+Na]$^+$)
$^1$H-NMR (300 MHz, CDCl$_3$) δ (ppm); 0.28-0.52 (m, 3H), 0.53-0.91 (m, 1H), 1.61 (s, 3H), 1.69-2.16 (m, 2H), 2.17-2.79 (m, 6H), 3.18-3.45 (m, 1H), 3.53-3.81 (m, 1H), 3.90 (s, 3H), 4.36-4.81 (m, 1H), 5.18-5.44 (m, 1H), 6.81-7.07 (m, 3H), 7.07-7.35 (m, 4H), 7.87-8.09 (m, 2H), 8.29-8.46 (m, 1H)

Example 29

Synthesis of (4R)-1-[5-chloro-1-{[4-methoxy-2-(trifluoromethoxy)phenyl]sulfonyl}-2-oxo-3-[2-(trifluoromethoxy)phenyl]-6-(trifluoromethyl)-2,3-dihydro-1H-indol-3-yl]-4-fluoro-N,N-dimethyl-L-prolinamide (levorotatory isomer)

Step 29-1: Synthesis of 5-chloro-3-hydroxy-3-[2-(trifluoromethoxy)phenyl]-6-(trifluoromethyl)-1,3-dihydro-2H-indol-2-one To a solution of 4.00 g of tert-butyl[4-chloro-3-(trifluoromethyl)phenyl]carbamate in Et$_2$O (30 ml) under cooling at −78° C. was added dropwise a solution of 1.6 mol/L tert-butyl lithium in n-pentane (21 ml), and the reaction mixture was stirred for 1 hour. Thereafter, the solution was warmed to −40° C. and was stirred under the same temperature condition for 2.5 hours. The solution was cooled again to −78° C., a solution of 4.25 g of ethyl oxo[2-(trifluoromethoxy)phenyl]acetate in THF (15 ml) was added dropwise to the reaction mixture and the reaction mixture was stirred under the same temperature condition for two hours. Thereafter, the solution was warmed to room temperature and stirred for 15 hours. To the reaction solution was added a saturated aqueous solution of NH$_4$Cl, the resulting mixture was extracted with EtOAc, the organic layer was washed with saturated brine, dried over MgSO$_4$ and the solvent was evaporated under reduced pressure. The residue was purified by column chromatography (silicagel 60; mobile phase: EtOAc/n-hexane=1/4; v/v) to obtain 3.57 g of the title compound (colorless powder).

MS (ESI neg.) m/z: 410 ([M−H]$^-$)

¹H-NMR (300 MHz, DMSO-d₆) δ (ppm); 7.20 (s, 1H), 7.22-7.31 (m, 2H), 7.47-7.56 (m, 2H), 8.05-8.13 (m, 1H), 10.99 (s, 1H)

Step 29-2: Synthesis of (4R)-1-[5-chloro-2-oxo-3-[2-(trifluoromethoxy)phenyl]-6-(trifluoromethyl)-2,3-dihydro-1H-indol-3-yl]-4-fluoro-N,N-dimethyl-L-prolinamide (levorotatory isomer and dextrorotatory isomer)

With 500 mg of the compound obtained in Step 29-1 and the compound obtained in Step 7-2-1 (1.45 mmol) as starting material, respectively 206 mg (Isomer A: pale yellow amorphous) and 174 mg (Isomer B: pale yellow amorphous) of two species of diastereoisomers of the title compound were obtained by a similar method to Step 28-2.

Isomer A: $[\alpha]_D^{28}$=−119° (c=0.101, CHCl₃)
MS (ESI pos.) m/z: 554 ([M+H]⁺), 576 ([M+Na]⁺), (ESI neg.) m/z: 552 ([M−H]⁻)
¹H-NMR (300 MHz, DMSO-d₆) δ (ppm); 1.75-2.00 (m, 1H), 2.36-2.60 (m, 1H), 2.40 (s, 3H), 2.56 (s, 3H), 3.09 (dd, J=20.9, 11.6 Hz, 1H), 3.57 (ddd, J=36.56, 12.0, 3.7 Hz, 1H), 4.70 (dd, J=8.6, 4.8 Hz, 1H), 5.19-5.49 (m, 1H), 7.09 (s, 1H), 7.21-7.31 (m, 1H), 7.37 (s, 1H), 7.49 (dd, J=6.1, 3.6 Hz, 2H), 8.15 (dd, J=6.1, 3.4 Hz, 1H), 10.89 (s, 1H)

Isomer B: $[\alpha]_D^{28}$=+51° (c=0.109, MeOH)
MS (ESI pos.) m/z: 554 ([M+H]⁺), 576 ([M+Na]⁺), (ESI neg.) m/z: 552 ([M−H]⁻)
¹H-NMR (300 MHz, DMSO-d₆) δ (ppm); 1.66-1.96 (m, 1H), 2.23-2.42 (m, 1H), 2.53 (s, 3H), 2.55 (s, 3H), 3.27-3.51 (m, 1H), 3.71-3.92 (m, 2H), 5.12-5.30 (m, 1H), 6.80 (s, 1H), 7.24 (s, 1H), 7.25-7.32 (m, 1H), 7.47-7.63 (m, 2H), 8.32 (dd, J=7.7, 1.9 Hz, 1H), 11.13 (s, 1H)

Step 29-3: Synthesis of (4R)-1-[5-chloro-1-{[4-methoxy-2-(trifluoromethoxy)phenyl]sulfonyl}-2-oxo-3-[2-(trifluoromethoxy)phenyl]-6-(trifluoromethyl)-2,3-dihydro-1H-indol-3-yl]-4-fluoro-N,N-dimethyl-L-prolinamide (levorotatory isomer)

With 100 mg of the compound obtained in Step 29-2 (Isomer B) and 63 mg of 4-methoxy-2-(trifluoromethoxy)benzene sulfonyl chloride as starting materials, 121 mg of the title compound (colorless solid) was obtained by a similar method to Example 2.

$[\alpha]_D^{22}$=−144° (c=0.211, CHCl₃)
MS (ESI pos.) m/z: 808 ([M+H]⁺), 830 ([M+Na]⁺), (ESI neg.) m/z: 806 ([M−H]⁻)
¹H-NMR (300 MHz, CDCl₃) δ (ppm); 1.70-1.95 (m, 1H), 2.09-2.25 (m, 1H), 2.44-2.50 (m, 3H), 2.77 (s, 3H), 3.27-3.48 (m, 1H), 3.62-3.77 (m, 1H), 3.89-3.98 (m, 1H), 3.91 (s, 3H), 4.87-5.11 (m, 1H), 6.85-6.89 (m, 1H), 6.95 (dd, J=9.0, 2.3 Hz, 1H), 7.02 (s, 1H), 7.12-7.19 (m, 1H), 7.35-7.48 (m, 2H), 8.33 (d, J=9.0 Hz, 1H), 8.40 (s, 1H), 8.46 (dd, J=7.8, 1.9 Hz, 1H)

Example 30

Synthesis of (4R)-1-(3-benzyl-5-chloro-1-{[4-methoxy-2-(trifluoromethoxy)phenyl]sulfonyl}-2-oxo-2,3-dihydro-1H-indol-3-yl)-4-fluoro-N,N-dimethyl-L-prolinamide Step 30-1: Synthesis of 3-benzyl-5-chloro-3-hydroxy-1,3-dihydro-2H-indol-2-one With 5.00 g of benzyl bromide and 1.50 g of 5-chloroisatin as starting material, 844 mg of the title compound (white solid) was obtained by a similar method to Step 21-1.

MS (ESI pos.) m/z: 296 ([M+Na]⁺), (ESI neg.) m/z: 272 ([M−H]⁻)
¹H-NMR (300 MHz, DMSO-d₆) δ (ppm); 2.86-3.26 (m, 2H), 6.25 (s, 1H), 6.60 (d, J=8.2 Hz, 1H), 6.92 (dd, J=6.5, 3.1 Hz, 2H), 7.04-7.27 (m, 4H), 10.19 (s, 1H)

Step 30-2: Synthesis of (4R)-1-(3-benzyl-5-chloro-2-oxo-2,3-dihydro-1H-indol-3-yl)-4-fluoro-N,N-dimethyl-L-prolinamide (diastereoisomer mixture)

With 200 mg of the compound obtained in Step 30-1 and 161 mg of the compound obtained in Step 7-2-1 as starting materials, 96 mg of a diastereoisomer mixture of the title compound (colorless solid) was obtained by a similar method to Step 21-2.

MS (ESI pos.) m/z: 416 ([M+H]⁺), 438 ([M+Na]⁺), (ESI neg.) m/z: 414 ([M−H]⁻)
¹H-NMR (300 MHz, DMSO-d₆) δ (ppm); 1.71-4.19 (m, 12H), 4.57-4.82 (m, 1H), 5.02-5.54 (m, 1H), 6.28-7.43 (m, 8H), 10.10-10.41 (m, 1H)

Step 30-3: Synthesis of (4R)-1-(3-benzyl-5-chloro-1-{[4-methoxy-2-(trifluoromethoxy)phenyl]sulfonyl}-2-oxo-2,3-dihydro-1H-indol-3-yl)-4-fluoro-N,N-dimethyl-L-prolinamide With 87 mg of the compound obtained in Step 30-2 and of 74 mg 4-methoxy-2-(trifluoromethoxy)benzene sulfonyl chloride as starting materials, 67 mg of the title compound (colorless solid) was obtained by a similar method to Example 2.

MS (ESI pos.) m/z: 670 ([M+H]⁺), 692 ([M+Na]⁺), (ESI neg.) m/z: 668 ([M−H]⁻)
¹H-NMR (300 MHz, CDCl₃) δ (ppm); 1.83-2.09 (m, 1H), 2.22-2.46 (m, 1H), 2.74-2.89 (m, 6H), 2.91-3.09 (m, 2H), 3.20 (d, J=12.9 Hz, 1H), 3.53-3.77 (m, 1H), 3.91 (s, 3H), 4.74 (t, J=7.5 Hz, 1H), 4.95-5.27 (m, 1H), 6.62-6.79 (m, 3H), 6.87-7.02 (m, 3H), 7.04-7.13 (m, 1H), 7.17-7.32 (m, 2H), 7.65 (d, J=8.4 Hz, 1H), 8.25 (d, J=9.0 Hz, 1H)

Example 31

Synthesis of (2S)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer)

With 500 mg of (2S)-1-[5-chloro-3-(2-methoxyphenyl)-2-oxo-2,3-dihydro-1H-indol-3-yl]-N,N-dimethylpiperidine-2-carboxamide, which is the compound described in Preparation 3.49 (Isomer B) of Publication No. WO01/98295 and 374 mg of 4-methoxy-2-(trifluoromethoxy)benzene sulfonyl chloride as starting materials, 322 mg of the title compound (colorless amorphous) was obtained by a similar method to Example 2.

$[\alpha]_D^{28}$=169° (c=0.198, CHCl₃)
MS (ESI pos.) m/z: 682 ([M+H]⁺)
¹H-NMR (300 MHz, CDCl₃) δ (ppm); 1.42-1.96 (m, 6H), 2.16-3.53 (m, 7H), 2.96 (s, 3H), 3.80-3.85 (m, 1H), 3.89 (s, 3H), 3.94-4.05 (m, 1H), 6.61-6.67 (m, 1H), 6.72 (d, J=2.3 Hz, 1H), 6.85-6.97 (m, 1H), 6.94 (dd, J=9.0, 2.3 Hz, 1H), 6.99-7.06 (m, 1H), 7.16-7.28 (m, 2H), 7.82-7.97 (m, 1H), 7.94 (d, J=8.7 Hz, 1H), 8.50 (d, J=8.86 Hz, 1H)

Example 32

Synthesis of (2S)-1-(5-chloro-3-(2-methoxyphenyl)-1-{[2-methoxy-4-(trifluoromethoxy)phenyl]sulfonyl}-2-oxo-2,3-dihydro-1H-indol-3-yl)-N,N-dimethylpiperidine-2-carboxamide (levorotatory isomer)

With 303 mg of (2S)-1-[5-chloro-3-(2-methoxyphenyl)-2-oxo-2,3-dihydro-1H-indol-3-yl]-N,N-dimethylpiperidine-2-carboxamide, which is the compound described in Preparation 3.49 (Isomer B) of the brochure Publication No. WO01/98295 and 245 mg of 2-methoxy-4-(trifluoromethoxy) benzene sulfonyl chloride as starting materials, 216 mg of the title compound (colorless amorphous) was obtained by a similar method to Example 1.

$[\alpha]_D^{25} = -179°$ (c=0.232, CHCl$_3$)
MS (ESI pos.) m/z: 682 ([M+H]$^+$), 704 ([M+Na]$^+$), (ESI neg.) m/z: 680 ([M−H]$^-$)
$^1$H-NMR (300 MHz, DMSO-d$_6$) δ (ppm); 1.15-1.98 (m, 6H), 2.20 (s, 3H), 2.52-2.84 (m, 7H), 3.69-3.90 (m, 5H), 6.72-6.87 (m, 2H), 7.08 (t, J=7.5 Hz, 1H), 7.20-7.39 (m, 3H), 7.48 (dd, J=8.9, 2.3 Hz, 1H), 7.78-7.95 (m, 2H), 8.18 (d, J=8.9 Hz, 1H)

Example 33

Synthesis of (2S)-1-[1-{[2,5-bis(2,2,2-trifluoroethoxy)phenyl]sulfonyl}-5-chloro-3-(2-methoxyphenyl)-2-oxo-2,3-dihydro-1H-indol-3-yl]-N,N-dimethylpiperidine-2-carboxamide (levorotatory isomer)

With 200 mg of (2S)-1-[5-chloro-3-(2-methoxyphenyl)-2-oxo-2,3-dihydro-1H-indol-3-yl]-N,N-dimethylpiperidine-2-carboxamide, which is the compound described in Preparation 3.49 (Isomer B) of the brochure No. WO01/98295, and 183 mg of 2,5-bis(2,2,2-trifluoroethoxy)benzene sulfonyl chloride as starting materials, 238 mg of the title compound (colorless amorphous) was obtained by a similar method to Example 2.

$[\alpha]_D^{22} = -203°$ (c=0.183, CHCl$_3$)
MS (ESI pos.) m/z: 764 ([M+H]$^+$)
$^1$H-NMR (300 MHz, CDCl$_3$) δ (ppm); 1.04-4.70 (m, 22H), 6.61-6.76 (m, 2H), 7.00-7.13 (m, 2H), 7.18-7.31 (m, 3H), 7.86-7.92 (m, 2H), 7.97-8.04 (m, 1H)

Example 34

Synthesis of (2S)-1-[5-chloro-1-{[4-methoxy-2-(trifluoromethoxy)phenyl]sulfonyl}-3-(2-naphthyl)-2-oxo-2,3-dihydro-1H-indol-3-yl]-N,N-dimethylpiperidine-2-carboxamide (levorotatory isomer)

Step 34-1: Synthesis of tert-butyl (2S)-2-[(dimethylamino)carbonyl]piperidine-1-carboxylate With 10.0 g of (2S)-1-(tert-butoxy carbonyl)piperidine-2-carboxylic acid as starting materials, 10.8 g of the title compound (colorless crystal) was obtained by a similar method to Step 6-1a.

MS (ESI pos.) m/z: 308 ([M−H]$^-$)
$^1$H-NMR (300 MHz, DMSO-d$_6$) δ (ppm); 3.14-3.78 (m, 9H), 3.52 (s, 3H), 3.90 (s, 3H), 4.08 (d, J=16.2 Hz, 1H), 6.90-7.07 (m, 3H), 7.10-7.19 (m, 4H), 7.27-7.37 (m, 2H), 7.62 (dd, J=7.9, 1.2 Hz, 1H), 7.72 (d, J=8.7 Hz, 1H), 8.14 (d, J=9.0 Hz, 1H), 8.25 (s, 1H), 8.27 (s, 1H)

Step 34-2 Synthesis of: (2S)—N,N-dimethylpiperidine-2-carboxamide trifluoroacetate With 1.67 g of the compound obtained in Step 34-1 as starting material, the title compound (crude form) was obtained by a similar method to Step 4-1. The present compound was used in the reaction of Step 34-4 without purification.

MS (ESI pos.) m/z: 157 ([M+H]$^+$), 179 ([M+Na]$^+$)
$^1$H-NMR (300 MHz, DMSO-d$_6$) δ (ppm); 1.32-1.49 (m, 1H), 1.51-1.81 (m, 4H), 1.97-2.08 (m, 1H), 2.82-3.05 (m, 1H), 2.89 (s, 3H), 3.02 (s, 3H), 3.18-3.28 (m, 1H), 4.25-4.37 (m, 1H), 8.46-8.65 (m, 1H), 8.78-8.94 (m, 1H),

Step 34-3: Synthesis of 5-chloro-3-hydroxy-3-(2-naphthyl)-1,3-dihydro-2H-indol-2-one With 11.10 g of 2-bromonaphthalene and 5.00 g of 5-chloroisatin as starting materials, 7.81 g of the title compound (yellow solid) was obtained by a similar method to Step 21-1.

MS (ESI pos.) m/z: 308 ([M−H]$^-$)
$^1$H-NMR (300 MHz, DMSO-d$_6$) δ (ppm); 6.90-7.01 (m, 2H), 7.14 (d, J=2.3 Hz, 1H), 7.28-7.39 (m, 2H), 7.45-7.57 (m, 2H), 7.79-7.98 (m, 4H), 10.64 (s, 1H)

Step 34-4: Synthesis of (2S)-1-[5-chloro-3-(2-naphthyl)-2-oxo-2,3-dihydro-1H-indol-3-yl]-N,N-dimethylpiperidine-2-carboxamide (levorotatory isomer)

From 2.02 g of the compound obtained in Step 34-3 and the compound obtained in Step 34-2 (6.51 mmol), respectively 1.77 g (Isomer A: beige amorphous) and 476 mg (Isomer B: light yellow amorphous) of two species of diastereoisomers of the title compound were obtained by a similar method to Step 21-2.

Isomer A: $[\alpha]_D^{25} = -127°$ (c=0.256, CHCl$_3$)
MS (ESI neg.) m/z: 446 ([M−H]$^-$)
$^1$H-NMR (300 MHz, DMSO-d$_6$) δ (ppm); 1.36-1.97 (m, 7H), 2.34 (s, 3H), 2.76 (s, 3H), 3.79-3.94 (m, 1'H), 4.08 (d, J=4.0 Hz, 1H), 6.87-6.93 (m, 1H), 7.28-7.35 (m, 2H), 7.42-7.57 (m, 3H), 7.78-7.97 (m, 4H), 10.73 (s, 1H)
Isomer B: $[\alpha]_D^{25} = -221°$ (c=0.204, CHCl$_3$)
MS (ESI neg.) m/z: 446 ([M−H]$^-$)
$^1$H-NMR (300 MHz, DMSO-d$_6$) δ (ppm); 1.34-2.01 (m, 7H), 2.19 (s, 3H), 2.64 (s, 3H), 3.83-4.15 (m, 2H), 6.85 (d, J=8.4 Hz, 1H), 7.14 (d, J=2.2 Hz, 1H), 7.22 (dd, J=8.4, 2.2 Hz, 1H), 7.45-7.55 (m, 3H), 7.74-7.98 (m, 4H), 10.62 (s, 1H)

Step 34-5: Synthesis of (2S)-1-[5-chloro-1-{[4-methoxy-2-(trifluoromethoxy)phenyl]sulfonyl}-3-(2-naphthyl)-2-oxo-2,3-dihydro-1H-indol-3-yl]-N,N-dimethylpiperidine-2-carboxamide (levorotatory isomer)

With 200 mg of the compound obtained in Step 34-4 (Isomer B) and 154 mg of 4-methoxy-2-(trifluoromethoxy)benzene sulfonyl chloride as starting materials, 198 mg of the title compound (colorless amorphous) was obtained by a similar method to Example 2.

$[\alpha]_D^{25} = -269°$ (c=0.183, CHCl$_3$)
MS (ESI pos.) m/z: 724 ([M+Na]$^+$)
$^1$H-NMR (300 MHz, DMSO-d$_6$) δ (ppm); 1.17-2.04 (m, 6H), 2.24 (s, 3H), 2.37-2.77 (m, 4H), 3.70-3.85 (m, 1H), 3.96-4.08 (m, 4H), 7.08-7.25 (m, 2H), 7.30-7.63 (m, 7H), 7.75-7.95 (m, 3H), 8.30 (d, J=9.0 Hz, 1H)

Example 35

Synthesis of (2S)-1-(5-chloro-1-{[4-methoxy-2-(trifluoromethoxy)phenyl]sulfonyl}-2-oxo-3-phenyl-2,3-dihydro-1H-indol-3-yl)-N,N-dimethylpiperidine-2-carboxamide (levorotatory isomer)

Step 35-1: Synthesis of (2S)-1-(5-chloro-2-oxo-3-phenyl-2,3-dihydro-1H-indol-3-yl)-N,N-dimethylpiperidine-2-carboxamide From 1.70 g of 5-chloro-3-hydroxy-3-phenyl-1,3-dihydro-2H-indol-2-one, which is the compound described in the Specification of U.S. Pat. No. 3,801,593 and the compound obtained in Step 34-2 (6.51 mmol), respectively 1.68 g (Isomer A: light yellow amorphous) and 412 mg (Isomer B: light yellow amorphous) of two species of diastereoisomers of the title compound were obtained by a similar method to Step 21-2.

Isomer A: $[\alpha]_D^{25}=-70°$ (c=0.242, CHCl$_3$)
MS (ESI pos.) m/z: 420 ([M+Na]$^+$), (ESI neg.) m/z: 396 ([M−H]$^-$)
$^1$H-NMR (300 MHz, DMSO-d$_6$) δ (ppm); 1.34-1.89 (m, 6H), 2.21-2.56 (m, 4H), 2.75 (s, 3H), 3.76-3.92 (m, 1H), 3.99-4.09, (m, 1H), 6.85 (d, J=8.2 Hz, 1H), 7.16-7.40 (m, 7H), 10.67 (s, 1H)

Isomer B: $[\alpha]_D^{25}=-263°$ (c=0.245, CHCl$_3$) MS (ESI pos.) m/z: 420 ([M+Na]$^+$), (ESI neg.) m/z: 396 ([M−H]$^-$)
$^1$H-NMR (300 MHz, DMSO-d$_6$) δ (ppm); 1.24-1.95 (m, 6H), 2.19 (s, 3H), 2.36-2.76 (m, 4H), 3.80-4.07 (m, 2H), 6.82 (d, J=8.4 Hz, 1H), 7.04 (d, J=2.2 Hz, 1H), 7.17-7.41 (m, 4H), 7.43-7.51 (m, 2H), 10.55 (s, 1H)

Step 35-2: Synthesis of (2S)-1-(5-chloro-1-{[4-methoxy-2-(trifluoromethoxy)phenyl]sulfonyl}-2-oxo-3-phenyl-2,3-dihydro-1H-indol-3-yl)-N,N-dimethylpiperidine-2-carboxamide (levorotatory isomer)

With 200 mg of the compound obtained in Step 35-1 (Isomer B) and 190 mg of 4-methoxy-2-(trifluoromethoxy)benzene sulfonyl chloride as starting materials, 106 mg of the title compound (colorless amorphous) was obtained by a similar method to Example 2.

$[\alpha]_D^{25}=-256°$ (c=0.222, CHCl$_3$)
MS (ESI pos.) m/z: 652 ([M+H]$^+$), 674 ([M+Na]$^+$)
$^1$H-NMR (300 MHz, DMSO-d$_6$) δ (ppm); 1.20-1.97 (m, 6H), 2.23 (s, 3H), 2.35-2.69 (m, 4H), 3.64-3.78 (m, 1H), 3.92-4.01 (m, 4H), 7.04-7.15 (m, 3H), 7.23-7.33 (m, 5H), 7.47 (dd, J=8.9, 2.3 Hz, 1H), 7.76 (d, J=8.9 Hz, 1H), 8.23 (d, J=8.9 Hz, 1H)

Example 36

Synthesis of (2S)-1-(5-chloro-1-{[4-methoxy-2-(trifluoromethoxy)phenyl]sulfonyl}-2-oxo-3-pyridin-2-yl-2,3-dihydro-1H-indol-3-yl)-N,N-dimethylpiperidine-2-carboxamide (levorotatory isomer)

Step 36-1: Synthesis of 5-chloro-3-hydroxy-3-pyridin-2-yl-1,3-dihydro-2H-indol-2-one With 10.0 g of 5-chloro-1H-indol-2,3-dione and 25.3 g of bromo pyridine as starting materials, 5.03 g of the title compound (orange color solid) was obtained by a similar method to Step 34-3.

MS (ESI pos.) m/z: 283 ([M+Na]$^+$), (ESI neg.) m/z: 259 ([M−H]$^-$)

$^1$H-NMR (200 MHz, DMSO-d$_6$) δ (ppm); 6.87 (d, J=8.4 Hz, 1H), 6.95-7.01 (m, 2H), 7.20-7.33 (m, 2H), 7.79-7.94 (m, 2H), 8.32-8.38 (m, 1H), 10.51 (s, 1H)

Step 36-2: Synthesis of (2S)-1-(5-chloro-2-oxo-3-pyridin-2-yl-2,3-dihydro-1H-indol-3-yl)-N,N-dimethylpiperidine-2-carboxamide (levorotatory isomer and dextrorotatory isomer)

With 1.70 g of the compound obtained in Step 36-1 as starting material, respectively 1.03 g (Isomer A: light yellow amorphous) and 1.52 g (Isomer B: light yellow amorphous) of two species of diastereoisomers of the title compound were obtained by a similar method to Step 34-4.

Isomer A: $[\alpha]_D^{25}=+111°$ (c=0.262, CHCl$_3$)
MS (ESI pos.) m/z: 421 ([M+Na]$^+$), (ESI neg.) m/z: 397 ([M−H]$^-$)
$^1$H-NMR (300 MHz, DMSO-d$_6$) δ (ppm); 1.37-1.86 (m, 6H), 2.35-2.61 (m, 4H), 2.75 (s, 3H), 3.76-3.90 (m, 1H), 4.03-4.10 (m, 1H), 6.78 (d, J=8.2 Hz, 1H), 7.07 (d, J=2.2 Hz, 1H), 7.19 (dd, J=8.2, 2.2 Hz, 1H), 7.25-7.32 (m, 1H), 7.83-7.92 (m, 1H), 7.99-8.06 (m, 1H), 8.31-8.36 (m, 1H), 10.64 (s, 1H)

Isomer B: $[\alpha]_D^{25}=-293°$ (c=0.232, CHCl$_3$)
MS (ESI pos.) m/z: 399 ([M+H]$^+$), 421 ([M+Na]$^+$), (ESI neg.) m/z: 397 ([M−H]$^-$)
$^1$H-NMR (300 MHz, DMSO-d$_6$) δ (ppm); 1.37-1.68 (m, 5H), 1.82-1.98 (m, 1H), 2.20 (s, 3H), 2.52-2.67 (m, 4H), 3.97-4.13 (m, 2H), 6.78 (d, J=8.4 Hz, 1H), 6.92 (d, J=2.2 Hz, 1H), 7.16-7.29 (m, 2H), 7.83-7.99 (m, 2H), 8.30-8.38 (m, 1H), 10.34 (s, 1H)

Step 36-3: Synthesis of (2S)-1-(5-chloro-1-{[4-methoxy-2-(trifluoromethoxy)phenyl]sulfonyl}-2-oxo-3-pyridin-2-yl-2,3-dihydro-1H-indol-3-yl)-N,N-dimethylpiperidine-2-carboxamide (levorotatory isomer)

With 300 mg of the compound obtained in Step 36-2 (Isomer B) as starting material, 202 mg of the title compound (light yellow amorphous) was obtained by a similar method to Example 2.

$[\alpha]_D^{25}=-297°$ (c=0.205, CHCl$_3$)
MS (ESI pos.) m/z: 653 ([M+H]$^+$), 675 ([M+Na]$^+$)
$^1$H-NMR (300 MHz, DMSO-d$_6$) δ (ppm); 1.30-1.74 (m, 5H), 1.81-2.02 (m, 1H), 2.24 (s, 3H), 2.41-2.71 (m, 4H), 3.82-3.97 (m, 4H), 4.06 (dd, J=5.9, 0.9 Hz, 1H), 7.04-7.12 (m, 1H), 7.13-7.27 (m, 3H), 7.42 (dd, J=8.9, 2.3 Hz, 1H), 7.73 (d, J=8.9 Hz, 1H), 7.80-7.94 (m, 2H), 8.04 (dd, J=4.6, 1.5 Hz, 1H), 8.17 (d, J=8.9 Hz, 1H)

Example 37

Synthesis of 2-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl isoindoline-1-carboxamide With 1.00 g of 2-[5-chloro-3-(2-methoxyphenyl)-2-oxo-2,3-dihydro-1H-indol-3-yl]-N,N-dimethyl isoindoline-1-carboxamide (diastereoisomer mixture), which is the compound described in Preparation 3.5 of the brochure Publication No. WO01/64668, and 692 mg of 4-methoxy-2-(trifluoromethoxy)benzene sulfonyl chloride as starting materials, 770 mg (Isomer mixture A, colorless amorphous) and 423 mg (Isomer mixture B, colorless amorphous) each of mixtures of diastereoisomers of the title compound were obtained by a similar method to Example 2.

Isomer mixture A: [α]$_D^{21}$=−783° (c=0.219, CHCl$_3$)
MS (ESI pos.) m/z: 716 ([M+H]$^+$)
$^1$H-NMR (300 MHz, CDCl$_3$) δ (ppm); 2.66 (s, 3H), 2.84 (s, 3H), 3.58 (s, 3H), 3.76 (s, 3H), 4.43-4.54 (m, 1H), 4.59-4.70 (m, 1H), 4.91-4.98 (m, 1H), 6.51 (s, 1H), 6.73 (dd, J=9.0, 2.3 Hz, 1H), 6.82 (d, J=8.1 Hz, 1H), 6.86-6.94 (m, 1H), 6.96 (d, J=2.3 Hz, 1H), 6.98-7.05 (m, 1H), 7.07-7.18 (m, 3H), 7.24-7.36 (m, 2H), 7.92 (d, J=8.7 Hz, 1H), 8.13 (d, J=9.0 Hz, 1H), 8.21 (d, J=6.8 Hz, 1H)

Isomer mixture B: [α]$_D^{21}$=−42.8° (c=0.185, CHCl$_3$)
MS (ESI pos.) m/z: 716 ([M+H]$^+$)
$^1$H-NMR (300 MHz, CDCl$_3$) δ (ppm); 2.46-3.02 (m, 3H), 2.63 (s, 3H), 3.27-3.94 (m, 4H), 3.84 (s, 3H), 4.36-4.50 (m, 1H), 5.86-6.02 (m, 1H), 6.49-8.49 (m, 12H), 6.81 (d, J=8.1 Hz, 1H), 7.90 (d, J=8.7 Hz, 1H)

Example 38

Synthesis of (3S)-2-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl-1,2,3,4-tetrahydroisoquinoline-3-carboxamide (levorotatory isomer)

From 1.00 g of (3S)-2-[5-chloro-3-(2-methoxyphenyl)-2-oxo-2,3-dihydro-1H-indol-3-yl]-N,N-dimethyl-1,2,3,4-tetrahydroisoquinoline-3-carboxamide (diastereoisomer mixture), which is the compound described in Preparation 3.1 of the brochure Publication No. WO01/64668, and 747 mg of 4-methoxy-2-(trifluoromethoxy)benzene sulfonyl chloride, respectively 190 mg (Isomer A, colorless amorphous) and 704 mg (Isomer B, colorless amorphous) of diastereoisomers of the title compound were obtained by a similar method to Example 2.

Isomer A: [α]$_D^{21}$=−731° (c=0.208, CHCl$_3$)
MS (ESI pos.) m/z: 730 ([M+H]$^+$)
$^1$H-NMR (300 MHz, CDCl$_3$) δ (ppm); 2.05-4.80 (m, 17H), 6.22-8.53 (m, 14H)

Isomer B: [α]$_D^{21}$=−94° (c=0.207, CHCl$_3$)
MS (ESI pos.) m/z: 730 ([M+Na]$^+$)
$^1$H-NMR (300 MHz, CDCl$_3$) δ (ppm); 2.21-5.20 (m, 17H), 6.16-8.59 (m, 14H)

Example 39

Synthesis of (3S)-2-(5-chloro-3-(2-methoxyphenyl)-1-{[2-methoxy-4-(trifluoromethoxy)phenyl]sulfonyl}-2-oxo-2,3-dihydro-1H-indol-3-yl)-N,N-dimethyl-1,2,3,4-tetrahydroisoquinoline-3-carboxamide (levorotatory isomer and dextrorotatory isomer)

With 498 mg of (3S)-2-[5-chloro-3-(2-methoxyphenyl)-2-oxo-2,3-dihydro-1H-indol-3-yl]-N,N-dimethyl-1,2,3,4-tetrahydroisoquinoline-3-carboxamide, which is the compound described in Preparation 3.1 of the brochure Publication No. WO01/64668, and 373 mg of 2-methoxy-4-(trifluoromethoxy)benzene sulfonyl chloride as starting materials, respectively 50 mg (Isomer A: colorless amorphous) and 230 mg (Isomer B: colorless amorphous) of two species of diastereoisomers, which are the title compounds, were obtained by a similar method to Example 1.

Isomer A: [α]$_D^{25}$=+132° (c=0.187, CHCl$_3$)
MS (ESI pos.) m/z: 730 ([M+H]$^+$), 752 ([M+Na]$^+$), (ESI neg.) m/z: 728 ([M−H]$^-$)
$^1$H-NMR (300 MHz, DMSO-d$_6$) δ (ppm); 1.93-2.10 (m, 1H), 2.42-2.81 (m, 8H), 3.22-3.65 (m, 4H), 3.72-4.58 (m, 4H), 6.57-7.59 (m, 11H), 7.73-8.31 (m, 3H)

Isomer B: [α]$_D^{25}$=−227° (c=0.228, CHCl$_3$)
MS (ESI pos.) m/z: 730 ([M+H]$^+$), 752 ([M+Na]$^+$), (ESI neg.) m/z: 728 ([M−H]$^-$)
$^1$H-NMR (300 MHz, DMSO-d$_6$) δ (ppm); 2.22-5.03 (m, 17H), 6.78-7.46 (m, 10H), 7.53 (dd, J=8.9, 2.3 Hz, 1H), 7.64 (dd, J=7.9, 1.6 Hz, 1H), 7.85 (d, J=8.9 Hz, 1H), 8.19 (d, J=8.6 Hz, 1H)

Example 40

Synthesis of (2S)-5'-chloro-3'-(2-methoxyphenyl)-1'-{[4-methoxy-2-(trifluoromethoxy)phenyl]sulfonyl}-N,N-dimethyl-2'-oxo-2,2',3,3'-tetrahydro-1'H-1,3'-biindole-2-carboxamide (levorotatory isomer)

With 400 mg of (2S)-5'-chloro-3'-(2-methoxyphenyl)-N,N-dimethyl-2'-oxo-2,2',3,3'-tetrahydro-1'H-1,3'-biindole-2-carboxamide, which is the compound described in Preparation 3.3 (−)-isomer of the brochure Publication No. WO01/64668 as starting material, 175 mg of the title compound (colorless amorphous) was obtained by a similar method to Example 2.

[α]$_D^{17}$=−318° (c=0.202, CHCl$_3$)
MS (ESI pos.) m/z: 716 ([M+H]$^+$), 738 ([M+Na]$^+$), (ESI neg.) m/z: 714 ([M−H]$^-$)
$^1$H-NMR (300 MHz, DMSO-d$_6$) δ (ppm); 2.39-2.78 (m, 7H), 3.44-3.62 (m, 4H), 3.89 (s, 3H), 5.19 (dd, J=11.8, 4.7 Hz, 1H), 6.23 (d, J=7.6 Hz, 1H), 6.39-6.52 (m, 1H), 6.60-6.73 (m, 1H), 6.83-7.07 (m, 4H), 7.15-7.35 (m, 3H), 7.39-7.52 (m, 2H), 7.71 (d, J=9.0 Hz, 1H), 8.22 (d, J=9.0 Hz, 1H)

Example 41

Synthesis of (3S)-4-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethylmorpholine-3-carboxamide (levorotatory isomer)

Step 41-1: Synthesis of tert-butyl (3S)-3-[(dimethylamino)carbonyl]-4-morpholine carboxylate With 1.16 g of (3S)-4-(tert-butoxy carbonyl)-3-morpholine carboxylic acid as starting material, 1.06 g of the title compound (colorless solid) was obtained by a similar method to Step 6-1a.
MS (ESI pos.) m/z: 281 ([M+Na]$^+$)
$^1$H-NMR (300 MHz, CDCl$_3$) δ (ppm); 1.46 (s, 9H), 2.98 (s, 3H), 3.03 (s, 3H), 3.39-4.21 (m, 6H), 4.53-4.89 (m, 1H)

Step 41-2: Synthesis of (3S)—N,N-dimethyl-3-morpholine carboxamide trifluoroacetate With 1.04 g of the compound obtained in Step 41-1 as starting material, 1.31 g of the title compound (crude form, pale yellow oil) was obtained by a similar method to Step 4-1. The present compound was used in the next reaction without purification.

Step 41-3: Synthesis of (3S)-4-[5-chloro-3-(2-methoxyphenyl)-2-oxo-2,3-dihydro-1H-indol-3-yl]-N,N-dimethylmorpholine-3-carboxamide (levorotatory isomer and dextrorotatory isomer)

To a suspension of 1.31 g of the compound obtained in Step 41-2 and 1.13 g of 3,5-dichloro-3-(2-methoxyphenyl)-1,3- dihydro-2H-indol-2-one in CHCl₃ (7 ml) was added 2.22 g of Et₃N under ice cooling. The solution was stirred at room temperature for 15 hours, then, the precipitated solid was collected by filtration, washed with water, and dried to obtain 168 mg (Isomer A: colorless amorphous).

The residue of the filtrate was purified by column chromatography (silicagel 60; mobile phase: CHCl₃/MeOH=9/1 to 4/1; v/v) to obtain 641 mg of the title compound (Isomer B: colorless amorphous).

Isomer A: $[\alpha]_D^{17}$=+124° (c=0.244, CHCl₃)
MS (ESI pos.) m/z: 430 ([M+H]⁺), 452 ([M+Na]⁺), (ESI neg.) m/z: 428 ([M−H]⁻)
¹H-NMR (300 MHz, DMSO-d₆) δ (ppm); 2.52-2.85 (m, 7H), 3.37-3.80 (m, 9H), 6.57-6.62 (m, 1H), 6.78 (d, J=8.1 Hz, 1H), 6.92 (dd, J=8.1, 0.9 Hz, 1H), 7.06-7.19 (m, 2H), 7.24-7.33 (m, 1H), 7.99 (d, J=7.3 Hz, 1H), 10.52 (s, 1H)

Isomer B: $[\alpha]_D^{17}$=−158° (c=0.192, CHCl₃)
MS (ESI pos.) m/z: 430 ([M+H]⁺), 452 ([M+Na]⁺), (ESI neg.) m/z: 428 ([M−H]⁻)
¹H-NMR (300 MHz, DMSO-d₆) δ (ppm); 2.24 (s, 3H), 2.42-2.63 (m, 4H), 3.42 (s, 3H), 3.52-3.66 (m, 1H), 3.71-3.92 (m, 4H), 4.05-4.19 (m, 1H), 6.68 (d, J=2.2 Hz, 1H), 6.75 (d, J=8.3 Hz, 1H), 6.91 (dd, J=8.3, 1.1 Hz, 1H), 7.03-7.12 (m, 1H), 7.19 (dd, J=8.3, 2.3 Hz, 1H), 7.23-7.32 (m, 1H), 7.94 (dd, J=7.7, 1.6 Hz, 1H), 10.17 (s, 1H)

Step 41-4: Synthesis of (3S)-4-(5-chloro-3-(2-methoxyphenyl)-1-{[4-methoxy-2-(trifluoromethoxy)phenyl]sulfonyl}-2-o xo-2,3-dihydro-1H-indol-3-yl)-N,N-dimethylmorpholine-3-carboxamide (levorotatory isomer)

With 381 mg of the compound obtained in Step 41-3 (Isomer B) as starting material, 188 mg of the title compound (colorless amorphous) was obtained by a similar method to Example 2.

$[\alpha]_D^{17}$=−169° (c=0.220, CHCl₃)
MS (ESI pos.) m/z: 684 ([M+H]⁺), 706 ([M+Na]⁺)
¹H-NMR (300 MHz, DMSO-d₆) δ (ppm); 2.22-2.61 (m, 7H), 3.14 (s, 3H), 3.43-3.98 (m, 9H), 6.84-6.91 (m, 2H), 7.05-7.13 (m, 2H), 7.24-7.35 (m, 2H), 7.44 (dd, J=8.8, 2.3 Hz, 1H), 7.72 (d, J=8.8 Hz, 1H), 7.90-8.02 (m, 1H), 8.26 (d, J=9.2 Hz, 1H)

Example 42

Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl azetidine-2-carboxamide (diastereoisomer mixture)

Step 42-1: Synthesis of 1-(tert-butoxy carbonyl) N,N-dimethyl azetidine-2-carboxamide With 500 mg of 1-(tert-butoxy carbonyl) azetidine-2-carboxylic acid as starting materials, 385 mg of the title compound (colorless oil) was obtained by a similar method to Step 6-1a.

MS (ESI pos.) m/z: 251 ([M+H]⁺)
¹H-NMR (300 MHz, CDCl₃) δ (ppm); 1.43 (s, 9H) 2.10-2.25 (m, 1H) 2.35-2.50 (m, 1H) 2.99 (s, 3H) 3.00 (s, 3H) 3.80-3.92 (m, 1H) 3.97-4.12 (m, 1H) 4.96 (dd, J=8.78, 5.36 Hz, 1H)

Step 42-2: Synthesis of 1-[5-chloro-3-(2-methoxyphenyl)-2-oxo-2,3-dihydro-1H-indol-3-yl]-N,N-dimethyl azetidine-2-carboxamide To a solution of 385 mg of the compound obtained in Step 42-1 in CHCl₃ (4 ml) was added TFA (0.65 ml), and the reaction mixture was stirred for two hours. After the end of the reaction and the solvent was evaporated under reduced pressure. To a solution of the obtained residue in CHCl₃ (5 ml) was added 408 mg of 3,5-dichloro-3-(2-methoxyphenyl)-1,3-dihydro-2H-indol-2-one and was slowly added dropwise Et₃N (2.0 ml) under ice cooling, then, the reaction mixture was stirred at room temperature for 10 hours. To the reaction solution was added water, the resulting mixture was extracted with CHCl₃, the organic layer was washed with saturated brine, dried over MgSO₄, then and the solvent was evaporated under reduced pressure. The residue was washed with Et₂O, and then filtered to obtain of 513 mg the title compound (colorless solid).

MS (ESI pos.) m/z: 400 ([M+H]⁺), 422 ([M+Na]⁺), (ESI neg.) m/z: 398 ([M−H]⁻)
¹H NMR (300 MHz, DMSO-d₆) δ (ppm); 1.67-3.47 (m, 4H), 2.38-2.50 (m, 3H), 2.63-2.70 (m, 3H), 3.48-3.53 (m, 3H), 3.85-5.15 (m, 1H), 6.55-7.32 (m, 6H), 7.70-7.90 (m, 1H), 10.64 (m, 1H), 10.77 (m, 1H)

Step 42-3: Synthesis of 1-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl azetidine-2-carboxamide (diastereoisomer mixture)

With 200 mg of the compound obtained in Step 42-2 and 160 mg of 4-methoxy-2-(trifluoromethoxy)benzene sulfonyl chloride as starting materials, 229 mg of a diastereoisomer mixture of the title compound (colorless amorphous) was obtained by a similar method to Example 2.

MS (ESI pos.) m/z: 654 ([M+H]⁺), 676 ([M+Na]⁺), (ESI neg.) m/z: 652 ([M−H]⁻)
¹H-NMR (300 MHz, CDCl₃) δ (ppm); 1.75-1.84 (m, 1H), 1.95-2.03 (m, 0.5H), 2.17-2.27 (m, 0.5H), 2.31 (s, 1.5H), 2.56-2.61 (m, 0.5H), 2.64 (s, 1.5H), 2.65 (s, 1.5H), 2.71 (s, 1.5H), 2.88-2.91 (m, 0.5H), 3.28 (s, 1.5H), 3.41-3.49 (m, 0.5H), 3.59 (s, 1.5H), 3.64-3.76 (m, 0.5H), 3.91 (s, 3H), 4.15-4.20 (m, 0.5H), 4.89-4.94 (m, 0.5H), 6.67-6.74 (m, 1H), 6.89-7.04 (m, 4H), 7.21-7.26 (m, 2H), 7.76-8.07 (m, 2H), 8.34-8.37 (m, 1H)

Example 43

Synthesis of 5-chloro-3-(2-methoxyphenyl)-1-{[4-methoxy-2-(trifluoromethoxy)phenyl]sulfonyl}-3-[2-oxo-2-(4-pyridin-4-yl piperazin-1-yl)ethyl]-1,3-dihydro-2H-indol-2-one hydrochloride 1.5 hydrate With 300 mg of 5-chloro-3-(2-methoxyphenyl)-3-[2-oxo-2-(4-pyridin-4-yl piperazin-1-yl)ethyl]-1,3-dihydro-2H-indol-2-one, which is the compound described in Example 1A of the brochure Publication No. WO03/008407, and 201 mg of 4-methoxy-2-(trifluoromethoxy)benzene sulfonyl chloride as starting materials, 382 mg of a free form of the title compound (pale yellow amorphous) was obtained by a similar method to Example 2. To a solution of 360 mg of the obtained free form in CHCl₃ (10 ml) was added a solution of 4 mol/L hydrochloric acid/EtOAc (0.62 ml), and the reaction mixture was stirred at room temperature for 3 hours. Thereafter, the solvent was evaporated under reduced pressure, IPA (5 ml) was added to the obtained residue, then the mixture stirred for 30 minutes while heating at 90° C. external temperature, then, the mixture was stirred at room temperature for 62 hours. The precipitated solid was collected by filtration to obtain 375 mg of the title compound (colorless solid).

MS (ESI pos.) m/z: 731 ([M+H]⁺)

¹H-NMR (300 MHz, DMSO-d₆) δ (ppm); 3.14-3.78 (m, 9H), 3.52 (s, 3H), 3.90 (s, 3H), 4.08 (d, J=16.2 Hz, 1H), 6.90-7.07 (m, 3H), 7.10-7.19 (m, 4H), 7.27-7.37 (m, 2H), 7.62 (dd, J=7.9, 1.2 Hz, 1H), 7.72 (d, J=8.7 Hz, 1H), 8.14 (d, J=9.0 Hz, 1H), 8.25 (s, 1H), 8.27 (s, 1H)

Example 44

Synthesis of 5-chloro-3-(2-methoxyphenyl)-1-{[4-methoxy-2-(trifluoromethoxy)phenyl]sulfonyl}-3-[2-oxo-2-(4-pyrazine-2-ylpiperazin-1-yl)ethyl]-1,3-dihydro-2H-indol-2-one With 300 mg of 5-chloro-3-(2-methoxyphenyl)-3-[2-oxo-2-(4-pyrazine-2-ylpiperazin-1-yl)ethyl]-1,3-dihydro-2H-indol-2-one, which is the compound described in Composes IV.1 of the brochure Publication No. WO03/008407, and 201 mg of 4-methoxy-2-(trifluoromethoxy)benzene sulfonyl chloride as starting materials, 424 mg of the title compound (pale yellow amorphous) was obtained by a similar method to Example 2.

MS (ESI pos.) m/z: 754 ([M+Na]⁺)
¹H-NMR (300 MHz, CDCl₃) δ (ppm); 3.23-3.71 (m, 10H), 3.69 (s, 3H), 3.88 (s, 3H), 6.81-6.89 (m, 3H), 6.92-6.99 (m, 1H), 7.01 (d, J=2.0 Hz, 1H), 7.19-7.33 (m, 3H), 7.86-7.94 (m, 2H), 8.04-8.13 (m, 2H), 8.26-8.30 (m, 1H)

Example 45

Synthesis of 5-chloro-3-(2-methoxyphenyl)-1-{[4-methoxy-2-(trifluoromethoxy)phenyl]sulfonyl}-3-[2-oxo-2-(4-pyrimidin-2-ylpiperazin-1-yl)ethyl]-1,3-dihydro-2H-indol-2-one Step 45-1: Synthesis of 5-chloro-3-(2-methoxyphenyl)-3-[2-oxo-2-(4-pyrimidin-2-ylpiperazin-1-yl)ethyl]-1,3-dihydro-2H-indol-2-one To a solution of 800 mg of [5-chloro-3-(2-methoxyphenyl)-2-oxo-2,3-dihydro-1H-indol-3-yl]acetic acid, which is the compound described in Preparation 1.1 of the brochure WO03/008407 and 488 mg of HOBt/H₂O in DMF (8 ml) was added 554 mg of EDC/HCl under ice cooling, then, the reaction mixture was warmed to room temperature and stirred at room temperature for 30 minutes. The solution was cooled with ice again, 433 mg of 2-piperazin-1-yl pyrimidine was added to the reaction solution, and after warming to room temperature, the reaction mixture was stirred at room temperature for 14 hours. To the reaction solution was added EtOAc, a saturated aqueous solution of K₂CO₃ and water, and the mixture was stirred for 30 minutes. Liquid separation was performed, the obtained aqueous layer was extracted with EtOAc, the combined organic layer was washed with water and saturated brine, then, was dried over MgSO₄, the drying agent was separated by filtration, then the solvent was evaporated under reduced pressure. The obtained residue was subjected to column chromatography (silicagel 60; mobile phase: CHCl₃/MeOH/OH=10/1/0.1; v/v/v) to obtain 1.09 g of the title compound (colorless solid).

MS (ESI pos.) m/z: 500 ([M+Na]⁺)
¹H-NMR (300 MHz, DMSO-d₆) δ (ppm); 3.07 (d, J=15.9 Hz, 1H), 3.28-3.79 (m, 8H), 3.60 (s, 3H), 3.90 (d, J=16.0 Hz, 1H), 6.65 (t, J=4.7 Hz, 1H), 6.77 (d, J=8.2 Hz, 1H), 6.92-7.01 (m, 2H), 7.11 (dd, J=8.2, 2.2 Hz, 1H), 7.20-7.32 (m, 2H), 7.40 (dd, J=8.2, 1.6 Hz, 1H), 8.35-8.41 (m, 2H), 10.53 (s, 1H)

Step 45-2: Synthesis of 5-chloro-3-(2-methoxyphenyl)-1-{[4-methoxy-2-(trifluoromethoxy)phenyl]sulfonyl}-3-[2-oxo-2-(4-pyrimidin-2-ylpiperazin-1-yl)ethyl]-1,3-dihydro-2H-indol-2-one With 300 mg of the compound obtained in Step 45-1 and 201 mg of 4-methoxy-2-(trifluoromethoxy)benzene sulfonyl chloride as starting materials, 402 mg of the title compound (colorless amorphous) was obtained by a similar method to Example 2.

MS (ESI pos.) m/z: 732 ([M+H]⁺)
¹H-NMR (300 MHz, CDCl₃) δ (ppm); 3.15-3.91 (m, 10H), 3.70 (s, 3H), 3.87 (s, 3H), 6.53 (t, J=4.8 Hz, 1H), 6.80-6.90 (m, 3H), 6.92-7.04 (m, 2H), 7.19-7.34 (m, 3H), 7.92 (d, J=8.9 Hz, 1H), 8.25-8.34 (m, 3H)

Example 46

Synthesis of 5-chloro-3-(2-methoxyphenyl)-1-{[4-methoxy-2-(trifluoromethoxy)phenyl]sulfonyl}-3-{2-oxo-2-[4-(1,3-thiazol-2-yl)piperazin-1-yl]ethyl}-1,3-dihydro-2H-indol-2-one Step 46-1: Synthesis of 5-chloro-3-(2-methoxyphenyl)-3-{2-oxo-2-[4-(1,3-thiazol-2-yl)piperazin-1-yl]ethyl}-1,3-dihydro-2H-indol-2-one With 800 mg of [5-chloro-3-(2-methoxyphenyl)-2-oxo-2,3-dihydro-1H-indol-3-yl]acetic acid, which is the compound described in Preparation 1.1 of the brochure Publication No. WO03/008407, and 449 mg of 1-(1,3-thiazol-2-yl)piperazine as starting materials, reaction manipulation and post-treatment were carried out by a similar method to Step 45-1, and the obtained residue was crystallized from EtOAc and n-hexane to obtain 976 mg of the title compound (colorless crystal).

MS (ESI pos.) m/z: 505 ([M+Na]⁺)
¹H-NMR (300 MHz, DMSO-d₆) δ (ppm); 3.08 (d, J=15.9 Hz, 1H), 3.15-3.67 (m, 8H), 3.60 (s, 3H), 3.89 (d, J=15.7 Hz, 1H), 6.76 (d, J=8.2 Hz, 1H), 6.87 (d, J=3.6 Hz, 1H), 6.92-6.99 (m, 2H), 7.11 (dd, J=8.2, 2.2 Hz, 1H), 7.18 (d, J=3.7 Hz, 1H), 7.20 (d, J=2.2 Hz, 1H), 7.23-7.31 (m, 1H), 7.40 (dd, J=8.1, 1.6 Hz, 1H), 10.53 (s, 1H)

Step 46-2: Synthesis of 5-chloro-3-(2-methoxyphenyl)-1-{[4-methoxy-2-(trifluoromethoxy)phenyl]sulfonyl}-3-{2-oxo-2-[4-(1,3-thiazol-2-yl)piperazin-1-yl]ethyl}-1,3-dihydro-2H-indol-2-one With 300 mg of the compound obtained in Step 46-1 and 200 mg of 4-methoxy-2-(trifluoromethoxy)benzene sulfonyl chloride as starting materials, 409 mg of the title compound (yellow amorphous) was obtained by a similar method to Example 2.

MS (ESI pos.) m/z: 737 ([M+H]⁺)
¹H-NMR (300 MHz, CDCl₃) δ (ppm); 3.18-3.74 (m, 10H), 3.69 (s, 3H), 3.88 (s, 3H), 6.60-6.64 (m, 1H), 6.80-7.04 (m, 5H), 7.18-7.34 (m, 4H), 7.92 (d, J=8.7 Hz, 1H), 8.25-8.32 (m, 1H)

Example 47

Synthesis of 5-chloro-3-(2-methoxyphenyl)-1-{[4-methoxy-2-(trifluoromethoxy)phenyl]sulfonyl}-3-[2-oxo-2-(4-pyridin-2-ylpiperazin-1-yl)ethyl]-1,3-dihydro-2H-indol-2-one Step 47-1: 5-chloro-3-(2-methoxyphenyl)-3-[2-oxo-2-(4-pyridin-2-ylpiperazin-1-yl)ethyl]-1,3-dihydro-2H-indol-2-one With 800 mg of [5-chloro-3-(2-methoxyphenyl)-2-oxo-2,3-dihydro-1H-indol-3-yl]acetic acid, which is the compound described in Preparation 1.1 of the brochure Publication No. WO03/008407, and 433 mg of 1-pyridin-2-ylpiperazine as starting materials, 1.00 g of the title compound (colorless solid) was obtained by a similar method to Step 45-1.

MS (ESI pos.) m/z: 477 ([M+H]$^+$)

$^1$H-NMR (300 MHz, DMSO-d$_6$) δ (ppm); 3.07 (d, J=15.9 Hz, 1H), 3.26-3.64 (m, 8H), 3.60 (s, 3H), 3.90 (d, J=15.7 Hz, 1H), 6.62-6.68 (m, 1H), 6.76 (d, J=8.2 Hz, 1H), 6.81 (d, J=8.6 Hz, 1H), 6.91-7.00 (m, 2H), 7.11 (dd, J=8.2, 2.2 Hz, 1H), 7.21 (d, J=2.2 Hz, 1H), 7.23-7.31 (m, 1H), 7.37-7.43 (m, 1H), 7.49-7.58 (m, 1H), 8.08-8.13 (m, 1H), 10.52 (s, 1H)

Step 47-2: Synthesis of 5-chloro-3-(2-methoxyphenyl)-1-{[4-methoxy-2-(trifluoromethoxy)phenyl]sulfonyl}-3-[2-oxo-2-(4-pyridin-2-ylpiperazin-1-yl) ethyl]-1,3-dihydro-2H-indol-2-one 2 hydrochloride 1 hydrate With 300 mg of the compound obtained in Step 47-1 and 201 mg of 4-methoxy-2-(trifluoromethoxy)benzene sulfonyl chloride as starting materials, 410 mg of free form of the title compound (pale yellow amorphous) was obtained by a similar method to Example 2. In a similar procedure to Example 43, 383 mg of the obtained free form underwent salt formation and was solidified to obtain 405 mg of the title compound (pale yellow solid).

MS (ESI pos.) m/z: 731 ([M+H]$^+$)

$^1$H-NMR (300 MHz, DMSO-d$_6$) δ (ppm); 3.10-4.14 (m, 10H), 3.53 (s, 3H), 3.90 (s, 3H), 6.79-7.24 (m, 7H), 7.27-7.36 (m, 2H), 7.64 (dd, J=7.9, 1.4 Hz, 1H), 7.72 (d, J=8.7 Hz, 1H), 7.76-7.91 (m, 1H), 8.06 (dd, J=5.9, 1.4 Hz, 1H), 8.14 (d, J=9.0 Hz, 1H)

Example 48

Synthesis of 5-chloro-3-(2-methoxyphenyl)-1-{[4-methoxy-2-(trifluoromethoxy)phenyl]sulfonyl}-3-[2-oxo-2-(4-pyridin-3-ylpiperazin-1-yl)ethyl]-1,3-dihydro-2H-indol-2-one Step 48-1: 5-chloro-3-(2-methoxyphenyl)-3-[2-oxo-2-(4-pyridin-3-ylpiperazin-1-yl)ethyl]-1,3-dihydro-2H-indol-2-one From 800 mg of [5-chloro-3-(2-methoxyphenyl)-2-oxo-2,3-dihydro-1H-indol-3-yl]acetic acid, which is the compound described in Preparation 1.1 of the brochure Publication No. WO03/008407, and 433 mg of 1-pyridin-3-ylpiperazine, 713 mg of the title compound (pale yellow amorphous) was obtained by a similar method to Step 45-1.

MS (ESI pos.) m/z: 499 ([M+Na]$^+$)

$^1$H-NMR (300 MHz, DMSO-d$_6$) δ (ppm); 2.87-3.95 (m, 10H), 3.61 (m, 3H), 6.76 (d, J=8.2 Hz, 1H), 6.90-6.99 (m, 2H), 7.10 (dd, J=8.2, 2.2 Hz, 1H), 7.16-7.36 (m, 4H), 7.37-7.43 (m, 1H), 8.01 (dd, J=4.4, 1.2 Hz, 1H), 8.26-8.32 (m, 1H), 10.52 (s, 1H)

Step 48-2: Synthesis of 5-chloro-3-(2-methoxyphenyl)-1-{[4-methoxy-2-(trifluoromethoxy)phenyl]sulfonyl}-3-[2-oxo-2-(4-pyridin-3-ylpiperazin-1-yl) ethyl]-1,3-dihydro-2H-indol-2-one hydrochloride 1.5 hydrate With 300 mg of the compound obtained in Step 48-1 and 201 mg of 4-methoxy-2-(trifluoromethoxy)benzene sulfonyl chloride as starting materials, 335 mg of free form of the title compound (yellow amorphous) was obtained by a similar method to Example 2. In a similar procedure to Example 43, by subjecting 310 mg of the obtained free form to salt formation and solidification, 307 mg of the title compound (pale yellow solid) was obtained.

MS (ESI pos.) m/z: 753 ([M+Na]$^+$)

$^1$H-NMR (300 MHz, DMSO-d$_6$) δ (ppm); 3.00-4.16 (m, 10H), 3.52 (s, 3H), 3.90 (s, 3H), 6.89-7.08 (m, 3H), 7.11-7.19 (m, 2H), 7.27-7.36 (m, 2H), 7.63 (dd, J=7.7, 1.3 Hz, 1H), 7.69-7.82 (m, 2H), 7.90-7.98 (m, 1H), 8.14 (d, J=9.0 Hz, 1H), 8.18 (d, J=4.8 Hz, 1H), 8.39 (d, J=2.8 Hz, 1H)

Example 49

Synthesis of 5-chloro-3-(2-methoxyphenyl)-1-{[4-methoxy-2-(trifluoromethoxy)phenyl]sulfonyl}-3-[2-oxo-2-(4-pyridazin-3-ylpiperazin-1-yl)ethyl]-1,3-dihydro-2H-indol-2-one Step 49-1: 5-chloro-3-(2-methoxyphenyl)-3-[2-oxo-2-(4-pyridazin-3-ylpiperazin-1-yl)ethyl]-1,3-dihydro-2H-indol-2-one With 800 mg of [5-chloro-3-(2-methoxyphenyl)-2-oxo-2,3-dihydro-1H-indol-3-yl]acetic acid, which is the compound described in Preparation 1.1 of the brochure Publication No. WO03/008407, and 677 mg of 3-piperazin-1-yl pyridazin as starting materials, 395 mg of the title compound (colorless solid) was obtained by a similar method to Step 45-1.

MS (ESI pos.) m/z: 500 ([M+Na]$^+$)

$^1$H-NMR (300 MHz, DMSO-d$_6$) δ (ppm); 3.09 (d, J=15.9 Hz, 1H), 3.26-3.68 (m, 8H), 3.60 (s, 3H), 3.91 (d, J=15.7 Hz, 1H), 6.77 (d, J=8.1 Hz, 1H), 6.93-6.99 (m, 2H), 7.11 (dd, J=8.2, 2.2 Hz, 1H), 7.20-7.31 (m, 3H), 7.36-7.43 (m, 2H), 8.57 (dd, J=4.5, 1.2 Hz, 1H), 10.53 (s, 1H)

Step 49-2: Synthesis of 5-chloro-3-(2-methoxyphenyl)-1-{[4-methoxy-2-(trifluoromethoxy)phenyl]sulfonyl}-3-[2-oxo-2-(4-pyridazin-3-ylpiperazin-1-yl)ethyl]-1,3-dihydro-2H-indol-2-one With 170 mg of the compound obtained in Step 49-1 and 114 mg of 4-methoxy-2-(trifluoromethoxy)benzene sulfonyl chloride as starting materials, 196 mg of the title compound (colorless amorphous) was obtained by a similar method to Example 2.

MS (ESI pos.) m/z: 732 ([M+H]$^+$)

$^1$H-NMR (300 MHz, CDCl$_3$) δ (ppm); 3.24-3.80 (m, 10H), 3.68 (s, 3H), 3.88 (s, 3H), 6.80-6.91 (m, 4H), 6.92-6.99 (m, 1H), 7.01 (d, J=2.0 Hz, 1H), 7.20-7.33 (m, 4H), 7.92 (d, J=8.7 Hz, 1H), 8.26-8.30 (m, 1H), 8.60-8.65 (m, 1H)

Example 50

Synthesis of 5-chloro-3-(2-methoxyphenyl)-1-{[2-methoxy-4-(trifluoromethoxy)phenyl]sulfonyl}-3-[2-oxo-2-(4-pyridin-4-yl piperazin-1-yl)ethyl]-1,3-dihydro-2H-indol-2-one With 150 mg of 5-chloro-3-(2-methoxyphenyl)-3-[2-oxo-2-(4-pyridin-4-yl piperazin-1-yl)ethyl]-1,3-dihydro-2H-indol-2-one, which is the compound described in EXAMPLE 1 of Publication No. WO03/008407, and 100 mg of 2-methoxy-4-(trifluoromethoxy)benzene sulfonyl chloride as starting materials, 73 mg of the title compound (colorless amorphous) was obtained by a similar method to Example 1.

MS (ESI pos.) m/z: 731 ([M+H]$^+$)

¹H-NMR (300 MHz, DMSO-d₆) δ (ppm); 3.10-3.73 (m, 15H), 4.08 (d, J=16.5 Hz, 1H), 6.83-7.24 (m, 7H), 7.27-7.36 (m, 2H), 7.60 (dd, J=8.2, 1.3 Hz, 1H), 7.76 (d, J=8.8 Hz, 1H), 8.07 (d, J=8.8 Hz, 1H), 8.19 (d, J=6.1 Hz, 2H)

Example 51

Synthesis of 5-chloro-3-(2-methoxyphenyl)-1-{[4-methoxy-2-(trifluoromethoxy)phenyl]sulfonyl}-3-[2-oxo-2-(4-pyridin-4-yl piperidin-1-yl)ethyl]-1,3-dihydro-2H-indol-2-one Step 51-1: Synthesis of 4-piperidin-4-yl pyridine To a solution of 5.00 g of 4,4'-bipyridine in 1 mol/L hydrochloric acid (32 ml) was added 299 mg of platinum oxide, and the reaction mixture was stirred under the conditions of 3.0 atm hydrogen and at 70° C. external temperature. After 3 hours, the solution was under ordinary temperature and ordinary pressure, then, 201 mg of platinum oxide was further added and the reaction was carried out under the conditions of 3.0 atm hydrogen and at 70° C. external temperature. After 4.5 hours, the solution was left to unattended for 16 hours in a state returned to under ordinary temperature and ordinary pressure. MeOH (30 ml) and 483 mg of platinum oxide were further added, and the mixture was stirred under the conditions of 3.0 atm hydrogen and 70° C. external temperature. The solution was stirred for 4 hours, then, filtered with celite, and the solvent of the filtrate was evaporated under reduced pressure. Then, a saturated aqueous solution of NaHCO₃ was added to the solution and the resulting mixture was extracted with a mixed solvent of CHCl₃:MeOH (10:1). The organic layer was evaporated under reduced pressure. Again, water was added to the solution, extracted with a mixed solvent of CHCl₃:MeOH (10:1), and the organic layer was evaporated under reduced pressure. The precipitated solid was washed with water and dried to obtain 390 mg of the title compound (colorless amorphous).

MS (ESI pos.) m/z: 163 ([M+H]⁺)
¹H-NMR (300 MHz, CDCl₃) δ (ppm); 1.55-1.74 (m, 3H), 1.79-1.89 (m, 2H), 2.55-2.68 (m, 1H), 2.69-2.81 (m, 2H), 3.16-3.25 (m, 2H), 7.12-7.16 (m, 2H), 8.49-8.54 (m, 2H)

Step 51-2: Synthesis of 5-chloro-3-(2-methoxyphenyl)-3-[2-oxo-2-(4-pyridin-4-yl piperidin-1-yl)ethyl]-1,3-dihydro-2H-indol-2-one To a solution of 720 mg of [5-chloro-3-(2-methoxyphenyl)-2-oxo-2,3-dihydro-1H-indol-3-yl]acetic acid, which is the compound described in Preparation 1.1 of the brochure WO03/008407 and 350 mg of 4-piperidin-4-yl pyridine obtained in Step 51-1 in CHCl₃ (15 ml) was added 500 mg of HOBt/H₂O, stirred for 15 minutes, then, 500 mg of EDC/HCl was added. The solution was stirred for 11 hours, then, water was added and the resulting mixture was extracted with CHCl₃. The organic layer was washed with water saturated brine, dried over Na₂SO₄, then, the drying agent was separated by filtration, and the solvent was evaporated under reduced pressure. The obtained residue was purified by column chromatography (first time: silicagel 60; mobile phase: CHCl₃/MeOH=9/1 to 5/1; second time: silica gel NH; mobile phase: CHCl₃/MeOH=19/1) to obtain 850 mg of the title compound (colorless amorphous).

MS (ESI pos.) m/z: 476 ([M+H]⁺), 498 ([M+Na]⁺), (ESI neg.) m/z: 474 ([M−H]⁻)
¹H-NMR (300 MHz, CDCl₃) δ (ppm); 1.35-2.00 (m, 4H), 2.43-2.77 (m, 2H), 3.03-3.40 (m, 2H), 3.72-3.85 (m, 3H), 3.92-4.11 (m, 2H), 4.63 (m, 1H), 6.73-7.47 (m, 9H), 8.13 (d, J=5.2 Hz, 1H), 8.52 (t, J=5.2 Hz, 2H)

Step 51-3: Synthesis of 5-chloro-3-(2-methoxyphenyl)-1-{[4-methoxy-2-(trifluoromethoxy)phenyl]sulfonyl}-3-[2-oxo-2-(4-pyridin-4-yl piperidin-1-yl)ethyl]-1,3-dihydro-2H-indol-2-one With 290 mg of the compound obtained in Step 51-2 and, 202 mg of 4-methoxy-2-(trifluoromethoxy)benzene sulfonyl chloride as starting materials, 150 mg of the title compound (colorless amorphous) was obtained by a similar method to Example 2.

MS (ESI pos.) m/z: 730 ([M+H]⁺), 752 ([M+Na]⁺), (ESI neg.) m/z: 728 ([M−H]⁻)
¹H-NMR (300 MHz, DMSO-d₆) δ (ppm): 0.92-1.81 (m, 4H), 2.23-2.79 (m, 2H), 2.92-3.38 (m, 2H), 3.48-3.63 (m, 3H), 3.74-4.23 (m, 6H), 6.89-7.23 (m, 7H), 7.25-7.41 (m, 2H), 7.59-7.68 (m, 1H), 7.74 (dd, J=8.7, 7.3 Hz, 1H), 8.14 (dd, J=9.0, 4.2 Hz, 1H), 8.41-8.53 (m, 2H)

Example 52

Synthesis of 5-chloro-3-(2-methoxyphenyl)-1-{[2-methoxy-4-(trifluoromethoxy)phenyl]sulfonyl}-3-[2-oxo-2-(4-pyridin-4-yl piperidin-1-yl)ethyl]-1,3-dihydro-2H-indol-2-one With 290 mg of 5-chloro-3-(2-methoxyphenyl)-3-[2-oxo-2-(4-pyridin-4-yl piperidin-1-yl)ethyl]-1,3-dihydro-2H-indol-2-one obtained in Step 51-2 and 195 mg of 2-methoxy-4-(trifluoromethoxy)benzene sulfonyl chloride as starting materials, 173 mg of the title compound (colorless amorphous) was obtained by a similar method to Example 1.

MS (ESI pos.) m/z: 730 ([M+H]⁺), 752 ([M+Na]⁺), (ESI neg.) m/z: 728 ([M−H]⁻)
¹H-NMR (300 MHz, DMSO-d₆) δ (ppm); 0.86-1.86 (m, 4H), 2.22-2.80 (m, 2H), 2.91-3.39 (m, 2H), 3.50-3.70 (m, 6H), 3.92-4.18 (m, 3H), 6.91-7.13 (m, 3H), 7.16-7.25 (m, 4H), 7.26-7.40 (m, 2H), 7.62 (dd, J=8.0, 1.3 Hz, 1H), 7.77 (dd, J=8.7, 2.1 Hz, 1H), 8.07 (dd, J=8.7, 4.0 Hz, 1H), 8.46 (d, J=5.1 Hz, 2H)

Example 53

Synthesis of 5-chloro-3-(2-methoxyphenyl)-1-{[4-methoxy-2-(trifluoromethoxy)phenyl]sulfonyl}-3-[2-oxo-2-(4-pyridin-4-yl piperazin-1-yl)ethoxy]-1,3-dihydro-2H-indol-2-one Step 53-1: Synthesis of methyl {[5-chloro-3-(2-methoxyphenyl)-2-oxo-2,3-dihydro-1H-indol-3-yl]oxy}acetate Under nitrogen atmosphere, to a solution of 12.9 g of methyl glycolate in THF (250 ml), under room temperature, was added 3.43 g of NaH, and the reaction mixture was stirred for 10 minutes at the same temperature. Under room temperature, 22.0 g of 3,5-dichloro-3-(2-methoxyphenyl)-1,3-dihydro-2H-indol-2-one was added to the reaction solution and the reaction mixture was stirred for 10 minutes. To the reaction solution was added EtOAc and water and the mixture was stirred for 5 minutes. Liquid separation was performed, the aqueous layer was extracted with EtOAc, the combined organic layer was washed with 1 mol/L hydrochloric acid and saturated brine, then, was dried over MgSO₄, the drying agent was separated by filtration, then, the solution was concentrated under reduced pressure. The obtained residue was purified by column chromatography (silicagel 60; mobile phase: EtOAc) to obtain 9.30 g of an orange solid. The obtained solid was crystallized from Et$_2$O to obtain 8.18 g of the title compound (pale yellow crystal).

MS (ESI pos.) m/z: 384 ([M+Na]$^+$)

$^1$H-NMR (300 MHz, DMSO-d$_6$) δ (ppm); 3.47 (s, 3H), 3.58 (s, 3H), 3.91 (d, J=15.5 Hz, 1H), 4.16 (d, J=15.5 Hz, 1H), 6.81 (d, J=2.3 Hz, 1H), 6.90 (d, J=8.2 Hz, 1H), 6.96 (dd, J=8.2, 0.9 Hz, 1H), 7.07-7.13 (m, 1H), 7.27-7.40 (m, 2H), 7.80 (dd, J=7.6, 1.7 Hz, 1H), 10.79 (s, 1H)

Step 53-2: Synthesis of {[5-chloro-3-(2-methoxyphenyl)-2-oxo-2,3-dihydro-1H-indol-3-yl]oxy}acetic acid To a suspension of 8.00 g of the compound obtained in Step 53-1 in MeOH (400 ml) was added an aqueous solution of 1.3 mol/L NaOH, and the reaction mixture was stirred at room temperature for 13 hours. The reaction solution was concentrated, under ice cooling, 3 mol/L hydrochloric acid was added until it became acidic. The obtained suspension was ultrasonicated for one hour, then, the insoluble matter was collected by filtration to obtain 7.31 g of the title compound (pale yellow solid).

MS (ESI pos.) m/z: 370 ([M+Na]$^+$), (ESI neg.) m/z: 346 ([M−H]$^−$)

$^1$H-NMR (300 MHz, DMSO-d$_6$) δ (ppm); 3.47 (s, 3H), 3.80 (d, J=15.7 Hz, 1H), 4.01 (d, J=15.7 Hz, 1H), 6.82 (d, J=2.2 Hz, 1H), 6.90 (d, J=8.2 Hz, 1H), 6.93-6.99 (m, 1H), 7.06-7.13 (m, 1H), 7.28-7.38 (m, 2H), 7.84 (dd, J=7.8, 1.7 Hz, 1H), 10.76 (s, 1H)

Step 53-3: 5-chloro-3-(2-methoxyphenyl)-3-[2-oxo-2-(4-pyridin-4-yl piperazin-1-yl)ethoxy]-1,3-dihydro-2H-indol-2-one From 900 mg of the compound obtained in Step 53-2 and 433 mg of 1-pyridin-4-yl piperazine, 940 mg of the title compound (colorless amorphous) was obtained by a similar method to Step 45-1.

MS (ESI pos.) m/z: 493 ([M+H]$^+$)

$^1$H-NMR (300 MHz, DMSO-d$_6$) δ (ppm); 3.23-3.63 (m, 8H), 3.46 (s, 3H), 3.86 (d, J=12.6 Hz, 1H), 4.12 (d, J=12.8 Hz, 1H), 6.78-6.98 (m, 5H), 7.03-7.13 (m, 1H), 7.26-7.39 (m, 2H), 7.85 (dd, J=7.8, 1.7 Hz, 1H), 8.15-8.19 (m, 2H), 10.82 (s, 1H)

Step 53-4: Synthesis of 5-chloro-3-(2-methoxyphenyl)-1-{[4-methoxy-2-(trifluoromethoxy)phenyl]sulfonyl}-3-[2-oxo-2-(4-pyridin-4-yl piperazin-1-yl)ethoxy]-1,3-dihydro-2H-indol-2-one With 300 mg of the compound obtained in Step 53-3 and 195 mg of 4-methoxy-2-(trifluoromethoxy)benzene sulfonyl chloride as starting materials, 321 mg of the title compound (yellow amorphous) was obtained by a similar method to Example 2.

MS (ESI pos.) m/z: 747 ([M+H]$^+$)

$^1$H-NMR (300 MHz, CDCl$_3$) δ (ppm); 3.11-4.22 (m, 10H), 3.52 (s, 3H), 3.88 (s, 3H), 6.56-7.13 (m, 7H), 7.23-7.44 (m, 2H), 7.77-7.86 (m, 1H), 7.93 (d, J=8.9 Hz, 1H), 8.19-8.40 (m, 3H)

Example 54

Synthesis of 5-chloro-3-(2-methoxyphenyl)-1-{[4-methoxy-2-(trifluoromethoxy)phenyl]sulfonyl}-3-[2-oxo-2-(4-pyridin-2-ylpiperazin-1-yl)ethoxy]-1,3-dihydro-2H-indol-2-one

Step 54-1: Synthesis of 5-chloro-3-(2-methoxyphenyl)-3-[2-oxo-2-(4-pyridin-2-ylpiperazin-1-yl)ethoxy]-1,3-dihydro-2H-indol-2-one With 900 mg of the compound obtained in Step 53-2 and 465 mg of 1-pyridin-2-ylpiperazine as starting materials, 1.01 g of the title compound (pale yellow amorphous) was obtained by a similar method to Step 45-1.

MS (ESI pos.) m/z: 493 ([M+H]$^+$)

$^1$H-NMR (300 MHz, DMSO-d$_6$) δ (ppm); 3.25-3.60 (m, 11H), 3.86 (d, J=12.4 Hz, 1H), 4.11 (d, J=12.6 Hz, 1H), 6.66 (dd, J=6.9, 5.2 Hz, 1H), 6.81-6.98 (m, 4H), 7.05-7.12 (m, 1H), 7.27-7.44 (m, 2H), 7.50-7.59 (m, 1H), 7.86 (dd, J=7.8, 1.7 Hz, 1H), 8.09-8.14 (m, 1H), 10.81 (s, 1H)

Step 54-2: Synthesis of 5-chloro-3-(2-methoxyphenyl)-1-{[4-methoxy-2-(trifluoromethoxy)phenyl]sulfonyl}-3-[2-oxo-2-(4-pyridin-2-ylpiperazin-1-yl)ethoxy]-1,3-dihydro-2H-indol-2-one hydrochloride 1 hydrate With 300 mg of the compound obtained in Step 54-1 and 201 mg of 4-methoxy-2-(trifluoromethoxy)benzene sulfonyl chloride as starting materials, 370 mg of free form of the title compound (yellow amorphous) was obtained by a similar method to Example 2. In a similar procedure to Example 43, by subjecting 335 mg of the obtained free form to salt formation and solidification, 314 mg of the title compound (colorless amorphous) was obtained.

MS (ESI pos.) m/z: 769 ([M+Na]$^+$)

$^1$H-NMR (300 MHz, DMSO-d$_6$) δ (ppm); 3.14-4.09 (m, 10H), 3.44 (s, 3H), 3.94 (s, 3H), 6.77-6.91 (m, 1H), 6.94-7.00 (m, 1H), 7.05-7.19 (m, 4H), 7.27 (dd, J=9.2, 2.3 Hz, 1H), 7.35-7.43 (m, 1H), 7.57 (dd, J=8.9, 2.3 Hz, 1H), 7.77-7.89 (m, 3H), 8.08 (dd, J=5.7, 1.3 Hz, 1H), 8.22 (d, J=9.0 Hz, 1H)

Example 55

Synthesis of 5-chloro-3-(2-methoxyphenyl)-1-{[4-methoxy-2-(trifluoromethoxy)phenyl]sulfonyl}-3-[2-oxo-2-(4-pyridin-3-ylpiperazin-1-yl)ethoxy]-1,3-dihydro-2H-indol-2-one hydrochloride 1 hydrate

Step 55-1: Synthesis of 5-chloro-3-(2-methoxyphenyl)-3-[2-oxo-2-(4-pyridin-3-ylpiperazin-1-yl)ethoxy]-1,3-dihydro-2H-indol-2-one With 900 mg of the compound obtained in Step 53-2 and 465 mg of 1-pyridin-3-ylpiperazine as starting material, 718 mg of the title compound (pale yellow amorphous) was obtained by a similar method to Step 45-1.

MS (ESI pos.) m/z: 493 ([M+H]$^+$)

$^1$H-NMR (300 MHz, DMSO-d$_6$) δ (ppm); 3.08-3.69 (m, 8H), 3.46 (s, 3H), 3.86 (d, J=12.4 Hz, 1H), 4.13 (d, J=12.4 Hz, 1H), 6.83-6.97 (m, 3H), 7.05-7.12 (m, 1H), 7.19-7.42 (m, 4H), 7.85 (dd, J=7.8, 1.7 Hz, 1H), 8.02 (dd, J=4.5, 1.2 Hz, 1H), 8.30 (d, J=2.8 Hz, 1H), 10.81 (s, 1H)

Step 55-2: Synthesis of 5-chloro-3-(2-methoxyphenyl)-1-{[4-methoxy-2-(trifluoromethoxy)phenyl]sulfonyl}-3-[2-oxo-2-(4-pyridin-3-ylpiperazin-1-yl)ethoxy]-1,3-dihydro-2H-indol-2-one hydrochloride 1 hydrate With 300 mg of the compound obtained in Step 55-1 and 201 mg of 4-methoxy-2-(trifluoromethoxy)benzene sulfonyl chloride as starting materials, 262 mg of free form of the title compound (yellow amorphous) was obtained by a similar method to Example 2. In a similar procedure to Example 43, by subjecting 237 mg of the obtained free form to salt formation and solidification, 211 mg of the title compound (colorless amorphous) was obtained.

MS (ESI pos.) m/z: 769 ([M+Na]$^+$)

$^1$H-NMR (300 MHz, DMSO-d$_6$) δ (ppm); 3.19-4.07 (m, 10H), 3.43 (s, 3H), 3.93 (s, 3H), 6.97 (d, J=8.2 Hz, 1H), 7.05-7.17 (m, 3H), 7.27 (dd, J=9.1, 2.4 Hz, 1H), 7.35-7.42 (m, 1H), 7.57 (dd, J=8.9, 2.3 Hz, 1H), 7.73-7.86 (m, 3H), 7.91-7.99 (m, 1H), 8.17-8.25 (m, 2H), 8.41 (d, J=2.8 Hz, 1H)

Example 56

Synthesis of N-(5-chloro-3-(2-methoxyphenyl)-1-{[4-methoxy-2-(trifluoromethoxy)phenyl]sulfonyl}-2-oxo-2,3-dihydro-1H-indol-3-yl)-4-pyridin-4-yl piperazine-1-carboxamide Step 56-1: Synthesis of 3-amino-5-chloro-3-(2-methoxyphenyl)-1-{[4-methoxy-2-(trifluoromethoxy)phenyl]sulfonyl}-1,3-dihydro-2H-indol-2-one With 5.54 g of 3-amino-5-chloro-3-(2-methoxyphenyl)-1,3-dihydro-2H-indol-2-one 5.00 g, 4-methoxy-2-(trifluoromethoxy)benzene sulfonyl chloride, which is the compound described in Preparation 1.18A of the brochure Publication No. WO03/008407, as starting materials, 4.99 g of the title compound (light yellow solid) was obtained by a similar method to Example 2.

MS (ESI pos.) m/z: 543 ([M+Na]$^+$)

$^1$H-NMR (200 MHz, CDCl$_3$) δ (ppm); 1.76 (s, 2H), 3.53 (s, 3H), 3.89 (s, 3H), 6.75 (dd, J=8.1, 1.1 Hz, 1H), 6.85-7.11 (m, 4H), 7.23-7.36 (m, 2H), 7.87-8.03 (m, 2H), 8.3 (d, J=8.8 Hz, 1H)

Step 56-2: Synthesis of phenyl (5-chloro-3-(2-methoxyphenyl)-1-{[4-methoxy-2-(trifluoromethoxy)phenyl]sulfonyl}-2-oxo-2,3-dihydro-1H-indol-3-yl)carbamate To a solution of 4.00 g of the compound obtained in Step 56-1 and 5.83 g of Py in CHCl$_3$ (30 ml) was added dropwise a solution of phenyl chloroformate (1.2 ml) in CHCl$_3$ (10 ml) under ice cooling over 5 minutes. The solution was stirred at the same temperature for 4 hours, then, EtOAc was added. The organic layer was washed with saturated brine, dried over Na$_2$SO$_4$, then, the drying agent was separated by filtration and the solvent was evaporated under reduced pressure. The obtained residue was purified by column chromatography (silicagel 60; mobile phase: CHCl$_3$/EtOAc=99/1 to 19/1; v/v) to obtain 4.24 g of the title compound (light yellow solid).

MS (ESI pos.) m/z: 663 ([M+H]$^+$), 685 ([M+Na]$^+$), (ESI neg.) m/z: 661 ([M−H]$^−$)

$^1$H-NMR (300 MHz, CDCl$_3$) δ (ppm); 3.81 (s, 3H), 3.89 (s, 3H), 6.54-7.40 (m, 14H), 7.90 (d, J=8.6 Hz, 1H), 8.25 (d, J=9.0 Hz, 1H)

Step 56-3: Synthesis of N-(5-chloro-3-(2-methoxyphenyl)-1-{[4-methoxy-2-(trifluoromethoxy)phenyl]sulfonyl}-2-oxo-2,3-dihydro-1H-indol-3-yl)-4-pyridin-4-yl piperazine-1-carboxamide A solution of 400 mg of the compound obtained in Step 56-2 and 200 mg of 1-pyridin-4-yl piperazine in CHCl$_3$ (4 ml) was stirred under heat at 90° C. (external temperature). The solution was stirred at the same temperature for 6 hours, then, was cooled to room temperature and purified by column chromatography (silicagel 60; mobile phase: CHCl$_3$/MeOH=99/1 to 99/5; v/v) to obtain 138 mg of the title compound (colorless amorphous).

MS (ESI pos.) m/z: 732 ([M+H]$^+$), (ESI neg.) m/z: 730 ([M−H]$^−$)

$^1$H-NMR (300 MHz, DMSO-d$_6$) δ (ppm); 3.16-3.46 (m, 8H), 3.63 (s, 3H), 3.91 (s, 3H), 6.82 (d, J=6.7 Hz, 2H), 6.96-7.07 (m, 3H), 7.11-7.25 (m, 2H), 7.29-7.41 (m, 2H), 7.54 (dd, J=7.8, 1.6 Hz, 1H), 7.67 (d, J=8.7 Hz, 1H), 7.76 (s, 1H), 8.10-8.25 (m, 3H)

Example 57

Synthesis of 5-chloro-3-(2-methoxyphenyl)-1-{[4-methoxy-2-(trifluoromethoxy)phenyl]sulfonyl}-2-oxo-2,3-dihydro-1H-indol-3-yl 4-pyridin-4-yl piperazine-1-carboxylate Step 57-1: Synthesis of 5-chloro-3-(2-methoxyphenyl)-1-{[4-methoxy-2-(trifluoromethoxy)phenyl]sulfonyl}-2-oxo-2,3-dihydro-1H-indol-3-ylphenyl carbonate With 2.50 g of compound obtained in Step 7-2-2 as starting material, 2.85 g of the title compound (colorless amorphous) was obtained by a similar method to Step 56-2.

MS (ESI pos.) m/z: 686 ([M+Na]$^+$)

$^1$H-NMR (300 MHz, CDCl$_3$) δ (ppm); 3.72 (s, 3H), 3.81 (s, 3H), 6.56-6.66 (m, 1H), 6.78-6.93 (m, 4H), 7.02-7.13 (m, 2H), 7.14-7.41 (m, 5H), 7.81 (dd, J=7.9, 1.7 Hz, 1H), 7.95 (d, J=8.9 Hz, 1H), 8.23 (d, J=8.9 Hz, 1H)

Step 57-2: Synthesis of 5-chloro-3-(2-methoxyphenyl)-1-{[4-methoxy-2-(trifluoromethoxy)phenyl]sulfonyl}-2-oxo-2,3-dihydro-1H-indol-3-yl 4-pyridin-4-yl piperazine-1-carboxylate With 300 mg of the compound obtained in Step 57-1 as starting material, 121 mg of the title compound (colorless amorphous) was obtained by a similar method to Step 56-3.

MS (ESI pos.) m/z: 733 ([M+H]$^+$), 755 ([M+Na]$^+$)

$^1$H-NMR (300 MHz, DMSO-d$_6$) δ (ppm); 3.06-3.87 (m, 11H), 3.92 (s, 3H), 6.80-6.87 (m, 2H), 6.96-7.05 (m, 2H), 7.08-7.25 (m, 3H), 7.35-7.51 (m, 2H), 7.72-7.86 (m, 2H), 8.11-8.23 (m, 3H)

Example 58

Synthesis of 5-chloro-3-(2-methoxyphenyl)-1-{[4-methoxy-2-(trifluoromethoxy)phenyl]sulfonyl}-3-{[2-oxo-2-(4-pyridin-4-yl piperazin-1-yl)ethyl]amino}-1,3-dihydro-2H-indol-2-one Step 58-1: Synthesis of tert-butyl N-(5-chloro-3-(2-methoxyphenyl)-1-{[4-methoxy-2-(trifluoromethoxy)phenyl]sulfonyl}-2-oxo-2,3-dihydro-1H-indol-3-yl) glycinate With 1.50 g of tert-butyl N-[5-chloro-3-(2-methoxyphenyl)-2-oxo-2,3-dihydro-1H-indol-3-yl]glycinate, which is the compound described in Preparation 1.28A of the brochure Publication No. WO03/008407, and 1.19 g of 4-methoxy-2-(trifluoromethoxy)benzene sulfonyl chloride as starting materials, 711 mg of the title compound (colorless amorphous) was obtained by a similar method to Example 2.

MS (ESI pos.) m/z: 657 ([M+H]$^+$)
$^1$H-NMR (300 MHz, CDCl$_3$) δ (ppm); 1.35 (s, 9H), 2.36-2.42 (m, 1H), 2.80-3.10 (m, 2H), 3.57 (s, 3H), 3.90 (d, J=0.78 Hz, 3H), 6.71-7.12 (m, 5H), 7.20-7.35 (m, 2H), 7.84-7.99 (m, 2H), 8.28 (d, J=8.9 Hz, 1H)

Step 58-2: Synthesis of N-(5-chloro-3-(2-methoxyphenyl)-1-{[4-methoxy-2-(trifluoromethoxy)phenyl]sulfonyl}-2-oxo-2,3-dihydro-1H-indol-3-yl) glycine With 598 mg of the compound obtained in Step 58-1 as starting material, 662 mg of the title compound (crude form light yellow amorphous) was obtained by a similar method to Step 4-1.

MS (ESI pos.) m/z: 601 ([M+H]$^+$), 623 ([M+Na]$^+$), (ESI neg.) m/z: 599 ([M−H]$^−$)
$^1$H-NMR (300 MHz, CDCl$_3$) δ (ppm); 3.17 (d, J=9.0 Hz, 2H), 3.60 (s, 3H), 3.89 (s, 3H), 6.78-7.09 (m, 5H), 7.25-7.36 (m, 2H), 7.82 (dd, J=7.9, 1.5 Hz, 1H), 7.94 (d, J=8.7 Hz, 1H), 8.27 (d, J=9.0 Hz, 1H)

Step 58-3: Synthesis of 5-chloro-3-(2-methoxyphenyl)-1-{[4-methoxy-2-(trifluoromethoxy)phenyl]sulfonyl}-3-{[2-oxo-2-(4-pyridin-4-yl piperazin-1-yl)ethyl]amino}-1,3-dihydro-2H-indol-2-one With 300 mg of the compound obtained in Step 58-2 and 89 mg of 1-pyridin-4-yl piperazine as starting material, 280 mg of the title compound (colorless amorphous) was obtained by a similar method to Step 51-2.

MS (ESI pos.) m/z: 746 ([M+H]$^+$)
$^1$H-NMR (300 MHz, CDCl$_3$) δ (ppm); 1.73 (s, 1H), 2.92 (dd, J=8.4, 2.6 Hz, 1H), 3.11-3.68 (m, 12H), 3.88 (s, 3H), 6.63 (d, J=5.8 Hz, 2H), 6.79 (d, J=8.2 Hz, 1H), 6.84-6.93 (m, 2H), 6.96 (d, J=1.7 Hz, 1H), 7.07 (t, J=7.5 Hz, 1H), 7.23-7.38 (m, 2H), 7.86-7.97 (m, 2H), 8.15-8.39 (m, 3H)

Example 59

Synthesis of 5-chloro-3-(2-methoxyphenyl)-1-{[4-methoxy-2-(trifluoromethoxy)phenyl]sulfonyl}-3-{[3-oxo-3-(4-pyridin-4-yl piperazin-1-yl) propyl]amino}-1,3-dihydro-2H-indol-2-one Step 59-1: Synthesis of tert-butyl N-(5-chloro-3-(2-methoxyphenyl)-1-{[4-methoxy-2-(trifluoromethoxy)phenyl]sulfonyl}-2-oxo-2,3-dihydro-1H-indol-3-yl)-β-alaninate With 1.50 g of tert-butyl N-[5-chloro-3-(2-methoxyphenyl)-2-oxo-2,3-dihydro-1H-indol-3-yl]-β-alaninate, which is the compound described in Preparation 1.29A of the brochure Publication No. WO03/008407, and 1.15 g of 4-methoxy-2-(trifluoromethoxy)benzene sulfonyl chloride as starting materials, 2.13 g of the title compound (light yellow solid) was obtained by a similar method to Example 2.

MS (ESI pos.) m/z: 671 ([M+H]$^+$), 693 ([M+Na]$^+$), (ESI neg.) m/z: 669 ([M−H]$^−$)
$^1$H-NMR (300 MHz, CDCl$_3$) δ (ppm); 1.40 (s, 9H), 2.15-2.35 (m, 5H), 3.58 (s, 3H), 3.90 (s, 3H), 6.71-7.08 (m, 5H), 7.21-7.33 (m, 2H), 7.82-7.97 (m, 2H), 8.29 (d, J=9.0 Hz, 1H)

Step 59-2: Synthesis of N-(5-chloro-3-(2-methoxyphenyl)-1-{[4-methoxy-2-(trifluoromethoxy)phenyl]sulfonyl}-2-oxo-2,3-dihydro-1H-indol-3-yl)-β-alanine With 2.00 g of the compound obtained in Step 59-1 as starting material, 1.37 g of the title compound (colorless solid) was obtained by a similar method to Step 4-1.

MS (ESI pos.) m/z: 615 ([M+H]$^+$), 637 ([M+Na]$^+$), (ESI neg.) m/z: 613 ([M−H]$^−$)
$^1$H-NMR (300 MHz, CDCl$_3$) δ (ppm); 2.25-2.49 (m, 4H), 3.61 (s, 3H), 3.88 (s, 3H), 6.75-7.08 (m, 5H), 7.24-7.37 (m, 2H), 7.77 (dd, J=7.9, 1.6 Hz, 1H), 7.93 (d, J=8.9 Hz, 1H), 8.29 (d, J=8.9 Hz, 1H)

Step 59-3: Synthesis of 5-chloro-3-(2-methoxyphenyl)-1-{[4-methoxy-2-(trifluoromethoxy)phenyl]sulfonyl}-3-{[3-oxo-3-(4-pyridin-4-yl piperazin-1-yl) propyl]amino}-1,3-dihydro-2H-indol-2-one With 308 mg of the compound obtained in Step 59-2 as starting material, 291 mg of the title compound (colorless amorphous) was obtained by a similar method to Step 58-3.

MS (ESI pos.) m/z: 760 ([M+H]$^+$)
$^1$H-NMR (300 MHz, CDCl$_3$) δ (ppm); 2.33-2.47 (m, 3H), 2.51-2.71 (m, 2H), 3.26-3.39 (m, 4H), 3.46-3.59 (m, 5H), 3.72 (s, 2H), 3.89 (s, 3H), 6.66 (d, J=6.4 Hz, 2H), 6.75 (d, J=7.6 Hz, 1H), 6.85-6.96 (m, 3H), 6.97-7.06 (m, 1H), 7.20-7.35 (m, 2H), 7.81-7.99 (m, 2H), 8.23-8.38 (m, 3H)

Example 60

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,4-trimethylpentan amide (levorotatory isomer)

Step 60-1: Synthesis of tert-butyl{(1S)-1-[(dimethylamino)carbonyl]-3-methyl-butyl}carbamate With 3.96 g of N-(tert-butoxy carbonyl)-L-leucine as starting material, 4.11 g of the title compound (colorless oil) was obtained by a similar method to Step 6-1a.

MS (ESI pos.) m/z: 281 ([M+Na]$^+$)
$^1$H-NMR (300 MHz, CDCl$_3$) δ (ppm); 0.93 (d, J=6.7 Hz, 3H), 1.00 (d, J=6.5 Hz, 3H), 1.29-1.55 (m, 11H), 1.65-1.81 (m, 1H), 2.92 (s, 3H), 3.08 (s, 3H), 4.60-4.73 (m, 1H), 5.19-5.30 (m, 1H)

Step 60-2: Synthesis of (2S)-2-amino-N,N,4-trimethylpentan amide trifluoroacetate With 4.05 g of the compound obtained in Step 60-1 as starting material, 9.49 g of the title compound (crude form)

was obtained by a similar method to Step 4-1. The present compound was used in the next reaction without purification.

MS (ESI pos.) m/z: 159 ([M+H]$^+$)

$^1$H-NMR (300 MHz, CDCl$_3$) δ (ppm); 0.95-1.03 (m, 6H), 1.50-1.62 (m, 1H), 1.69-1.85 (m, 2H), 3.00 (s, 3H), 3.07 (s, 3H), 4.42-4.53 (m, 1H), 7.62 (s, 3H)

Step 60-3: Synthesis of (2S)-2-{[5-chloro-3-(2-methoxyphenyl)-2-oxo-2,3-dihydro-1H-indol-3-yl]amino}-N,N,4-trimethylpentan amide (levorotatory isomer and dextrorotatory isomer)

With 4.40 of 3,5-dichloro-3-(2-methoxyphenyl)-1,3-dihydro-2H-indol-2-one and the compound obtained in Step 60-2 (crude form) as starting material, respectively 2.09 g (Isomer A: colorless powder) and 3.26 g (Isomer B: colorless powder) of two species of diastereoisomers of the title compound were obtained by a similar method to Step 4-2.

Isomer A: $[\alpha]_D^{25}$=+161° (c=0.146, CHCl$_3$)

MS (ESI pos.) m/z: 430 ([M+H]$^+$)

$^1$H-NMR (300 MHz, DMSO-d$_6$) δ (ppm); 0.81-0.94 (m, 6H), 0.98-1.13 (m, 1H), 1.24-1.37 (m, 1H), 1.87-2.04 (m, 1H), 2.61 (s, 6H), 3.14 (d, J=9.3 Hz, 1H), 3.33-3.44 (m, 1H), 3.47 (s, 3H), 6.69 (d, J=2.2 Hz, 1H), 6.83 (d, J=8.3 Hz, 1H), 6.93 (dd, J=8.2, 1.1 Hz, 1H), 7.01-7.09 (m, 1H), 7.18 (dd, J=8.3, 2.3 Hz, 1H), 7.26-7.34 (m, 1H), 7.85 (dd, J=7.8, 1.7 Hz, 1H), 10.58 (s, 1H)

Isomer B: $[\alpha]_D^{25}$=–131° (c=0.230, CHCl$_3$)

MS (ESI pos.) m/z: 430 ([M+H]$^+$)

$^1$H-NMR (300 MHz, CDCl$_3$) δ (ppm); 0.64 (d, J=6.7 Hz, 3H), 0.92 (d, J=6.80 Hz, 3H), 0.98-1.10 (m, 1H), 1.44-1.57 (m, 1H), 1.91-2.10 (m, 1H), 2.65 (s, 3H), 2.87 (s, 3H), 3.35-3.44 (m, 1H), 3.51 (s, 3H), 6.74-6.84 (m, 2H), 6.92 (d, J=2.0 Hz, 1H), 7.03-7.12 (m, 1H), 7.16 (dd, J=8.2, 2.2 Hz, 1H), 7.24-7.34 (m, 1H), 7.89 (s, 1H), 8.10-8.21 (m, 1H)

Step 60-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino-N,N,4-trimethylpentan amide (levorotatory isomer)

With 2.26 g of the compound obtained in Step 60-3 (Isomer B) and 1.55 g of 4-methoxy-2-(trifluoromethoxy)benzene sulfonyl chloride as starting material, 3.15 g of the title compound (colorless amorphous) was obtained by a similar method to Example 2.

$[\alpha]_D^{26}$=–131° (c=0.258, CHCl$_3$)

MS (ESI pos.) m/z: 706 ([M+Na]$^+$)

$^1$H-NMR (300 MHz, CDCl$_3$) δ (ppm); 0.51 (d, J=6.5 Hz, 3H), 0.84 (d, J=6.7 Hz, 3H), 0.96-1.09 (m, 1H), 1.27-1.40 (m, 1H), 1.69-1.85 (m, 1H), 2.71 (s, 3H), 2.96 (s, 3H), 3.09 (s, 3H), 3.26-3.37 (m, 2H), 3.89 (s, 3H), 6.65 (dd, J=8.2, 0.9 Hz, 1H), 6.84-6.95 (m, 3H), 7.03 (td, J=7.5, 1.1 Hz, 1H), 7.19-7.33 (m, 2H), 7.93 (d, J=8.9 Hz, 1H), 8.02 (dd, J=7.8, 1.7 Hz, 1H), 8.38 (d, J=9.3 Hz, 1H)

Example 61

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer)

Step 61-1: Synthesis of tert-butyl[(1S)-2-(dimethylamino)-1-methyl-2-oxo ethyl]carbamate With 3.97 g of N-(tert-butoxy carbonyl)-L-alanine as starting material, 3.53 g of the title compound (colorless oil) was obtained by a similar procedure to Step 60-1.

MS (ESI pos.) m/z: 239 ([M+Na]$^+$)

$^1$H-NMR (300 MHz, CDCl$_3$) δ (ppm); 1.30 (d, J=6.8 Hz, 3H), 1.44 (s, 9H), 2.97 (s, 3H), 3.07 (s, 3H), 4.55-4.71 (m, 1H), 5.51 (d, J=5.9 Hz, 1H)

Step 61-2: Synthesis of (2S)-2-amino-N,N-dimethylpropanamide trifluoroacetate With 3.47 g of the compound obtained in Step 61-1 as starting material, 8.71 g of the title compound (crude form) was obtained by a similar procedure to Step 60-2.

MS (ESI pos.) m/z: 117 ([M+H]$^+$)

$^1$H-NMR (300 MHz, DMSO-d$_6$) δ (ppm); 1.31 (m, 3H), 2.89 (s, 3H), 3.02 (s, 3H), 4.26-4.42 (m, 1H), 8.10 (s, 3H)

Step 61-3: Synthesis of (2S)-2-{[5-chloro-3-(2-methoxyphenyl)-2-oxo-2,3-dihydro-1H-indol-3-yl]amino}-N,N-dimethyl propanamide (levorotatory isomer and dextrorotatory isomer)

From 4.48 g of 3,5-dichloro-3-(2-methoxyphenyl)-1,3-dihydro-2H-indol-2-one and the compound obtained in Step 61-2 (16.0 mmol, crude form) as starting materials, respectively 1.75 g (Isomer A, colorless amorphous) and 1.64 g (Isomer B, colorless powder) of two species of diastereoisomers of the title compound were obtained by a similar method to Step 4-2.

Isomer A: $[\alpha]_D^{26}$=+166° (c=0.223, CHCl$_3$)

MS (ESI pos.) m/z: 388 ([M+H]$^+$)

$^1$H-NMR (200 MHz, CDCl$_3$) δ (ppm); 1.31 (d, J=7.0 Hz, 3H), 2.92 (s, 6H), 3.54 (s, 3H), 4.00 (q, J=6.9 Hz, 1H), 6.67 (d, J=8.4 Hz, 1H), 6.81 (d, J=7.0 Hz, 1H), 6.89 (d, J=1.8 Hz, 1H), 7.03-7.15 (m, 2H), 7.26-7.37 (m, 1H), 7.62 (s, 1H), 7.99-8.08 (m, 1H)

Isomer B: $[\alpha]_D^{26}$=–97° (c=0.244, CHCl$_3$)

MS (ESI pos.) m/z: 388 ([M+H]$^+$)

$^1$H NMR (200 MHz, DMSO-d$_6$) δ (ppm); 1.01 (d, J=6.6 Hz, 3H), 2.69 (s, 6H), 3.11-3.19 (m, 1H), 3.42 (s, 3H), 3.42-3.53 (m, 1H), 6.73-6.82 (m, 2H), 6.89 (d, J=8.4 Hz, 1H), 7.00-7.10 (m, 1H), 7.21 (dd, J=7.9, 2.2 Hz, 1H), 7.24-7.35 (m, 1H), 7.88 (dd, J=7.9, 1.8 Hz, 1H), 10.50 (s, 1H)

Step 61-4: Synthesis of ((2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer)

With 0.95 g of the compound obtained in Step 61-3 (Isomer B) as starting material, 1.06 g of the title compound (colorless amorphous) was obtained by a similar procedure to Example 2.

$[\alpha]_D^{26}$=119° (c=0.216, CHCl$_3$)

MS (ESI pos.) m/z: 664 ([M+Na]$^+$)

$^1$H-NMR (300 MHz, CDCl$_3$) δ (ppm); 0.92 (d, J=6.7 Hz, 3H), 2.72 (s, 3H), 2.94 (s, 3H), 3.28 (m, 4H), 3.56 (q, J=6.7 Hz, 1H), 3.89 (s, 3H), 6.70 (d, J=8.2 Hz, 1H), 6.84-6.95 (m, 3H), 7.01 (td, J=7.5, 1.1 Hz, 1H), 7.20-7.33 (m, 2H), 7.80 (dd, J=7.9, 1.6 Hz, 1H), 7.91 (d, J=8.7 Hz, 1H), 8.34 (d, J=8.9 Hz, 1H)

Example 62

Synthesis of 2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylacetamide

Step 62-1: Synthesis of tert-butyl[2-(dimethylamino)-2-oxo ethyl]carbamate

With 3.94 g of N-(tert-butoxy carbonyl)-glycine as starting material, 2.74 g of the title compound (colorless solid) was obtained by a similar procedure to Step 60-1.

MS (ESI pos.) m/z: 223 ([M+Na]$^+$)

$^1$H-NMR (300 MHz, CDCl$_3$) δ (ppm); 1.46 (s, 9H), 2.97 (s, 3H), 2.99 (s, 3H), 3.95 (d, J=4.4 Hz, 2H), 5.52 (s, 1H)

Step 62-2: Synthesis of 2-amino-N,N-dimethylacetamide trifluoroacetate

With 1.58 g of the compound obtained in Step 62-1 as starting material, 3.96 g of the title compound (crude form) was obtained by a similar procedure to Step 60-2.

MS (ESI pos.) m/z: 103 ([M+H]$^+$)

$^1$H-NMR (300 MHz, DMSO-d$_6$) δ (ppm); 2.90 (s, 3H), 2.94 (s, 3H), 3.84 (q, J=5.7 Hz, 2H), 8.06 (s, 3H)

Step 62-3: Synthesis of 2-{[5-chloro-3-(2-methoxyphenyl)-2-oxo-2,3-dihydro-1H-indol-3-yl]amino}-N,N-dimethylacetamide With 2.01 g of 3,5-dichloro-3-(2-methoxyphenyl)-1,3-dihydro-2H-indol-2-one and the compound obtained in Step 62-2 (7.81 mmol, crude form) as starting material, 1.91 g of the title compound (colorless powder) was obtained by a similar method to Step 4-2.

MS (ESI pos.) m/z: 374 ([M+H]$^+$)

$^1$H-NMR (300 MHz, CDCl$_3$) δ (ppm); 2.86 (s, 3H), 2.94 (s, 3H), 3.41 (d, J=16.0 Hz, 1H), 3.57 (s, 3H), 3.72 (d, J=16.2 Hz, 1H), 6.78 (d, J=8.2 Hz, 1H), 6.83 (dd, J=8.2, 1.1 Hz, 1H), 6.94 (d, J=2.2 Hz, 1H), 7.05-7.12 (m, 1H), 7.14 (dd, J=8.2, 2.2 Hz, 1H), 7.27-7.37 (m, 1H), 7.96 (dd, J=7.8, 1.7 Hz, 1H), 8.00-8.08 (m, 1H)

Step 62-4: Synthesis of 2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylacetamide With 1.34 g of the compound obtained in Step 62-3 as starting material, 1.90 g of the title compound (colorless amorphous) was obtained by a similar procedure to Example 2.

MS (ESI pos.) m/z: 650 ([M+Na]$^+$)

$^1$H-NMR (300 MHz, CDCl$_3$) δ (ppm); 2.72 (s, 3H), 2.77 (s, 3H), 3.09 (d, J=15.9 Hz, 1H), 3.35 (d, J=16.0 Hz, 1H), 3.57 (s, 3H), 3.90 (s, 3H), 6.78 (dd, J=8.2, 0.9 Hz, 1H), 6.86-6.98 (m, 3H), 7.05 (td, J=7.5, 0.9 Hz, 1H), 7.24-7.34 (m, 2H), 7.88-7.94 (m, 2H), 8.24 (d, J=8.9 Hz, 1H)

Example 63

Synthesis of ((2S,3S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,3-trimethylpentan amide (levorotatory isomer)

Step 63-1: Synthesis of tert-butyl{(1S,2S)-1-[(dimethylamino)carbonyl]-2-methyl-butyl}carbamate With 4.00 g of N-(tert-butoxy carbonyl)-L-isoleucine as starting material, 4.86 g of the title compound (colorless oil) was obtained by a similar procedure to Step 60-1.

MS (ESI pos.) m/z: 259 ([M+H]$^+$)

$^1$H-NMR (300 MHz, CDCl$_3$) δ (ppm); 0.88 (t, J=7.4 Hz, 3H), 0.93 (d, J=6.8 Hz, 3H), 1.02-1.22 (m, 1H), 1.43 (s, 9H), 1.47-1.61 (m, 1H), 1.62-1.76 (m, 1H), 2.97 (s, 3H), 3.11 (s, 3H), 4.49 (dd, J=9.3, 6.8 Hz, 1H), 5.19-5.32 (m, 1H)

Step 63-2: Synthesis of (2S,3S)-2-amino-N,N,3-trimethylpentan amide trifluoroacetate With 4.00 g of the compound obtained in Step 63-1 as starting material, 9.49 g of the title compound (crude form) was obtained by a similar procedure to Step 60-2.

MS (ESI pos.) m/z: 159 ([M+H]$^+$)

$^1$H-NMR (300 MHz, CDCl$_3$) δ (ppm); 0.95 (t, J=7.4 Hz, 3H), 1.07 (d, J=7.0 Hz, 3H), 1.13-1.32 (m, 1H), 1.46-1.62 (m, 1H), 1.87-2.04 (m, 1H), 3.02 (s, 3H), 3.10 (s, 3H), 4.34-4.42 (m, 1H), 7.43-7.62 (m, 3H)

Step 63-3: Synthesis of (2S,3S)-2-{[5-chloro-3-(2-methoxyphenyl)-2-oxo-2,3-dihydro-1H-indol-3-yl]amino}-N,N,3-trim ethylpentan amide (levorotatory isomer and dextrorotatory isomer)

With 3.98 g of 3,5-dichloro-3-(2-methoxyphenyl)-1,3-dihydro-2H-indol-2-one and the compound obtained in Step 63-2 (15.5 mmol, crude form) as starting materials, respectively 1.28 g (Isomer A, colorless powder) and 2.60 g (Isomer B, colorless powder) of two species of diastereoisomers of the title compound were obtained by a similar method to Step 4-2.

Isomer A: [α]$_D^{28}$=+155° (c=0.194, CHCl$_3$)

MS (ESI pos.) m/z: 430 ([M+H]$^+$)

$^1$H-NMR (300 MHz, DMSO-d$_6$) δ (ppm); 0.74-0.85 (m, 6H), 1.02-1.16 (m, 1H), 1.34-1.45 (m, 1H), 1.58-1.72 (m, 1H), 2.54 (s, 3H), 2.56 (s, 3H), 3.10 (dd, J=9.3, 6.2 Hz, 1H), 3.49 (s, 3H), 6.70 (d, J=2.2 Hz, 1H), 6.83 (d, J=8.2 Hz, 1H), 6.94 (dd, J=8.2, 1.1 Hz, 1H), 7.04 (td, J=7.6, 1.2 Hz, 1H), 7.17 (dd, J=8.2, 2.2 Hz, 1H), 7.26-7.34 (m, 1H), 7.74 (dd, J=7.8, 1.6 Hz, 1H), 10.60 (s, 1H)

Isomer B: [α]$_D^{28}$=−125° (c=0.194, CHCl$_3$)

MS (ESI pos.) m/z: 430 ([M+H]$^+$)

$^1$H-NMR (300 MHz, DMSO-d$_6$) δ (ppm); 0.64 (d, J=6.8 Hz, 3H), 0.70 (t, J=7.5 Hz, 3H), 1.07-1.20 (m, 1H), 1.31-1.41 (m, 1H), 1.60-1.70 (m, 1H), 2.63 (s, 3H), 2.76 (s, 3H), 2.89-3.00 (m, 2H), 3.43 (s, 3H), 6.73 (d, J=2.2 Hz, 1H), 6.84 (d, J=8.2 Hz, 1H), 6.90 (dd, J=8.2, 1.1 Hz, 1H), 7.08 (td, J=7.5, 1.2 Hz, 1H), 7.24 (dd, J=8.3, 2.3 Hz, 1H), 7.27-7.35 (m, 1H), 8.02 (dd, J=7.8, 1.7 Hz, 1H), 10.50 (s, 1H)

Step 63-4: Synthesis of (2S,3S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,3-trimethylpentan amide (levorotatory isomer)

With 2.23 g of the compound obtained in Step 63-3 (Isomer B) as starting material, 2.28 g of the title compound (colorless amorphous) was obtained by a similar procedure to Example 2.

$[\alpha]_D^{28}$=−108° (c=0.199, CHCl$_3$)

MS (ESI pos.) m/z: 684 ([M+H]$^+$)

$^1$H-NMR (300 MHz, CDCl$_3$) δ (ppm); 0.71 (d, J=6.8 Hz, 3H), 0.76 (t, J=7.4 Hz, 3H), 0.97-1.14 (m, 1H), 1.32-1.44 (m, 1H), 1.58-1.68 (m, 1H), 2.70 (s, 3H), 2.96 (s, 3H), 3.06 (s, 3H), 3.10-3.18 (m, 1H), 3.26-3.34 (m, 1H), 3.88 (s, 3H), 6.64 (dd, J=8.2, 0.9 Hz, 1H), 6.83-6.94 (m, 3H), 7.03 (td, J=7.6, 1.1 Hz, 1H), 7.19-7.33 (m, 2H), 7.93 (d, J=8.9 Hz, 1H), 8.02 (dd, J=7.8, 1.7 Hz, 1H), 8.37 (d, J=9.3 Hz, 1H), Example 64

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-phenylpropanamide (levorotatory isomer)

Step 64-1: Synthesis of tert-butyl[(1S)-1-benzyl-2-(dimethylamino)-2-oxo ethyl]carbamate With 5.00 g of N-(tert-butoxy carbonyl)-L-phenylalanine as starting material, 6.36 g of the title compound (colorless oil) was obtained by a similar procedure to Step 60-1.

MS (ESI pos.) m/z: 293 ([M+H]$^+$)

$^1$H-NMR (300 MHz, CDCl$_3$) δ (ppm); 1.41 (s, 9H), 2.62 (s, 3H), 2.86 (s, 3H), 2.87-3.07 (m, 2H), 4.72-4.92 (m, 1H), 5.36-5.50 (m, 1H), 7.13-7.33 (m, 5H)

Step 64-2: Synthesis of (2S)-2-amino-N,N-dimethyl-3-phenylpropanamide trifluoroacetate With 4.92 g of the compound obtained in Step 64-1 as starting material, 10.48 g of the title compound (crude form) was obtained by a similar procedure to Step 60-2.

MS (ESI pos.) m/z: 193 ([M+H]$^+$)

$^1$H-NMR (300 MHz, CDCl$_3$) δ (ppm); 2.62 (s, 3H), 2.92 (s, 3H), 3.03-3.16 (m, 1H), 3.17-3.28 (m, 1H), 4.65-4.77 (m, 1H), 7.11-7.23 (m, 2H), 7.28-7.38 (m, 3H), 7.69 (s, 3H)

Step 64-3: Synthesis of (2S)-2-{[5-chloro-3-(2-methoxyphenyl)-2-oxo-2,3-dihydro-1H-indol-3-yl]amino}-N,N-dimethyl-3-phenylpropanamide (levorotatory isomer and dextrorotatory isomer)

With 3.90 g of 3,5-dichloro-3-(2-methoxyphenyl)-1,3-dihydro-2H-indol-2-one and the compound obtained in Step 64-2 (16.8 mmol, crude form) as starting material, respectively 1.91 g (Isomer A, colorless powder) and 2.99 g (Isomer B, colorless amorphous) of two species of diastereoisomers of the title compound were obtained by a similar method to Step 4-2.

Isomer A: $[\alpha]_D^{28}$=+147° (c=0.215, CHCl$_3$)

MS (ESI pos.) m/z: 486 ([M+Na]$^+$)

$^1$H-NMR (300 MHz, DMSO-d$_6$) δ (ppm); 2.54 (s, 3H), 2.67 (s, 3H), 2.68-2.83 (m, 2H), 2.87 (d, J=10.0 Hz, 1H), 3.42 (s, 3H), 3.80-3.93 (m, 1H), 6.62 (d, J=2.2 Hz, 1H), 6.73 (td, J=7.6, 1.0 Hz, 1H), 6.80 (d, J=8.2 Hz, 1H), 6.83-6.88 (m, 1H), 7.15-7.38 (m, 8H), 10.40 (s, 1H)

Isomer B: $[\alpha]_D^{28}$=−88, (c=0.242, CHCl$_3$)

MS (ESI pos.) m/z: 486 ([M+Na]$^+$)

$^1$H-NMR (300 MHz, CDCl$_3$) δ (ppm); 2.29 (s, 3H), 2.69-2.94 (m, 5H), 3.26 (d, J=9.2 Hz, 1H), 3.50 (s, 3H), 3.67-3.79 (m, 1H), 6.56 (d, J=2.2 Hz, 1H), 6.72-6.81 (m, 2H), 6.95-7.05 (m, 1H), 7.06-7.14 (m, 3H), 7.15-7.33 (m, 5H), 7.89 (dd, J=7.8, 1.7 Hz, 1H), 8.77 (s, 1H)

Step 64-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-phenylpropanamide (levorotatory isomer)

With 1.59 g of the compound obtained in Step 64-3 (Isomer B) as starting material, 1.89 g of the title compound (colorless amorphous) was obtained by a similar procedure to Example 2.

$[\alpha]_D^{28}$=147° (c=0.233, CHCl$_3$)

MS (ESI pos.) m/z: 718 ([M+H]$^+$)

$^1$H-NMR (300 MHz, CDCl$_3$) δ (ppm); 2.21 (dd, J=12.8, 6.8 Hz, 1H), 2.28 (s, 3H), 2.52-2.61 (m, 1H), 2.87 (s, 3H), 3.28 (s, 3H), 3.57-3.73 (m, 4H), 6.44 (d, J=2.0 Hz, 1H), 6.68 (dd, J=8.2, 0.9 Hz, 1H), 6.79-6.88 (m, 2H), 6.91-7.02 (m, 3H), 7.14-7.30 (m, 5H), 7.76 (dd, J=7.7, 1.6 Hz, 1H), 7.89 (d, J=8.9 Hz, 1H), 8.37 (d, J=9.3 Hz, 1H)

Example 65

Synthesis of ((2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-hydroxy-N,N-dimethylpropanamide (levorotatory isomer and dextrorotatory isomer)

Step 65-1: Synthesis of tert-butyl[(1S)-2-(dimethylamino)-1-(hydroxymethyl)-2-oxo ethyl]carbamate With 3.90 g of N-(tert-butoxy carbonyl)-L-serine as starting material, 1.96 g of the title compound (colorless solid) was obtained by a similar procedure to Step 60-1.

MS (ESI pos.) m/z: 255 ([M+Na]$^+$)

$^1$H-NMR (200 MHz, CDCl$_3$) δ (ppm); 1.45 (s, 9H), 2.98 (s, 3H), 3.13 (s, 3H), 3.39 (dd, J=7.5, 4.8 Hz, 1H), 3.64-3.89 (m, 2H), 4.60-4.74 (m, 1H), 5.67 (d, J=7.5 Hz, 1H)

Step 65-2: Synthesis of (2S)-2-amino-3-hydroxy-N,N-dimethylpropanamide trifluoroacetate With 1.86 g of the compound obtained in Step 65-1 as starting material, 4.60 g of the title compound (crude form) was obtained by a similar procedure to Step 60-2.

MS (ESI pos.) m/z: 133 ([M+H]$^+$)

$^1$H-NMR (300 MHz, DMSO-d$_6$) δ (ppm); 2.89 (s, 3H), 3.04 (s, 3H), 3.56-3.65 (m, 1H), 3.70-3.79 (m, 1H), 4.30-4.37 (m, 1H), 8.09 (s, 3H)

Step 65-3: Synthesis of ((2S)-2-{[5-chloro-3-(2-methoxyphenyl)-2-oxo-2,3-dihydro-1H-indol-3-yl]amino}-3-hydroxy-N,N-dimethylpropanamide (diastereoisomer mixture)

With 2.04 g of 3,5-dichloro-3-(2-methoxyphenyl)-1,3-dihydro-2H-indol-2-one and the compound obtained in Step 65-2 (8.00 mmol, crude form) as starting materials, 1.87 g of a diastereoisomer mixture of the title compound (colorless amorphous) was obtained by a similar method to Step 4-2.
MS (ESI pos.) m/z: 404 ([M+H]$^+$)
$^1$H-NMR (300 MHz, DMSO-d$_6$) δ (ppm); 2.65-2.79 (m, 6H), 2.95 and 3.02 (each m, 1H), 3.23-3.83 (m, 6H), 4.73 and 4.90 (each m, 1H), 6.68-6.96 (m, 3H), 6.99-7.11 (m, 1H), 7.16-7.34 (m, 2H), 7.94 and 8.05 (each dd, J=7.8, 1.7 Hz, 1H), 10.45 and 10.54 (each s, 1H)

Step 65-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-hydroxy-N,N-dimethylpropanamide (levorotatory isomer and dextrorotatory isomer)

With 0.88 g of the compound obtained in Step 65-3 and 0.649 g of 4-methoxy-2-(trifluoromethoxy)benzene sulfonyl chloride as starting materials, respectively 140 mg (Isomer A, colorless amorphous) and 170 mg (Isomer B, colorless amorphous) of two species of diastereoisomers of the title compound were obtained by a similar method to Example 2.
Isomer A: $[α]_D^{24}$=+145° (c=0.219, CHCl$_3$)
MS (ESI pos.) m/z: 658 ([M+H]$^+$)
$^1$H-NMR (300 MHz, DMSO-d$_6$) δ (ppm); 2.36 (s, 3H), 2.70 (s, 3H), 2.90 (d, J=9.6 Hz, 1H), 3.35-3.44 (m, 5H), 3.67-3.77 (m, 1H), 3.90 (s, 3H), 4.94-5.00 (m, 1H), 6.85 (d, J=2.2 Hz, 1H), 6.92 (dd, J=8.2, 0.9 Hz, 1H), 7.05-7.15 (m, 2H), 7.21 (dd, J=9.1, 2.4 Hz, 1H), 7.29-7.39 (m, 1H), 7.47 (dd, J=8.8, 2.4 Hz, 1H), 7.80 (d, J=8.9 Hz, 1H), 8.12 (d, J=9.0 Hz, 1H), 8.18 (dd, J=7.8, 1.7 Hz, 1H)
Isomer B: $[α]_D^{28}$=−103° (c=0.211, CHCl$_3$)
MS (ESI pos.) m/z: 658 ([M+H]$^+$)
$^1$H-NMR (300 MHz, DMSO-d$_6$) δ (ppm); 2.68 (s, 3H), 2.76 (s, 3H), 3.10 (s, 3H), 3.13-3.31 (m, 3H), 3.36-3.46 (m, 1H), 3.93 (s, 3H), 4.77 (t, J=5.9 Hz, 1H), 6.85 (dd, J=8.4, 0.9 Hz, 1H), 6.95 (d, J=2.2 Hz, 1H), 7.02-7.11 (m, 1H), 7.13-7.19 (m, 1H), 7.23-7.37 (m, 2H), 7.50 (dd, J=8.9, 2.3 Hz, 1H), 7.80 (d, J=8.9 Hz, 1H), 7.93 (dd, J=7.9, 1.7 Hz, 1H), 8.21 (d, J=9.0 Hz, 1H)

Example 66

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-4-(methylthio) butanamide (levorotatory isomer)

Step 66-1: Synthesis of tert-butyl[(1S)-1-[(dimethylamino)carbonyl]-3-(methylthio) propyl]carbamate With 4.00 g of N-(tert-butoxy carbonyl)-L-methionine as starting material, 4.22 g of the title compound (colorless oil) was obtained by a similar procedure to Step 60-1.
MS (ESI pos.) m/z: 277 ([M+H]$^+$)
$^1$H-NMR (200 MHz, CDCl$_3$) δ (ppm); 1.44 (s, 9H), 1.71-2.03 (m, 2H), 2.11 (s, 3H), 2.48-2.63 (m, 2H), 2.97 (s, 3H), 3.11 (s, 3H), 4.71-4.88 (m, 1H), 5.39-5.50 (m, 1H)

Step 66-2: Synthesis of (2S)-2-amino-N,N-dimethyl-4-(methylthio) butanamide trifluoroacetate With 3.00 g of the compound obtained in Step 66-1 as starting material, 6.38 g of the title compound (crude form) was obtained by a similar procedure to Step 60-2.
MS (ESI pos.) m/z: 177 ([M+H]$^+$)
$^1$H-NMR (300 MHz, CDCl$_3$) δ (ppm); 2.08-2.20 (m, 5H), 2.63-2.72 (m, 2H), 3.02 (s, 3H), 3.12 (s, 3H), 4.69 (t, J=6.1 Hz, 1H), 7.91 (s, 3H)

Step 66-3: Synthesis of (2S)-2-{[5-chloro-3-(2-methoxyphenyl)-2-oxo-2,3-dihydro-1H-indol-3-yl]amino}-N,N-dimethyl-4-(methylthio) butanamide (levorotatory isomer and dextrorotatory isomer)

With 1.90 g of 3,5-dichloro-3-(2-methoxyphenyl)-1,3-dihydro-2H-indol-2-one and the compound obtained in Step 66-2 (7.48 mmol, crude form) as starting materials, respectively 1.17 g (Isomer A, pale yellow amorphous) and 1.49 g (Isomer B, pale yellow amorphous) of two species of diastereoisomers of the title compound were obtained by a similar method to Step 4-2.
Isomer A: $[α]_D^{28}$=+155° (c=0.240, CHCl$_3$)
MS (ESI pos.) m/z: 470 ([M+Na]$^+$)
$^1$H-NMR (300 MHz, CDCl$_3$) δ (ppm); 1.76-1.99 (m, 2H), 2.14 (s, 3H), 2.59-2.73 (m, 1H), 2.75-2.85 (m, 1H), 2.87 (s, 3H), 2.90 (s, 3H), 3.04-3.16 (m, 1H), 3.55 (s, 3H), 3.96-4.06 (m, 1H), 6.65 (d, J=8.2 Hz, 1H), 6.81 (dd, J=8.2, 1.0 Hz, 1H), 6.91 (d, J=2.2 Hz, 1H), 7.01-7.15 (m, 2H), 7.30 (td, J=7.8, 1.7 Hz, 1H), 8.00 (dd, J=7.8, 1.7 Hz, 1H), 8.54 (s, 1H)
Isomer B: $[α]_D^{28}$=−115° (c=0.235, CHCl$_3$)
MS (ESI pos.) m/z: 470 ([M+Na]$^+$)
$^1$H-NMR (300 MHz, CDCl$_3$) δ (ppm); 1.53-1.69 (m, 1H), 1.69-1.88 (m, 1H), 2.05 (s, 3H), 2.57-2.77 (m, 2H), 2.73 (s, 3H), 2.88 (s, 3H), 3.33 (m, 1H), 3.49 (s, 3H), 3.57-3.72 (m, 1H), 6.74-6.84 (m, 2H), 6.92 (d, J=2.0 Hz, 1H), 7.02-7.11 (m, 1H), 7.14 (dd, J=8.2, 2.2 Hz, 1H), 7.24-7.33 (m, 1H), 8.08 (dd, J=7.8, 1.7 Hz, 1H), 8.99 (s, 1H)

Step 66-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-4-(methylthio) butanamide (levorotatory isomer)

With 1.19 g of the compound obtained in Step 66-3 (Isomer B) as starting material, 1.59 g of the title compound (colorless amorphous) was obtained by a similar procedure to Example 2.
$[α]_D^{28}$=−119° (c=0.227, CHCl$_3$)
MS (ESI pos.) m/z: 702 ([M+H]$^+$)
$^1$H-NMR (300 MHz, CDCl$_3$) δ (ppm); 1.44-1.75 (m, 2H), 2.00 (s, 3H), 2.45-2.53 (m, 2H), 2.78 (s, 3H), 2.97 (s, 3H), 3.09 (s, 3H), 3.43 (s, 1H), 3.54 (m, 1H), 3.89 (s, 3H), 6.65 (dd, J=8.2, 1.1 Hz, 1H), 6.83-6.94 (m, 3H), 6.98-7.07 (m, 1H), 7.20-7.34 (m, 2H), 7.88-8.00 (m, 2H), 8.32-8.39 (m, 1H)

Example 67

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N1,N1-dimethylsuccinamide (diastereoisomer mixture)

Step 67-1: Synthesis of tert-butyl{(1S)-3-amino-1-[(dimethylamino)carbonyl]-3-oxo propyl}carbamate With 3.00 g of (2S)-4-amino-2-[(tert-butoxy carbonyl)amino]-4-oxo butanoic acid as starting material, 1.30 g of the title compound (colorless amorphous) was obtained by a similar procedure to Step 60-1.

MS (ESI pos.) m/z: 282 ([M+Na]$^+$)

$^1$H-NMR (300 MHz, CDCl$_3$) δ (ppm); 1.43 (s, 9H), 2.51-2.61 (m, 1H), 2.62-2.74 (m, 1H), 2.96 (s, 3H), 3.16 (s, 3H), 4.92-5.09 (m, 1H), 5.72 (s, 1H), 5.80-6.00 (m, 1H), 6.65 (s, 1H)

Step 67-2: Synthesis of (2S)-2-amino-N1,N1-dimethylsuccinamide trifluoroacetate

With 1.00 g of the compound obtained in Step 67-1 as starting material, 2.42 g of the title compound (crude form) was obtained by a similar procedure to Step 60-2.

MS (ESI pos.) m/z: 160 ([M+H]$^+$)

$^1$H-NMR (200 MHz, DMSO-d$_6$) δ (ppm); 2.40-2.56 (m, 1H), 2.58-2.73 (m, 1H), 2.89 (s, 3H), 3.02 (s, 3H), 4.49-4.63 (m, 1H), 7.23 (s, 1H), 7.67 (s, 1H), 8.12 (s, 3H)

Step 67-3: Synthesis of (2S)-2-{[5-chloro-3-(2-methoxyphenyl)-2-oxo-2,3-dihydro-1H-indol-3-yl]amino}-N1,N1-dimethylsuccinamide (diastereoisomer mixture)

With 1.08 g of 3,5-dichloro-3-(2-methoxyphenyl)-1,3-dihydro-2H-indol-2-one and the compound obtained in Step 67-2 (15.5 mmol, crude form) as starting materials, 576 mg of the title compound (colorless amorphous) was obtained by a similar method to Step 4-2.

MS (ESI pos.) m/z: 453 ([M+Na]$^+$)

$^1$H-NMR (300 MHz, CDCl$_3$) δ (ppm); 2.23-2.57 (m, 2H), 2.63-2.71 (m, 3H), 2.76-2.86 (m, 3H), 3.51-3.64 (m, 3H), 3.77-4.19 (m, 1H), 6.74-6.87 (m, 2H), 6.95-7.17 (m, 3H), 7.21-7.36 (m, 2H), 7.74-7.97 (m, 1H), 9.13-9.71 (m, 1H)

Step 67-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N1,N1-dimethylsuccinamide (diastereoisomer mixture)

With 296 mg of the compound obtained in Step 67-3 and 204 mg of 4-methoxy-2-(trifluoromethoxy)benzene sulfonyl chloride as starting materials, 263 mg of the title compound (colorless amorphous) was obtained by a similar method to Example 2.

MS (ESI pos.) m/z: 685 ([M+H]$^+$)

$^1$H-NMR (300 MHz, CDCl$_3$) δ (ppm); 2.14-2.36 (m, 2H), 2.53 and 2.75 (each s, 3H), 2.69 and 2.97 (each s, 3H), 3.20 and 3.59 (each s, 3H), 3.82-3.95 (m, 4H), 5.12 and 5.32 (each s, 1H), 6.19 and 6.43 (each s, 1H), 6.65-7.13 (m, 5H), 7.21-7.37 (m, 2H), 7.73-7.99 (m, 2H), 8.21 and 8.35 (each d, J=8.9 Hz, 1H)

Example 68

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N1,N1-dimethylpentanediamide (levorotatory isomer)

Step 68-1: Synthesis of tert-butyl{(1S)-4-amino-1-[(dimethylamino)carbonyl]-4-oxo-butyl}carbamate With 3.00 g of (2S)-5-amino-2-[(tert-butoxy carbonyl)amino]-5-oxo pentanoic acid as starting material, 1.57 g of the title compound (colorless solid) was obtained by a similar procedure to Step 60-1.

MS (ESI pos.) m/z: 296 ([M+Na]$^+$)

$^1$H-NMR (300 MHz, CDCl$_3$) δ (ppm); 1.44 (s, 9H), 1.62-1.78 (m, 1H), 2.00-2.15 (m, 1H), 2.22-2.45 (m, 2H), 2.96 (s, 3H), 3.07 (s, 3H) 4.62 (ddd, J=10.4, 8.1, 2.6 Hz, 1H), 5.49 (s, 1H), 5.64-5.77 (m, 1H), 6.55 (s, 1H)

Step 68-2: Synthesis of (2S)-2-amino-N1,N1-dimethylpentanediamide trifluoroacetate With 1.00 g of the compound obtained in Step 68-1 as starting material, 2.25 g of the title compound (crude form) was obtained by a similar procedure to Step 60-2.

MS (ESI pos.) m/z: 196 ([M+Na]$^+$)

$^1$H-NMR (200 MHz, DMSO-d$_6$) δ (ppm); 1.72-2.42 (m, 4H), 2.81-3.09 (m, 6H), 4.30-4.56 (m, 1H), 6.85-8.24 (m, 5H)

Step 68-3: Synthesis of (2S)-2-{[5-chloro-3-(2-methoxyphenyl)-2-oxo-2,3-dihydro-1H-indol-3-yl]amino}-N1,N1-dimethylpentanediamide (levorotatory isomer and dextrorotatory isomer)

With 1.03 g of 3,5-dichloro-3-(2-methoxyphenyl)-1,3-dihydro-2H-indol-2-one and the compound obtained in Step 68-2 (3.66 mmol, crude form) as starting materials, respectively 168 mg (Isomer A, colorless amorphous) and 204 mg (Isomer B, colorless amorphous) of two species of diastereoisomers of the title compound were obtained by a similar method to Step 4-2.

Isomer A: $[α]_D^{28}$=+118° (c=0.250, CHCl$_3$)

MS (ESI pos.) m/z: 467 ([M+Na]$^+$)

$^1$H-NMR (300 MHz, CDCl$_3$) δ (ppm); 1.44-1.60 (m, 1H), 1.82-1.99 (m, 1H), 2.22-2.34 (m, 1H), 2.68 (s, 3H), 2.75 (s, 3H), 2.85-3.00 (m, 1H), 3.30 (m, 1H), 3.58 (s, 3H), 3.83-4.06 (m, 1H), 5.88 (s, 1H), 6.61 (d, J=8.1 Hz, 1H), 6.82 (dd, J=8.2, 1.1 Hz, 1H), 6.98-7.12 (m, 3H), 7.24-7.33 (m, 1H), 7.75 (dd, J=7.8, 1.6 Hz, 1H), 10.98 (s, 1H)

Isomer B: $[α]_D^{28}$=−111° (c=0.184, MeOH)

MS (ESI pos.) m/z: 467 ([M+Na]$^+$)

$^1$H-NMR (300 MHz, DMSO-d$_6$) δ (ppm); 1.33-1.47 (m, 1H), 1.47-1.61 (m, 1H), 2.09-2.31 (m, 2H), 2.65 (s, 3H), 2.72 (s, 3H), 3.22-3.39 (m, 2H), 3.41 (s, 3H), 6.59 (s, 1H), 6.75-6.84 (m, 2H), 6.89 (dd, J=8.2, 0.9 Hz, 1H), 7.07 (td, J=7.5, 1.1 Hz, 1H), 7.16-7.36 (m, 3H), 8.04 (dd, J=7.7, 1.6 Hz, 1H), 10.43 (s, 1H)

Step 68-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N1,N1-dimethylpentanediamide (levorotatory isomer)

With 88 mg of the compound obtained in Step 68-3 (Isomer B) as starting material, 80 mg of the title compound (colorless amorphous) was obtained by a similar procedure to Example 2.

$[α]_D^{27}$=−141° (c=0.187, CHCl$_3$)

MS (ESI pos.) m/z: 721 ([M+Na]$^+$)

$^1$H-NMR (300 MHz, CDCl$_3$) δ (ppm); 1.44-1.81 (m, 2H), 2.19-2.29 (m, 1H), 2.32-2.47 (m, 1H), 2.84 (s, 3H), 2.97 (s, 3H), 3.10 (s, 3H), 3.42-3.52 (m, 1H), 3.89 (s, 3H), 5.14 (s, 1H), 5.48 (s, 1H), 6.61-6.71 (m, 1H), 6.80-6.95 (m, 3H), 6.96-7.08 (m, 1H), 7.20-7.33 (m, 2H), 7.83-7.90 (m, 1H), 7.92 (d, J=8.9 Hz, 1H), 8.35 (d, J=9.0 Hz, 1H)

Example 69

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,N',N'-tetramethyl succinamide (levorotatory isomer)

Step 69-1: Synthesis of tert-butyl{(1S)-3-(dimethylamino)-1-[(dimethylamino)carbonyl]-3-oxopropyl}carbamate With 4.00 g of N-(tert-butoxy carbonyl)-L-aspartic acid as starting material, 3.09 g of the title compound (colorless oil) was obtained by a similar method to Step 6-1a.

MS (ESI pos.) m/z: 288 ([M+H]$^+$)

$^1$H-NMR (300 MHz, CDCl$_3$) δ (ppm); 1.43 (s, 9H), 2.63 (dd, J=16.2, 3.9 Hz, 1H), 2.90 (s, 3H), 2.93-2.99 (m, 1H), 2.97 (s, 3H), 3.00 (s, 3H), 3.22 (s, 3H), 4.97-5.11 (m, 1H), 5.26 (d, J=9.0 Hz, 1H)

Step 69-2: Synthesis of (2S)-2-amino-N,N,N',N'-tetramethylsuccinamide trifluoroacetate With 2.00 g of the compound obtained in Step 69-1 as starting material, 5.34 g of the title compound (crude form) was obtained by a similar procedure to Step 60-2.

MS (ESI pos.) m/z: 188 ([M+H]$^+$)

$^1$H-NMR (300 MHz, DMSO-d$_6$) δ (ppm); 2.60-2.73 (m, 1H), 2.88 (s, 3H), 2.89-2.94 (m, 4H), 2.96 (s, 3H), 3.01 (s, 3H), 4.49-4.60 (m, 1H), 8.06 (s, 3H)

Step 69-3: Synthesis of (2S)-2-{[5-chloro-3-(2-methoxyphenyl)-2-oxo-2,3-dihydro-1H-indol-3-yl]amino}-N,N,N',N'-tetramethyl succinamide (levorotatory isomer and dextrorotatory isomer)

With 1.95 g of 3,5-dichloro-3-(2-methoxyphenyl)-1,3-dihydro-2H-indol-2-one and the compound obtained in Step 69-2 (6.96 mmol, crude form) as starting materials, respectively 0.92 g (Isomer A: colorless powder) and 1.48 g (Isomer B: colorless powder) of two species of diastereoisomers of the title compound were obtained by a similar method to Step 4-2.

Isomer A: [α]$_D^{28}$=+139° (c=0.204, CHCl$_3$)

MS (ESI pos.) m/z: 481 ([M+Na]$^+$)

$^1$H-NMR (300 MHz, CDCl$_3$) δ (ppm); 2.49 (dd, J=14.5, 5.4 Hz, 1H), 2.76 (dd, J=14.6, 7.8 Hz, 1H), 2.88 (s, 6H), 3.03 (s, 3H), 3.12 (s, 3H), 3.56 (s, 3H), 4.28 (dd, J=7.5, 5.5 Hz, 1H), 6.71 (d, J=8.2 Hz, 1H), 6.79 (dd, J=8.2, 1.0 Hz, 1H), 6.90 (d, J=2.2 Hz, 1H), 6.99-7.12 (m, 2H), 7.23-7.33 (m, 1H), 7.82 (dd, J=7.8, 1.7 Hz, 1H), 8.24 (s, 1H)

Isomer B: [α]$_D^{27}$=−95° (c=0.222, CHCl$_3$)

MS (ESI pos.) m/z: 481 ([M+Na]$^+$)

$^1$H-NMR (300 MHz, DMSO-d$_6$) δ (ppm); 2.27-2.39 (m, 1H), 2.43-2.48 (m, 1H), 2.68 (s, 3H), 2.71 (s, 3H), 2.78 (s, 3H), 2.95 (s, 3H), 3.11 (d, J=9.5 Hz, 1H), 3.43 (s, 3H), 3.72-3.82 (m, 1H), 6.71 (d, J=2.3 Hz, 1H), 6.79-6.93 (m, 2H), 7.04 (td, J=7.5, 1.1 Hz, 1H), 7.18-7.33 (m, 2H), 7.92 (dd, J=7.8, 1.7 Hz, 1H), 10.50 (s, 1H)

Step 69-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,N',N'-tetramethyl succinamide (levorotatory isomer)

With 0.72 g of the compound obtained in Step 69-3 (Isomer B) as starting material, 0.99 g of the title compound (colorless amorphous) was obtained by a similar procedure to Example 2.

[α]$_D^{27}$=−98° (c=0.211, CHCl$_3$)

MS (ESI pos.) m/z: 713 ([M+H]$^+$)

$^1$H-NMR (300 MHz, CDCl$_3$) δ (ppm); 2.37-2.54 (m, 2H), 2.78 (s, 3H), 2.89 (s, 3H), 2.93 (s, 3H), 2.97 (s, 3H), 3.19 (s, 3H), 3.89 (s, 3H), 3.98 (t, J=6.6 Hz, 1H), 6.67 (dd, J=8.2, 1.1 Hz, 1H), 6.82-6.94 (m, 3H), 7.01 (td, J=7.6, 1.2 Hz, 1H), 7.20-7.34 (m, 2H), 7.84-7.96 (m, 2H), 8.30-8.40 (m, 1H)

Example 70

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,N',N'-tetramethylpentanediamide (levorotatory isomer)

Step 70-1: Synthesis of tert-butyl{(1S)-4-(dimethylamino)-1-[(dimethylamino)carbonyl]-4-oxobutyl}carbamate With 4.00 g of N-(tert-butoxy carbonyl)-L-glutamic acid as starting material, 3.21 g of the title compound (colorless solid) was obtained by a similar procedure to Step 69-1.

MS (ESI pos.) m/z: 302 ([M+H]$^+$)

$^1$H-NMR (300 MHz, CDCl$_3$) δ (ppm); 1.43 (s, 9H), 1.56-1.71 (m, 1H), 2.08-2.22 (m, 1H), 2.23-2.35 (m, 1H), 2.45-2.60 (m, 1H), 2.94-2.97 (m, 6H), 2.98 (s, 3H), 3.19 (s, 3H), 4.57-4.71 (m, 1H), 5.52 (d, J=8.2 Hz, 1H)

Step 70-2: Synthesis of (2S)-2-amino-N,N,N',N'-tetramethylpentanediamide trifluoroacetate With 1.70 g of the compound obtained in Step 70-1 as starting material, 4.23 g of the title compound (crude form) was obtained by a similar procedure to Step 60-2.

MS (ESI pos.) m/z: 202 ([M+H]$^+$)

$^1$H-NMR (300 MHz, DMSO-d$_6$) δ (ppm); 1.71-1.89 (m, 1H), 1.90-2.04 (m, 1H), 2.37-2.49 (m, 2H), 2.84 (s, 3H), 2.90 (s, 3H), 2.94 (s, 3H), 3.09 (s, 3H), 4.29-4.41 (m, 1H), 8.10 (s, 3H)

Step 70-3: Synthesis of (2S)-2-{[5-chloro-3-(2-methoxyphenyl)-2-oxo-2,3-dihydro-1H-indol-3-yl]amino}-N,N,N',N'-tetramethylpentanediamide (levorotatory isomer and dextrorotatory isomer)

With 1.58 g of 3,5-dichloro-3-(2-methoxyphenyl)-1,3-dihydro-2H-indol-2-one and the compound obtained in Step 70-2 (5.64 mmol, crude form) as starting materials, respectively 0.64 g (Isomer A, colorless powder) and 1.14 g (Isomer B, colorless powder) of two species of diastereoisomers of the title compound were obtained by a similar method to Step 4-2.

Isomer A: [α]$_D^{27}$=+163° (c=0.196, CHCl$_3$)

MS (ESI pos.) m/z: 495 ([M+Na]$^+$)

$^1$H-NMR (300 MHz, DMSO-d$_6$) δ (ppm); 1.27-1.42 (m, 1H), 1.63-1.76 (m, 1H), 2.19-2.33 (m, 1H), 2.63 (s, 3H), 2.67-2.78 (m, 4H), 2.83 (s, 3H), 2.97 (s, 3H), 3.37-3.46 (m, 1H), 3.49 (s, 3H), 6.72 (d, J=2.2 Hz, 1H), 6.82 (d, J=8.2 Hz, 1H), 6.93 (dd, J=8.2, 0.9 Hz, 1H), 7.01 (td, J=7.5, 1.1 Hz, 1H), 7.18 (dd, J=8.2, 2.2 Hz, 1H), 7.25-7.34 (m, 1H), 7.71 (dd, J=7.8, 1.7 Hz, 1H), 10.48 (s, 1H)

Isomer B: $[\alpha]_D^{27}$=−91° (c=0.209, CHCl$_3$)

MS (ESI pos.) m/z: 473 ([M+H]$^+$)

$^1$H-NMR (300 MHz, CDCl$_3$) δ (ppm); 1.43-1.58 (m, 1H), 1.74-1.86 (m, 1H), 2.22-2.34 (m, 1H), 2.64-2.78 (m, 1H), 2.83 (s, 3H), 2.90 (s, 3H), 3.01 (s, 3H), 3.02 (s, 3H), 3.49 (s, 3H), 3.52-3.61 (m, 2H), 6.71-6.86 (m, 3H), 7.01-7.17 (m, 2H), 7.22-7.36 (m, 1H), 8.06 (dd, J=7.7, 1.6 Hz, 1H), 8.13 (s, 1H)

Step 70-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,N',N'-tetramethylpentanediamide (levorotatory isomer)

With 0.50 g of the compound obtained in Step 70-3 (Isomer B) as starting material, 721 mg of the title compound (colorless amorphous) was obtained by a similar procedure to Example 2.

$[\alpha]_D^{27}$=136° (c=0.185, CHCl$_3$)

MS (ESI pos.) m/z: 727 ([M+H]$^+$)

$^1$H-NMR (300 MHz, CDCl$_3$) δ (ppm); 1.40-1.54 (m, 1H), 1.69-1.82 (m, 1H), 2.20-2.32 (m, 1H), 2.49-2.65 (m, 1H), 2.86 (s, 3H), 2.97 (s, 3H), 2.99-3.03 (m, 9H), 3.39-3.48 (m, 1H), 3.60-3.72 (m, 1H), 3.89 (s, 3H), 6.64 (d, J=8.2 Hz, 1H), 6.74 (d, J=2.3 Hz, 1H), 6.85-6.92 (m, 2H), 7.04 (td, J=7.6, 1.1 Hz, 1H), 7.20-7.36 (m, 2H), 7.92 (d, J=8.9 Hz, 1H), 8.01 (dd, J=7.8, 1.7 Hz, 1H), 8.36 (d, J=8.6 Hz, 1H)

Example 71

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(methyl)amino]-N,N-dimethylpropanamide (levorotatory isomer)

Step 71-1: Synthesis of tert-butyl[(1S)-2-(dimethylamino)-1-methyl-2-oxo ethyl]methyl carbamate With 2.50 g of N-(tert-butoxy carbonyl)-N-methyl-L-alanine as starting material, 2.70 g of the title compound (colorless oil) was obtained by a similar procedure to Step 60-1.

MS (ESI pos.) m/z: 253 ([M+Na]$^+$)

$^1$H-NMR (300 MHz, CDCl$_3$) δ (ppm); 1.27 (d, J=6.8 Hz, 3H), 1.47 (s, 9H), 2.74 (s, 3H), 2.96 (s, 3H), 3.02 (s, 3H), 4.77-5.18 (m, 1H)

Step 71-2: Synthesis of (2S)—N,N-dimethyl-2-(methyl amino) propanamide trifluoroacetate With 1.35 g of the compound obtained in Step 71-1 as starting material, 2.94 g of the title compound (crude form) was obtained by a similar procedure to Step 60-2.

MS (ESI pos.) m/z: 131 ([M+H]$^+$)

$^1$H-NMR (300 MHz, DMSO-d$_6$) δ (ppm); 1.33 (d, J=6.8 Hz, 3H), 2.90 (s, 3H), 3.01 (s, 3H), 4.27-4.43 (m, 1H), 8.69 (s, 1H), 8.93 (s, 1H)

Step 71-3: Synthesis of (2S)-2-[[5-chloro-3-(2-methoxyphenyl)-2-oxo-2,3-dihydro-1H-indol-3-yl](methyl)amino]-N,N-dimethylpropanamide (levorotatory isomer and dextrorotatory isomer)

With 1.64 g of 3,5-dichloro-3-(2-methoxyphenyl)-1,3-dihydro-2H-indol-2-one and the compound obtained in Step 71-2 (5.86 mmol, crude form) as starting materials, respectively 0.90 g (Isomer A, colorless amorphous) and 1.41 g (Isomer B, colorless amorphous) of two species of diastereoisomers of the title compound were obtained by a similar method to Step 4-2.

Isomer A: $[\alpha]_D^{27}$=+102° (c=0.176, CHCl$_3$)

MS (ESI pos.) m/z: 402 ([M+H]$^+$)

$^1$H-NMR (300 MHz, CDCl$_3$) δ (ppm); 1.15-1.35 (m, 3H), 2.58 (s, 3H), 2.88-3.04 (m, 5H), 3.56 (s, 3H), 3.82-4.00 (m, 1H), 6.76-6.90 (m, 3H), 6.97-7.20 (m, 2H), 7.21-7.33 (m, 1H), 7.76-7.98 (m, 1H), 8.39 (s, 1H)

Isomer B: $[\alpha]_D^{27}$=−106° (c=0.220, CHCl$_3$)

MS (ESI pos.) m/z: 402 ([M+H]$^+$)

$^1$H-NMR (300 MHz, CDCl$_3$) δ (ppm); 1.23-1.32 (m, 3H), 2.50-2.68 (m, 6H), 2.83-2.98 (m, 3H), 3.56 (s, 3H), 4.25-4.40 (m, 1H), 6.72-6.93 (m, 3H), 6.97-7.19 (m, 2H), 7.22-7.34 (m, 1H), 7.77-7.96 (m, 1H), 8.21-8.39 (m, 1H)

Step 71-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(methyl)amino]-N,N-dimethylpropanamide (levorotatory isomer)

With 0.66 g of the compound obtained in Step 71-3 (Isomer B) as starting material, 0.77 g of the title compound (colorless amorphous) was obtained by a similar procedure to Example 2.

$[\alpha]_D^{27}$=−176° (c=0.190, CHCl$_3$)

MS (ESI pos.) m/z: 656 ([M+H]$^+$)

$^1$H-NMR (300 MHz, CDCl$_3$) δ (ppm); 0.71-1.01 (m, 3H), 2.32 (s, 3H), 2.47 (s, 3H), 2.92 (s, 3H), 3.53 (s, 3H), 3.90 (s, 3H), 4.18-4.34 (m, 1H), 6.77 (d, J=8.4 Hz, 1H), 6.86-7.03 (m, 4H), 7.19-7.31 (m, 2H), 7.66 (d, J=7.6 Hz, 1H), 7.89 (d, J=8.9 Hz, 1H), 8.34 (d, J=8.6 Hz, 1H)

Example 72

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(1H-indol-3-yl)-N,N-dimethylpropanamide (levorotatory isomer)

Step 72-1: Synthesis of tert-butyl[(1S)-2-(dimethylamino)-1-(1H-indol-3-ylmethyl)-2-oxo ethyl]carbamate With 4.00 g of N-(tert-butoxy carbonyl)-L-tryptophan as starting material, 4.08 g of the title compound (pale yellow solid) was obtained by a similar procedure to Step 60-1.

MS (ESI pos.) m/z: 354 ([M+Na]$^+$)

$^1$H-NMR (300 MHz, CDCl$_3$) δ (ppm); 1.43 (s, 9H), 2.53 (s, 3H), 2.77 (s, 3H), 3.07-3.23 (m, 2H), 4.85-5.01 (m, 1H), 5.51

(d, J=8.4 Hz, 1H), 7.02 (d, J=2.2 Hz, 1H), 7.06-7.23 (m, 2H), 7.33 (d, J=7.9 Hz, 1H), 7.62 (d, J=7.8 Hz, 1H), 8.28 (s, 1H)

Step 72-2: Synthesis of (2S)-2-amino-3-(1H-indol-3-yl)-N,N-dimethylpropanamide trifluoroacetate With 2.50 g of the compound obtained in Step 72-1 as starting material, 5.47 g of the title compound (crude form) was obtained by a similar procedure to Step 60-2.
MS (ESI pos.) m/z: 232 ([M+H]$^+$)
$^1$H-NMR (300 MHz, CDCl$_3$) δ (ppm); 2.85 (s, 3H), 2.87 (s, 3H), 3.21-3.40 (m, 2H), 4.64-4.78 (m, 1H), 7.08-7.28 (m, 3H), 7.34-7.41 (m, 2H), 7.42-7.68 (m, 3H), 8.40 (s, 1H)

Step 72-3: Synthesis of (2S)-2-{[5-chloro-3-(2-methoxyphenyl)-2-oxo-2,3-dihydro-1H-indol-3-yl]amino}-3-(1H-indol-3-yl)-N,N-dimethylpropanamide (levorotatory isomer and dextrorotatory isomer)

With 2.02 g of 3,5-dichloro-3-(2-methoxyphenyl)-1,3-dihydro-2H-indol-2-one and the compound obtained in Step 72-2 (7.54 mmol, crude form) as starting materials, respectively 0.96 g (Isomer A, colorless solid) and 1.64 g (Isomer B, pale brownish red amorphous) of two species of diastereoisomers of the title compound were obtained by a similar method to Step 4-2.
Isomer A: [α]$_D^{24}$=+120° (c=0.152, MeOH)
MS (ESI pos.) m/z: 525 ([M+Na]$^+$)
$^1$H-NMR (300 MHz, DMSO-d$_6$) δ (ppm); 2.40 (s, 3H), 2.59 (s, 3H), 2.90-2.97 (m, 3H), 3.43 (s, 3H), 3.87-3.98 (m, 1H), 6.66 (d, J=2.2 Hz, 1H), 6.71 (td, J=7.5, 1.1 Hz, 1H), 6.79 (d, J=8.2 Hz, 1H), 6.86 (dd, J=8.2, 0.9 Hz, 1H), 6.90-6.98 (m, 1H), 7.06 (td, J=7.6, 1.0 Hz, 1H), 7.10-7.26 (m, 3H), 7.35 (d, J=8.1 Hz, 1H), 7.45 (d, J=7.8 Hz, 1H), 7.61 (dd, J=7.7, 1.6 Hz, 1H), 10.42 (s, 1H), 10.83-10.89 (m, 1H)
Isomer B: [α]$_D^{27}$=-97° (c=0.223, CHCl$_3$)
MS (ESI pos.) m/z: 525 ([M+Na]$^+$)
$^1$H-NMR (300 MHz, DMSO-d$_6$) δ (ppm); 2.07 (s, 3H), 2.61 (s, 3H), 2.77-2.85 (m, 2H), 3.21 (d, J=8.4 Hz, 1H), 3.42 (s, 3H), 3.46-3.57 (m, 1H), 6.60 (d, J=2.2 Hz, 1H), 6.80 (d, J=8.2 Hz, 1H), 6.83-6.92 (m, 2H), 6.95 (d, J=2.3 Hz, 1H), 6.97-7.11 (m, 3H), 7.21 (dd, J=8.3, 2.3 Hz, 1H), 7.24-7.34 (m, 2H), 7.93 (dd, J=7.8, 1.7 Hz, 1H), 10.50 (s, 1H), 10.76 (d, J=1.6 Hz, 1H)

Step 72-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(1H-indol-3-yl)-N,N-dimethylpropanamide (levorotatory isomer)

With 0.76 g of the compound obtained in Step 72-3 (Isomer B) as starting material, 0.70 g of the title compound (colorless amorphous) was obtained by a similar procedure to Example 2.
[α]$_D^{27}$=-174° (c=0.230, CHCl$_3$)
MS (ESI pos.) m/z: 779 ([M+Na]$^+$)
$^1$H-NMR (300 MHz, DMSO-d$_6$) δ (ppm); 2.16 (s, 3H), 2.52-2.62 (m, 1H), 2.65 (s, 3H), 2.67-2.77 (m, 1H), 3.10 (s, 3H), 3.41 (d, J=8.4 Hz, 1H), 3.53 (m, 1H), 3.80 (s, 3H), 6.47 (d, J=2.3 Hz, 1H), 6.78-6.87 (m, 1H), 6.88-7.07 (m, 4H), 7.06-7.14 (m, 1H), 7.18-7.34 (m, 4H), 7.41 (dd, J=8.8, 2.4 Hz, 1H), 7.74 (d, J=8.9 Hz, 1H), 7.84 (dd, J=7.8, 1.6 Hz, 1H), 8.23 (d, J=9.2 Hz, 1H), 10.78 (d, J=2.0 Hz, 1H)

Example 73

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(1,3-thiazol-4-yl) propanamide (levorotatory isomer)

Step 73-1: Synthesis of tert-butyl[(1S)-2-(dimethylamino)-2-oxo-1-(1,3-thiazol-4-ylmethyl)ethyl]carbamate With 2.98 g of N-(tert-butoxy carbonyl)-3-(1,3-thiazol-4-yl)-L-alanine as starting material, 3.42 g of the title compound (colorless solid) was obtained by a similar procedure to Step 60-1.
MS (ESI pos.) m/z: 322 ([M+Na]$^+$)
$^1$H-NMR (300 MHz, CDCl$_3$) δ (ppm); 1.38 (s, 9H), 2.93 (s, 3H), 2.99 (s, 3H), 3.04-3.14 (m, 1H), 3.16-3.25 (m, 1H), 4.95-5.06 (m, 1H), 5.47 (d, J=9.2 Hz, 1H), 7.09 (d, J=2.0 Hz, 1H), 8.76 (d, J=1.9 Hz, 1H)

Step 73-2: Synthesis of (2S)-2-amino-N,N-dimethyl-3-(1,3-thiazol-4-yl) propanamide trifluoroacetate With 2.00 g of the compound obtained in Step 73-1 as starting material, 5.28 g of the title compound (crude form) was obtained by a similar procedure to Step 60-2.
MS (ESI pos.) m/z: 200 ([M+H]$^+$)
$^1$H-NMR (300 MHz, DMSO-d$_6$) δ (ppm); 2.84 (s, 3H), 2.85 (s, 3H), 3.20 (d, J=6.5 Hz, 2H), 4.58-4.72 (m, 1H), 7.52 (d, J=1.9 Hz, 1H), 8.19 (s, 3H), 9.12 (d, J=2.0 Hz, 1H)

Step 73-3: Synthesis of (2S)-2-{[5-chloro-3-(2-methoxyphenyl)-2-oxo-2,3-dihydro-1H-indol-3-yl]amino}-N,N-dimethyl-3-(1,3-thiazol-4-yl)propanamide8 levorotatory isomer, dextrorotatory isomer)

With 1.87 g of 3,5-dichloro-3-(2-methoxyphenyl)-1,3-dihydro-2H-indol-2-one and the compound obtained in Step 73-2 (6.68 mmol, crude form) as starting materials, respectively 0.71 g (Isomer A, colorless powder) and 1.29 g (Isomer B, colorless amorphous) of two species of diastereoisomers of the title compound were obtained by a similar method to Step 4-2.
Isomer A: [α]$_D^{27}$=+93° (c=0.205, CHCl$_3$)
MS (ESI pos.) m/z: 471 ([M+H]$^+$)
$^1$H-NMR (300 MHz, DMSO-d$_6$) δ (ppm); 2.69 (s, 3H), 2.73 (s, 3H), 2.80-2.88 (m, 2H), 2.95 (d, J=9.9 Hz, 1H), 3.42 (s, 3H), 4.01-4.11 (m, 1H), 6.61 (d, J=2.2 Hz, 1H), 6.66-6.74 (m, 1H), 6.78-6.88 (m, 2H), 7.13-7.26 (m, 3H), 7.51 (d, J=2.0 Hz, 1H), 9.07 (d, J=2.0 Hz, 1H), 10.41 (s, 1H)
Isomer B: [α]$_D^{27}$=-72° (c=0.201, CHCl$_3$)
MS (ESI pos.) m/z: 471 ([M+H]$^+$)
$^1$H-NMR (300 MHz, DMSO-d$_6$) δ (ppm); 2.61-2.88 (m, 8H), 3.38 (s, 3H), 3.55 (t, J=6.8 Hz, 1H), 6.03 (d, J=2.3 Hz, 1H), 6.75-6.91 (m, 2H), 6.94-7.04 (m, 1H), 7.11-7.32 (m, 2H), 7.44 (d, J=2.0 Hz, 1H), 7.85 (dd, J=7.8, 1.6 Hz, 1H), 8.88 (d, J=2.0 Hz, 1H), 10.45 (s, 1H)

Step 73-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(1,3-thiazol-4-yl) propanamide (levorotatory isomer)

With 0.79 g of the compound obtained in Step 73-3 (Isomer B) as starting material, 0.87 g of the title compound (colorless amorphous) was obtained by a similar procedure to Example 2.

$[\alpha]_D^{27}$=−102° (c=0.216, CHCl$_3$)

MS (ESI pos.) m/z: 747 ([M+Na]$^+$)

$^1$H-NMR (300 MHz, CDCl$_3$) δ (ppm); 2.69-2.90 (m, 5H), 2.98 (s, 3H), 3.02 (s, 3H), 3.47-3.71 (m, 2H), 3.85 (s, 3H), 6.07 (d, J=2.0 Hz, 1H), 6.60 (dd, J=8.2, 1.0 Hz, 1H), 6.83-6.92 (m, 2H), 6.95-7.05 (m, 1H), 7.09 (d, J=2.0 Hz, 1H), 7.14-7.30 (m, 2H), 7.80-7.94 (m, 2H), 8.37 (d, J=9.3 Hz, 1H), 8.67 (d, J=2.0 Hz, 1H)

Example 74

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl butanamide (levorotatory isomer)

Step 74-1: Synthesis of (2S)-2-[(tert-butoxy carbonyl)amino]butanoic acid

In an aqueous solution of 2 mol/L NaOH (30 ml), 3.00 g of (2S)-2-amino butanoic acid was dissolved, THF (10 ml) and (Boc)$_2$O (25 ml) were added, and the solution was stirred at room temperature for 4 hours. EtOAc was added, liquid separation was performed, the pH of the aqueous layer was adjusted to 2 with 1 mol/L hydrochloric acid, and then, this was extracted with EtOAc. The organic layers were combined, washed with water and saturated brine, dried over MgSO$_4$, then, the drying agent was separated by filtration, and the solvent was evaporated under reduced pressure to obtain 4.50 g of the title compound. The present compound was used in the next reaction without purification.

MS (ESI pos.) m/z: 226 ([M+Na]$^+$)

$^1$H-NMR (300 MHz, CDCl$_3$) δ (ppm); 0.99 (t, J=7.5 Hz, 3H), 1.45 (s, 9H), 1.65-1.82 (m, 1H), 1.84-2.01 (m, 1H), 4.20-4.34 (m, 1H), 5.00 (d, J=7.6 Hz, 1H)

Step 74-2: Synthesis of tert-butyl{(1S)-1-[(dimethylamino)carbonyl]propyl}carbamate With 3.39 g of the compound obtained in Step 74-1 as starting material, 3.50 g of the title compound (colorless oil) was obtained by a similar procedure to Step 60-1.

MS (ESI pos.) m/z: 253 ([M+Na]$^+$)

$^1$H-NMR (300 MHz, CDCl$_3$) δ (ppm); 0.94 (t, J=7.5 Hz, 3H), 1.44 (s, 9H), 1.47-1.84 (m, 2H), 2.97 (s, 3H), 3.08 (s, 3H), 4.49-4.64 (m, 1H), 5.40 (d, J=7.8 Hz, 1H)

Step 74-3: Synthesis of (2S)-2-amino-N,N-dimethyl butanamide trifluoroacetate

With 2.08 g of the compound obtained in Step 74-2 as starting material, 4.14 g of the title compound (crude form) was obtained by a similar procedure to Step 60-2.

MS (ESI pos.) m/z: 131 ([M+H]$^+$)

$^1$H-NMR (300 MHz, CDCl$_3$) δ (ppm); 1.04 (t, J=7.5 Hz, 3H), 1.81-2.03 (m, 2H), 3.00 (s, 3H), 3.07 (s, 3H), 4.39-4.50 (m, 1H), 7.72 (s, 3H)

Step 74-4: Synthesis of (2S)-2-{[5-chloro-3-(2-methoxyphenyl)-2-oxo-2,3-dihydro-1H-indol-3-yl]amino}-N,N-dimethyl butanamide (levorotatory isomer and dextrorotatory isomer)

With 2.42 g of 3,5-dichloro-3-(2-methoxyphenyl)-1,3-dihydro-2H-indol-2-one and the compound obtained in Step 74-3 (9.03 mmol, crude form) as starting materials, respectively 1.1 μg (Isomer A, colorless powder) and 1.77 g (Isomer B, colorless powder) of two species of diastereoisomers of the title compound were obtained by a similar method to Step 4-2.

Isomer A: $[\alpha]_D^{27}$=+142° (c=0.235, CHCl$_3$)

MS (ESI pos.) m/z: 402 ([M+H]$^+$)

$^1$H-NMR (300 MHz, DMSO-d$_6$) δ (ppm); 0.85 (t, J=7.4 Hz, 3H), 1.41-1.64 (m, 2H), 2.67 (s, 3H), 2.71 (s, 3H), 3.01 (d, J=9.3 Hz, 1H), 3.47 (s, 3H), 3.52-3.62 (m, 1H), 6.70 (d, J=2.0 Hz, 1H), 6.82 (d, J=8.2 Hz, 1H). 6.93 (dd, J=8.2, 1.1 Hz, 1H), 7.01-7.12 (m, 1H), 7.19 (dd, J=8.2, 2.2 Hz, 1H), 7.26-7.36 (m, 1H), 7.90 (dd, J=7.8, 1.7 Hz, 1H), 10.46 (s, 1H)

Isomer B: $[\alpha]_D^{27}$=−150° (c=0.223, CHCl$_3$)

MS (ESI pos.) m/z: 402 ([M+H]$^+$)

$^1$H-NMR (300 MHz, DMSO-d$_6$) δ (ppm); 0.79 (t, J=7.4 Hz, 3H), 1.24-1.38 (m, 2H), 2.66 (s, 3H), 2.73 (s, 3H), 3.03-3.11 (m, 1H), 3.13-3.22 (m, 1H), 3.43 (s, 3H), 6.77 (d, J=2.2 Hz, 1H), 6.82-6.87 (m, 1H), 6.90 (dd, J=8.2, 0.9 Hz, 1H), 7.02-7.11 (m, 1H), 7.23 (dd, J=8.3, 2.3 Hz, 1H), 7.26-7.35 (m, 1H), 7.99 (dd, J=7.8, 1.7 Hz, 1H), 10.51 (s, 1H)

Step 74-5: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl butanamide (levorotatory isomer)

With 0.80 g of the compound obtained in Step 74-4 (Isomer B) as starting material, 1.08 g of the title compound (colorless amorphous) was obtained by a similar procedure to Example 2.

$[\alpha]_D^{27}$=−154° (c=0.214, CHCl$_3$)

MS (ESI pos.) m/z: 678 ([M+Na]$^+$)

$^1$H-NMR (300 MHz, CDCl$_3$) δ (ppm); 0.70-0.78 (m, 3H), 1.22-1.34 (m, 2H), 2.71 (s, 3H), 2.96 (s, 3H), 3.16-3.37 (m, 5H), 3.89 (s, 3H), 6.68 (dd, J=8.2, 1.1 Hz, 1H), 6.83-6.95 (m, 3H), 6.96-7.07 (m, 1H), 7.19-7.35 (m, 2H), 7.86-8.00 (m, 2H), 8.36 (d, J=8.7 Hz, 1H)

Example 75

Synthesis of 1-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl cyclohexane carboxamide Step 75-1: Synthesis of 1-[(tert-butoxy carbonyl)amino]cyclohexane carboxylic acid With 3.00 g of 1-amino cyclohexane carboxylic acid as starting material, 1.12 g of the title compound (colorless solid) was obtained by a similar procedure to Step 74-1.

MS (ESI pos.) m/z: 266 ([M+Na]$^+$)

$^1$H-NMR (300 MHz, CDCl$_3$) δ (ppm); 1.22-1.52 (m, 11H), 1.56-1.72 (m, 4H), 1.79-1.94 (m, 2H), 1.95-2.08 (m, 2H), 4.80 (s, 1H)

Step 75-2: Synthesis of tert-butyl{1-[(dimethylamino)carbonyl]cyclohexyl}carbamate With 1.06 g of the compound obtained in Step 75-1 as starting material, 0.78 g of the title compound (colorless amorphous) was obtained by a similar procedure to Step 60-1.

MS (ESI pos.) m/z: 293 ([M+Na]$^+$)

$^1$H-NMR (300 MHz, CDCl$_3$) δ (ppm); 1.17-1.51 (m, 12H), 1.53-1.78 (m, 3H), 1.81-2.05 (m, 4H), 3.05 (s, 6H), 4.74-5.02 (m, 1H)

Step 75-3: Synthesis of 1-amino-N,N-dimethyl cyclohexane carboxamide trifluoroacetate With 0.69 g of the compound obtained in Step 75-2 as starting material, 1.17 g of the title compound (crude form) was obtained by a similar procedure to Step 60-2.
MS (ESI pos.) m/z: 171 ([M+H]$^+$)
$^1$H-NMR (300 MHz, CDCl$_3$) δ (ppm); 1.23-1.41 (m, 1H), 1.49-1.71 (m, 2H), 1.83-2.08 (m 5H), 2.11-2.28 (m, 2H), 3.15 (s, 6H), 7.70 (s, 3H)

Step 75-4: Synthesis of 1-{[5-chloro-3-(2-methoxyphenyl)-2-oxo-2,3-dihydro-1H-indol-3-yl]amino}-N,N-dimethyl cyclohexane carboxamide With 0.72 g of 3,5-dichloro-3-(2-methoxyphenyl)-1,3-dihydro-2H-indol-2-one and the compound obtained in Step 75-3 (2.55 mmol, crude form) as starting materials, 0.24 g of the title compound (pale yellow solid) was obtained by a similar method to Step 4-2.
MS (ESI pos.) m/z: 442 ([M+H]$^+$)
$^1$H-NMR (300 MHz, CDCl$_3$) δ (ppm); 1.13-1.30 (m, 3H), 1.36-1.60 (m, 4H), 2.22-2.36 (m, 1H), 2.38-2.53 (m, 2H), 2.69 (s, 3H), 3.48 (s, 3H), 3.60 (s, 3H), 6.70 (d, J=2.2 Hz, 1H), 6.75-6.83 (m, 2H), 7.04 (td, J=7.7, 1.2 Hz, 1H), 7.15 (dd, J=8.2, 2.2 Hz, 1H), 7.24-7.32 (m, 1H), 8.05 (dd, J=7.9, 1.6 Hz, 1H), 8.29 (s, 1H)

Step 75-5: Synthesis of 1-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl cyclohexane carboxamide With 142 mg of the compound obtained in Step 75-4 as starting material, 133 mg of the title compound (colorless powder) was obtained by a similar procedure to Example 2.
MS (ESI pos.) m/z: 696 ([M+H]$^+$)
$^1$H-NMR (300 MHz, DMSO-d$_6$) δ (ppm); 0.54-0.68 (m, 1H), 0.79-1.01 (m, 3H), 1.20-1.56 (m, 4H), 1.75-1.84 (m, 1H), 2.19-2.30 (m, 1H), 2.56 (s, 3H), 3.13 (s, 1H), 3.37 (s, 3H), 3.54 (s, 3H), 3.93 (s, 3H), 6.61 (d, J=2.3 Hz, 1H), 6.82-6.90 (m, 1H), 7.02-7.12 (m, 2H), 7.22-7.36 (m, 2H), 7.41 (dd, J=8.8, 2.4 Hz, 1H), 7.73 (d, J=8.9 Hz, 1H), 8.09 (dd, J=7.9, 1.5 Hz, 1H), 8.23 (d, J=9.0 Hz, 1H)

Example 76

Synthesis of 1-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl cyclopentane carboxamide

Step 76-1: Synthesis of 1-[(tert-butoxy carbonyl)amino]cyclopentane carboxylic acid With 3.00 g of 1-aminocyclopentane carboxylic acid as starting material, 1.19 g of the title compound (colorless solid) was obtained by a similar procedure as Step 74-1.
MS (ESI pos.) m/z: 252 ([M+Na]$^+$)
$^1$H-NMR (300 MHz, CDCl$_3$) δ (ppm); 1.45 (s, 9H), 1.79 (m, 4H), 1.95 (m, 2H), 2.20-2.37 (m, 2H), 4.94 (s, 1H)

Step 76-2: Synthesis of tert-butyl{1-[(dimethylamino)carbonyl]cyclopentyl}carbamate With 1.13 g of the compound obtained in Step 76-1 as starting material, 0.96 g of the title compound (colorless amorphous) was obtained by a similar procedure as Step 60-1.

MS (ESI pos.) m/z: 279 ([M+Na]$^+$)
$^1$H-NMR (300 MHz, CDCl$_3$) δ (ppm); 1.42 (s, 9H), 1.63-1.87 (m, 6H), 2.29-2.44 (m, 2H), 3.03 (s, 6H), 4.75-5.43 (m, 1H)

Step 76-3: Synthesis of 1-amino-N,N-dimethyl cyclopentane carboxamide trifluoroacetate With 0.74 g of the compound obtained in Step 76-2 as starting material, 1.09 g of the title compound (crude form) was obtained by a similar procedure to Step 60-2.
MS (ESI pos.) m/z: 157 ([M+H]$^+$)
$^1$H-NMR (300 MHz, CDCl$_3$) δ (ppm); 1.95-2.24 (m, 6H), 2.26-2.42 (m, 2H), 3.03 (s, 6H), 7.65 (s, 3H)

Step 76-4: Synthesis of 1-{[5-chloro-3-(2-methoxyphenyl)-2-oxo-2,3-dihydro-1H-indol-3-yl]amino}-N,N-dimethyl cyclopentane carboxamide With 0.81 g of 3,5-dichloro-3-(2-methoxyphenyl)-1,3-dihydro-2H-indol-2-one and the compound obtained in Step 76-3 (2.89 mmol, crude form) as starting materials, 0.27 g of the title compound (pale yellow solid) was obtained by a similar method to Step 4-2.
MS (ESI pos.) m/z: 450 ([M+Na]$^+$)
$^1$H-NMR (300 MHz, DMSO-d$_6$) δ (ppm); 1.20-1.39 (m, 2H), 1.45-1.66 (m, 3H), 1.92-2.04 (m, 2H), 2.18-2.33 (m, 1H), 2.54 (s, 3H), 3.06 (s, 1H), 3.37 (s, 3H), 3.46 (s, 3H), 6.48 (d, J=2.3 Hz, 1H), 6.74 (d, J=8.2 Hz, 1H), 6.85 (dd, J=8.2, 1.2 Hz, 1H), 7.04 (td, J=7.6, 1.2 Hz, 1H), 7.14 (dd, J=8.2, 2.2 Hz, 1H), 7.22-7.31 (m, 1H), 8.09 (dd, J=7.9, 1.6 Hz, 1H), 10.47 (s, 1H)

Step 76-5: Synthesis of 1-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl cyclopentane carboxamide With 176 mg of the compound obtained in Step 76-4 as starting material, 165 mg of the title compound (colorless powder) was obtained by a similar procedure as Example 2.
MS (ESI pos.) m/z: 682 ([M+H]$^+$)
$^1$H-NMR (300 MHz, DMSO-d$_6$) δ (ppm); 0.75-0.90 (m, 1H), 0.95-1.30 (m, 3H), 1.33-1.49 (m, 1H), 1.83-2.04 (m, 3H), 2.56 (s, 3H), 3.41-3.49 (m, 3H), 3.54 (s, 1H), 3.93 (s, 3H), 6.58 (d, J=2.3 Hz, 1H), 6.86 (dd, J=8.3, 1.0 Hz, 1H), 7.03-7.13 (m, 2H), 7.22-7.35 (m, 2H), 7.40 (dd, J=8.9, 2.3 Hz, 1H), 7.73 (d, J=8.7 Hz, 1H), 8.10 (dd, J=7.9, 1.7 Hz, 1H), 8.22 (d, J=9.0 Hz, 1H)

Example 77

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(1H-imidazol-4-yl)-N,N-dimethylpropanamide (levorotatory isomer)

Step 77-1: Synthesis of tert-butyl[(1S)-2-(dimethylamino)-1-(1H-imidazol-4-ylmethyl)-2-oxo ethyl]carbamate With 2.50 g of (2S)-2-[(tert-butoxy carbonyl)amino]-3-(1H-imidazol-4-yl) propanoic acid as starting material, 1.98 g of the title compound (colorless amorphous) was obtained by a similar procedure as Step 60-1.
MS (ESI pos.) m/z: 283 ([M+H]$^+$)

¹H-NMR (300 MHz, CDCl₃) δ (ppm); 1.42 (s, 9H), 2.89-3.09 (m, 8H), 4.77-4.88 (m, 1H), 5.48 (d, J=7.9 Hz, 1H), 6.85 (d, J=0.9 Hz, 1H), 7.55 (d, J=0.9 Hz, 1H)

Step 77-2: Synthesis of (2S)-2-amino-3-(1H-imidazol-4-yl)-N,N-dimethylpropanamide trifluoroacetate With 1.49 g of the compound obtained in Step 77-1 as starting material, 3.71 g of the title compound (crude form) was obtained by a similar procedure to Step 60-2.

MS (ESI pos.) m/z: 183 ([M+H]⁺)

¹H-NMR (300 MHz, DMSO-d₆) δ (ppm); 2.90 (s, 3H), 3.00-3.12 (m, 4H), 3.15-3.25 (m, 1H), 4.56-4.69 (m, 1H), 7.46 (d, J=0.9 Hz, 1H), 8.26 (s, 3H), 9.06 (d, J=1.4 Hz, 1H)

Step 77-3: Synthesis of (2S)-2-{[5-chloro-3-(2-methoxyphenyl)-2-oxo-2,3-dihydro-1H-indol-3-yl]amino}-3-(1H-imidazol-4-yl)-N,N-dimethylpropanamide (levorotatory isomer and dextrorotatory isomer)

With 1.48 g of 3,5-dichloro-3-(2-methoxyphenyl)-1,3-dihydro-2H-indol-2-one and the compound obtained in Step 77-2 (5.28 mmol, crude form) as starting materials, respectively 0.57 g (Isomer A, colorless powder) and 0.88 g (Isomer B, colorless powder) of two species of diastereoisomers of the title compound were obtained by a similar method to Step 4-2.

Isomer A: $[\alpha]_D^{24}=+117°$ (c=0.177, MeOH)

MS (ESI pos.) m/z: 454 ([M+H]⁺)

¹H-NMR (300 MHz, MeOH-d₄) δ (ppm); 2.66 (s, 3H), 2.72 (s, 3H), 2.77-2.83 (m, 2H), 3.53 (s, 3H), 3.98 (t, J=7.2 Hz, 1H), 6.78 (d, J=2.2 Hz, 1H), 6.83-6.97 (m, 4H), 7.16 (dd, J=8.2, 2.2 Hz, 1H), 7.21-7.31 (m, 1H), 7.57 (d, J=7.9 Hz, 1H), 7.62 (d, J=1.1 Hz, 1H)

Isomer B: $[\alpha]_D^{27}=-105°$ (c=0.229, CHCl₃)

MS (ESI pos.) m/z: 454 ([M+H]⁺)

¹H-NMR (300 MHz, MeOH-d₄) δ (ppm); 2.59-2.78 (m, 5H), 2.83 (s, 3H), 3.47 (s, 3H), 3.49-3.56 (m, 1H), 6.32 (d, J=2.2 Hz, 1H), 6.80-6.90 (m, 3H), 7.04 (td, J=7.6, 1.2 Hz, 1H), 7.13-7.19 (m, 1H), 7.22-7.33 (m, 1H), 7.53 (d, J=1.2 Hz, 1H), 8.03 (dd, J=7.8, 1.7 Hz, 1H)

Step 77-4: Synthesis of tert-butyl 4-[(2S)-2-{[5-chloro-3-(2-methoxyphenyl)-2-oxo-2,3-dihydro-1H-indol-3-yl]amino}-3-(dimethylamino)-3-oxo propyl]-1H-imidazole-1-carboxylate (levorotatory isomer)

To a solution of 300 mg of the compound obtained in Step 77-3 (Isomer B) in THF (5 ml) was added (Boc)₂O (0.17 ml) and the reaction mixture was stirred at room temperature for 12 hours. Hexane was added, the precipitated crystal was collected by filtration, this was subjected to column chromatography (silicagel 60; mobile phase: CHCl₃/MeOH=9/1; v/v) to obtain 283 mg of the title compound (colorless amorphous).

$[\alpha]_D^{27}=-62°$ (c=0.252, CHCl₃)

MS (ESI pos.) m/z: 554 ([M+H]⁺)

¹H-NMR (200 MHz, CDCl₃) δ (ppm); 1.61 (s, 9H), 2.57-2.69 (m, 2H), 2.81 (s, 3H), 2.87 (s, 3H), 3.40-3.56 (m, 4H), 3.60-3.77 (m, 1H), 6.46 (d, J=2.2 Hz, 1H), 6.72 (t, J=7.7 Hz, 2H), 6.94-7.13 (m, 2H), 7.18-7.35 (m, 2H), 7.90 (s, 1H), 7.97 (dd, J=7.9, 1.8 Hz, 1H), 8.24 (s, 1H)

Step 77-5: Synthesis of tert-butyl 4-[(2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(dimethylamino)-3-oxo propyl]-1H-imidazole-1-carboxylate (levorotatory isomer)

With 200 mg of the compound obtained in Step 77-4 as starting material, 218 mg of the title compound (colorless amorphous) was obtained by a similar procedure to Example 2. $[\alpha]_D^{27}=-102°$ (c=0.183, CHCl₃)

MS (ESI pos.) m/z: 830 ([M+H]⁺)

¹H-NMR (300 MHz, CDCl₃) δ (ppm); 1.60 (s, 9H), 2.47-2.55 (m, 2H), 2.87 (s, 3H), 2.97 (s, 3H), 3.05 (s, 3H), 3.48-3.65 (m, 2H), 3.86 (s, 3H), 6.28 (d, J=2.2 Hz, 1H), 6.62 (dd, J=8.3, 0.9 Hz, 1H), 6.80-6.91 (m, 2H), 6.97-7.06 (m, 1H), 7.16-7.27 (m, 3H), 7.81-7.93 (m, 2H), 7.99 (dd, J=7.6, 1.7 Hz, 1H), 8.31-8.42 (m, 1H)

Step 77-6: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(1H-imidazol-4-yl)-N,N-dimethylpropanamide (levorotatory isomer)

To 122 mg of the compound obtained in 77-5 was added a solution of 4 mol/L hydrochloric acid/EtOAc (4 ml) under ice cooling, then the solution was stirred for 30 minutes under ice cooling, and thereafter was stirred at room temperature for two hours. The solution was cooled on ice, then, an aqueous solution of saturated K₂CO₃ was added, and the mixture was stirred. Saturated aqueous solution of K₂CO₃ and EtOAc were added, liquid separation was performed, and the aqueous layer was extracted with EtOAc. The organic layers were combined, washed with saturated brine, then, dried with Na₂SO₄, the drying agent was separated by filtration, the solvent was evaporated. The residue was subjected to column chromatography (silicagel 60; mobile phase: CHCl₃/acetone=2/1; v/v) to obtain 57 mg of the title compound (colorless powder).

$[\alpha]_D^{27}=-129°$ (c=0.104, CHCl₃)

MS (ESI pos.) m/z: 708 ([M+H]⁺)

¹H-NMR (300 MHz, CDCl₃) δ (ppm); 2.47-2.71 (m, 5H), 2.93 (s, 3H), 3.17-3.36 (m, 4H), 3.69-3.87 (m, 4H), 6.54-6.62 (m, 1H), 6.67-6.76 (m, 2H), 6.77-6.87 (m, 2H), 6.92-7.04 (m, 1H), 7.20-7.34 (m, 2H), 7.48 (d, J=0.9 Hz, 1H), 7.63-7.76 (m, 1H), 7.90 (d, J=8.9 Hz, 1H), 8.32 (d, J=8.9 Hz, 1H)

Example 78

Synthesis of tert-butyl [(5S)-5-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-6-(dimethylamino)-6-oxo hexyl]carbamate

Step 78-1: Synthesis of N²-[(benzyl oxy)carbonyl]-N⁶-(tert-butoxy carbonyl)-N,N-dimethyl-L-lysinamide With 4.00 g of (2S)-2-{[(benzyl oxy)carbonyl]amino}-6-[(tert-butoxy carbonyl)amino]hexanoic acid as starting materials, 4.65 g of the title compound (colorless oil) was obtained by a similar procedure as Step 60-1.

MS (ESI pos.) m/z: 430 ([M+Na]⁺)

¹H-NMR (300 MHz, CDCl₃) δ (ppm); 1.29-1.64 (m, 15H), 2.96 (s, 3H), 3.05-3.13 (m, 5H), 4.55-4.72 (m, 2H), 5.09 (s, 2H), 5.70 (d, 1H), 7.28-7.39 (m, 5H)

Step 78-2: Synthesis of tert-butyl[(5S)-5-amino-6-(dimethylamino)-6-oxo hexyl]carbamate Under nitrogen atmosphere, palladium-activated carbon (10% Pd, 0.30 g) was added to a solution of 2.75 g of the compound obtained in Step 78-1 in EtOH (30 ml) and the inside of the reaction system was displaced with hydrogen gas. The solution was stirred at room temperature for two hours, then, the reaction solution was filtered, and the solvent was filtered out under reduced pressure to obtain 1.97 g of residue (pale yellow oil). The present compound was used in the next reaction without purification.

MS (ESI pos.) m/z: 274 ([M+H]⁺)

¹H-NMR (300 MHz, CDCl₃) δ (ppm); 1.28-1.67 (m, 15H), 2.92-3.20 (m, 9H), 3.60-3.71 (m, 1H), 4.68 (m, 1H)

Step 78-3: Synthesis of tert-butyl [(5S)-5-{[5-chloro-3-(2-methoxyphenyl)-2-oxo-2,3-dihydro-1H-indol-3-yl]amino}-6-(dimethylamino)-6-oxo hexyl]carbamate (levorotatory isomer and dextrorotatory isomer)

With 1.73 g of 3,5-dichloro-3-(2-methoxyphenyl)-1,3-dihydro-2H-indol-2-one and the compound obtained in Step 78-2 (6.76 mmol, crude form) as starting materials respectively 0.90 g (Isomer A, colorless amorphous) and 1.69 g (Isomer B, colorless amorphous) of two species of diastereoisomers of the title compound were obtained by a similar method to Step 4-2.

Isomer A: $[\alpha]_D^{27}$=+114° (c=0.193, CHCl₃)

MS (ESI pos.) m/z: 545 ([M+H]⁺)

¹H-NMR (300 MHz, CDCl₃) δ (ppm); 1.36-1.67 (m, 15H), 2.86 (s, 3H), 2.90 (s, 3H), 2.98-3.07 (m, 1H), 3.11-3.22 (m, 2H), 3.54 (s, 3H), 3.80-3.93 (m, 1H), 4.67 (m, 1H), 6.64 (d, J=8.24 Hz, 1H), 6.81 (dd, J=8.24, 0.93 Hz, 1H), 6.85-6.94 (m, 1H), 7.00-7.16 (m, 2H), 7.21-7.36 (m, 1H), 8.05 (dd, J=7.77, 1.55 Hz, 1H), 8.47 (s, 1H)

Isomer B: $[\alpha]_D^{27}$=−19° (c=0.203, CHCl₃)

MS (ESI pos.) m/z: 567 ([M+Na]⁺)

¹H-NMR (300 MHz, CDCl₃) δ (ppm); 1.27-1.59 (m, 15H), 2.67 (s, 3H), 2.87 (s, 3H), 3.02-3.15 (m, 2H), 3.22 (m, 1H), 3.37-3.57 (m, 4H), 4.64 (m, 1H), 6.71-6.85 (m, 1H), 6.91 (d, J=2.18 Hz, 1H), 7.00-7.11 (m, 1H), 7.14 (dd, J=8.24, 2.18 Hz, 1H), 7.23-7.37 (m, 1H), 8.04 (d, J=8.08 Hz, 1H), 8.77 (s, 1H)

Step 78-4: Synthesis of tert-butyl [(5S)-5-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-6-(dimethylamino)-6-oxo hexyl] carbamate (levorotatory isomer)

With 0.74 g of the compound obtained in Step 78-3 (Isomer B) as starting material, 860 mg of the title compound (colorless amorphous) was obtained by a similar procedure as Example 2.

$[\alpha]_D^{27}$−117° (c=0.208, CHCl₃)

MS (ESI pos.) m/z: 799 ([M+H]⁺)

¹H-NMR (300 MHz, CDCl₃) δ (ppm); 1.10-1.40 (m, 6H), 1.43 (s, 9H), 2.72 (s, 3H), 2.96 (s, 3H), 2.98-3.10 (m, 2H), 3.13 (s, 3H), 3.26-3.39 (m, 2H), 3.89 (s, 3H), 4.53 (m, 1H), 6.66 (dd, J=8.2, 0.9 Hz, 1H), 6.85-6.96 (m, 3H), 7.02 (td, J=7.6, 1.0 Hz, 1H), 7.19-7.35 (m, 2H), 7.86-8.00 (m, 2H), 8.36 (d, J=9.2 Hz, 1H)

Example 79

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(2-hydroxyethyl)amino]-N,N-dimethylpropanamide (levorotatory isomer)

Step 79-1: Synthesis of benzyl[(1S)-2-(dimethylamino)-1-methyl-2-oxo ethyl]carbamate With 3.00 g of N-[(benzyl oxy)carbonyl]-L-alanine as starting material, 3.38 g of the title compound (colorless oil) was obtained by a similar procedure to Step 60-1.

MS (ESI pos.) m/z: 273 ([M+Na]⁺)

¹H-NMR (300 MHz, CDCl₃) δ (ppm); 1.33 (d, J=6.8 Hz, 3H), 2.97 (s, 3H), 3.06 (s, 3H), 4.62-4.74 (m, 1H), 5.10 (s, 2H), 5.76-5.88 (m, 1H), 7.25-7.39 (m, 5H)

Step 79-2: Synthesis of benzyl[2-(benzyl oxy)ethyl][(1S)-2-(dimethylamino)-1-methyl-2-oxo ethyl]carbamate Under nitrogen atmosphere, to a solution of 2.78 g of the compound obtained in Step 79-1 in DMF (30 ml) was added 0.66 g of NaH under ice cooling. The solution was stirred at room temperature for one hour, then, 3.58 g of [(2-bromoethoxy)methyl]benzene was added. The solution was stirred at room temperature for two hours, then, water was added, and the resulting mixture was extracted with EtOAc. The organic layers were combined, washed with saturated brine and dried over MgSO₄, then, the drying agent was separated by filtration and the solvent was evaporated under reduced pressure. The obtained residue was purified by column chromatography (silicagel 60; mobile phase: n-hexane/EtOAc=2/3; v/v) to obtain 3.22 g of the title compound (pale yellow oil).

MS (ESI pos.) m/z: 385 ([M+H]⁺)

¹H-NMR (300 MHz, CDCl₃) δ (ppm); 1.31 (d, J=7.0 Hz, 3H), 2.71-3.04 (m, 6H), 3.40-3.66 (m, 4H), 4.38-4.54 (m, 2H), 4.84-5.24 (m, 3H), 7.22-7.39 (m, 10H)

Step 79-3: Synthesis of (2S)-2-[(2-hydroxy ethyl)amino]-N,N-dimethylpropanamide

Under nitrogen atmosphere, to a solution of 2.75 g of the compound obtained in Step 79-2 in EtOH (30 ml) was added palladium-activated carbon (10% Pd, 0.30 g), and the inside of the reaction system was displaced with hydrogen gas. The solution was stirred for 24 hours at 45° C., then, the reaction solution was filtered, and the solvent was filtered out under reduced pressure. To a solution of the obtained residue in EtOH (30 ml) solution was added palladium-activated carbon (10% Pd, 0.30 g), and the reaction system was displaced with hydrogen gas, again. The solution was stirred for one day at 45° C., then, the reaction solution was filtered, and the solvent was evaporated under reduced pressure. The obtained residue was purified by column chromatography (silicagel 60; mobile phase: CHCl₃/MeOH=9/1 to 4/1; v/v) to obtain 734 mg of the title compound (colorless oil).

MS (ESI pos.) m/z: 161 ([M+H]⁺)

¹H-NMR (300 MHz, CDCl₃) δ (ppm); 1.23 (d, J=7.0 Hz, 3H), 2.41-2.53 (m, 2H), 2.61 (ddd, J=12.4, 6.8, 4.6 Hz, 1H), 2.74 (ddd, J=12.5, 5.4, 4.0 Hz, 1H), 3.00 (s, 3H), 3.05 (s, 3H), 3.48-3.63 (m, 3H)

Step 79-4: Synthesis of (2S)-2-[[5-chloro-3-(2-methoxyphenyl)-2-oxo-2,3-dihydro-1H-indol-3-yl](2-hydroxy ethyl)amino]-N,N-dimethylpropanamide (levorotatory isomer and dextrorotatory isomer)

With 1.17 g of 3,5-dichloro-3-(2-methoxyphenyl)-1,3-dihydro-2H-indol-2-one and the compound obtained in Step 79-3 (4.18 mmol, crude form) as starting materials, respectively 0.92 g (Isomer A, colorless solid) and 0.66 g (Isomer B, colorless amorphous) of two species of diastereoisomers of the title compound were obtained by a similar method to Step 4-2.

Isomer A: $[\alpha]_D^{27}$=−189° (c=0.247, CHCl$_3$)
MS (ESI pos.) m/z: 432 ([M+H]$^+$)
$^1$H-NMR (300 MHz, DMSO-d$_6$) δ (ppm); 1.18 (d, J=6.5 Hz, 3H), 2.42 (s, 3H), 2.67-2.77 (m, 4H), 2.88-3.03 (m, 1H), 3.15-3.31 (m, 2H), 3.51 (s, 3H), 4.34-4.49 (m, 1H), 5.35 (s, 1H), 6.79 (d, J=8.2 Hz, 1H), 6.86-6.91 (m, 1H), 6.96 (dd, J=8.2, 0.9 Hz, 1H), 7.02 (td, J=7.5, 1.1 Hz, 1H), 7.15-7.22 (m, 1H), 7.25-7.33 (m, 1H), 7.52-7.62 (m, 1H), 10.54 (s, 1H)

Isomer B: $[\alpha]_D^{27}$=+182° (c=0.205, CHCl$_3$)
MS (ESI pos.) m/z: 432 ([M+H]$^+$)
$^1$H-NMR (300 MHz, DMSO-d$_6$) δ (ppm); 1.21 (d, J=6.5 Hz, 3H), 2.66-2.78 (m, 8H), 2.98-3.29 (m, 2H), 3.50 (s, 3H), 3.68-3.89 (m, 1H), 4.71-4.79 (m, 1H), 6.70-6.76 (m, 1H), 6.82 (d, J=8.2 Hz, 1H), 6.94 (dd, J=8.3, 1.0 Hz, 1H), 7.08 (m, 1H), 7.22 (dd, J=8.4, 2.2 Hz, 1H), 7.25-7.33 (m, 1H), 7.48-8.03 (m, 1H), 10.46 (s, 1H)

Step 79-5: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(2-hydroxyethyl)amino]-N,N-dimethylpropanamide (levorotatory isomer)

With 450 mg of the compound obtained in Step 79-4 (Isomer A) as starting material, 80 mg of the title compound (colorless amorphous) was obtained by a similar procedure to Example 2.

$[\alpha]_D^{24}$=142° (c=0.178, CHCl$_3$)
MS (ESI pos.) m/z: 686 ([M+H]$^+$)
$^1$H-NMR (300 MHz, DMSO-d$_6$) δ (ppm); 0.84 (d, J=7.0 Hz, 3H), 2.20-2.30 (m, 3H), 2.43-2.47 (m, 2H), 2.78 (s, 3H), 3.03-3.22 (s, 3H), 3.36-3.49 (m, 2H), 3.93 (s, 3H), 4.19-4.33 (m, 1H), 5.21-5.31 (m, 1H), 6.88-7.09 (m, 3H), 7.09-7.16 (m, 1H), 7.22-7.38 (m, 2H), 7.41-7.59 (m, 2H), 7.67-7.82 (m, 1H), 8.24 (d, J=9.2 Hz, 1H)

Example 80

Synthesis of Methyl (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)oxy]propanoate (levorotatory isomer)

Step 80-1: Synthesis of methyl (2S)-2-{[5-chloro-3-(2-methoxyphenyl)-2-oxo-2,3-dihydro-1H-indol-3-yl]oxy}propanoate (levorotatory isomer)

Under nitrogen atmosphere, to a solution of 2.03 g of (S)methyl lactate in THF (30 ml) was added 0.94 g of NaH. To the reaction solution was added THF (20 ml) and the reaction mixture was stirred under ice cooling for 30 minutes. Therein 3.00 g of 3,5-dichloro-3-(2-methoxyphenyl)-1,3-dihydro-2H-indol-2-one was added, and the solution was stirred at room temperature for one hour. A saturated aqueous solution of NaHCO$_3$ was added to the reaction solution, and the mixture was extracted with EtOAc, the organic layers were combined, washed with water and saturated brine, then, dried over MgSO$_4$, the drying agent was separated by filtration and the solvent was evaporated under reduced pressure. The obtained residue was purified by column chromatography (silicagel 60; mobile phase: CHCl$_3$/MeOH=25/1; v/v, and CHCl$_3$/EtOAc=2/1; v/v) to obtain 1.29 g of one species among the diastereoisomers of the title compound (pale yellow solid).

$[\alpha]_D^{23}$=−73° (c=0.246, CHCl$_3$)
MS (ESI pos.) m/z: 398 ([M+Na]$^+$)
$^1$H-NMR (300 MHz, DMSO-d$_6$) δ (ppm); 1.29 (d, J=6.8 Hz, 3H), 3.42 (s, 3H), 3.47 (s, 3H), 4.05-4.14 (m, 1H), 6.84-6.96 (m, 3H), 7.04-7.12 (m, 1H), 7.25-7.38 (m, 2H), 7.72 (dd, J=7.8, 1.7 Hz, 1H), 10.69 (s, 1H)

Step 80-2: Synthesis of methyl (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)oxy]propanoate (levorotatory isomer)

With 300 mg of the compound obtained in Step 80-1 as starting material, 349 mg of the title compound (colorless amorphous) was obtained by a similar procedure to Example 2.

$[\alpha]_D^{23}$=−113° (c=0.217, CHCl$_3$)
MS (ESI pos.) m/z: 647 ([M+NH$_4$]$^+$)
$^1$H-NMR (300 MHz, CDCl$_3$) δ (ppm); 1.18 (d, J=6.7 Hz, 3H), 3.49 (s, 3H), 3.51 (s, 3H), 3.90 (s, 3H), 4.03 (q, J=6.7 Hz, 1H), 6.76 (dd, J=8.2, 1.1 Hz, 1H), 6.85-6.95 (m, 2H), 6.98 (d, J=2.3 Hz, 1H), 7.00-7.10 (m, 1H), 7.23-7.38 (m, 2H), 7.80 (dd, J=7.9, 1.6 Hz, 1H), 7.95 (d, J=8.7 Hz, 1H), 8.29 (d, J=8.7 Hz, 1H)

Example 81

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)oxy]-N,N-dimethylpropanamide (levorotatory isomer)

Step 81-1: Synthesis of (2S)-2-{[5-chloro-3-(2-methoxyphenyl)-2-oxo-2,3-dihydro-1H-indol-3-yl]oxy}propanoic acid (levorotatory isomer)

To a mixed solution of 0.50 g of the compound obtained in Step 80-1 in MeOH (10 ml)-THF (10 ml) was added water (5 ml) and 1.00 g of K$_2$CO$_3$. The solution was stirred at room temperature for 24 hours, then, reaction solution was concentrated under vacuum. To the solution was added 1.0 mol/L hydrochloric acid (50 ml), extracted with CHCl$_3$, then, the organic layer was washed with saturated brine, dried over MgSO$_4$, the drying agent was separated by filtration and the solvent was evaporated under reduced pressure. The obtained residue was purified by column chromatography (silicagel 60; mobile phase: CHCl$_3$/MeOH=5/1; v/v) to obtain 0.48 g of the title compound (pale yellow amorphous).

$[\alpha]_D^{23}$=−88° (c=0.243, CHCl$_3$)
MS (ESI pos.) m/z: 384 ([M+Na]$^+$)
$^1$H-NMR (300 MHz, CDCl$_3$) δ (ppm); 1.46 (d, J=6.8 Hz, 3H), 3.54 (s, 3H), 3.87-3.96 (m, 1H), 6.80-6.91 (m, 2H), 6.95 (d, J=2.2 Hz, 1H), 7.05-7.13 (m, 1H), 7.22-7.28 (m, 1H), 7.29-7.38 (m, 1H), 7.89 (dd, J=7.7, 1.6 Hz, 1H), 9.65 (s, 1H)

Step 81-2: Synthesis of (2S)-2-{[5-chloro-3-(2-methoxyphenyl)-2-oxo-2,3-dihydro-1H-indol-3-yl]oxy}-N,N-dimethylpropanamide (levorotatory isomer)

With 0.41 g of the compound obtained in Step 81-1 as starting material, 356 mg of the title compound (colorless solid) was obtained by a similar procedure to Step 60-1.

$[\alpha]_D^{23}$=−13.4° (c=0.179, CHCl$_3$)
MS (ESI neg.) m/z: 387 ([M−H]$^+$)
$^1$H-NMR (300 MHz, DMSO-d$_6$) δ (ppm); 1.21 (d, J=6.7 Hz, 3H), 2.64 (s, 3H), 2.90 (s, 3H), 3.42 (s, 3H), 4.34-4.44 (m, 1H), 6.79-6.86 (m, 1H), 6.87-6.97 (m, 2H), 7.03-7.12 (m, 1H), 7.20-7.38 (m, 2H), 7.73 (dd, J=7.7, 1.6 Hz, 1H), 10.64 (s, 1H)

Step 81-3: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)oxy]-N,N-dimethylpropanamide (levorotatory isomer)

With 298 mg of the compound obtained in Step 81-2 as starting material, 449 mg of the title compound (colorless amorphous) was obtained by a similar procedure to Example 2.
$[\alpha]_D^{24}$=−109° (c=0.227, CHCl$_3$)
MS (ESI pos.) m/z: 643 ([M+H]$^+$)
$^1$H-NMR (300 MHz, CDCl$_3$) δ (ppm); 1.10 (d, J=6.7 Hz, 3H), 2.72 (s, 3H), 2.83 (s, 3H), 3.54 (s, 3H), 3.89 (s, 3H), 4.38 (q, J=6.5 Hz, 1H), 6.78 (dd, J=8.3, 0.9 Hz, 1H), 6.87-6.95 (m, 2H), 6.96-7.08 (m, 2H), 7.25-7.37 (m, 2H), 7.72 (dd, J=7.8, 1.7 Hz, 1H), 7.92 (d, J=8.9 Hz, 1H), 8.18-8.31 (m, 1H)

Example 82

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,3-trimethyl butanamide (levorotatory isomer)

Step 82-1: Synthesis of benzyl{(1S)-1-[(dimethylamino)carbonyl]-2-methyl propyl}carbamate With 3.00 g of (2S)-2-{[(benzyl oxy)carbonyl]amino}-3-methyl butanoic acid as starting material, 3.47 g of the title compound (colorless oil) was obtained by a similar procedure to Step 60-1.
MS (ESI pos.) m/z: 301 ([M+Na]$^+$)
$^1$H-NMR (300 MHz, CDCl$_3$) δ (ppm); 0.90 (d, J=6.7 Hz, 3H), 0.98 (d, J=6.8 Hz, 3H), 1.90-2.03 (m, 1H), 2.97 (s, 3H), 3.10 (s, 3H), 4.53 (dd, J=9.2, 5.8 Hz, 1H), 5.04-5.14 (m, 2H), 5.57 (d, J=8.7 Hz, 1H), 7.28-7.38 (m, 5H)

Step 82-2: Synthesis of (2S)-2-amino-N,N,3-trimethyl butanamide

A suspension of 2.04 g of the compound obtained in Step 82-1 and 0.3 g of 10% palladium-carbon in EtOH (20 ml) was stirred at room temperature for two hours under hydrogen atmosphere. The insoluble matter was separated by filtration and the filtrate was concentrated to obtain 1.05 g of the title compound (pale yellow oil).
MS (ESI pos.) m/z: 145 ([M+H]$^+$)
$^1$H-NMR (300 MHz, CDCl$_3$) δ (ppm); 0.92 (d, J=6.8 Hz, 3H), 0.97 (d, J=6.8 Hz, 3H), 1.79-1.92 (m, 1H), 2.98 (s, 3H), 3.05 (s, 3H), 3.49 (d, J=5.4 Hz, 1H)

Step 82-3: (2S)-2-{[5-chloro-3-(2-methoxyphenyl)-2-oxo-2,3-dihydro-1H-indol-3-yl]amino}-N,N,3-trimethyl butanamide (levorotatory isomer and dextrorotatory isomer) Synthesis of With 1.92 g of 3,5-dichloro-3-(2-methoxyphenyl)-1,3-dihydro-2H-indol-2-one and 0.99 g of the compound obtained in Step 82-2 as starting materials, respectively 1.07 g (Isomer A, pale yellow solid) and 1.73 g (Isomer B, colorless solid) of two species of diastereoisomers of the title compound were obtained by a similar method to Step 4-2.
Isomer A: $[\alpha]_D^{26}$=+92° (c=0.211, CHCl$_3$)
MS (ESI pos.) m/z: 416 ([M+H]$^+$)
$^1$H-NMR (300 MHz, DMSO-d$_6$) δ (ppm); 0.83-0.90 (m, 6H), 1.58-1.72 (m, 1H), 2.55 (s, 3H), 2.59 (s, 3H), 3.11 (dd, J=9.3, 5.3 Hz, 1H), 3.25 (d, J=9.5 Hz, 1H), 3.49 (s, 3H), 6.69 (d, J=2.2 Hz, 1H), 6.80-6.85 (m, 1H), 6.94 (dd, J=8.2, 1.1 Hz, 1H), 7.01-7.08 (m, 1H), 7.15-7.20 (m, 1H), 7.26-7.34 (m, 1H), 7.79 (dd, J=7.9, 1.6 Hz, 1H), 10.57 (s, 1H)
Isomer B: $[\alpha]_D^{26}$=−154° (c=0.224, CHCl$_3$)
MS (ESI pos.) m/z: 416 ([M+H]$^+$)
$^1$H-NMR (300 MHz, DMSO-d$_6$) δ (ppm); 0.69 (d, J=6.8 Hz, 3H), 0.87 (d, J=6.7 Hz, 3H), 1.49-1.62 (m, 1H), 2.64 (s, 3H), 2.75 (s, 3H), 2.85-2.93 (m, 1H), 2.96-3.02 (m, 1H), 3.32 (s, 3H), 3.43 (s, 3H), 6.74 (d, J=2.2 Hz, 1H), 6.84 (d, J=8.2 Hz, 1H), 6.90 (dd, J=8.2, 1.1 Hz, 1H), 7.03-7.14 (m, 1H), 7.24 (dd, J=8.2, 2.3 Hz, 1H), 7.27-7.39 (m, 1H), 8.05 (dd, J=7.8, 1.7 Hz, 1H), 10.49 (s, 1H)

Step 82-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,3-trimethyl butanamide (levorotatory isomer)

With 0.63 g of the compound obtained in Step 82-3 (Isomer A) as starting material, 0.63 g of the title compound (colorless amorphous) was obtained by a similar procedure to Example 2.
$[\alpha]_D^{26}$=−150° (c=0.201, CHCl$_3$)
MS (ESI pos.) m/z: 670 ([M+H]$^+$)
$^1$H-NMR (200 MHz, CDCl$_3$) δ (ppm); 0.73 (d, J=7.0 Hz, 3H), 0.85 (d, J=7.0 Hz, 3H), 1.48-1.70 (m, 1H), 2.70 (s, 3H), 2.96 (s, 3H), 3.03-3.17 (m, 4H), 3.24-3.36 (m, 1H), 3.89 (s, 3H), 6.64 (d, J=7.0 Hz, 1H), 6.85-6.95 (m, 3H), 7.03 (t, J=7.0 Hz, 1H), 7.17-7.35 (m, 2H), 7.92 (d, J=8.8 Hz, 1H), 8.04 (dd, J=7.5, 1.8 Hz, 1H), 8.37 (d, J=9.2 Hz, 1H)

Example 83

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(4-pyridinyl) propanamide (levorotatory isomer)

Step 83-1: Synthesis of 9H-fluorene-9-ylmethyl [(1S)-2-(dimethylamino)-2-oxo-1-(4-pyridinylmethyl)ethyl]carbamate With 2.50 g of (2S)-2-{[(9H-fluorene-9-yl methoxy)carbonyl]amino}-3-(4-pyridinyl) propanoic acid as starting material, 2.07 g of the title compound (colorless amorphous) was obtained by a similar procedure to Step 60-1.
MS (ESI pos.) m/z: 438 ([M+Na]$^+$)
$^1$H-NMR (300 MHz, CDCl$_3$) δ (ppm); 2.81 (s, 3H), 2.91 (s, 3H), 2.93-3.08 (m, 2H), 4.19 (t, J=6.8 Hz, 1H), 4.28-4.47 (m, 2H), 4.86-5.00 (m, 1H), 5.69 (d, J=8.2 Hz, 1H), 7.11 (d, J=5.9 Hz, 2H), 7.28-7.35 (m, 2H), 7.41 (t, J=7.4 Hz, 2H), 7.57 (d, J=7.5 Hz, 2H), 7.77 (d, J=7.6 Hz, 2H), 8.52 (d, J=5.6 Hz, 2H)

Step 83-2: Synthesis of (2S)-2-amino-N,N-dimethyl-3-(4-pyridinyl) propanamide

To a solution of 1.61 g of the compound obtained in Step 83-1 in a mixed solution of MeOH and THF (25 ml 4:1; v/v)

was added a solution of 2 mol/L dimethylamine MeOH (5.8 ml) and the reaction mixture was stirred at room temperature for 24 hours. The reaction solution was concentrated under vacuum, and the obtained residue was purified by column chromatography (silicagel 60; mobile phase: CHCl$_3$/MeOH=9/1 to 5/1; v/v) to obtain 0.59 g of the title compound (brown oil).

MS (ESI pos.) m/z: 194 ([M+H]$^+$)

$^1$H-NMR (300 MHz, CDCl$_3$) δ (ppm); 2.72-2.80 (m, 1H), 2.86 (s, 3H), 2.88-3.00 (m, 4H), 3.94 (dd, J=7.5, 6.5 Hz, 1H), 7.12-7.17 (m, 2H), 8.51-8.57 (m, 2H)

Step 83-3: Synthesis of (2S)-2-{[5-chloro-3-(2-methoxyphenyl)-2-oxo-2,3-dihydro-1H-indol-3-yl]amino}-N,N-dimethyl-3-(4-pyridinyl) propanamide With 0.78 g of 3,5-dichloro-3-(2-methoxyphenyl)-1,3-dihydro-2H-indol-2-one and 0.54 g of the compound obtained in Step 83-2 as starting materials, 268 mg of a diastereoisomer mixture of the title compound (pale yellow amorphous) was obtained by a similar method to Step 4-2.

MS (ESI pos.) m/z: 465 ([M+H]$^+$)

$^1$H-NMR (300 MHz, CDCl$_3$) δ (ppm); 2.40 and 2.69 (each s, 3H), 2.76-2.88 (m, 5H), 3.03 and 3.28 (each d, J=10.6 Hz and 9.2 Hz, 1H), 3.52 and 3.53 (each s, 3H), 3.75-3.87 and 4.08-4.18 (each m, 1H), 6.57-7.30 (m, 8H), 7.35 and 7.78 (each dd, J=7.7, 1.8 Hz and 7.9, 1.6 Hz, 1H), 7.83 and 8.09 (each s, 1H), 8.47-8.52 and 8.55-8.60 (each m, 1H)

Step 83-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(4-pyridinyl) propanamide (levorotatory isomer)

With 223 mg of the diastereoisomer mixture obtained in Step 83-3 as starting material, 180 mg of a single isomer of the title compound (pale yellow amorphous) was obtained by a similar procedure to Example 2.

[α]$_D^{25}$=−174° (c=0.124, CHCl$_3$)

MS (ESI pos.) m/z: 719 ([M+H]$^+$)

$^1$H NMR (300 MHz, CDCl$_3$) δ (ppm); 2.28 (dd, J=12.9, 7.0 Hz, 1H), 2.41 (s, 3H), 2.59 (dd, J=12.7, 7.1 Hz, 1H), 2.91 (s, 3H), 3.09 (d, J=9.0 Hz, 1H), 3.25 (s, 3H), 3.64-3.77 (m, 4H), 6.41 (d, J=2.3 Hz, 1H), 6.64-6.72 (m, 1H), 6.79-6.88 (m, 2H), 6.89-6.94 (m, 2H), 6.94-7.02 (m, 1H), 7.19-7.32 (m, 2H), 7.71 (dd, J=7.8, 1.7 Hz, 1H), 7.90 (d, J=8.7 Hz, 1H), 8.37 (d, J=8.7 Hz, 1H), 8.42-8.51 (m, 2H)

Example 84

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(2-pyridinyl) propanamide (levorotatory isomer)

Step 84-1: Synthesis of 9H-fluorene-9-ylmethyl [(1S)-2-(dimethylamino)-2-oxo-1-(2-pyridinylmethyl)ethyl]carbamate With 2.11 g of (2S)-2-{[(9H-fluorene-9-ylmethoxy)carbonyl]amino}-3-(2-pyridinyl) propanoic acid as starting materials, 1.57 g of the title compound (purple chromatic amorphous) was obtained by a similar procedure to Step 60-1.

MS (ESI pos.) m/z: 416 ([M+H]$^+$)

$^1$H-NMR (300 MHz, CDCl$_3$) δ (ppm); 2.93 (s, 3H), 3.02 (s, 3H), 3.05-3.14 (m, 1H), 3.16-3.26 (m, 1H), 4.14-4.20 (m, 1H), 4.22-4.38 (m, 2H), 5.08-5.21 (m, 1H), 5.81 (d, J=8.9 Hz, 1H), 7.12-7.20 (m, 2H), 7.27-7.34 (m, 2H), 7.35-7.45 (m, 2H), 7.52-7.63 (m, 3H), 7.76 (d, J=7.3 Hz, 2H), 8.51-8.57 (m, 1H)

Step 84-2: Synthesis of (2S)-2-amino-N,N-dimethyl-3-(2-pyridinyl) propanamide

To a solution of 1.47 g of the compound obtained in Step 84-1 in a mixed solution of MeOH and THF (25 ml 4:1; v/v) was added a solution of 2 mol/L dimethylamine MeOH (5.8 ml) and the reaction solution was stirred at room temperature for 24 hours. The reaction solution was concentrated under vacuum and the obtained residue was purified by column chromatography (silicagel 60; mobile phase: CHCl$_3$/MeOH=9/1 to 5/1; v/v) to obtain 0.60 g of the title compound (brown oil).

MS (ESI pos.) m/z: 194 ([M+H]$^+$)

$^1$H-NMR (300 MHz, CDCl$_3$) δ (ppm); 2.86 (dd, J=13.5, 8.6 Hz, 1H), 2.95 (s, 3H), 3.01 (s, 3H), 3.10 (dd, J=13.6, 5.1 Hz, 1H), 4.27 (dd, J=8.6, 5.1 Hz, 1H), 7.12-7.21 (m, 2H), 7.57-7.66 (m, 1H), 8.53-8.62 (m, 1H)

Step 84-3: Synthesis of (2S)-2-{[5-chloro-3-(2-methoxyphenyl)-2-oxo-2,3-dihydro-1H-indol-3-yl]amino}-N,N-dimethyl-3-(2-pyridinyl) propanamide (levorotatory isomer)

With 878 mg of 3,5-dichloro-3-(2-methoxyphenyl)-1,3-dihydro-2H-indol-2-one and 0.55 g of the compound obtained in Step 84-2 as starting materials, 0.38 g (Isomer A, pale yellow amorphous) and 0.61 g (Isomer B, pale yellow amorphous) of the respective diastereoisomers of the title compound sere obtained by a similar method to Step 4-2.

Isomer A: [α]$_D^{25}$=−1.80° (c=0.208, CHCl$_3$)

MS (ESI pos.) m/z: 465 ([M+H]$^+$)

$^1$H-NMR (300 MHz, DMSO-d$_6$) δ (ppm); 2.70 (s, 3H), 2.72-2.87 (m, 5H), 2.97 (d, J=10.3 Hz, 1H), 3.41 (s, 3H), 4.06-4.17 (m, 1H), 6.48-6.61 (m, 2H), 6.77-6.87 (m, 2H), 6.97 (dd, J=7.8, 1.7 Hz, 1H), 7.12-7.23 (m, 2H), 7.28-7.39 (m, 2H), 7.75-7.84 (m, 1H), 8.49-8.57 (m, 1H), 10.39 (s, 1H)

Isomer B: [α]$_D^{25}$=−6.40° (c=0.195, CHCl$_3$)

MS (ESI pos.) m/z: 465 ([M+H]$^+$)

$^1$H-NMR (300 MHz, DMSO-d$_6$) δ (ppm); 2.68 (d, J=6.7 Hz, 2H), 2.71 (s, 3H), 2.74 (s, 3H), 3.19 (d, J=9.5 Hz, 1H), 3.36 (s, 3H), 3.53-3.64 (m, 1H), 5.78 (d, J=2.3 Hz, 1H), 6.76 (d, J=8.2 Hz, 1H), 6.83 (dd, J=8.2, 0.9 Hz, 1H), 6.92-7.01 (m, 1H), 7.13 (dd, J=8.2, 2.2 Hz, 1H), 7.17-7.28 (m, 2H), 7.34 (d, J=7.8 Hz, 1H), 7.67-7.76 (m, 1H), 7.80 (dd, J=7.8, 1.7 Hz, 1H), 8.33-8.37 (m, 1H), 10.44 (s, 1H)

Step 84-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(2-pyridinyl) propanamide (levorotatory isomer)

With 0.32 g of the compound obtained in Step 84-3 (Isomer B) as starting material, 180 mg of the title compound (pale yellow amorphous) was obtained by a similar procedure to Example 2.

[α]$_D^{25}$=−0.530° (c=0.187, CHCl$_3$)

MS (ESI pos.) m/z: 719 ([M+H]$^+$)

$^1$H-NMR (300 MHz, CDCl$_3$) δ (ppm); 2.65-2.75 (m, 1H), 2.76-2.84 (m, 1H), 2.86 (s, 3H), 2.98 (s, 6H), 3.55 (d, J=9.6

Hz, 1H), 3.67-3.78 (m, 1H), 3.85 (s, 3H), 5.88 (d, J=2.3 Hz, 1H), 6.57 (dd, J=8.2, 0.9 Hz, 1H), 6.82-6.87 (m, 2H), 6.92-7.01 (m, 1H), 7.09-7.25 (m, 4H), 7.61 (dt, J=7.6, 1.9 Hz, 1H), 7.83-7.90 (m, 2H), 8.38 (d, J=8.7 Hz, 1H), 8.40-8.45 (m, 1H)

Example 85

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(3-pyridinyl) propanamide (levorotatory isomer)

Step 85-1: Synthesis of 9H-fluorene-9-ylmethyl [(1S)-2-(dimethylamino)-2-oxo-1-(3-pyridinylmethyl)ethyl]carbamate With 1.97 g of (2S)-2-{[(9H-fluorene-9-ylmethoxy)carbonyl]amino}-3-(3-pyridinyl) propanoic acid as starting material, 1.79 g of the title compound (colorless amorphous) was obtained by a similar procedure to Step 60-1.
MS (ESI pos.) m/z: 438 ([M+Na]$^+$)
$^1$H-NMR (300 MHz, CDCl$_3$) δ (ppm); 2.80 (s, 3H), 2.87-3.09 (m, 5H), 4.19 (t, J=6.9 Hz, 1H), 4.29-4.43 (m, 2H), 4.86-4.95 (m, 1H), 5.73 (d, J=8.1 Hz, 1H), 7.21 (dd, J=8.0, 4.9 Hz, 1H), 7.28-7.36 (m, 2H), 7.40 (t, J=7.5 Hz, 2H), 7.50 (d, J=7.8 Hz, 1H), 7.58 (dd, J=7.4, 0.9 Hz, 2H), 7.77 (d, J=7.6 Hz, 2H), 8.42-8.45 (m, 1H), 8.48-8.53 (m, 1H)

Step 85-2: Synthesis of (2S)-2-amino-N,N-dimethyl-3-(3-pyridinyl) propanamide

To a solution of 1.67 g of the compound obtained in Step 85-1 in a mixed solution of MeOH and THF (25 ml 4:1; v/v) was added a solution of 2 mol/L dimethylamine in MeOH (6.0 ml) and the reaction solution was stirred at room temperature for 24 hours. The reaction solution was concentrated under vacuum, the obtained residue was purified by column chromatography (silicagel 60; mobile phase: CHCl$_3$/MeOH=9/1 to 5/1; v/v, 0.1% NH$_4$OH content) to obtain 0.66 g of the title compound (brown oil).
MS (ESI pos.) m/z: 194 ([M+H]$^+$)
$^1$H-NMR (300 MHz, CDCl$_3$) δ (ppm); 2.72-2.85 (m, 4H), 2.86-3.00 (m, 4H), 3.91 (dd, J=7.3, 6.7 Hz, 1H), 7.21-7.27 (m, 1H), 7.52-7.58 (m, 1H), 8.46-8.52 (m, 2H)

Step 85-3: Synthesis of (2S)-2-{[5-chloro-3-(2-methoxyphenyl)-2-oxo-2,3-dihydro-1H-indol-3-yl]amino}-N,N-dimethyl-3-(3-pyridinyl) propanamide (levorotatory isomer and dextrorotatory isomer)

With 1.82 g of 3,5-dichloro-3-(2-methoxyphenyl)-1,3-dihydro-2H-indol-2-one and 0.61 g of the compound obtained in Step 85-2 as starting materials, 246 mg (Isomer A, yellow amorphous) and 536 mg (Isomer B, pale yellow amorphous) of the respective diastereoisomers of the title compound were obtained by a similar method to Step 4-2.
Isomer A: [α]$_D^{25}$=+115° (c=0.205, CHCl$_3$)
MS (ESI pos.) m/z: 465 ([M+H]$^+$)
$^1$H-NMR (300 MHz, CDCl$_3$) δ (ppm); 2.70 (s, 3H), 2.79-3.04 (m, 6H), 3.52 (s, 3H), 4.05-4.18 (m, 1H), 6.63 (d, J=8.2 Hz, 1H), 6.73-6.86 (m, 3H), 7.07 (dd, J=8.2, 2.2 Hz, 1H), 7.19-7.32 (m, 2H), 7.36 (dd, J=7.8, 1.7 Hz, 1H), 7.55-7.61 (m, 1H), 7.95 (s, 1H), 8.50-8.53 (m, 1H), 8.56 (dd, J=4.8, 1.7 Hz, 1H)
Isomer B: [α]$_D^{25}$=−117° (c=0.221, CHCl$_3$)
MS (ESI pos.) m/z: 487 ([M+Na]$^+$)
$^1$H-NMR (300 MHz, CDCl$_3$) δ (ppm); 2.46 (s, 3H), 2.72-2.83 (m, 2H), 2.85 (s, 3H), 3.37 (d, J=9.0 Hz, 1H), 3.50 (s, 3H), 3.62-3.72 (m, 1H), 6.49 (d, J=2.2 Hz, 1H), 6.73-6.79 (m, 2H), 6.98-7.05 (m, 1H), 7.10 (dd, J=8.2, 2.2 Hz, 1H), 7.16-7.30 (m, 2H), 7.39-7.45 (m, 1H), 7.86 (dd, J=7.9, 1.6 Hz, 1H), 8.40-8.42 (m, 1H), 8.48 (dd, J=4.8, 1.6 Hz, 1H), 8.53 (s, 1H)

Step 85-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-3-(3-pyridinyl) propanamide (levorotatory isomer)

With 357 mg of the compound obtained in Step 85-3 (Isomer B) as starting material, 331 mg of the title compound (colorless amorphous) was obtained by a similar procedure to Example 2.
[α]$_D^{25}$=168° (c=0.203, CHCl$_3$)
MS (ESI pos.) m/z: 719 ([M+H]$^+$)
$^1$H-NMR (300 MHz, CDCl$_3$) δ (ppm); 2.32 (dd, J=13.4, 7.5 Hz, 1H), 2.45 (s, 3H), 2.58 (dd, J=12.8, 6.8 Hz, 1H), 2.93 (s, 3H), 3.18-3.24 (m, 4H), 3.56-3.65 (m, 1H), 3.75 (s, 3H), 6.35 (d, J=2.3 Hz, 1H), 6.67 (dd, J=8.2, 1.1 Hz, 1H), 6.82-6.91 (m, 2H), 6.95-7.05 (m, 1H), 7.11-7.33 (m, 4H), 7.77 (dd, J=7.8, 1.7 Hz, 1H), 7.89 (d, J=8.7 Hz, 1H), 8.26-8.29 (m, 1H), 8.37 (d, J=9.0 Hz, 1H), 8.46 (dd, J=4.9, 1.6 Hz, 1H)

Example 86

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(4-hydroxyphenyl)-N,N-dimethylpropanamide (levorotatory isomer)

Step 86-1: Synthesis of tert-butyl[(1S)-2-(dimethylamino)-1-(4-hydroxy benzyl)-2-oxo ethyl]carbamate With 3.00 g of (2S)-2-[(tert-butoxy carbonyl)amino]-3-(4-hydroxyphenyl) propanoic acid as starting material, 2.43 g of the title compound (colorless amorphous) was obtained by a similar procedure to Step 60-1.
MS (ESI pos.) m/z: 331 ([M+Na]$^+$)
$^1$H-NMR (300 MHz, CDCl$_3$) δ (ppm); 1.41 (s, 9H), 2.63-2.94 (m, 8H), 4.72-4.85 (m, 1H), 5.46 (d, J=8.7 Hz, 1H), 6.74 (d, J=8.4 Hz, 2H), 6.88 (s, 1H), 6.99 (d, J=8.4 Hz, 2H)

Step 86-2: Synthesis of tert-butyl[(1S)-1-[4-(benzyl oxy)benzyl]-2-(dimethylamino)-2-oxo ethyl]carbamate A solution of 2.62 g of the compound obtained in Step 86-1 in DMF (30 ml) was added sequentially 1.29 g of K$_2$CO$_3$ and benzyl bromide (1.1 ml), and the reaction mixture was stirred at room temperature for 3 hours. The solution was cooled on ice, then, a saturated aqueous solution of NaHCO$_3$ was added, and the mixture was extracted with EtOAc. The combined organic layer was washed with water and saturated brine, dried over MgSO$_4$, then, the drying agent was separated by filtration and the solvent was evaporated under reduced pressure. The obtained residue was purified by column chromatography (silicagel 60; mobile phase: n-hexane/EtOAc=1/1; v/v) to obtain 2.36 g of the title compound (colorless oil).
MS (ESI pos.) m/z: 421 ([M+Na]$^+$)

¹H-NMR (300 MHz, CDCl₃) δ (ppm); 1.41 (s, 9H), 2.61 (s, 3H), 2.81-2.96 (m, 5H), 4.71-4.82 (m, 1H), 5.04 (s, 2H), 5.40 (d, J=8.7 Hz, 1H), 6.85-6.93 (m, 2H), 7.05-7.12 (m, 2H), 7.27-7.45 (m, 5H)

Step 86-3: Synthesis of (2S)-2-amino-3-[4-(benzyl oxy)phenyl]-N,N-dimethylpropanamide trifluoroacetate To a solution of 2.00 g of the compound obtained in Step 86-2 in CHCl₃ (30 ml) was added TFA (6 ml) under ice cooling, then, the reaction solution was stirred at room temperature for 13 hours. The reaction solution was concentrated under reduced pressure to obtain 3.47 g of the title compound (yellow oil form, crude form).
MS (ESI pos.) m/z: 298 ([M+H]⁺)
¹H-NMR (300 MHz, CDCl₃) δ (ppm); 2.58 (s, 3H), 2.86 (s, 3H), 2.98-3.07 (m, 1H), 3.08-3.18 (m, 1H), 4.59 (t, J=7.4 Hz, 1H), 5.04 (s, 2H), 6.88-6.97 (m, 2H), 7.05-7.11 (m, 2H), 7.27-7.51 (m, 8H)

Step 86-4: Synthesis of (2S)-3-[4-(benzyl oxy)phenyl]-2-{[5-chloro-3-(2-methoxyphenyl)-2-oxo-2,3-dihydro-1H-indol-3-yl]amino}-N,N-dimethylpropanamide (levorotatory isomer and dextrorotatory isomer)

With 4.58 g of 3,5-dichloro-3-(2-methoxyphenyl)-1,3-dihydro-2H-indol-2-one and the compound obtained in Step 86-3 (5.02 mmol, crude form) as starting materials, 1.09 g (Isomer A, yellow solid) and 1.67 g (Isomer B, colorless amorphous) of the respective diastereoisomers of the title compound were obtained by a similar method to Step 4-2.
Isomer A: [α]$_D^{26}$=+109° (c=0.221, CHCl₃)
MS (ESI pos.) m/z: 570 ([M+H]⁺)
¹H-NMR (300 MHz, DMSO-d₆) δ (ppm); 2.54 (s, 3H), 2.58-2.77 (m, 5H), 2.83 (d, J=10.0 Hz, 1H), 3.42 (s, 3H), 3.75-3.86 (m, 1H), 5.12 (s, 2H), 6.62 (d, J=2.3 Hz, 1H), 6.65-6.73 (m, 1H), 6.77-6.88 (m, 2H), 6.92-6.99 (m, 2H), 7.07-7.15 (m, 2H), 7.15-7.25 (m, 2H), 7.28-7.53 (m, 6H), 10.40 (s, 1H)
Isomer B: [α]$_D^{26}$=−80° (c=0.224, CHCl₃)
MS (ESI neg.) m/z: 568 ([M−H]⁻)
¹H-NMR (300 MHz, DMSO-d₆) δ (ppm); 2.48 (s, 3H), 2.70 (s, 3H), 3.12 (d, J=8.9 Hz, 1H), 3.24-3.31 (m, 1H), 3.39 (s, 3H), 5.06 (s, 2H), 6.14 (d, J=2.2 Hz, 1H), 6.77 (d, J=8.4 Hz, 1H), 6.83-6.92 (m, 3H), 6.95-7.04 (m, 3H), 7.15 (dd, J=8.2, 2.3 Hz, 1H), 7.22-7.46 (m, 6H), 7.90 (dd, J=7.7, 1.6 Hz, 1H), 10.47 (s, 1H)

Step 86-5: Synthesis of (2S)-3-[4-(benzyl oxy)phenyl]-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer)

With 597 mg of the compound obtained in Step 86-4 (Isomer B) as starting material, 582 mg of the title compound (colorless amorphous) was obtained by a similar procedure to Example 2.
[α]$_D^{25}$=−128° (c=0.209, CHCl₃)
MS (ESI pos.) m/z: 824 ([M+H]⁺)
¹H-NMR (300 MHz, CDCl₃) δ (ppm); 2.14 (dd, J=13.3, 7.2 Hz, 1H), 2.28 (s, 3H), 2.44-2.54 (m, 1H), 2.86 (s, 3H), 3.29 (s, 3H), 3.61 (t, J=7.2 Hz, 1H), 3.66 (s, 3H), 5.03 (s, 2H), 6.47 (d, J=2.0 Hz, 1H), 6.68 (dd, J=8.2, 1.1 Hz, 1H), 6.77-6.90 (m, 6H), 6.93-7.03 (m, 1H), 7.18-7.46 (m, 7H), 7.76 (dd, J=7.8, 1.7 Hz, 1H), 7.89 (d, J=8.7 Hz, 1H), 8.36 (d, J=9.3 Hz, 1H)

Step 86-6: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-3-(4-hydroxyphenyl)-N,N-dimethylpropanamide (levorotatory isomer)

A suspension of 347 mg of the compound obtained in Step 86-5 and 30 mg of 10% palladium-carbon in EtOH (10 ml) was stirred at room temperature for 48 hours under hydrogen atmosphere. The insoluble matter was separated by filtration, and the filtrate was concentrated under reduced pressure. The obtained residue was purified by column chromatography (silicagel 60; mobile phase: n-hexane/EtOAc=2/3; v/v) to obtain 183 mg of the title compound (colorless amorphous).
[α]$_D^{25}$=164° (c=0.191, CHCl₃)
MS (ESI pos.) m/z: 756 ([M+Na]⁺)
¹H-NMR (300 MHz, CDCl₃) δ (ppm); 2.12 (dd, J=12.8, 6.5 Hz, 1H), 2.28 (s, 3H), 2.48 (dd, J=12.9, 8.1 Hz, 1H), 2.85 (s, 3H), 3.29 (s, 3H), 3.61-3.69 (m, 4H), 6.18 (s, 1H), 6.51 (d, J=2.2 Hz, 1H), 6.64-6.74 (m, 3H), 6.74-6.88 (m, 4H), 6.91-7.01 (m, 1H), 7.18-7.32 (m, 2H), 7.75 (dd, J=7.8, 1.6 Hz, 1H), 7.89 (d, J=8.9 Hz, 1H), 8.34 (d, J=8.9 Hz, 1H)

Example 87

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-2-phenyl acetamide (levorotatory isomer)

Step 87-1: Synthesis of benzyl[(1S)-2-(dimethylamino)-2-oxo-1-phenylethyl]carbamate With 2.50 g of (2S)-{[(benzyl oxy)carbonyl]amino}(phenyl)acetic acid as starting material, 2.49 g of the title compound (colorless solid) was obtained by a similar procedure to Step 60-1.
MS (ESI pos.) m/z: 335 ([M+Na]⁺)
¹H-NMR (300 MHz, CDCl₃) δ (ppm); 2.88 (s, 3H), 2.98 (s, 3H), 4.97-5.03 (m, 1H), 5.08-5.14 (m, 1H), 5.58 (d, J=7.5 Hz, 1H), 6.35 (d, J=7.2 Hz, 1H), 7.27-7.43 (m, 10H)

Step 87-2: Synthesis of (2S)-2-amino-N,N-dimethyl-2-phenyl acetamide

A suspension of 1.67 g of the compound obtained in Step 87-1 and 0.17 g of 10% palladium-carbon in EtOH (20 ml) was stirred at room temperature for 14 hours under hydrogen atmosphere. The stirred solution was added with THF (1 ml) and stirred at room temperature for 1 hour under hydrogen atmosphere. The insoluble matter was separated by filtration and the filtrate was concentrated under reduced pressure to obtain 0.97 g of the title compound (pale yellow solid, crude form).
MS (ESI pos.) m/z: 179 ([M+H]⁺)
¹H-NMR (300 MHz, CDCl₃) δ (ppm); 2.02 (s, 2H), 2.85 (s, 3H), 2.99 (s, 3H), 4.72 (s, 1H), 7.25-7.40 (m, 5H)

Step 87-3: Synthesis of (2S)-2-{[5-chloro-3-(2-methoxyphenyl)-2-oxo-2,3-dihydro-1H-indol-3-yl]amino}-N,N-dimethyl-2-phenyl acetamide (levorotatory isomer and dextrorotatory isomer)

With 1.45 g of 3,5-dichloro-3-(2-methoxyphenyl)-1,3-dihydro-2H-indol-2-one and 0.92 g of the compound obtained in Step 87-2 (5.16 mmol, crude form) as starting materials, 1.09 g (Isomer A, colorless amorphous) and 1.31 g (Isomer B, colorless amorphous) of the respective diastereoisomers of the title compound were obtained by a similar method to Step 4-2.

Isomer A: $[\alpha]_D^{26}=+131°$ (c=0.220, CHCl$_3$)
MS (ESI pos.) m/z: 450 ([M+H]$^+$)
$^1$H-NMR (300 MHz, CDCl$_3$) δ (ppm); 2.85 (s, 3H), 2.92 (s, 3H), 3.58 (s, 3H), 3.62 (d, J=9.8 Hz, 1H), 4.99-5.06 (m, 1H), 6.70 (d, J=8.2 Hz, 1H), 6.75-6.88 (m, 2H), 7.02-7.15 (m, 2H), 7.26-7.43 (m, 6H), 7.92-7.99 (m, 1H), 8.22 (s, 1H)

Isomer B: $[\alpha]_D^{26}=-13.0°$ (c=0.194, CHCl$_3$)
MS (ESI pos.) m/z: 472 ([M+Na]$^+$)
$^1$H-NMR (300 MHz, CDCl$_3$) δ (ppm); 2.66 (s, 3H), 2.85 (s, 3H), 3.54 (s, 3H), 4.50 (s, 1H), 6.68 (d, J=2.0 Hz, 1H), 6.76-6.85 (m, 2H), 7.01-7.15 (m, 4H), 7.17-7.33 (m, 4H), 8.01-8.11 (m, 1H), 8.64 (s, 1H)

Step 87-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethyl-2-phenyl acetamide (levorotatory isomer)

With 0.73 g of the compound obtained in Step 87-3 (Isomer B) as starting material, 0.90 g of the title compound (colorless amorphous) was obtained by a similar procedure to Example 2.

$[\alpha]_D^{25}=-1.90°$ (c=0.206, CHCl$_3$)
MS (ESI pos.) m/z: 726 ([M+Na]$^+$)
$^1$H-NMR (300 MHz, CDCl$_3$) δ (ppm); 2.66 (s, 3H), 2.89 (s, 3H), 3.36 (s, 3H), 3.91 (s, 3H), 4.05 (s, 1H), 4.37 (s, 1H), 6.55 (d, J=2.3 Hz, 1H), 6.70 (d, J=8.2 Hz, 1H), 6.78-6.83 (m, 1H), 6.88-7.05 (m, 4H), 7.06-7.15 (m, 3H), 7.17-7.29 (m, 2H), 7.90 (d, J=8.7 Hz, 1H), 7.97 (dd, J=7.8, 1.7 Hz, 1H), 8.32 (d, J=9.0 Hz, 1H)

Example 88

(4R)-1-(3-(1,3-benzodioxol-4-yl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer) Synthesis of Step 88-1: tert-butyl (2S,4R)-2-[(dimethylamino)carbonyl]-4-hydroxypyrrolidine-1-carboxylate Synthesis of With 18.6 g of (4R)-1-(tert-butoxy carbonyl)-4-hydroxy-L-proline as starting material, 13.0 g of the title compound (colorless solid) was obtained by a similar method to Step 6-1a.

MS (ESI pos.) m/z: 281 ([M+Na]$^+$)
$^1$H-NMR (300 MHz, CDCl$_3$) δ (ppm); 1.40 & 1.45 (each-s, 9H), 1.95-2.36 (m, 3H), 2.97 & 2.98 (each-s, 3H), 3.08 & 3.13 (each-s, 3H), 3.41-3.62 (m, 1H), 3.63-3.76 (m, 1H), 4.46-4.60 (m, 1H), 4.69-4.87 (m, 1H)

Step 88-2: Synthesis of (4R)-4-hydroxy-N,N-dimethyl-L-prolinamide hydrochloride

To a solution of 11.0 g of the compound obtained in Step 88-1 in EtOAc (100 ml) was added dropwise a solution of 4 mol/l hydrochloric acid in EtOAc (100 ml) over 20 minutes. The solution was stirred at room temperature for two hours and then the solvent was evaporated under reduced pressure. EtOAc was added, and the solution was stirred for 30 minutes. Thereafter, the precipitated solid was filtered and then dried to obtain 8.21 g of the title compound (colorless solid).

$^1$H-NMR (300 MHz, DMSO-d$_6$) δ (ppm); 1.79-1.94 (m, 1H), 2.30-2.42 (m, 1H), 2.91 (s, 3H), 3.01 (s, 3H), 3.03-3.12 (m, 1H), 3.25-3.38 (m, 1H), 4.35-4.49 (m, 1H), 4.66 (dd, J=10.3, 7.5 Hz, 1H), 5.58 (d, J=3.4 Hz, 1H), 9.01-9.58 (m, 2H)

Step 88-3: Synthesis of (4R)-1-[3-(1,3-benzodioxol-4-yl)-5-chloro-2-oxo-2,3-dihydro-1H-indol-3-yl]-4-hydroxy-N,N-dimethyl-L-prolinamide From 1.00 g of 3-(1,3-benzodioxol-4-yl)-5-chloro-3-hydroxy-1,3-dihydro-2H-indol-2-one and 650 mg of (4R)-4-hydroxy-N,N-dimethyl-L-prolinamide hydrochloride, respectively 51 mg (Isomer A: pale orange amorphous) and 53 mg (Isomer B: pale orange amorphous) of diastereoisomers of the title compound were obtained by a similar method to Step 21-2.

Isomer A: MS (ESI pos.) m/z: 444 ([M+H]$^+$), 466 ([M+Na]$^+$), (ESI neg.) m/z: 443 ([M−H]$^-$)
$^1$H-NMR (300 MHz, CDCl$_3$) δ (ppm); 1.87-2.08 (m, 1H), 2.27 (dd, J=13.4, 6.5 Hz, 1H), 2.73 (s, 3H), 2.92 (s, 3H), 3.48-3.71 (m, 3H), 3.91 (dd, J=11.04 6.7 Hz, 1H), 4.26-4.47 (m, 1H), 5.89 (dd, J=27.8, 1.4 Hz, 2H), 6.69-6.98 (m, 3H), 7.09-7.38 (m, 3H), 9.13-9.32 (m, 1H)

Isomer B: MS (ESI pos.) m/z: 444 ([M+H]$^+$), 466 ([M+Na]$^+$), (ESI neg.) m/z: 443 ([M−H]$^-$)
$^1$H-NMR (300 MHz, CDCl$_3$) δ (ppm); 1.91-2.01 (m, 1H), 2.10-2.22 (m, 1H), 2.58 (s, 3H), 2.62-2.71 (m, 4H), 2.82-2.92 (m, 1H), 3.54-3.69 (m, 1H), 4.39-4.52 (m, 1H), 4.87 (dd, J=8.2, 6.5 Hz, 1H), 6.01 (dd, J=11.2, 1.4 Hz, 2H), 6.74-6.84 (m, 3H), 6.99-7.07 (m, 1H), 7.14 (dd, J=8.2, 2.2 Hz, 1H), 7.60 (d, J=2.2 Hz, 1H), 8.35 (s, 1H)

Step 88-4: Synthesis of (4R)-1-(3-(1,3-benzodioxol-4-yl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 50 mg of the compound obtained in Step 88-3 (Isomer B) and 36 mg of 4-methoxy-2-(trifluoromethoxy benzene) sulfonyl chloride as starting materials, 56 mg of the title compound (colorless amorphous) was obtained by a similar method to Example 2.

$[\alpha]_D^{25}=-184°$ (c=0.336, CHCl$_3$)
MS (ESI pos.) m/z: 698 ([M+H]$^+$), 720 ([M+Na]$^+$), (ESI neg.) m/z: 696 ([M−H]$^-$)
$^1$H-NMR (300 MHz, CDCl$_3$) δ (ppm); 1.85-1.96 (m, 1H), 2.02-2.13 (m, 1H), 2.23-2.32 (m, 1H), 2.51 (s, 3H), 2.60-2.70 (m, 4H), 3.57 (dd, J=10.3, 4.0 Hz, 1H), 3.91 (s, 3H), 4.37-4.47 (m, 1H), 4.61 (dd, J=8.6, 5.6 Hz, 1H), 5.69 (dd, J=27.7, 1.4 Hz, 2H), 6.69-6.77 (m, 2H), 6.80-6.91 (m, 2H), 6.96 (dd, J=9.0, 2.3 Hz, 1H), 7.23-7.30 (m, 1H), 7.43 (d, J=2.2 Hz, 1H), 7.90 (d, J=8.7 Hz, 1H), 8.40 (d, J=9.0 Hz, 1H)

Example 89

Synthesis of (4R)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 89-1: Synthesis of (4R)-4-hydroxy-N,N-dimethyl-L-prolinamide trifluoroacetate With 316 mg of the compound obtained in Step 6-1a as starting material, the title compound was obtained by a similar method to Step 4-1. The obtained crude form was subjected to the next reaction without purification.
MS (ESI pos.) m/z: 159 ([M+H]$^+$)
$^1$H-NMR (300 MHz, CDCl$_3$) δ (ppm); 1.89-2.04 (m, 1H), 2.61-2.76 (m, 1H), 3.05 (s, 3H), 3.08 (s, 3H), 3.32-3.48 (m, 1H), 3.69-3.85 (m, 1H), 4.69-4.83 (m, 1H), 4.93-5.10 (m, 1H)

Step 89-2: Synthesis of (4R)-1-[5-chloro-3-(2,3-dihydro-1-benzofuran-7-yl)-2-oxo-2,3-dihydro-1H-indol-3-yl]-4-hydroxy-N,N-dimethyl-L-prolinamide (diastereoisomer mixture)

From 308 mg of the compound obtained in Step 25-1 and (4R)-4-hydroxy-N,N-dimethyl-L-prolinamide trifluoroacetate (1.22 mmol), 287 mg of a diastereoisomer mixture of the title compound (colorless amorphous) was obtained by a similar method to Step 21-2.
MS (ESI pos.) m/z: 464 ([M+Na]$^+$), (ESI neg.) m/z: 440 ([M−H]$^−$)
$^1$H-NMR (300 MHz, CDCl$_3$) δ (ppm); 1.83-2.27 (m, 4H), 2.56-2.81 (m, 6H), 2.97-3.27 (m, 2H), 3.57-3.96 (m, 1H), 4.32-4.80 (m, 3H), 6.67-8.26 (m, 7H)

Step 89-3: Synthesis of (4R)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 125 mg of the compound obtained in Step 89-2 (diastereoisomer mixture) and 98 mg of 4-methoxy-2-(trifluoromethoxy)benzene sulfonyl chloride as starting materials, respectively 32 mg (Isomer A: colorless amorphous) and 4 mg (Isomer B: colorless powder) two species of diastereoisomers of the title compound were obtained by a similar method to Example 2.
Isomer A: [α]$_D^{25}$=+109° (c=0.169, CHCl$_3$)
MS (ESI pos.) m/z: 718 ([M+Na]$^+$), (ESI neg.) m/z: 694 ([M−H]$^−$)
$^1$H-NMR (300 MHz, CDCl$_3$) δ (ppm); 1.75-1.91 (m, 1H), 1.97-2.10 (m, 1H), 2.52 (s, 3H), 2.72 (s, 3H), 2.99 (t, J=8.8 Hz, 2H), 3.44-3.59 (m, 2H), 3.86-4.17 (m, 6H), 4.32 (br. s., 1H), 6.87-6.98 (m, 3H), 7.01-7.10 (m, 2H), 7.22-7.29 (m, 1H), 7.85-7.95 (m, 2H), 8.32 (d, J=8.9 Hz, 1H)
Isomer B: [α]$_D^{25}$=−189° (c=0.054, CHCl$_3$)
MS (ESI pos.) m/z: 718 ([M+Na]$^+$), (ESI neg.) m/z: 694 ([M−H]$^−$)
$^1$H-NMR (300 MHz, CDCl$_3$) δ (ppm); 1.81-2.13 (m, 2H), 2.51 (s, 3H), 2.59-2.69 (m, 1H), 2.66 (s, 3H), 3.04-3.14 (m, 2H), 3.48-3.58 (m, 3H), 3.91 (s, 3H), 4.20-4.44 (m, 3H), 4.56-4.65 (m, 1H), 6.74 (t, 1H), 6.86-6.91 (m, 1H), 6.96 (dd, J=9.0, 2.3 Hz, 1H), 7.03-7.13 (m, 2H), 7.23 (dd, J=8.7, 2.3 Hz, 1H), 7.41 (d, J=2.2 Hz, 1H), 7.88 (d, J=8.7 Hz, 1H), 8.41 (d, J=8.9 Hz, 1H)

Example 90

Synthesis of (2S)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer)

Step 90-1: Synthesis of (2S)-1-[5-chloro-3-(2,3-dihydro-1-benzofuran-7-yl)-2-oxo-2,3-dihydro-1H-indol-3-yl]-N,N-dimethylpiperidine-2-carboxamide (diastereoisomer mixture)

For 500 mg of the compound obtained in Step 25-1 and of (2S)—N,N-dimethylpiperidine-2-carboxamide trifluoroacetate (1.99 mmol), 547 mg of a diastereoisomer mixture of the title compound (colorless amorphous) was obtained by a similar method to Step 21-2.
MS (ESI pos.) m/z: 462 ([M+Na]$^+$), (ESI neg.) m/z: 438 ([M−H]$^−$)
$^1$H-NMR (300 MHz, CDCl$_3$) δ (ppm); 1.42-2.00 (m, 7H), 2.27 (br. s., 2H), 2.76 (br. s., 4H), 2.88-3.81 (m, 3H), 3.94-4.50 (m, 4H), 6.72-7.17 (m, 5H), 7.56-7.77 (m, 1H), 8.43-8.67 (m, 1H)

Step 90-2: Synthesis of (2S)-1-(5-chloro-3-(2,3-dihydro-1-benzofuran-7-yl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer)

With 299 mg of the compound obtained in Step 90-1 (diastereoisomer mixture) and 237 mg of 4-methoxy-2-(trifluoromethoxy)benzene sulfonyl chloride as starting materials, 93 mg of the title compound (colorless amorphous) was obtained by a similar method to Example 2.
[α]$_D^{25}$=159° (c=0.480, CHCl$_3$)
MS (ESI pos.) m/z: 716 ([M+Na]$^+$)
$^1$H-NMR (300 MHz, CDCl$_3$) δ (ppm); 1.44-1.94 (m, 7H), 2.24 (br. s., 2H), 2.76-3.04 (m, 6H), 3.44-3.62 (m, 1H), 3.77-3.95 (m, 5H), 3.99-4.17 (m, 1H), 6.76-7.05 (m, 5H), 7.20-7.30 (m, 1H), 7.51-7.66 (m, 1H), 7.96 (d, J=8.9 Hz, 1H), 8.47 (d, J=8.9 Hz, 1H)

Example 91

Synthesis of (4R)-1-(3-(1,3-benzodioxol-4-yl)-5-iodo-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer, levorotatory isomer)

Step 91-1: Synthesis of 3-(1,3-benzodioxol-4-yl)-3-hydroxy-5-iodo-1,3-dihydro-2H-indol-2-one With 2.70 g of 4-bromo-1,3-benzodioxol and 9.00 g of 5-iodoisatin as starting materials, 3.44 g of the title compound (orange color solid) was obtained by a similar method to Step 21-1.
MS (ESI pos.) m/z: 418 ([M+Na]$^+$), (ESI neg.) m/z: 394 ([M−H]$^−$)

¹H-NMR (300 MHz, DMSO-d₆) δ (ppm); 5.77-5.83 (m, 2H), 6.71 (d, J=8.1 Hz, 1H), 6.78-6.96 (m, 3H), 7.20-7.29 (m, 2H), 7.55 (dd, J=8.1, 1.9 Hz, 1H), 10.58 (brs, 1H)

Step 91-2: Synthesis of (4R)-1-[3-(1,3-benzodioxol-4-yl)-5-iodin-2-oxo-2,3-dihydro-1H-indol-3-yl]-4-hydroxy-N,N-dimethyl-L-prolinamide From 1.00 g of the compound obtained in Step 91-1 and 591 mg of (4R)-4-hydroxy-N,N-dimethyl-L-prolinamide hydrochloride, 1.14 g of the title compound (pale yellow amorphous) was obtained by a similar method to Step 28-2.
MS (ESI pos.) m/z: 536 ([M+H]⁺), (ESI neg.) m/z: 534 ([M−H]⁻)
¹H-NMR (300 MHz, CDCl₃) δ (ppm); 1.50-2.28 (m, 3H), 2.53-2.96 (m, 7H), 3.52-4.91 (m, 3H), 5.78-6.04 (m, 2H), 6.55-7.93 (m, 7H)

Step 91-3: Synthesis of (4R)-1-(3-(1,3-benzodioxol-4-yl)-5-iodo-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer, levorotatory isomer)

With 315 mg of the compound obtained in Step 91-2 and 206 mg of 4-methoxy-2-(trifluoromethoxy)benzene sulfonyl chloride as starting materials, respectively 149 mg (Isomer A: colorless solid) and 124 mg (Isomer B: colorless amorphous) of two species of diastereoisomers of the title compound were obtained by a similar method to Example 2.
Isomer A: [α]_D^25=−153° (c=0.749, CHCl₃)
MS (ESI pos.) m/z: 812 ([M+Na]⁺), (ESI neg.) m/z: 788 ([M−H]⁻)
¹H-NMR (300 MHz, CDCl₃) δ (ppm); 1.82-1.96 (m, 1H), 2.02-2.14 (m, 1H), 2.26-2.41 (m, 1H), 2.52 (s, 3H), 2.58-2.65 (m, 1H), 2.66 (s, 3H), 3.57 (dd, J=10.3, 4.0 Hz, 1H), 3.91 (s, 3H), 4.43 (brs, 3H), 4.60 (dd, J=8.6, 5.4 Hz, 1H), 5.67 (dd, J=34.0, 1.4 Hz, 1H), 6.67-6.78 (m, 2H), 6.80-6.91 (m, 2H), 6.96 (dd, J=8.9, 2.4 Hz, 1H), 7.56-7.63 (m, 2H), 7.67-7.77 (m, 2H), 8.40 (d, J=9.0 Hz, 1H)
Isomer B: [α]_D^25=+68° (c=0.168, CHCl₃)
MS (ESI pos.) m/z: 812 ([M+Na]⁺), (ESI neg.) m/z: 788 ([M−H]⁻)
¹H-NMR (300 MHz, CDCl₃) δ (ppm); 1.75-1.90 (m, 2H), 1.96-2.09 (m, 1H), 2.51 (s, 3H), 2.79 (s, 3H), 3.40-3.57 (m, 2H), 3.86-3.97 (m, 1H), 3.91-3.94 (m, 3H), 4.33 (brs, 1H), 5.45 (dd, J=39.3, 1.6 Hz, 2H), 6.71 (dd, J=7.5, 0.9 Hz, 1H), 6.83-6.99 (m, 3H), 7.40 (d, J=1.9 Hz, 1H), 7.53-7.68 (m, 2H), 7.71-7.79 (m, 1H), 8.31 (d, J=9.0 Hz, 1H)

Example 92

Synthesis of (4R)-1-(3-(1,3-benzodioxol-4-yl)-5-bromo-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 92-1: Synthesis of 3-(1,3-benzodioxol-4-yl)-5-bromo-3-hydroxy-1,3-dihydro-2H-indol-2-one With 2.25 g of 5-bromoisatin and a Grignard reagent (1 mol/L solution; 15 ml), which was prepared in a similar procedure to Step 91-1, as starting materials, 2.67 g of the title compound (orange color solid) was obtained by a similar method to Step 21-1.

MS (ESI pos.) m/z: 370 ([M+Na]⁺), (ESI neg.) m/z: 346 ([M−H]⁻)
¹H-NMR (300 MHz, DMSO-d₆) δ (ppm); 5.80 (dd, J=4.8, 0.9 Hz, 2H), 6.78-6.97 (m, 3H), 7.10 (d, J=2.2 Hz, 1H), 7.25 (dd, J=7.4, 1.9 Hz, 1H), 7.39 (dd, J=8.2, 2.0 Hz, 1H), 10.60 (brs, 1H)

Step 92-2: Synthesis of (4R)-1-[3-(1,3-benzodioxol-4-yl)-5-bromo-2-oxo-2,3-dihydro-1H-indol-3-yl]-4-hydroxy-N,N-dimethyl-L-prolinamide From 1.00 g of the compound obtained in Step 92-1 and 670 mg of (4R)-4-hydroxy-N,N-dimethyl-L-prolinamide hydrochloride, 1.22 g of a diastereo mixture of the title compound (colorless solid) was obtained by a similar method to Step 28-2.
MS (ESI pos.) m/z: 488 ([M+H]⁺), (ESI neg.) m/z: 486 ([M−H]⁻)
¹H-NMR (300 MHz, CDCl₃) δ (ppm); 1.58-2.35 (m, 3H), 2.48-3.19 (m, 7H), 3.54-4.94 (m, 4H), 5.75-6.08 (m, 2H), 6.64-7.78 (m, 7H)

Step 92-3: Synthesis of (4R)-1-(3-(1,3-benzodioxol-4-yl)-5-bromo-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 318 mg of the compound obtained in Step 92-2 and 227 mg of 4-methoxy-2-(trifluoromethoxy)benzene sulfonyl chloride as starting materials, respectively 135 mg (Isomer A: colorless solid) and 100 mg (Isomer B: colorless solid) of two species of diastereoisomers of the title compound were obtained by a similar method to Example 2.
Isomer A: [α]_D^25=−137° (c=0.382, CHCl₃)
MS (ESI pos.) m/z: 742 ([M+H]⁺), (ESI neg.) m/z: 740 ([M−H]⁻)
¹H-NMR (300 MHz, CDCl₃) δ (ppm); 1.83-1.97 (m, 1H), 2.02-2.14 (m, 1H), 2.24-2.41 (m, 1H), 2.48-2.55 (m, 3H), 2.59-2.65 (m, 1H), 2.66 (s, 3H), 3.57 (dd, J=10.3, 4.1 Hz, 1H), 3.86-3.96 (m, 3H), 4.42 (brs, 1H), 4.61 (dd, J=8.6, 5.4 Hz, 1H), 5.68 (dd, J=30.2, 1.4 Hz, 2H), 6.68-6.76 (m, 2H), 6.80-6.91 (m, 2H), 6.96 (dd, J=9.0, 2.3 Hz, 1H), 7.41 (dd, J=8.9, 2.2 Hz, 1H), 7.56 (d, J=2.0 Hz, 1H), 7.84 (d, J=8.7 Hz, 1H), 8.40 (d, J=9.0 Hz, 1H)
Isomer B: [α]_D^25=+96° (c=0.520, CHCl₃)
MS (ESI pos.) m/z: 764 ([M+Na]⁺), (ESI neg.) m/z: 740 ([M−H]⁻)
¹H-NMR (300 MHz, CDCl₃) δ (ppm); 1.77-1.89 (m, 2H), 1.97-2.09 (m, 7.1 Hz, 1H), 2.51 (s, 3H), 2.76 (s, 3H), 3.39-3.58 (m, 2H), 3.87-3.97 (m, 1H), 3.91-3.95 (m, 1H), 4.34 (brs, 1H), 5.45 (dd, J=36.8, 1.7 Hz, 2H), 6.71 (dd, J=7.8, 1.0 Hz, 1H), 6.84-6.99 (m, 3H), 7.24 (d, J=2.2 Hz, 1H), 7.44 (dd, J=8.8, 2.3 Hz, 1H), 7.59 (dd, J=8.2, 1.2 Hz, 1H), 7.87 (d, J=8.9 Hz, 1H), 8.31 (d, J=9.0 Hz, 1H)

Example 93

Synthesis of (4R)-1-(3-(1,3-benzodioxol-4-yl)-5-fluoro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 93-1: Synthesis of 3-(1,3-benzodioxol-4-yl)-5-fluoro-3-hydroxy-1,3-dihydro-2H-indol-2-one With 1.64 g, of 5-fluoroisatin and a Grignard reagent (1 mol/L; 15 ml), which was prepared in a similar procedure to Step 91-1, as starting materials, 1.85 g of the title compound (black brown solid) was obtained by a similar method to Step 21-1.

MS (ESI pos.) m/z: 310 ([M+Na]$^+$), (ESI neg.) m/z: 286 ([M−H]$^−$)

$^1$H-NMR (300 MHz, DMSO-d$_6$) δ (ppm); 5.79 (dd, J=11.3, 0.9 Hz, 2H), 6.70-6.97 (m, 4H), 6.99-7.11 (m, 1H), 7.24 (dd, J=7.2, 2.1 Hz, 1H), 10.47 (brs, 1H)

Step 93-2: Synthesis of (4R)-1-[3-(1,3-benzodioxol-4-yl)-5-fluoro-2-oxo-2,3-dihydro-1H-indol-3-yl]-4-hydroxy-N,N-dimethyl-L-prolinamide From 1.00 g of the compound obtained in Step 93-1 and 813 mg of (4R)-4-hydroxy-N,N-dimethyl-L-prolinamide hydrochloride, 1.04 g of a diastereoisomer mixture of the title compound (orange color solid) was obtained by a similar method to Step 21-2.

MS (ESI pos.) m/z: 428 ([M+H]$^+$), (ESI neg.) m/z: 426 ([M−H]$^−$)

$^1$H-NMR (300 MHz, CDCl$_3$) δ (ppm); 1.89-5.01 (m, 13H), 5.77-6.10 (m, 2H), 6.68-7.49 (m, 6H), 8.34-9.22 (m, 1H)

Step 93-3: Synthesis of (4R)-1-(3-(1,3-benzodioxol-4-yl)-5-fluoro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 305 mg of the compound obtained in Step 93-2 and 249 mg of 4-methoxy-2-(trifluoromethoxy)benzene sulfonyl chloride as starting materials, respectively 149 mg (Isomer A: colorless amorphous) and 75 mg (Isomer B: colorless amorphous) of two species of diastereoisomers of the title compound were obtained by a similar method to Example 2.

Isomer A: $[α]_D^{25}$=−233° (c=0.332, CHCl$_3$)

MS (ESI pos.) m/z: 682 ([M+H]$^+$), (ESI neg.) m/z: 680 ([M−H]$^−$)

$^1$H-NMR (300 MHz, CDCl$_3$) δ (ppm); 1.84-2.13 (m, 2H), 2.31-2.46 (m, 1H), 2.46-2.54 (m, 3H), 2.55-2.65 (m, 1H), 2.68 (s, 3H), 3.54 (dd, J=10.2, 4.3 Hz, 1H), 3.83-3.97 (m, 3H), 4.43 (brs, 1H), 4.65 (dd, J=8.6, 5.3 Hz, 1H), 5.68 (dd, J=23.7, 1.5 Hz, 2H), 6.62-7.05 (m, 7H), 7.20 (dd, J=7.8, 2.8 Hz, 1H), 7.92 (dd, J=9.0, 4.5 Hz, 1H), 8.39 (d, J=9.0 Hz, 1H)

Isomer B: $[α]_D^{25}$=+81° (c=0.320, CHCl$_3$)

MS (ESI pos.) m/z: 704 ([M+Na]$^+$), (ESI neg.) m/z: 680 ([M−H]$^−$)

$^1$H-NMR (300 MHz, CDCl$_3$) δ (ppm); 1.73-1.94 (m, 1H), 1.94-2.14 (m, 1H), 2.49-2.58 (m, 3H), 2.62-2.77 (m, 3H), 3.37-3.60 (m, 2H), 3.83-4.04 (m, 3H), 4.34 (brs, 1H), 5.45 (dd, J=32.4, 1.6 Hz, 2H), 6.59-7.11 (m, 6H), 7.57 (dd, J=8.2, 1.0 Hz, 1H), 7.85-8.09 (m, 1H), 8.32 (d, J=9.0 Hz, 1H)

Example 94

Synthesis of (4R)-1-(3-(1,3-benzodioxol-4-yl)-1-{[4-methoxy-2-(trifluoromethoxy)phenyl]sulfonyl}-5-nitro-2-oxo-2,3-dihydro-1H-indol-3-yl)-4-hydroxy-N,N-dimethyl-L-prolinamide (levorotatory isomer)

Step 94-1: Synthesis of 3-(1,3-benzodioxol-4-yl)-3-hydroxy-5-nitro-1,3-dihydro-2H-indol-2-one With 1.91 g of 5-nitrosatin and a Grignard reagent (1 mol/L; 15 ml), which was prepared by a similar procedure to Step 91-1, as starting materials, 1.73 g of the title compound (yellow solid) was obtained by a similar method to Step 21-1.

MS (ESI pos.) m/z: 337 ([M+Na]$^+$), (ESI neg.) m/z: 313 ([M−H]$^−$)

$^1$H-NMR (300 MHz, DMSO-d$_6$) δ (ppm); 5.78 (dd, J=16.3, 0.9 Hz, 2H), 6.85-7.16 (m, 3H), 7.32 (dd, J=7.7, 1.6 Hz, 1H), 7.80 (d, J=2.3 Hz, 1H), 8.21 (dd, J=8.7, 2.5 Hz, 1H), 11.22 (brs, 1H)

Step 94-2: Synthesis of (4R)-1-[3-(1,3-benzodioxol-4-yl)-5-nitro-2-oxo-2,3-dihydro-1H-indol-3-yl]-4-hydroxy-N,N-dimethyl-L-prolinamide To a solution of 1.00 g of the compound obtained in Step 94-1 and Py (0.31 ml) in CHCl$_3$ (10.5 ml) was added thionyl chloride (0.27 ml) under ice cooling, and the reaction mixture was stirred for 30 minutes under the same condition. To the reaction solution was added water, the reaction mixture was extracted with CHCl$_3$, the combined organic layer was dried over MgSO$_4$, then, the drying agent was separated by filtration and the filtrate was concentrated. To a suspension of the obtained residue and 738 mg of (4R)-4-hydroxy-N,N-dimethyl-L-prolinamide hydrochloride in CHCl$_3$ (10.5 ml) was added dropwise Et$_3$N (2.2 ml) then the reaction mixture was stirred for 14 hours under the same conditions. The reaction solution was added with water and the precipitated insoluble matter was collected by filtration to obtain 400 mg of the title compound (Isomer A) (colorless solid). The filtrate was concentrated and the obtained residue was purified by column chromatography (silicagel 60; mobile phase: CHCl$_3$/MeOH=9/1; v/v) to obtain 702 mg of the title compound (Isomer B) (brown solid).

Isomer A: MS (ESI pos.) m/z: 477 ([M+Na]$^+$), (ESI neg.) m/z: 453 ([M−H]$^−$)

$^1$H-NMR (300 MHz, DMSO-d$_6$) δ (ppm); 1.67-1.94 (m, 2H), 2.36 (s, 3H), 2.58 (s, 3H), 3.16-3.39 (m, 2H), 3.61-3.74 (m, 1H), 4.16-4.34 (m, 1H), 4.71 (d, J=4.5 Hz, 1H), 5.86 (dd, J=4.7, 0.9 Hz, 2H), 6.80-7.11 (m, 3H), 7.45 (d, J=8.1 Hz, 1H), 7.65 (d, J=2.3 Hz, 1H), 8.13 (dd, J=8.7, 2.3 Hz, 1H), 11.40 (brs, 1H)

Isomer B: MS (ESI pos.) m/z: 477 ([M+Na]$^+$), (ESI neg.) m/z: 453 ([M−H]$^−$)

$^1$H-NMR (300 MHz, DMSO-d$_6$) δ (ppm); 1.63-2.02 (m, 2H), 2.43 (s, 3H), 2.53 (s, 3H), 3.13-3.40 (m, 2H), 4.30-4.46 (m, 1H), 4.60-4.78 (m, 1H), 4.87 (d, J=4.8 Hz, 1H), 5.72-5.95 (m, 2H), 6.75-7.07 (m, 3H), 7.30 (t, J=4.7 Hz, 1H), 7.95 (d, J=2.3 Hz, 1H), 8.04-8.21 (m, 1H), 11.31 (brs, 1H)

Step 94-3: Synthesis of (4R)-1-(3-(1,3-benzodioxol-4-yl)-1-{[4-methoxy-2-(trifluoromethoxy)phenyl]sulfonyl}-5-nitro-2-oxo-2,3-dihydro-1H-indol-3-yl)-4-hydroxy-N,N-dimethyl-L-prolinamide (levorotatory isomer)

With 279 mg of the compound obtained in Step 94-2 (Isomer B) and 214 mg of 4-methoxy-2-(trifluoromethoxy)benzene sulfonyl chloride as starting materials, 163 mg of the title compound (pale yellow solid) was obtained by a similar method to Example 2.

$[α]_D^{25}$=−193° (c=0.320, CHCl$_3$)

MS (ESI pos.) m/z: 709 ([M+H]$^+$), (ESI neg.) m/z: 707 ([M−H]$^−$)

$^1$H-NMR (300 MHz, CDCl$_3$) δ (ppm); 1.83-1.95 (m, 1H), 2.10-2.24 (m, 1H), 2.44-2.54 (m, 1H), 2.52 (s, 3H), 2.62 (s, 3H), 2.73 (d, J=10.3 Hz, 1H), 3.57 (dd, J=10.3, 3.9 Hz, 1H), 3.88-3.96 (m, 3H), 4.39 (brs, 1H), 4.59 (dd, J=8.6, 5.8 Hz, 1H), 5.74 (dd, J=32.6, 1.2 Hz, 2H), 6.71-6.78 (m, 2H), 6.82-

6.91 (m, 2H), 6.99 (dd, J=9.2, 2.3 Hz, 1H), 8.08-8.16 (m, 1H), 8.17-8.25 (m, 1H), 8.33 (d, J=2.3 Hz, 1H), 8.41 (d, J=9.0 Hz, 1H)

Example 95

Synthesis of (4R)-1-(3-(1,3-benzodioxol-4-yl)-6-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 95-1: Synthesis of 3-(1,3-benzodioxol-4-yl)-6-chloro-3-hydroxy-1,3-dihydro-2H-indol-2-one With 1.81 g of 6-chloroisatin and a Grignard reagent (1 mol/L solution; 15 ml), which was prepared by a similar procedure to Step 91-1, as starting materials, 1.33 g of the title compound (pale yellow solid) was obtained by a similar method to Step 21-1.
MS (ESI pos.) m/z: 304 ([M+H]$^+$), (ESI neg.) m/z: 302 ([M−H]$^-$)
$^1$H-NMR (300 MHz, DMSO-d$_6$) δ (ppm); 5.78 (dd, J=7.9, 0.9 Hz, 2H), 6.78 (s, 1H), 6.84-6.96 (m, 3H), 6.98-7.03 (m, 1H), 7.26 (dd, J=7.5, 1.8 Hz, 1H), 10.61 (brs, 1H)

Step 95-2: Synthesis of (4R)-1-[3-(1,3-benzodioxol-4-yl)-6-chloro-2-oxo-2,3-dihydro-1H-indol-3-yl]-4-hydroxy-N,N-dimethyl-L-prolinamide From 800 mg of the compound obtained in Step 95-1 and 1.03 g of (4R)-4-hydroxy-N,N-dimethyl-L-prolinamide hydrochloride, 727 mg of a diastereoisomer mixture of the title compound (colorless amorphous) was obtained by a similar method to Step 28-2.
MS (ESI pos.) m/z: 466 ([M+Na]$^+$), (ESI neg.) m/z: 442 ([M−H]$^-$)
$^1$H-NMR (300 MHz, DMSO-d$_6$) δ (ppm); 1.59-1.94 (m, 2H), 2.21-2.62 (m, 6H), 3.03-3.41 (m, 4H), 3.61-4.89 (m, 3H), 5.76-5.93 (m, 2H), 6.71-7.43 (m, 6H), 10.62-10.94 (m, 1H)

Step 95-3: Synthesis of (4R)-1-(3-(1,3-benzodioxol-4-yl)-6-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 442 mg of the compound obtained in Step 95-2 (diastereoisomer mixture) and 347 mg, of 4-methoxy-2-(trifluoromethoxy)benzene sulfonyl chloride as starting materials, respectively 210 mg (Isomer A: colorless amorphous) and 177 mg (Isomer B: colorless solid) of two species of diastereoisomers of the title compound were obtained by a similar method to Example 2.
Isomer A: [α]$_D^{25}$=−195° (c=0.746, CHCl$_3$)
MS (ESI pos.) m/z: 720 ([M+Na]$^+$), (ESI neg.) m/z: 696 ([M−H]$^-$)
$^1$H-NMR (300 MHz, CDCl$_3$) δ (ppm); 1.83-1.97 (m, 1H), 1.99-2.14 (m, 6H), 2.26-2.40 (m, 1H), 2.49 (s, 3H), 2.58-2.66 (m, 1H), 2.69 (s, 3H), 3.54 (dd, J=10.3, 4.3 Hz, 1H), 3.91 (s, 3H), 4.36-4.51 (m, 1H), 4.61 (dd, J=8.6, 5.2 Hz, 1H), 5.63 (dd, J=32.3, 1.5 Hz, 2H), 6.67-6.75 (m, 2H), 6.83-7.00 (m, 3H), 7.07 (dd, J=8.2, 1.9 Hz, 1H), 7.34 (d, J=8.1 Hz, 1H), 8.00 (d, J=1.9 Hz, 1H), 8.39 (d, J=9.0 Hz, 1H)
Isomer B: [α]$_D^{25}$=+126° (c=0.364, CHCl$_3$)
MS (ESI pos.) m/z: 720 ([M+Na]$^+$), (ESI neg.) m/z: 696 ([M−H]$^-$)
$^1$H-NMR (300 MHz, CDCl$_3$) δ (ppm); 1.65-2.13 (m, 3H), 2.56 (s, 3H), 2.59-2.67 (m, 3H), 3.39-3.61 (m, 2H), 3.91-4.01 (m, 1H), 3.93 (s, 3H), 4.34 (brs, 1H), 5.41 (dd, J=38.4, 1.7 Hz, 2H), 6.69 (dd, J=7.8, 1.1 Hz, 1H), 6.80-7.15 (m, 5H), 7.57 (dd, J=8.1, 1.1 Hz, 1H), 8.02 (s, 1H), 8.32 (d, J=9.1 Hz, 1H)

Example 96

Synthesis of (2S)-1-(3-(4-methoxyphenyl)-1-{[4-methoxy-2-(trifluoromethoxy)phenyl]sulfonyl}-5-methyl-2-oxo-2,3-dihydro-1H-indol-3-yl)-N,N-dimethylpiperidine-2-carboxamide (levorotatory isomer)

Step 96-1: Synthesis of 3-hydroxy-3-(4-methoxyphenyl)-5-methyl-1,3-dihydro-2H-indol-2-one With 5.61 g of 4-bromoanisole and 3.23 g of 5-methyl isatin as starting materials, 4.38 g of the title compound (light brown solid) was obtained by a similar method to Step 21-1.
MS (ESI pos.) m/z: 252 ([M+Na]$^+$), (ESI neg.) m/z: 268 ([M−H]$^-$)
$^1$H-NMR (300 MHz, DMSO-d$_6$) δ (ppm); 2.22 (s, 3H), 3.71 (s, 3H), 6.46 (s, 1H), 6.77 (d, J=7.9 Hz, 1H), 6.83-6.93 (m, 3H), 7.01-7.06 (m, 1H), 7.14-7.21 (m, 2H), 10.23 (s, 1H)

Step 96-2: Synthesis of (2S)-1-[3-(4-methoxyphenyl)-5-methyl-2-oxo-2,3-dihydro-1H-indol-3-yl]-N,N-dimethylpiperidine-2-carboxamide (levorotatory isomer)

From 808 mg of the compound obtained in Step 96-1 and 508 mg of (2S)—N,N-dimethylpiperidine-2-carboxamide hydrochloride, respectively 620 mg (Isomer A: orange color amorphous) and 221 mg (Isomer B: orange color amorphous) of two species of diastereoisomers of the title compound were obtained by a similar method to Step 21-2.
Isomer A: [α]$_D^{25}$=−191° (c=0.304, CHCl$_3$)
MS (ESI pos.) m/z: 430 ([M+Na]$^+$), (ESI neg.) m/z: 406 ([M−H]$^-$)
$^1$H-NMR (300 MHz, DMSO-d$_6$) δ (ppm); 1.31-1.82 (m, 7H), 2.22-2.31 (m, 6H), 2.70 (s, 3H), 3.71 (s, 3H), 3.77-3.90 (m, 1H), 3.95-4.03 (m, 1H), 6.68-6.74 (m, 1H), 6.81-6.90 (m, 2H), 6.95-7.04 (m, 2H), 7.22-7.31 (m, 2H), 10.34 (s, 1H)
Isomer B: [α]$_D^{25}$=−301° (c=0.608, CHCl$_3$)
MS (ESI pos.) m/z: 430 ([M+Na]$^+$), (ESI neg.) m/z: 406 ([M−H]$^-$)
$^1$H-NMR (300 MHz, DMSO-d$_6$) δ (ppm); 1.30-2.32 (m, 13H), 2.61 (s, 3H), 3.72 (s, 3H), 3.80-4.10 (m, 2H), 6.67 (d, J=7.8 Hz, 1H), 6.78-7.04 (m, 4H), 7.31-7.40 (m, 2H), 10.24 (s, 1H)

Step 96-3: Synthesis of (2S)-1-(3-(4-methoxyphenyl)-1-{[4-methoxy-2-(trifluoromethoxy)phenyl]sulfonyl}-5-methyl-2-oxo-2,3-dihydro-1H-indol-3-yl)-N,N-dimethylpiperidine-2-carboxamide (levorotatory isomer)

With 100 mg of the compound obtained in Step 96-2 (Isomer B) and 80 mg of 4-methoxy-2-(trifluoromethoxy)benzene sulfonyl chloride as starting materials, 131 mg of the title compound (colorless amorphous) was obtained by a similar method to Example 2.
[α]$_D^{25}$=−273° (c=0.415, CHCl$_3$)
MS (ESI pos.) m/z: 662 ([M+H]$^+$), 684 ([M+Na]$^+$)

¹H-NMR (300 MHz, CDCl₃) δ (ppm); 1.21-1.93 (m, 6H), 2.20 (s, 3H), 2.26 (s, 3H), 2.53-2.67 (m, 1H), 2.84 (s, 3H), 3.73 (s, 3H), 3.84-4.04 (m, 5H), 6.67-6.76 (m, 2H), 6.82-6.98 (m, 3H), 7.00-7.12 (m, 3H), 7.83 (d, J=8.4 Hz, 1H), 8.42 (d, J=9.0 Hz, 1H)

Example 97

Synthesis of (4R)-1-(5-chloro-3-(5-chloro-2-methoxyphenyl)-1-{[4-methoxy-2-(trifluoromethoxy)phenyl]sulfonyl}-4-methyl-2-oxo-2,3-dihydro-1H-indol-3-yl)-4-hydroxy-N,N-dimethyl-L-prolinamide (levorotatory isomer and dextrorotatory isomer)

Step 97-1: Synthesis of 5-chloro-3-(5-chloro-2-methoxyphenyl)-3-hydroxy-4-methyl-1,3-dihydro-2H-indol-2-one With 4.75 g of 2-bromo-4-chloro-1-methoxy benzene and 1.96 g of 5-chloro-4-methyl-1H-indol-2,3-dione as starting materials, 2.43 g of the title compound (yellow solid) was obtained by a similar method to Step 21-1.

MS (ESI neg.) m/z: 336 ([M−H]⁻)

¹H-NMR (300 MHz, DMSO-d₆) δ (ppm); 1.87 (s, 3H), 3.41 (s, 3H), 6.70 (dd, J=8.2, 0.4 Hz, 1H), 6.78 (s, 1H), 6.93 (d, J=8.7 Hz, 1H), 7.25 (dd, J=8.2, 0.4 Hz, 1H), 7.35 (dd, J=8.7, 2.8 Hz, 1H), 7.83 (d, J=2.8 Hz, 1H), 10.48 (s, 1H)

Step 97-2: (4R)-1-[5-chloro-3-(5-chloro-2-methoxyphenyl)-4-methyl-2-oxo-2,3-dihydro-1H-indol-3-yl]-4-hydroxy-N,N-dimethyl-L-prolinamide Synthesis of From 1.20 g of the compound obtained in Step 97-1 and 691 mg of (4R)-4-hydroxy-N,N-dimethyl-L-prolinamide hydrochloride, 1.48 g of the title compound (diastereoisomer mixture: brown amorphous) was obtained by a similar method to Step 21-2.

MS (ESI pos.) m/z: 500 ([M+Na]⁺), (ESI neg.) m/z: 476 ([M−H]⁻)

¹H-NMR (300 MHz, DMSO-d₆) δ (ppm); 1.51-5.08 (m, 19H), 6.55-8.74 (m, 5H), 10.50-11.14 (m, 1H)

Step 97-3: Synthesis of (4R)-1-(5-chloro-3-(5-chloro-2-methoxyphenyl)-1-{[4-methoxy-2-(trifluoromethoxy)phenyl]sulfonyl}-4-methyl-2-oxo-2,3-dihydro-1H-indol-3-yl)-4-hydroxy-N,N-dimethyl-L-prolinamide (levorotatory isomer and dextrorotatory isomer)

With 300 mg of Step the compound obtained in Step 97-2 and 200 mg of 4-methoxy-2-(trifluoromethoxy)benzene sulfonyl chloride as starting materials, respectively 105 mg (Isomer A: orange color amorphous) and 98 mg (Isomer B: orange color amorphous) of two species of diastereoisomers of the title compound were obtained by a similar method to Example 2.

Isomer A: $[\alpha]_D^{25}$=−221° (c=0.139, CHCl₃)

MS (ESI pos.) m/z: 732 ([M+H]⁺), 754 ([M+Na]⁺), (ESI neg.) m/z: 730 ([M−H]⁻)

¹H-NMR (300 MHz, CDCl₃) δ (ppm); 1.46-3.99 (m, 21H), 4.57-4.70 (m, 1H), 6.63-6.71 (m, 1H), 6.84-6.97 (m, 2H), 7.18 (dd, J=8.7, 2.6 Hz, 1H), 7.33 (d, J=8.9 Hz, 1H), 7.80 (d, J=8.9 Hz, 2H), 8.21-8.40 (m, 1H)

Isomer B: $[\alpha]_D^{25}$=+124° (c=0.209, CHCl₃)

MS (ESI pos.) m/z: 732 ([M+H]⁺), 754 ([M+Na]⁺), (ESI neg.) m/z: 730 ([M−H]⁻)

¹H-NMR (300 MHz, CDCl₃) δ (ppm); 1.01-1.18 (m, 1H), 1.71-1.93 (m, 2H), 1.96 (s, 3H), 2.39 (s, 3H), 2.69 (s, 3H), 3.44 (s, 3H), 3.50-3.67 (m, 2H), 3.91 (s, 3H), 4.08 (dd, J=9.6, 7.0 Hz, 1H), 4.20-4.27 (m, 1H), 6.66 (d, J=8.7 Hz, 1H), 6.88-6.95 (m, 2H), 7.21 (dd, J=8.7, 2.6 Hz, 1H), 7.38 (d, J=8.9 Hz, 1H), 7.88 (d, J=8.9 Hz, 1H), 8.02 (d, J=2.6 Hz, 1H), 8.26 (d, J=9.0 Hz, 1H)

Example 98

Synthesis of (4R)-1-(4,5-dichloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 98-1: Synthesis of 4,5-dichloro-3-hydroxy-3-(2-methoxy-5-methylphenyl)-1,3-dihydro-2H-indol-2-one With 3.02 g of 2-bromo-1-methoxy-4-methyl benzene and 1.50 g of 4,5-dichloroisatin as starting materials, 1.23 g of the title compound (yellow solid) was obtained by a similar method to Step 21-1.

MS (ESI pos.) m/z: 360 ([M+Na]⁺), (ESI neg.) m/z: 336 ([M−H]⁻)

¹H-NMR (200 MHz, DMSO-d₆) δ (ppm); 2.31 (s, 3H), 3.38 (s, 3H), 6.64-6.87 (m, 3H), 7.00-7.13 (m, 1H), 7.42 (d, J=8.4 Hz, 1H), 7.68 (d, J=2.2 Hz, 1H), 10.61 (s, 1H)

Step 98-2: Synthesis of (4R)-1-[4,5-dichloro-3-(2-methoxy-5-methylphenyl)-2-oxo-2,3-dihydro-1H-indol-3-yl]-4-hydroxy-N,N-dimethyl-L-prolinamide (diastereoisomer mixture)

With 600 mg of the compound obtained in Step 98-1 and 345 mg of (4R)-4-hydroxy-N,N-dimethyl-L-prolinamide hydrochloride, 530 mg of the title compound (diastereoisomer mixture: brown amorphous) was obtained by a similar method to Step 21-2.

MS (ESI pos.) m/z: 478 ([M+H]⁺), 500 ([M+Na]⁺), (ESI neg.) m/z: 476 ([M−H]⁻)

¹H-NMR (300 MHz, DMSO-d₆) δ (ppm); 1.54-5.07 (m, 19H), 6.69-6.88 (m, 2H), 6.94-7.21 (m, 1H), 7.59-8.08 (m, 2H), 10.75 (s, 1H)

Step 98-3: Synthesis of (4R)-1-(4,5-dichloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 250 mg of the compound obtained in Step 98-2 and 170 mg of 4-methoxy-2-(trifluoromethoxy)benzene sulfonyl chloride as starting materials, respectively 93 mg (Isomer A: colorless amorphous) and 88 mg (Isomer B: colorless amorphous) of two species of diastereoisomers of the title compound were obtained by a similar method to Example 2.

Isomer A: $[\alpha]_D^{25}$=−230° (c=0.170, CHCl₃)

MS (ESI pos.) m/z: 732 ([M+H]⁺), 754 ([M+Na]⁺), (ESI neg.) m/z: 731 ([M−H]⁻)

¹H-NMR (300 MHz, CDCl₃) δ (ppm); 1.42-1.99 (m, 4H), 2.28 (s, 3H), 2.51 (s, 3H), 2.60-2.90 (m, 3H), 3.43 (s, 4H), 3.78-4.00 (m, 3H), 4.48-4.83 (m, 2H), 6.62 (d, J=8.4 Hz, 1H), 6.82-7.11 (m, 3H), 7.41 (d, J=8.9 Hz, 1H), 7.74-8.02 (m, 2H), 8.36 (d, J=8.7 Hz, 1H)

Isomer B: $[\alpha]_D^{25}$=+114° (c=0.199, CHCl₃)

MS (ESI pos.) m/z: 732 ([M+H]⁺), 754 ([M+Na]⁺), (ESI neg.) m/z: 730 ([M−H]⁻)

¹H-NMR (300 MHz, CDCl₃) δ (ppm); 1.22-1.51 (m, 1H), 1.77-1.94 (m, 2H), 2.34 (s, 3H), 2.53 (s, 3H), 2.71 (s, 3H), 3.40-3.57 (m, 4H), 3.63-3.72 (m, 1H), 3.91 (s, 3H), 4.05 (t, J=8.0 Hz, 1H), 4.24-4.32 (m, 1H), 6.63 (d, J=8.4 Hz, 1H), 6.88-6.96 (m, 2H), 7.01-7.08 (m, 1H), 7.47 (d, J=8.9 Hz, 1H), 7.80-7.87 (m, 1H), 7.98 (d, J=8.9 Hz, 1H), 8.27 (d, J=9.3 Hz, 1H)

Example 99

Synthesis of (4R)-1-[5-chloro-1-{[4-methoxy-2-(trifluoromethoxy)phenyl]sulfonyl}-3-(2-methylphenyl)-2-oxo-2,3-dihydro-1H-indol-3-yl]-4-hydroxy-N,N-dimethyl-L-prolinamide (levorotatory isomer)

Step 99-1: Synthesis of (4R)-1-[5-chloro-3-(2-methylphenyl)-2-oxo-2,3-dihydro-1H-indol-3-yl]-4-hydroxy-N,N-dimethyl-L-prolinamide (levorotatory isomer and dextrorotatory isomer)

From 820 mg of 5-chloro-3-hydroxy-3-(2-methylphenyl)-1,3-dihydro-2H-indol-2-one, which is the compound described in Preparation 14 of the brochure Publication No. WO09518105, and 591 mg of (4R)-4-hydroxy-N,N-dimethyl-L-prolinamide hydrochloride, respectively 535 mg (Isomer A: orange color amorphous) and 223 mg (Isomer B: orange color amorphous) of two species of diastereoisomers of the title compound were obtained by a similar method to Step 21-2.

Isomer A: $[\alpha]_D^{25}$=+241° (c=0.930, CHCl₃)
MS (ESI pos.) m/z: 414 ([M+H]⁺), 436 ([M+Na]⁺), (ESI neg.) m/z: 412 ([M−H]⁻)
¹H-NMR (300 MHz, DMSO-d₆) δ (ppm); 1.55-2.02 (m, 4H), 2.34-2.65 (m, 7H), 2.98-3.25 (m, 2H), 3.59-3.76 (m, 1H), 4.16-4.33 (m, 1H), 4.67 (d, J=4.2 Hz, 1H), 6.34-6.68 (m, 1H), 6.89 (d, J=8.4 Hz, 1H), 7.02-7.46 (m, 5H), 10.88 (s, 1H)

Isomer B: $[\alpha]_D^{25}$=−248° (c=0.960, CHCl₃)
MS (ESI pos.) m/z: 414 ([M+H]⁺), 436 ([M+Na]⁺), (ESI neg.) m/z: 412 ([M−H]⁻)
¹H-NMR (300 MHz, DMSO-d₆) δ (ppm); 1.56-2.72 (m, 13H), 4.25-5.02 (m, 3H), 6.70-7.36 (m, 6H), 7.80-8.07 (m, 1H), 10.76 (s, 1H)

Step 99-2: Synthesis of (4R)-1-[5-chloro-1-{[4-methoxy-2-(trifluoromethoxy)phenyl]sulfonyl}-3-(2-methylphenyl)-2-oxo-2,3-dihydro-1H-indol-3-yl]-4-hydroxy-N,N-dimethyl-L-prolinamide (levorotatory isomer)

With 150 mg of the compound obtained in Step 99-1 (Isomer B) and 120 mg of 4-methoxy-2-(trifluoromethoxy)benzene sulfonyl chloride as starting materials, 88 mg of the title compound (yellow amorphous) was obtained by a similar method to Example 2.

$[\alpha]_D^{25}$=−212° (c=0.245, CHCl₃)
MS (ESI pos.) m/z: 668 ([M+H]⁺), 690 ([M+Na]⁺), (ESI neg.) m/z: 666 ([M−H]⁻)
¹H-NMR (300 MHz, CDCl₃) δ (ppm); 1.26-3.71 (m, 14H), 3.91 (s, 3H), 4.47-4.82 (m, 2H), 6.75-7.44 (m, 7H), 7.85-8.12 (m, 2H), 8.36 (d, J=9.0 Hz, 1H)

Example 100

Synthesis of (4R)-1-(5-chloro-3-(2,4-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 150 mg of (4R)-1-[5-chloro-3-(2,4-dimethoxyphenyl)-2-oxo-2,3-dihydro-1H-indol-3-yl]-4-hydroxy-N,N-dimethyl-L-prolinamide (levorotatory compound), which is the compound described in Preparation 3.39 of brochure Publication No. WO01/055130 and 110 mg of 4-methoxy-2-(trifluoromethoxy)benzene sulfonyl chloride as starting materials, 91 mg of the title compound (yellow amorphous) was obtained by a similar method to Example 2.

$[\alpha]_D^{25}$=−184° (c=0.237, CHCl₃)
MS (ESI pos.) m/z: 714 ([M+H]⁺), 736 ([M+Na]⁺), (ESI neg.) m/z: 712 ([M−H]⁻)
¹H-NMR (300 MHz, CDCl₃) δ (ppm); 1.05-2.56 (m, 7H), 2.77 (s, 3H), 3.11-3.32 (m, 1H), 3.58 (s, 3H), 3.73-3.83 (m, 3H), 3.86-3.96 (m, 3H), 4.47-4.94 (m, 2H), 6.23-6.57 (m, 2H), 6.77-7.34 (m, 4H), 7.62-7.99 (m, 2H), 8.26-8.41 (m, 1H)

Example 101

Synthesis of (4R)-1-(5-chloro-3-(2-ethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 101-1: Synthesis of (4R)-1-[5-chloro-3-(2-ethoxyphenyl)-2-oxo-2,3-dihydro-1H-indol-3-yl]-4-hydroxy-N,N-dimethyl-L-prolinamide (levorotatory isomer and dextrorotatory isomer)

From 1.00 g of 5-chloro-3-(2-ethoxyphenyl)-3-hydroxy-1,3-dihydro-2H-indol-2-one, which is the compound described in Preparation 1.2 of the brochure Publication No. WO2003/008407, and 640 mg of (4R)-4-hydroxy-N,N-dimethyl-L-prolinamide hydrochloride, respectively 298 mg (Isomer A: orange color amorphous) and 706 mg (Isomer B: orange color amorphous) of two species of diastereoisomers of the title compound were obtained by a similar method to Step 21-2.

Isomer A: $[\alpha]_D^{25}$=+21.0° (c=0.143, CHCl₃)
MS (ESI pos.) m/z: 444 ([M+H]⁺), 466 ([M+Na]⁺), (ESI neg.) m/z: 442 ([M−H]⁻)
¹H-NMR (300 MHz, DMSO-d₆) δ (ppm); 1.05 (t, J=7.0 Hz, 3H), 1.58-1.90 (m, 2H), 2.44 (s, 3H), 2.57 (s, 3H), 3.07-3.27 (m, 2H), 3.57-3.86 (m, 3H), 4.15-4.33 (m, 1H), 4.51-4.67 (m, 1H), 6.45 (d, J=2.3 Hz, 1H), 6.74-6.93 (m, 2H), 6.98-7.38 (m, 3H), 8.04 (dd, J=7.8, 1.9 Hz, 1H), 10.50 (s, 1H)

Isomer B: $[\alpha]_D^{25}$=−193° (c=0.842, CHCl₃)
MS (ESI pos.) m/z: 444 ([M+H]⁺), 466 ([M+Na]⁺), (ESI neg.) m/z: 442 ([M−H]⁻)
¹H-NMR (300 MHz, DMSO-d₆) δ (ppm); 0.93-1.20 (m, 3H), 1.54-3.24 (m, 10H), 3.58-3.92 (m, 2H), 4.28-4.50 (m, 1H), 4.63-4.90 (m, 2H), 6.62-7.02 (m, 4H), 7.07-7.35 (m, 2H), 7.83 (dd, J=4.6, 3.8 Hz, 1H), 10.44 (s, 1H)

Step 101-2: Synthesis of (4R)-1-(5-chloro-3-(2-ethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 150 mg of the compound obtained in Step 101-1 (Isomer B) and 110 mg of 4-methoxy-2-(trifluoromethoxy)

benzene sulfonyl chloride as starting materials, 110 mg of the title compound (colorless amorphous) was obtained by a similar method to Example 2.

$[\alpha]_D^{25}$=−168° (c=0.188, CHCl$_3$)

MS (ESI pos.) m/z: 698 ([M+H]$^+$), 720 ([M+Na]$^+$), (ESI neg.) m/z: 696 ([M−H]$^−$)

$^1$H-NMR (300 MHz, CDCl$_3$) δ (ppm); 1.08-2.26 (m, 7H), 2.36 (s, 3H), 2.75 (s, 3H), 3.04-3.20 (m, 1H), 3.77-4.11 (m, 5H), 4.56-4.86 (m, 2H), 6.71-7.12 (m, 6H), 7.15-7.32 (m, 2H), 7.69-7.83 (m, 1H), 7.89 (d, J=8.5 Hz, 1H)

Example 102

Synthesis of (4R)-1-(5-chloro-3-(2,5-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 102-1: Synthesis of (4R)-1-[5-chloro-3-(2,5-dimethoxyphenyl)-2-oxo-2,3-dihydro-1H-indol-3-yl]-4-hydroxy-N,N-dimethyl-L-prolinamide (levorotatory isomer and dextrorotatory isomer)

From 1.00 g of 5-chloro-3-(2,5-dimethoxyphenyl)-3-hydroxy-1,3-dihydro-2H-indol-2-one, which is the compound described in Preparation 1.17 of the brochure Publication No. WO03/008407, and 609 mg of (4R)-4-hydroxy-N,N-dimethyl-L-prolinamide hydrochloride, respectively 280 mg (Isomer A: orange color amorphous) and 541 mg (Isomer B: orange color amorphous) of two species of diastereoisomers of the title compound were obtained by a similar method to Step 21-2.

Isomer A: $[\alpha]_D^{25}$=+105° (c=0.211, CHCl$_3$)

MS (ESI pos.) m/z: 482 ([M+Na]$^+$), (ESI neg.) m/z: 458 ([M−H]$^−$)

$^1$H-NMR (300 MHz, DMSO-d$_6$) δ (ppm); 1.56-2.06 (m, 2H), 2.35-2.70 (m, 6H), 3.02-3.85 (m, 9H), 4.15-4.31 (m, 1H), 4.56-4.64 (m, 1H), 6.44-6.54 (m, 1H), 6.71-6.96 (m, 3H), 7.10-7.25 (m, 1H), 7.64-7.79 (m, 1H), 10.54 (s, 1H)

Isomer B: $[\alpha]_D^{25}$=−263° (c=0.562, CHCl$_3$)

MS (ESI pos.) m/z: 482 ([M+Na]$^+$), (ESI neg.) m/z: 458 ([M−H]$^−$)

$^1$H-NMR (300 MHz, DMSO-d$_6$) δ (ppm); 1.56-4.96 (m, 19H), 6.72-6.91 (m, 4H), 7.17 (dd, J=8.0, 2.3 Hz, 1H), 7.36-7.64 (m, 1H), 10.50 (s, 1H)

Step 102-2: Synthesis of (4R)-1-(5-chloro-3-(2,5-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 150 mg of the compound obtained in Step 102-1 (Isomer B) and 110 mg of 4-methoxy-2-(trifluoromethoxy)benzene sulfonyl chloride as starting materials, 61 mg of the title compound (colorless amorphous) was obtained by a similar method to Example 2.

$[\alpha]_D^{25}$=−248° (c=0.065, CHCl$_3$)

MS (ESI pos.) m/z: 714 ([M+H]$^+$), 736 ([M+Na]$^+$), (ESI neg.) m/z: 712 ([M−H]$^−$)

$^1$H-NMR (300 MHz, CDCl$_3$) δ (ppm); 1.03-4.21 (m, 20H), 4.48-4.94 (m, 2H), 6.58-7.61 (m, 7H), 7.90 (d, J=8.7 Hz, 1H), 8.35 (d, J=8.7 Hz, 1H)

Example 103

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 103-1: Synthesis of 5-chloro-3-hydroxy-3-(2-methoxy-5-methylphenyl)-1,3-dihydro-2H-indol-2-one With 4.36 g of 3-bromo-4-methoxy toluene and 2.81 g of 5-chloroisatin as starting materials, 4.27 g of the title compound (light brown solid) was obtained by a similar method to Step 21-1.

MS (ESI pos.) m/z: 326 ([M+Na]$^+$), (ESI neg.) m/z: 302 ([M−H]$^−$)

$^1$H-NMR (300 MHz, DMSO-d$_6$) δ (ppm); 2.32 (s, 3H), 3.38 (s, 3H), 6.57 (s, 1H), 6.72-6.87 (m, 3H), 7.04-7.12 (m, 1H), 7.20 (dd, J=8.2, 2.3 Hz, 1H), 7.62 (d, J=2.3 Hz, 1H), 10.40 (s, 1H)

Step 103-2: Synthesis of (4R)-1-[5-chloro-3-(2-methoxy-5-methylphenyl)-2-oxo-2,3-dihydro-1H-indol-3-yl]-4-hydroxy-N,N-dimethyl-L-prolinamide (levorotatory isomer and dextrorotatory isomer)

From 1.00 g of the compound obtained in Step 103-1 and 641 mg of (4R)-4-hydroxy-N,N-dimethyl-L-prolinamide hydrochloride, respectively 211 mg (Isomer A: orange color amorphous) and 387 mg (Isomer B: orange color amorphous) of two species of diastereoisomers of the title compound were obtained by a similar method to Step 21-2.

Isomer A: $[\alpha]_D^{25}$=+175° (c=0.136, CHCl$_3$)

MS (ESI pos.) m/z: 444 ([M+H]$^+$), 466 ([M+Na]$^+$), (ESI neg.) m/z: 442 ([M−H]$^−$)

$^1$H-NMR (300 MHz, DMSO-d$_6$) δ (ppm); 1.54-1.91 (m, 2H), 2.31-2.61 (m, 9H), 3.09-3.28 (m, 2H), 3.44 (s, 3H), 3.66 (dd, J=8.7, 6.1 Hz, 1H), 4.16-4.32 (m, 1H), 4.51-4.59 (m, 1H), 6.47-6.53 (m, 1H), 6.80 (dd, J=8.2, 2.5 Hz, 2H), 7.07 (dd, J=8.1, 2.3 Hz, 1H), 7.16 (dd, J=8.2, 2.3 Hz, 1H), 7.83 (d, J=2.2 Hz, 1H), 10.54 (s, 1H)

Isomer B: $[\alpha]_D^{25}$=−214° (c=0.266, CHCl$_3$)

MS (ESI pos.) m/z: 444 ([M+H]$^+$), 466 ([M+Na]$^+$), (ESI neg.) m/z: 442 ([M−H]$^−$)

$^1$H-NMR (300 MHz, DMSO-d$_6$) δ (ppm); 1.51-1.95 (m, 2H), 2.12-3.15 (m, 10H), 3.47 (s, 3H), 4.30-4.52 (m, 2H), 4.70-4.95 (m, 2H), 6.70-6.88 (m, 3H), 6.97-7.26 (m, 2H), 7.65 (d, J=1.6 Hz, 1H), 10.51 (s, 1H)

Step 103-3: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 100 mg of the compound obtained in Step 103-2 (Isomer B) and 80 mg of 4-methoxy-2-(trifluoromethoxy)benzene sulfonyl chloride as starting materials, 53 mg of the title compound (colorless amorphous) was obtained by a similar method to Example 2.

$[\alpha]_D^{25}$=−186° (c=0.447, CHCl$_3$)

MS (ESI pos.) m/z: 698 ([M+H]$^+$), (ESI neg.) m/z: 696 ([M−H]$^−$)

¹H-NMR (300 MHz, CDCl₃) δ (ppm); 1.04-2.04 (m, 4H), 2.15-2.57 (m, 6H), 2.68-3.75 (m, 7H), 3.90 (s, 3H), 4.52-4.91 (m, 2H), 6.67 (d, J=8.2 Hz, 1H), 6.83-7.40 (m, 5H), 7.56-7.74 (m, 1H), 7.89 (d, J=8.9 Hz, 1H), 8.34 (d, J=8.9 Hz, 1H)

Example 104

Synthesis of (4R)-1-[5-chloro-1-{[4-methoxy-2-(trifluoromethoxy)phenyl]sulfonyl}-2-oxo-3-(2-vinylphenyl)-2,3-dihydro-1H-indol-3-yl]-4-hydroxy-N,N-dimethyl-L-prolinamide (levorotatory isomer)

Step 104-1: Synthesis of 5-chloro-3-hydroxy-3-(2-vinylphenyl)-1,3-dihydro-2H-indol-2-one With 10.0 g of 1-bromo-2-vinyl benzene and 4.72 g of 5-chloroisatin as starting materials, 5.71 g of the title compound (light brown solid) was obtained by a similar method to Step 21-1.
MS (ESI pos.) m/z: 308 ([M+Na]⁺)
¹H-NMR (300 MHz, DMSO-d₆) δ (ppm); 5.04 (dd, J=10.9, 1.4 Hz, 1H), 5.45 (dd, J=17.2, 1.5 Hz, 1H), 6.47-6.60 (m, 1H), 6.84-6.94 (m, 3H), 7.27-7.46 (m, 4H), 7.74 (dd, J=7.2, 1.6 Hz, 1H), 10.67 (brs, 1H)

Step 104-2: Synthesis of (4R)-1-[5-chloro-2-oxo-3-(2-vinylphenyl)-2,3-dihydro-1H-indol-3-yl]-4-hydroxy-N,N-dimethyl-L-prolinamide (levorotatory isomer and dextrorotatory isomer)

From 1.50 g of the compound obtained in Step 104-1 and 1.53 g of (4R)-4-hydroxy-N,N-dimethyl-L-prolinamide hydrochloride, respectively 555 mg (Isomer A: brown solid) and 394 mg (Isomer B: brown solid) of two species of diastereoisomers of the title compound were obtained by a similar method to Step 21-2.
Isomer A: $[\alpha]_D^{25}$=+331° (c=0.070, CHCl₃)
MS (ESI pos.) m/z: 426 ([M+H]⁺)
¹H-NMR (300 MHz, DMSO-d₆) δ (ppm); 1.70 (s, 1H), 1.78-1.91 (m, 1H), 2.36-2.61 (m, 6H), 2.89-3.05 (m, 1H), 3.11-3.40 (m, 1H), 3.65 (dd, J=9.1, 5.1 Hz, 1H), 4.15-4.28 (m, 1H), 4.69 (d, J=5.0 Hz, 1H), 5.04-5.95 (m, 2H), 6.81-9.25 (m, 8H), 10.95 (brs, 1H)
Isomer B: $[\alpha]_D^{25}$=−137° (c=0.561, CHCl₃)
MS (ESI pos.) m/z: 426 ([M+H]⁺)
¹H-NMR (300 MHz, DMSO-d₆) δ (ppm); 1.64-1.75 (m, 1H), 1.77-1.93 (m, 1H), 2.35 (s, 3H), 2.54 (s, 3H), 2.71-2.87 (m, 1H), 3.08-3.21 (m, 1H), 4.38-4.50 (m, 1H), 4.53-4.64 (m, 1H), 4.85 (d, J=4.4 Hz, 1H), 5.15 (dd, J=11.0, 1.6 Hz, 1H), 5.46 (d, J=0.6 Hz, 1H), 6.81-6.86 (m, 1H), 7.13-7.64 (m, 7H), 10.81 (brs, 1H)

Step 104-3: Synthesis of (4R)-1-[5-chloro-1-{[4-methoxy-2-(trifluoromethoxy)phenyl]sulfonyl}-2-oxo-3-(2-vinylphenyl)-2,3-dihydro-1H-indol-3-yl]-4-hydroxy-N,N-dimethyl-L-prolinamide (levorotatory isomer)

With 200 mg of the compound obtained in Step 104-2 (Isomer B) as starting material, 47 mg of the title compound (colorless amorphous) was obtained by a similar procedure to Example 2.
$[\alpha]_D^{25}$=−205° (c=0.101, CHCl₃)
MS (ESI pos.) m/z: 680 ([M+H]⁺)
¹H-NMR (300 MHz, CDCl₃) δ (ppm); 1.73 (d, J=2.5 Hz, 1H), 1.87-1.98 (m, 1H), 2.28-2.44 (m, 1H), 2.35 (s, 3H), 2.69 (s, 3H), 3.34-3.43 (m, 1H), 3.91 (s, 3H), 4.58-4.72 (m, 2H), 4.96 (d, J=12.0 Hz, 1H), 5.20 (dd, J=17.3, 1.6 Hz, 1H), 6.69-6.81 (m, 1H), 6.88-6.91 (m, 1H), 6.95 (dd, J=9.0, 2.3 Hz, 1H), 7.16-7.30 (m, 5H), 7.65-7.72 (m, 1H), 7.91 (d, J=8.7 Hz, 1H), 8.36 (d, J=9.0 Hz, 1H)

Example 105

Synthesis of (4R)-1-[5-bromo-1-{[4-methoxy-2-(trifluoromethoxy)phenyl]sulfonyl}-3-(2-methylphenyl)-2-oxo-2,3-dihydro-1H-indol-3-yl]-4-hydroxy-N,N-dimethyl-L-prolinamide (levorotatory isomer)

Step 105-1: Synthesis of 5-bromo-3-hydroxy-3-(2-methylphenyl)-1,3-dihydro-2H-indol-2-one With 9.58 g of 1-bromo-2-methyl benzene and 4.52 g of 5-bromoisatin as starting materials, 3.19 g of the title compound (brown solid) was obtained by a similar method to Step 21-1.
MS (ESI pos.) m/z: 340 ([M+Na]⁺)
¹H-NMR (300 MHz, DMSO-d₆) δ (ppm); 1.81 (s, 3H), 6.80 (s, 1H), 6.82-6.92 (m, 2H), 7.09 (d, J=0.6 Hz, 1H), 7.18-7.33 (m, 2H), 7.44 (dd, J=8.2, 2.0 Hz, 1H), 7.85 (dd, J=7.8, 1.4 Hz, 1H), 10.72 (brs, 1H)

Step 105-2: Synthesis of (4R)-1-[5-bromo-3-(2-methylphenyl)-2-oxo-2,3-dihydro-1H-indol-3-yl]-4-hydroxy-N,N-dimethyl-L-prolinamide (levorotatory isomer and dextrorotatory isomer)

From 3.00 g of the compound obtained in Step 105-1 and 2.02 g of (4R)-4-hydroxy-N,N-dimethyl-L-prolinamide hydrochloride, respectively 1.62 g (Isomer A: yellow amorphous) and 777 mg (Isomer B: brown amorphous) of two species of diastereoisomers of the title compound were obtained by a similar method to Step 21-2.
Isomer A; $[\alpha]_D^{25}$=+224° (c=0.233, CHCl₃)
MS (ESI pos.) m/z: 480 ([M+Na]⁺)
¹H-NMR (300 MHz, CDCl₃) δ (ppm); 1.60 (s, 3H), 1.77-2.19 (m, 2H), 2.72 (s, 3H), 2.87 (s, 3H), 3.15-3.37 (m, 1H), 3.48-3.58 (m, 1H), 3.62-3.72 (m, 1H), 3.96-4.08 (m, 1H), 4.32-4.41 (m, 1H), 6.76-7.44 (m, 6H), 8.17-8.28 (m, 1H), 9.26 (brs, 1H)
Isomer B; $[\alpha]_D^{25}$=−214° (c=0.354, CHCl₃)
MS (ESI pos.) m/z: 480 ([M+Na]⁺)
¹H-NMR (300 MHz, CDCl₃) δ (ppm); 1.46-4.96 (m, 16H), 6.49-8.69 (m, 8H)

Step 105-3: Synthesis of (4R)-1-[5-bromo-1-{[4-methoxy-2-(trifluoromethoxy)phenyl]sulfonyl}-3-(2-methylphenyl)-2-oxo-2,3-dihydro-1H-indol-3-yl]-4-hydroxy-N,N-dimethyl-L-prolinamide (levorotatory isomer)

With 621 mg of the compound obtained in Step 105-2 (Isomer B) as starting material, 478 mg of the title compound (pale brown amorphous) was obtained by a similar procedure to Example 2.
$[\alpha]_D^{25}$=−407° (c=0.029, CHCl₃)
MS (ESI neg.) m/z: 710 ([M−H]⁻)
¹H-NMR (300 MHz, CDCl₃) δ (ppm); 1.34-2.09 (m, 6H), 2.35 (brs, 3H), 2.72 (s, 3H), 3.05-3.64 (m, 1H), 3.91 (s, 3H), 4.45-4.82 (m, 2H), 6.81-6.99 (m, 3H), 7.07-7.35 (m, 3H), 7.44 (dd, J=8.7, 2.2 Hz, 1H), 7.83-8.13 (m, 1H), 7.89 (d, J=8.7 Hz, 1H), 8.35 (d, J=8.9 Hz, 1H)

Example 106

Synthesis of (4R)-4-hydroxy-1-[5-iodo-1-{[4-methoxy-2-(trifluoromethoxy)phenyl]sulfonyl}-3-(2-methylphe nyl)-2-oxo-2,3-dihydro-1H-indol-3-yl]-N,N-dimethyl-L-prolinamide (levorotatory isomer)

Step 106-1: Synthesis of 3-hydroxy-5-iodo-3-(2-methylphenyl)-1,3-dihydro-2H-indol-2-one With 5.46 g of 5-iodoisatin and 1-bromo-2-methyl benzene as starting materials, 5.87 g of the title compound (brown solid) was obtained by a similar method to Step 21-1.

MS (ESI pos.) m/z: 388 ([M+H]$^+$)

$^1$H-NMR (300 MHz, DMSO-d$_6$) δ (ppm); 1.80 (s, 3H), 6.74-6.80 (m, 2H), 7.03-7.11 (m, 2H), 7.18-7.33 (m, 2H), 7.60 (dd, J=8.2, 1.8 Hz, 1H), 7.85 (dd, J=7.7, 1.3 Hz, 1H), 10.70 (brs, 1H)

Step 106-2: Synthesis of (4R)-4-hydroxy-1-[5-iodo-3-(2-methylphenyl)-2-oxo-2,3-dihydro-1H-indol-3-yl]-N,N-dimethyl-L-prolinamide From 3.00 g of the compound obtained in Step 106-1 and 1.92 g of (4R)-4-hydroxy-N,N-dimethyl-L-prolinamide hydrochloride, respectively 2.26 g (Isomer A: yellow amorphous) and 730 mg (Isomer B: brownish red amorphous) of two species of diastereoisomers of the title compound were obtained by a similar method to Step 21-2.

Isomer A; MS (ESI pos.) m/z: 528 ([M+Na$^+$]

$^1$H-NMR (300 MHz, CDCl$_3$) δ (ppm); 1.78-2.23 (m, 2H) 2.00 (s, 3H) 2.74 (s, 3H) 2.95 (s, 3H) 3.36-3.79 (m, 3H) 3.94-4.17 (m, 1H) 4.37 (brs, 1H) 6.71 (d, J=8.2 Hz, 1H) 6.95-7.43 (m, 4H) 7.44-7.59 (m, 1H) 8.05-8.24 (m, 1H) 9.83 (brs, 3H)

Isomer B; MS (ESI pos.) m/z: 528 ([M+Na$^+$]

$^1$H-NMR (300 MHz, CDCl$_3$) δ (ppm); 1.56-4.28 (m, 13H) 4.56-5.05 (m, 2H) 6.00-6.78 (m, 1H) 6.95-8.02 (m, 6H) 10.00-10.89 (m, 1H)

Step 106-3: Synthesis of (4R)-4-hydroxy-1-[5-iodo-1-{[4-methoxy-2-(trifluoromethoxy)phenyl]sulfonyl}-3-(2-methylphe nyl)-2-oxo-2,3-dihydro-1H-indol-3-yl]-N,N-dimethyl-L-prolinamide (levorotatory isomer)

With 621 mg of the compound obtained in Step 106-2 (Isomer B) as starting material, 478 mg of the title compound (pale brown amorphous) was obtained by a similar procedure to Example 2.

$[α]_D^{29}$=−216° (c=0.127, CHCl$_3$)

MS (ESI pos.) m/z: 760 ([M+H]$^+$)

$^1$H-NMR (300 MHz, CDCl$_3$) δ (ppm); 1.51 (s, 3H), 1.59-1.67 (m, 1H), 1.70-1.82 (m, 1H), 1.97-2.08 (m, 1H), 2.50 (s, 3H), 2.80-2.83 (m, 3H), 3.26-3.35 (m, 1H), 3.39-3.49 (m, 1H), 3.92 (s, 3H), 3.95-4.04 (m, 1H), 4.30 (brs, 1H), 6.84-6.89 (m, 1H), 6.94 (dd, J=9.0, 2.3 Hz, 2H), 7.12-7.22 (m, 2H), 7.30-7.41 (m, 1H), 7.63-7.71 (m, 1H), 7.75-7.83 (m, 1H), 8.30 (d, J=9.0 Hz, 1H), 8.39-8.49 (m, 1H)

Example 107

Synthesis of (4R)-1-(3-(1,3-benzodioxol-4-yl)-1-{[4-methoxy-2-(trifluoromethoxy)phenyl]sulfonyl}-5-methy l-2-oxo-2,3-dihydro-1H-indol-3-yl)-4-hydroxy-N,N-dimethyl-L-prolinamide (levorotatory isomer and dextrorotatory isomer)

Step 107-1: Synthesis of 3-(1,3-benzodioxol-4-yl)-3-hydroxy-5-methyl-1,3-dihydro-2H-indol-2-one With 7.80 g of 4-bromo-1,3-benzodioxol and 1.61 g of 5-methyl isatin as starting materials, 1.95 g of the title compound (brown solid) was obtained by a similar method to Step 21-1.

MS (ESI pos.) m/z: 306 ([M+Na]$^+$)

$^1$H-NMR (300 MHz, DMSO-d$_6$) δ (ppm); 2.17 (s, 3H), 5.78 (d, J=2.2 Hz, 2H), 6.58 (s, 1H), 6.72 (d, J=7.8 Hz, 1H), 6.78-6.94 (m, 3H), 6.99 (dd, J=7.8, 0.8 Hz, 1H), 7.25 (dd, J=7.8, 1.6 Hz, 1H), 10.30 (br. s., 1H)

Step 107-2: Synthesis of (4R)-1-[3-(1,3-benzodioxol-4-yl)-5-methyl-2-oxo-2,3-dihydro-1H-indol-3-yl]-4-hydroxy-N,N-dimethyl-L-prolinamide From 800 mg of the compound obtained in Step 107-1 and 659 mg of (4R)-4-hydroxy-N,N-dimethyl-L-prolinamide hydrochloride, 2.26 g of a diastereoisomer mixture of the title compound (brown amorphous) was obtained by a similar method to Step 21-2.

MS (ESI pos.) m/z: 424 ([M+H]$^+$)

$^1$H-NMR (300 MHz, CDCl$_3$) δ (ppm) 1.58-5.03 (m, 15H), 5.74-6.05 (m, 2H), 6.67-7.56 (m, 6H), 8.22-8.88 (m, 1H)

Step 107-3: Synthesis of (4R)-1-(3-(1,3-benzodioxol-4-yl)-1-{[4-methoxy-2-(trifluoromethoxy) phenyl]sulfonyl}-5-methy l-2-oxo-2,3-dihydro-1H-indol-3-yl)-4-hydroxy-N,N-dimethyl-L-prolinamide (levorotatory isomer and dextrorotatory isomer)

With 384 mg of the compound obtained in Step 107-2 (diastereoisomer mixture) and 317 mg of 4-methoxy-2-(trifluoromethoxy)benzene sulfonyl chloride as starting materials, respectively 59 mg (Isomer A: colorless solid) and 77 mg (Isomer B: colorless solid) of the diastereoisomers of the title compound were obtained by a similar method to Example 2.

Isomer A; $[α]_D^{25}$=−191° (c=0.092, CHCl$_3$)

MS (ESI pos.) m/z: 678 ([M+H]$^+$)

$^1$H-NMR (300 MHz, CDCl$_3$) δ (ppm); 1.85-2.79 (m, 10H), 3.55 (dd, J=10.2, 4.4 Hz, 1H), 3.87-3.95 (m, 3H), 4.42-4.72 (m, 2H), 5.54-5.96 (m, 2H), 6.64-7.33 (m, 7H), 7.78-8.01 (m, 1H), 8.25-8.44 (m, 1H)

Isomer B; $[α]_D^{25}$=+67° (c=0.112, CHCl$_3$)

MS (ESI pos.) m/z: 678 ([M+H]$^+$)

$^1$H-NMR (300 MHz, CDCl$_3$) δ (ppm); 1.76-1.88 (m, 1H), 1.95-2.07 (m, 1H), 2.16-2.29 (m, 4H), 2.23 (s, 3H), 2.46 (s, 3H), 2.63 (s, 3H), 3.41-3.60 (m, 2H), 3.85-4.02 (m, 1H), 3.91-3.94 (m, 3H), 4.33 (br. s., 1H), 5.43 (dd, J=34.2, 1.6 Hz, 2H), 6.64-7.29 (m, 6H), 7.61 (dd, J=8.2, 1.2 Hz, 1H), 7.84 (d, J=8.4 Hz, 1H), 8.33 (d, J=9.0 Hz, 1H)

Example 108

Synthesis of (4R)-1-(3-(1,3-benzodioxol-4-yl)-5-cyano-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 108-1: Synthesis of 3-(1,3-benzodioxol-4-yl)-3-hydroxy-2-oxo indoline-5-carbonitrile With 1.70 g of 2,3-dioxo indoline-5-carbonitrile and 1,3-benzodioxol-4-yl bromide (13 ml) as starting materials, 1.37 g of the title compound (brown solid) was obtained by a similar method to Step 21-1.

MS (ESI neg.) m/z: 293 ([M−H]$^-$)

$^1$H-NMR (300 MHz, DMSO-d$_6$) δ (ppm); 5.78 (dd, J=14.6, 0.9 Hz, 2H), 6.55-8.16 (m, 6H), 10.96 (brs, 1H)

Step 108-2: Synthesis of (4R)-1-[3-(1,3-benzodioxol-4-yl)-5-cyano-2-oxo-2,3-dihydro-1H-indol-3-yl]-4-hydroxy-N,N-dimethyl-L-prolinamide From 800 mg of the compound obtained in Step 108-1 and 635 mg of (4R)-4-hydroxy-N,N-dimethyl-L-prolinamide hydrochloride, 285 mg of a diastereoisomer mixture of the title compound (colorless amorphous) was obtained by a similar method to Step 21-2.

MS (ESI pos.) m/z: 435 ([M+H]$^+$)

$^1$H-NMR (300 MHz, CDCl$_3$) δ (ppm); 1.81-2.09 (m, 1H), 2.14-2.41 (m, 1H), 2.53-3.25 (m, 7H), 3.45-3.77 (m, 2H), 3.78-4.89 (m, 2H), 5.81-6.13 (m, 2H), 6.73-7.20 (m, 4H), 7.41-7.95 (m, 2H), 8.93-10.60 (m, 1H)

Step 108-3: Synthesis of (4R)-1-(3-(1,3-benzodioxol-4-yl)-5-cyano-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 254 mg of the compound obtained in Step 108-2 (diastereoisomer mixture) and 204 mg of 4-methoxy-2-(trifluoromethoxy)benzene sulfonyl chloride as starting materials, respectively 99 mg (Isomer A: colorless solid) and 120 mg (Isomer B: colorless solid) of the diastereoisomers of the title compound were obtained by a similar method to Example 2.

Isomer A; $[\alpha]_D^{25}$=−188° (c=0.134, CHCl$_3$)

MS (ESI pos.) m/z: 689 ([M+H]$^+$)

$^1$H-NMR (300 MHz, CDCl$_3$) δ (ppm); 1.83-1.95 (m, 1H), 2.07-2.19 (m, 1H), 2.32-2.43 (m, 1H), 2.54 (s, 3H), 2.61-2.67 (m, 3H), 2.67-2.72 (m, 1H), 3.55 (dd, J=10.3, 3.9 Hz, 1H), 3.87-3.97 (m, 3H), 4.39 (brs, 1H), 4.55 (dd, J=8.6, 5.7 Hz, 1H), 5.72 (dd, J=23.2, 1.5 Hz, 2H), 6.68-6.92 (m, 4H), 6.98 (dd, J=9.0, 2.3 Hz, 1H), 7.60 (dd, J=8.7, 1.9 Hz, 1H), 7.75 (d, J=1.4 Hz, 1H), 8.08 (d, J=8.7 Hz, 1H), 8.40 (d, J=9.0 Hz, 1H)

Isomer B; $[\alpha]_D^{25}$=+113° (c=0.107, CHCl$_3$)

MS (ESI pos.) m/z: 689 ([M+H]$^+$)

$^1$H-NMR (300 MHz, CDCl$_3$) δ (ppm); 1.70-1.89 (m, 2H), 1.99-2.10 (m, 1H), 2.54 (s, 3H), 2.71 (s, 3H), 3.41-3.58 (m, 2H), 3.85-3.96 (m, 1H), 3.94 (s, 3H), 4.34 (brs, 1H), 5.46 (dd, J=34.0, 1.6 Hz, 2H), 6.74 (dd, J=7.8, 1.1 Hz, 1H), 6.86-7.02 (m, 3H), 7.42 (d, J=1.6 Hz, 1H), 7.54-7.66 (m, 2H), 8.11 (d, J=8.7 Hz, 1H), 8.32 (d, J=9.0 Hz, 1H)

Example 109

Synthesis of tert-butyl 4-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-3-[(dimethylamino)carbonyl]piperazine-1-carboxylate

Step 109-1: Synthesis of 1-[(benzyl oxy)carbonyl]-4-(tert-butoxy carbonyl) piperazine-2-carboxylic acid To a mixed solution of 2.03 g of 2-piperazine carboxylic acid/2 hydrochloric acid in 1,4-dioxane (10 ml) and water (10 ml) was added an aqueous solution of 4 mol/L NaOH (5 ml) under ice cooling, and 2.40 g of (Boc)$_2$O was added dropwise over 10 minutes. The solution was stirred at room temperature for one hour, then was ice cooled again. An aqueous solution of 4 mol/L NaOH (3 ml) was added to the reaction mixture and ice-bathed, and 1.87 g of benzyl chloroformate was added dropwise over 10 minutes. The solution was stirred at room temperature for one hour, then was ice cooled again, and 4 mol/L hydrochloric acid was added to set to pH=6. The resulting solution was extracted with EtOAc, the combined organic layer was washed in saturated brine and dried over Na$_2$SO$_4$, then, the drying agent was separated by filtration, and the solvent was evaporated under reduced pressure to obtain 4.01 g of the title compound (crude form). The present compound was used in the next reaction without purification.

MS (ESI pos.) m/z: 365 ([M+H]$^+$), 387 ([M+Na]$^+$), (ESI neg.) m/z: 363 ([M−H]$^-$)

$^1$H-NMR (600 MHz, CDCl$_3$) δ (ppm); 1.40-1.43 (m, 9H), 2.70-3.40 (m, 3H), 3.70 (s, 1H), 3.85-4.07 (m, 2H), 4.51-4.88 (m, 2H), 5.07-5.24 (m, 2H), 7.26-7.39 (m, 5H)

Step 109-2: Synthesis of 4-tert-butyl 1-benzyl 2-[(dimethylamino)carbonyl]piperazine-1,4-dicarboxylate With 4.01 g of the compound obtained in Step 109-1 as starting material, 3.16 g of the title compound was obtained by a similar method to Step 6-1a.

MS (ESI pos.) m/z: 392 ([M+H]$^+$), 414 ([M+Na]$^+$)

$^1$H-NMR (600 MHz, CDCl$_3$) δ (ppm); 1.37-1.50 (m, 9H), 2.76-3.34 (m, 7H), 3.68-4.29 (m, 6H), 4.69-5.22 (m, 2H), 7.27-7.41 (m, 5H)

Step 109-3: Synthesis of tert-butyl 3-[(dimethylamino)carbonyl]piperazine-1-carboxylate With 3.10 g of the compound obtained in Step 109-2 as starting material, 2.44 g of the title compound was obtained by a similar method to Step 11-4. The present compound was used in the next reaction without purification.

MS (ESI pos.) m/z: 258 ([M+H]$^+$), 280 ([M+Na]$^+$)

$^1$H-NMR (200 MHz, CDCl$_3$) δ (ppm); 1.47 (s, 9H), 2.51-3.17 (m, 11H), 3.53-4.22 (m, 3H)

Step 109-4: Synthesis of 3,5-dichloro-3-(2-methoxy-5-methylphenyl)-1,3-dihydro-2H-indol-2-one Under nitrogen atmosphere, to a suspension of 200 g of the compound obtained in Step 103-1 and 78.1 g of Py in CHCl$_3$ (2 L) was added dropwise 117.5 g of thionyl chloride over one hour. The solution was stirred at the same temperature for one hour, then, was poured into water (1.5 L), the solution was stirred for one hour, and liquid separation was performed. The aqueous layer was extracted with CHCl$_3$, the combined organic layer was washed with saturated brine then dried over MgSO$_4$, the drying agent was separated by filtration, and then the solvent was evaporated under reduced pressure. The residue was washed with Et$_2$O (1.2 L) by stirring, then the solid was collected by filtration to obtain 198.3 g of the title compound.

MS (ESI neg.) m/z: 320 ([M−H]$^-$)

$^1$H-NMR (600 MHz, DMSO-d$_6$) δ (ppm); 2.33 (s, 3H), 3.41 (s, 3H), 6.86 (d, J=8.25 Hz, 1H), 6.90 (d, J=8.71 Hz, 1H), 6.92 (d, J=1.83 Hz, 1H), 7.18 (dd, J=8.25, 2.29 Hz, 1H), 7.27 (dd, J=8.25, 2.29 Hz, 1H), 7.67 (d, J=1.83 Hz, 1H), 10.92 (s, 1H)

Step 109-5: Synthesis of tert-butyl 4-[5-chloro-3-(2-methoxy-5-methylphenyl)-2-oxo-2,3-dihydro-1H-indol-3-yl]-3-[(dimethylamino)carbonyl]piperazine-1-carboxylate With 2.43 g of the compound obtained in Step 109-3 and 2.43 g of the compound obtained in Step 109-4 as starting materials, 1.78 g of the title compound was obtained by a similar method to Step 4-2.

MS (ESI pos.) m/z: 543 ([M+H]$^+$), 565 ([M+Na]$^+$), (ESI neg.) m/z: 541 ([M−H]$^-$)

$^1$H-NMR (600 MHz, CDCl$_3$) δ (ppm); 1.43 (s, 9H), 2.29-2.35 (m, 2H), 2.37-2.46 (m, 5H), 2.73-2.87 (m, 5H), 3.38-3.96 (m, 7H), 6.70 (d, J=8.25 Hz, 1H), 6.73-6.85 (m, 2H), 6.97-7.16 (m, 2H), 7.86-7.95 (m, 1H), 8.10-8.22 (m, 1H)

Step 109-6 Synthesis of tert-butyl 4-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-3-[(dimethylamino)carbonyl]piperazine-1-carboxylate With 1.70 g of the compound obtained in Step 109-5 and 1.00 g of 4-methoxy-2-(trifluoromethoxy)benzene sulfonyl chloride as starting material, 2.01 g of the title compound (amorphous) was obtained by a similar procedure to Example 2.

MS (ESI pos.) m/z: 797 ([M+H]$^+$), 819 ([M+Na]$^+$)

$^1$H-NMR (600 MHz, CDCl$_3$) δ (ppm); 1.39 (s, 9H), 2.20-2.49 (m, 2H), 2.65-2.96 (m, 5H), 2.99-3.10 (m, 3H), 3.50-3.77 (m, 3H), 3.78-4.19 (m, 3H), 6.54-6.60 (m, 1H), 6.67 (d, J=8.25 Hz, 1H), 6.75 (s, 1H), 6.85 (d, J=17.42 Hz, 1H), 6.93 (dd, J=8.71, 2.29 Hz, 1H), 7.02 (d, J=7.79 Hz, 1H), 7.11 (s, 1H), 7.21-7.30 (m, 1H), 7.56 (s, 1H), 7.63 (s, 1H), 7.84-7.95 (m, 1H), 8.31 (d, J=8.25 Hz, 1H)

Example 110

Synthesis of 1-(5-chloro-3-(2-methoxy-5-methylphenyl)-1-{[4-methoxy-2-(trifluoromethoxy)phenyl]sulfonyl. }-2-oxo-2,3-dihydro-1H-indol-3-yl)-N,N-dimethylpiperazine-2-carboxamide To a solution of 800 mg of the compound obtained in Step 109-6 in THF (10 ml) was added a solution of 4 mol/L hydrochloric acid/1,4-dioxane (20 ml) and the reaction mixture was stirred for two hours. The solution was poured into a saturated aqueous solution of NaHCO$_3$, to set to pH=8, and the resulting mixture was extracted with EtOAc, the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=10/1 to 5/1; v/v) to obtain 533 mg of the title compound.

MS (ESI pos.) m/z: 697 ([M+H]$^+$)

$^1$H-NMR (600 MHz, CDCl$_3$) δ (ppm); 1.59-1.79 (m, 1H), 2.11-2.24 (m, 3H), 2.31 (s, 3H), 2.59-2.65 (m, 1H), 2.77-2.93 (m, 7H), 3.01 (d, J=13.30 Hz, 1H), 3.18 (dd, J=13.53, 4.81 Hz, 1H), 3.41-3.55 (m, 1H), 3.62 (d, J=4.59 Hz, 1H), 3.84 (s, 3H), 3.97-4.05 (m, 1H), 6.50 (d, J=8.25 Hz, 1H), 6.73 (d, J=2.29 Hz, 1H), 6.85 (s, 1H), 6.89 (dd, J=9.17, 2.29 Hz, 1H), 6.96 (d, J=8.25 Hz, 1H), 7.20-7.24 (m, 1H), 7.60 (s, 1H), 7.90 (d, J=8.71 Hz, 1H), 8.44 (d, J=9.17 Hz, 1H)

Example 111

Synthesis of 1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N,4-trimethylpiperazine-2-carboxamide To a solution of 100 mg of the compound obtained in Example 110, 14 mg of an aqueous solution of 37% formaldehyde and 18 mg of acetic acid in CHCl$_3$ (2 ml) was added 37 mg of sodium triacetoxy borohydride and the reaction mixture was stirred for one hour. To the solution was added a saturated aqueous solution of NaHCO$_3$, the resulting mixture was extracted with EtOAc, the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=20/1 to 5/1; v/v) to obtain 91 mg of the title compound.

MS (ESI pos.) m/z: 711 ([M+H]$^+$), 733 ([M+Na]$^+$)

$^1$H-NMR (600 MHz, CDCl$_3$) δ (ppm); 1.83-1.90 (m, 2H), 2.05-2.11 (m, 2H), 2.16-2.21 (m, 3H), 2.22-2.27 (m, 1H), 2.29-2.43 (m, 3H), 2.53-2.72 (m, 3H), 2.72-2.81 (m, 2H), 2.98 (s, 1H), 3.30-3.34 (m, 3H), 3.51 (s, 1H), 3.73-3.79 (m, 1H), 3.85-3.96 (m, 3H), 6.63 (d, J=8.25 Hz, 1H), 6.74 (s, 1H), 6.86 (s, 1H), 6.93 (d, J=8.71 Hz, 1H), 7.03 (d, J=8.25 Hz, 1H), 7.21-7.27 (m, 1H), 7.67 (s, 1H), 7.89 (d, J=8.71 Hz, 1H), 8.43 (d, J=8.71 Hz, 1H)

Example 112

Synthesis of 1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-pyridin-4-yl piperazine-2-carboxamide A solution of 100 mg of the compound obtained in Example 110 and 91 mg of 4-bromopyridine in 1-methyl-2-pyrrolidone (1 ml) was stirred for one hour at 100° C. To the solution was added water and the resulting mixture was extracted with EtOAc, the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=10/1 to 4/1; v/v) to obtain 15 mg of the title compound.

MS (ESI pos.) m/z: 774 ([M+H]$^+$)

$^1$H-NMR (600 MHz, CDCl$_3$) δ (ppm); 2.26 (s, 4H), 2.30-2.50 (m, 3H), 2.59-2.89 (m, 1H), 2.97-3.04 (m, 1H), 3.04-3.18 (m, 3H), 3.56 (s, 3H), 3.62 (s, 3H), 3.87 (s, 1H), 3.96-4.05 (m, 1H), 4.74 (s, 1H), 6.22 (d, J=6.42 Hz, 2H), 6.59 (s, 1H), 6.70 (d, J=8.25 Hz, 1H), 6.85 (dd, J=9.17, 2.29 Hz, 1H), 7.04-7.08 (m, 1H), 7.14 (d, J=2.29 Hz, 1H), 7.26-7.30 (m, 1H), 7.52-7.56 (m, 1H), 7.90 (d, J=8.71 Hz, 1H), 8.15 (d, J=6.42 Hz, 2H), 8.28 (d, J=9.17 Hz, 2H)

Example 113

Synthesis of benzyl(2S)-1-(5-chloro-3-(2-methoxyphenyl)-1-{[4-methoxy-2-(trifluoromethoxy)phenyl]sulfon yl}-2-oxo-2,3-dihydro-1H-indol-3-yl) piperidine-2-carboxylate (levorotatory isomer)

Step 113-1: Synthesis of benzyl(2S)-1-[5-chloro-3-(2-methoxyphenyl)-2-oxo-2,3-dihydro-1H-indol-3-yl]piperidine-2-car boxylate (levorotatory isomer)

With 2.19 g of 3,5-dichloro-3-(2-methoxyphenyl)-1,3-dihydro-2H-indol-2-one and 2.00 g of benzyl(2S)piperidine-2-carboxylic acid hydrochloride, which is the compound described in Example X of the brochure Publication No. WO98/42342, as starting materials, 3.54 g of the title compound (amorphous) was obtained by a similar method to Step 4-2.

$[\alpha]_D^{25}$=−139° (c=0.415, CHCl$_3$)

MS (ESI pos.) m/z: 491 ([M+H]$^+$), 513 ([M+Na]$^+$), (ESI neg.) m/z: 489 ([M−H]$^+$)

$^1$H-NMR (600 MHz, CDCl$_3$) δ (ppm); 1.33-1.43 (m, 1H), 1.61-1.72 (m, 3H), 1.84-1.99 (m, 2H), 3.02 (d, J=11.92 Hz, 1H), 3.46-3.66 (m, 5H), 4.90-5.02 (m, 1H), 5.07-5.15 (m, 1H), 6.34 (d, J=7.79 Hz, 1H), 6.60-6.80 (m, 3H), 6.97-7.13 (m, 2H), 7.20-7.38 (m, 6H), 7.91 (d, J=7.79 Hz, 1H)

Step 113-2: Synthesis of benzyl(2S)-1-(5-chloro-3-(2-methoxyphenyl)-1-{[4-methoxy-2-(trifluoromethoxy)phenyl]sulfon yl}-2-oxo-2,3-dihydro-1H-indol-3-yl)piperidine-2-carboxylate (levorotatory isomer)

With 2.00 g of the compound obtained in Step 113-1 and 1.42 g of 4-methoxy-2-(trifluoromethoxy)benzene sulfonyl chloride as starting material, 1.74 g of the title compound (amorphous) was obtained by a similar procedure to Example 2.

$[\alpha]_D^{25}$=−139° (c=0.470, CHCl$_3$)

MS (ESI pos.) m/z: 745 ([M+H]$^+$), 767 ([M+Na]$^+$)

$^1$H-NMR (200 MHz, CDCl$_3$) δ (ppm); 1.09-1.29 (m, 2H), 1.54 (s, 4H), 1.70-2.02 (m, 1H), 2.88-3.20 (m, 1H), 3.36 (s, 3H), 3.53-3.66 (m, 1H), 3.86 (s, 3H), 4.72-4.86 (m, 1H), 4.98-5.08 (m, 1H), 6.65-6.81 (m, 2H), 6.84-7.12 (m, 3H), 7.12-7.37 (m, 7H), 7.86-7.97 (m, 2H), 8.44 (d, J=9.23 Hz, 1H)

Example 114

Synthesis of (2S)-1-(5-chloro-3-(2-methoxyphenyl)-1-{[4-methoxy-2-(trifluoromethoxy)phenyl]sulfonyl}-2-o xo-2,3-dihydro-1H-indol-3-yl)piperidine-2-carboxylic acid (levorotatory isomer)

Under hydrogen atmosphere, a suspension of 1.58 g of the compound obtained in Step 113-2 and 400 mg of 10% palladium-carbon in EtOAc (30 ml) was stirred at room temperature for 15 hours. The insoluble matter was filtered with celite, and was concentrated under reduced pressure. The residue was purified by column chromatography (silicagel 60N; mobile phase: n-hexane/EtOAc=3/2; v/v) to obtain 1.14 g of the title compound (amorphous).

$[\alpha]_D^{25}$=−141° (c=0.141, CHCl$_3$)

MS (ESI pos.) m/z: 655 ([M+H]$^+$), 677 ([M+Na]$^+$), (ESI neg.) m/z: 653 ([M−H]$^+$), $^1$H-NMR (200 MHz, CDCl$_3$) δ (ppm); 1.19-2.13 (m, 6H), 2.81-3.22 (m, 2H), 3.32 (s, 3H), 3.55-3.77 (m, 1H), 3.90 (s, 3H), 6.68-6.82 (m, 1H), 6.82-7.16 (m, 4H), 7.19-7.35 (m, 3H), 7.72-7.86 (m, 1H), 7.93 (d, J=9.23 Hz, 1H), 8.38 (d, J=9.23 Hz, 1H)

Example 115

Synthesis of 5-chloro-3-(2-methoxyphenyl)-1-{[4-methoxy-2-(trifluoromethoxy)phenyl]sulfonyl}-3-{(2S)-2-[(4-pyridin-4-yl piperazin-1-yl)carbonyl] piperidin-1-yl}-1,3-dihydro-2H-indol-2-one With 75 mg of the compound obtained in Example 114 and 39 mg of 1-(4-pyridyl)piperazine as starting materials, 55 mg of the title compound (amorphous) was obtained by a similar procedure to Step 109-2.

MS (ESI pos.) m/z: 800 ([M+H]$^+$)

$^1$H-NMR (600 MHz, CDCl$_3$) δ (ppm); 1.47-1.82 (m, 6H), 1.87-1.96 (m, 1H), 2.71-2.95 (m, 5H), 2.98-3.55 (m, 5H), 3.78-3.98 (m, 6H), 6.53-6.66 (m, 3H), 6.70 (d, J=2.29 Hz, 1H), 6.88 (s, 1H), 6.94 (dd, J=9.17, 2.29 Hz, 1H), 7.03 (t, J=7.57 Hz, 1H), 7.14 (dd, J=8.71, 2.29 Hz, 1H), 7.18-7.23 (m, 1H), 7.84 (d, J=9.17 Hz, 1H), 7.86-7.89 (m, 1H), 8.22-8.33 (m, 2H), 8.49 (d, J=9.17 Hz, 1H)

Example 116

Synthesis of (2S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer)

Step 116-1: Synthesis of (2S)-1-[5-chloro-3-(2-methoxy-5-methylphenyl)-2-oxo-2,3-dihydro-1H-indol-3-yl]-N,N-dimeth ylpiperidine-2-carboxamide (levorotatory isomer and dextrorotatory isomer)

From 4.00 g of the compound obtained in Step 103-1 and (4R)-4-hydroxy-N,N-dimethyl-L-prolinamide trifluoroacetate (14.5 mmol), respectively 1.24 g (Isomer A: brown amorphous) and 3.43 g (Isomer B: brown amorphous) of two species of diastereoisomers of the title compound were obtained by a similar method to Step 21-2.

Isomer A: $[\alpha]_D^{25}$=+176° (c=0.335, CHCl$_3$)

MS (ESI pos.) m/z: 442 ([M+H]$^+$), 464 ([M+Na]$^+$), (ESI neg.) m/z: 440 ([M−H]$^-$)

$^1$H-NMR (300 MHz, DMSO-d$_6$) δ (ppm); 1.32-4.18 (m, 21H), 6.61 (s, 1H), 6.76 (dd, J=9.8, 8.2 Hz, 2H), 7.06 (dd, J=8.3, 2.1 Hz, 1H), 7.14 (dd, J=8.2, 2.2 Hz, 1H), 7.70 (s, 1H), 10.45 (s, 1H)

Isomer B: $[\alpha]_D^{25}$=−247° (c=0.265, CHCl$_3$)

MS (ESI pos.) m/z: 442 ([M+H]$^+$), 464 ([M+Na]$^+$), (ESI neg.) m/z: 440 ([M−H]$^-$)

$^1$H-NMR (300 MHz, DMSO-d$_6$) δ (ppm); 1.32-2.00 (m, 6H), 2.16 (s, 3H), 2.33 (s, 3H), 2.54-2.71 (m, 4H), 3.36 (s, 3H), 3.79-3.97 (m, 2H), 6.63 (d, J=1.7 Hz, 1H), 6.76 (dd, J=12.0, 8.2 Hz, 2H), 7.05 (dd, J=8.2, 2.3 Hz, 1H), 7.17 (dd, J=8.2, 2.1 Hz, 1H), 7.66 (s, 1H), 10.07 (s, 1H)

Step 116-2: Synthesis of (2S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer)

With 500 mg of the compound obtained in Step 116-1 (Isomer B) and 365 mg of 4-methoxy-2-(trifluoromethoxy)benzene sulfonyl chloride as starting materials, 396 mg of the title compound (colorless amorphous) was obtained by a similar method to Example 2.
$[\alpha]_D^{25}$=−210° (c=0.332, CHCl$_3$)
MS (ESI pos.) m/z: 696 ([M+H]$^+$), 718 ([M+Na]$^+$)
$^1$H-NMR (600 MHz, CDCl$_3$) δ (ppm); 1.39-1.99 (m, 4H), 2.20-2.56 (m, 7H), 2.75-3.02 (m, 7H), 3.35-3.65 (m, 1H), 3.81 (d, J=5.0 Hz, 1H), 3.88 (s, 3H), 3.99 (t, J=12.2 Hz, 1H), 6.53 (d, J=8.7 Hz, 1H), 6.75 (d, J=2.3 Hz, 1H), 6.88 (s, 1H), 6.93 (dd, J=9.2, 2.3 Hz, 1H), 6.99 (dd, J=8.5, 1.6 Hz, 1H), 7.25 (dd, J=8.7, 2.3 Hz, 1H), 7.66 (d, J=1.8 Hz, 1H), 7.93 (d, J=9.2 Hz, 1H), 8.49 (d, J=8.7 Hz, 1H)

Example 117

Synthesis of (2S)-1-(5-chloro-3-(2,5-dimethoxyphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer and dextrorotatory isomer)

Step 117-1: Synthesis of (2S)-1-[5-chloro-3-(2,5-dimethoxyphenyl)-2-oxo-2,3-dihydro-1H-indol-3-yl]-N,N-dimethylpiper idine-2-carboxamide From 1.30 g of the compound obtained in Step 102-1 and 940 mg of (4R)-4-hydroxy-N,N-dimethyl-L-prolinamide hydrochloride, 1.64 g of the title compound (diastereoisomer mixture: colorless amorphous) was obtained by a similar method to Step 21-2.
MS (ESI pos.) m/z: 458 ([M+H]$^+$), 480 ([M+Na]$^+$), (ESI neg.) m/z: 456 ([M−H]$^−$)
$^1$H-NMR (600 MHz, DMSO-d$_6$) δ (ppm); 1.22-4.11 (m, 19H), 6.60-6.94 (m, 4H), 7.07-7.29 (m, 1H), 7.49 (s, 1H), 9.95-10.64 (m, 1H)

Step 117-2: Synthesis of (2S)-1-(5-chloro-3-(2,5-dimethoxyphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer and dextrorotatory isomer)

With 900 mg of the compound obtained in Step 117-1 and 682 mg of 4-methoxy-2-(trifluoromethoxy)benzene sulfonyl chloride as starting materials, respectively 104 mg (Isomer A: colorless amorphous) and 430 mg (Isomer B: colorless amorphous) of two species of diastereoisomers of the title compound were obtained by a similar method to Example 2.
Isomer A: $[\alpha]_D^{25}$=+98.1° (c=0.415, CHCl$_3$)
MS (ESI pos.) m/z: 712 ([M+H]$^+$), 734 ([M+Na]$^+$)
$^1$H-NMR (499 MHz, CDCl$_3$) δ (ppm); 1.36-4.25 (m, 24H), 6.52-8.53 (m, 9H)
Isomer B: $[\alpha]_D^{25}$=−222° (c=0.259, CHCl$_3$)
MS (ESI pos.) m/z: 712 ([M+H]$^+$), 734 ([M+Na]$^+$)
$^1$H-NMR (499 MHz, CDCl$_3$) δ (ppm); 1.48-1.93 (m, 7H), 2.25 (s, 3H), 2.76-3.02 (m, 6H), 3.66-4.11 (m, 8H), 6.58 (d, J=8.8 Hz, 1H), 6.69-6.79 (m, 2H), 6.83-7.04 (m, 2H), 7.19-7.36 (m, 1H), 7.52 (d, J=3.0 Hz, 1H), 7.93 (d, J=8.8 Hz, 1H), 8.49 (d, J=8.8 Hz, 1H)

Example 118

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-pyrrolo[2,3-b]pyridin-3-yl)-4-hydroxy-N,N-dimethyl-L-prolinamide (levorotatory isomer and dextrorotatory isomer)

Step 118-1: Synthesis of ethyl (2-amino-5-chloro pyridin-3-yl)(methylthio)acetate Under nitrogen atmosphere, to a suspension of 20.3 g of 5-chloro pyridin-2-amine in MeCN (400 ml)-THF (30 ml) was added dropwise under salt-ice cooling 17.2 g of perchloric acid t-butyl ester over 5 minutes. The solution was stirred at the same temperature for one hour, then, a solution of 21.2 g of methyl thioethyl acetate in MeCN (50 ml) was added dropwise over 30 minutes, then, 16.0 g of Et$_3$N was added dropwise over 10 minutes. After the end of dropwise addition, the solution was warmed to room temperature over one hour. To the reaction solution was added water and CHCl$_3$, liquid separation was performed, and the aqueous layer was extracted with CHCl$_3$. The combined organic layer was washed with saturated brine, dried over MgSO$_4$, then, the drying agent was separated by filtration and solvent was evaporated under reduced pressure. The obtained residue was purified by column chromatography (silicagel 60; mobile phase: EtOAc/n-hexane=1/4 to 1/1; v/v) to obtain 8.18 g of the title compound (brown solid).
MS (ESI pos.) m/z: 261 ([M+H]$^+$)
$^1$H-NMR (600 MHz, CDCl$_3$) δ (ppm); 1.23-1.29 (m, 3H), 2.03 (s, 3H), 4.18-4.27 (m, 2H), 4.40-4.45 (m, 1H), 5.00 (brs, 2H), 7.57 (d, J=2.8 Hz, 1H), 8.00 (d, J=2.3 Hz, 1H)

Step 118-2: Synthesis of 5-chloro-3-(methylthio)-1,3-dihydro-2H-pyrrolo[2,3-b]pyridin-2-one The compound that is obtained in Step 118-1, 7.50 g was stirred at 70° C. for two hours in 6.0 mol/L hydrochloric acid (100 ml). After the solution was stood to cool, Et$_2$O (100 ml) was added to the solution, then, was set to pH=10 with a saturated aqueous solution of NaHCO$_3$ under ice cooling. Liquid separation was performed and the aqueous layer was extracted with CHCl$_3$. The solution was dried over MgSO$_4$, then, the drying agent was separated by filtration and the solvent was evaporated under reduced pressure. The obtained residue (2.40 g, brown solid) was subjected to the next step without purification.
MS (ESI pos.) m/z: 236 ([M+Na]$^+$)
$^1$H-NMR (600 MHz, CDCl$_3$) δ (ppm); 2.12 (s, 3H), 4.32 (s, 1H), 7.60-7.65 (m, 1H), 7.83-7.95 (m, 1H), 8.14 (s, 1H)

Step 118-3: Synthesis of 3,5-dichloro-3-(methylthio)-1,3-dihydro-2H-pyrrolo[2,3-b]pyridin-2-one A suspension of 2.40 g of the compound that is obtained at Step 118-2 and 1.64 g of N-chloro succinimide in carbon tetrachloride (100 ml) was heat-refluxed for two hours. After the solution was let to cool down, the insoluble matter was separated by filtration, and the filtrate was concentrated under reduced pressure. The obtained residue (2.97 g, brown solid) was subjected to the next step without purification.

¹H-NMR (600 MHz, CDCl₃) δ (ppm); 2.52 (s, 3H), 7.69 (d, J=2.3 Hz, 1H), 7.74 (brs, 1H), 8.17 (d, J=2.3 Hz, 1H)

Step 118-4: Synthesis of
5-chloro-1H-pyrrolo[2,3-b]pyridin-2,3-dione

To a suspension of 2.23 g of mercury oxide and 1.45 g of boron trifluoride-Et₂O complex in 20% hydrous THF (104 ml) was added dropwise a solution of 2.90 g of the compound that is obtained at Step 118-3 in THF (200 ml) over 15 minutes, then, the reaction mixture was stirred at room temperature for two hours. The reaction solution was filtered with celite, EtOAc and water was added to the filtrate, and liquid separation was performed. The organic layer was washed with saturated brine and dried over MgSO₄, then, the drying agent was separated by filtration, and the filtrate was concentrated under reduced pressure. The obtained residue was purified by column chromatography (silicagel 60; mobile phase: EtOAc/n-hexane=3/7; v/v) to obtain a brown solid (1.20 g). The obtained solid was washed by stirring in IPE, then, the solid was collected by filtration to obtain 920 mg of the title compound (brown solid).

MS (ESI neg.) m/z: 181 ([M−H]⁻)
¹H-NMR (600 MHz, DMSO-d₆) δ (ppm); 8.03 (d, J=2.8 Hz, 1H), 8.42 (d, J=2.3 Hz, 1H), 11.73 (s, 1H)

Step 118-5: Synthesis of 5-chloro-3-hydroxy-3-(2-methoxy-5-methylphenyl)-1,3-dihydro-2H-pyrrolo[2,3-b]pyridin-2-one With 1.49 g of 2-bromo-4-methyl anisole and 900 mg of the compound obtained in Step 118-4 as starting materials, 1.23 g of the title compound (brown solid) was obtained by a similar method to Step 21-1.

MS (ESI pos.) m/z: 327 ([M+Na]⁺)
¹H-NMR (600 MHz, DMSO-d₆) δ (ppm); 2.29 (s, 3H), 3.37 (s, 3H), 6.77 (d, J=8.3 Hz, 1H), 6.79 (s, 1H), 7.06-7.09 (m, 1H), 7.20 (d, J=2.3 Hz, 1H), 7.58 (d, J=2.3 Hz, 1H), 8.06 (d, J=2.3 Hz, 1H), 11.10 (s, 1H)

Step 118-6: Synthesis of 5-chloro-3-hydroxy-3-(2-methoxy-5-methylphenyl)-1-{[4-methoxy-2-(trifluoromethoxy)phenyl]sulfonyl}-1,3-dihydro-2H-pyrrolo[2,3-b]pyridin-2-one With 1.18 g of the compound obtained in Step 118-5 and 1.24 g of 4-methoxy-2-(trifluoromethoxy)benzene sulfonyl chloride as starting materials, 565 mg of the title compound (brown gummy substance) was obtained by a similar method to Example 2.

MS (ESI pos.) m/z: 581 ([M+Na]⁺)
¹H-NMR (600 MHz, CDCl₃) δ (ppm); 2.34 (s, 3H), 3.23 (s, 1H), 3.67 (s, 3H), 3.89 (s, 3H), 6.72 (d, J=8.3 Hz, 1H), 6.85-6.87 (m, 1H), 6.92 (dd, J=9.2, 2.3 Hz, 1H), 7.12-7.15 (m, 1H), 7.37 (d, J=2.3 Hz, 1H), 7.49 (d, J=2.3 Hz, 1H), 8.19 (d, J=2.3 Hz, 1H), 8.28 (d, J=9.2 Hz, 1H)

Step 118-7: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-pyrrolo[2,3-b]pyridin-3-yl)-4-hydroxy-N,N-dimethyl-L-prolinami de (levorotatory isomer and dextrorotatory isomer)

Under nitrogen atmosphere, to a solution of 280 mg of the compound obtained in Step 118-6 in CHCl₃ (2.8 ml) was added sequentially 107 mg of methanesulfonic acid anhydride and Et₃N (104 mg), then, the reaction mixture was stirred for 30 minutes under the same condition. Under nitrogen atmosphere, to a suspension of (4R)-4-hydroxy-N,N-dimethyl-L-prolinamide trifluoroacetate (2.57 mmol) in CHCl₃ (5 ml) was added Et₃N (520 mg) under dry ice-acetone cooling. To the reaction solution was added dropwise over 30 seconds the reaction solution of the mesyl form prepared above, then the reaction mixture was warmed to room temperature over two hours. To the reaction solution was added water and CHCl₃, liquid separation was performed, and the aqueous layer was extracted with CHCl₃. The combined organic layer was washed with saturated brine, dried over MgSO₄, then, the drying agent was separated by filtration and the filtrate was concentrated. The obtained residue was separated and purified by column chromatography (silicagel 60; mobile phase: CHCl₃/MeOH/NH₄OH=95/5/0.5; v/v/v) to obtain respectively 33 mg (Isomer A: brown amorphous) and 24 mg (Isomer B: pale brown amorphous) of two species of diastereoisomers of the title compound.

Isomer A: $[\alpha]_D^{25}$=+14.9° (c=0.104, CHCl₃)
MS (ESI pos.) m/z: 699 ([M+H]⁺), 721 ([M+Na]⁺)
¹H-NMR (600 MHz, CDCl₃) δ (ppm); 1.76-1.82 (m, 1H), 1.99-2.04 (m, 1H), 2.37 (s, 3H), 2.41 (s, 3H), 2.66 (s, 3H), 3.44-3.48 (m, 1H), 3.53-3.58 (m, 1H), 3.55 (s, 3H), 3.82-3.92 (m, 1H), 3.91 (s, 3H), 3.93-3.98 (m, 1H), 4.27-4.30 (m, 1H), 6.67 (d, J=8.3 Hz, 1H), 6.88-6.90 (m, 1H), 6.94 (dd, J=9.2, 2.3 Hz, 1H), 7.05-7.08 (m, 1H), 7.29 (d, J=2.3 Hz, 1H), 7.90 (d, J=1.8 Hz, 1H), 8.18 (d, J=2.3 Hz, 1H), 8.31 (d, J=8.7 Hz, 1H)

Isomer B: $[\alpha]_D^{25}$=−15.7° (c=0.132, CHCl₃)
MS (ESI pos.) m/z: 699 ([M+H]⁺), 721 ([M+Na]⁺)
¹H-NMR (600 MHz, CDCl₃) δ (ppm); 1.22-3.94 (m, 5H), 2.28 (s, 3H), 2.46 (s, 3H), 2.82 (s, 3H), 3.71 (s, 3H), 3.90 (s, 3H), 4.71-4.79 (m, 1H), 4.86-4.97 (m, 1H), 6.71 (d, J=8.3 Hz, 1H), 6.89 (s, 1H), 6.94 (dd, J=9.2, 2.3 Hz, 1H), 7.05-7.08 (m, 1H), 7.45 (s, 1H), 7.62 (s, 1H), 8.14 (d, J=2.3 Hz, 1H), 8.34 (d, J=9.2 Hz, 1H)

Example 119

Synthesis of (4R)-1-[5-chloro-1-[(2,4-dimethoxyphenyl)sulfonyl]-3-(2-methoxy-5-methylphenyl)-2-oxo-2,3-dihydro-1H-pyrrolo[2,3-b]pyridin-3-yl]-4-hydroxy-N,N-dimethyl-L-prolinamide (levorotatory isomer and dextrorotatory isomer)

Step 119-1: Synthesis of 5-chloro-1-[(2,4-dimethoxyphenyl)sulfonyl]-3-hydroxy-3-(2-methoxy-5-methylphenyl)-1,3-dihy dro-2H-pyrrolo[2,3-b]pyridin-2-one With 2.00 g of the compound obtained in Step 118-5 and 1.72 g of 4-methoxy-2-(trifluoromethoxy)benzene sulfonyl chloride as starting materials, 1.27 g of the title compound (brown amorphous) was obtained by a similar method to Example 2.

MS (ESI pos.) m/z: 505 ([M+H]⁺), 527 ([M+Na]⁺), (ESI neg.) m/z: 503 ([M−H]⁻)
¹H-NMR (200 MHz, CDCl₃) δ (ppm); 2.35 (s, 3H), 3.69 (s, 3H), 3.74 (s, 3H), 3.83-3.90 (m, 4H), 6.41 (d, J=2.2 Hz, 1H), 6.60 (dd, J=9.0, 2.4 Hz, 1H), 6.74 (d, J=8.4 Hz, 1H), 7.08-7.20

(m, 1H), 7.35-7.41 (m, 1H), 7.44 (d, J=1.8 Hz, 1H), 8.13 (d, J=8.8 Hz, 1H), 8.20-8.25 (m, 1H)

Step 119-2: Synthesis of (4R)-1-[5-chloro-1-[(2,4-dimethoxyphenyl)sulfonyl]-3-(2-methoxy-5-methylphenyl)-2-oxo-2,3-dihydro-1H-pyrrolo[2,3-b]pyridin-3-yl]-4-hydroxy-N,N-dimethyl-L-prolinamide (levorotatory isomer and dextrorotatory isomer)

To a solution of 500 mg of the compound obtained in Step 119-1 and 200 mg of $Et_3N$ in $CHCl_3$ (5 ml) was added 207 mg of methane sulfonic acid anhydride under ice cooling. The solution was stirred at the same temperature for 20 minutes, then, 1.90 g of $Et_3N$ was added. Thereafter, a solution of (4R)-4-hydroxy-N,N-dimethyl-L-prolinamide trifluoroacetate (4.95 mmol) in $CHCl_3$ (5 ml) was added dropwise at the same temperature. The solution was stirred at the same temperature for one hour, then, was gradually warmed and stirred for 30 minutes under room temperature conditions, then, was poured into a saturated aqueous solution of $NH_4Cl$ and extracted with $CHCl_3$. The combined organic layer was washed with saturated brine, dried over $Na_2SO_4$, then, the drying agent was separated by filtration and the solvent was evaporated under reduced pressure. The obtained residue was separated and purified by column chromatography (first time: silicagel 60N; mobile phase: $CHCl_3$/MeOH=10/0 to 9/1; v/v, first time: silicagel 60N; mobile phase: EtOAc/MeOH=10/0 to 9/1; v/v) to obtain respectively 7.6 mg (Isomer A: brown amorphous) and 18.9 mg (Isomer B: brown amorphous) of two species of diastereoisomers of the title compound.

Isomer A: $[\alpha]_D^{25}$=−121° (c=0.063, $CHCl_3$)
MS (ESI pos.) m/z: 645 ([M+H]$^+$), 667 ([M+Na]$^+$), (ESI neg.) m/z: 643 ([M−H]$^-$)
$^1$H-NMR (600 MHz, $CDCl_3$) δ (ppm); 1.79-4.06 (m, 23H), 4.72-4.97 (m, 2H), 6.45 (d, J=2.3 Hz, 1H), 6.62 (dd, J=9.2, 2.3 Hz, 1H), 6.72 (d, J=8.3 Hz, 1H), 7.06 (dd, J=8.5, 2.1 Hz, 1H), 7.41-7.62 (m, 2H), 8.17 (d, J=9.2 Hz, 1H), 8.22 (d, J=2.3 Hz, 1H)

Isomer B: $[\alpha]_D^{25}$=+19.5° (c=0.082, $CHCl_3$)
MS (ESI pos.) m/z: 645 ([M+H]$^+$), 667 ([M+Na]$^+$), (ESI neg.) m/z: 643 ([M−H]$^-$)
$^1$H-NMR (600 MHz, $CDCl_3$) δ (ppm); 1.80-2.63 (m, 13H), 3.56-3.70 (m, 4H), 3.89 (s, 3H), 3.97-4.04 (m, 4H), 4.36 (t, J=3.2 Hz, 1H), 6.47 (d, J=1.8 Hz, 1H), 6.64 (dd, J=8.9, 2.1 Hz, 1H), 6.71 (d, J=8.3 Hz, 1H), 7.08 (dd, J=8.3, 2.3 Hz, 1H), 7.30 (d, J=2.8 Hz, 1H), 7.86 (d, J=1.8 Hz, 1H), 8.11 (d, J=2.3 Hz, 1H), 8.20 (d, J=8.7 Hz, 1H)

Example 120

Synthesis of (4R)-1-(5-bromo-3-(2-methoxy-5-methylphenyl)-1-{[4-methoxy-2-(trifluoromethoxy)phenyl]sulfonyl}-2-oxo-2,3-dihydro-1H-pyrrolo[2,3-b]pyridin-3-yl)-4-hydroxy-N,N-dimethyl-L-prolinamide (levorotatory isomer)

Step 120-1: Synthesis of (2-amino-5-bromopyridin-3-yl)(methylthio)ethyl acetate

Under nitrogen atmosphere, to a suspension of 50.0 g of 2-amino-5-bromopyridine in methylene chloride (1 L) was added dropwise 31.4 g of perchloric acid tert-butyl ester over 20 minutes at −60° C. After stirring at the same temperature for 30 minutes, 38.8 g of ethyl (methylthio) acetate was added dropwise to the solution over 30 minutes at the same temperature, and the reaction mixture was stirred at −40° C. for 3 hours. 29.2 g of $Et_3N$ was added dropwise to the solution over 10 minutes at −60° C., and the reaction mixture was stirred at room temperature for one hour. A water (1 L) suspension was added, liquid separation was performed, and the aqueous layer was extracted with $CHCl_3$. The combined organic layer was washed with saturated brine, dried over $MgSO_4$, then, the drying agent was separated by filtration and the organic layer was concentrated under reduced pressure. The residue was purified by column chromatography (silicagel 60N; mobile phase: n-hexane/EtOAc=2/1 to 1/1; v/v) to obtain 31.2 g of the title compound.

MS (ESI pos.) m/z: 305 ([M+H−1]$^+$), 307 ([M+H+1]$^+$), 329 ([M+Na+1]$^+$), 327 ([M+Na−1]$^+$), (ESI neg.) m/z: 303 ([M−H−1]$^+$), 305 ([M−H+1]$^+$)
$^1$H-NMR (200 MHz, $CDCl_3$) δ (ppm); 1.25-1.33 (m, 3H), 1.63-1.77 (m, 2H), 2.75-2.79 (m, 3H), 4.18-4.31 (m, 2H), 5.00-5.08 (m, 1H), 7.68 (d, J=2.20 Hz, 1H), 8.09 (d, J=2.20 Hz, 1H)

Step 120-2: Synthesis of 5-bromo-3-(methylthio)-1,3-dihydro-2H-pyrrolo[2,3-b]pyridin-2-one A mixture of 61.0 g of the compound obtained in Step 120-1 and 6.0 mol/L hydrochloric acid (300 ml) was stirred at 100° C. for two hours. The insoluble matter was separated by filtration, the residue was added with water (500 ml), the precipitated solid was washed by stirring, and then the solid was collected by filtration to obtain 20.8 g of the title compound.

MS (ESI neg.) m/z: 259 ([M−H+1]$^-$), 257 ([M−H−1]$^-$)
$^1$H-NMR (200 MHz, DMSO-$d_6$) δ (ppm); 1.73-2.20 (m, 3H), 4.70 (s, 1H), 7.83 (s, 1H), 8.25 (s, 1H), 11.38 (s, 1H)

Step 120-3: Synthesis of 5-bromo-1H-pyrrolo[2,3-b]pyridin-2,3-dione

To a suspension of 17.0 g of the compound obtained in Step 120-2 in tetrachloride (360 ml) was added 10.2 g of N-chloro succinimide, and the reaction mixture was stirred at 100° C. for one hour. The insoluble matter was filtered with celite, concentrated under reduced pressure to obtain 17.0 g of residue. To a mixed solution of 12.5 g of mercury oxide and 8.21 g of $Et_2O$ complex of boron trifluoride in THF (160 ml) and water (40 ml) was added dropwise a solution of the obtained residue in THF (20 ml) under ice cooling. After stirring at the same temperature for one hour, the insoluble matter was filtered with celite, water was added, and the solution was extracted three times with EtOAc. The combined organic layer was washed with saturated brine, dried over $MgSO_4$, then, the drying agent was separated by filtration, and the organic layer was concentrated under reduced pressure. The obtained residue was washed by stirring in EtOAc (50 ml), then, the solid was collected by filtration to obtain 10.2 g of the title compound.

MS (ESI neg.) m/z: 227 ([M+H]$^-$), 225 ([M−H]$^-$)
$^1$H-NMR (200 MHz, DMSO-$d_6$) δ (ppm); 8.06-8.26 (m, 1H), 8.42-8.69 (m, 1H), 11.76 (s, 1H)

Step 120-4: Synthesis of 5-bromo-3-hydroxy-3-(2-methoxy-5-methylphenyl)-1,3-dihydro-2H-pyrrolo[2,3-b]pyridin-2-one With 2.00 g of the compound obtained in Step 120-3 and 2.26 g of 3-bromo-4-methoxy toluene as starting materials, 1.80 g of the title compound was obtained by a similar method to Step 21-1.

MS (ESI pos.) m/z: 349 ([M+H−1]+), 351 ([M+H+1]+), 371 ([M+Na−1]+), ([M+Na+1]+), (ESI neg.) m/z: 347 ([M−H−1]−), 349 ([M−H+1]−)
¹H-NMR (200 MHz, DMSO-d₆) δ (ppm); 2.32 (s, 3H), 3.30 (s, 1H), 3.41 (s, 3H), 6.82 (s, 1H), 7.04-7.16 (m, 1H), 7.31 (d, J=2.20 Hz, 1H), 7.61 (d, J=2.20 Hz, 1H), 8.18 (d, J=2.20 Hz, 1H), 11.12 (s, 1H)

Step 120-5: Synthesis of 5-bromo-3-hydroxy-3-(2-methoxy-5-methylphenyl)-1-{[4-methoxy-2-(trifluoromethoxy)phenyl]sulfonyl}-1,3-dihydro-2H-pyrrolo[2,3-b]pyridin-2-one With 900 mg of the compound obtained in Step 120-4 and 898 mg of 4-methoxy-2-(trifluoromethoxy)benzene sulfonyl chloride as starting material, 297 mg of the title compound was obtained by a similar procedure to Example 2.
¹H-NMR (200 MHz, CDCl₃) δ (ppm); 2.36 (s, 4H), 3.68 (s, 3H), 3.90 (s, 3H), 6.69-6.80 (m, 1H), 6.83-6.99 (m, 2H), 7.10-7.19 (m, 2H), 7.46-7.52 (m, 2H), 8.23-8.34 (m, 1H)

Step 120-6: Synthesis of (4R)-1-(5-bromo-3-(2-methoxy-5-methylphenyl)-1-{[4-methoxy-2-(trifluoromethoxy)phenyl]sulfonyl}-2-oxo-2,3-dihydro-1H-pyrrolo[2,3-b]pyridin-3-yl)-4-hydroxy-N,N-dimethyl-L-prolinamide (levorotatory isomer)

To a solution of 290 mg of the compound obtained in Step 120-5 and 97 mg of Et₃N in CHCl₃ (2 ml), on ice, was added 101 mg of methanesulfonic acid anhydride and the reaction mixture was stirred at room temperature for one hour. The solution was cooled again under ice cooling, 97 mg of Et₃N and 261 mg of (4R)-4-hydroxy-N,N-dimethyl-L-prolinamide trifluoroacetate was added, and the reaction mixture was stirred at room temperature for two hours. A saturated aqueous solution of NaHCO₃ was poured, and the solution was extracted with EtOAc. The organic layer was washed with saturated brine, dried over Na₂SO₄, then, the drying agent was separated by filtration and the solvent was evaporated under reduced pressure. The obtained residue was purified by thin layer chromatography (silicagel 60 F₂₅₄; 1 mm thick; mobile phase: CHCl₃/MeOH=9/1; v/v) to obtain 6 mg of the title compound (amorphous).
[α]$_D^{25}$=−96.3° (c=0.214, CHCl₃)
MS (ESI pos.) m/z: 765 ([M+Na−1]+), 767 ([M+Na+1]+), (ESI neg.) m/z: 741 ([M−H−1]−), 743 ([M−H+1]−)
¹H-NMR (600 MHz, CDCl₃) δ (ppm); 1.47-1.68 (m, 1H), 1.83-1.92 (m, 1H), 1.93-2.08 (m, 1H), 2.27 (s, 3H), 2.28-2.42 (m, 1H), 2.45 (s, 3H), 2.76-2.89 (m, 3H), 3.12-3.27 (m, 1H), 3.70 (s, 3H), 3.88 (s, 3H), 4.69-4.77 (m, 1H), 4.85-4.96 (m, 1H), 6.70 (d, J=8.71 Hz, 1H), 6.88 (s, 1H), 6.93 (dd, J=9.17, 2.29 Hz, 1H), 7.04-7.07 (m, 1H), 7.56 (s, 1H), 7.60 (s, 1H), 8.23 (d, J=2.29 Hz, 1H), 8.32 (d, J=9.17 Hz, 1H)

Example 121

Synthesis of (4R)-1-[5-bromo-1-[(2,4-dimethoxyphenyl)sulfonyl]-3-(2-methoxy-5-methylphenyl)-2-oxo-2,3-dihydro-1H-pyrrolo[2,3-b]pyridin-3-yl]-4-hydroxy-N,N-dimethyl-L-prolinamide (levorotatory isomer and dextrorotatory isomer)

Step 121-1: Synthesis of 5-bromo-1-[(2,4-dimethoxyphenyl)sulfonyl]-3-hydroxy-3-(2-methoxy-5-methylphenyl)-1,3-dihydro-2H-pyrrolo[2,3-b]pyridin-2-one With 800 mg of the compound obtained in Step 120-4 and 592 mg of 2,4-dimethoxy benzene sulfonyl chloride as starting materials, 389 mg of the title compound was obtained by a similar procedure to Example 2.
MS (ESI pos.) m/z: 571 ([M+Na−1]+), 573 ([M+Na+1]+), (ESI neg.) m/z: 547 ([M−H−1]−), 549 ([M−H+1]−)
¹H-NMR (200 MHz, CDCl₃) δ (ppm); 2.35 (s, 3H), 3.68 (s, 3H), 3.74 (s, 3H), 3.87 (s, 3H), 6.42 (d, J=2.20 Hz, 1H), 6.58 (d, J=2.20 Hz, 1H), 6.62 (d, J=2.20 Hz, 1H), 6.72 (s, 1H), 6.76 (s, 1H), 7.08-7.14 (m, 1H), 7.14-7.19 (m, 1H), 7.40-7.47 (m, 1H), 7.49 (d, J=2.20 Hz, 1H), 8.13 (d, J=8.79 Hz, 1H), 8.32 (d, J=2.20 Hz, 1H)

Step 121-2: (4R)-1-[5-bromo-1-[(2,4-dimethoxyphenyl)sulfonyl]-3-(2-methoxy-5-methylphenyl)-2-oxo-2,3-dihydro-1H-pyrrolo[2,3-b]pyridin-3-yl]-4-hydroxy-N,N-dimethyl-L-prolinamide (levorotatory isomer and dextrorotatory isomer) Synthesis of With 300 mg of the compound obtained in Step 121-1 and 281 mg of (4R)-4-hydroxy-N,N-dimethyl-L-prolinamide trifluoroacetate as starting materials, respectively 9 mg (Isomer A: amorphous) and 10 mg (Isomer B: amorphous) of two species of diastereoisomers of the title compound were obtained by a similar procedure to Step 120-6.
Isomer A:
[α]$_D^{25}$=+47.9° (c=0.722, CHCl₃)
MS (ESI pos.) m/z: 689 ([M+H−1]+), 691 ([M+H+1]+), 711 ([M+Na−1]+), 713 ([M+Na+1]+), (ESI neg.) m/z: 687 ([M−H−1]−), 689 ([M−H+1]−)
¹H-NMR (200 MHz, CDCl₃) δ (ppm); 1.60-1.73 (m, 1H), 1.75-1.87 (m, 1H), 2.10-2.18 (m, 1H), 2.29 (s, 3H), 2.38 (s, 3H), 2.61 (s, 3H), 3.58-3.67 (m, 2H), 3.89 (s, 3H), 3.99 (s, 3H), 4.31-4.40 (m, 1H), 6.46 (d, J=2.20 Hz, 1H), 6.64 (dd, J=9.01, 2.42 Hz, 1H), 6.71 (d, J=8.35 Hz, 1H), 7.02-7.13 (m, 2H), 7.42 (d, J=2.20 Hz, 1H), 7.82-7.86 (m, 1H), 8.21 (d, J=2.20 Hz, 1H)
Isomer B:
[α]$_D^{25}$=−95.3° (c=0.590, CHCl₃)
MS (ESI pos.) m/z: 689 ([M+H−1]+), 691 ([M+H+1]+), 711 ([M+Na−1]+), 713 ([M+Na+1]+)
¹H-NMR (600 MHz, CDCl₃) δ (ppm); 1.63-1.72 (m, 2H), 1.80-1.87 (m, 1H), 2.12-2.19 (m, 1H), 2.26 (s, 3H), 2.40 (s, 3H), 2.84 (s, 3H), 3.10-3.16 (m, 1H), 3.73 (s, 3H), 3.81 (s, 3H), 3.86 (s, 3H), 4.74-4.80 (m, 1H), 4.90-4.94 (m, 1H), 6.44 (d, J=2.29 Hz, 1H), 6.61 (dd, J=8.71, 2.29 Hz, 1H), 6.71 (d, J=8.71 Hz, 1H), 7.05 (dd, J=8.25, 2.29 Hz, 1H), 7.54-7.58 (m, 2H), 8.16 (d, J=8.71 Hz, 1H), 8.30 (d, J=2.29 Hz, 1H)

Example 122

Synthesis of (4R)-1-(5-bromo-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 122-1: Synthesis of 5-bromo-3-hydroxy-3-(2-methoxy-5-methylphenyl)-1,3-dihydro-2H-indol-2-one With 56.3 g of 3-bromo-4-methoxy toluene and 45.2 g of 5-bromoisatin as starting materials, 62.8 g of the title compound was obtained by a similar method to Step 21-1.
MS (ESI pos.) m/z: 370 ([M+Na−1]+), 372 ([M+Na+1]+), (ESI neg.) m/z 346 ([M−H−1]−), 348 ([M−H+1]−)

¹H-NMR (200 MHz, CDCl₃) δ (ppm); 2.34 (s, 3H), 3.52 (s, 1H), 3.63 (s, 3H), 6.70-6.82 (m, 2H), 7.07-7.16 (m, 1H), 7.23 (d, J=2.20 Hz, 1H), 7.37 (dd, J=8.35, 1.76 Hz, 1H), 7.45-7.54 (m, 2H)

Step 122-2: Synthesis of (4R)-1-[5-bromo-3-(2-methoxy-5-methylphenyl)-2-oxo-2,3-dihydro-1H-indol-3-yl]-4-hydroxy-N,N-dimethyl-L-prolinamide (levorotatory isomer)

From 62.8 g of the compound obtained in Step 122-1 and 60.8 g of (4R)-4-hydroxy-N,N-dimethyl-L-prolinamide trifluoroacetate, 13.1 g of one among the isomers of the title compound was obtained by a similar method to Step 28-2.
$[\alpha]_D^{25}$=−225° (c=0.208, CHCl₃)
MS (ESI pos.) m/z: 488 ([M+H−1]⁺), 490 ([M+H+1]⁺), 510 ([M+Na−1]⁺), 512 ([M+Na+1]⁺), (ESI neg.) m/z: 486 ([M−H−1]⁻), 488 ([M−H+1]⁻)
¹H-NMR (600 MHz, CDCl₃) δ (ppm); 1.91-2.09 (m, 3H), 2.29-2.32 (m, 3H), 2.50-2.60 (m, 3H), 2.72-2.86 (m, 3H), 2.96-3.10 (m, 1H), 3.27-3.45 (m, 1H), 3.54-3.61 (m, 3H), 4.54-4.68 (m, 1H), 4.84-5.03 (m, 1H), 6.64-6.73 (m, 2H), 7.01-7.05 (m, 1H), 7.13-7.19 (m, 1H), 7.22 (dd, J=8.25, 1.83 Hz, 1H), 7.68 (s, 1H), 9.08 (s, 1H)

Step 122-3: Synthesis of (4R)-1-(5-bromo-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 5.00 g of the compound obtained in Step 122-2 and 3.28 g of 4-methoxy-2-(trifluoromethoxy)benzene sulfonyl chloride as starting material, 6.76 g of the title compound (amorphous) was obtained by a similar method to Example 2.
$[\alpha]_D^{25}$=155° (c=0.612, CHCl₃)
MS (ESI pos.) m/z: 742 ([M+H−1]⁺), 744 ([M+H+1]⁺), 764 ([M+Na−1]⁺), 766 ([M+Na+1]⁺), (ESI neg.) m/z: 740 ([M−H−1]⁻), 742 ([M+H+1]⁻)
¹H-NMR (600 MHz, CDCl₃) δ (ppm); 1.75-1.86 (m, 4H), 2.24-2.29 (m, 3H), 2.34-2.44 (m, 3H), 2.71-2.88 (m, 3H), 3.09-3.26 (m, 1H), 3.48-3.65 (m, 3H), 3.88 (s, 3H), 4.55-4.66 (m, 1H), 4.68-4.81 (m, 1H), 6.65 (d, J=8.25 Hz, 1H), 6.84-6.88 (m, 1H), 6.90-6.95 (m, 1H), 6.99-7.04 (m, 1H), 7.21-7.30 (m, 1H), 7.35-7.42 (m, 1H), 7.50-7.67 (m, 1H), 7.81 (d, J=8.71 Hz, 1H), 8.22-8.37 (m, 1H)

Example 123

Synthesis of (4R)-1-(5-iodo-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 123-1: Synthesis of 5-iodo-3-hydroxy-3-(2-methoxy-5-methylphenyl)-1,3-dihydro-2H-indol-2-one Under nitrogen atmosphere, to a suspension of 54.6 g of 5-iodoisatin in THF (1 L) was added 8.80 g of NaH and the reaction mixture was stirred for one hour. Thereafter, a solution of bromo(2-methoxy-5-methylphenyl)magnesium in THF (20 ml), which was prepared similarly to Step 122-1, was added dropwise over 20 minutes. The solution was stirred at the same temperature for one hour, then, a saturated aqueous solution of NH₄Cl (500 ml) and water (500 ml) were added, the precipitated solid was washed by stirring, then the solid was collected by filtration to obtain 50.8 g of the title compound.
MS (ESI pos.) m/z: 418 ([M+Na]⁺), (ESI neg.) m/z: 394 ([M−H]⁻)
¹H-NMR (600 MHz, DMSO-d₆) δ (ppm); 2.29 (s, 3H), 3.54-3.60 (m, 3H), 6.49-6.51 (m, 1H), 6.65 (d, J=7.79 Hz, 1H), 6.74 (d, J=8.25 Hz, 1H), 6.95-6.98 (m, 1H), 7.03-7.07 (m, 1H), 7.46 (dd, J=8.25, 1.83 Hz, 1H), 7.58 (d, J=1.83 Hz, 1H), 10.35 (s, 1H)

Step 123-2: (4R)-1-[5-iodo-3-(2-methoxy-5-methylphenyl)-2-oxo-2,3-dihydro-1H-indol-3-yl]-4-hydroxy-N, N-dimethyl-L-prolinamide Synthesis of From 39.5 of the compound obtained in Step 123-1 and 46.1 g of (4R)-4-hydroxy-N,N-dimethyl-L-prolinamide trifluoroacetate, 16.8 g of one of the isomers of the title compound was obtained by a similar procedure to Step 28-2.
MS (ESI pos.) m/z: 536 ([M+H]⁺), 558 ([M+Na]⁺), (ESI neg.) m/z: 534 ([M−H]⁻),
¹H-NMR (600 MHz, CDCl₃) δ (ppm); 2.18-2.23 (m, 1H), 2.31 (s, 3H), 2.53 (s, 3H), 2.74-2.82 (m, 3H), 3.34-3.48 (m, 1H), 3.61 (s, 3H), 3.71-3.76 (m, 3H), 4.64-4.71 (m, 1H), 4.87-4.99 (m, 1H), 6.58 (d, J=8.25 Hz, 1H), 6.71 (d, J=8.25 Hz, 1H), 7.02-7.06 (m, 1H), 7.37 (s, 1H), 7.42-7.46 (m, 1H), 7.69 (s, 1H), 8.12 (s, 1H)

Step 123-3: Synthesis of (4R)-1-(5-iodo-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 16.7 g of the compound obtained in Step 123-2 and 9.97 g of 4-methoxy-2-(trifluoromethoxy)benzene sulfonyl chloride as starting material, 20.2 g of the title compound (amorphous) was obtained by a similar procedure to Example 2.
$[\alpha]_D^{25}$=115° (c=0.633, CHCl₃)
MS (ESI pos.) m/z: 790 ([M+H]⁺), 812 ([M+Na]⁺), (ESI neg.) m/z: 788 ([M−H]⁻)
¹H-NMR (600 MHz, CDCl₃) δ (ppm); 1.90-2.07 (m, 1H), 2.27 (s, 3H), 2.33-2.43 (m, 6H), 2.74-2.87 (m, 3H), 3.11-3.26 (m, 1H), 3.50-3.68 (m, 3H), 3.88 (s, 3H), 4.58-4.66 (m, 1H), 4.69-4.80 (m, 1H), 6.66 (d, J=8.25 Hz, 1H), 6.85-6.88 (m, 1H), 6.93 (dd, J=8.94, 2.52 Hz, 1H), 7.00-7.05 (m, 1H), 7.17 (d, J=7.79 Hz, 1H), 7.38-7.47 (m, 1H), 7.54-7.65 (m, 1H), 7.70 (d, J=8.71 Hz, 1H), 8.29-8.36 (m, 1H)

Example 124

Synthesis of (4R)-4-hydroxy-1-(3-(2-methoxy-5-methylphenyl)-1-{[4-methoxy-2-(trifluoromethoxy)phenyl]sulfonyl}-2-oxo-5-pyridin-4-yl-2,3-dihydro-1H-indol-3-yl)-N,N-dimethyl-L-prolinamide (levorotatory isomer)

Under nitrogen atmosphere, to a mixed solution of 500 mg of the compound obtained in Step 123-3, 156 mg of 4-pyridyl boronic acid and 335 mg of Na₂CO₃ in water (3 ml), EtOH (3 ml) and toluene (6 ml) was added 73 mg of tetrakis triphenylphosphine palladium⁰. After one hour refluxing, water and EtOAc were added, liquid separation was performed, the organic layer was washed with saturated brine and dried over Na₂SO₄, then, the drying agent was separated by filtration and the solvent was evaporated under reduced pressure. The obtained residue was purified by column chromatography (silicagel 60N; mobile phase: CHCl$_3$/MeOH=20/1 to 10/1; v/v) to obtain 321 mg of the title compound (amorphous).

[α]$_D^{25}$=−107° (c=0.520, CHCl$_3$)
MS (ESI pos.) m/z: 741 ([M+H]$^+$), 763 ([M+Na]$^+$), (ESI neg.) m/z: 739 ([M−H]$^−$),
$^1$H-NMR (300 MHz, CDCl$_3$) δ (ppm); 1.22-1.29 (m, 3H), 2.28 (s, 3H), 2.40 (s, 3H), 2.83 (s, 3H), 3.05-3.59 (s, 5H), 3.89 (s, 3H), 4.57-4.74 (m, 1H), 4.76-4.93 (m, 1H), 6.66 (d, J=8.24 Hz, 1H), 6.86-6.90 (m, 1H), 6.96 (dd, J=8.94, 2.41 Hz, 1H), 6.99-7.05 (m, 1H), 7.38-7.44 (m, 3H), 7.58 (dd, J=8.70, 2.02 Hz, 1H), 7.71 (s, 1H), 8.06 (d, J=8.70 Hz, 1H), 8.36 (d, J=9.01 Hz, 1H), 8.58-8.62 (m, 2H)

Example 125

Synthesis of (4R)-4-hydroxy-1-(3-(2-methoxy-5-methylphenyl)-1-{[4-methoxy-2-(trifluoromethoxy)phenyl]sulfonyl}-2-oxo-5-piperidin-1-yl-2,3-dihydro-1H-indol-3-yl)-N,N-dimethyl-L-prolinamide (levorotatory isomer)

Under nitrogen atmosphere, a solution of 500 mg of the compound obtained in Step 123-3, 109 mg of piperidine and 183 mg of tert-butoxy sodium in toluene (5 ml) was added with 51 mg of tri tert-butylphosphine and 14 mg of palladium acetate. After stirring at 100° C. for one hour, the solution was added to a saturated aqueous solution of NH$_4$Cl and extracted with EtOAc; the combined organic layer was washed with a saturated aqueous solution of NaHCO$_3$ and saturated brine, then, dried over Na$_2$SO$_4$; the drying agent was separated by filtration and the solvent was evaporated under reduced pressure. The obtained residue was purified by column chromatography (silicagel 60N; mobile phase: CHCl$_3$/MeOH=20/1 to 10/1; v/v) to obtain 115 mg of the title compound (amorphous).

[α]$_D^{25}$=−87° (c=0.361, CHCl$_3$)
MS (CI pos.) m/z: 747 ([M+H]$^+$)
$^1$H-NMR (600 MHz, CDCl$_3$) δ (ppm); 1.42-1.48 (m, 3H), 1.52-1.65 (m, 4H), 2.09-2.20 (m, 1H), 2.29 (s, 3H), 2.50 (d, J=14.67 Hz, 1H), 2.66-2.73 (m, 1H), 2.75 (s, 3H), 2.84-2.95 (m, 4H), 3.01 (s, 3H), 3.55 (dd, J=14.67, 3.21 Hz, 1H), 3.59 (s, 3H), 3.79 (s, 3H), 5.16-5.25 (m, 2H), 6.45 (d, J=2.29 Hz, 1H), 6.50 (d, J=2.75 Hz, 1H), 6.56 (dd, J=9.17, 2.29 Hz, 1H), 6.62 (dd, J=8.94, 2.52 Hz, 1H), 6.69 (d, J=8.25 Hz, 1H), 7.04 (dd, J=8.02, 2.06 Hz, 1H), 7.12 (d, J=9.17 Hz, 1H), 7.78 (d, J=1.83 Hz, 1H), 8.00 (d, J=8.71 Hz, 1H)

Example 126

Synthesis of (4R)-1-(5-cyano-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 126-1: Synthesis of 3-hydroxy-3-(2-methoxy-5-methylphenyl)-2-oxo indoline-5-carbonitrile With 7.06 g of 2-bromo-1-methoxy-4-methyl benzene and 4.03 g of 2,3-dioxo indoline-5-carbonitrile as starting materials, 3.50 g of the title compound (brown amorphous) was obtained by a similar method to Step 21-1.
MS (ESI pos.) m/z: 295 ([M+H]$^+$), 317 ([M+Na]$^+$), (ESI neg.) m/z: 293 ([M−H]$^−$)
$^1$H-NMR (600 MHz, CDCl$_3$) δ (ppm); 2.33 (s, 3H) 3.57 (s, 3H) 3.97 (brs, 1H) 6.73 (d, J=8.3 Hz, 1H) 6.94 (d, J=8.3 Hz, 1H) 7.12 (dd, J=8.7, 2.3 Hz, 1H) 7.32-7.35 (m, 1H) 7.50 (d, J=1.8 Hz, 1H) 7.53 (dd, J=8.3, 1.8 Hz, 1H) 8.50 (brs, 1H)

Step 126-2: (4R)-1-[5-cyano-3-(2-methoxy-5-methylphenyl)-2-oxo-2,3-dihydro-1H-indol-3-yl]-4-hydroxy-N,N-dimethyl-L-prolinamide (levorotatory isomer and dextrorotatory isomer) Synthesis of From 3.50 g of the compound obtained in Step 126-1 and 2.78 g of (4R)-4-hydroxy-N,N-dimethyl-L-prolinamide hydrochloride, respectively 1.26 g (Isomer A: brown solid) and 1.47 g (Isomer B: brown amorphous) of two species of diastereoisomers of the title compound were obtained by a similar method to Step 28-2.

Isomer A: [α]$_D^{29}$=+265° (c=0.107, CHCl$_3$)
MS (ESI pos.) m/z: 435 ([M+H]$^+$), 457 ([M+Na]$^+$), (ESI neg.) m/z: 433 ([M−H]$^−$)
$^1$H-NMR (600 MHz, CDCl$_3$) δ (ppm); 1.84-1.91 (m, 1H) 2.05-2.11 (m, 1H) 2.39 (s, 3H) 2.66 (s, 3H) 2.96-3.03 (m, 3H) 3.54-3.58 (m, 5H) 3.73 (d, J=12.4 Hz, 1H) 3.99 (dd, J=10.6, 6.9 Hz, 1H) 4.35-4.38 (m, 1H) 6.73 (d, J=8.3 Hz, 1H) 6.93 (d, J=8.3 Hz, 1H) 7.09 (dd, 2H) 7.45 (d, J=7.8 Hz, 1H) 7.66-7.77 (m, 1H) 9.47-9.84 (m, 1H)

Isomer B: [α]$_D^{29}$=−251° (c=0.118, CHCl$_3$)
MS (ESI pos.) m/z: 435 ([M+H]$^+$), 457 ([M+Na]$^+$), (ESI neg.) m/z: 433 ([M−H]$^−$)
$^1$H-NMR (600 MHz, CDCl$_3$) δ (ppm); 1.88-1.94 (m, 1H) 1.95-2.11 (m, 1H) 2.29 (s, 3H) 2.58 (s, 3H) 2.74 (s, 3H) 3.02-3.60 (m, 3H) 3.52 (s, 3H) 4.57-4.64 (m, 1H) 4.84 (brs, 1H) 6.68 (d, J=7.8 Hz, 1H) 6.75-6.80 (m, 1H) 7.03 (d, J=7.8 Hz, 1H) 7.22-7.29 (m, 1H) 7.38 (d, J=7.3 Hz, 1H) 7.63 (s, 1H) 9.51 (brs, 1H)

Step 126-3-A: Synthesis of (4R)-1-(5-cyano-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer)

With 391 mg of the compound obtained in Step 126-2 and 272 mg of 4-methoxy-2-(trifluoromethoxy)benzene sulfonyl chloride as starting materials, 581 mg of the title compound (colorless amorphous) was obtained by a similar method as Example 2.

[α]$_D^{28}$=+144° (c=0.103, CHCl$_3$)
MS (ESI pos.) m/z: 689 ([M+H]$^+$), 711 ([M+Na]$^+$), (ESI neg.) m/z: 687 ([M−H]$^−$)
$^1$H-NMR (600 MHz, CDCl$_3$) δ (ppm); 1.67-1.72 (m, 1H) 1.86-1.92 (m, 1H) 2.39 (s, 3H) 2.45 (s, 3H) 2.72 (s, 3H) 3.38-3.49 (m, 2H) 3.45 (s, 3H) 3.81 (dd, J=9.63, 7.34 Hz, 1H) 3.91 (s, 3H) 4.16-4.22 (m, 1H) 6.64 (d, J=8.25 Hz, 1H) 6.90 (s, 1H) 6.94 (dd, J=9.17, 2.29 Hz, 1H) 7.06 (d, J=6.88 Hz, 1H) 7.23-7.28 (m, 1H) 7.59 (dd, J=8.71, 1.83 Hz, 1H) 7.98 (brs, 1H) 8.09 (d, J=8.71 Hz, 1H) 8.28 (d, J=9.17 Hz, 1H)

Step 126-3-B: Synthesis of (4R)-1-(5-cyano-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 485 mg of the compound obtained in Step 126-2 (Isomer B) as starting material, 583 mg of the title compound (colorless amorphous) was obtained by a similar method to Example 2.

[α]$_D^{28}$=−185° (c=0.102, CHCl$_3$)
MS (ESI pos.) m/z: 689 ([M+H]$^+$), 711 ([M+Na]$^+$), (ESI neg.) m/z: 687 ([M−H]$^−$)

¹H-NMR (600 MHz, CDCl₃) δ (ppm); 1.77-1.84 (m, 1H) 1.92-2.14 (m, 1H) 2.28 (s, 3H) 2.41 (s, 3H) 2.71-2.86 (m, 3H) 3.07-3.27 (m, 2H) 3.47-3.68 (m, 4H) 3.88 (s, 3H) 4.56-4.64 (m, 1H) 4.67-4.79 (m, 1H) 6.66 (d, J=8.3 Hz, 1H) 6.85-6.88 (m, 1H) 6.94 (dd, J=9.2, 2.3 Hz, 1H) 7.04 (dd, J=8.3, 2.3 Hz, 1H) 7.38-7.46 (m, 1H) 7.57 (dd, J=8.3, 1.8 Hz, 1H) 7.59-7.70 (m, 1H) 8.06 (d, J=8.7 Hz, 1H) 8.32 (d, J=8.3 Hz, 1H)

Example 127

Synthesis of 3-{(2S,4R)-2-[(dimethylamino)carbonyl]-4-hydroxypyrrolidin-1-yl}-3-(2-methoxy-5-methylphenyl)-1-{[4-methoxy-2-(trifluoromethoxy)phenyl]sulfonyl}-2-oxo indoline-5-carboxylic acid (levorotatory isomer)

A solution of 200 mg of the compound obtained in Step 126-3 in concentrated hydrochloric acid (6 ml) was heat-refluxed for two hours. After the reaction, the solution was concentrated under reduced pressure, and the residue was purified by column chromatography (silicagel 60; mobile phase: MeOH/CHCl₃=2/98 to 5/95; v/v) to obtain 111 mg of the title compound (colorless amorphous).

$[\alpha]_D^{24}$=−156° (c=0.109, CHCl₃)
MS (ESI pos.) m/z: 689 ([M+H]⁺), 711 ([M+Na]⁺), (ESI neg.) m/z: 687 ([M−H]⁻)
¹H-NMR (600 MHz, CDCl₃) δ (ppm); 1.45-1.63 (m, 1H) 1.79-2.04 (m, 2H) 2.20 (s, 3H) 2.45 (s, 3H) 2.82 (brs, 3H) 3.03-3.15 (m, 1H) 3.63 (brs, 3H) 3.87 (s, 3H) 4.72-4.88 (m, 2H) 6.67 (d, J=8.25 Hz, 1H) 6.83-6.86 (m, 1H) 6.93 (dd, J=9.17, 2.29 Hz, 1H) 6.99-7.01 (m, 1H) 7.69 (brs, 1H) 7.98-8.07 (m, 3H) 8.31 (d, J=9.17 Hz, 1H)

Example 128

Synthesis of 3-{(2S,4R)-2-[(dimethylamino)carbonyl]-4-hydroxypyrrolidin-1-yl}-3-(2-methoxy-5-methylphenyl)-1-{[4-methoxy-2-(trifluoromethoxy)phenyl]sulfonyl}-2-oxo indoline-5-carboxamide (levorotatory isomer)

Concentrated hydrochloric acid (4 ml) was added to 40 mg of the compound obtained in Step 126-4, and the solution was stirred at room temperature for 15 hours. The reaction solution was poured in NaHCO₃, and extraction was carried out in EtOAc. The extract was dried over Na₂SO₄, then, the drying agent was separated by filtration and the solvent was evaporated under reduced pressure. The title compound in the amounts of 35 mg (light brown solid) was obtained.

$[\alpha]_D^{25}$=151° (c=0.186, CHCl₃)
MS (ESI pos.) m/z: 707 ([M+H]⁺)

¹H-NMR (600 MHz, CDCl₃) δ (ppm); 1.16-6.15 (m, 18H), 3.88 (s, 3H), 6.60-6.67 (m, 1H), 6.85-6.88 (m, 1H), 6.91-6.95 (m, 1H), 6.98-7.04 (m, 1H), 7.46-7.88 (m, 3H), 7.99-8.05 (m, 1H), 8.28-8.36 (m, 1H)

Example 129

Synthesis of (4R)-4-hydroxy-1-(3-(2-methoxy-5-methylphenyl)-1-{[4-methoxy-2-(trifluoromethoxy)phenyl]sulfonyl}-5-nitro-2-oxo-2,3-dihydro-1H-indol-3-yl)-N,N-dimethyl-L-prolinamide (levorotatory isomer and dextrorotatory isomer)

Step 129-1: Synthesis of 3-hydroxy-3-(2-methoxy-5-methylphenyl)-5-nitro-1,3-dihydro-2H-indol-2-one With 10.0 g of 2-bromo-4-methyl anisole and 6.00 g of 5-nitroisatin as starting materials, 9.40 g of the title compound (brown solid) was obtained by a similar method to Step 21-1.
MS (ESI neg.) m/z: 313 ([M−H]⁻)
¹H-NMR (600 MHz, DMSO-d₆) δ (ppm); 2.35 (s, 3H), 3.38 (s, 3H), 6.77-6.88 (m, 2H), 7.00-7.07 (m, 1H), 7.12 (dd, J=8.3, 2.3 Hz, 1H), 7.53-7.60 (m, 1H), 7.67 (s, 1H), 8.02-8.30 (m, 1H), 11.04 (s, 1H)

Step 129-2: Synthesis of (4R)-4-hydroxy-1-[3-(2-methoxy-5-methylphenyl)-5-nitro-2-oxo-2,3-dihydro-1H-indol-3-yl]-N,N-dimethyl-L-prolinamide From 5.00 g of the compound obtained in Step 129-1 and 3.40 g of (4R)-4-hydroxy-N,N-dimethyl-L-prolinamide hydrochloride, 3.00 g of the title compound (diastereoisomer mixture: yellow solid) was obtained by a similar method to Step 21-2.
MS (ESI pos.) m/z: 455 ([M+H]⁺), 477 ([M+Na]⁺), (ESI neg.) m/z: 453 ([M−H]⁻)
¹H-NMR (600 MHz, DMSO-d₆) δ (ppm); 1.63-1.93 (m, 2H), 2.24-2.65 (m, 7H), 3.21 (t, J=4.6 Hz, 1H), 3.42-3.47 (m, 3H), 3.62-5.00 (m, 4H), 6.79-6.85 (m, 1H), 6.94-7.03 (m, 1H), 7.05-7.12 (m, 1H), 7.36 (d, J=2.3 Hz, 1H), 7.59 (d, J=2.3 Hz, 1H), 7.70-7.93 (m, 1H), 8.05-8.21 (m, 2H), 11.01-11.28 (m, 1H)

Step 129-3: Synthesis of (4R)-4-hydroxy-1-(3-(2-methoxy-5-methylphenyl)-1-{[4-methoxy-2-(trifluoromethoxy)phenyl]sulfonyl}-5-nitro-2-oxo-2,3-dihydro-1H-indol-3-yl)-N,N-dimethyl-L-prolinamide (levorotatory isomer and dextrorotatory isomer)

With 1.90 g of the compound obtained in Step 129-2 (diastereoisomer mixture) and 1.34 g of 4-methoxy-2-(trifluoromethoxy)benzene sulfonyl chloride as starting materials, respectively 1.52 g (Isomer A: yellow amorphous) and 1.01 g (Isomer B: yellow amorphous) of two species of diastereoisomers of the title compound were obtained by a similar method to Example 2.
Isomer A: $[\alpha]_D^{25}$=+121° (c=0.217, CHCl₃)
MS (ESI pos.) m/z: 731 ([M+Na]⁺), (ESI neg.) m/z: 707 ([M−H]⁻)
¹H-NMR (600 MHz, CDCl₃) δ (ppm); 1.67-1.98 (m, 2H), 2.41 (s, 3H), 2.49 (s, 3H), 2.57 (s, 3H), 3.39-3.51 (m, 4H), 3.82 (dd, J=9.4, 7.1 Hz, 1H), 3.92 (s, 3H), 4.19-4.23 (m, 1H), 6.65 (d, J=8.3 Hz, 1H), 6.89-6.93 (m, 1H), 6.95 (dd, J=8.9, 2.5 Hz, 1H), 7.07 (dd, J=8.3, 1.8 Hz, 1H), 7.81 (d, J=2.3 Hz, 1H), 8.01 (d, J=14.7 Hz, 1H), 8.13-8.17 (m, 1H), 8.19-8.25 (m, 1H), 8.30 (d, J=8.7 Hz, 1H)
Isomer B: $[\alpha]_D^{25}$=−69.9° (c=0.269, CHCl₃)
MS (ESI pos.) m/z: 709 ([M+H]⁺), 731 ([M+Na]⁺), (ESI neg.) m/z: 707 ([M−H]⁻)
¹H-NMR (600 MHz, CDCl₃) δ (ppm); 1.71-3.72 (m, 17H), 3.90 (s, 3H), 4.51-4.84 (m, 2H), 6.67 (d, J=8.3 Hz, 1H), 6.88

(s, 1H), 6.96 (dd, J=9.2, 2.3 Hz, 1H), 7.05 (dd, J=8.3, 2.3 Hz, 1H), 7.65-7.75 (m, 1H), 7.97-8.04 (m, 1H), 8.12 (d, J=8.7 Hz, 1H), 8.20 (dd, J=9.2, 2.3 Hz, 1H), 8.34 (d, J=9.2 Hz, 1H)

Example 130

(4R)-1-(5-amino-3-(2-methoxy-5-methylphenyl)-1-{[4-methoxy-2-(trifluoromethoxy)phenyl]s ulfonyl}-2-oxo-2,3-dihydro-1H-indol-3-yl)-4-hydroxy-N,N-dimethyl-L-prolinamide (levorotatory isomer) Synthesis of Under nitrogen atmosphere, to a solution of 500 mg of the compound obtained in Step 129-3 (Isomer B) in acetic acid (7 ml) was added 394 mg of iron and then the reaction mixture was warmed to an external temperature of 70° C. After stirring at the same temperature for 10 hours, the solution was cooled to room temperature. The solid was filtered out, and the filtrate was extracted with CHCl$_3$. The organic layer was washed with a saturated aqueous solution of NaHCO$_3$, and saturated brine, in this order; then, after drying over Na$_2$SO$_4$, the drying agent was removed by filtration and the solvent was evaporated under reduced pressure. The obtained residue was purified by column chromatography (Chromatorex NH; mobile phase: CHCl$_3$/MeOH=14/1 to 10/1; v/v) to obtain 251 mg of the title compound (brown amorphous).
$[\alpha]_D^{25}$=−134° (c=0.297, CHCl$_3$)
MS (ESI pos.) m/z: 679 ([M+H]$^+$), 701 ([M+Na]$^+$), (ESI neg.) m/z: 677 ([M−H]$^−$)
$^1$H-NMR (600 MHz, CDCl$_3$) δ (ppm); 1.49 (m, 1H), 1.69-1.92 (m, 3H), 1.98-2.12 (m, 1H), 2.25 (s, 3H), 2.38 (s, 3H), 2.81 (s, 3H), 3.15 (s, 1H), 3.61 (m, 4H), 3.87 (s, 3H), 4.52-4.65 (m, 1H), 4.81 (s, 1H), 6.49 (s, 1H), 6.57 (dd, J=8.7, 2.8 Hz, 1H), 6.62-6.67 (m, 1H), 6.87 (d, J=1.8 Hz, 1H), 6.92 (dd, J=8.9, 2.5 Hz, 1H), 6.99 (dd, J=8.3, 1.8 Hz, 1H), 7.54-7.63 (m, 1H), 7.68 (d, J=8.7 Hz, 1H), 8.31 (d, J=8.7 Hz, 1H)

Example 131

Synthesis of (4S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 131-1: Synthesis of (4S)-1-[5-chloro-3-(2-methoxy-5-methylphenyl)-2-oxo-2,3-dihydro-1H-indol-3-yl]-4-hydroxy-N,N-dimethyl-L-prolinamide From 1.30 g of the compound obtained in Step 103-1 and (4S)-4-hydroxy-N,N-dimethyl-L-prolinamide trifluoroacetate (4.68 mmol), 1.62 g of the title compound (diastereoisomer mixture: colorless amorphous) was obtained by a similar method to Step 21-2.
MS (ESI pos.) m/z: 444 ([M+H]$^+$), 466 ([M+Na]$^+$), (ESI neg.) m/z: 442 ([M−H]$^−$)
$^1$H-NMR (300 MHz, DMSO-d$_6$) δ (ppm); 1.37-2.98 (m, 13H), 3.36-3.65 (m, 4H), 3.92-4.13 (m, 4H), 4.98-5.22 (m, 1H), 5.94-7.91 (m, 6H), 10.47-10.73 (m, 1H)

Step 131-2: Synthesis of (4S)-1-(5-chloro-3-(2-methoxy-5-methylphenyl)-1-{[4-methoxy-2-(trifluoromethoxy)phenyl]sulf onyl}-2-oxo-2,3-dihydro-1H-indol-3-yl)-4-hydroxy-N,N-dimethyl-L-prolinamide (levorotatory isomer and dextrorotatory isomer)

With 1.00 g of the compound obtained in Step 131-1 and 785 mg of 4-methoxy-2-(trifluoromethoxy)benzene sulfonyl chloride as starting materials, respectively 263 mg (Isomer A: orange color amorphous) and 201 mg (Isomer B: orange color amorphous) of two species of diastereoisomers of the title compound were obtained by a similar method to Example 2.
Isomer A: $[\alpha]_D^{25}$=+81.2° (c=0.161, CHCl$_3$)
MS (ESI pos.) m/z: 698 ([M+H]$^+$), 719 ([M+Na]$^+$), (ESI neg.) m/z: 696 ([M−H]$^−$)
$^1$H-NMR (499 MHz, CDCl$_3$) δ (ppm); 1.33-1.94 (m, 3H), 2.35 (s, 3H), 2.37 (s, 3H), 2.80 (s, 3H), 3.04 (dd, J=10.7, 3.0 Hz, 1H), 3.22 (dd, J=10.4, 1.8 Hz, 1H), 3.38 (s, 3H), 3.72 (d, J=10.1 Hz, 1H), 3.92 (s, 3H), 4.04-4.18 (m, 1H), 6.63 (d, J=8.2 Hz, 1H), 6.88-6.91 (m, 2H), 6.97 (dd, J=9.0, 2.3 Hz, 1H), 7.03 (dd, J=8.4, 2.3 Hz, 1H), 7.28 (dd, J=8.8, 2.1 Hz, 1H), 7.89 (d, J=8.8 Hz, 2H), 8.33 (d, J=9.1 Hz, 1H)
Isomer B: $[\alpha]_D^{25}$=−72.8° (c=0.497, CHCl$_3$)
MS (ESI pos.) m/z: 698 ([M+H]$^+$), 719 ([M+Na]$^+$), (ESI neg.) m/z: 696 ([M−H]$^−$)
$^1$H-NMR (499 MHz, CDCl$_3$) δ (ppm); 1.57 (s, 2H), 1.74-1.90 (m, 1H), 2.05-2.16 (m, 1H), 2.38 (s, 3H), 2.43 (s, 3H), 2.77 (s, 3H), 3.31-3.48 (m, 4H), 3.73 (m, 1H), 3.85-3.98 (m, 4H), 4.87-5.03 (m, 1H), 6.65 (d, J=8.2 Hz, 1H), 6.85-6.95 (m, 2H), 7.04 (dd, J=8.2, 1.8 Hz, 1H), 7.25-7.29 (m, 1H), 7.79-8.06 (m, 2H), 8.32 (d, J=8.8 Hz, 1H)

Example 132

Synthesis of (4S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

Step 132-1: Synthesis of (4S)-1-[5-chloro-3-(2-methoxy-5-methylphenyl)-2-oxo-2,3-dihydro-1H-indol-3-yl]-4-fluoro-N, N-dimethyl-L-prolinamide (levorotatory isomer and dextrorotatory isomer)

From 610 mg of the compound obtained in Step 103-1 and (4S)-4-fluoro-N,N-dimethyl-L-prolinamide trifluoroacetate (2.21 mmol), respectively 184 mg (Isomer A: colorless amorphous) and 293 mg (Isomer B: colorless amorphous) of two species of diastereoisomers of the title compound were obtained by a similar method to Step 21-2.
Isomer A: $[\alpha]_D^{25}$=+179° (c=0.196, CHCl$_3$)
MS (ESI pos.) m/z: 446 ([M+H]$^+$), 468 ([M+Na]$^+$), (ESI neg.) m/z: 444 ([M−H]$^−$)
$^1$H-NMR (300 MHz, DMSO-d$_6$) δ (ppm); 1.63-1.95 (m, 1H), 2.13-2.61 (m, 9H), 3.24-3.35 (m, 1H), 3.36-3.54 (m, 4H), 3.74-3.97 (m, 2H), 4.91-5.41 (m, 1H), 6.51 (d, J=2.2 Hz, 1H), 6.69-6.96 (m, 2H), 6.97-7.29 (m, 2H), 7.82 (d, J=2.0 Hz, 1H), 10.50 (s, 1H)
Isomer B: $[\alpha]_D^{25}$=−294° (c=0.134, CHCl$_3$)
MS (ESI pos.) m/z: 446 ([M+H]$^+$), 468 ([M+Na]$^+$), (ESI neg.) m/z: 444 ([M−H]$^−$)
$^1$H-NMR (300 MHz, DMSO-d$_6$) δ (ppm); 1.74-3.82 (m, 16H), 4.60-4.74 (m, 1H), 5.12-5.46 (m, 1H), 6.69-6.88 (m, 3H), 7.06 (dd, J=7.7, 2.3 Hz, 1H), 7.17 (dd, J=8.2, 2.3 Hz, 1H), 7.69 (s, 1H), 10.32 (s, 1H)

Step 132-2: Synthesis of (4S)-1-(5-chloro-3-(2-methoxy-5-methylphenyl)-1-{[4-methoxy-2-(trifluoromethoxy)phenyl]sulf onyl}-2-oxo-2,3-dihydro-1H-indol-3-yl)-4-fluoro-N,N-dimethyl-L-prolinamide (levorotatory isomer)

With 200 mg of the compound obtained in Step 132-1 (Isomer B) and 160 mg of 4-methoxy-2-(trifluoromethoxy)

benzene sulfonyl chloride as starting materials, 62 mg of the title compound (colorless amorphous) was obtained by a similar method to Example 2.

$[\alpha]_D^{25}$=−200° (c=0.077, CHCl$_3$)

MS (ESI pos.) m/z: 700 ([M+H]$^+$), 722 ([M+Na]$^+$)

$^1$H-NMR (499 MHz, CDCl$_3$) δ (ppm); 1.61-5.53 (m, 21H), 6.53-7.44 (m, 6H), 7.52-8.47 (m, 3H)

Example 133

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-D-prolinamide (levorotatory isomer and dextrorotatory isomer)

Step 133-1: Synthesis of (4R)-1-[5-chloro-3-(2-methoxy-5-methylphenyl)-2-oxo-2,3-dihydro-1H-indol-3-yl]-4-hydroxy-N,N-dimethyl-D-prolinamide (diastereoisomer mixture)

With 1.51 g of the compound that is obtained at Step 109-4 and (4R)-4-hydroxy-N,N-dimethyl-D-prolinamide trifluoroacetate (4.68 mmol) as starting materials, 1.63 g of the title compound (diastereoisomer mixture: light brown solid) was obtained by a similar method to Step 4-2.

MS (ESI pos.) m/z: 444 ([M+H]$^+$), 466 ([M+Na]$^+$), (ESI neg.) m/z: 442 ([M−H]$^−$)

$^1$H-NMR (600 MHz, DMSO-d$_6$) δ (ppm); 1.42-1.55 (m, 1H), 2.03-2.94 (m, 12H), 3.33-3.60 (m, 4H), 3.91-4.23 (m, 1H), 4.89-5.28 (m, 1H), 5.98-7.29 (m, 5H), 7.48-7.95 (m, 1H), 10.45-10.75 (m, 1H)

Step 133-2: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-D-prolinamide (levorotatory isomer and dextrorotatory isomer)

With 700 mg of the compound obtained in Step 133-1 and 505 mg of 4-methoxy-2-(trifluoromethoxy)benzene sulfonyl chloride as starting materials, respectively 219 mg (Isomer A: colorless amorphous) and 314 mg (Isomer B: colorless amorphous) of two species of diastereoisomers of the title compound were obtained by a similar method to Example 2.

Isomer A: $[\alpha]_D^{25}$=−114° (c=0.293, CHCl$_3$)

MS (ESI pos.) m/z: 698 ([M+H]$^+$), 720 ([M+Na]$^+$), (ESI neg.) m/z: 696 ([M−H]$^−$)

$^1$H-NMR (600 MHz, CDCl$_3$) δ (ppm); 1.59-1.69 (m, 1H), 1.80-1.91 (m, 1H), 2.35-2.40 (m, 7H), 2.82 (s, 3H), 3.06 (d, J=1.8 Hz, 1H), 3.24 (d, J=10.1 Hz, 1H), 3.39 (s, 3H), 3.73 (d, J=10.1 Hz, 1H), 3.93 (s, 3H), 4.13 (s, 1H), 6.64 (d, J=8.3 Hz, 1H), 6.85-7.09 (m, 4H), 7.18-7.40 (m, 1H), 7.90 (d, J=9.2 Hz, 2H), 8.34 (d, J=9.2 Hz, 1H)

Isomer B: $[\alpha]_D^{25}$=+139° (c=0.359, CHCl$_3$)

MS (ESI pos.) m/z: 698 ([M+H]$^+$), 720 ([M+Na]$^+$), (ESI neg.) m/z: 696 ([M−H]$^−$)

$^1$H-NMR (600 MHz, CDCl$_3$) δ (ppm); 1.54-1.67 (m, 2H), 2.22-2.27 (m, 1H), 2.32 (d, J=1.5 Hz, 6H), 2.86 (s, 4H), 3.60 (s, 3H), 3.91 (s, 4H), 4.93 (d, J=8.7 Hz, 1H), 6.68 (d, J=8.3 Hz, 1H), 6.82-6.86 (m, 1H), 6.93 (dd, J=9.2, 2.3 Hz, 1H), 7.06 (dd, J=8.7, 1.8 Hz, 1H), 7.14 (d, J=2.3 Hz, 1H), 7.22-7.28 (m, 1H), 7.63 (s, 1H), 7.84 (d, J=8.7 Hz, 1H), 8.30 (d, J=9.2 Hz, 1H)

Example 134

Synthesis of (4S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-D-prolinamide (dextrorotatory isomer)

Step 134-1: Synthesis of (4S)-1-[5-chloro-3-(2-methoxy-5-methylphenyl)-2-oxo-2,3-dihydro-1H-indol-3-yl]-4-hydroxy-N,N-dimethyl-D-prolinamide (levorotatory isomer and dextrorotatory isomer)

With 1.51 g of the compound that is obtained at Step 109-4 and (4S)-4-hydroxy-N,N-dimethyl-D-prolinamide trifluoroacetate (4.68 mmol) as starting materials, respectively 728 mg (Isomer A: colorless solid) and 770 mg (Isomer B: light orange color amorphous) of two species of diastereoisomers of the title compound were obtained by a similar method to Step 4-2.

Isomer A: $[\alpha]_D^{25}$=−213° (c=0.280, CHCl$_3$)

MS (ESI pos.) m/z: 444 ([M+H]$^+$), 466 ([M+Na]$^+$), (ESI neg.) m/z: 442 ([M−H]$^−$)

$^1$H-NMR (600 MHz, DMSO-d$_6$) δ (ppm); 1.61-1.69 (m, 1H), 1.77-1.88 (m, 1H), 2.30-2.63 (m, 9H), 3.12-3.25 (m, 2H), 3.44 (s, 3H), 3.66 (dd, J=8.9, 6.2 Hz, 1H), 4.18-4.26 (m, 1H), 4.54 (d, J=4.6 Hz, 1H), 6.50 (d, J=2.3 Hz, 1H), 6.80 (dd, J=8.5, 4.8 Hz, 2H), 7.04-7.09 (m, 1H), 7.16 (dd, J=8.3, 2.3 Hz, 1H), 7.82 (s, 1H), 10.53 (s, 1H)

Isomer B: $[\alpha]_D^{25}$=+237° (c=0.522, CHCl$_3$)

MS (ESI pos.) m/z: 444 ([M+H]$^+$), 466 ([M+Na]$^+$), (ESI neg.) m/z: 442 ([M−H]$^−$)

$^1$H-NMR (600 MHz, DMSO-d$_6$) δ (ppm); 1.60-1.89 (m, 2H), 2.24 (s, 3H), 2.39-2.46 (m, 3H), 2.58-3.22 (m, 5H), 3.47 (s, 3H), 4.36-4.48 (m, 1H), 4.69-4.88 (m, 2H), 6.74-6.83 (m, 3H), 7.04 (dd, J=8.5, 2.1 Hz, 1H), 7.17 (dd, J=8.3, 2.3 Hz, 1H), 7.65 (s, 1H), 10.50 (s, 1H)

Step 134-2: Synthesis of (4S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-D-prolinamide (dextrorotatory isomer)

With 300 mg of the compound obtained in Step 134-1 (Isomer B) and 220 mg of 4-methoxy-2-(trifluoromethoxy) benzene sulfonyl chloride as starting materials, 340 mg of the title compound (colorless amorphous) was obtained by a similar method to Example 2.

$[\alpha]_D^{25}$=+168° (c=0.415, CHCl$_3$)

MS (ESI pos.) m/z: 698 ([M+H]$^+$), 720 ([M+Na]$^+$), (ESI neg.) m/z: 696 ([M−H]$^−$)

$^1$H-NMR (600 MHz, CDCl$_3$) δ (ppm); 1.32-2.16 (m, 4H), 2.28 (s, 3H), 2.40 (s, 3H), 2.81 (s, 3H), 3.01-3.37 (m, 1H), 3.51-3.67 (m, 3H), 3.89 (s, 3H), 4.55-4.87 (m, 2H), 6.66 (d, J=8.3 Hz, 1H), 6.85-6.88 (m, 1H), 6.94 (dd, J=8.7, 2.3 Hz, 1H), 7.03 (dd, J=8.3, 2.3 Hz, 1H), 7.13 (s, 1H), 7.24 (dd, J=8.7, 2.3 Hz, 1H), 7.60 (s, 1H), 7.88 (d, J=8.7 Hz, 1H), 8.33 (d, J=8.7 Hz, 1H)

Example 135

Synthesis of Methyl (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-L-prolinate (levorotatory isomer)

Step 135-1: Synthesis of methyl (4R)-1-[5-chloro-3-(2-methoxy-5-methylphenyl)-2-oxo-2,3-dihydro-1H-indol-3-yl]-4-hydroxy-L-prolinate (levorotatory isomer and dextrorotatory isomer)

From 1.30 g of the compound obtained in Step 103-1 and methyl (4R)-4-hydroxy-L-prolinate trifluoroacetate (4.69 mmol), respectively 583 mg (Isomer A: light yellow amorphous) and 706 mg (Isomer B: orange color amorphous) of two species of diastereoisomers of the title compound were obtained by a similar method to Step 21-2.

Isomer A: $[\alpha]_D^{25}=+116°$ (c=0.210, CHCl$_3$)
MS (ESI pos.) m/z: 431 ([M+H]$^+$), 453 ([M+Na]$^+$), (ESI neg.) m/z: 429 ([M−H]$^−$)
$^1$H-NMR (300 MHz, DMSO-d$_6$) δ (ppm); 1.74-2.30 (m, 2H), 2.36 (s, 3H), 3.10-3.28 (m, 2H), 3.44 (s, 3H), 3.53-3.84 (m, 3H), 4.12-5.45 (m, 3H), 6.48 (d, J=2.2 Hz, 1H), 6.81 (dd, J=10.3, 8.2 Hz, 2H), 7.09 (dd, J=8.2, 2.4 Hz, 1H), 7.17 (dd, J=8.3, 2.3 Hz, 1H), 7.67 (s, 1H), 10.58 (s, 1H)

Isomer B: $[\alpha]_D^{25}=-223°$ (c=0.752, CHCl$_3$)
MS (ESI pos.) m/z: 431 ([M+H]$^+$), 453 ([M+Na]$^+$), (ESI neg.) m/z: 429 ([M−H]$^−$)

$^1$H-NMR (300 MHz, DMSO-d$_6$) δ (ppm); 1.68-2.04 (m, 2H), 2.15-2.59 (m, 6H), 2.89-3.09 (m, 1H), 3.36-3.56 (m, 4H), 4.21-4.38 (m, 2H), 5.00 (d, J=4.5 Hz, 1H), 6.73-6.87 (m, 3H), 7.04 (dd, J=8.3, 2.3 Hz, 1H), 7.18 (dd, J=8.3, 2.1 Hz, 1H), 7.62 (s, 1H), 10.51 (s, 1H)

Step 135-2: Synthesis of methyl (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-L-prolinate (levorotatory isomer)

With 300 mg of the compound obtained in Step 135-1 (Isomer B) and 240 mg of 4-methoxy-2-(trifluoromethoxy)benzene sulfonyl chloride as starting materials, 213 mg of the title compound (colorless amorphous) was obtained by a similar method to Example 2.

$[\alpha]_D^{25}=-148°$ (c=0.341, CHCl$_3$)
MS (ESI pos.) m/z: 685 ([M+H]$^+$), 707 ([M+Na]$^+$), (ESI neg.) m/z: 683 ([M−H]$^−$)
$^1$H-NMR (500 MHz, CDCl$_3$) δ (ppm); 1.32-2.02 (m, 4H), 2.28 (s, 3H), 3.13-3.28 (m, 1H), 3.40-3.60 (m, 6H), 3.89 (s, 3H), 4.22-4.53 (m, 2H), 6.67 (d, J=8.5 Hz, 1H), 6.86-6.88 (m, 1H), 6.94 (dd, J=8.8, 2.4 Hz, 1H), 7.00-7.04 (m, 1H), 7.06 (s, 1H), 7.17-7.38 (m, 1H), 7.50-7.65 (m, 1H), 7.88 (d, J=8.8 Hz, 1H), 8.34 (d, J=8.8 Hz, 1H)

Example 136

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

Step 136-1: Synthesis of (4R)-1-[5-chloro-3-(2-methoxy-5-methylphenyl)-2-oxo-2,3-dihydro-1H-indol-3-yl]-4-fluoro-N,N-dimethyl-L-prolinamide (levorotatory isomer and dextrorotatory isomer)

From 1.30 g of the compound obtained in Step 103-1 and (4R)-4-fluoro-N,N-dimethyl-L-prolinamide trifluoroacetate (4.69 mmol), respectively 596 mg (Isomer A: yellow solid) and 834 mg (Isomer B: orange color amorphous) of two species of diastereoisomers of the title compound were obtained by a similar method to Step 21-2.

Isomer A: $[\alpha]_D^{25}=+116°$ (c=0.105, CHCl$_3$)
MS (ESI pos.) m/z: 446 ([M+H]$^+$), 468 ([M+Na]$^+$), (ESI neg.) m/z: 444 ([M−H]$^−$)
$^1$H-NMR (300 MHz, DMSO-d$_6$) δ (ppm); 1.60-2.35 (m, 2H), 2.33-2.61 (m, 7H), 2.73-3.16 (m, 1H), 3.43 (s, 3H), 3.61-4.13 (m, 3H), 5.00-5.61 (m, 2H), 6.51 (d, J=2.2 Hz, 1H), 6.81 (d, J=8.4 Hz, 2H), 6.96-7.32 (m, 2H), 7.82 (d, J=2.0 Hz, 1H), 10.50 (s, 1H)

Isomer B: $[\alpha]_D^{25}=-200°$ (c=0.509, CHCl$_3$)
MS (ESI pos.) m/z: 446 ([M+H]$^+$), 468 ([M+Na]$^+$), (ESI neg.) m/z: 444 ([M−H]$^−$)
$^1$H-NMR (300 MHz, DMSO-d$_6$) δ (ppm); 1.70-3.19 (m, 11H), 3.36-3.72 (m, 4H), 4.57-4.79 (m, 2H), 5.08-5.53 (m, 1H), 6.66-6.95 (m, 3H), 6.98-7.26 (m, 2H), 7.69 (s, 1H), 10.33 (s, 1H)

Step 136-2: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-fluoro-N,N-dimethyl-L-prolinamide (levorotatory isomer)

With 300 mg of the compound obtained in Step 136-1 (Isomer B) and 230 mg of 4-methoxy-2-(trifluoromethoxy)benzene sulfonyl chloride as starting materials, 198 mg of the title compound (colorless amorphous) was obtained by a similar method to Example 2.

$[\alpha]_D^{25}=-59°$ (c=0.380, CHCl$_3$)
MS (ESI pos.) m/z: 700 ([M+H]$^+$), 722 ([M+Na]$^+$)
$^1$H-NMR (500 MHz, CDCl$_3$) δ (ppm); 1.19-4.01 (m, 18H), 4.20-5.52 (m, 3H), 6.57-7.36 (m, 6H), 7.53-8.47 (m, 3H)

Example 137

Synthesis of (3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl acetate (levorotatory isomer)

Step 137-1: Synthesis of tert-butyl (2S,4R)-2-[(dimethylamino)carbonyl]-4-hydroxypyrrolidine-1-carboxylate To a solution of 3.00 g of the compound that is obtained at Step 6-1a and 354 mg of DMAP in THF (15 ml) was added 2.37 g of acetic anhydride and the reaction mixture was stirred at room temperature for 3 hours. To the reaction solution was added EtOH, and the reaction mixture was stirred for 30 minutes, then, and the reaction mixture was concentrated under reduced pressure. EtOAc was added to the obtained residue and dissolved; after washing with a saturated aqueous solution of NH$_4$Cl and with saturated brine, and dried over MgSO$_4$, the drying agent was separated by filtration, and the filtrate was concentrated. The obtained residue was purified by column chromatography (silicagel 60; mobile phase: CHCl$_3$/MeOH/NH$_4$OH=20/0/0 to 20/1/0.1; v/v/v) to obtain 3.45 g of the title compound (pale yellow solid).

MS (ESI pos.) m/z: 301 ([M+H]$^+$), 323 ([M+Na]$^+$)

$^1$H-NMR (300 MHz, CDCl$_3$) δ (ppm); 1.38-1.48 (m, 9H), 2.07 (s, 3H), 2.11-2.35 (m, 2H), 2.95-3.02 (m, 3H), 3.05-3.15 (m, 3H), 3.54-3.83 (m, 2H), 4.65-4.85 (m, 1H), 5.27-5.35 (m, 1H)

Step 137-2: Synthesis of
(3R,5S)-5-[(dimethylamino)carbonyl]pyrrolidin-3-yl
acetate trifluoroacetate From 1.32 g of the compound obtained in Step 137-1, 2.62 g of the title compound (pale yellow oil) was obtained by a similar procedure to Step 4-1. The resultant compound was subjected to the next step without purification.

MS (ESI pos.) m/z: 201 ([M+H]$^+$)

$^1$H-NMR (300 MHz, DMSO-d$_6$) δ (ppm); 2.02-2.17 (m, 1H), 2.04 (s, 3H), 2.47-2.65 (m, 1H), 2.91 (s, 3H), 3.00 (s, 3H), 3.29-3.39 (m, 1H), 3.43-3.58 (m, 1H), 4.67-4.80 (m, 1H), 5.26-5.34 (m, 1H), 8.78 (brs, 1H), 9.85 (brs, 1H)

Step 137-3: Synthesis of (3R,5S)-1-[5-chloro-3-(2-methoxy-5-methylphenyl)-2-oxo-2,3-dihydro-1H-indol-3-yl]-5-[(dimet hylamino)carbonyl]pyrrolidin-3-yl acetate (levorotatory isomer and dextrorotatory isomer)

To a solution of 1.29 g of the compound that is obtained at Step 109-4 and the compound that is obtained at Step 137-2 (4.40 mmol) in CHCl$_3$ (12.9 ml) was added dropwise 2.43 g of Et$_3$N under ice cooling over 30 seconds, then, the reaction mixture was stirred at room temperature for 12 hours. To the reaction solution was added 5% K$_2$CO$_3$ and the reaction mixture was stirred for 10 minutes, then, liquid separation was performed and the aqueous layer was extracted with CHCl$_3$. The combined organic layer was washed with saturated brine, dried over MgSO$_4$, then, the drying agent was separated by filtration and the filtrate was concentrated. To the obtained residue was added CHCl$_3$, the solution was stirred under ice cooling for 30 minutes, then the insoluble matter was separated by filtration, one among two species of diastereoisomers of the title compound (colorless solid, isomer A, 545 mg) was obtained. The filtrate was concentrated, the obtained residue was purified by column chromatography (silicagel 60; mobile phase: CHCl$_3$/MeOH=100/0 to 98/2; v/v) to obtain 1.01 g of one of the two species of diastereoisomers of the title compound (pale brown amorphous, isomer B).

Isomer A: $[α]_D^{25}$=+178° (c=0.110, CHCl$_3$)

MS (ESI pos.) m/z: 486 ([M+H]$^+$)

$^1$H-NMR (300 MHz, DMSO-d$_6$) δ (ppm); 1.75-1.87 (m, 1H), 1.97 (s, 3H), 2.04-2.14 (m, 1H), 2.36 (s, 3H), 2.50 (s, 3H), 2.57 (s, 3H), 3.29-3.46 (m, 1H), 3.42 (s, 3H), 3.64-3.71 (m, 1H), 3.73-3.83 (m, 1H), 4.93-4.99 (m, 1H), 6.51 (d, J=2.3 Hz, 1H), 6.75-6.88 (m, 2H), 7.03-7.13 (m, 1H), 7.18 (dd, J=8.2, 2.2 Hz, 1H), 7.81 (d, J=2.2 Hz, 1H), 10.54 (s, 1H)

Isomer B: $[α]_D^{25}$=−225° (c=0.551, CHCl$_3$)

MS (ESI pos.) m/z: 486 ([M+H]$^+$)

$^1$H-NMR (300 MHz, DMSO-d$_6$) δ (ppm); 1.85-1.95 (m, 1H), 2.00-3.53 (m, 6H), 2.05 (s, 3H), 2.28 (s, 3H), 2.43 (s, 3H), 3.45 (s, 3H), 4.58-4.84 (m, 1H), 5.15-5.29 (m, 1H), 6.72-6.93 (m, 3H), 7.07 (dd, J=8.3, 2.3 Hz, 1H), 7.18 (dd, J=8.4, 2.2 Hz, 1H), 7.61-7.73 (m, 1H), 10.44 (s, 1H)

Step 137-4: Synthesis of (3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl acetate (levorotatory isomer)

With 500 mg of the compound obtained in Step 137-3 (Isomer B) and 329 mg of 4-methoxy-2-(trifluoromethoxy)benzene sulfonyl chloride as starting materials, 526 mg of the title compound (colorless amorphous) was obtained by a similar method to Example 2.

$[α]_D^{25}$=176° (c=0.231, CHCl$_3$)

MS (ESI pos.) m/z: 740 ([M+H]$^+$), 762 ([M+Na]$^+$)

$^1$H-NMR (300 MHz, CDCl$_3$) δ (ppm); 1.33-4.95 (m, 8H), 2.30 (s, 3H), 2.41-2.44 (m, 3H), 2.78 (brs, 3H), 3.49 (brs, 3H), 3.91 (s, 3H), 5.37 (brs, 1H), 6.65 (d, J=8.2 Hz, 1H), 6.88 (s, 1H), 6.95 (dd, J=9.0, 2.3 Hz, 1H), 7.00-7.17 (m, 2H), 7.19-7.33 (m, 1H), 7.67 (brs, 1H), 7.86 (d, J=8.7 Hz, 1H), 8.33-8.45 (m, 1H)

Example 138

Synthesis of (3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl propionate (levorotatory isomer)

Step 138-1: Synthesis of tert-butyl (2S,4R)-2-[(dimethylamino)carbonyl]-4-(propionyl oxy)pyrrolidine-1-carboxylate From 200 g of the compound that is obtained at Step 6-1a, 23.6 g of DMAP and 23.6 g of anhydrous propionic acid, 177 g of the title compound (pale yellow solid) was obtained by a similar method to Step 137-1.

MS (ESI pos.) m/z: 315 ([M+H]$^+$), 337 ([M+Na]$^+$)

$^1$H-NMR (600 MHz, CDCl$_3$) δ (ppm); 1.08-1.17 (m, 3H), 1.35-1.50 (m, 9H), 2.13-2.37 (m, 4H), 2.92-3.02 (m, 3H), 3.04-3.15 (m, 3H), 3.62 (dd, J=66.0, 12.4 Hz, 1H), 3.73-3.83 (m, 1H), 4.63-4.85 (m, 1H), 5.27-5.34 (m, 1H)

Step 138-2: Synthesis of
(3R,5S)-5-[(dimethylamino)carbonyl]pyrrolidin-3-yl
propionate trifluoro acetate From 176 g of the compound obtained in Step 138-1, the title compound (yellow oil 304 g) was obtained by a similar procedure to Step 4-1. The resultant compound was subjected to the next step without purification.

MS (ESI pos.) m/z: 215 ([M+H]$^+$)

$^1$H-NMR (600 MHz, DMSO-d$_6$) δ (ppm); 0.99-1.04 (m, 3H), 2.05-2.11 (m, 1H), 2.28-2.33 (m, 2H), 2.48-2.56 (m, 1H), 2.88 (s, 3H), 2.97 (s, 3H), 3.30 (d, J=12.8 Hz, 1H), 3.45-3.51 (m, 1H), 4.65-4.74 (m, 1H), 5.23-5.34 (m, 1H), 8.76 (brs, 1H), 9.85 (brs, 1H)

Step 138-3: Synthesis of (3R,5S)-1-[5-chloro-3-(2-methoxy-5-methylphenyl)-2-oxo-2,3-dihydro-1H-indol-3-yl]-5-[(dimethylamino)carbonyl]pyrrolidin-3-yl propionate (levorotatory isomer and dextrorotatory isomer)

To a solution of 2.79 g of the compound obtained in Step 109-4 and the compound obtained in Step 138-2 (9.54 mmol) in CHCl$_3$ (27.9 ml) was added dropwise under ice cooling 5.27 g of Et$_3$N over 30 seconds and then the reaction mixture was stirred at room temperature for 12 hours. The precipitate was separated by filtration to obtain a mixture of one of two species of diastereoisomers of the title compound (Isomer A) and Et$_3$N hydrochloride (colorless solid, 1.38 g). To the filtrate was added 5% K$_2$CO$_3$ and the solution was stirred for 10 minutes, then liquid separation was performed, and the aqueous layer was extracted with CHCl$_3$. The combined organic layer was washed with saturated brine, dried over MgSO$_4$, then, the drying agent was separated by filtration, the filtrate was concentrated to obtain a brown amorphous (3.3 μg). To the obtained residue was added EtOAc, the solution was stirred on ice for 30 minutes, then the insoluble matter was separated by filtration to obtain one of two species of diastereoisomers of the title compound (colorless solid, isomer A, 407 mg). The filtrate was concentrated to obtain 2.13 g of one of the two species of diastereoisomers of the title compound (brown solid, isomer B).

Isomer A: [α]$_D^{25}$=+134° (c=0.329, CHCl$_3$)

MS (ESI pos.) m/z: 500 ([M+H]$^+$), 522 ([M+Na]$^+$)

$^1$H-NMR (600 MHz, DMSO-d$_6$) δ (ppm); 0.98 (t, J=7.3 Hz, 3H), 1.75-1.82 (m, 1H), 2.02-2.09 (m, 1H), 2.18-3.42 (m, 4H), 2.19-2.36 (m, 2H), 2.33 (s, 3H), 2.54 (s, 3H), 3.38 (s, 3H), 3.64 (d, J=12.4 Hz, 1H), 3.75 (dd, J=9.9, 6.6 Hz, 1H), 4.93-4.96 (m, 1H), 6.47 (d, J=2.3 Hz, 1H), 6.74-6.80 (m, 2H), 7.04 (dd, J=8.5, 2.1 Hz, 1H), 7.14 (dd, J=8.5, 2.1 Hz, 1H), 7.78 (d, J=1.8 Hz, 1H), 10.49 (s, 1H)

Isomer B: [α]$_D^{25}$=−224° (c=0.390, CHCl$_3$)

MS (ESI pos.) m/z: 500 ([M+H]$^+$), 522 ([M+Na]$^+$)

$^1$H-NMR (600 MHz, DMSO-d$_6$) δ (ppm); 0.96-1.05 (m, 3H), 1.85-1.91 (m, 1H), 1.97-2.16 (m, 1H), 2.20-3.47 (m, 7H), 2.24 (s, 3H), 2.39 (s, 3H), 3.41 (s, 3H), 4.65 (brs, 1H), 5.17-5.23 (m, 1H), 6.70-6.83 (m, 3H), 7.03 (dd, J=8.3, 2.3 Hz, 1H), 7.14 (dd, J=8.3, 2.3 Hz, 1H), 7.62 (s, 1H), 10.41 (brs, 1H)

Step 138-4: Synthesis of (3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl propionate (levorotatory isomer)

With 113 g of the compound that is obtained by a similar method to Step 138-3 (Isomer B) and 75.5 g of 4-methoxy-2-(trifluoromethoxy)benzene sulfonyl chloride as starting materials, 152 g of the title compound (pale yellow amorphous) was obtained by a similar method to Example 2.

[α]$_D^{25}$=143° (c=0.389, CHCl$_3$)

MS (ESI pos.) m/z: 754 ([M+H]$^+$), 776 ([M+Na]$^+$)

$^1$H-NMR (600 MHz, CDCl$_3$) δ (ppm); 0.99-1.22 (m, 3H), 1.33-3.79 (m, 9H), 1.95-1.97 (m, 3H), 2.29 (s, 3H), 2.40-2.42 (m, 3H), 3.89 (s, 3H), 4.68-4.83 (m, 1H), 5.31-5.50 (m, 1H), 6.64 (d, J=7.8 Hz, 1H), 6.76-7.31 (m, 1H), 6.84-6.89 (m, 1H), 6.92-6.97 (m, 1H), 7.00-7.03 (m, 1H), 7.19-7.27 (m, 1H), 7.57-7.76 (m, 1H), 7.84 (d, J=8.7 Hz, 1H), 8.30-8.43 (m, 1H)

Example 139

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(3-hydroxypropoxy)-N,N-dimethyl-L-prolinamide (levorotatory isomer)

Step 139-1 Synthesis of tert-butyl (2S,4R)-4-(3-{[tert-butyl(dimethyl)silyl]oxy}propoxy)-2-[(dimethylamino)carbonyl]pyrrolidine-1-carboxylate Under nitrogen atmosphere, to a suspension of 1.55 g of NaH in THF (100 ml) was added 10.0 g of tert-butyl (2S,4S)-2-[(dimethylamino)carbonyl]-4-hydroxypyrrolidine-1-carboxylate and the reaction mixture was stirred at 50° C. for one hour. Thereafter, at the same temperature, solution of 23.2 g of (3-iodopropyl)-tert-butyl-dimethyl silane in THF (10 ml) was added, and the solution was refluxed for two hours. The solution was poured into water and the resulting mixture was extracted with EtOAc; the organic layer was washed with saturated brine and dried over MgSO$_4$, then, the drying agent was separated by filtration and the solvent was evaporated under reduced pressure. The obtained residue was purified by column chromatography (silicagel 60N; mobile phase: n-hexane/EtOAc=1/1 to 0/1; v/v) to obtain 2.10 g of the title compound.

MS (ESI pos.) m/z: 431 ([M+H]$^+$), 453 ([M+Na]$^+$)

$^1$H-NMR (200 MHz, CDCl$_3$) δ (ppm); 0.03-0.10 (m, 6H), 0.89 (s, 9H), 1.35-1.54 (m, 9H), 1.67-1.88 (m, 3H), 1.95-2.30 (m, 3H), 2.92-3.14 (m, 6H), 3.40-3.55 (m, 2H), 3.58-3.82 (m, 2H), 3.95-4.26 (m, 1H), 4.59-4.84 (m, 1H)

Step 139-2 Synthesis of tert-butyl(2S,4R)-2-[(dimethylamino)carbonyl]-4-(3-hydroxypropoxy)pyrrolidine-1-carboxylate To a solution of 2.10 g of the compound obtained in Step 139-1 in THF (100 ml) was added a solution 1 mol/L TBAF in THF (10 ml) under ice cooling and the reaction mixture was stirred at room temperature for two hours. Water was poured, the solution was extracted twice with CHCl$_3$; the combined organic layer was washed with saturated brine and dried over MgSO$_4$, then, the drying agent was separated by filtration and the solvent was evaporated under reduced pressure. The obtained residue was purified by column chromatography (silicagel 60N; mobile phase: CHCl$_3$/MeOH=20/1 to 10/1; v/v) to obtain 1.79 g of the title compound.

$^1$H-NMR (200 MHz, CDCl$_3$) δ (ppm); 1.39-1.48 (m, 9H), 1.59-2.32 (m, 5H), 2.93-3.17 (m, 6H), 3.31-3.81 (m, 6H), 4.05-4.30 (m, 1H), 4.61-4.84 (m, 1H)

Step 139-3 Synthesis of (4R)-4-(3-hydroxypropoxy)-N,N-dimethyl-L-prolinamide trifluoroacetate With 1.78 g of the compound obtained in Step 139-2 as starting material, 3.10 g of the title compound (crude form) obtained by a similar procedure to Step 4-1. The present compound was used in the next reaction without purification.

MS (ESI pos.) m/z: 217 ([M+H]$^+$)

$^1$H-NMR (200 MHz, DMSO-d$_6$) δ (ppm); 1.43-1.74 (m, 1H), 1.77-2.04 (m, 1H), 2.91 (s, 3H), 3.00 (s, 3H), 3.06-3.38 (m, 6H), 3.41-3.58 (m, 3H), 4.18-4.28 (m, 1H), 4.47 (t, J=6.37 Hz, 1H), 4.54-4.72 (m, 1H)

Step 139-4 Synthesis of (4R)-1-[5-chloro-3-(2-methoxy-5-methylphenyl)-2-oxo-2,3-dihydro-1H-indol-3-yl]-4-(3-hydroxypropoxy)-N,N-dimethyl-L-prolinamide With 1.57 g of the compound obtained in Step 109-4 and 3.10 g of the compound obtained in Step 139-3 as starting materials, 880 mg of the title compound obtained by a similar procedure to Step 4-2.

MS (ESI pos.) m/z: 502 ([M+H]$^+$), 524 ([M+Na]$^+$), (ESI neg.) m/z: 500 ([M−H]$^−$)

$^1$H-NMR (600 MHz, CDCl$_3$) δ (ppm); 1.58-1.68 (m, 2H), 1.72-1.86 (m, 2H), 1.93-2.17 (m, 3H), 2.28-2.36 (m, 3H), 2.37-2.58 (m, 3H), 2.73-2.93 (m, 3H), 3.22-3.47 (m, 1H), 3.49-3.63 (m, 3H), 3.66-3.81 (m, 3H), 4.28-4.42 (m, 1H), 4.81-5.10 (m, 1H), 6.69 (d, J=8.25 Hz, 1H), 6.72 (d, J=8.25 Hz, 1H), 7.00-7.05 (m, 2H), 7.10 (dd, J=8.25, 2.29 Hz, 1H), 7.72 (s, 1H), 7.91-7.97 (m, 1H)

Step 139-5: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(3-hydroxypropoxy)-N,N-dimethyl-L-prolinamide (levorotatory isomer)

With 870 mg of the compound obtained in Step 139-4 and 603 mg of 4-methoxy-2-(trifluoromethoxy)benzene sulfonyl chloride as starting materials, 390 mg of the title compound (amorphous) was obtained by a similar procedure to Example 2.

[α]$_D^{25}$=−122° (c=0.452, CHCl$_3$)

MS (ESI pos.) m/z: 756 ([M+H]$^+$), 778 ([M+Na]$^+$), (ESI neg.) m/z: 754 ([M−H]$^−$)

$^1$H-NMR (600 MHz, CDCl$_3$) δ (ppm); 1.22-1.40 (m, 1H), 1.52-2.01 (m, 4H), 2.27 (s, 3H), 2.33-2.40 (m, 3H), 2.76-2.89 (m, 3H), 3.08-3.20 (m, 1H), 3.42-3.52 (m, 3H), 3.56-3.73 (m, 5H), 3.90 (s, 3H), 4.34-4.47 (m, 1H), 4.66-4.84 (m, 1H), 6.65 (d, J=8.25 Hz, 1H), 6.92-6.96 (m, 2H), 7.00-7.04 (m, 1H), 7.08-7.18 (m, 1H), 7.23 (dd, J=8.71, 2.29 Hz, 1H), 7.58 (s, 1H), 7.86 (d, J=9.17 Hz, 1H), 8.26-8.35 (m, 1H)

Example 140

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[3-(dimethylamino)propoxy]-N,N-dimethyl-L-prolinamide (levorotatory isomer)

To a solution of 222 mg of IBX in DMSO (2.2 ml) was added 150 mg of the compound obtained Step 139-5 and the reaction mixture was stirred at room temperature for two hours. A saturated aqueous solution of NaHCO$_3$ was added to the solution and the resulting mixture was extracted with EtOAc. The organic layer was washed with water and with saturated brine, dried over Na$_2$SO$_4$, then, the drying agent was separated by filtration, and the solvent was evaporated under reduced pressure to obtain 138 mg of residue. To a solution of the obtained residue, 82 mg of and aqueous solution 50% dimethylamine and 55 mg of acetic acid in CHCl$_3$ (2 ml) was added 43 mg of sodium triacetoxy borohydride under ice cooling and the reaction mixture was stirred for one hour. To the solution was added a saturated aqueous solution of NaHCO$_3$ and the resulting mixture was extracted with EtOAc; the organic layer was washed with saturated brine, dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=10/1 to 2/1; v/v) obtained 53 mg of the title compound.

[α]$_D^{25}$=−67.1° (c=0.143, CHCl$_3$)

MS (ESI pos.) m/z: 783 ([M+H]$^+$)

$^1$H-NMR (600 MHz, CDCl$_3$) δ (ppm); 1.47-2.01 (m, 6H), 2.16-2.47 (m, 12H), 2.75-2.92 (m, 3H), 3.05-3.19 (m, 1H), 3.26-3.37 (m, 3H), 3.52-3.68 (m, 3H), 3.89 (s, 3H), 4.28-4.46 (m, 1H), 4.69-4.82 (m, 1H), 6.64 (d, J=7.79 Hz, 1H), 6.87 (s, 1H), 6.93 (dd, J=8.94, 2.52 Hz, 1H), 7.00-7.04 (m, 1H), 7.06-7.14 (m, 1H), 7.21-7.24 (m, 1H), 7.50-7.65 (m, 1H), 7.83-7.87 (m, 1H), 8.27-8.38 (m, 1H)

Example 141

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2-hydroxyethoxy)-N,N-dimethyl-L-prolinamide (levorotatory isomer)

Step 141-1 Synthesis of tert-butyl (2S,4R)-4-(2-{[tert-butyl(dimethyl)silyl]oxy}ethoxy)-2-[(dimethylamino)carbonyl]pyrrolidine-1-carboxylate With 10.0 g of tert-butyl (2S,4R)-2-[(dimethylamino)carbonyl]-4-hydroxypyrrolidine-1-carboxylate and 32.2 g of (2-iodoethyl)-tert-butyl-dimethyl silane as starting materials, 5.50 g of the title compound was obtained by a similar procedure to Step 139-1.

$^1$H-NMR (200 MHz, CDCl$_3$) δ (ppm); 0.06 (s, 6H), 0.85-0.91 (m, 9H), 1.42 (d, J=10.99 Hz, 9H), 1.94-2.30 (m, 3H), 2.92-3.17 (m, 6H), 3.45-3.59 (m, 2H), 3.61-3.80 (m, 3H), 4.13-4.29 (m, 1H), 4.61-4.83 (m, 1H)

Step 141-2 Synthesis of tert-butyl (2S,4R)-2-[(dimethylamino)carbonyl]-4-(2-hydroxyethoxy)pyrrolidine-1-carboxylate With 5.50 g of the compound obtained in Step 141-1 as starting material, 3.25 g of the title compound was obtained by a similar procedure to Step 139-2.

MS (ESI pos.) m/z: 303 ([M+H]$^+$)

$^1$H-NMR (200 MHz, CDCl$_3$) δ (ppm); 1.20-1.80 (m, 9H), 2.07-2.23 (m, 4H), 2.94-3.16 (m, 6H), 3.33-3.79 (m, 5H), 4.13-4.32 (m, 1H), 4.46-4.87 (m, 1H)

Step 141-3 Synthesis of (4R)-4-(2-hydroxyethoxy)-N,N-dimethyl-L-prolinamide trifluoroacetate With 3.24 g of the compound obtained in Step 141-2 as starting material, 5.60 g of the title compound (crude form) obtained by a similar procedure to Step 4-1. The present compound was used in the next reaction without purification.

MS (ESI pos.) m/z: 203 ([M+H]$^+$)

$^1$H-NMR (200 MHz, DMSO-d$_6$) δ (ppm); 1.77-2.05 (m, 1H), 2.22-2.46 (m, 1H), 2.54-2.69 (m, 1H), 2.92 (s, 3H), 3.01 (s, 3H), 3.26-3.41 (m, 2H), 3.41-3.54 (m, 2H), 3.67-3.86 (m, 1H), 4.13-4.82 (m, 2H), 8.50-8.86 (m, 1H), 9.70-9.96 (m, 1H)

Step 141-4 Synthesis of (4R)-1-[5-chloro-3-(2-methoxy-5-methylphenyl)-2-oxo-2,3-dihydro-1H-indol-3-yl]-4-(2-hydroxyethoxy)-N,N-dimethyl-L-prolinamide With 4.25 g of the compound obtained in Step 109-4 and 5.60 g of the compound obtained in Step 141-3 as starting materials, 1.55 g of the title compound obtained by a similar procedure to Step 4-2.

MS (ESI pos.) m/z: 488 ([M+H]⁺), 510 ([M+Na]⁺), (ESI neg.) m/z: 486 ([M−H]⁻)
¹H-NMR (200 MHz, CDCl₃) δ (ppm); 1.79-1.93 (m, 4H), 1.95-2.22 (m, 3H), 2.24-2.89 (m, 9H), 3.12-4.04 (m, 5H), 4.21-4.45 (m, 1H), 4.94-5.14 (m, 1H), 6.62-6.77 (m, 1H), 6.94-7.19 (m, 2H), 7.76 (d, J=2.20 Hz, 1H), 7.89-8.14 (m, 1H), 8.33-8.45 (m, 1H), 8.35-8.47 (m, 1H)

Step 141-5 Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2-hydroxyethoxy)-N,N-dimethyl-L-prolinamide (levorotatory isomer)

With 750 mg of the compound obtained in Step 141-4 and 491 mg of 4-methoxy-2-(trifluoromethoxy)benzene sulfonyl chloride as starting material, 49 mg of the title compound (amorphous) was obtained by a similar procedure to Example 2. $[\alpha]_D^{25}$=−113° (c=0.150, CHCl₃)
MS (ESI pos.) m/z: 756 ([M+H]⁺), 778 ([M+Na]⁺), (ESI neg.) m/z: 754 ([M−H]⁻)
¹H-NMR (600 MHz, CDCl₃) δ (ppm); 1.64-2.12 (m, 2H), 2.24-2.29 (m, 2H), 2.32-2.42 (m, 3H), 2.76-2.90 (m, 3H), 3.09-3.22 (m, 1H), 3.36-3.42 (m, 3H), 3.42-3.50 (m, 3H), 3.51-3.68 (m, 4H), 3.89 (s, 3H), 4.34-4.55 (m, 1H), 4.68-4.80 (m, 1H), 6.63-6.68 (m, 1H), 6.86-6.97 (m, 2H), 7.00-7.05 (m, 1H), 7.21-7.29 (m, 2H), 7.53-7.62 (m, 1H), 7.86 (d, J=9.17 Hz, 1H), 8.30-8.36 (m, 1H)

Example 142

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[2-(dimethylamino)ethoxy]-N,N-dimethyl-L-prolinamide (levorotatory isomer)

To a solution of 200 mg of the compound obtained in Step 141-5 and 50 mg of Et₃N in CHCl₃ (2 ml) was added 34 mg of methane sulfonyl chloride under ice cooling and the reaction mixture was stirred at room temperature for one hour. To the solution was added a saturated aqueous solution of NaHCO₃ and the resulting mixture was extracted with EtOAc; the organic layer was washed with saturated brine and dried over Na₂SO₄, then, the drying agent was separated by filtration and the solvent was evaporated under reduced pressure. To a solution of the obtained residue in CHCl₃ (2 ml) was added an aqueous solution of 50% dimethylamine (4.35 ml) and the reaction mixture was stirred at 90° C. for two hours under sealed conditions. To the solution was added a saturated aqueous solution of NaHCO₃ and the resulting mixture was extracted with EtOAc; the organic layer was washed with saturated brine and dried over Na₂SO₄, then, the drying agent was separated by filtration and the solvent was evaporated under reduced pressure. The obtained residue was purified by column chromatography (silicagel 60N; mobile phase: CHCl₃/MeOH=20/1 to 5/1; v/v) obtained 61 mg of the title compound.
$[\alpha]_D^{25}$=−114° (c=0.086, CHCl₃)
MS (ESI pos.) m/z: 769 ([M+H]⁺)
¹H-NMR (600 MHz, CDCl₃) δ (ppm); 1.18-2.01 (m, 2H), 2.16-2.48 (m, 15H), 2.75-2.88 (m, 3H), 3.03-3.18 (m, 1H), 3.32-3.66 (m, 5H), 3.89 (s, 3H), 4.33-4.52 (m, 1H), 4.70-4.80 (m, 1H), 6.64 (d, J=8.25 Hz, 1H), 6.86-6.89 (m, 1H), 6.92 (dd, J=8.94, 2.52 Hz, 1H), 7.00-7.03 (m, 1H), 7.07-7.16 (m, 1H), 7.22 (dd, J=8.48, 2.52 Hz, 1H), 7.54-7.65 (m, 1H), 7.85 (d, J=8.71 Hz, 1H), 8.28-8.37 (m, 1H)

Example 143

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2-cyano ethoxy)-N,N-dimethyl-L-prolinamide Step 143-1 Synthesis of tert-butyl (2S,4R)-2-[(dimethylamino)carbonyl]-4-(2-ethoxy-2-oxo ethoxy) pyrrolidine-1-carboxylate With 20.0 g of tert-butyl (2S,4S)-2-[(dimethylamino)carbonyl]-4-hydroxypyrrolidine-1-carboxylate and 25.9 g of bromoethyl acetate as starting material, 12.3 g of the title compound obtained by a similar procedure to Step 139-1.
MS (ESI pos.) m/z: 345 ([M+H]⁺), 367 ([M+Na]⁺)
¹H-NMR (200 MHz, CDCl₃) δ (ppm): 1.29 (t, J=7.03 Hz, 3H), 1.36-1.53 (m, 9H), 1.89-2.50 (m, 2H), 2.85-3.24 (m, 6H), 3.47-3.87 (m, 2H), 3.93-4.40 (m, 5H), 4.64-4.88 (m, 1H)

Step 143-2 Synthesis of tert-butyl (2S,4R)-2-[(dimethylamino)carbonyl]-4-(2-hydroxyethoxy)pyrrolidine-1-carboxylate Under nitrogen atmosphere, to a solution of 2.00 g of the compound obtained in Step 143-1 in THF (40 ml) was added 360 mg of LAH at −40° C., and the reaction mixture was stirred at −10° C. for one hour. To the solution was added sodium sulfate 10 hydrate and the reaction mixture was stirred at room temperature for one hour. The insoluble matter was filtered with celite, the solvent was evaporated under reduced pressure to obtain 2.02 g of the title compound.

Step 143-3 Synthesis of tert-butyl (2S,4R)-4-(2-cyano ethoxy)-2-[(dimethylamino)carbonyl]pyrrolidine-1-carboxylate To a solution of 3.00 g of the compound obtained in Step 143-2 and 2.01 g of Et₃N in CHCl₃ (30 ml) was added 1.36 g of methane sulfonyl chloride under ice cooling and the reaction mixture was stirred at room temperature for one hour. To the solution was added a saturated aqueous solution of NaHCO₃ and the resulting mixture was extracted with EtOAc; the organic layer was washed with saturated brine and dried over Na₂SO₄, then, the drying agent was separated by filtration and the solvent was evaporated under reduced pressure. To a solution of the obtained residue in MeCN (40 ml) was added 2.58 g potassium cyanide and 260 mg of 18-crown-6-ether, and the reaction mixture was refluxed for two hours. To the solution was added water and the resulting mixture was extracted with EtOAc; the organic layer was washed with saturated brine and dried over Na₂SO₄, then, the drying agent was separated by filtration and the solvent was evaporated under reduced pressure. The obtained residue was purified by column chromatography (silicagel 60N; mobile phase: EtOAc) obtained 1.22 g of the title compound.
¹H-NMR (200 MHz, CDCl₃) δ (ppm); 1.41 (t, J=9.89 Hz, 9H), 1.93-2.36 (m, 4H), 2.86-3.22 (m, 6H), 3.36-3.82 (m, 4H), 4.53 (s, 1H), 4.65-4.92 (m, 1H)

Step 143-4 (4R)-1-[5-chloro-3-(2-methoxy-5-methylphenyl)-2-oxo-2,3-dihydro-1H-indol-3-yl]-4-(2-cyano ethoxy)-N,N-dimethyl-L-prolinamide With 1.20 g of the compound obtained in Step 143-3 and 1.24 g of the compound obtained in Step 109-4 as starting materials, 725 mg of the title compound obtained by a similar method to Step 42-2.

MS (ESI pos.) m/z: 497 ([M+H]⁺), 519 ([M+Na]⁺), (ESI neg.) m/z: 495 ([M−H]⁻)
¹H-NMR (200 MHz, CDCl₃) δ (ppm); 1.86-2.22 (m, 2H), 2.29-2.66 (m, 9H), 2.71-2.90 (m, 3H), 3.33-3.71 (m, 6H), 4.34-4.57 (m, 1H), 4.77-5.02 (m, 1H), 6.64-6.82 (m, 2H), 6.95-7.20 (m, 3H), 7.71 (d, J=1.76 Hz, 1H), 7.99-8.12 (m, 1H)

Step 143-5 Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2-cyano ethoxy)-N,N-dimethyl-L-prolinamide With 720 mg of the compound obtained in Step 143-4 and 506 mg of 4-methoxy-2-(trifluoromethoxy)benzene sulfonyl chloride as starting materials, 720 mg of the title compound (amorphous) was obtained by a similar procedure to Example 2.

MS (ESI pos.) m/z: 751 ([M+H]⁺), 773 ([M+Na]⁺)
¹H-NMR (600 MHz, CDCl₃) δ (ppm); 1.30-1.40 (m, 2H), 1.75-2.00 (m, 2H), 2.24-2.30 (m, 3H), 2.33-2.40 (m, 3H), 2.43-2.52 (m, 3H), 2.77-2.91 (m, 3H), 3.07-3.16 (m, 1H), 3.45-3.69 (m, 3H), 3.90 (s, 3H), 4.38-4.52 (m, 1H), 4.75-4.92 (m, 1H), 6.66 (d, J=7.79 Hz, 1H), 6.92-6.95 (m, 2H), 7.03 (dd, J=8.25, 2.29 Hz, 1H), 7.08-7.17 (m, 1H), 7.22-7.24 (m, 1H), 7.52-7.61 (m, 1H), 7.86 (d, J=8.71 Hz, 1H), 8.27-8.35 (m, 1H)

Example 144

Synthesis of (4R)-4-(3-amino-3-oxopropoxy)-1-(5-chloro-3-(2-methoxy-5-methylphenyl)-1-{[4-methoxy-2-(t rifluoromethoxy)phenyl]sulfonyl}-2-oxo-2,3-dihydro-1H-indol-3-yl)-N,N-dimethyl-L-prolinamide (levorotatory isomer)

A mixed solution of 300 mg of the compound obtained in Step 143-5 and 12 mol/L hydrochloric acid was stirred at 50° C. for 4 hours. To the solution was added water and the resulting mixture was extracted with EtOAc; the organic layer was washed with a saturated aqueous solution of NaHCO₃ and with a saturated brine and dried over Na₂SO₄, then, the drying agent was separated by filtration and the solvent was evaporated under reduced pressure. The obtained residue was purified by column chromatography (silicagel 60N; mobile phase: CHCl₃/MeOH=9/1; v/v) obtained 50 mg of the title compound.

$[\alpha]_D^{25}$=−80.0° (c=0.111, CHCl₃)
MS (ESI pos.) m/z: 769 ([M+H]⁺), 791 ([M+Na]⁺), (ESI neg.) m/z: 767 ([M−H]⁻)
¹H-NMR (600 MHz, CDCl₃) δ (ppm); 1.37-1.53 (m, 1H), 1.65-1.78 (m, 1H), 1.81-2.13 (m, 2H), 2.27 (s, 3H), 2.34-2.44 (m, 6H), 2.75-2.90 (m, 3H), 3.13-3.27 (m, 1H), 3.45-3.64 (m, 5H), 3.90 (s, 3H), 4.38-4.51 (m, 1H), 4.72-4.86 (m, 1H), 6.64 (d, J=8.25 Hz, 1H), 6.87-6.89 (m, 1H), 6.94 (dd, J=9.17, 2.29 Hz, 1H), 7.02 (dd, J=8.71, 2.29 Hz, 1H), 7.06-7.19 (m, 1H), 7.24 (dd, J=8.71, 2.29 Hz, 1H), 7.54-7.62 (m, 1H), 7.85 (d, J=8.71 Hz, 1H), 8.30-8.35 (m, 1H)

Example 145

Synthesis of 3-({(3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl}oxy) propanoic acid A mixed solution of 100 mg of the compound obtained in Step 143-5 and 12 mol/L hydrochloric acid was stirred at 80° C. for two hours. To the solution was added water and the resulting mixture was extracted with EtOAc; the organic layer was washed with saturated brine and dried over Na₂SO₄, then, the drying agent was separated by filtration and the solvent was evaporated under reduced pressure. The obtained residue was purified by column chromatography (silicagel 60N; mobile phase: CHCl₃/MeOH=9/1 to 4/1; v/v) to obtain 10 mg of the title compound.

MS (ESI pos.) m/z: 770 ([M+H]⁺), 792 ([M+Na]⁺), (ESI neg.) m/z: 768 ([M−H]⁻)
¹H-NMR (600 MHz, CDCl₃) δ (ppm); 1.17-1.28 (m, 2H), 1.72-1.80 (m, 1H), 1.83-1.94 (m, 1H), 2.24 (s, 3H), 2.32-2.38 (m, 3H), 2.41-2.52 (m, 3H), 2.76-2.87 (m, 3H), 3.03-3.11 (m, 1H), 3.47-3.65 (m, 5H), 3.86-3.89 (m, 2H), 4.34-4.44 (m, 1H), 4.70-4.79 (m, 1H), 6.63 (d, J=8.25 Hz, 1H), 6.87 (s, 1H), 6.90 (dd, J=8.94, 2.52 Hz, 1H), 6.99 (dd, J=8.25, 1.83 Hz, 1H), 7.05-7.14 (m, 1H), 7.17-7.22 (m, 1H), 7.48-7.57 (m, 1H), 7.83 (d, J=8.71 Hz, 1H), 8.24-8.33 (m, 1H)

Example 146

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(cyano methoxy)-N,N-dimethyl-L-prolinamide (levorotatory isomer)

Step 146-1: Synthesis of tert-butyl (2S,4R)-4-(cyano methoxy)-2-[(dimethylamino)carbonyl]pyrrolidine-1-carboxylate To a solution of 10.0 g of tert-butyl (2S,4R)-2-[(dimethylamino)carbonyl]-4-hydroxypyrrolidine-1-carboxylate in THF (80 ml) was added 1.54 g of NaH. The solution was stirred at room temperature for 10 minutes. To the reaction solution was added bromo acetonitrile (9.37 ml), then, the reaction mixture was refluxed for one hour. After concentration under reduced pressure, the obtained residue was purified by column chromatography (silicagel 60; mobile phase: EtOAc) to obtain 4.00 g of the title compound (brown oil).

MS (ESI pos.) m/z: 320 ([M+Na]⁺)
¹H-NMR (200 MHz, CDCl₃) δ (ppm); 1.41 &1.46 (each-s, 9H), 2.03-2.42 (m, 2H), 2.97 &2.99 (each-s, 3H), 3.09 & 3.14 (each-s, 3H), 3.51-3.83 (m, 2H), 4.09-4.48 (m, 3H), 4.62-4.86 (m, 1H)

Step 146-2: Synthesis of (4R)-4-(cyano methoxy)-N,N-dimethyl-L-prolinamide trifluoroacetate With 4.00 g of the compound obtained in Step 146-1 as starting material, 5.00 g of the title compound (crude form brown oil) was obtained by a similar method to Step 4-1. The present compound was used in the next reaction without purification.

MS (ESI pos.) m/z: 198 ([M+H]⁺)
¹H-NMR (200 MHz, CDCl₃) δ (ppm); 1.96-2.18 (m, 1H), 2.66-2.87 (m, 1H), 3.06 (s, 3H), 3.10 (s, 3H), 3.39-3.59 (m, 1H), 3.80-4.64 (m, 4H), 4.96-5.15 (m, 1H)

Step 146-3: Synthesis of (4R)-1-[5-chloro-3-(2-methoxy-5-methylphenyl)-2-oxo-2,3-dihydro-1H-indol-3-yl]-4-(cyano methoxy)-N,N-dimethyl-L-prolinamide With 4.00 g of the compound that is obtained at Step 109-4 and 5.00 g of the compound obtained in Step 146-2 as starting materials, respectively 660 mg (Isomer A: colorless solid) and 900 mg (Isomer B: colorless amorphous) of two species of diastereoisomers of the title compound were obtained by a similar method to Step 4-2.

Isomer A: MS (ESI pos.) m/z: 505 ([M+Na]$^+$)
$^1$H-NMR (600 MHz, CDCl$_3$) δ (ppm); 1.94-2.00 (m, 1H), 2.09-2.15 (m, 1H), 2.41 (s, 3H), 2.48 (s, 3H), 2.73 (s, 3H), 3.51 (s, 3H), 3.86-3.94 (m, 2H), 4.12 (d, J=16.0 Hz, 1H), 4.20-4.24 (m, 1H), 4.31 (d, J=16.0 Hz, 3H), 6.70 (d, J=8.3 Hz, 1H), 6.74 (d, J=8.3 Hz, 1H), 6.87 (d, J=1.8 Hz, 1H), 7.07 (d, J=8.3 Hz, 1H), 7.12 (d, J=8.3 Hz, 1H), 8.02 (s, 1H)

Isomer B: MS (ESI pos.) m/z: 505 ([M+Na]$^+$)
$^1$H-NMR (600 MHz, CDCl$_3$) δ (ppm); 2.03-2.25 (m, 2H), 2.33 (s, 3H), 2.52 (s, 3H), 2.63-2.88 (m, 3H), 3.52-3.62 (m, 1H), 3.57 (s, 3H), 4.09-4.62 (m, 5H), 6.68-6.78 (m, 2H), 6.94-7.14 (m, 4H), 7.68 (s, 1H)

Step 146-4: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(cyano methoxy)-N,N-dimethyl-L-prolinamide (levorotatory isomer)

With 900 mg of the compound obtained in Step 146-3 (Isomer B) as starting material, 620 mg of the title compound (colorless amorphous) was obtained by a similar method to Example 2.

[α]$_D^{25}$=−145° (c=0.186, CHCl$_3$)
MS (ESI pos.) m/z: 737 ([M+H]$^+$)
$^1$H-NMR (600 MHz, CDCl$_3$) δ (ppm); 1.27-4.89 (m, 20H), 3.91 (s, 3H), 6.66 (d, J=7.8 Hz, 1H), 6.89 (s, 1H), 6.93-6.96 (m, 1H), 7.00-7.14 (m, 2H), 7.22-7.26 (m, 1H), 7.46-7.58 (m, 1H), 7.88 (d, J=8.7 Hz, 1H), 8.26-8.36 (m, 1H)

Example 147

Synthesis of (4R)-4-(2-amino-2-oxo ethoxy)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-L-prolinamide (levorotatory isomer)

Concentrated hydrochloric acid (5 ml) was added to 250 mg of the compound obtained in Step 146-4 and the solution was stirred at room temperature for one hour. The solution was poured into a saturated aqueous solution of NaHCO$_3$, the resulting mixture was extracted with EtOAc then, dried over Na$_2$SO$_4$, then, the drying agent was separated by filtration and the solvent was evaporated under reduced pressure. The obtained residue was purified by column chromatography (silicagel 60; mobile phase: CHCl$_3$/MeOH=18/1; v/v) to obtain 220 mg of the title compound (colorless amorphous).
[α]$_D^{25}$=−162° (c=0.310, CHCl$_3$)
MS (ESI pos.) m/z: 755 ([M+H]$^+$)
$^1$H-NMR (600 MHz, CDCl$_3$) δ (ppm); 1.41-4.95 (m, 20H), 3.88 (s, 3H), 6.39-6.49 (m, 1H), 6.65 (d, J=8.3 Hz, 1H), 6.85 (s, 1H), 6.91-6.95 (m, 1H), 7.00-7.16 (m, 2H), 7.21-7.29 (m, 1H), 7.56-7.63 (m, 1H), 7.87 (d, J=8.7 Hz, 1H), 8.27-8.36 (m, 1H)

Example 148

Synthesis of ({(3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl]pyrrolidin-3-yl}oxy) acetic acid (levorotatory isomer)

Concentrated hydrochloric acid (5 ml) was added to 100 mg of the compound obtained in Example 147, the mixture was refluxed for two hours. After the mixture was cooled, the reaction solution was poured into a saturated aqueous solution of NaHCO$_3$, the resulting mixture was extracted with EtOAc and then dried over Na$_2$SO$_4$; the drying agent was separated by filtration and the solvent was evaporated under reduced pressure. The obtained residue was purified by preparative TLC plate (1 mm; mobile phase: CHCl$_3$/MeOH=8/1; v/v) to obtain 20 mg of the title compound (light yellow solid).

[α]$_D^{25}$=−170° (c=0.074, CHCl$_3$)
MS (ESI pos.) m/z: 756 ([M+H]$^+$)
$^1$H-NMR (600 MHz, CDCl$_3$) δ (ppm); 1.11-4.86 (m, 14H), 2.26 (s, 3H), 2.38 (s, 3H), 3.88 (s, 3H), 6.66 (d, J=8.3 Hz, 1H), 6.86-6.96 (m, 2H), 6.99-7.16 (m, 2H), 7.21-7.28 (m, 1H), 7.47-7.60 (m, 1H), 7.87 (d, J=8.7 Hz, 1H), 8.24-8.35 (m, 1H)

Example 149

Synthesis of (4R)-4-(allyloxy)-1-[5-chloro-3-(2-methoxy-5-methylphenyl)-2-oxo-2,3-dihydro-1H-indol-3-yl]-N,N-dimethyl-L-prolinamide (levorotatory isomer)

Step 149-1: Synthesis of tert-butyl (2S,4R)-4-(allyloxy)-2-[(dimethylamino)carbonyl]pyrrolidine-1-carboxylate To a solution of 9.6 g of tert-butyl (2S,4R)-2-[(dimethylamino)carbonyl]-4-hydroxypyrrolidine-1-carboxylate in THF (100 ml) was added 937 mg of NaH and the reaction mixture was stirred at 60° C. for one hour. After returning to room temperature, 12.5 g of allyl iodide was added to the reaction solution, and the reaction mixture was refluxed for one hour. To the reaction solution was added water and the resulting mixture was extracted with EtOAc, then was washed with saturated brine. The organic layer was dried over Na$_2$SO$_4$, then the drying agent was separated by filtration and the solvent was evaporated under reduced pressure. The obtained residue was purified by column chromatography (silicagel 60; mobile phase: CHCl$_3$/MeOH=18/1 to 9/1; v/v) to obtain 6.70 g of the title compound (light brown oil).

MS (ESI pos.) m/z: 229 ([M+H]$^+$)
$^1$H-NMR (600 MHz, CDCl$_3$) δ (ppm); 1.37&1.42 (each-s, 9H), 1.98-2.08 (m, 1H), 2.13-2.24 (m, 1H), 2.93&2.94 (each-s, 3H), 3.04&3.09 (each-s, 3H), 3.60-3.71 (m, 2H), 3.88-4.03 (m, 2H), 4.10-4.25 (m, 1H), 4.63-4.79 (m, 1H), 5.12-5.29 (m, 2H), 5.81-5.93 (m, 1H)

Step 149-2: Synthesis of (4R)-4-(allyloxy)-N,N-dimethyl-L-prolinamide trifluoroacetate With 6.70 g of the compound obtained in Step 149-1 as starting material, 6.70 g of the title compound (crude form light brown oil) was obtained by a similar method to Step 4-1. The present compound was used in the next reaction without purification.

MS (ESI pos.) m/z: 129 ([M+H]$^+$)
$^1$H-NMR (600 MHz, CDCl$_3$) δ (ppm); 1.91-2.00 (m, 1H), 2.60-2.69 (m, 1H), 3.05 (s, 3H), 3.10 (s, 3H), 3.37-3.46 (m, 1H), 3.77-3.85 (m, 1H), 3.91-4.09 (m, 2H), 4.33-4.39 (m, 1H), 5.06-5.14 (m, 1H), 5.20-5.31 (m, 2H), 5.78-5.89 (m, 1H)

Step 149-3: (4R)-4-(allyloxy)-1-[5-chloro-3-(2-methoxy-5-methylphenyl)-2-oxo-2,3-dihydro-1H-indol-3-yl]-N,N-dimethyl-L-prolinamide Synthesis of With 6.60 g of the compound that is obtained at Step 109-4 and 6.70 g of (4R)-4-(allyloxy)-N,N-dimethyl-L-prolinamide trifluoroacetate as starting materials, respectively 1.0 g (Isomer A: colorless solid) and 5.1 g (Isomer B: brown amorphous) of two species of diastereoisomers of the title compound were obtained by a similar method to Step 4-2.

Isomer A: MS (ESI pos.) m/z: 484 ([M+H]$^+$)

$^1$H-NMR (600 MHz, CDCl$_3$) δ (ppm); 1.89-1.96 (m, 1H), 2.02-2.09 (m, 1H), 2.41 (s, 3H), 2.49 (s, 3H), 2.73 (s, 3H), 3.39-3.44 (m, 1H), 3.50 (s, 3H), 3.68-3.73 (m, 1H), 3.80-3.86 (m, 1H), 3.88-3.94 (m, 1H), 4.04-4.09 (m, 1H), 4.12-4.18 (m, 1H), 5.10-5.15 (m, 1H), 5.21-5.27 (m, 1H), 5.85-5.94 (m, 1H), 6.67-6.75 (m, 2H), 6.82-6.86 (m, 1H), 7.03-7.11 (m, 2H), 8.02 (s, 1H), 8.20-8.26 (m, 1H)

Isomer B: MS (ESI pos.) m/z: 484 ([M+H]$^+$)

$^1$H-NMR (600 MHz, CDCl$_3$) δ (ppm); 1.83-4.98 (m, 11H), 2.31 (s, 3H), 2.50 (s, 3H), 3.56 (s, 3H), 5.09-5.32 (m, 2H), 5.80-5.95 (m, 1H), 6.65-6.77 (m, 2H), 6.96-7.14 (m, 3H), 7.68-7.82 (m, 1H), 8.01-8.19 (m, 1H)

Step 149-4: Synthesis of (4R)-4-(allyloxy)-1-[5-chloro-3-(2-methoxy-5-methylphenyl)-2-oxo-2,3-dihydro-1H-indol-3-yl]-N,N-dimethyl-L-prolinamide (levorotatory isomer)

With 5.1 g of the compound obtained in Step 149-3 (Isomer B) and 593 mg of 4-methoxy-2-(trifluoromethoxy)benzene sulfonyl chloride as starting materials, 4.70 g of the title compound (colorless solid) was obtained by a similar method to Example 2.

[α]$_D^{25}$=151° (c=0.332, CHCl$_3$)

MS (ESI pos.) m/z: 738 ([M+H]$^+$)

$^1$H-NMR (600 MHz, CDCl$_3$) δ (ppm); 1.13-4.82 (m, 14H), 2.16 (s, 3H), 2.26 (s, 3H), 3.86 (s, 3H), 5.02-5.25 (m, 2H), 5.71-5.84 (m, 1H), 6.62-6.67 (m, 1H), 6.84 (s, 1H), 6.90-6.94 (m, 1H), 7.00-7.04 (m, 1H), 7.07-7.16 (m, 1H), 7.19-7.25 (m, 1H), 7.52-7.61 (m, 1H), 7.87 (d, J=8.7 Hz, 1H), 8.21-8.36 (m, 1H)

Example 150

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(2,3-dihydroxy propoxy)-N,N-dimethyl-L-prolinamide (diastereoisomer mixture)

To a solution of 1.0 g of the compound obtained in Step 149-4 in water (2.8 ml) and MeCN (7.8 ml) was added an aqueous solution of 50% N-methyl morpholine (0.56 ml) and osmium tetroxide (4% aqueous solution, 0.43 ml) and the reaction mixture was stirred overnight at room temperature. 82 mg of sodium hydrogen sulfite was added to the reaction solution and the mixture was stirred at room temperature for one hour. After filtration with celite, the filtrate was concentrated under reduced pressure. Water was added to the residue and the resulting mixture was extracted with EtOAc. The extract was dried over Na$_2$SO$_4$, then, the drying agent was separated by filtration and the solvent was evaporated under reduced pressure. The obtained residue was purified by column chromatography (silicagel 60; mobile phase: CHCl$_3$/MeOH=18/1; v/v) to obtain 756 mg of the title compound (colorless solid).

MS (ESI pos.) m/z: 772 ([M+H]$^+$)

$^1$H-NMR (600 MHz, CDCl$_3$) δ (ppm); 1.17-4.89 (m, 19H), 2.27 (s, 3H), 2.37 (s, 3H), 3.90 (s, 3H), 6.59-6.70 (m, 1H), 6.88-6.98 (m, 2H), 6.96-7.06 (m, 1H), 7.05-7.17 (m, 1H), 7.18-7.31 (m, 1H), 7.48-7.63 (m, 1H), 7.85 (d, J=8.7 Hz, 1H), 8.26-8.41 (m, 1H)

Example 151

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[3-(diethylamino)propoxy]-N,N-dimethyl-L-prolinamide (levorotatory isomer)

Step 151-1: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-(3-hydroxypropoxy)-N,N-dimethyl-L-prolinamide To a solution of 100 mg of the compound obtained in Step 149-4 in THF (3 ml) was added a 0.5M 9-borabicyclo[3.3.1] nonane THF solution (3.20 ml) and the reaction mixture was stirred for 3 hours at 50° C. After returning to room temperature, an aqueous solution of 3 mol/L sodium acetate, 30% hydrogen peroxide water (0.32 ml) and water (2 ml) were added, and the solution was stirred for 15 hours as is. Water was added to the reaction solution, and the resulting mixture was extracted with EtOAc, and then washed with saturated brine. The organic layer was dried over Na$_2$SO$_4$, then, the drying agent was separated by filtration and the solvent was evaporated under reduced pressure. The obtained residue was purified with a preparative TLC plate (1 mm; mobile phase: CHCl$_3$/MeOH=18/1; v/v) to obtain 65 mg of the title compound (colorless oil).

MS (ESI pos.) m/z: 756 ([M+H]$^+$)

$^1$H-NMR (600 MHz, CDCl$_3$) δ (ppm); 1.11-4.89 (m, 18H), 2.27 (s, 3H), 2.35 (s, 3H), 3.90 (s, 3H), 6.65 (d, J=8.3 Hz, 1H), 6.90-6.97 (m, 2H), 6.99-7.04 (m, 1H), 7.07-7.18 (m, 1H), 7.20-7.25 (m, 1H), 7.51-7.64 (m, 1H), 7.86 (d, J=9.2 Hz, 1H), 8.24-8.38 (m, 1H)

Step 151-2: Synthesis of 3-({(3R,5S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-5-[(dimethylamino)carbonyl] pyrrolidin-3-yl}oxy) propyl methane sulfonate To a solution of 3.20 g of the compound obtained in Step 151-1 in CHCl$_3$ (30 ml) was added Et$_3$N (0.57 ml) under ice cooling and was added dropwise methane sulfonyl chloride (0.19 ml). The solution was stirred at room temperature for one hour. A saturated aqueous solution of NaHCO$_3$ was added to the reaction solution and the resulting mixture was extracted with EtOAc. The extract was dried over Na$_2$SO$_4$, then, the drying agent was separated by filtration and the solvent was evaporated under reduced pressure. The title compound in the amounts of 4.20 g (light yellow oil) was obtained. The present compound was used in the next reaction without purification.

MS (ESI pos.) m/z: 834 ([M+H]$^+$)

Step 151-3: Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[3-(diethylamino)propoxy]-N,N-dimethyl-L-prolinamide (levorotatory isomer)

To a solution of 1.00 g of the compound obtained in Step 151-2 in CHCl$_3$ (5 ml) was added 739 mg of diethyl amine and the reaction mixture was stirred at 80° C. for 3 hours. A saturated aqueous solution of NaHCO$_3$ was added to the reaction solution and the resulting mixture was extracted with EtOAc. The extract was dried over Na$_2$SO$_4$, then, the drying agent was separated by filtration and the solvent was evaporated under reduced pressure. The obtained residue was purified with a preparative TLC plate (2 mm; mobile phase: CHCl$_3$/MeOH=8/1; v/v) to obtain 220 mg of the title compound (colorless amorphous).

[α]$_D^{25}$=−131° (c=0.208, CHCl$_3$)
MS (ESI pos.) m/z: 811 ([M+H]$^+$)
$^1$H-NMR (600 MHz, CDCl$_3$) δ (ppm); 0.91-4.83 (m, 34H), 3.89 (s, 3H), 6.60-6.67 (m, 1H), 6.86 (s, 1H), 6.90-6.95 (m, 1H), 6.99-7.04 (m, 1H), 7.07-7.15 (m, 1H), 7.20-7.24 (m, 1H), 7.51-7.63 (m, 1H), 7.85 (d, J=8.7 Hz, 1H), 8.25-8.39 (m, 1H)

Example 152

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-{3-[ethyl(methyl)amino]propoxy}-N,N-dimethyl-L-prolinamide (levorotatory isomer)

With 1.00 g of the compound obtained in Step 151-2 and 590 mg of ethylmethylamine as starting materials, 220 mg of the title compound (light yellow amorphous) was obtained by a similar method to Step 151-3.

[α]$_D^{25}$=−136° (c=0.284, CHCl$_3$)
MS (ESI pos.) m/z: 797 ([M+H]$^+$)
$^1$H-NMR (600 MHz, CDCl$_3$) δ (ppm); 3.88 (s, 3H), 6.64 (d, J=8.7 Hz, 1H), 6.86 (s, 1H), 6.90-6.96 (m, 1H), 6.98-7.06 (m, 1H), 7.06-7.17 (m, 1H), 7.19-7.25 (m, 1H), 7.51-7.65 (m, 1H), 7.85 (d, J=8.7 Hz, 1H), 8.25-8.38 (m, 1H)

Example 153

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-(3-piperidin-1-ylpropoxy)-L-prolinamide (levorotatory isomer)

With 1.00 g of the compound obtained in Step 151-2 and 850 mg of piperidine as starting material, 300 mg of the title compound (colorless amorphous) was obtained by a similar method to Step 151-3.

[α]$_D^{25}$=−136° (c=0.298, CHCl$_3$)
MS (ESI pos.) m/z: 823 ([M+H]$^+$)
$^1$H-NMR (600 MHz, CDCl$_3$) δ (ppm); 1.08-4.84 (m, 34H), 3.87 (s, 3H), 6.63 (d, J=7.8 Hz, 1H), 6.86 (s, 1H), 6.91 (d, J=8.7 Hz, 1H), 7.00 (d, J=7.8 Hz, 1H), 7.05-7.16 (m, 1H), 7.21 (d, J=8.7 Hz, 1H), 7.40-7.70 (m, 1H), 7.84 (d, J=8.7 Hz, 1H), 8.13-8.42 (m, 1H)

Example 154

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-[3-(4-methylpiperazin-1-yl)propoxy]-L-prolinamide (levorotatory isomer)

With 1.00 g of the compound obtained in Step 151-2 and 1.00 g of 1-methylpiperazine as starting material, 300 mg of the title compound (colorless amorphous) was obtained by a similar method to Step 151-3.

[α]$_D^{25}$=132° (c=0.232, CHCl$_3$)
MS (ESI pos.) m/z: 838 ([M+H]$^+$)
$^1$H-NMR (600 MHz, CDCl$_3$) δ (ppm); 1.09-4.84 (m, 25H), 3.86 (s, 3H), 6.63 (d, J=7.8 Hz, 1H), 6.84 (s, 1H), 6.87-6.93 (m, 1H), 6.97-7.02 (m, 1H), 7.03-7.16 (m, 1H), 7.17-7.24 (m, 1H), 7.45-7.66 (m, 1H), 7.84 (d, J=8.7 Hz, 1H), 8.19-8.41 (m, 1H)

Example 155

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-(3-morpholin-4-ylpropoxy)-L-prolinamide (levorotatory isomer)

With 150 mg of the compound obtained in Step 139-5 and 86 mg of morpholine as starting materials, 50 mg of the title compound (amorphous) was obtained by a similar procedure to Example 141.

[α]$_D^{25}$=−125° (c=0.407, CHCl$_3$)
MS (ESI pos.) m/z: 825 ([M+H]$^+$), (ESI neg.) m/z: 823 ([M−H]$^-$)
$^1$H-NMR (600 MHz, CDCl$_3$) δ (ppm); 1.14-1.30 (m, 1H), 1.52-1.81 (m, 4H), 1.81-1.93 (m, 1H), 2.16-2.47 (m, 12H), 2.80 (s, 3H), 3.01-3.13 (m, 1H), 3.20-3.35 (m, 3H), 3.51-3.61 (m, 2H), 3.65 (s, 3H), 3.86 (s, 3H), 4.26-4.41 (m, 1H), 4.65-4.79 (m, 1H), 6.62 (d, J=8.25 Hz, 1H), 6.84 (s, 1H), 6.90 (dd, J=9.17, 2.29 Hz, 1H), 6.99 (dd, J=8.25, 2.29 Hz, 1H), 7.04-7.13 (m, 1H), 7.20 (dd, J=8.71, 1.83 Hz, 1H), 7.50-7.59 (m, 1H), 7.83 (d, J=8.71 Hz, 1H), 8.20-8.35 (m, 1H)

Example 156

Synthesis of 1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethyl-4-oxo-L-prolinamide (levorotatory isomer)

With 3.00 g of the compound obtained in Step 103-3 as starting material, 2.57 g of the title compound (amorphous) obtained by a similar procedure to Step 140-1.

[α]$_D^{25}$=−136° (c=0.212, CHCl$_3$)
MS (ESI pos.) m/z: 696 ([M+H]$^+$), (ESI neg.) m/z: 694 ([M−H]$^-$)
$^1$H-NMR (600 MHz, CDCl$_3$) δ (ppm); 1.81-2.20 (m, 3H), 2.29 (s, 3H), 2.42-2.54 (m, 3H), 2.56-2.74 (m, 1H), 2.84-2.97 (m, 3H), 3.50-3.73 (m, 3H), 3.90 (s, 3H), 4.67-4.86 (m, 1H), 6.67-6.75 (m, 1H), 6.84 (s, 1H), 6.91 (dd, J=8.71, 2.29 Hz, 1H), 7.05-7.11 (m, 2H), 7.28 (dd, J=9.17, 2.29 Hz, 1H), 7.48-7.59 (m, 1H), 7.88 (d, J=8.71 Hz, 1H), 8.16-8.33 (m, 1H)

Example 157

Synthesis of benzyl(4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-L-prolinate Step 157-1: Synthesis of 2-benzyl 1-tert-butyl (2S,4R)-4-hydroxypyrrolidine-1,2-dicarboxylate To a solution of (4R)-1-(tert-butoxy carbonyl)-4-hydroxy-L-proline in DMF (80 ml) was added 5.4 g of NaHCO$_3$ and 11.1 g of benzyl bromide and the reaction mixture was stirred at 60° C. for 5 hours. Water was added to the reaction solution and the resulting mixture was extracted with EtOAc. The extract was dried over Na$_2$SO$_4$, then, the drying agent was separated by filtration and the solvent was evaporated under reduced pressure. The obtained residue was purified by column chromatography (silicagel 60; mobile phase: hexane/EtOAc=1/1 to CHCl$_3$/MeOH=8/1; v/v) to obtain 10.0 g of the title compound (colorless oil).

MS (ESI pos.) m/z: 344 ([M+Na]$^+$)
$^1$H-NMR (200 MHz, CDCl$_3$) δ (ppm); 1.31-1.50 (m, 9H), 1.97-2.16 (m, 1H), 2.18-2.43 (m, 1H), 3.35-3.70 (m, 2H), 4.36-4.58 (m, 2H), 5.03-5.34 (m, 2H), 7.29-7.41 (m, 5H)

Step 157-2: Synthesis of benzyl(4R)-4-hydroxy-L-prolinate hydrochloride

To a solution of 10.0 g of the compound obtained in Step 157-1 in EtOAc (49 ml) was added a solution of 4 mol/L hydrochloric acid/EtOAc (39 ml). The solution was stirred at room temperature for one hour. The precipitated crystal was filtered, and the crystal was washed with EtOAc. The title compound in the amount of 6.70 g (colorless solid) was obtained.

MS (ESI pos.) m/z: 322 ([M+H]$^+$)
$^1$H-NMR (200 MHz, DMSO-d$_6$) δ (ppm); 1.97-2.31 (m, 2H), 3.02-3.14 (m, 1H), 3.30-3.46 (m, 1H), 4.37-4.62 (m, 2H), 5.20 (d, J=12.3 Hz, 1H), 5.28 (d, J=12.3 Hz, 1H), 7.32-7.50 (m, 5H)

Step 157-3: Synthesis of benzyl(4R)-1-[5-chloro-3-(2-methoxy-5-methylphenyl)-2-oxo-2,3-dihydro-1H-indol-3-yl]-4-hydroxy-L-prolinate With 5.00 g of the compound that is obtained at Step 109-4 and 6.7 g of the compound obtained in Step 157-2 as starting materials, respectively 0.30 g (Isomer A: light yellow amorphous) and 2.6 g (Isomer B: light yellow amorphous) of two species of diastereoisomers of the title compound were obtained by a similar method to Step 4-2.

Isomer A: MS (ESI pos.) m/z: 507 ([M+H]$^+$)
$^1$H-NMR (600 MHz, CDCl$_3$) δ (ppm); 1.87-1.95 (m, 1H), 2.15-2.23 (m, 1H), 2.39 (s, 3H), 2.95-3.00 (m, 1H), 3.55 (s, 3H), 3.57-3.66 (m, 2H), 4.29-4.34 (m, 1H), 4.69 (d, J=12.4 Hz, 1H), 4.91 (d, J=12.4 Hz, 1H), 6.69-6.73 (m, 2H), 6.89-6.92 (m, 1H), 7.01-7.09 (m, 2H), 7.20-7.24 (m, 2H), 7.27-7.38 (m, 3H), 7.86 (s, 1H), 7.97 (s, 1H)

Isomer B: MS (ESI pos.) m/z: 507 ([M+H]$^+$)
$^1$H-NMR (600 MHz, CDCl$_3$) δ (ppm); 1.49-5.04 (m, 8H), 2.26 (s, 3H), 3.58 (s, 3H), 6.60 (d, J=8.7 Hz, 1H), 6.73 (d, J=8.3 Hz, 1H), 6.99-7.11 (m, 3H), 7.19-7.24 (m, 2H), 7.27-7.38 (m, 3H), 7.65 (s, 1H), 8.40-8.62 (m, 1H)

Step 157-4: Synthesis of benzyl(4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-L-prolinate With 2.6 g of the compound obtained in Step 157-3 (Isomer B) and 1.79 g of 4-methoxy-2-(trifluoromethoxy)benzenesulfonyl chloride as starting materials, 2.8 g of the title compound (colorless amorphous) was obtained by a similar method to Example 2.

MS (ESI pos.) m/z: 761 ([M+H]$^+$)
$^1$H-NMR (600 MHz, CDCl$_3$) δ (ppm); 1.85-5.05 (m, 14H), 3.87 (s, 3H), 6.64-6.68 (m, 1H), 6.84-6.87 (m, 1H), 6.91-6.94 (m, 1H), 6.98-7.01 (m, 1H), 7.04-7.09 (m, 1H), 7.14-7.18 (m, 2H), 7.20-7.24 (m, 1H), 7.27-7.32 (m, 3H), 7.55-7.63 (m, 1H), 7.84-7.88 (m, 1H)

Example 158

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-L-proline (levorotatory isomer)

To a solution of 2.8 g of the compound obtained in Step 157-4 in EtOAc (50 ml) was added 700 mg of 10% palladium-carbon and the reaction mixture was stirred at room temperature for 8 hours under hydrogen atmosphere. After filtration with celite, the filtrate was concentrated under reduced pressure. The obtained residue was purified by column chromatography (silicagel 60; mobile phase: n-hexane/EtOAc=1/1 to CHCl$_3$/MeOH=9/1; v/v) to obtain 620 mg of the title compound (colorless amorphous).

[α]$_D^{25}$=−151° (c=0.280, CHCl$_3$)
MS (ESI pos.) m/z: 671 ([M+H]$^+$)
$^1$H-NMR (600 MHz, CDCl$_3$) δ (ppm); 1.82-1.98 (m, 1H), 2.08-2.15 (m, 1H), 2.18 (s, 3H), 2.23-2.36 (m, 1H), 3.15-3.23 (m, 1H), 3.57 (s, 3H), 3.89 (s, 3H), 4.25-4.30 (m, 1H), 4.34-4.42 (m, 1H), 6.70 (d, J=8.3 Hz, 1H), 6.85 (s, 1H), 6.91-6.98 (m, 1H), 7.00-7.06 (m, 1H), 7.24-7.36 (m, 3H), 7.87 (d, J=8.7 Hz, 1H), 8.31 (d, J=8.7 Hz, 1H)

Example 159

Synthesis of 5-chloro-3-{(2S,4R)-4-hydroxy-2-[(4-methylpiperazin-1-yl)carbonyl]pyrrolidin-1-yl}-3-(2-methoxy-5-methylphenyl)-1-{[4-methoxy-2-(trifluoromethoxy)phenyl]sulfonyl}-1,3-dihydro-2H-indol-2-one (levorotatory isomer)

To 100 mg of compound obtained in Example 158 in DMF (1.0 ml) were added 46 mg of HOBt/H$_2$O, 57 mg of EDC/HCl and 30 mg of 1-methylpiperazine, and the solution was stirred at room temperature for 4 hours. A saturated aqueous solution of NaHCO$_3$ was added to the reaction solution and the resulting mixture was extracted with EtOAc. The extract was dried over Na$_2$SO$_4$, then, the drying agent was separated by filtration and the solvent was evaporated under reduced pressure. The obtained residue was purified by column chromatography (Chromatorex NH; mobile phase: EtOAc to CHCl$_3$/MeOH=8/1; v/v) to obtain 100 mg of the title compound (colorless amorphous).

[α]$_D^{25}$=−168° (c=0.240, CHCl$_3$)
MS (ESI pos.) m/z: 753 ([M+H]$^+$)
$^1$H-NMR (600 MHz, CDCl$_3$) δ (ppm); 1.26-4.89 (m, 23H), 3.86 (s, 3H), 6.63 (d, J=8.3 Hz, 1H), 6.84 (s, 1H), 6.88-6.94 (m, 1H), 6.95-7.02 (m, 1H), 7.03-7.15 (m, 1H), 7.17-7.26 (m, 1H), 7.48-7.73 (m, 1H), 7.84 (d, J=8.7 Hz, 1H), 8.27-8.37 (m, 1H)

Example 160

(4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N-[2-(dimethylamino)ethyl]-4-hydroxy-N-methyl-L-prolinamide (levorotatory isomer) Synthesis of With 100 mg of the compound obtained in Example 158 and 30 mg of N,N,N'-trimethyl-ethane-1,2-diamine as starting materials, 70 mg of the title compound (colorless amorphous) was obtained by a similar method to Example 159.

[α]$_D^{25}$=−192° (c=0.192, CHCl$_3$)
MS (ESI pos.) m/z: 755 ([M+H]$^+$)

¹H-NMR (600 MHz, CDCl₃) δ (ppm); 1.21-4.75 (m, 25H), 3.87 (s, 3H), 6.60-6.70 (m, 1H), 6.80-7.24 (m, 5H), 7.50-7.67 (m, 1H), 7.86 (d, J=8.7 Hz, 1H), 8.22-8.37 (m, 1H)

Example 161

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-bis(2-hydroxy ethyl)-L-prolinamide (levorotatory isomer)

With 100 mg of compound obtained in Example 158 and 32 mg of diethanol amine as starting materials, 15 mg of the title compound (colorless amorphous) was obtained by a similar method to Example 159.
[α]$_D^{25}$=171° (c=0.086, CHCl₃)
MS (FAB pos.) m/z: 758 ([M+H]⁺)
¹H-NMR (500 MHz, CDCl₃) δ (ppm); 1.51-4.48 (m, 17H), 2.27 (s, 3H), 3.89 (S, 3H), 6.66 (d, J=8.4 Hz, 1H), 6.87 (s, 1H), 6.91-6.97 (m, 1H), 6.99-7.09 (m, 2H), 7.22-7.27 (m, 1H), 7.53-7.65 (m, 1H), 7.87 (d, J=8.4 Hz, 1H), 8.33 (d, J=8.4 Hz, 1H)

Example 162

Synthesis of tert-butyl{1-[(4R)-1-(5-chloro-3-(2-methoxy-5-methylphenyl)-1-{[4-methoxy-2-(trifluorometho xy)phenyl]sulfonyl}-2-oxo-2,3-dihydro-1H-indol-3-yl)-4-hydroxy-L-prolyl]azetidin-3-yl}carbamate With 200 mg of compound obtained in Example 158 and 103 mg of azetidin-3-yl-carbamic acid tert-butyl ester as starting materials, 114 mg of the title compound (colorless amorphous) was obtained by a similar method to Example 159.
MS (ESI pos.) m/z: 825 ([M+H]⁺)
¹H-NMR (600 MHz, CDCl₃) δ (ppm); 1.11-4.84 (m, 24H), 3.88 (s, 3H), 6.68-6.75 (m, 1H), 6.86 (s, 1H), 6.90-6.96 (m, 1H), 7.06-7.17 (m, 1H), 7.20-7.25 (m, 1H), 7.62-7.76 (m, 1H), 7.88 (t, J=8.9 Hz, 1H), 8.30 (d, J=9.2 Hz, 1H)

Example 163

Synthesis of 3-{(2S,4R)-2-[(3-amino azetidin-1-yl)carbonyl]-4-hydroxypyrrolidin-1-yl}-5-chloro-3-(2-methoxy-5-methylphenyl)-1-{[4-methoxy-2-(trifluoromethoxy)phenyl]sulfonyl}-1,3-dihydro-2H-indol-2-one (levorotatory isomer)

Concentrated hydrochloric acid was added to 200 mg of compound obtained in Example 162, and the solution was stirred at room temperature for 30 minutes. The solution was poured into saturated NaHCO₃ and the resulting mixture was extracted with EtOAc. The extract was dried over Na₂SO₄, then, the drying agent was separated by filtration and the solvent was evaporated under reduced pressure. The title compound in the amount of 144 mg (colorless amorphous) was obtained.
[α]$_D^{25}$=−162° (c=0.250, CHCl₃)
MS (ESI pos.) m/z: 725 ([M+H]⁺)
¹H-NMR (500 MHz, CDCl₃) δ (ppm); 1.10-4.64 (m, 17H), 3.89 (s, 3H), 6.70 (t, J=8.8 Hz, 1H), 6.86 (s, 1H), 6.91-6.96 (m, 1H), 7.04-7.14 (m, 2H), 7.21-7.26 (m, 1H), 7.64-7.76 (m, 1H), 7.85-7.91 (m, 1H), 8.31 (d, J=9.2 Hz, 1H)

Example 164

Synthesis of 5-chloro-3-((2S,4R)-2-{[3-(dimethylamino) azetidin-1-yl]carbonyl}-4-hydroxypyrrolidin-1-yl)-3-(2-methoxy-5-methylphenyl)-1-{[4-methoxy-2-(trifluoromethoxy)phenyl]sulfonyl}-1,3-dihydro-2H-indol-2-one (levorotatory isomer)

A mixed solution of 100 mg of the compound obtained in Example 163, 37% formalin (2 ml) and formic acid (1 ml) was stirred at 80° C. for 4 hours. The reaction solution was poured into a saturated aqueous solution of NaHCO₃ and the resulting mixture was extracted with EtOAc. The extract was dried over Na₂SO₄, then, the drying agent was separated by filtration and the solvent was evaporated under reduced pressure. The obtained residue was purified with a preparative TLC plate (2 mm; mobile phase: CHCl₃/MeOH=8/1; v/v) to obtain 103 mg of the title compound (colorless amorphous).
[α]$_D^{25}$=−173° (c=0.198, CHCl₃)
MS (ESI pos.) m/z: 753 ([M+H]⁺)
¹H-NMR (600 MHz, CDCl₃) δ (ppm); 1.17-4.74 (m, 23H), 3.87 (s, 3H), 6.64-6.72 (m, 1H), 6.82-6.87 (m, 1H), 6.90-6.94 (m, 1H), 7.00-7.16 (m, 2H), 7.20-7.25 (m, 1H), 7.57-7.69 (m, 1H), 7.84-7.90 (m, 1H)

Example 165

Synthesis of 3-[(2S,4R)-2-(azetidin-1-ylcarbonyl)-4-hydroxypyrrolidin-1-yl]-5-chloro-3-(2-methoxy-5-methy lphenyl)-1-{[4-methoxy-2-(trifluoromethoxy)phenyl]sulfonyl}-1,3-dihydro-2H-indol-2-one (levorotatory isomer)

Step 165-1: Synthesis of 3-[(2S,4R)-2-(azetidin-1-ylcarbonyl)-4-hydroxypyrrolidin-1-yl]-5-chloro-3-(2-methoxy-5-methylphenyl)-1,3-dihydro-2H-indol-2-one From 30.0 g of the compound that is obtained at Step 109-4 and (3R,5S)-5-(azetidin-1-ylcarbonyl)pyrrolidin-3-ol trifluoroacetate (3.72 mmol), respectively 130 mg (Isomer A: brown amorphous) and 508 mg (Isomer B: pale red amorphous) of two species of diastereoisomers of the title compound were obtained by a similar method to Step 28-2.
Isomer A: MS (ESI pos.) m/z: 456 ([M+H]⁺), 478 ([M+Na]⁺), (ESI neg.) m/z: 454 ([M−H]⁻)
¹H-NMR (600 MHz, CDCl₃) δ (ppm); 1.83-1.90 (m, 1H) 1.97-2.24 (m, 3H) 2.29-2.35 (m, 1H) 2.39 (s, 3H) 3.36-3.45 (m, 1H) 3.52-3.55 (m, 2H) 3.56 (s, 3H) 3.61-3.67 (m, 1H) 3.77-3.82 (m, 3H) 4.05-4.13 (m, 1H) 4.30-4.33 (m, 1H) 6.71 (d, J=8.3 Hz, 1H) 6.81 (d, J=8.3 Hz, 1H) 7.06 (d, J=9.6 Hz, 1H) 7.20 (dd, J=8.3, 2.3 Hz, 1H) 7.87 (s, 1H) 8.17-8.29 (m, 1H)
Isomer B: MS (ESI pos.) m/z: 456 ([M+H]⁺), 478 ([M+Na]⁺), (ESI neg.) m/z: 454 ([M−H]⁻)
¹H-NMR (600 MHz, CDCl₃) δ (ppm); 1.81-2.69 (m, 6H) 2.39 (s, 3H) 2.99-3.44 (m, 2H) 3.54-3.67 (m, 3H) 3.73-3.91 (m, 3H) 4.39-4.57 (m, 1H) 4.58-4.66 (m, 1H) 6.71-6.80 (m, 2H) 7.03-7.18 (m, 3H) 7.76 (s, 1H) 8.78 (brs, 1H)

Step 165-2: Synthesis of 3-[(2S,4R)-2-(azetidin-1-ylcarbonyl)-4-hydroxypyrrolidin-1-yl]-5-chloro-3-(2-methoxy-5-methy lphenyl)-1-{[4-methoxy-2-(trifluoromethoxy)phenyl]sulfonyl}-1,3-dihydro-2H-indol-2-one With 496 mg of the compound obtained in Step 160-1 (Isomer B) as starting material, 383 mg of the title compound (colorless amorphous) was obtained by a similar method to Example 2.

[α]$_D^{28}$=−179° (c=0.131, CHCl$_3$)

MS (ESI pos.) m/z: 710 ([M+H]$^+$), 732 ([M+Na]$^+$), (ESI neg.) m/z: 708 ([M−H]$^−$)

$^1$H-NMR (600 MHz, CDCl$_3$) δ (ppm); 1.58-1.85 (m, 4H) 1.87-2.05 (m, 2H) 2.38 (s, 3H) 2.70-2.88 (m, 1H) 2.99-3.16 (m, 1H) 3.59 (brs, 3H) 3.70-3.76 (m, 1H) 3.76-3.83 (m, 1H) 3.85-3.94 (m, 1H) 3.87 (s, 3H) 4.24-4.34 (m, 1H) 4.55-4.62 (m, 1H) 6.69 (d, J=8.3 Hz, 1H) 6.84-6.87 (m, 1H) 6.92 (dd, J=9.2, 2.3 Hz, 1H) 7.08 (d, J=6.9 Hz, 1H) 7.12 (brs, 1H) 7.23 (dd, J=8.7, 2.3 Hz, 1H) 7.67 (s, 1H) 7.87 (d, J=8.7 Hz, 1H) 8.29 (d, J=8.7 Hz, 1H)

Example 166

Synthesis of (4R)-1-(5-chloro-3-(2-methoxy-5-methylphenyl)-2-oxo-1-{[2-(trifluoromethoxy)phenyl]sulfonyl}-2,3-dihydro-1H-indol-3-yl)-4-hydroxy-N,N-dimethyl-L-prolinamide (levorotatory isomer)

With 150 mg of the compound that is obtained at Step 103-2 (Isomer B) and 100 mg of 2-(trifluoromethoxy)benzene sulfonyl chloride as starting materials, 111 mg of the title compound (colorless amorphous) was obtained by a similar method to Example 2.

[α]$_D^{25}$=−273° (c=0.415, CHCl$_3$)

MS (ESI pos.) m/z: 668 ([M+H]$^+$), 690 ([M+Na]$^+$), (ESI neg.) m/z: 666 ([M−H]$^−$)

$^1$H-NMR (600 MHz, CDCl$_3$) δ (ppm); 1.16-2.15 (m, 7H), 2.28 (s, 3H), 2.39 (s, 3H), 2.57-3.35 (m, 4H), 3.58 (s, 2H), 4.53-4.83 (m, 2H), 6.67 (d, J=8.3 Hz, 1H), 7.03 (dd, J=8.3, 2.3 Hz, 1H), 7.09-7.20 (m, 1H), 7.22-7.31 (m, 1H), 7.41 (d, J=8.3 Hz, 1H), 7.50 (t, J=7.8 Hz, 1H), 7.56-7.66 (m, 1H), 7.68-7.75 (m, 1H), 7.90 (d, J=8.7 Hz, 1H), 8.43 (d, J=6.4 Hz, 1H)

Example 167

Synthesis of (4R)-1-(5-chloro-3-(2-methoxy-5-methylphenyl)-2-oxo-1-{[4-(trifluoromethoxy)phenyl]sulfonyl}-2,3-dihydro-1H-indol-3-yl)-4-hydroxy-N,N-dimethyl-L-prolinamide (levorotatory isomer)

With 100 mg of the compound obtained in Step 103-2 (Isomer B) and 65 mg of 4-(trifluoromethoxy)benzene sulfonyl chloride as starting materials, 70 mg of the title compound (colorless amorphous) was obtained by a similar method to Example 2.

[α]$_D^{25}$=−154° (c=0.272, CHCl$_3$)

MS (ESI pos.) m/z: 668 ([M+H]$^+$), 690 ([M+Na]$^+$), (ESI neg.) m/z: 666 ([M−H]$^−$)

$^1$H-NMR (600 MHz, CDCl$_3$) δ (ppm); 1.86 (d, J=9.2 Hz, 2H), 2.16-3.94 (m, 15H), 4.53-4.89 (m, 2H), 6.63 (d, J=7.8 Hz, 1H), 7.00-7.14 (m, 2H), 7.22-7.31 (m, 1H), 7.39 (d, J=8.7 Hz, 2H), 7.49-7.98 (m, 2H), 8.31 (s, 2H)

Example 168

Synthesis of (4R)-1-(5-chloro-3-(2-methoxy-5-methylphenyl)-2-oxo-1-{[3-(trifluoromethoxy)phenyl]sulfonyl}-2,3-dihydro-1H-indol-3-yl)-4-hydroxy-N,N-dimethyl-L-prolinamide (levorotatory isomer)

With 150 mg of the compound obtained in Step 103-2 (Isomer B) and 100 mg of 3-(trifluoromethoxy)benzene sulfonyl chloride as starting materials, 117 mg of the title compound (colorless amorphous) was obtained by a similar method to Example 2.

[α]$_D^{25}$=−143° (c=0.270, CHCl$_3$)

MS (ESI pos.) m/z: 668 ([M+H]$^+$), 690 ([M+Na]$^+$), (ESI neg.) m/z: 666 ([M−H]$^−$)

$^1$H-NMR (600 MHz, CDCl$_3$) δ (ppm); 1.35-1.95 (m, 4H), 2.23-2.36 (m, 3H), 2.39-2.52 (m, 3H), 2.54-3.58 (m, 8H), 4.40-4.98 (m, 2H), 6.55-6.72 (m, 1H), 6.93-7.16 (m, 2H), 7.19-7.34 (m, 1H), 7.47-7.56 (m, 1H), 7.58-7.68 (m, 1H), 7.70-7.89 (m, 1H), 8.00-8.34 (m, 2H)

Example 169

Synthesis of (4R)-1-(5-chloro-3-(2-methoxy-5-methyl pyridin-3-yl)-1-{[4-methoxy-2-(2,2,2-trifluoroethoxy)phenyl]sulfonyl}-2-oxo-2,3-dihydro-1H-indol-3-yl)-4-hydroxy-N,N-dimethyl-L-prolinamide Step 169-1: Synthesis of 5-chloro-3-hydroxy-3-(2-methoxy-5-methyl pyridin-3-yl)-1,3-dihydro-2H-indol-2-one (levorotatory isomer)

Under nitrogen atmosphere and under dry ice-acetone cooling, tert-butyl lithium (64.0 ml; 1.42 mol/L n-pentane solution) was added to THF (150 ml), then, mesityl bromide (6.57 ml) was added dropwise over 2 minutes. The solution was stirred for one hour under the same conditions. 4.07 g of 2-methoxy-5-methylpyridine was added dropwise to the solution over 3 minutes and then the reaction mixture was stirred under ice cooling for one hour and at room temperature for 30 minutes. The solution was dry ice-acetone-cooled again, a suspension of 3.00 g of 5-chloroisatin in THF (75 ml) was added dropwise over 2 minutes, then the reaction mixture was warmed to room temperature and was stirred for 18 hours. To the reaction solution was added a saturated aqueous solution of NH$_4$Cl and EtOAc, then liquid separation was performed, the aqueous layer was extracted with EtOAc, the combined organic layer was washed with saturated brine, dried over MgSO$_4$, then, the drying agent was separated by filtration, and the filtrate was concentrated under reduced pressure. The obtained residue was purified by column chromatography (silicagel 60; mobile phase: CHCl$_3$/MeOH/NH$_4$OH=97/3/0.3; v/v/v) to obtain 2.05 g of the title compound (yellow solid).

MS (ESI pos.) m/z: 305 ([M+H]$^+$), 327 ([M+Na]$^+$)

$^1$H-NMR (600 MHz, DMSO-d$_6$) δ (ppm): 2.27 (s, 3H), 3.48 (s, 3H), 6.76-6.77 (m, 1H), 6.79-6.81 (m, 1H), 6.82 (d, J=8.3 Hz, 1H), 7.21 (dd, J=8.3, 2.3 Hz, 1H), 7.88 (s, 1H), 7.95 (d, J=1.8 Hz, 1H), 10.49 (s, 1H)

Step 169-2: Synthesis of (4R)-1-[5-chloro-3-(2-methoxy-5-methyl pyridin-3-yl)-2-oxo-2,3-dihydro-1H-indol-3-yl]-4-hydroxy-N,N-dimethyl-L-prolinamide From 2.00 g of the compound obtained in Step 169-1 and (4R)-4-hydroxy-N,N-dimethyl-L-prolinamide trifluoroacetate (6.89 mmol), respectively 500 mg (Isomer A: colorless amorphous) and 600 mg (Isomer B: colorless amorphous) of two species of diastereoisomers of the title compound were obtained by a similar method to Step 28-2.

Isomer A: MS (ESI pos.) m/z: 467 ([M+Na]$^+$)

$^1$H-NMR (200 MHz, CDCl$_3$) δ (ppm): 1.77-1.98 (m, 1H), 2.00-2.21 (m, 1H), 2.36 (s, 3H), 2.60 (s, 3H), 2.72 (s, 3H), 2.93-3.08 (m, 1H), 3.59 (d, J=3.1 Hz, 1H), 3.65 (s, 1H), 3.72 (s, 3H), 3.87-4.08 (m, 1H), 4.30-4.44 (m, 1H), 6.80 (d, J=8.4

Hz, 1H), 6.94 (d, J=2.2 Hz, 1H), 7.17 (dd, J=8.4, 2.2 Hz, 1H), 7.91 (d, J=1.8 Hz, 1H), 8.25 (s, 1H), 8.31-8.44 (m, 1H)

Isomer B: MS (ESI pos.) m/z: 467 ([M+Na]$^+$)

$^1$H-NMR (200 MHz, CDCl$_3$) δ (ppm); 1.82-2.20 (m, 2H), 2.28 (s, 3H), 2.39-2.50 (m, 1H), 2.53-2.68 (m, 4H), 2.75 (s, 3H), 3.37-3.53 (m, 1H), 3.78 (s, 3H), 4.54-4.70 (m, 1H), 4.80-4.96 (m, 1H), 6.76 (d, J=8.4 Hz, 1H), 7.08 (d, J=2.2 Hz, 1H), 7.14 (dd, J=8.4, 2.2 Hz, 1H), 7.89 (d, J=2.2 Hz, 1H), 8.06 (d, J=2.2 Hz, 1H), 8.40 (s, 1H)

Step 169-3: Synthesis of 1-methoxy-3-(2,2,2-trifluoroethoxy)benzene

A suspension of 5.00 g of 3-methoxy phenol, 10.0 g of 2,2,2-trifluoroethyl iodide and 20.0 g of cesium carbonate in DMF (15 ml) was stirred at 80° C. for two hours. The solution was added with water and extracted with Et$_2$O; the organic layer was washed in saturated brine, then, was dried in MgSO$_4$, the drying agent was separated by filtration and solvent was evaporated under reduced pressure obtained 6.60 g of the title compound.

MS (CI+ pos.) m/z: 207 ([M+H]$^+$)

$^1$H-NMR (200 MHz, CDCl$_3$) δ (ppm); 3.75-3.85 (m, 3H), 4.33 (q, J=8.35 Hz, 2H), 6.44-6.70 (m, 3H), 7.07-7.32 (m, 1H)

Step 169-4: Synthesis of 4-methoxy-2-(2,2,2-trifluoroethoxy)benzene sulfonyl chloride To a solution of 5.00 g of the compound obtained in Step 169-4 in carbon tetrachloride (25 ml) was added dropwise under ice cooling 4.58 g of trimethylsilyl chloro sulfonate over 30 minutes. After stirring at room temperature for 30 minutes, water was added, and the solution was extracted with CHCl$_3$. The aqueous layer was filtered with celite, the filtrate was neutralized in an aqueous solution of 2 mol/L KOH (PH=9), the solvent was evaporated under reduced pressure to obtain 6.10 g. Phosphorus oxychloride (30 ml) was added to the obtained residue and the reaction mixture was stirred at an external temperature of 100° C. for one hour. The solution was poured into ice water and the resulting mixture was extracted with Et$_2$O; the organic layer was washed with water and with saturated brine, and then was dried over MgSO$_4$, the drying agent was separated by filtration, and then the solvent was evaporated under reduced pressure. The obtained residue was purified by column chromatography (silicagel 60N; mobile phase: EtOAc/n-hexane=1/10 to 1/4; v/v) to obtain 444 mg of the title compound 4-methoxy-2-(2,2,2,-trifluoroethoxy)benzene sulfonyl chloride and 641 mg of 2-methoxy-4-(2,2,2,-trifluoroethoxy)benzene sulfonyl chloride.

4-methoxy-2-(2,2,2,-trifluoroethoxy)benzene sulfonyl chloride $^1$H-NMR (200 MHz, CDCl$_3$) δ (ppm); 3.92 (s, 3H), 4.54 (q, J=7.91 Hz, 2H), 6.54 (d, J=2.20 Hz, 1H), 6.67 (dd, J=9.01, 2.42 Hz, 1H), 7.95 (d, J=9.23 Hz, 1H)

2-methoxy-4-(2,2,2,-trifluoroethoxy)benzene sulfonyl chloride $^1$H-NMR (200 MHz, CDCl$_3$) δ (ppm); 4.05 (s, 3H), 4.45 (q, J=7.76 Hz, 2H), 6.57 (dd, J=9.01, 2.42 Hz, 1H), 6.67 (d, J=2.20 Hz, 1H), 7.95 (d, J=8.79 Hz, 1H)

Step 169-5: Synthesis of (4R)-1-(5-chloro-3-(2-methoxy-5-methyl pyridin-3-yl)-1-{[4-methoxy-2-(2,2,2-trifluoroethoxy)phenyl]sulfonyl}-2-oxo-2,3-dihydro-1H-indol-3-yl)-4-hydroxy-N,N-dimethyl-L-prolinamide (levorotatory isomer)

With 200 mg of the compound obtained in Step 169-3 (Isomer B) and 150 mg of 4-methoxy-2-(2,2,2,-trifluoroethoxy)benzene sulfonyl chloride obtained in Step 169-5 as starting materials, 182 mg of the title compound (amorphous) was obtained by a similar procedure to Example 2.

[α]$_D^{25}$=−195° (c=0.427, CHCl$_3$)

MS (ESI pos.) m/z: 713 ([M+H]$^+$), 735 ([M+Na]$^+$), (ESI neg.) m/z: 711 ([M−H]$^-$)

$^1$H-NMR (200 MHz, CDCl$_3$) δ (ppm); 1.40-1.65 (m, 2H), 1.81-1.94 (m, 2H), 1.95-2.09 (m, 3H), 2.23 (s, 3H), 2.46 (s, 3H), 2.84 (s, 3H), 3.76-3.88 (s, 8H), 6.41 (d, J=2.20 Hz, 1H), 6.73 (dd, J=9.23, 2.20 Hz, 1H), 7.04 (d, J=2.20 Hz, 1H), 7.23-7.33 (m, 1H), 7.84-7.96 (m, 3H), 8.26 (d, J=9.23 Hz, 1H)

Example 170

Synthesis of (4R)-1-[5-chloro-1-{[2-(difluoromethoxy)-4-methoxyphenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer)

Step 170-1 Synthesis of 1-(difluoromethoxy)-3-methoxy benzene 2.67 g of methyl iodide was stirred on ice in a suspension of 2.00 g of 3-difluoromethoxy phenol and 2.60 g of K$_2$CO$_3$ in DMF (10 ml) at room temperature for two hours. Water was added to the solution and the resulting mixture was extracted with Et$_2$O; the organic layer was washed with saturated brine and then dried over MgSO$_4$; the drying agent was separated by filtration, and the solvent was evaporated under reduced pressure obtained 46.0 g of the title compound (crude form).

MS (CI+ pos.) m/z: 175 ([M+H]$^+$), MS (EI+ pos.) m/z: 174 ([M]$^+$)

$^1$H-NMR (600 MHz, CDCl$_3$) δ (ppm); 3.80 (s, 3H), 6.50 (t, J=74.05 Hz, 1H), 6.66 (t, J=2.52 Hz, 1H), 6.70 (dd, J=8.48, 2.06 Hz, 1H), 6.75 (dd, J=8.25, 3.21 Hz, 1H), 7.25 (t, J=8.25 Hz, 1

Step 170-2 Synthesis of a mixture of 2-(difluoromethoxy)-4-methoxy benzene sulfonyl chloride and 4-(difluoromethoxy)-2-methoxy benzene sulfonyl chloride With 600 mg of the compound obtained in Step 170-1 as starting material, 300 mg of a mixture of the title compound was obtained by a similar procedure to Step G1-2.

$^1$H-NMR (500 MHz, CDCl$_3$) δ (ppm); 3.92 (s, 3H), 6.66 (t, 1H), 6.83-6.87 (m, 1H), 6.88-6.92 (m, 1H), 7.98 (d, J=9.17 Hz, 1H)

Step 170-3 Synthesis of (4R)-1-[5-chloro-1-{[2-(difluoromethoxy)-4-methoxyphenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer)

With 65 mg of (4R)-1-[5-chloro-3-(2-methoxy pyridin-3-yl)-2-oxo-2,3-dihydro-1H-indol-3-yl]-4-hydroxy-N,N-dimethyl-L-prolinamide, which is the compound described in Example 5 of the brochure Publication No. WO2005030755, and 40 mg of the compound obtained in Step 170-2 as starting materials, 51 mg of the title compound (amorphous) was obtained by a similar procedure to Example 2.

$[\alpha]_D^{25}$=−233° (c=0.080, CHCl$_3$)

MS (ESI pos.) m/z: 667 ([M+H]$^+$), 689 ([M+Na]$^+$), (ESI neg.) m/z: 665 ([M−H]$^-$)

$^1$H-NMR (200 MHz, CDCl$_3$) δ (ppm); 1.61 (s, 2H), 1.82-1.99 (m, 1H), 2.27-2.40 (m, 1H), 2.46 (s, 3H), 2.72-2.80 (m, 3H), 3.19-3.35 (m, 1H), 3.59-3.83 (m, 3H), 3.89 (s, 3H), 4.38-4.83 (m, 2H), 6.20-7.08 (m, 5H), 7.23-7.34 (m, 1H), 7.89 (d, J=8.79 Hz, 1H), 8.07 (dd, J=4.83, 2.20 Hz, 1H), 8.12-8.20 (m, 1H), 8.30 (d, J=9.23 Hz, 1H)

Example 171

Synthesis of (4R)-1-(5-chloro-3-(2-methoxy-5-methylphenyl)-1-{[4-methoxy-2-(2,2,2-trifluoroethoxy)phenyl]sulfonyl}-2-oxo-2,3-dihydro-1H-indol-3-yl)-4-hydroxy-N,N-dimethyl-L-prolinamide (levorotatory isomer)

With 141 mg of the compound obtained in Step 103-2 (Isomer B) and 102 mg of 4-methoxy-2-(2,2,2-trifluoroethoxy)benzene sulfonyl chloride as starting materials, 166 mg of the title compound (colorless amorphous) was obtained by a similar method to Example 2.

$[\alpha]_D^{29}$=−208° (c=0.104, CHCl$_3$)

MS (ESI pos.) m/z: 712 ([M+H]$^+$), 734 ([M+Na]$^+$), (ESI neg.) m/z: 710 ([M−H]$^-$)

$^1$H-NMR (600 MHz, CDCl$_3$) δ (ppm); 1.62-1.72 (m, 2H) 1.95-2.06 (m, 1H) 2.25 (s, 3H) 2.34 (s, 3H) 2.82 (s, 3H) 2.99-3.09 (m, 1H) 3.61-3.69 (m, 1H) 3.65 (brs, 3H) 3.86 (s, 3H) 4.22-4.30 (m, 1H) 4.40-4.48 (m, 1H) 4.66-4.73 (m, 1H) 4.75 (d, J=9.6 Hz, 1H) 6.39 (d, J=2.3 Hz, 1H) 6.66 (d, J=8.3 Hz, 1H) 6.70 (dd, J=8.7, 2.3 Hz, 1H) 6.99-7.03 (m, 1H) 7.07 (d, J=1.8 Hz, 1H) 7.22-7.26 (m, 1H) 7.50-7.56 (m, 1H) 7.90 (d, J=8.7 Hz, 1H) 8.23 (d, J=8.7 Hz, 1H)

Example 172

Synthesis of (4R)-1-{5-chloro-3-(2-methoxy-5-methyl pyridin-3-yl)-2-oxo-1-[(2,4,5-trimethoxyphenyl)sulfonyl]-2,3-dihydro-1H-indol-3-yl}-4-hydroxy-N,N-dimethyl-L-prolinamide (levorotatory isomer)

Step 172-1: Synthesis of 2,4,5-trimethoxy benzene sulfonyl chloride

To a solution of 10.0 g of 1,3,4-trimethoxy benzene in CHCl$_3$ (100 ml) was added dropwise 6.90 g of chlorosulfonic acid over 10 minutes under ice cooling. After stirring at room temperature for two hours, the solution was poured into ice water and the resulting mixture was extracted with CHCl$_3$. The aqueous layer was filtered with celite, the filtrate was neutralized with an aqueous solution of 2 mol/L KOH (pH=9), and the solvent was evaporated under reduced pressure to obtain 7.81 g. Phosphorus oxychloride (30 ml) was added to the obtained residue and the reaction mixture was stirred at an external temperature of 100° C. for one hour. The solution was poured into ice water and the resulting mixture was extracted with Et$_2$O; the organic layer was washed with water and with saturated brine and then dried over MgSO$_4$; the drying agent was separated by filtration, and then the solvent was evaporated under reduced pressure. The obtained residue was purified by column chromatography (silicagel 60N; mobile phase: EtOAc/n-hexane=1/10 to 1/2; v/v) to obtain 1.80 g of the title compound.

$^1$H-NMR (600 MHz, CDCl$_3$) δ (ppm); 3.88 (s, 3H), 3.98 (s, 3H), 4.03 (s, 3H), 6.58 (s, 1H), 7.38 (s, 1H)

Step 172-2: Synthesis of (4R)-1-{5-chloro-3-(2-methoxy-5-methyl pyridin-3-yl)-2-oxo-1-[(2,4,5-trimethoxyphenyl)sulfonyl]-2,3-dihydro-1H-indol-3-yl}-4-hydroxy-N,N-dimethyl-L-prolinamide (levorotatory isomer)

With 100 mg of the compound that is obtained at Step 169-2 (Isomer B) and 66.0 mg of 2,4,5-trimethoxy benzene sulfonyl chloride as starting materials, 65.0 mg of the title compound (pale yellow amorphous) was obtained by a similar method to Example 2.

$[\alpha]_D^{25}$=166° (c=0.202, CHCl$_3$)

MS (ESI pos.) m/z: 675 ([M+H]$^+$), 697 ([M+Na]$^+$)

$^1$H-NMR (600 MHz, CDCl$_3$) δ (ppm); 1.37-3.99 (m, 4H), 2.21 (s, 3H), 2.46 (s, 3H), 2.81 (s, 3H), 3.06-3.19 (m, 1H), 3.68 (s, 3H), 3.70 (s, 3H), 3.91 (s, 3H), 3.93 (s, 3H), 4.54-4.63 (m, 1H), 4.75-4.83 (m, 1H), 6.47 (s, 1H), 7.07 (d, J=2.3 Hz, 1H), 7.24-7.29 (m, 1H), 7.66 (s, 1H), 7.79-7.97 (m, 3H)

Example 173

Synthesis of (4R)-1-{5-chloro-3-(2-methoxy-5-methyl pyridin-3-yl)-2-oxo-1-[(2,3,4-trimethoxyphenyl)sulfonyl]-2,3-dihydro-1H-indol-3-yl}-4-hydroxy-N,N-dimethyl-L-prolinamide (levorotatory isomer)

Step 173-1 Synthesis of 2,3,4-trimethoxy benzene sulfonyl chloride

To a solution of 10.0 g of 1,2,3-trimethoxy benzene in CHCl$_3$ (100 ml) was added dropwise 6.90 g of chlorosulfonic acid over 10 minutes under ice cooling. After stirring at room temperature for two hours, the solution was poured into ice water and the resulting mixture was extracted with CHCl$_3$. The aqueous layer was filtered with celite, the filtrate was neutralized with an aqueous solution of 2 mol/L KOH (pH=9), and the solvent was evaporated under reduced pressure to obtain 1.40 g. Phosphorus oxychloride (7 ml) was added to the obtained residue and the mixture was stirred at external temperature of 100° C. for one hour. The solution was poured into ice water, the resulting mixture was extracted with Et$_2$O, the organic layer was washed with water and with saturated brine and then dried over MgSO$_4$; the drying agent was separated by filtration, and then the solvent was evaporated under reduced pressure. The obtained residue was purified by column chromatography (silicagel 60N; mobile phase: EtOAc/n-hexane=1/10 to 1/4; v/v) to obtain 450 mg of the title compound.

MS (CI+ pos.) m/z: 267 ([M+H]$^+$), MS (EI+ pos.) m/z: 266 ([M]$^+$)

$^1$H-NMR (200 MHz, CDCl$_3$) δ (ppm); 3.92 (s, 3H), 3.97 (s, 3H), 4.14 (s, 3H), 6.74 (d, J=8.79 Hz, 1H), 7.69 (d, J=8.79 Hz, 1H)

Step 173-2: Synthesis of (4R)-1-{5-chloro-3-(2-methoxy-5-methyl pyridin-3-yl)-2-oxo-1-[(2,3,4-trimethoxyphenyl)sulfonyl]-2,3-dihydro-1H-indol-3-yl}-4-hydroxy-N,N-dimethyl-L-prolinamide (levorotatory isomer)

With 150 mg of the compound obtained in Step 169-3 and 108 mg of the compound obtained in Step 173-1 as starting materials, 69 mg of the title compound (amorphous) was obtained by a similar procedure to Example 2.

$[\alpha]_D^{25}$=163° (c=0.280, CHCl$_3$)

MS (ESI pos.) m/z: 675 ([M+H]$^+$), 697 ([M+Na]$^+$), (ESI neg.) m/z: 673 ([M–H]$^-$)

$^1$H-NMR (200 MHz, CDCl$_3$) δ (ppm); 1.35-2.18 (m, 5H), 2.23-2.28 (m, 3H), 2.47-2.52 (m, 3H), 2.81-2.87 (m, 3H), 3.71-3.78 (m, 3H), 3.82-3.87 (m, 3H), 3.92-3.97 (m, 3H), 3.96-4.02 (m, 3H), 4.41-4.92 (m, 2H), 6.81 (d, J=9.23 Hz, 1H), 7.04-7.15 (m, 1H), 7.17-7.36 (m, 2H), 7.71-8.05 (m, 3H)

Example 174

Synthesis of (4R)-1-{5-chloro-3-(2-methoxy-5-methyl pyridin-3-yl)-2-oxo-1-[(2,4,6-trimethoxyphenyl) sulfonyl]-2,3-dihydro-1H-indol-3-yl}-4-hydroxy-N,N-dimethyl-L-prolinamide (levorotatory isomer)

With 150 mg of the compound obtained in Step 169-3 and 108 mg of (2,4,6-trimethoxyphenyl)sulfonyl chloride, which is which is the compound described in Preparation Method 89 of the brochure Publication No. WO2004/026292, as starting materials, 142 mg of the title compound (amorphous) was obtained by a similar procedure to Example 2.

$[\alpha]_D^{25}$=–148° (c=0.317, CHCl$_3$)

MS (ESI pos.) m/z: 675 ([M+H]$^+$), 697 ([M+Na]$^+$), (ESI neg.) m/z: 673 ([M–H]$^-$)

$^1$H-NMR (200 MHz, CDCl$_3$) δ (ppm); 1.75-1.89 (m, 1H), 2.05 (s, 3H), 2.23 (s, 3H), 2.48 (s, 3H), 2.85 (s, 3H), 3.08-3.24 (m, 1H), 3.79 (s, 6H), 3.82 (s, 3H), 3.84 (s, 3H), 4.31-4.98 (m, 2H), 6.11 (s, 2H), 7.12 (d, J=2.20 Hz, 1H), 7.21-7.31 (m, 2H), 7.82-7.95 (m, 2H)

Example 175

Synthesis of (4R)-1-{5-chloro-3-(2-methoxy-5-methylphenyl)-2-oxo-1-[(2,4,6-trimethoxyphenyl)sulfonyl]-2,3-dihydro-1H-indol-3-yl}-4-hydroxy-N,N-dimethyl-L-prolinamide (levorotatory isomer)

With 200 mg of the compound that is obtained at Step 103-2 (Isomer B) and 132 mg of 2,4,6-trimethoxy benzene sulfonyl chloride as starting materials, 34 mg of the title compound (pale yellow amorphous) was obtained by a similar method to Example 2.

$[\alpha]_D^{25}$=130° (c=0.171, CHCl$_3$)

MS (ESI pos.) m/z: 674 ([M+H]$^+$), 696 ([M+Na]$^+$)

$^1$H NMR (600 MHz, CDCl$_3$) δ (ppm); 1.45-1.53 (m, 1H), 1.77 (dd, J=11.7, 6.2 Hz, 1H), 1.92-2.00 (m, 1. H), 2.25 (s, 3H), 2.36 (s, 3H), 2.84 (s, 3H), 3.08-3.14 (m, 1H), 3.68 (s, 3H), 3.73-3.89 (m, 1H), 3.77 (s, 6H), 3.82 (s, 3H), 4.66-4.73 (m, 1H), 4.90 (d, J=9.2 Hz, 1H), 6.09 (s, 2H), 6.64 (d, J=8.3 Hz, 1H), 7.00 (dd, J=8.3, 2.3 Hz, 1H), 7.15 (d, J=1.8 Hz, 1H), 7.22 (dd, J=8.7, 2.3 Hz, 1H), 7.54-7.56 (m, 1H), 7.83 (d, J=8.7 Hz, 1H)

Example 176

Synthesis of (4R)-1-{5-chloro-3-(2-methoxy-5-methylphenyl)-2-oxo-1-[(2,3,4-trimethoxyphenyl)sulfonyl]-2,3-dihydro-1H-indol-3-yl}-4-hydroxy-N,N-dimethyl-L-prolinamide (levorotatory isomer)

With 200 mg of the compound that is obtained at Step 103-2 (Isomer B) and 132 mg of 2,3,4-trimethoxy benzene sulfonyl chloride as starting materials, 122 mg of the title compound (pale yellow amorphous) was obtained by a similar method to Example 2.

$[\alpha]_D^{25}$=–186° (c=0.266, CHCl$_3$)

MS (ESI pos.) m/z: 674 ([M+H]$^+$), 696 ([M+Na]$^+$)

$^1$H-NMR (600 MHz, CDCl$_3$) δ (ppm); 1.50-1.70 (m, 1H), 1.82-1.88 (m, 1H), 2.10-2.22 (m, 1H), 2.23-2.63 (m, 1H), 2.26 (s, 3H), 2.38 (s, 3H), 2.82 (s, 3H), 3.13-3.22 (m, 1H), 3.61 (s, 3H), 3.84 (s, 3H), 3.92 (s, 3H), 3.97 (s, 3H), 4.56-4.65 (m, 1H), 4.82-4.89 (m, 1H), 6.66 (d, J=8.3 Hz, 1H), 6.78 (d, J=9.2 Hz, 1H), 7.00-7.03 (m, 1H), 7.15 (d, J=2.3 Hz, 1H), 7.22 (dd, J=8.7, 2.3 Hz, 1H), 7.60 (s, 1H), 7.78 (d, J=8.7 Hz, 1H), 7.93 (d, J=9.2 Hz, 1H)

Example 177

Synthesis of (4R)-1-{5-chloro-3-(2-methoxy-5-methylphenyl)-2-oxo-1-[(2,4,5-trimethoxyphenyl)sulfonyl]-2,3-dihydro-1H-indol-3-yl}-4-hydroxy-N,N-dimethyl-L-prolinamide (levorotatory isomer)

With 150 mg of the compound that is obtained at Step 103-2 (Isomer B) and 98.5 mg of 2,4,5-trimethoxy benzene sulfonyl chloride as starting materials, 64 mg of the title compound (pale yellow amorphous) was obtained by a similar method to Example 2.

$[\alpha]_D^{25}$=–185° (c=0.312, CHCl$_3$)

MS (ESI pos.) m/z: 674 ([M+H]$^+$), 696 ([M+Na]$^+$)

$^1$H-NMR (600 MHz, CDCl$_3$) δ (ppm); 1.20-3.99 (m, 4H), 2.25 (s, 3H), 2.36 (s, 3H), 2.82 (s, 3H), 3.03-3.12 (m, 1H), 3.64 (s, 3H), 3.66 (s, 3H), 3.90 (s, 3H), 3.93 (s, 3H), 4.62-4.69 (m, 1H), 4.78-4.84 (m, 1H), 6.46 (s, 1H), 6.66 (d, J=8.3 Hz, 1H), 7.00-7.02 (m, 1H), 7.13 (s, 1H), 7.22-7.26 (m, 1H), 7.56 (s, 1H), 7.66 (s, 1H), 7.87 (d, J=8.7 Hz, 1H)

Example 178

Synthesis of (2S)-1-(5-chloro-3-(2-methoxyphenyl)-1-[(2,4-dithyl thio-phenyl)sulfonyl]-2-oxo-2,3-dihydro-1H-indol-3-yl)-N,N-dimethylpiperidine-2-carboxamide (levorotatory isomer)

With 500 mg of (2S)-1-[5-chloro-3-(2-methoxyphenyl)-2-oxo-2,3-dihydro-1H-indol-3-yl]-N,N-dimethylpiperidine-2-carboxamide, which is the compound described in Preparation 3.49 (Isomer B) of Publication No. WO01/98295, and 374 mg of 2,4-dimethyl thio benzene sulfonyl chloride as starting materials, 322 mg of the title compound (colorless amorphous) was obtained by a similar method to Example 2.

$[\alpha]_D^{25}$=–177° (c=0.115, CHCl$_3$)

MS (ESI pos.) m/z: 682 ([M+Na]$^+$), 660 ([M+H]$^+$)

$^1$H-NMR (300 MHz, DMSO-d$_6$) δ ppm; 1.02-4.23 (m, 21H), 3.32 (s, 3H), 6.77 (d, J=2.0 Hz, 2H), 7.03-7.13 (m, 1H), 7.17 (s, 1H), 7.22-7.33 (m, 2H), 7.43 (s, 1H), 7.83-7.97 (m, 2H), 8.12 (d, J=8.5 Hz, 1H)

Example 179

Synthesis of (4R)-1-(5-chloro-3-(2-methoxy-5-methylphenyl)-1-{[4-(methylthio)-2-(trifluoromethoxy) phenyl]sulfonyl}-2-oxo-2,3-dihydro-1H-indol-3-yl)-4-hydroxy-N,N-dimethyl-L-prolinamide (levorotatory isomer)

Step 179-1 Synthesis of 1-(methylthio)-3-(trifluoromethoxy)benzene

With 2.50 g of 3-(trifluoromethoxy)thio phenol as starting material, 2.35 g of the title compound was obtained by a similar procedure to Step 170-1.

MS (CI+ pos.) m/z: 209 ([M+H]$^+$)

¹H-NMR (200 MHz, CDCl₃) δ (ppm); 2.49 (s, 3H) 6.93-7.02 (m, 1H) 7.07 (s, 1H) 7.12-7.20 (m, 1H) 7.30 (t, J=7.91 Hz, 1H)

Step 179-2 Synthesis of 4-(methylthio)-2-(trifluoromethoxy)benzene sulfonyl chloride and 2-(methylthio)-4-(trifluoromethoxy)benzene sulfonyl chloride To a solution of 1.00 g of the compound obtained in Step 179-1 in CHCl₃ (10 ml) was added dropwise 3.36 g of chlorosulfonic acid in CHCl₃ (10 ml) over 30 minutes under ice cooling. After stirring at room temperature for one hour, the solution was poured into ice water and the resulting mixture was extracted with CHCl₃. The organic layer was washed with a saturated aqueous solution of NaHCO₃ and with saturated brine and then dried over MgSO₄; the drying agent was separated by filtration, and then the solvent was evaporated under reduced pressure. The obtained residue was purified by column chromatography (silicagel 60N; mobile phase: EtOAc/n-hexane=1/10 to 1/5; v/v) to obtain 340 mg of 4-(methylthio)-2-(trifluoromethoxy)benzene sulfonyl chloride (179-2-a) and 212 mg of 2-(methylthio)-4-(trifluoromethoxy)benzene sulfonyl chloride (179-2-b).

4-(methylthio)-2-(trifluoromethoxy)benzene sulfonyl chloride (179-2-a)

¹H-NMR (200 MHz, CDCl₃) δ (ppm); 2.57 (s, 3H) 7.12-7.38 (m, 2H) 7.95 (d, J=9.23 Hz, 1H)

2-(methylthio)-4-(trifluoromethoxy)benzene sulfonyl chloride (179-2-b)

¹H-NMR (200 MHz, CDCl₃) δ (ppm); 2.61 (s, 3H), 7.05-7.21 (m, 2H) 8.13 (d, J=8.79 Hz, 1H)

Step 179-3 Synthesis of 4R)-1-(5-chloro-3-(2-methoxy-5-methylphenyl)-1-{[4-(methylthio)-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 444 mg of the compound obtained in Step 103-2 (Isomer B) and 337 mg of 4-(methylthio)-2-(trifluoromethoxy)benzene sulfonyl chloride obtained in Step 179-2 as starting materials, 425 mg of the title compound (amorphous) was obtained. by a similar procedure to Example 2

$[α]_D^{25}$=−191° (c=0.425, CHCl₃)

MS (ESI pos.) m/z: 714 ([M+H]⁺), 736 ([M+Na]⁺), (ESI neg.) m/z 712 ([M−H]⁻)

¹H-NMR (600 MHz, CDCl₃) δ (ppm); 1.15-1.22 (m, 1H), 1.35-1.49 (m, 1H), 1.75-1.85 (m, 1H), 1.90-2.02 (m, 1H), 2.27 (s, 3H), 2.39 (s, 3H), 2.51 (s, 3H), 2.80 (s, 3H), 3.12-3.24 (m, 1H), 3.47-3.64 (m, 3H), 4.56-4.65 (m, 1H), 4.69-4.81 (m, 1H), 6.65 (d, J=8.25 Hz, 1H), 7.02 (dd, J=8.25, 1.83 Hz, 1H), 7.08-7.15 (m, 2H), 7.20-7.24 (m, 2H), 7.49-7.65 (m, 1H), 7.86 (d, J=8.71 Hz, 1H), 8.25 (d, J=7.34 Hz, 1H)

Example 180

Synthesis of (4R)-1-(5-chloro-3-(2-methoxy-5-methylphenyl)-1-{[4-(methyl sulfinyl)-2-(trifluoromethoxy)phenyl]sulfonyl}-2-oxo-2,3-dihydro-1H-indol-3-yl)-4-hydroxy-N, N-dimethyl-L-prolinamide (180-a) and (4R)-1-(5-chloro-3-(2-methoxy-5-methylphenyl)-1-{[4-(methyl sulfonyl)-2-(trifluoromethoxy)phenyl]sulfonyl}-2-oxo-2,3-dihydro-1H-indol-3-yl)-4-hydroxy-N, N-dimethyl-L-prolinamide (180-b)

To a solution of 340 mg of Oxone in water (2 ml) was added dropwise a solution of 200 mg of the compound obtained in Step 179-3 in EtOH (2 ml) under ice cooling and the reaction mixture was stirred at room temperature for one hour. Water was added to the solution and the resulting mixture was extracted with CHCl₃. The organic layer was washed with a saturated aqueous solution of NaHCO₃ and with a saturated brine and then dried over MgSO₄; the drying agent was separated by filtration, and then the solvent was evaporated under reduced pressure. The obtained residue was purified by column chromatography (silicagel 60N; mobile phase: CHCl₃/MeOH=50/1 to 10/1; v/v) to obtain respectively 80 mg (180-a: amorphous) and 9 mg (180-b: amorphous) of two species of compounds of the title compound.

180-a: MS (ESI pos.) m/z: 730 ([M+H]⁺), 752 ([M+Na]⁺), (ESI neg.) m/z: 728 ([M−H]⁻)

¹H-NMR (600 MHz, CDCl₃) δ (ppm); 1.11-1.24 (m, 1H), 1.53-1.72 (m, 2H), 1.79-1.93 (m, 1H), 2.26 (s, 3H), 2.38 (s, 3H), 2.66-2.85 (m, 6H), 3.08-3.17 (m, 1H), 3.63 (s, 3H), 4.50-4.62 (m, 1H), 4.62-4.72 (m, 1H), 6.62-6.69 (m, 1H), 7.03 (d, J=8.25 Hz, 1H), 7.09-7.17 (m, 1H), 7.22-7.28 (m, 1H), 7.52-7.62 (m, 2H), 7.74 (s, 1H), 7.88 (d, J=9.17 Hz, 1H), 8.48-8.60 (m, 1H)

180-b: MS (ESI pos.) m/z: 746 ([M+H]⁺), 768 ([M+Na]⁺), (ESI neg.) m/z: 744 ([M−H]⁻)

¹H-NMR (600 MHz, CDCl₃) δ (ppm); 0.96-1.15 (m, 1H), 1.50-1.97 (m, 2H), 2.21-2.27 (m, 3H), 2.32-2.42 (m, 3H), 2.62-2.69 (m, 1H), 2.71-2.82 (m, 3H), 2.85-2.96 (m, 1H), 3.08 (s, 3H), 3.51-3.68 (m, 3H), 4.49-4.66 (m, 2H), 6.67 (d, J=8.25 Hz, 1H), 7.00-7.16 (m, 2H), 7.23-7.29 (m, 2H), 7.49-7.58 (m, 1H), 7.83-7.90 (m, 1H), 8.00-8.03 (m, 1H), 8.60 (s, 1H)

Example 181

Synthesis of (4R)-1-[5-chloro-1-{[3,4-dimethoxy-5-(trifluoromethoxy)phenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer)

Step 181-1: Synthesis of 1-[bromo (difluoro) methoxy]-2,3-dimethoxy benzene

To a solution of 5.0 g of 2,3-dimethoxy phenol in 1,3-dimethyl-2-imidazolidinone (65 ml) was added 7.28 g of potassium tert-butoxide, and was added dropwise a solution of 41.5 g of dibromo difluoromethane in 1,3-dimethyl-2-imidazolidinone (20 ml) over 30 minutes. The solution was stirred at 55° C. for 3 hours, and then water was added and the resulting mixture was extracted with Et₂O. The organic layer was sequentially washed with 1 mol/L hydrochloric acid, water, and saturated brine, dried over MgSO₄, then, the drying agent was separated by filtration and the solvent was evaporated under reduced pressure. The obtained residue was purified by column chromatography (silicagel 60; mobile phase: EtOAc/n-hexane=1/9 to 1/4; v/v) to obtain 2.21 g of the title compound (colorless oil).

MS (EI pos.) m/z: 282 ([M]⁺)

¹H-NMR (600 MHz, CDCl₃) δ (ppm); 3.88 (s, 3H) 3.90 (s, 3H) 6.85-6.88 (m, 1H) 6.90-6.94 (m, 1H) 7.03 (t, J=8.48 Hz, 1H)

Step 181-2: Synthesis of
1,2-dimethoxy-3-(trifluoromethoxy)benzene

To a solution of 2.21 g of the compound obtained in Step 181-1 in IPE (20 ml) was added a pyridine hydrofluoride complex (10 ml) and 1.44 g of mercury oxide and the reaction mixture was stirred at room temperature for 5 hours. After the reaction, water was added to the solution and the resulting mixture was extracted with Et₂O. The organic layer was sequentially washed with an aqueous solution of 1 mol/L NaOH, water, and saturated brine, dried over MgSO₄, then, the drying agent was separated by filtration and the solvent was evaporated under reduced pressure. The obtained residue was purified by column chromatography (silicagel 60; mobile phase: EtOAc/n-hexane=1/4; v/v) to obtain 1.09 g of the title compound (colorless oil).

MS (EI pos.) m/z: 222 ([M]⁺)

¹H-NMR (600 MHz, CDCl₃) δ (ppm); 3.88 (s, 3H) 3.88 (s, 3H) 6.83-6.87 (m, 2H) 7.02 (t, J=8.25 Hz, 1H)

Step 181-3: Synthesis of 3,4-dimethoxy-5-(trifluoromethoxy)benzene sulfonyl chloride (Isomer A) and 3,4-dimethoxy-2-(trifluoromethoxy)benzene sulfonyl chloride (Isomer B)

With 1.09 g of the compound obtained in Step 181-2 as starting material, 1.13 g (colorless oil form; isomer A) and 363 mg (colorless oil form; isomer B) of the title compounds were obtained by a similar method to Step 169-5.

Isomer A: ¹H-NMR (600 MHz, CDCl₃) δ (ppm); 3.99 (s, 3H) 4.03 (s, 3H) 7.46 (d, J=1.83 Hz, 1H) 7.57 (s, 1H)

Isomer B: ¹H-NMR (600 MHz, CDCl₃) δ (ppm); 3.90 (s, 3H) 3.97 (s, 3H) 6.92 (d, J=9.17 Hz, 1H) 7.78 (d, J=9.17 Hz, 1H)

Step 181-4: Synthesis of (4R)-1-[5-chloro-1-{[3,4-dimethoxy-5-(trifluoromethoxy)phenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer)

With 128 mg of the compound described in C of Example 5 of the brochure Publication No. WO2005/030755 and 100 mg of the compound obtained in Step 181-3 (Isomer A) as starting materials, 144 mg of the title compound (colorless amorphous) was obtained by a similar method to Example 2.

$[\alpha]_D^{30}$=138° (c=0.106, CHCl₃)

MS (ESI pos.) m/z: 715 ([M+H]⁺), 737 ([M+Na]⁺), (ESI neg.) m/z: 713 ([M−H]⁻)

¹H-NMR (600 MHz, CDCl₃) δ (ppm); 1.63-5.02 (m, 4H) 1.76-1.86 (m, 1H) 1.87-2.10 (m, 1H) 2.42 (s, 3H) 2.45-2.60 (m, 3H) 3.32 (s, 3H) 3.89 (s, 3H) 3.89 (s, 3H) 4.43-4.50 (m, 1H) 6.83-6.93 (m, 2H) 7.17-7.24 (m, 1H) 7.66-7.67 (m, 1H) 7.69 (d, J=8.71 Hz, 1H) 7.74-7.84 (m, 1H) 7.99 (dd, J=5.04, 1.83 Hz, 1H) 8.14-8.32 (m, 1H)

Example 182

Synthesis of (4R)-1-[5-chloro-1-{[3,4-dimethoxy-2-(trifluoromethoxy)phenyl]sulfonyl}-3-(2-methoxy pyridin-3-yl)-2-oxo-2,3-dihydro-1H-indol-3-yl]-4-hydroxy-N,N-dimethyl-L-prolinamide (levorotatory isomer)

With 128 mg of compound described in C of Example 5 of the brochure Publication No. WO2005/030755 and 100 mg of the compound obtained in Step 181-3 (Isomer B) as starting materials, 62 mg of the title compound (colorless amorphous) was obtained by a similar method to Example 2.

$[\alpha]_D^{30}$=150° (c=0.102, CHCl₃)

MS (ESI pos.) m/z: 715 ([M+H]⁺), 737 ([M+Na]⁺), (ESI neg.) m/z: 713 ([M−H]⁻)

¹H-NMR (600 MHz, CDCl₃) δ (ppm); 1.64-1.78 (m, 1H) 1.85-1.92 (m, 1H) 2.44 (s, 3H) 2.71 (s, 3H) 3.25-3.38 (m, 1H) 3.46-3.61 (m, 1H) 3.60-3.75 (m, 3H) 3.88 (s, 3H) 3.97 (s, 3H) 4.49-4.55 (m, 1H) 4.60-4.74 (m, 1H) 6.88 (dd, J=7.34, 5.04 Hz, 1H) 6.96-7.03 (m, 2H) 7.26 (dd, J=8.71, 2.29 Hz, 1H) 7.90 (d, J=9.17 Hz, 1H) 8.04 (dd, J=5.04, 1.83 Hz, 1H) 8.10-8.22 (m, 2H)

Example 183

Synthesis of (4R)-1-[5-chloro-1-{[3,4-dimethoxy-5-(trifluoromethoxy)phenyl]sulfonyl}-3-(2-methoxy-5-methylphenyl)-2-oxo-2,3-dihydro-1H-indol-3-yl]-4-hydroxy-N,N-dimethyl-L-prolinamide (levorotatory isomer)

With 131 mg of the compound obtained in Step 103-2 (Isomer B) and 100 mg of the compound obtained in Step 181-3 (Isomer A) as starting materials, 122 mg of the title compound (colorless amorphous) was obtained by a similar method to Example 2.

$[\alpha]_D^{30}$=136° (c=0.109, CHCl₃)

MS (ESI pos.) m/z: 728 ([M+H]⁺), 750 ([M+Na]⁺), (ESI neg.) m/z: 726 ([M−H]⁻)

¹H-NMR (600 MHz, CDCl₃) δ (ppm); 1.48-1.74 (m, 3H) 1.77-1.88 (m, 1H) 2.28 (s, 3H) 2.44 (s, 3H) 2.64-2.85 (m, 2H) 3.11-3.70 (m, 4H) 3.93 (s, 3H) 3.95 (s, 3H) 4.52-4.96 (m, 2H) 6.64 (d, J=8.25 Hz, 2H) 7.01-7.14 (m, 2H) 7.21-7.29 (m, 1H) 7.49-7.96 (m, 4H)

Example 184

Synthesis of (4R)-1-[5-chloro-1-{[3,4-dimethoxy-2-(trifluoromethoxy)phenyl]sulfonyl}-3-(2-methoxy-5-methylphenyl)-2-oxo-2,3-dihydro-1H-indol-3-yl]-4-hydroxy-N,N-dimethyl-L-prolinamide (levorotatory isomer)

With 131 mg of the compound obtained in Step 103-2 (Isomer B) and 100 mg of the compound obtained in Step 181-3 (Isomer B) as starting materials, 60 mg of the title compound (colorless amorphous) was obtained by a similar method to Example 2.

$[\alpha]_D^{30}$=−144° (c=0.111, CHCl₃)

MS (ESI pos.) m/z: 728 ([M+H]⁺), 750 ([M+Na]⁺), (ESI neg.) m/z: 726 ([M−H]⁻)

¹H-NMR (600 MHz, CDCl₃) δ (ppm); 1.77-1.84 (m, 1H) 1.92-2.00 (m, 1H) 2.26 (s, 3H) 2.33-2.41 (m, 3H) 2.72-2.85 (m, 3H) 3.10-3.26 (m, 1H) 3.43-3.51 (m, 1H) 3.51-3.69 (m, 3H) 3.87 (s, 3H) 3.96 (s, 3H) 4.56-4.65 (m, 1H) 4.66-4.82 (m, 1H) 6.64 (d, J=8.25 Hz, 1H) 6.97 (d, J=9.17 Hz, 1H) 7.00-

7.03 (m, 1H) 7.08-7.15 (m, 1H) 7.23 (dd, J=8.71, 2.29 Hz, 1H) 7.56-7.66 (m, 1H) 7.88 (d, J=8.71 Hz, 1H) 8.10 (d, J=8.25 Hz, 2H)

Example 185

Synthesis of (4R)-1-{5-chloro-3-(2-methoxy-5-methylphenyl)-1-[(2-methoxy-4-nitrophenyl)sulfonyl]-2-oxo-2,3-dihydro-1H-indol-3-yl}-4-hydroxy-N,N-dimethyl-L-prolinamide (levorotatory isomer)

With 444 mg of the compound obtained in Step 103-2 (Isomer B) and 306 mg of 2-methoxy-4-nitrobenzene sulfonyl chloride as starting materials, 420 mg of the title compound (amorphous) was obtained by a similar procedure to Example 2.

$[\alpha]_D^{25}$=−221° (c=0.354, CHCl$_3$)
MS (ESI pos.) m/z: 659 ([M+H]$^+$), 681 ([M+Na]$^+$), (ESI neg.) m/z: 657 ([M−H]$^-$)
$^1$H-NMR (600 MHz, CDCl$_3$) δ (ppm); 1.13-1.23 (m, 1H), 1.52-1.62 (m, 1H), 1.67 (dd, J=10.32, 5.73 Hz, 1H), 1.85-1.96 (m, 1H), 2.29 (s, 3H), 2.33-2.41 (m, 3H), 2.83 (s, 3H), 3.09 (s, 1H), 3.70 (s, 3H), 3.83 (s, 3H), 4.58-4.70 (m, 1H), 4.74 (d, J=9.17 Hz, 1H), 6.71 (d, J=8.71 Hz, 1H), 7.06 (dd, J=8.25, 1.83 Hz, 1H), 7.19 (s, 1H), 7.30 (dd, J=8.71, 2.29 Hz, 1H), 7.57 (s, 1H), 7.82 (d, J=1.83 Hz, 1H), 7.89 (d, J=8.71 Hz, 1H), 7.97 (dd, J=8.71, 2.29 Hz, 1H), 8.42 (d, J=8.71 Hz, 1H)

Example 186

Synthesis of (4R)-1-{5-chloro-3-(2-methoxy-5-methylphenyl)-1-[(4-methoxy-2-nitrophenyl)sulfonyl]-2-oxo-2,3-dihydro-1H-indol-3-yl}-4-hydroxy-N,N-dimethyl-L-prolinamide (levorotatory isomer)

With 444 mg of the compound obtained in Step 103-2 (Isomer B) and 306 mg of 4-methoxy-2-nitrobenzene sulfonyl chloride as starting materials, 436 mg of the title compound (amorphous) was obtained by a similar procedure to Example 2.

$[\alpha]_D^{25}$=−98.8° (c=0.334, CHCl$_3$)
MS (ESI pos.) m/z: 659 ([M+H]$^+$), 681 ([M+Na]$^+$), (ESI neg.) m/z: 657 ([M−H]$^-$)
$^1$H-NMR (600 MHz, CDCl$_3$) δ (ppm); 1.06-1.19 (m, 1H), 1.38-1.49 (m, 1H), 1.77-1.83 (m, 1H), 2.13-2.23 (m, 1H), 2.26 (s, 3H), 2.42 (s, 3H), 2.73-2.92 (m, 3H), 3.13-3.25 (m, 1H), 3.49-3.66 (m, 3H), 3.92 (s, 3H), 4.46-4.52 (m, 1H), 4.68-4.81 (m, 1H), 6.64 (d, J=8.25 Hz, 1H), 7.01 (dd, J=8.25, 1.83 Hz, 1H), 7.06-7.12 (m, 1H), 7.18 (dd, J=8.94, 2.52 Hz, 1H), 7.23-7.28 (m, 2H), 7.55-7.65 (m, 1H), 7.68 (d, J=8.71 Hz, 1H), 8.49-8.58 (m, 1H)

Example 187

Synthesis of (4R)-1-[5-chloro-1-{[4-(hydroxyamino)-2-methoxyphenyl]sulfonyl}-3-(2-methoxy-5-methylphenyl)-2-oxo-2,3-dihydro-1H-indol-3-yl]-4-hydroxy-N,N-dimethyl-L-prolinamide (levorotatory isomer)

With 300 mg of the compound obtained in Example 185 as starting material, 216 mg of the title compound (amorphous) was obtained by a similar procedure to Example 114.

$[\alpha]_D^{25}$=−189° (c=0.428, CHCl$_3$)
MS (ESI pos.) m/z: 645 ([M+H]$^+$), 667 ([M+Na]$^+$), (ESI neg.) m/z 643 ([M−H]$^-$)
$^1$H-NMR (600 MHz, CDCl$_3$) δ (ppm); 1.25-1.34 (m, 1H), 1.54-1.68 (m, 2H), 1.74-1.98 (m, 2H), 2.24-2.28 (m, 3H), 2.31-2.37 (m, 3H), 2.85 (s, 3H), 3.00-3.08 (m, 1H), 3.58 (s, 3H), 3.64-3.73 (m, 3H), 4.52-4.62 (m, 1H), 4.83 (d, J=7.34 Hz, 1H), 6.46-6.57 (m, 2H), 6.68 (d, J=8.25 Hz, 1H), 6.99-7.06 (m, 2H), 7.12-7.19 (m, 1H), 7.22-7.26 (m, 1H), 7.49 (s, 1H), 7.89 (d, J=8.71 Hz, 1H), 7.99-8.05 (m, 1H)

Example 188

Synthesis of (4R)-1-[1-[(4-amino-2-methoxyphenyl)sulfonyl]-5-chloro-3-(2-methoxy-5-methylphenyl)-2-oxo-2,3-dihydro-1H-indol-3-yl]-4-hydroxy-N,N-dimethyl-L-prolinamide (levorotatory isomer)

A suspension of 450 mg of the compound obtained in Example 185 and 381 mg of iron in acetic acid (5 ml) was stirred at 80° C. for one hour. Water was added to the solution and the resulting mixture was extracted with EtOAc; the organic layer was washed with a saturated aqueous solution of NaHCO$_3$ and with saturated brine, dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=20/1 to 10/1; v/v) to obtain 301 mg of the title compound (amorphous).

$[\alpha]_D^{25}$=−211° (c=0.405, CHCl$_3$)
MS (ESI pos.) m/z: 629 ([M+H]$^+$), (ESI neg.) m/z: 627 ([M−H]$^+$)
$^1$H-NMR (600 MHz, CDCl$_3$) δ (ppm); 1.34-1.46 (m, 1H), 1.50-1.69 (m, 3H), 1.75-1.83 (m, 1H), 1.86-1.96 (m, 1H), 2.26 (s, 3H), 2.35 (s, 3H), 2.83 (s, 3H), 3.05-3.15 (m, 1H), 3.57-3.62 (m, 3H), 3.62-3.69 (m, 3H), 4.62-4.69 (m, 1H), 4.86 (d, J=8.71 Hz, 1H), 6.10 (s, 1H), 6.29 (dd, J=8.48, 2.06 Hz, 1H), 6.67 (d, J=8.25 Hz, 1H), 7.02 (d, J=8.25 Hz, 1H), 7.11-7.17 (m, 1H), 7.20-7.29 (m, 1H), 7.55 (s, 1H), 7.89 (d, J=8.71 Hz, 1H), 7.97 (d, J=8.71 Hz, 1H)

Example 189

Synthesis of (4R)-1-{5-chloro-3-(2-methoxy-5-methylphenyl)-1-[(2-methoxy-4-methylphenyl)sulfonyl]-2-oxo-2,3-dihydro-1H-indol-3-yl}-4-hydroxy-N,N-dimethyl-L-prolinamide (levorotatory isomer)

With 444 mg of the compound obtained in Step 103-2 (Isomer B), 265 mg of 2-methoxy-4-methyl benzene sulfonyl chloride as starting material, 450 mg of the title compound (amorphous) was obtained by a similar procedure to Example 2.

$[\alpha]_D^{25}$=−196° (c=0.370, CHCl$_3$)
MS (ESI pos.) m/z: 628 ([M+H]$^+$), 650 ([M+Na]$^+$), (ESI neg.) m/z: 626 ([M−H]$^-$)
$^1$H-NMR (600 MHz, CDCl$_3$) δ (ppm); 1.28-1.36 (m, 1H), 1.61 (s, 1H), 1.74 (dd, J=11.46, 5.96 Hz, 1H), 1.86-1.98 (m, 1H), 2.26 (s, 3H), 2.33 (s, 3H), 2.40 (s, 3H), 2.81 (s, 3H), 3.06-3.11 (m, 1H), 3.62 (s, 3H), 3.66 (s, 3H), 4.61-4.68 (m, 1H), 4.81 (d, J=9.17 Hz, 1H), 6.66 (d, J=8.25 Hz, 1H), 6.75 (s, 1H), 6.92 (d, J=8.25 Hz, 1H), 7.01 (dd, J=8.25, 2.29 Hz, 1H), 7.14 (d, J=2.29 Hz, 1H), 7.24 (d, J=2.29 Hz, 1H), 7.56 (s, 1H), 7.88 (d, J=8.71 Hz, 1H), 8.09 (d, J=8.25 Hz, 1H)

Example 190

Synthesis of (4R)-1-(5-chloro-3-[5-(dimethylamino)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 190-1: Synthesis of 3-bromo-4-methoxy aniline

Under nitrogen atmosphere, to a solution of 24.0 g of 2-bromo-1-methoxy-4-nitrobenzene in acetic acid (960 ml) was added 57.0 g of iron then the reaction mixture was warmed to an external temperature of 70° C. over 50 minutes (internal temperature: 63.5° C.). After stirring at the same temperature for 8 hours, the solution was cooled to room temperature. The solid was filtered out, and the filtrate was extracted with $CHCl_3$. The organic layer was washed with a saturated aqueous solution of $NaHCO_3$ and with saturated brine, in this order, then, dried over $Na_2SO_4$, and then, the drying agent was removed by filtration and the solvent was evaporated under reduced pressure to obtain 13.1 g of the title compound (brown oil).

MS (ESI pos.) m/z: 202 ([M+H]$^+$)
$^1$H-NMR (200 MHz, $CDCl_3$) δ (ppm); 3.44 (bs, 2H), 3.81 (s, 3H), 6.54-6.66 (m, 1H), 6.70-6.80 (m, 1H), 6.93 (d, J=2.6 Hz, 1H)

Step 190-2: Synthesis of 3-bromo-4-methoxy-N,N-dimethyl aniline

Under nitrogen atmosphere, to a solution of 12.6 g of the compound obtained in Step 190-1 in MeOH (150 ml), under room temperature, was added 25.0 g of an aqueous solution of 37% formaldehyde and the reaction mixture was stirred for one hour. At the same temperature, 44.0 g of sodium triacetoxy borohydride was added to the solution and the resulting mixture was stirred for 17 hours. A saturated aqueous solution of $NaHCO_3$ was added to the solution and the resulting mixture was extracted with EtOAc. The organic layer was washed with saturated brine, dried over $Na_2SO_4$, then, the drying agent was removed by filtration and the solvent was evaporated under reduced pressure. The obtained residue was separated and purified by column chromatography (silicagel 60N; mobile phase: hexane/EtOAc=9/1 to 0/10; v/v) to obtain 7.40 g of the title compound (colorless solid).

MS (ESI pos.) m/z: 230 ([M+H]$^+$)
$^1$H-NMR (200 MHz, $CDCl_3$) δ (ppm); 2.87 (s, 6H), 3.83 (s, 3H), 6.62-6.72 (m, 1H), 6.79-6.90 (m, 1H), 6.97 (d, J=3.1 Hz, 1H)

Step 190-3: Synthesis of 5-chloro-3-[5-(dimethylamino)-2-methoxyphenyl]-3-hydroxy-1,3-dihydro-2H-indol-2-one With 500 mg of the compound obtained in Step 190-2 and 270 mg of 5-chloroisatin as starting materials, 397 mg of the title compound (brown solid) was obtained by a similar method to Step 21-1.

MS (ESI pos.) m/z: 355 ([M+Na]$^+$), (ESI neg.) m/z: 331 ([M−H]$^-$)
$^1$H-NMR (600 MHz, DMSO-$d_6$) δ (ppm): 2.88 (s, 3H), 3.30 (s, 3H), 3.32 (s, 3H), 6.56 (s, 1H), 6.66 (dd, J=8.7, 3.2 Hz, 1H), 6.75-6.78 (m, 2H), 6.82 (d, J=8.3 Hz, 1H), 7.20 (dd, J=8.3, 2.3 Hz, 1H), 7.28 (d, J=3.2 Hz, 1H), 10.37 (s, 1H)

Step 190-4: Synthesis of (4R) 1-{5-chloro-3-[5-(dimethylamino)-2-methoxyphenyl]-2-oxo-2,3-dihydro-1H-indol-3-yl}-4-hydroxy-N,N-dimethyl-L-prolinamide From 100 mg of the compound obtained in Step 190-3 and 60 mg of (4R)-4-hydroxy-N,N-dimethyl-L-prolinamide hydrochloride, 73 mg of the title compound (diastereoisomer mixture: brown amorphous) was obtained by a similar method to Step 21-2.

MS (ESI pos.) m/z: 473 ([M+H]$^+$), 495 ([M+Na]$^+$), (ESI neg.) m/z: 471 ([M−H]$^-$)
$^1$H-NMR (600 MHz, DMSO-$d_6$) δ (ppm); 1.52-4.95 (m, 22H), 6.31-8.13 (m, 6H), 10.43-10.58 (m, 1H)

Step 190-5: Synthesis of (4R)-1-(5-chloro-3-[5-(dimethylamino)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 50 mg of the compound obtained in Step 190-4 and 35 mg of 4-methoxy-2-(trifluoromethoxy)benzene sulfonyl chloride as starting materials, respectively 15 mg (Isomer A: orange color amorphous) and 19 mg (Isomer B: orange color amorphous) of two species of diastereoisomers of the title compound were obtained by a similar method to Example 2.

Isomer A: $[\alpha]_D^{25}$=+108° (c=0.262, $CHCl_3$)
MS (ESI pos.) m/z: 727 ([M+H]$^+$), 749 ([M+Na]$^+$), (ESI neg.) m/z: 725 ([M−H]$^-$)
$^1$H-NMR (600 MHz, $CDCl_3$) δ (ppm); 1.23-1.37 (m, 2H), 1.67-1.75 (m, 1H), 1.90 (dd, J=12.8, 7.3 Hz, 1H), 2.45 (s, 3H), 2.76 (s, 3H), 2.98 (s, 6H), 3.37-3.52 (m, 6H), 3.85-3.92 (m, 2H), 4.18-4.21 (m, 1H), 6.63-6.70 (m, 2H), 6.88-6.91 (m, 1H), 6.93 (dd, J=9.2, 2.3 Hz, 1H), 6.98 (d, J=2.3 Hz, 1H), 7.23-7.29 (m, 1H), 7.73-7.80 (m, 1H), 7.92 (d, J=8.7 Hz, 1H), 8.30 (d, J=8.7 Hz, 1H)

Isomer B: $[\alpha]_D^{25}$=−167° (c=0.220, $CHCl_3$)
MS (ESI pos.) m/z: 727 ([M+H]$^+$), 749 ([M+Na]$^+$), (ESI neg.) m/z: 725 ([M−H]$^-$)
$^1$H-NMR (600 MHz, $CDCl_3$) δ (ppm); 1.08-2.13 (m, 4H), 2.31-2.50 (m, 3H), 2.71-2.83 (m, 3H), 2.83-2.97 (m, 6H), 3.05-3.61 (m, 4H), 3.82-3.93 (m, 3H), 4.52-4.64 (m, 1H), 4.76-4.89 (m, 1H), 6.60 (dd, J=8.7, 2.3 Hz, 1H), 6.65-6.74 (m, 1H), 6.83-6.91 (m, 1H), 6.94 (dd, J=8.7, 2.3 Hz, 1H), 7.08-7.37 (m, 3H), 7.88 (d, J=8.7 Hz, 1H), 8.34 (d, J=7.8 Hz, 1H)

Example 191

Synthesis of (4R)-1-(5-chloro-3-(2-methoxy-5-morpholin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 191-1: Synthesis of 4-(3-bromo-4-methoxyphenyl) morpholine

Under nitrogen atmosphere, to a solution of 20.0 g of 2-bromo-4-iodoanisole in toluene (250 ml) was added morpholine (6.12 ml), 1.29 g of tri-tert-butyl phosphine, 13.5 g of sodium tert-butoxide, and 359 mg of palladium acetate (II), and the reaction mixture was stirred for two hours at 45° C. Water and EtOAc were added to the reaction solution, liquid separation was performed and the aqueous layer was extracted with EtOAc. The combined organic layer was washed with saturated brine, dried over MgSO$_4$, then, the drying agent was separated by filtration, and the filtrate was concentrated under reduced pressure. The obtained residue was purified by column chromatography (Chromatorex NH; mobile phase: n-hexane/EtOAc=10/1 to 3/1; v/v) to obtain 3.94 g of the title compound (colorless powder).

MS (ESI pos.) m/z: 272 ([M+H]$^+$)

$^1$H-NMR (600 MHz, CDCl$_3$) δ (ppm); 3.00-3.09 (m, 4H), 3.80-3.88 (m, 7H), 6.80-6.90 (m, 2H), 7.13 (d, J=2.3 Hz, 1H)

Step 191-2: Synthesis of 5-chloro-3-hydroxy-3-(2-methoxy-5-morpholin-4-ylphenyl)-1,3-dihydro-2H-indol-2-one With 2.00 g of the compound obtained in Step 191-1 and 953 mg of 5-chloroisatin as starting materials, 1.52 g of the title compound (pale yellow amorphous) was obtained by a similar method to Step 21-1.

MS (ESI pos.) m/z: 375 ([M+H]$^+$), 397 ([M+Na]$^+$)

$^1$H-NMR (600 MHz, CDCl$_3$) δ (ppm); 3.07-3.21 (m, 4H), 3.60 (s, 3H), 3.92-4.00 (m, 4H), 4.63 (s, 1H), 6.79 (d, J=8.3 Hz, 1H), 6.80-6.83 (m, 1H), 6.87 (dd, J=9.2, 2.3 Hz, 1H), 7.09 (d, J=2.3 Hz, 1H), 7.23 (dd, J=8.3, 2.3 Hz, 1H), 7.58 (d, J=2.8 Hz, 1H), 8.24 (s, 1H)

Step 191-3: Synthesis of 3,5-dichloro-3-(2-methoxy-5-morpholin-4-ylphenyl)-1,3-dihydro-2H-indol-2-one With 1.48 g of the compound obtained in Step 191-2 as starting material, 1.44 g of the title compound (pink amorphous) was obtained by a similar method to Step 28-2.

MS (ESI neg.) m/z: 391 ([M−H]$^−$)

$^1$H-NMR (600 MHz, CDCl$_3$) δ (ppm); 3.12-3.24 (m, 4H), 3.48 (s, 4H), 3.85-3.97 (m, 4H), 6.77 (d, J=8.7 Hz, 1H), 6.84 (d, J=8.3 Hz, 1H), 6.90-6.99 (m, 1H), 6.97 (d, J=2.3 Hz, 1H), 7.19 (dd, J=8.3, 1.8 Hz, 1H), 7.68 (s, 1H), 8.40 (s, 1H)

Step 191-4: Synthesis of (4R)-1-[5-chloro-3-(2-methoxy-5-morpholin-4-ylphenyl)-2-oxo-2,3-dihydro-1H-indol-3-yl]-4-hydroxy-N,N-dimethyl-L-prolinamide (levorotatory isomer and dextrorotatory isomer)

With 1.36 g of the compound obtained in Step 191-3 and (4R)-4-hydroxy-N,N-dimethyl-L-prolinamide trifluoroacetate (4.87 mmol) as starting materials, 589 mg (Isomer A, yellow amorphous) and 703 mg (Isomer B, pale yellow amorphous) were obtained by a similar method to Step 4-2.

Isomer A: $[α]_D^{25}$=+276° (c=0.399, CHCl$_3$)

MS (ESI pos.) m/z: 515 ([M+H]$^+$), 537 ([M+Na]$^+$)

$^1$H-NMR (600 MHz, CDCl$_3$) δ (ppm); 1.77-1.85 (m, 1H), 2.07 (dd, J=13.3, 6.0 Hz, 1H), 2.58-2.69 (m, 6H), 3.08-3.24 (m, 5H), 3.46-3.56 (m, 1H), 3.50 (s, 3H), 3.69 (d, J=12.4 Hz, 1H), 3.82-3.95 (m, 5H), 4.32 (d, J=3.2 Hz, 1H), 6.69-6.82 (m, 2H), 6.79 (dd, J=8.7, 2.8 Hz, 1H), 6.89 (s, 1H), 7.09 (dd, J=8.3, 2.3 Hz, 1H), 7.78 (s, 1H), 8.65 (s, 1H)

Isomer B: $[α]_D^{25}$=−250° (c=0.553, CHCl$_3$)

MS (ESI pos.) m/z: 515 ([M+H]$^+$), 537 ([M+Na]$^+$)

$^1$H-NMR (600 MHz, CDCl$_3$) δ (ppm); 1.74-3.94 (m, 11H), 3.05-3.18 (m, 4H), 3.53 (s, 3H), 3.80-3.92 (m, 4H), 4.62 (s, 1H), 4.89-5.14 (m, 1H), 6.68-6.81 (m, 3H), 6.93-7.11 (m, 1H), 7.07 (dd, J=8.3, 2.3 Hz, 1H), 7.45-7.70 (m, 1H), 9.17 (s, 1H)

Step 191-5: Synthesis of (4R)-1-(5-chloro-3-(2-methoxy-5-morpholin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 200 mg of the compound that is obtained at Step 191-4 (Isomer B) and 124 mg of 4-methoxy-2-(trifluoromethoxy)benzene sulfonyl chloride as starting materials, 168 mg of the title compound (pale brown amorphous) was obtained by a similar method to Example 2.

$[α]_D^{25}$=−179° (c=0.221, CHCl$_3$)

MS (ESI pos.) m/z: 769 ([M+H]$^+$), 791 ([M+Na]$^+$)

$^1$H-NMR (600 MHz, CDCl$_3$) δ (ppm); 1.15-3.67 (m, 9H), 2.48 (s, 3H), 3.02-3.22 (m, 5H), 3.46-3.62 (m, 1H), 3.82-3.94 (m, 7H), 4.51-4.60 (m, 1H), 4.78-4.86 (m, 1H), 6.69-6.73 (m, 1H), 6.76 (dd, J=8.9, 2.1 Hz, 1H), 6.87 (s, 1H), 6.94 (dd, J=9.2, 2.3 Hz, 1H), 7.10-7.17 (m, 1H), 7.24 (dd, J=8.7, 2.3 Hz, 1H), 7.36-7.45 (m, 1H), 7.88 (d, J=9.2 Hz, 1H), 8.30-8.38 (m, 1H)

Example 192

Synthesis of (4R)-1-(5-chloro-3-(2-methoxy-5-pyridin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 192-1: Synthesis of 4-(3-bromo-4-methoxyphenyl)pyridine

Under nitrogen atmosphere, a solution of 20.0 g of 2-bromo-4-iodine-1-methoxy benzene, 8.64 g of pyridine-4-boronic acid, 2.22 g of tetrakis (triphenyl phosphine) palladium$^0$, 6.76 g of Na$_2$CO$_3$, and 24.3 g of cesium fluoride in a mixed solution of MeCN-water (200 ml, 3/7; v/v) was heat refluxed for 8 hours. After let to cool down, water and EtOAc were added, liquids were separated and the aqueous layer was extracted with EtOAc. The combined organic layer was washed with saturated brine and dried over MgSO$_4$, then, the drying agent was filtered out, and the filtrate was concentrated under reduced pressure. The obtained residue was purified by column chromatography (Chromatorex NH; mobile phase: EtOAc/n-hexane=8/92; v/v) to obtain 4.27 g of the title compound (colorless solid).

MS (ESI pos.) m/z: 264 ([M+H]$^+$)

$^1$H-NMR (600 MHz, CDCl$_3$) δ (ppm); 3.95 (s, 3H), 7.00 (d, J=8.3 Hz, 1H), 7.44 (d, J=6.0 Hz, 2H), 7.57 (dd, J=8.3, 2.3 Hz, 1H), 7.84 (d, J=2.3 Hz, 1H), 8.63 (d, J=3.7 Hz, 2H)

Step 192-2: Synthesis of 5-chloro-3-hydroxy-3-(2-methoxy-5-pyridin-4-ylphenyl)-1,3-dihydro-2H-indol-2-one Under nitrogen atmosphere and under dry ice-acetone cooling, a solution of 4.00 g of the compound obtained in Step 192-1 in THF (63 ml) was added dropwise with n-butyl lithium (9.96 ml, 1.52 mol/L n-hexane solution) over 2 minutes. Under the same condition, the solution was stirred for one hour, then let to stand (preparation of lithiation reagent).

Under nitrogen atmosphere to a suspension of 1.33 g of 5-chloroisatin in THF (31.5 ml) was added 555 mg of NaH under ice cooling and the reaction mixture was stirred for one hour under the same conditions. To the reaction solution was added dropwise the lithiation reagent prepared above over 5 minutes and the reaction solution was stirred for one hour under ice cooling. An aqueous solution of saturated $NH_4Cl$ and EtOAc were added to the reaction solution; liquid separation was performed and the aqueous layer was extracted with EtOAc. The combined organic layer was washed with saturated brine, dried over $MgSO_4$, then, the drying agent was separated by filtration, and the filtrate was concentrated under reduced pressure. The obtained residue was purified by column chromatography (Chromatorex NH; mobile phase: $CHCl_3$/MeOH/$NH_4OH$=97/3/0.3 to 90/10/0.9; v/v/v) to obtain 1.85 g of the title compound (pale brown solid).

MS (ESI pos.) m/z: 367 ([M+H]$^+$)
$^1$H-NMR (600 MHz, DMSO-$d_6$) δ (ppm); 3.49 (s, 3H), 6.76-6.78 (m, 1H), 6.81-6.86 (m, 2H), 7.02 (d, J=8.7 Hz, 1H), 7.20 (dd, J=8.3, 2.3 Hz, 1H), 7.67-7.71 (m, 2H), 7.74 (dd, J=8.5, 2.5 Hz, 1H), 8.20 (d, J=2.8 Hz, 1H), 8.60 (d, J=6.0 Hz, 2H), 10.46 (s, 1H)

Step 192-3: Synthesis of (4R)-1-[5-chloro-3-(2-methoxy-5-pyridin-4-ylphenyl)-2-oxo-2,3-dihydro-1H-indol-3-yl]-4-hydroxy-N,N-dimethyl-L-prolinamide (levorotatory isomer and dextrorotatory isomer)

From 1.83 g of the compound obtained in Step 192-2 and (4R)-4-hydroxy-N,N-dimethyl-L-prolinamide trifluoroacetate (5.49 mmol), respectively 670 mg (Isomer A, yellow amorphous) and 950 mg (Isomer B, pale yellow amorphous) of two species of diastereoisomers of the title compound were obtained by a similar method to Step 21-2.

Isomer A: $[α]_D^{25}$=+278° (c=0.502, $CHCl_3$)
MS (ESI pos.) m/z: 507 ([M+H]$^+$), 529 ([M+Na]$^+$)
$^1$H-NMR (600 MHz, DMSO-$d_6$) δ (ppm); 1.62-1.68 (m, 1H), 1.77-1.86 (m, 1H), 2.40 (s, 3H), 2.58 (s, 3H), 3.11-3.21 (m, 2H), 3.52 (s, 3H), 3.55-3.70 (m, 1H), 4.22-4.28 (m, 1H), 4.59-4.62 (m, 1H), 6.45-6.49 (m, 1H), 6.80 (d, J=8.3 Hz, 1H), 7.04 (d, J=8.7 Hz, 1H), 7.17 (dd, J=8.3, 2.3 Hz, 1H), 7.68-7.71 (m, 2H), 7.73 (dd, J=8.5, 2.5 Hz, 1H), 8.58 (d, J=2.3 Hz, 1H), 8.62-8.66 (m, 2H), 10.56 (s, 1H)

Isomer B: $[α]_D^{25}$=−308° (c=0.661, $CHCl_3$)
MS (ESI pos.) m/z: 507 ([M+H]$^+$), 529 ([M+Na]$^+$)
$^1$H-NMR (600 MHz, DMSO-$d_6$) δ (ppm); 1.56-1.64 (m, 1H), 1.65-3.58 (m, 4H), 2.29 (s, 3H), 2.35 (brs, 3H), 3.50 (s, 3H), 4.26-4.39 (m, 1H), 4.57-5.00 (m, 1H), 6.68-6.76 (m, 1H), 6.83-6.88 (m, 1H), 6.98 (d, J=8.7 Hz, 1H), 7.08-7.15 (m, 1H), 7.66-7.74 (m, 3H), 8.10-8.42 (m, 1H), 8.49-8.53 (m, 2H), 10.56 (brs, 1H)

Step 192-4: Synthesis of (4R)-1-(5-chloro-3-(2-methoxy-5-pyridin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 500 mg of a compound (Isomer B) that is obtained by a similar method to Step 192-3 and 315 mg of 4-methoxy-2-(trifluoromethoxy)benzene sulfonyl chloride as starting materials, 325 mg of the title compound (pale brown amorphous) was obtained by a similar method to Example 2.

$[α]_D^{25}$=−217° (c=0.441, $CHCl_3$)
MS (ESI pos.) m/z: 761 ([M+H]$^+$), 783 ([M+Na]$^+$)
$^1$H-NMR (600 MHz, $CDCl_3$) δ (ppm); 1.14-3.81 (m, 14H), 3.89 (s, 3H), 4.53-4.64 (m, 1H), 4.74-4.88 (m, 1H), 6.85-6.91 (m, 2H), 6.94 (dd, J=9.2, 2.3 Hz, 1H), 7.05-7.19 (m, 1H), 7.24-7.29 (m, 1H), 7.60-7.70 (m, 3H), 7.90 (d, J=8.3 Hz, 1H), 8.21-8.39 (m, 2H), 8.57-8.69 (m, 1H)

Example 193

Synthesis of (4R)-1-(5-chloro-3-(2-methoxy-5-piperidin-1-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 193-1: Synthesis of 1-(3-bromo-4-methoxyphenyl)piperidine

From 20.0 g of 2-bromo-4-iodoanisole, 1.72 g of the title compound (black solid) was obtained by a similar procedure to Step 191-1.

MS (CI pos.) m/z: 271 ([M+H]$^+$)
$^1$H-NMR (600 MHz, $CDCl_3$) δ (ppm); 1.44-1.58 (m, 2H), 1.59-1.74 (m, 4H), 2.93-3.02 (m, 4H), 3.79 (s, 3H), 6.73-6.85 (m, 2H), 7.11 (d, J=1.8 Hz, 1H)

Step 193-2: Synthesis of 5-chloro-3-hydroxy-3-(2-methoxy-5-piperidin-1-ylphenyl)-1,3-dihydro-2H-indol-2-one From 924 mg of 5-chloroisatin, 650 mg of the title compound (pale brown amorphous) was obtained by a similar procedure to Step 192-2.

MS (ESI pos.) m/z: 373 ([M+H]$^+$), 395 ([M+Na]$^+$)
$^1$H-NMR (600 MHz, DMSO-$d_6$) δ (ppm); 1.47-1.52 (m, 2H), 1.60-1.66 (m, 4H), 2.99-3.06 (m, 4H), 3.29 (s, 3H), 6.52-6.54 (m, 1H), 6.70-6.74 (m, 2H), 6.77-6.81 (m, 2H), 7.17 (dd, J=8.3, 2.3 Hz, 1H), 7.41 (d, J=2.8 Hz, 1H), 10.35 (s, 1H)

Step 193-3: Synthesis of 3,5-dichloro-3-(2-methoxy-5-piperidin-1-ylphenyl)-1,3-dihydro-2H-indol-2-one From 620 mg of the compound obtained in Step 193-2 1.10 g of the title compound (crude form, brown solid) was obtained by a similar procedure to Step 192-3. The resultant compound was subjected to the next step without purification.

Step 193-4: Synthesis of (4R)-1-[5-chloro-3-(2-methoxy-5-piperidin-1-ylphenyl)-2-oxo-2,3-dihydro-1H-indol-3-yl]-4-hydroxy-N,N-dimethyl-L-prolinamide (levorotatory isomer and dextrorotatory isomer)

With 1.10 g of the compound obtained in Step 193-3 and (4R)-4-hydroxy-N,N-dimethyl-L-prolinamide trifluoroacetate (1.83 mmol) as starting materials, respectively 202 mg (Isomer A, brown amorphous) and 343 mg (Isomer B, brown amorphous) of two species of diastereoisomers of the title compound were obtained by a similar procedure to Step 4-2.

Isomer A: $[α]_D^{25}$=+260° (c=0.355, $CHCl_3$)
MS (ESI pos.) m/z: 513 ([M+H]$^+$), 535 ([M+Na]$^+$)
$^1$H-NMR (600 MHz, DMSO-$d_6$) δ (ppm); 1.48-1.54 (m, 2H), 1.58-1.71 (m, 5H), 1.75-1.82 (m, 1H), 2.40 (s, 3H), 2.54 (s, 3H), 3.00-3.12 (m, 5H), 3.17 (dd, J=9.9, 5.7 Hz, 1H), 3.35 (s, 3H), 3.61 (dd, J=8.7, 6.0 Hz, 1H), 4.16-4.22 (m, 1H), 4.54 (d, J=4.6 Hz, 1H), 6.46 (d, J=2.3 Hz, 1H), 6.72-6.81 (m, 3H), 7.13 (dd, J=8.3, 2.3 Hz, 1H), 7.71 (d, J=2.3 Hz, 1H), 10.47 (s, 1H)

Isomer B: $[α]_D^{25}$=−173° (c=0.283, $CHCl_3$)
MS (ESI pos.) m/z: 513 ([M+H]$^+$), 535 ([M+Na]$^+$)

¹H-NMR (600 MHz, DMSO-d₆) δ (ppm); 1.44-3.43 (m, 23H), 4.30-4.38 (m, 1H), 4.66-4.83 (m, 2H), 6.70-6.82 (m, 3H), 7.12-7.15 (m, 1H), 7.17 (dd, J=8.3, 2.3 Hz, 1H), 7.41 (d, J=3.2 Hz, 1H), 10.34 (s, 1H)

Step 193-5: Synthesis of (4R)-1-(5-chloro-3-(2-methoxy-5-piperidin-1-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

From 300 mg of the compound that is obtained at Step 193-4 (Isomer B) and 187 mg of 4-methoxy-2-(trifluoromethoxy)benzene sulfonyl chloride, 179 mg of the title compound (brown amorphous) was obtained by a similar method to Example 2.

$[\alpha]_D^{25}$=−157° (c=0.390, CHCl₃)

MS (ESI pos.) m/z: 767 ([M+H]⁺), 789 ([M+Na]⁺)

¹H-NMR (600 MHz, CDCl₃) δ (ppm); 1.01-3.96 (m, 24H), 3.87 (s, 3H), 4.52-4.64 (m, 1H), 4.72-4.85 (m, 1H), 6.68 (d, J=8.7 Hz, 1H), 6.75-6.84 (m, 1H), 6.86 (s, 1H), 6.91-6.97 (m, 1H), 7.08-7.19 (m, 1H), 7.20-7.27 (m, 1H), 7.29-7.41 (m, 1H), 7.85-7.91 (m, 1H), 8.22-8.47 (m, 1H)

Example 194

Synthesis of (4R)-1-(5-chloro-3-[4-(dimethylamino)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 194-1: Synthesis of 4-bromo-3-methoxy-N,N-dimethyl aniline

With 8.00 g of 4-bromo-3-methoxy aniline as starting material, 7.57 g of the title compound (yellow solid) was obtained by a similar method to Step 190-2.

MS (ESI pos.) m/z: 229 ([M−1]⁺), 231 ([M+1]⁺)

¹H-NMR (300 MHz, CDCl₃) δ (ppm); 2.94 (s, 6H), 3.88 (s, 3H), 6.15-6.28 (m, 2H), 7.31 (d, J=8.7 Hz, 1H)

Step 194-2: Synthesis of 5-chloro-3-[4-(dimethylamino)-2-methoxyphenyl]-3-hydroxy-1,3-dihydro-2H-indol-2-one With 1.97 g of 5-chloroisatin and 4.99 g of the compound obtained in Step 194-1 as starting materials, 1.52 g of the title compound (pale yellow amorphous) was obtained by a similar method to Step 21-1.

MS (ESI pos.) m/z: 660 ([M+H]⁺), 682 ([M+Na]⁺)

¹H-NMR (300 MHz, DMSO-d₆) δ (ppm); 1.02-4.23 (m, 19H), 3.32 (s, 3H), 6.77 (d, J=2.0 Hz, 2H), 7.03-7.13 (m, 1H), 7.17 (s, 1H), 7.22-7.33 (m, 2H), 7.43 (s, 1H), 7.83-7.97 (m, 2H), 8.12 (d, J=8.5 Hz, 1H)

Step 194-3: Synthesis of (4R)-1-{5-chloro-3-[4-(dimethylamino)-2-methoxyphenyl]-2-oxo-2,3-dihydro-1H-indol-3-yl}-4-hydroxy-N,N-dimethyl-L-prolinamide From 500 mg of the compound obtained in Step 194-2 and 350 mg of (4R)-4-hydroxy-N,N-dimethyl-L-prolinamide hydrochloride, 277 mg of a mixture of two species of diastereoisomers of the title compound (brown amorphous) was obtained by a similar method to Step 21-2.

MS (ESI pos.) m/z: 708 ([M+H]⁺), 730 ([M+Na]⁺), (ESI neg.) m/z: 706 ([M−H]⁻)

¹H-NMR (600 MHz, CDCl₃) δ (ppm); 1.79-4.34 (m, 22H) 6.11-7.93 (m, 7H)

Step 194-4: Synthesis of (4R)-1-(5-chloro-3-[4-(dimethylamino)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 276 mg of the compound obtained in Step 194-3 and 178 mg of 4-methoxy-2-(trifluoromethoxy)benzene sulfonyl chloride as starting materials, respectively 140 mg (Isomer A: pale yellow amorphous) and 69.2 mg (Isomer B: yellow amorphous) of two species of diastereoisomers of the title compound were obtained by a similar method to Example 2.

Isomer A: $[\alpha]_D^{28}$=+144° (c=0.108, CHCl₃)

MS (ESI pos.) m/z: 727 ([M+H]⁺), 749 ([M+Na]⁺), (ESI neg.) m/z: 725 ([M−H]⁻)

¹H-NMR (600 MHz, CDCl₃) δ (ppm); 1.64-1.73 (m, 1H) 1.85 (dd, J=12.2, 8.0 Hz, 1H) 2.43 (s, 3H) 2.73 (s, 3H) 2.91 (s, 6H) 3.43-3.47 (m, 2H) 3.48 (s, 3H) 3.77-3.93 (m, 2H) 3.89 (s, 3H) 4.12-4.21 (m, 1H) 6.05 (d, J=2.3 Hz, 1H) 6.40 (dd, J=8.7, 2.8 Hz, 1H) 6.88 (s, 1H) 6.92 (dd, J=9.2, 2.3 Hz, 1H) 6.96 (d, J=2.3 Hz, 1H) 7.22 (dd, J=8.7, 2.3 Hz, 1H) 7.89 (d, J=8.7 Hz, 1H) 7.96 (d, J=8.7 Hz, 1H) 8.28 (d, J=9.2 Hz, 1H)

Isomer B: $[\alpha]_D^{28}$=−68.9° (c=0.101, CHCl₃)

MS (ESI pos.) m/z: 727 ([M+H]⁺), 749 ([M+Na]⁺), (ESI neg.) m/z: 725 ([M−H]⁻)

¹H-NMR (600 MHz, CDCl₃) δ (ppm); 1.81-1.86 (m, 1H) 1.99-2.12 (m, 1H) 2.39 (s, 3H) 2.75 (s, 3H) 2.90 (s, 6H) 2.91-2.97 (m, 1H) 3.09-3.22 (m, 1H) 3.57 (brs, 3H) 3.87 (s, 3H) 3.88-3.91 (m, 1H) 4.54-4.59 (m, 1H) 4.81 (brs, 1H) 6.04 (d, J=2.39 Hz, 1H) 6.26 (dd, J=8.7, 2.3 Hz, 1H) 6.84-6.86 (m, 1H) 6.92 (dd, J=9.2, 2.3 Hz, 1H) 7.08-7.12 (m, 1H) 7.19 (dd, J=9.2, 2.3 Hz, 1H) 7.50-7.57 (m, 1H) 7.84 (d, J=9.2 Hz, 1H) 8.32 (d, J=9.2 Hz, 1H)

Example 195

Synthesis of (4R)-1-(5-chloro-3-{5-[(dimethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 195-1: Synthesis of 1-(3-bromo-4-methoxyphenyl)-N,N-dimethyl methane amine

To a solution of 10.0 g of 3-bromo-4-methoxy benzaldehyde in MeOH (155 ml) was added an aqueous solution of 50% dimethylamine (2.52 ml) and the reaction mixture was stirred at room temperature for 30 minutes. Thereafter, to the solution was added 4.38 g of sodium cyanoborohydride, the reaction mixture was stirred for 15 hours under the same temperature condition, and the reaction solution was concentrated under reduced pressure. Water was added to the residue and extracted with CHCl₃; the organic layer was washed with saturated brine and dried over MgSO₄, then, the drying agent was separated by filtration and the solvent was evaporated under reduced pressure. The obtained residue was purified by column chromatography (silicagel 60; mobile phase: EtOAc/ hexane=1/1, then, MeOH/CHCl₃=1/9; v/v) to obtain 2.20 g of the title compound (colorless oil).

Step 195-2: Synthesis of 5-chloro-3-{5-[(dimethylamino)methyl]-2-methoxyphenyl}-3-hydroxy-1,3-dihydro-2H-indol-2-one With 2.00 g of the compound obtained in Step 195-1 and 1.24 g of 5-chloroisatin as starting material, 637 mg of the title compound (pale red solid) was obtained by a similar method to Step 21-1.

MS (ESI pos.) m/z: 347 ([M+H]$^+$), 369 ([M+Na]$^+$), (ESI neg.) m/z: 345 ([M−H]$^−$)

$^1$H-NMR (600 MHz, DMSO-d$_6$) δ (ppm); 2.14 (s, 6H) 3.34-3.36 (m, 2H) 3.38 (s, 3H) 6.66-6.68 (m, 1H) 6.79 (d, J=4.1 Hz, 1H) 6.80 (d, J=3.7 Hz, 1H) 7.14 (dd, J=8.3, 2.3 Hz, 1H) 7.17 (dd, J=8.3, 2.3 Hz, 1H) 7.72 (d, J=2.3 Hz, 1H) 10.38 (brs, 1H)

Step 195-3: Synthesis of (4R)-1-(5-chloro-3-{5-[(dimethylamino)methyl]-2-methoxyphenyl}-2-oxo-2,3-dihydro-1H-indol-3-yl)-4-hydroxy-N,N-dimethyl-L-prolinamide From 545 mg of the compound obtained in Step 195-2 and 367 mg of (4R)-4-hydroxy-N,N-dimethyl-L-prolinamide hydrochloride, 567 mg of a mixture of two species of diastereoisomers of the title compound (colorless amorphous) was obtained by a similar method to Step 28-2.

MS (ESI pos.) m/z: 487 ([M+H]$^+$), (ESI neg.) m/z: 485 ([M−H]$^−$)

$^1$H-NMR (600% MHz, CDCl₃) δ (ppm); 1.59-4.80 (m, 24H) 6.46-7.92 (m, 6H) 10.44-10.55 (m, 1H)

Step 195-4: Synthesis of (4R)-1-(5-chloro-3-{5-[(dimethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 556 mg of the compound obtained in Step 195-3 and 348 mg of 4-methoxy-2-(trifluoromethoxy)benzene sulfonyl chloride as starting materials, respectively 68 mg (Isomer A: colorless amorphous) and 74 mg (Isomer B: colorless amorphous) of two species of diastereoisomers of the title compound were obtained by a similar method to Example 2.

Isomer A: [α]$_D^{29}$=−175° (c=0.116, CHCl₃)

MS (ESI pos.) m/z: 741 ([M+H]$^+$), (ESI neg.) m/z: 739 ([M−H]$^−$)

$^1$H-NMR (600 MHz, CDCl₃) δ (ppm); 1.72-5.10 (m, 27H) 6.61-6.75 (m, 1H) 6.85-6.89 (m, 1H) 6.92 (dd, J=8.9, 2.5 Hz, 1H) 6.97-7.18 (m, 2H) 7.22 (dd, J=8.7, 2.3 Hz, 1H) 7.85 (d, J=8.7 Hz, 1H) 8.17-8.56 (m, 2H)

Isomer B: [α]$_D^{29}$=+137° (c=0.108, CHCl₃)

MS (ESI pos.) m/z: 741 ([M+H]$^+$), (ESI neg.) m/z: 739 ([M−H]$^−$)

$^1$H-NMR (600 MHz, CDCl₃) δ (ppm); 1.67-1.73 (m, 1H) 1.85-1.90 (m, 1H) 2.13-2.29 (m, 5H) 2.25 (s, 3H) 2.43 (s, 3H) 2.74 (s, 3H) 3.37-3.53 (m, 3H) 3.49 (s, 3H) 3.85-3.89 (m, 1H) 3.90 (s, 3H) 4.17-4.20 (m, 1H) 6.69 (d, J=8.7 Hz, 1H) 6.88-6.90 (m, 1H) 6.91-6.94 (m, 2H) 7.16 (dd, J=8.5, 2.1 Hz, 1H) 7.26 (dd, J=8.9, 2.5 Hz, 1H) 7.91 (d, J=8.7 Hz, 1H) 8.13 (d, J=1.8 Hz, 1H) 8.28 (d, J=8.7 Hz, 1H)

Example 196

Synthesis of (4R)-1-(5-chloro-3-(5-formyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 196-1: Synthesis of 2-(3-bromo-4-methoxyphenyl)-1,3-dioxolane

A solution of 53.0 g of 3-bromo-4-methoxy benzaldehyde, 18.4 g of ethylene glycol, and 4.24 g of p-toluene sulfonic acid/1 hydrate in benzene was refluxed for 5 hours while taking water out of the system. After the mixture was cooled, the reaction solution was poured into a saturated aqueous solution of NaHCO₃, liquid separation was performed, and the aqueous layer was extracted with benzene. The combined organic layer was washed with saturated brine and dried over MgSO₄, then, the drying agent was separated by filtration and the filtrate was concentrated under reduced pressure. The obtained residue was purified by column chromatography (Chromatorex NH; mobile phase: EtOAc/n-hexane=1/9; v/v) to obtain 59.1 g of the title compound (colorless oil) was obtained.

MS (CI pos.) m/z: 259 ([M+H]$^+$)

$^1$H-NMR (600 MHz, CDCl₃) δ (ppm); 3.86 (s, 3H), 3.93-4.12 (m, 4H), 5.69 (s, 1H), 6.85 (d, J=8.7 Hz, 1H), 7.33 (dd, J=8.5, 2.1 Hz, 1H), 7.63 (d, J=2.3 Hz, 1H)

Step 196-2: Synthesis of 5-chloro-3-[5-(1,3-dioxolan-2-yl)-2-methoxyphenyl]-3-hydroxy-1,3-dihydro-2H-indol-2-one With 30.0 g of the compound obtained in Step 196-1 and 17.52 g of 5-chloroisatin as starting materials, 15.3 g of the title compound (yellow solid) was obtained by a similar method to Step 21-1.

MS (ESI pos.) m/z: 362 ([M+H]$^+$), 384 ([M+Na]$^+$)

$^1$H-NMR (600 MHz, CDCl₃) δ (ppm); 3.69 (s, 3H), 3.95-4.16 (m, 4H), 5.77 (s, 1H), 6.68-6.79 (m, 1H), 6.84-7.01 (m, 1H), 7.12-7.20 (m, 1H), 7.32-7.41 (m, 1H), 7.76-7.89 (m, 1H), 9.93 (s, 1H)

Step 196-3: Synthesis of (4R)-1-[5-chloro-3-(5-formyl-2-methoxyphenyl)-2-oxo-2,3-dihydro-1H-indol-3-yl]-4-hydroxy-N,N-dimethyl-L-prolinamide (levorotatory isomer and dextrorotatory isomer)

From 1.00 g of the compound obtained in Step 196-2 and (4R)-4-hydroxy-N,N-dimethyl-L-prolinamide trifluoroacetate (2.51 mmol), respectively 81 mg (Isomer A, yellow amorphous) and 158 mg (Isomer B, brown amorphous) of two species of diastereoisomers of the title compound were obtained by a similar method to Step 21-2.

Isomer A: [α]$_D^{25}$=+254° (c=0.179, CHCl₃)

MS (ESI pos.) m/z: 458 ([M+H]$^+$), 480 ([M+Na]$^+$)

$^1$H-NMR (600 MHz, DMSO-d₆) δ (ppm); 1.59-4.64 (m, 16H), 6.42-6.47 (m, 1H), 6.73-6.83 (m, 1H), 7.04-7.22 (m, 2H), 7.86 (dd, J=8.5, 2.1 Hz, 1H), 8.56 (d, J=1.8 Hz, 1H), 9.94 (s, 1H), 10.60 (s, 1H)

Isomer B: [α]$_D^{25}$=−229° (c=0.216, CHCl₃)

MS (ESI pos.) m/z: 458 ([M+H]$^+$), 480 ([M+Na]$^+$)

¹H-NMR (600 MHz, DMSO-d₆) δ (ppm); 1.62-1.70 (m, 1H), 1.73-1.89 (m, 1H), 2.32-4.44 (m, 12H), 4.65-4.77 (m, 1H), 4.84-4.88 (m, 1H), 6.73-6.80 (m, 1H), 6.87 (d, J=2.3 Hz, 1H), 7.07-7.11 (m, 1H), 7.14-7.18 (m, 1H), 7.78-7.83 (m, 1H), 8.39-8.49 (m, 1H), 9.81 (s, 1H), 10.53 (brs., 1H)

Step 196-4: Synthesis of (4R)-1-(5-chloro-3-(5-formyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 350 mg of the compound obtained in Step 196-3 (Isomer B) and 223 mg of 4-methoxy-2-(trifluoromethoxy) benzene sulfonyl chloride as starting materials, 171 mg of the title compound (yellow amorphous) was obtained by a similar method to Example 2.
$[\alpha]_D^{25}=-187°$ (c=0.440, CHCl₃)
MS (ESI pos.) m/z: 712 ([M+H]⁺), 734 ([M+Na]⁺)
¹H-NMR (600 MHz, CDCl₃) δ (ppm); 1.20-3.95 (m, 4H), 1.80-1.88 (m, 1H), 2.43 (s, 3H), 2.67 (s, 3H), 3.70 (s, 3H), 3.89 (s, 3H), 4.48-4.82 (m, 2H), 6.85-6.96 (m, 1H), 6.87-6.90 (m, 2H), 6.94 (dd, J=8.9, 2.5 Hz, 1H), 6.97-7.13 (m, 1H), 7.21-7.29 (m, 1H), 7.85 (d, J=9.6 Hz, 1H), 7.89 (d, J=8.7 Hz, 1H), 8.29-8.37 (m, 1H), 9.91 (s, 1H)

Example 197

Synthesis of (4R)-1-(5-chloro-3-[2-methoxy-5-(morpholin-4-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

A solution of 160 mg of the compound obtained in Step 196-4, 39 mg of morpholine, and 67 mg of acetic acid in CHCl₃ (1.6 ml) was stirred at room temperature for 30 minutes. Thereafter, to the solution was added 105 mg of sodium triacetoxy borohydride and the reaction mixture was stirred at room temperature for one hour. CHCl₃ and saturated aqueous solution of NaHCO₃ were added to the reaction solution, then liquid separation was performed and the aqueous layer was extracted with CHCl₃. The combined organic layer was washed with saturated brine and dried over MgSO₄, then, the drying agent was separated by filtration, and the filtrate was concentrated under reduced pressure. The obtained residue was purified by column chromatography (Chromatorex NH; mobile phase: CHCl₃/MeOH/NH₄OH=99/1/0.1; v/v/v) to obtain 159 mg of the title compound (colorless amorphous).
$[\alpha]_D^{25}=-179°$ (c=0.271, CHCl₃)
MS (ESI pos.) m/z: 783 ([M+H]⁺), 805 ([M+Na]⁺)
¹H-NMR (600 MHz, CDCl₃) δ (ppm); 1.71-3.89 (m, 21H), 2.36 (s, 3H), 3.84 (s, 3H), 4.32-4.86 (m, 2H), 6.57-6.72 (m, 1H), 6.80-7.30 (m, 3H), 6.84 (s, 1H), 6.88 (dd, J=9.2, 2.3 Hz, 1H), 7.17-7.20 (m, 1H), 7.81-7.85 (m, 1H), 8.19-8.44 (m, 1H)

Example 198

Synthesis of (4R)-1-(5-chloro-3-[2-methoxy-5-(piperidin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

Step 198-1: Synthesis of 3-(3,5-dichloro-2-oxo-2,3-dihydro-1H-indol-3-yl)-4-methoxy benzaldehyde With 14.1 g of the compound obtained in Step 196-2 as starting material, 26.3 g of the title compound (crude form) was obtained by a similar procedure to Step 192-3. The resultant compound was subjected to the next step without purification.

Step 198-2: Synthesis of (4R)-1-[5-chloro-3-(5-formyl-2-methoxyphenyl)-2-oxo-2,3-dihydro-1H-indol-3-yl]-4-hydroxy-N,N-dimethyl-L-prolinamide With 26.3 g of the compound obtained in Step 198-1 and (4R)-4-hydroxy-N,N-dimethyl-L-prolinamide trifluoroacetate (35.1 mmol) as starting materials, 12.5 g of a diastereoisomer mixture of the title compound (colorless amorphous) was obtained by a similar method to Step 4-2.
MS (ESI pos.) m/z: 502 ([M+H]⁺), (ESI neg.) m/z: 500 ([M−H]⁻)
¹H-NMR (600 MHz, CDCl₃) δ (ppm); 1.81-5.06 (m, 20H) 5.68-5.86 (m, 1H) 6.71-7.14 (m, 4H) 7.37-7.45 (m, 1H) 7.96-8.20 (m, 1H) 8.51 (brs, 0.6H) 8.76 (brs, 0.4H)

Step 198-3: Synthesis of (4R)-1-(5-chloro-3-(5-formyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 10.9 g of the compound obtained in Step 198-2 and 6.63 g of 4-methoxy-2-(trifluoromethoxy)benzene sulfonyl chloride as starting materials, 6.76 g of a mixture of two species of diastereoisomers of the title compound (colorless amorphous) was obtained by a similar method to Example 2.
MS (ESI pos.) m/z: 712 ([M+H]⁺), 734 ([M+Na]⁺), (ESI neg.) m/z: 710 ([M−H]⁻)
¹H-NMR (600 MHz, CDCl₃) δ (ppm); 1.68-4.62 (m, 19H) 6.86-8.80 (m, 9H) 9.90 (s, 0.4H) 10.03 (s, 0.6H)

Step 198-4: Synthesis of (4R)-1-(5-chloro-3-[2-methoxy-5-(piperidin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

To a solution of 500 mg of the compound obtained in Step 198-3 in CHCl₃ (3.5 ml) was added piperidine (0.14 ml) and acetic acid (0.24 ml), and the reaction mixture was stirred for 30 minutes. To the solution was added 327 mg of sodium triacetoxy borohydride, and the reaction mixture was further stirred for 15 hours. After the end of the reaction, water was added to the solution and the resulting mixture was extracted with CHCl₃. The organic layer was washed with saturated brine and dried over MgSO₄, then, the drying agent was separated by filtration and the solvent was evaporated under reduced pressure. The obtained residue was purified by column chromatography (silicagel 60; mobile phase: MeOH/CHCl₃=1/99; v/v) to obtain respectively 94 mg (Isomer A: colorless amorphous) and 217 mg (Isomer B: colorless amorphous) of two species of diastereoisomers of the title compound.
Isomer A: $[\alpha]_D^{29}=-184°$ (c=0.113, CHCl₃)
MS (ESI pos.) m/z: 781 ([M+H]⁺), (ESI neg.) m/z: 779 ([M−H]⁻)
¹H-NMR (600 MHz, CDCl₃) δ (ppm); 1.08-3.67 (m, 25H) 3.74-3.84 (m, 1H) 3.87 (s, 3H) 4.34-4.68 (m, 2H) 6.58-6.73 (m, 1H) 6.86-6.90 (m, 1H) 6.91 (dd, J=8.9, 2.1 Hz, 1H) 6.99-7.12 (m, 2H) 7.21 (dd, J=9.2, 2.3 Hz, 1H) 7.85 (d, J=8.7 Hz, 1H) 8.32-8.54 (m, 2H)
Isomer B: $[\alpha]_D^{30}=+141°$ (c=0.123, CHCl₃)
MS (ESI pos.) m/z: 781 ([M+H]⁺), (ESI neg.) m/z: 779 ([M−H]⁻)

¹H-NMR (600 MHz, CDCl₃) δ (ppm); 1.08-2.70 (m, 16H) 2.74 (s, 3H) 3.35-3.40 (m, 1H) 3.45-3.54 (m, 6H) 3.84-3.88 (m, 1H) 3.89 (s, 3H) 4.17-4.21 (m, 1H) 6.66 (d, J=8.3 Hz, 1H) 6.87-6.89 (m, 1H) 6.90-6.93 (m, 2H) 7.14 (dd, J=8.3, 1.8 Hz, 1H) 7.24-7.27 (m, 1H) 7.90 (d, J=9.2 Hz, 1H) 8.15 (d, J=1.8 Hz, 1H) 8.27 (d, J=9.2 Hz, 1H)

Example 199

Synthesis of (4R)-1-(5-chloro-3-[2-methoxy-5-(pyrrolidin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

With 500 mg of the compound obtained in Step 198-3 and 150 mg of pyrrolidine as starting materials, respectively 228 mg (Isomer A, colorless amorphous) and 90 mg (Isomer B, colorless amorphous) of two species of diastereoisomers of the title compound were obtained by a similar method to Example 197.

Isomer A: $[\alpha]_D^{25}$=+106° (c=0.341, CHCl₃)
MS (ESI pos.) m/z: 767 ([M+H]⁺)
¹H-NMR (600 MHz, CDCl₃) δ (ppm); 1.73-1.81 (m, 4H), 1.82-1.94 (m, 2H), 2.41 (s, 3H), 2.45-2.56 (m, 5H), 2.71 (s, 3H), 3.35-3.50 (m, 3H), 3.45 (s, 3H), 3.57-3.74 (m, 1H), 3.81-3.91 (m, 1H), 3.87 (s, 3H), 4.14-4.17 (m, 1H), 6.66 (d, J=8.3 Hz, 1H), 6.85-6.92 (m, 3H), 7.17-7.26 (m, 2H), 7.88 (d, J=9.2 Hz, 1H), 8.09-8.12 (m, 1H), 8.25 (d, J=9.2 Hz, 1H)

Isomer B: $[\alpha]_D^{25}$=−122° (c=0.255, CHCl₃)
MS (ESI pos.) m/z: 767 ([M+H]⁺)
¹H-NMR (600 MHz, CDCl₃) δ (ppm); 1.16-4.17 (m, 15H), 4.32-4.79 (m, 2H), 6.62-6.74 (m, 1H), 6.85-7.34 (m, 3H), 6.86-6.89 (m, 1H), 6.90-6.95 (m, 1H), 7.20-7.32 (m, 1H), 7.83-7.91 (m, 1H), 8.28-8.49 (m, 1H)

Example 200

Synthesis of (4R)-1-(5-chloro-3-{2-methoxy-5-[(4-methylpiperazin-1-yl)methyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

From 500 mg of the compound obtained in Step 198-3 and 211 mg of 1-methylpiperazine, respectively 235 mg (Isomer A, colorless amorphous) and 122 mg (Isomer B, colorless amorphous) of two species of diastereoisomers of the title compound were obtained by a similar procedure to Example 199.

Isomer A: $[\alpha]_D^{25}$=+113° (c=0.280, CHCl₃)
MS (ESI pos.) m/z: 796 ([M+H]⁺)
¹H-NMR (600 MHz, CDCl₃) δ (ppm); 1.56-2.78 (m, 10H), 1.84-1.91 (m, 1H), 2.29 (s, 3H), 2.44 (s, 3H), 2.73 (s, 3H), 3.36-3.49 (m, 2H), 3.46-3.48 (m, 3H), 3.49-3.60 (m, 2H), 3.83-3.88 (m, 1H), 3.89 (s, 3H), 4.17-4.20 (m, 1H), 6.67 (d, J=8.3 Hz, 1H), 6.87-6.89 (m, 1H), 6.90-6.94 (m, 2H), 7.16-7.19 (m, 1H), 7.24-7.27 (m, 1H), 7.90 (d, J=8.7 Hz, 1H), 8.10-8.12 (m, 1H), 8.27 (d, J=9.2 Hz, 1H)

Isomer B: $[\alpha]_D^{25}$=−146° (c=0.390, CHCl₃)
MS (ESI pos.) m/z: 796 ([M+H]⁺)
¹H-NMR (600 MHz, CDCl₃) δ (ppm); 1.20-3.98 (m, 28H), 3.87 (s, 3H), 4.41-4.78 (m, 2H), 6.58-7.32 (m, 3H), 6.61-6.74 (m, 1H), 6.86-6.94 (m, 2H), 7.19-7.34 (m, 1H), 7.81-7.94 (m, 1H), 8.24-8.52 (m, 1H)

Example 201

Synthesis of tert-butyl 4-[3-(5-chloro-3-{(2S,4R)-2-[(dimethylamino)carbonyl]-4-hydroxypyrrolidin-1-yl}-1-{[4-methoxy-2-(trifluoromethoxy)phenyl]sulfonyl}-2-oxo-2,3-dihydro-1H-indol-3-yl)-4-methoxybenzyl]piperazine-1-carboxylate With 500 mg of the compound obtained in Step 198-2 and 262 mg of tert-butylpiperazine-1-carboxylate as starting materials, respectively 388 mg (Isomer A: colorless amorphous) and 162 mg (Isomer B: colorless amorphous) of two species of diastereoisomers of the title compound were obtained by a similar method to Step 198-4.

Isomer A: $[\alpha]_D^{29}$=−147° (c=0.106, CHCl₃)
MS (ESI pos.) m/z: 882 ([M+H]⁺), (ESI neg.) m/z: 880 ([M−H]⁻)
¹H-NMR (600 MHz, CDCl₃) δ (ppm); 1.38-3.43 (m, 12H) 1.43 (s, 9H) 1.83-1.89 (m, 1H) 2.41 (s, 3H) 2.72 (s, 3H) 3.46 (s, 3H) 3.52 (d, J=4.6 Hz, 2H) 3.82-3.86 (m, 1H) 3.88 (s, 3H) 4.15-4.19 (m, 1H) 6.66 (d, J=8.3 Hz, 1H) 6.85-6.87 (m, 1H) 6.88-6.91 (m, 2H) 7.14 (dd, J=8.3, 2.3 Hz, 1H) 7.23-7.25 (m, 1H) 7.89 (d, J=8.7 Hz, 1H) 8.11 (d, J=2.3 Hz, 1H) 8.25 (d, J=9.2 Hz, 1H)

Isomer B:
MS (ESI pos.) m/z: 882 ([M+H]⁺), 904 ([M+Na]⁺), (ESI neg.) m/z: 880 ([M−H]⁻)
¹H-NMR (600 MHz, CDCl₃) δ (ppm); 1.42-1.47 (m, 9H) 1.77-3.51 (m, 25H) 3.84-3.89 (m, 3H) 4.29-4.61 (m, 1H) 6.53-7.24 (m, 7H) 7.81-7.90 (m, 1H) 8.16-8.48 (m, 1H)

Example 202A

Synthesis of (4R)-1-(5-chloro-3-[2-methoxy-5-(piperazin-1-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer)

To a suspension of 116 mg of compound obtained in Example 201 (Isomer A) in water (1.5 ml) was added a solution of 4 mol/L hydrochloric acid in dioxane (1.5 ml) and the reaction mixture was stirred for 3 hours. After the reaction, the solution was concentrated under reduced pressure, CHCl₃ and a saturated aqueous solution of NaHCO₃ were added to the residue, and liquid separation was performed. The organic layer was washed with saturated brine and dried over MgSO₄, then, the drying agent was separated by filtration and the solvent was evaporated under reduced pressure. The obtained residue was purified by column chromatography (Chromatorex NH; mobile phase: MeOH/CHCl₃=5/95; v/v) to obtain 66.8 mg of the title compound (colorless amorphous).

$[\alpha]_D^{30}$=+148° (c=0.113, CHCl₃)
MS (ESI pos.) m/z: 782 ([M+H]⁺), (ESI neg.) m/z: 780 ([M−H]⁻)
¹H-NMR (600 MHz, CDCl₃) δ (ppm); 1.67-1.74 (m, 1H) 1.85-1.90 (m, 1H) 2.08-2.48 (m, 5H) 2.44 (s, 3H) 2.74 (s, 3H) 2.91 (t, J=4.8 Hz, 4H) 3.35-3.40 (m, 1H) 3.43-3.49 (m, 1H) 3.48 (s, 3H) 3.52-3.54 (m, 2H) 3.60-3.78 (m, 1H) 3.86 (dd, J=9.4, 7.1 Hz, 1H) 3.90 (s, 3H) 4.17-4.22 (m, 1H) 6.67 (d, J=8.3 Hz, 1H) 6.87-6.90 (m, 1H) 6.90-6.94 (m, 2H) 7.16 (dd, J=8.5, 2.1 Hz, 1H) 7.24-7.27 (m, 1H) 7.91 (d, J=8.7 Hz, 1H) 8.14 (d, J=2.3 Hz, 1H) 8.28 (d, J=8.7 Hz, 1H)

Example 202B

Synthesis of (4R)-1-(5-chloro-3-[2-methoxy-5-(piperazin-1-ylmethyl)phenyl]-1-{[4-methoxy-2-(trifluoromet hoxy)phenyl]sulfonyl}-2-oxo-2,3-dihydro-1H-indol-3-yl)-4-hydroxy-N,N-dimethyl-L-prolinamide (levorotatory isomer)

With 120 mg of the compound obtained in Example 201 (Isomer B) as starting material, 87.1 mg of the title compound (colorless amorphous) was obtained by a similar method to Step 202A.

$[\alpha]_D^{30}$=−173° (c=0.113, CHCl$_3$)

MS (ESI pos.) m/z: 782 ([M+H]$^+$), (ESI neg.) m/z: 780 ([M−H]$^−$)

$^1$H-NMR (600 MHz, CDCl$_3$) δ (ppm); 1.34-4.91 (m, 30H) 6.56-8.49 (m, 9H)

Example 203

Synthesis of (4R)-1-(5-chloro-3-[5-(hydroxymethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer and dextrorotatory isomer)

To a solution of 2.00 g of the compound obtained in Step 198-3 in MeOH (20 ml) was added 54 mg of NaBH$_4$, and the reaction mixture was stirred for one hour, then, the reaction mixture was poured into a saturated aqueous solution of NH$_4$Cl and resulting mixture was extracted with EtOAc; the combined organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=20/1 to 9/1; v/v) to obtain respectively 386 mg (Isomer A: amorphous) and 388 mg (Isomer B: amorphous) of two species of diastereoisomers of the title compound.

Isomer A: $[\alpha]_D^{25}$=+107° (c=0.260, CHCl$_3$)

MS (ESI pos.) m/z: 714 ([M+H]$^+$), 736 ([M+Na]$^+$), (ESI neg.) m/z: 712 ([M−H]$^−$)

$^1$H-NMR (600 MHz, CDCl$_3$) δ (ppm); 1.21-1.29 (m, 1H), 1.54-1.96 (m, 3H), 2.43 (s, 3H), 2.74 (s, 3H), 3.34-3.57 (m, 5H), 3.83-3.97 (m, 4H), 4.16-4.20 (m, 1H), 4.71 (s, 2H), 6.72 (d, J=8.25 Hz, 1H), 6.88-6.90 (m, 1H), 6.91-6.94 (m, 2H), 7.24 (dd, 1H), 7.27 (dd, J=8.71, 2.29 Hz, 1H), 7.92 (d, J=9.17 Hz, 1H), 8.22 (d, J=2.29 Hz, 1H), 8.28 (d, J=9.17 Hz, 1H)

Isomer B: $[\alpha]_D^{25}$=−160° (c=0.160, CHCl$_3$)

MS (ESI pos.) m/z: 714 ([M+H]$^+$), 736 ([M+Na]$^+$), (ESI neg.) m/z: 712 ([M−H]$^−$)

$^1$H-NMR (600 MHz, CDCl$_3$) δ (ppm); 1.84-1.89 (m, 1H) 1.98-2.10 (m, 1H) 2.47-2.50 (m, 4H) 2.64-2.80 (m, 3H) 3.11-3.27 (m, 1H) 3.50-3.68 (m, 5H) 3.88 (s, 3H) 4.42-4.49 (m, 1H) 4.54-4.60 (m, 1H) 4.63-4.70 (m, 1H) 4.77-4.94 (m, 1H) 6.72 (d, J=7.8 Hz, 1H) 6.85-6.88 (m, 1H) 6.93 (dd, J=8.9, 2.5 Hz, 1H) 7.10-7.16 (m, 1H) 7.16-7.21 (m, 1H) 7.21-7.31 (m, 1H) 7.85-8.03 (m, 2H) 8.27-8.42 (m, 1H)

Example 204

Synthesis of (4R)-1-(5-chloro-3-{5-[(diethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide Step 204-1: Synthesis of (3-bromo-4-methoxyphenyl)methanol (levorotatory isomer)

To a mixed solution of 100 g of 3-bromo-para-anisaldehyde in MeOH (700 ml) and THF (100 ml), on ice, was added 7.50 g of NaBH$_4$. After the solution was warmed to room temperature and stirred for two hours, acetone was added. The reaction solution was concentrated under reduced pressure, water and EtOAc were added to the residue, and liquid separation was performed. The organic layer was washed with saturated brine and dried over MgSO$_4$, then, the drying agent was separated by filtration and the solvent was evaporated under reduced pressure. The obtained residue was purified by column chromatography (silicagel 60; mobile phase: EtOAc/n-hexane=1/1; v/v) to obtain 99.8 g of the title compound (colorless solid).

MS (EI pos.) m/z: 216 ([M]$^+$)

$^1$H-NMR (600 MHz, CDCl$_3$) δ (ppm); 3.89 (s, 3H) 4.60 (s, 2H) 6.86-6.89 (m, 1H) 7.24-7.28 (m, 1H) 7.55 (s, 1H)

Step 204-2: Synthesis of [(3-bromo-4-methoxybenzyl)oxy] (tert-butyl) dimethyl silane To a solution of 98.8 g of the compound obtained in Step 204-1 in DMF (455 ml) was added 72.0 g of TBSCl and 62.0 g of imidazole under ice cooling, and the reaction mixture was stirred for 10 minutes. The solution was warmed to room temperature then stirred for two hours, water and Et$_2$O were added and liquid separation was performed. The organic layer was washed with saturated brine and dried over MgSO$_4$, then, the drying agent was separated by filtration and the solvent was evaporated under reduced pressure. n-hexane was used on the obtained solid residue for a recovery by filtration to obtain 152 g of the title compound.

MS (ESI neg.) m/z: 329 ([M−H]$^−$)

$^1$H-NMR (600 MHz, CDCl$_3$) δ (ppm); 0.08 (s, 6H) 0.92 (s, 9H) 3.87 (s, 3H) 4.64 (s, 2H) 6.85 (d, J=8.3 Hz, 1H) 7.21 (dd, J=8.5, 2.1 Hz, 1H) 7.49 (d, J=2.3 Hz, 1H)

Step 204-3: Synthesis of 3-[5-({[tert-butyl(dimethyl) silyl]oxy}methyl)-2-methoxyphenyl]-5-chloro-3-hydroxy-1,3-dihydro-2H-indol-2-one With 100 g of the compound obtained in Step 204-2 and 45.8 g of 5-chloroisatin as starting material, 66.2 g of the title compound (opal solid) was obtained by a similar method to Step 21-1.

MS (ESI pos.) m/z: 456 ([M+Na]$^+$), (ESI neg.) m/z: 432 ([M−H]$^−$)

$^1$H-NMR (600 MHz, DMSO-d$_6$) δ (ppm); 0.06-0.08 (m, 6H) 0.88 (s, 9H) 3.26 (s, 1H) 3.39 (s, 3H) 4.68 (d, J=2.8 Hz, 2H) 6.67 (d, J=1.8 Hz, 1H) 6.81 (dd, J=17.0, 8.3 Hz, 2H) 7.16-7.20 (m, 2H) 7.76 (d, J=1.8 Hz, 1H) 10.38 (brs, 1H)

Step 204-4: Synthesis of (4R)-1-{3-[5-({[tert-butyl (dimethyl)silyl]oxy}methyl)-2-methoxyphenyl]-5-chloro-2-oxo-2,3-dihydro-1H-indol-3-yl}-4-hydroxy-N,N-dimethyl-L-prolinamide With 50.0 g of the compound obtained in Step 204-3 and (4R)-4-hydroxy-N,N-dimethyl-L-prolinamide trifluoroacetate (138 mmol) as starting materials, respectively 5.25 g (Isomer A: colorless amorphous) and 14.9 g (Isomer B: colorless amorphous) of two species of diastereoisomers of the title compound and a mixture of isomers A and B (11.0 g) were obtained by a similar method to Step 28-2.

Isomer A: MS (ESI pos.) m/z: 574 ([M+H]$^+$), 596 ([M+Na]$^+$), (ESI neg.) m/z: 572 ([M−H]$^-$)

$^1$H-NMR (600 MHz, CDCl$_3$) δ (ppm); 0.12 (s, 6H) 0.95 (s, 9H) 1.83-1.89 (m, 1H) 2.12 (dd, J=13.5, 5.7 Hz, 1H) 2.68 (s, 3H) 2.82 (brs, 3H) 3.38-3.45 (m, 1H) 3.53-3.57 (m, 1H) 3.58 (s, 3H) 3.66-3.71 (m, 1H) 3.97 (dd, J=11.0, 6.4 Hz, 1H) 4.32-4.36 (m, 1H) 4.78 (s, 2H) 6.79 (dd, J=8.5, 4.4 Hz, 2H) 6.85-6.88 (m, 1H) 7.12 (dd, J=8.3, 2.3 Hz, 1H) 7.27 (dd, J=8.3, 2.3 Hz, 1H) 7.94 (brs, 1H) 8.93 (brs, J=3.7 Hz, 1H)

Isomer B: MS (ESI pos.) m/z: 574 ([M+H]$^+$), 596 ([M+Na]$^+$), (ESI neg.) m/z: 572 ([M−H]$^-$)

$^1$H-NMR (600 MHz, CDCl$_3$) δ (ppm); 0.06-0.07 (m, 6H) 0.89 (s, 9H) 1.86-1.91 (m, 1H) 2.05-2.10 (m, 2H) 2.17-2.23 (m, 2H) 2.45-2.48 (m, 2H) 2.49 (s, 3H) 2.59-2.73 (m, 3H) 3.57 (s, 3H) 4.98 (t, J=8.0 Hz, 2H) 6.67 (d, J=8.3 Hz, 1H) 6.76 (d, J=8.3 Hz, 1H) 6.93-7.01 (m, 1H) 7.05 (dd, J=8.3, 2.3 Hz, 1H) 7.25 (d, J=8.7 Hz, 1H) 7.66-7.83 (m, 1H) 8.43 (s, 1H)

Step 204-5: Synthesis of (4R) 1-{5-chloro-3-[5-(hydroxymethyl)-2-methoxyphenyl]-2-oxo-2,3-dihydro-1H-indol-3-yl}-4-hydroxy-N,N-dimethyl-L-prolinamide With 12.9 g of the compound obtained in Step 204-4 (Isomer B) as starting material, 5.10 g of the title compound (colorless amorphous) was obtained by a similar method to Step 139-2.

MS (ESI pos.) m/z: 482 ([M+Na]$^+$), (ESI neg.) m/z: 458 ([M−H]$^-$)

$^1$H-NMR (600 MHz, CDCl$_3$) δ (ppm); 1.60-1.67 (m, 1H) 1.85-1.91 (m, 1H) 1.97-2.15 (m, 1H) 2.56 (s, 3H) 2.61-2.69 (m, 3H) 3.30-3.35 (m, 2H) 3.55 (brs, 3H) 4.37-4.49 (m, 1H) 4.53-4.69 (m, 2H) 4.76-5.11 (m, 1H) 6.71 (dd, J=15.6, 8.3 Hz, 2H) 6.95-7.03 (m, 1H) 7.05 (dd, J=8.3, 2.3 Hz, 1H) 7.16 (dd, J=8.3, 2.3 Hz, 1H) 7.94-8.16 (m, 1H) 8.70-8.91 (m, 1H)

Step 204-6: Synthesis of (4R)-1-(5-chloro-3-[5-(hydroxymethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 3.09 g of the compound obtained in Step 204-5 and 2.05 g of 4-methoxy-2-(trifluoromethoxy)benzene sulfonyl chloride as starting materials, 2.68 g of the title compound (colorless amorphous) was obtained by a similar method to Example 2.

[α]$_D^{25}$=−160° (c=0.160, CHCl$_3$)

MS (ESI pos.) m/z: 714 ([M+H]$^+$), 736 ([M+Na]$^+$), (ESI neg.) m/z: 712 ([M−H]$^-$)

$^1$H-NMR (600 MHz, CDCl$_3$) δ (ppm); 1.84-1.89 (m, 1H) 1.98-2.10 (m, 1H) 2.47-2.50 (m, 4H) 2.64-2.80 (m, 3H) 3.11-3.27 (m, 1H) 3.50-3.68 (m, 5H) 3.88 (s, 3H) 4.42-4.49 (m, 1H) 4.54-4.60 (m, 1H) 4.63-4.70 (m, 1H) 4.77-4.94 (m, 1H) 6.72 (d, J=7.8 Hz, 1H) 6.85-6.88 (m, 1H) 6.93 (dd, J=8.9, 2.5 Hz, 1H) 7.10-7.16 (m, 1H) 7.16-7.21 (m, 1H) 7.21-7.31 (m, 1H) 7.85-8.03 (m, 2H) 8.27-8.42 (m, 1H)

Step 204-7: Synthesis of (4R)-1-(5-chloro-3-(5-formyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide To a solution of 1.16 g of the compound obtained in Step 204-6 in CHCl$_3$ (8.1 ml) was added 5.62 g of manganese dioxide and the reaction mixture was stirred for 15 hours. After the reaction, the solution was filtered with celite, and the filtrate was concentrated under reduced pressure. The obtained residue was purified by column chromatography (silicagel 60; mobile phase: MeOH/CHCl$_3$=2/98; v/v) to obtain 975 mg of the title compound (colorless amorphous).

MS (ESI pos.) m/z: 712 ([M+H]$^+$), (ESI neg.) m/z: 710 ([M−H]$^-$)

$^1$H-NMR (600 MHz, CDCl$_3$) δ (ppm); 1.27-4.76 (m, 2H) 1.74-1.85 (m, 1H) 1.94-2.16 (m, 1H) 2.28-2.49 (m, 3H) 2.51-2.73 (m, 3H) 3.08-3.39 (m, 1H) 3.49-3.79 (m, 3H) 3.85 (s, 3H) 4.47-4.56 (m, 1H) 4.57-4.79 (m, 1H) 6.82-6.86 (m, 2H) 6.90 (dd, J=8.9, 2.5 Hz, 1H) 6.93-7.11 (m, 1H) 7.20-7.27 (m, 1H) 7.80 (d, J=8.3 Hz, 1H) 7.84 (d, J=8.7 Hz, 1H) 8.22-8.64 (m, 2H) 9.86 (s, 1H)

Step 204-8: Synthesis of (4R)-1-(5-chloro-3-{5-[(diethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 101 mg of the compound obtained in Step 204-7 and diethyl amine (18 μl) as starting material, 31.0 mg of the title compound (colorless amorphous) was obtained by a similar method to Step 195-1.

MS (ESI pos.) m/z: 769 ([M+H]$^+$), (ESI neg.) m/z: 767 ([M−H]$^-$)

$^1$H-NMR (600 MHz, CDCl$_3$) δ (ppm); 0.79-4.83 (m, 31H) 6.58-8.52 (m, 9H)

Example 205

Synthesis of (4R)-1-(5-chloro-3-(5-{[ethyl(methyl)amino]methyl}-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 105 mg of the compound obtained in Step 204-1 and methylethyl amine (63 μl) as starting materials, 53.1 mg of the title compound (colorless amorphous) was obtained by a similar method to Step 195-1.

[α]$_D^{30}$=−179° (c=0.088, CHCl$_3$)

MS (ESI pos.) m/z: 755 ([M+H]$^+$), 777 ([M+Na]$^+$), (ESI neg.) m/z: 753 ([M−H]$^-$)

$^1$H-NMR (600 MHz, CDCl$_3$) δ (ppm); 0.98-4.85 (m, 29H) 6.57-8.45 (m, 9H)

Example 206

Synthesis of (4R)-1-(5-chloro-3-{2-methoxy-5-[(methyl amino)methyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 200 mg of the compound obtained in Step 204-1 and a solution of 40% methylamine in MeOH (0.2 ml) as starting materials, 124 mg of the title compound (colorless amorphous) was obtained by a similar method to Step 195-1.

$[\alpha]_D^{30}$=−175° (c=0.092, CHCl$_3$)

MS (ESI pos.) m/z: 727 ([M+H]$^+$), (ESI neg.) m/z: 725 ([M−H]$^−$)

$^1$H-NMR (600 MHz, CDCl$_3$) δ (ppm); 1.09-3.83 (m, 20H) 3.87 (s, 3H) 4.34-4.87 (m, 2H) 6.62-6.73 (m, 1H) 6.87 (s, 1H) 6.92 (dd, J=8.9, 2.1 Hz, 1H) 6.94-7.19 (m, 2H) 7.20-7.23 (m, 1H) 7.60-7.81 (m, 1H) 7.81-7.89 (m, 1H) 8.22-8.46 (m, 1H)

Example 207

Synthesis of (4R)-1-(5-chloro-3-{5-[(cyclopropylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

To a solution of 250 mg of the compound obtained in Step 196-5, 40 mg of cyclopropyl amine and 42 mg of acetic acid in CHCl$_3$ (3 ml) was added 149 mg of sodium triacetoxy borohydride under ice cooling and the reaction mixture was stirred for one hour. A saturated aqueous solution of NaHCO$_3$ was added, the solution was extracted with EtOAc, the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=9/1 to 4/1; v/v) to obtain 199 mg of the title compound.

$[\alpha]_D^{25}$=−160° (c=0.045, CHCl$_3$)

MS (ESI pos.) m/z: 753 ([M+H]$^+$), 775 ([M+Na]$^+$), (ESI neg.) m/z: 751 ([M−H]$^−$)

$^1$H-NMR (600 MHz, CDCl$_3$) δ (ppm); 0.23-0.60 (m, 4H), 1.56-1.99 (m, 6H), 2.09-2.18 (m, 1H), 2.36-2.61 (m, 3H), 2.66-2.93 (m, 3H), 3.05-3.65 (m, 3H), 3.69-3.75 (m, 1H), 3.76-3.85 (m, 1H), 3.88 (s, 3H), 4.42-4.60 (m, 1H), 4.69-4.84 (m, 1H), 6.64-6.72 (m, 1H), 6.87 (s, 1H), 6.93 (dd, J=9.17, 2.29 Hz, 1H), 6.98-7.12 (m, 1H), 7.17 (d, J=8.25 Hz, 1H), 7.22 (dd, J=8.71, 2.29 Hz, 1H), 7.69-7.82 (m, 1H), 7.86 (d, J=8.71 Hz, 1H), 8.28-8.42 (m, 1H)

Example 208

Synthesis of (4R)-1-(5-chloro-3-(5-{[cyclopropyl(methyl)amino]methyl}-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 180 mg of the compound obtained in Example 207 and 39 mg of an aqueous solution of 37% formaldehyde as starting materials, 80 mg of the title compound (amorphous) was obtained by a similar procedure to Example 111.

$[\alpha]_D^{25}$=174° (c=0.365, CHCl$_3$)

MS (ESI pos.) m/z: 767 ([M+H]$^+$), 789 ([M+Na]$^+$), (ESI neg.) m/z: 765 ([M−H]$^−$)

$^1$H-NMR (600 MHz, CDCl$_3$) δ (ppm); 0.23-0.60 (m, 4H), 1.12-1.33 (m, 1H), 1.76-1.86 (m, 5H), 2.04-2.12 (m, 2H), 2.19 (s, 3H), 2.34-2.92 (m, 6H), 3.29-3.79 (m, 3H), 3.85-3.92 (m, 3H), 4.41-4.83 (m, 2H), 6.58-6.75 (m, 1H), 6.87 (s, 1H), 6.92 (dd, J=9.17, 2.29 Hz, 1H), 6.96-7.18 (m, 2H), 7.22 (dd, J=8.71, 2.29 Hz, 1H), 7.59-7.80 (m, 1H), 7.86 (d, J=8.71 Hz, 1H), 8.28-8.44 (m, 1H)

Example 209

Synthesis of (4R)-1-(5-chloro-3-[5-(1-hydroxyethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide To a solution of 1.20 g of the compound obtained in Step 203-1 in THF (8.4 ml), under a temperature condition of −78° C., was added dropwise a solution of 0.84 mol/L methyl magnesium iodide in Et$_2$O (7 ml) over 15 minutes and the reaction mixture was stirred under the same temperature condition for two hours. The solution was stirred further for one hour under ice cooling, a saturated aqueous solution of NH$_4$Cl and CHCl$_3$ were added, and liquid separation was performed. The organic layer was washed with water and with saturated brine and dried over MgSO$_4$, then, the drying agent was separated by filtration and the solvent was evaporated under reduced pressure. The obtained residue was purified by column chromatography (silicagel 60; mobile phase: MeOH/CHCl$_3$=2/98; v/v) to obtain 1.03 g of the title compound (colorless amorphous).

MS (ESI pos.) m/z: 728 ([M+H]$^+$), 750 ([M+Na]$^+$), (ESI neg.) m/z: 726 ([M−H]$^−$)

$^1$H-NMR (600 MHz, CDCl$_3$) δ (ppm); 1.19-4.92 (m, 24H) 6.67-8.42 (m, 9H)

Example 210

Synthesis of (4R)-1-(3-(5-acetyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 943 mg of the compound obtained in Example 209 as starting material, 682 mg of the title compound (colorless amorphous) was obtained by a similar method to Step 204-1.

$[\alpha]_D^{30}$=−178° (c=0.121, CHCl$_3$)

MS (ESI pos.) m/z: 726 ([M+H]$^+$), 748 ([M+Na]$^+$), (ESI neg.) m/z: 724 ([M−H]$^−$)

$^1$H-NMR (600 MHz, CDCl$_3$) δ (ppm); 1.49-1.65 (m, 3H) 1.78-1.88 (m, 1H) 1.96-2.15 (m, 1H) 2.35-2.52 (m, 3H) 2.61-2.77 (m, 2H) 2.63 (s, 3H) 3.08-3.35 (m, 1H) 3.51-3.82 (m, 3H) 3.88 (s, 3H) 4.49-4.57 (m, 1H) 4.66-4.89 (m, 1H) 6.82 (d, J=9.2 Hz, 1H) 6.88 (s, 1H) 6.94 (dd, J=9.2, 2.3 Hz, 1H) 6.99-7.13 (m, 1H) 7.21-7.32 (m, 1H) 7.85-7.99 (m, 2H) 8.25-8.41 (m, 1H) 8.41-8.64 (m, 1H)

Example 211

Synthesis of (4R)-1-(5-chloro-3-[5-(1-hydroxy-1-methylethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 129 mg of the compound obtained in Example 210 as starting material, 59.6 mg of the title compound (colorless amorphous) was obtained by a similar method to Example 209.

MS (ESI pos.) m/z: 742 ([M+H]$^+$), 764 ([M+Na]$^+$), (ESI neg.) m/z: 740 ([M−H]$^−$) $[\alpha]_D^{25}$=−118° (c=0.092, CHCl$_3$)

$^1$H-NMR (600 MHz, CDCl$_3$) δ (ppm); 1.02-3.92 (m, 20H) 3.87 (s, 3H) 4.28-4.59 (m, 2H) 4.62-4.90 (m, 1H) 6.69 (d, J=8.3 Hz, 1H) 6.87 (s, 1H) 6.92 (d, J=8.3 Hz, 1H) 6.99-7.17

(m, 1H) 7.22 (d, J=8.7 Hz, 1H) 7.27 (d, J=7.8 Hz, 1H) 7.73-7.93 (m, 1H) 7.94-8.13 (m, 1H) 8.20-8.51 (m, 1H)

Example 212

Synthesis of (4R)-1-[5-chloro-1-{[4-methoxy-2-(trifluoromethoxy)phenyl]sulfonyl}-3-(2-methoxy-5-vinylphenyl)-2-oxo-2,3-dihydro-1H-indol-3-yl]-4-hydroxy-N,N-dimethyl-L-prolinamide (levorotatory isomer)

Under nitrogen atmosphere, to a solution of 3.00 g of methyl triphenyl phosphonium bromide in THF (50 ml) was added solution of 1.59 mol/L n-butyl lithium in n-hexane (5.30 ml) under ice cooling and the reaction mixture was stirred at room temperature for one hour. The solution was cooled by ice, 1.00 g of the compound obtained in Example 196-5 was added and the reaction mixture was stirred at room temperature for two hours. A saturated aqueous solution of NH$_4$Cl was added, the solution was extracted with EtOAc, the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=50/1 to 20/1; v/v) to obtain 801 mg of the title compound (amorphous).
[α]$_D^{25}$=−212° (c=0.312, CHCl$_3$)
MS (ESI pos.) m/z: 710 ([M+H]$^+$), 732 ([M+Na]$^+$), (ESI neg.) m/z: 708 ([M−H]$^+$)
$^1$H-NMR (600 MHz, CDCl$_3$) δ (ppm); 1.31-1.48 (m, 1H), 1.65-1.83 (m, 2H), 2.37 (s, 3H), 2.67-2.81 (m, 3H), 3.09-3.20 (m, 1H), 3.52-3.67 (m, 3H), 3.86-3.88 (m, 3H), 4.56-4.68 (m, 1H), 4.71-4.81 (m, 1H), 5.16 (d, J=11.00 Hz, 1H), 5.72 (d, J=16.96 Hz, 1H), 6.60 (dd, J=17.42, 11.00 Hz, 1H), 6.71 (d, J=8.71 Hz, 1H), 6.86-6.87 (m, 1H), 6.93 (dd, J=9.17, 2.29 Hz, 1H), 7.06-7.15 (m, 1H), 7.21-7.27 (m, 1H), 7.42-7.48 (m, 2H), 7.48-7.56 (m, 1H), 7.80-7.94 (m, 1H), 8.27-8.34 (m, 1H)

Example 213

Synthesis of (4R)-1-(5-chloro-3-(5-ethyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 300 mg of the compound obtained in Example 212 as starting material, 151 mg of the title compound (amorphous) was obtained by a similar procedure to Example 114.
[α]$_D^{25}$=−170° (c=0.401, CHCl$_3$)
MS (ESI pos.) m/z: 712 ([M+H]$^+$), 734 ([M+Na]$^+$), (ESI neg.) m/z: 710 ([M−H]$^-$)
$^1$H-NMR (600 MHz, CDCl$_3$) δ (ppm); 1.18 (t, J=7.57 Hz, 3H), 1.27-1.84 (m, 1H), 2.15 (s, 3H), 2.35-2.46 (m, 3H), 2.51-2.63 (m, 2H), 2.69-2.83 (m, 3H), 3.11-3.27 (m, 1H), 3.45-3.62 (m, 3H), 3.85-3.89 (m, 3H), 4.54-4.62 (m, 1H), 4.68-4.81 (m, 1H), 6.67 (d, J=8.71 Hz, 1H), 6.86 (s, 1H), 6.92 (dd, J=9.17, 2.29 Hz, 1H), 7.04 (dd, J=8.25, 2.29 Hz, 1H), 7.07-7.15 (m, 1H), 7.22 (dd, J=9.17, 2.29 Hz, 1H), 7.41-7.75 (m, 1H), 7.86 (d, J=8.71 Hz, 1H), 8.32 (d, J=8.25 Hz, 1H)

Example 214

Synthesis of (4R)-1-(5-chloro-3-{2-methoxy-5-[propa-1-en-1-yl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 300 mg of the compound obtained in Step 196-5 and 782 mg of ethyl triphenyl phosphonium bromide as starting materials, 305 mg of the title compound (amorphous) was obtained by a similar procedure to Example 212.
MS (ESI pos.) m/z: 724 ([M+H]$^+$), 746 ([M+Na]$^+$), (ESI neg.) m/z: 722 ([M−H]$^-$)
$^1$H-NMR (600 MHz, CDCl$_3$) δ (ppm); 1.05-1.25 (m, 3H), 1.74-1.90 (m, 2H), 1.93-2.03 (m, 1H), 2.21-2.31 (m, 3H), 2.67-2.83 (m, 3H), 3.10-3.24 (m, 1H), 3.53-3.71 (m, 3H), 3.87 (s, 3H), 4.47-4.88 (m, 2H), 5.64-5.76 (m, 1H), 6.12-6.37 (m, 1H), 6.69 (dd, J=32.55, 8.71 Hz, 1H), 6.85 (s, 1H), 6.92 (dd, J=9.17, 2.29 Hz, 1H), 7.04-7.16 (m, 2H), 7.18-7.27 (m, 1H), 7.40-7.54 (m, 1H), 7.68-7.75 (m, 1H), 7.86 (dd, J=8.71, 3.21 Hz, 1H), 8.25-8.35 (m, 1H)

Example 215

Synthesis of (4R)-1-(5-chloro-3-(2-methoxy-5-propylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 303 mg of the compound obtained in Example 214 as starting material, 105 mg of the title compound (amorphous) was obtained by a similar procedure to Example 114.
[α]$_D^{25}$=−184° (c=0.325, CHCl$_3$)
MS (ESI pos.) m/z: 726 ([M+H]$^+$), 748 ([M+Na]$^+$), (ESI neg.) m/z: 724 ([M−H]$^-$)
$^1$H-NMR (600 MHz, CDCl$_3$) δ (ppm); 0.92 (t, J=7.34 Hz, 3H), 1.10-1.22 (m, 1H), 1.39-1.65 (m, 3H), 1.74-1.86 (m, 1H), 1.97-2.14 (m, 1H), 2.42 (s, 3H), 2.50 (t, J=7.57 Hz, 2H), 2.78 (s, 3H), 3.12-3.29 (m, 1H), 3.46-3.65 (m, 3H), 3.88 (s, 3H), 4.52-4.64 (m, 1H), 4.68-4.82 (m, 1H), 6.67 (d, J=8.25 Hz, 1H), 6.86 (s, 1H), 6.93 (dd, J=9.17, 2.29 Hz, 1H), 7.02 (dd, J=8.25, 2.29 Hz, 1H), 7.06-7.14 (m, 1H), 7.23 (dd, J=8.71, 2.29 Hz, 1H), 7.57-7.65 (m, 1H), 7.87 (d, J=8.71 Hz, 1H), 8.33 (d, J=8.25 Hz, 1H)

Example 216

Synthesis of (4R)-1-(5-chloro-3-[5-(2-hydroxyethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer)

Step 216-1: Synthesis of ethyl (3-bromo-4-methoxyphenyl)acetate

To a solution of 50.0 g of ethyl(3-bromo-4-methoxyphenyl)acetonitrile in EtOH (300 ml) was added concentrated hydrochloric acid (300 ml), and the reaction mixture was refluxed for two hours. The solvent was evaporated under reduced pressure, then, extraction was carried out with EtOAc. The extract was dried over Na$_2$SO$_4$, then, the drying agent was separated by filtration and the solvent was evaporated under reduced pressure. The title compound in the amounts of 70.0 g (light yellow oil) was obtained.
MS (ESI pos.) m/z: 273 ([M+H]$^+$)
$^1$H-NMR (200 MHz, CDCl$_3$) δ (ppm); 1.26 (t, J=7.5 Hz, 3H), 3.53 (s, 2H), 3.88 (s, 3H), 4.15 (q, J=7.5 Hz, 2H), 6.85 (d, J=8.4 Hz, 1H), 7.19 (dd, J=8.4, 1.8 Hz, 1H), 7.48 (d, J=1.8 Hz, 1H)

Step 216-2: Synthesis of 2-(3-bromo-4-methoxyphenyl)ethanol

To a solution of 10.7 g of LAH in THF (600 ml) was added dropwise a solution of 70.0 g of ethyl(3-bromo-4-methoxyphenyl)acetate in THF (200 ml) at an internal temperature of −12 to −3° C. After stirring at an internal of 0° C. or lower for one hour, Na₂SO₄/10 hydrate was added slowly. After foaming ended, filtration was carried out. The filtrate was concentrated under reduced pressure to obtain 45.0 g of the title compound (light yellow oil).

MS (CI pos.) m/z: 231 ([M+H]⁺)

¹H-NMR (200 MHz, CDCl₃) δ (ppm); 2.79 (t, J=6.6 Hz, 2H), 3.82 (t, J=6.6 Hz, 2H), 3.88 (s, 3H), 6.85 (d, J=8.4 Hz, 1H), 7.13 (dd, J=8.4, 2.2 Hz, 1H), 7.42 (d, J=2.2 Hz, 1H)

Step 216-3: Synthesis of [2-(3-bromo-4-methoxyphenyl)ethoxy](tert-butyl) dimethyl silane To a solution 45.0 g of the compound obtained in Step 216-2 in DMF (50 ml) was added 29.0 g of imidazole and 32.0 g of TBSCl, and stirred at room temperature for 16 hours. Water was added to the solution, and the resulting mixture was extracted with Et₂O. The extract was dried over Na₂SO₄, then, the drying agent was separated by filtration and the solvent was evaporated under reduced pressure. The obtained residue was purified by column chromatography (silicagel 60; mobile phase: n-hexane/EtOAc=10/1; v/v) to obtain 62.0 g of the title compound (colorless oil).

MS (CI pos.) m/z: 347 ([M+H]⁺)

¹H-NMR (200 MHz, CDCl₃) δ (ppm); 0.89 (s, 9H), 2.75 (t, J=6.8 Hz, 2H), 3.78 (t, J=6.8 Hz, 2H), 3.89 (s, 3H), 6.83 (d, J=8.4 Hz, 1H), 7.12 (dd, J=8.4, 2.0 Hz, 1H), 7.42 (d, J=2.0 Hz, 1H)

Step 216-4: Synthesis of 3-[5-(2-{[tert-butyl(dimethyl) silyl]oxy}ethyl)-2-methoxyphenyl]-5-chloro-3-hydroxy-1,3-dihydro-2H-indol-2-one With 20.0 g of the compound obtained in Step 217-3 and 7.50 g of 5-chloro-isatin as starting materials, 8.00 g of the title compound (light brown solid) was obtained by a similar method to Step 21-1.

MS (ESI neg.) m/z: 446 ([M−H]⁻)

¹H-NMR (200 MHz, CDCl₃) δ (ppm); 0.02 (s, 6H), 0.89 (s, 9H), 2.81 (t, J=6.8 Hz, 2H), 3.81 (t, J=6.8 Hz, 2H), 6.72-6.84 (m, 2H), 7.05 (d, J=2.2 Hz, 1H), 7.17 (d, 2H), 7.56 (d, J=2.2 Hz, 1H), 8.27 (s, 1H)

Step 216-5: Synthesis of (4R)-1-{3-[5-(2-{[tert-butyl (dimethyl) silyl]oxy}ethyl)-2-methoxyphenyl]-5-chloro-2-oxo-2,3-dihydro-1H-indol-3-yl}-4-hydroxy-N,N-dimethyl-L-prolinamide From 8.00 g of the compound obtained in Step 217-4 and 11.4 g of (4R)-4-hydroxy-N,N-dimethyl-L-prolinamide trifluoroacetate, respectively 1.0 g (Isomer A: light yellow solid) and 4.0 g (Isomer B: purple amorphous) of two species of diastereoisomers of the title compound were obtained by a similar method to Step 21-2.

Isomer A: MS (ESI pos.) m/z: 588 ([M+H]⁺)

¹H-NMR (600 MHz, CDCl₃) δ (ppm); 0.01 (s, 6H), 0.88 (s, 9H), 1.81-1.89 (m, 1H), 2.07-2.14 (m, 1H), 2.68 (s, 3H), 2.69-2.92 (m, 5H), 3.57 (s, 1H), 3.57 (s, 3H), 3.64-3.72 (m, 1H), 3.83 (t, J=7.1 Hz, 2H), 3.92-3.99 (m, 1H), 4.32-4.36 (m, 1H), 6.70-6.82 (m, 2H), 6.87-6.93 (m, 1H), 7.09-7.15 (m, 2H), 7.83-7.90 (m, 1H)

Isomer B: MS (ESI pos.) m/z: 588 ([M+H]⁺)

¹H-NMR (600 MHz, CDCl₃) δ (ppm); 0.00 (s, 6H), 0.86 (s, 9H), 1.88-4.68 (m, 16H), 3.58 (s, 3H), 6.69-6.77 (m, 2H), 6.96-7.13 (m, 3H), 7.68-7.81 (m, 1H), 9.28-9.40 (m, 1H)

Step 216-6: Synthesis of (4R)-1-(3-[5-(2-{[tert-butyl (dimethyl) silyl]oxy}ethyl)-2-methoxyphenyl]-5-chloro-1-{[4-methoxy-2-(trifluoromethoxy)phenyl] sulfonyl}-2-oxo-2,3-dihydro-1H-indol-3-yl)-4-hydroxy-N,N-dimethyl-L-prolinamide (Isomer A)

With 1.00 g of the compound obtained in Step 217-6 (Isomer A) and 593 mg of 4-methoxy-2-(trifluoromethoxy)benzene sulfonyl chloride as starting materials, 1.00 g of the title compound (colorless amorphous) was obtained by a similar method as Example 2.

MS (ESI pos.) m/z: 842 ([M+H]⁺)

¹H-NMR (600 MHz, CDCl₃) δ (ppm); −0.01 (s, 6H), 0.85 (s, 9H), 1.67-1.74 (m, 1H), 1.84-1.91 (m, 1H), 2.45 (s, 3H), 2.73 (s, 3H), 2.78-2.92 (m, 2H), 3.36-3.52 (m, 2H), 3.47 (S, 3H), 3.81 (t, J=6.6 Hz, 2H), 3.84-3.89 (m, 1H), 3.90 (s, 3H), 4.13-4.22 (m, 1H), 6.66 (d, J=8.3 Hz, 1H), 6.88-6.96 (m, 3H), 7.08-7.12 (m, 1H), 7.23-7.29 (m, 1H), 7.91 (d, J=8.7 Hz, 1H), 7.97 (s, 1H), 8.28 (d, J=8.7 Hz, 1H)

Step 216-7: Synthesis of (4R)-1-(5-chloro-3-[5-(2-hydroxy ethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer)

To a solution of 500 mg of the compound obtained in Step 216-6 in THF (5.0 ml) was added dropwise a solution of 1 mol/L TBAF/THF (2.6 ml) under ice cooling. The solution was stirred at room temperature for two hours. Water was added to the reaction solution and the resulting mixture was extracted with EtOAc. The extract was dried over Na₂SO₄, then, the drying agent was separated by filtration and the solvent was evaporated under reduced pressure. The obtained residue was purified by column chromatography (silicagel 60; mobile phase: CHCl₃/MeOH=8/1; v/v) to obtain 320 mg of the title compound (light yellow solid).

$[\alpha]_D^{25}$=+115° (c=0.418, CHCl₃)

MS (ESI pos.) m/z: 728 ([M+H]⁺)

¹H-NMR (600 MHz, CDCl₃) δ (ppm); 1.64-1.73 (m, 1H), 1.83-1.94 (m, 1H), 2.44 (s, 3H), 2.75 (s, 3H), 2.84-2.99 (m, 2H), 3.47 (s, 2H), 3.47 (S, 3H), 3.83-3.94 (m, 3H), 3.90 (s, 3H), 4.16-4.21 (m, 1H), 6.69 (d, J=8.3 Hz, 1H), 6.87-6.95 (m, 3H), 7.09-7.13 (m, 1H), 7.24-7.29 (m, 1H), 7.91 (d, J=8.7 Hz, 1H), 8.09 (s, 1H), 8.28 (d, J=9.2 Hz, 1H)

Example 217

Synthesis of (4R)-1-(5-chloro-3-[5-(2-hydroxy ethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 217-1: Synthesis of (4R)-1-(3-[5-(2-{[tert-butyl (dimethyl) silyl]oxy}ethyl)-2-methoxyphenyl]-5-chloro-1-{[4-methoxy-2-(trifluoromethoxy)phenyl] sulfonyl}-2-oxo-2,3-dihydro-1H-indol-3-yl)-4-hydroxy-N,N-dimethyl-L-prolinamide (Isomer B)

With 4.0 g of the compound obtained in Step 216-5 (Isomer B) as starting material, 5.0 g of the title compound (pale purple amorphous) was obtained by a similar method to Example 2.

MS (ESI pos.) m/z: 842 ([M+H]⁺)

¹H-NMR (600 MHz, CDCl₃) δ (ppm); −0.01 (s, 6H), 0.84 (s, 9H), 1.55-4.85 (m, 19H), 3.88 (s, 3H), 6.67 (d, J=8.3 Hz, 1H), 6.86 (s, 1H), 6.91-6.95 (m, 1H), 7.04-7.13 (m, 2H), 7.20-7.24 (m, 1H), 7.54-7.68 (m, 1H), 7.87 (d, J=8.7 Hz, 1H), 8.26-8.39 (m, 1H)

Step 217-2: Synthesis of (4R)-1-(5-chloro-3-[5-(2-hydroxy ethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 5.0 g of the compound obtained in Step 217-1 as starting material, 3.7 g of the title compound (light yellow amorphous) was obtained by a similar method to Step 216-7.
$[\alpha]_D^{25}$=−176° (c=0.252, CHCl$_3$)
MS (ESI pos.) m/z: 728 ([M+H]$^+$)
$^1$H-NMR (600 MHz, CDCl$_3$) δ (ppm); 1.23-4.91 (m, 19H), 3.86 (s, 3H), 6.67 (d, J=8.3 Hz, 1H), 6.85 (s, 1H), 6.89-6.95 (m, 1H), 7.02-7.15 (m, 2H), 7.19-7.23 (m, 1H), 7.65-7.79 (m, 1H), 7.85 (d, J=8.7 Hz, 1H), 8.26-8.38 (m, 1H)

Example 218

Synthesis of (4R)-1-(5-chloro-3-[2-methoxy-5-(2-oxo ethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (Isomer A)

To DMSO (1.70 ml) was added 79 mg of IBX and the reaction mixture was stirred at room temperature for 10 minutes, and after dissolution, 170 mg of the compound obtained in Step 216-8 was added. The solution was stirred at room temperature overnight. A saturated aqueous solution of NaHCO$_3$ was added to the reaction solution and the resulting mixture was extracted with EtOAc. After washing in water saturated brine, drying was carried out in Na$_2$SO$_4$. The drying agent was separated by filtration and the solvent was evaporated under reduced pressure.
The title compound in the amount of 158 mg (pale orange amorphous) was obtained.
MS (ESI pos.) m/z: 726 ([M+H]$^+$)
$^1$H-NMR (600 MHz, CDCl$_3$) δ (ppm); 1.65-1.72 (m, 1H), 1.84-1.92 (m, 1H), 2.44 (s, 3H), 2.74 (s, 3H), 3.38-3.58 (m, 2H), 3.50 (s, 3H), 3.90 (s, 5H), 3.90 (s, 3H), 4.15-4.24 (m, 1H), 6.74 (d, J=8.3 Hz, 1H), 6.84-7.12 (m, 4H), 7.24-7.33 (m, 1H), 7.92 (d, J=9.2 Hz, 1H), 8.09 (s, 1H), 8.28 (d, J=9.2 Hz, 1H), 9.78 (s, 1H)

Example 219

Synthesis of (4R)-1-(5-chloro-3-[2-methoxy-5-(2-oxo ethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (Isomer B)

With 2.00 g of the compound obtained in Step 217-2 as starting material, 2.00 g of the title compound (light yellow amorphous) was obtained by a similar procedure to Example 218.
MS (ESI pos.) m/z: 726 ([M+H]$^+$)
$^1$H-NMR (600 MHz, CDCl$_3$) δ (ppm); 1.50-4.90 (m, 18H), 3.88 (s, 3H), 6.69-7.32 (m, 6H), 7.58-7.73 (m, 1H), 7.79-7.95 (m, 1H), 8.29-8.41 (m, 1H), 9.69-9.77 (m, 1H)

Example 220

Synthesis of (4R)-1-(5-chloro-3-{5-[2-(dimethylamino)ethyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (dextrorotatory isomer)

A mixed solution of 150 mg of the compound obtained in Example 218, a solution of 2 mol/L dimethylamine in THF (0.22 ml), 63 mg of acetic acid, 95 mg of sodium triacetoxy borohydride, in CHCl$_3$ (1.5 ml) was stirred at room temperature for one hour. A saturated aqueous solution of NaHCO$_3$ was added to the reaction solution, and the resulting mixture was extracted with CHCl$_3$. The extract was dried over Na$_2$SO$_4$, then, the drying agent was separated by filtration and the solvent was evaporated under reduced pressure. Purification was carried out by a preparative TLC plate (1 mm; mobile phase: CHCl$_3$/MeOH=8/1; v/v) to obtain 75 mg of the title compound (colorless solid).
$[\alpha]_D^{25}$=+114° (c=0.144, CHCl$_3$)
MS (ESI pos.) m/z: 755 ([M+H]$^+$)
$^1$H-NMR (600 MHz, CDCl$_3$) δ (ppm); 1.67-1.74 (m, 1H), 1.84-1.92 (m, 1H), 2.32 (s, 6H), 2.46 (s, 3H), 2.52-2.62 (m, 2H), 2.73 (s, 3H), 2.75-2.91 (m, 2H), 3.36-3.49 (m, 2H), 3.46 (s, 3H), 3.90 (s, 3H), 3.84-3.93 (m, 1H), 4.18-4.22 (m, 1H), 6.67 (d, J=8.3 Hz, 1H), 6.87-6.97 (m, 3H), 7.07-7.12 (m, 1H), 7.24-7.28 (m, 1H), 7.91 (d, J=8.7 Hz, 1H), 7.97-8.00 (m, 1H), 8.28 (d, J=9.2 Hz, 1H)

Example 221

Synthesis of (4R)-1-(5-chloro-3-{5-[2-(dimethylamino)ethyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 500 mg of the compound obtained in Example 219, a solution of 2 mol/L dimethylamine in THF (0.76 ml) as starting material, 300 mg of the title compound (light yellow amorphous) was obtained by a similar method to Example 220.
$[\alpha]_D^{25}$=−163° (c=0.246, CHCl$_3$)
MS (ESI pos.) m/z: 755 ([M+H]$^+$)
$^1$H-NMR (600 MHz, CDCl$_3$) δ (ppm); 1.29-3.73 (m, 23H), 3.86 (s, 3H), 4.39-4.81 (m, 2H), 6.57-6.72 (m, 1H), 6.80-6.97 (m, 2H), 6.97-7.14 (m, 2H), 7.21 (d, J=7.3 Hz, 1H), 7.49-7.74 (m, 1H), 7.84 (d, J=8.7 Hz, 1H), 8.25-8.41 (m, 1H)

Example 222

Synthesis of (4R)-1-(5-chloro-3-[2-methoxy-5-(2-morpholin-4-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 500 mg of the compound obtained in Example 219 and morpholine (0.13 ml) as starting material, 300 mg of the title compound (colorless amorphous) was obtained by a similar method to Example 220.
$[\alpha]_D^{25}$=−170° (c=0.154, CHCl$_3$)
MS (ESI pos.) m/z: 797 ([M+H]$^+$)
$^1$H-NMR (600 MHz, CDCl$_3$) δ (ppm); 1.31-3.68 (m, 23H), 3.70 (s, 3H), 3.86 (s, 3H), 4.45-4.83 (m, 1H), 6.66 (d, J=8.3

Hz, 1H), 6.77-6.97 (m, 2H), 7.00-7.15 (m, 2H), 7.18-7.25 (m, 1H), 7.55-7.75 (m, 1H), 7.85 (d, J=8.7 Hz, 1H), 8.23-8.42 (m, 1H)

Example 223

Synthesis of (4R)-1-(5-chloro-3-{2-methoxy-5-[2-(4-methylpiperazin-1-yl)ethyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 500 mg of the compound obtained in Example 219 and 1-methylpiperazine (0.17 ml) as starting material, 287 mg of the title compound (light yellow amorphous) was obtained by a similar method to Example 220.

$[\alpha]_D^{25}$=160° (c=0.168, CHCl$_3$)

MS (ESI pos.) m/z: 810 ([M+H]$^+$)

$^1$H-NMR (600 MHz, CDCl$_3$) δ (ppm); 1.62-2.03 (m, 2H), 2.25-3.78 (m, 24H), 2.29 (s, 3H), 3.87 (S, 32H), 4.44-4.81 (m, 1H), 6.67 (d, J=8.7 Hz, 1H), 6.87 (s, 1H), 6.90-6.96 (m, 1H), 7.02-7.16 (m, 2H), 7.19-7.24 (m, 1H), 7.48-7.75 (m, 1H), 7.86 (d, J=9.2 Hz, 1H), 8.15-8.49 (m, 1H)

Example 224

Synthesis of (4R)-1-(5-chloro-3-{5-[2-(diethylamino)ethyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 500 mg of the compound obtained in Example 219 and diethyl amine (0.16 ml) as starting materials, 180 mg of the title compound (light yellow amorphous) was obtained by a similar method to Example 220.

$[\alpha]_D^{25}$=−163° (c=0.200, CHCl$_3$)

MS (ESI pos.) m/z: 783 ([M+H]$^+$)

$^1$H-NMR (600 MHz, CDCl$_3$) δ (ppm); 0.98 (t, J=7.1 Hz, 6H), 3.81 (s, 23H), 3.81 (s, 3H), 6.61 (d, J=7.8 Hz, 1H), 6.81 (s, 1H), 6.83-6.90 (m, 1H), 6.93-7.11 (m, 2H), 7.11-7.19 (m, 1H), 7.47-7.72 (m, 1H), 7.80 (d, J=9.2 Hz, 1H), 8.18-8.38 (m, 1H)

Example 225

Synthesis of (4R)-1-(5-chloro-3-[2-methoxy-5-(2-piperidin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 600 mg of the compound obtained in Example 219 and 129 mg of piperidine as starting materials, 250 mg of the title compound (light yellow amorphous) was obtained by a similar method to Example 220.

$[\alpha]_D^{25}$=−162° (c=0.148, CHCl$_3$)

MS (ESI pos.) m/z: 795 ([M+H]$^+$), MS (ESI neg.) m/z: 793 ([M−H]$^-$)

$^1$H-NMR (600 MHz, CDCl$_3$) δ (ppm); 1.27-4.87 (m, 30H), 3.86 (s, 3H), 6.58-6.73 (m, 1H), 6.86 (s, 1H), 6.90-6.98 (m, 1H), 6.99-7.16 (m, 2H), 7.15-7.24 (m, 1H), 7.50-7.73 (m, 1H), 7.85 (d, J=9.2 Hz, 1H), 8.24-8.46 (m, 1H)

Example 226

Synthesis of (4R)-1-(5-chloro-3-[2-methoxy-5-(2-pyrrolidin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 350 mg of the compound obtained in Example 219 and 75 mg of pyrrolidine as starting materials, 110 mg of the title compound (pale orange amorphous) was obtained by a similar method to Example 220.

$[\alpha]_D^{25}$=−161° (c=0.212, CHCl$_3$)

MS (ESI pos.) m/z: 781 ([M+H]$^+$)

$^1$H-NMR (600 MHz, CDCl$_3$) δ (ppm); 1.08-4.95 (m, 27H), 3.87 (s, 3H), 6.57-6.76 (m, 1H), 6.80-7.36 (m, 5H), 7.49-7.77 (m, 1H), 7.85 (d, J=8.7 Hz, 1H), 8.25-8.50 (m, 1H)

Example 227

Synthesis of (4R)-1-(5-chloro-3-(5-{2-[ethyl(methyl)amino]ethyl}-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

To a suspension of 2.00 g of the compound obtained in Example 219 and Et$_3$N (0.77 ml) in CHCl$_3$ (20 ml) was added dropwise methane sulfonyl chloride (0.26 ml). The solution was stirred at room temperature for one hour. A saturated aqueous solution of NaHCO$_3$ was added to the reaction solution and the resulting mixture was extracted with CHCl$_3$. The extract was dried over Na$_2$SO$_4$, then, the drying agent was separated by filtration, the solvent was evaporated under reduced pressure to obtain 2.5 g of residue (crude form, colorless amorphous). To a solution of 800 mg of the obtained compound in CHCl$_3$ (8.0 ml) was added 1.0 g of ethylmethylamine and the reaction mixture was stirred at 80° C. for 6 hours. After being returned to room temperature, the solution was diluted in CHCl$_3$, washed with water and dried over Na$_2$SO$_4$, then the drying agent was separated by filtration and the solvent was evaporated under reduced pressure. The obtained residue was purified by a preparative TLC plate (2 mm; mobile phase: CHCl$_3$/MeOH=18/1; v/v) to obtain 200 mg of the title compound (colorless amorphous).

$[\alpha]_D^{25}$=−166° (c=0.212, CHCl$_3$)

MS (ESI pos.) m/z: 769 ([M+H]$^+$)

$^1$H-NMR (600 MHz, CDCl$_3$) δ (ppm); 1.06 (t, J=7.3 Hz, 3H), 1.35-4.85 (m, 24H), 3.87 (s, 3H), 6.64-6.71 (m, 1H), 6.84-7.24 (m, 5H), 7.48-7.78 (m, 1H), 7.86 (d, J=8.7 Hz, 1H), 8.20-8.46 (m, 1H)

Example 228

Synthesis of tert-butyl 4-{2-[3-(5-chloro-3-{(2S,4R)-2-[(dimethylamino)carbonyl]-4-hydroxypyrrolidin-1-yl}-1-{[4-methoxy-2-(trifluoromethoxy)phenyl]sulfonyl}-2-oxo-2,3-dihydro-1H-indol-3-yl)-4-methoxyphenyl]ethyl}piperazine-1-carboxylate With 2.00 g of the compound obtained in Example 219 and 3.3 g of piperazine-1-carboxylic acid tert-butyl ester as starting materials, 120 mg of the title compound (colorless oil) was obtained by a similar procedure to Example 227.

MS (ESI pos.) m/z: 896 ([M+H]$^+$)
$^1$H-NMR (600 MHz, CDCl$_3$) δ (ppm); 1.45 (s, 9H), 1.49-4.86 (m, 27H), 3.88 (s, 3H), 6.63-6.71 (m, 1H), 6.82-7.25 (m, 5H), 7.45-7.79 (m, 1H), 7.86 (d, J=8.7 Hz, 1H), 8.26-8.41 (m, 1H)

Example 229

Synthesis of (4R)-1-(5-chloro-3-[2-methoxy-5-(2-piperazin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Concentrated hydrochloric acid (3.0 ml) was added to 120 mg of the compound obtained in Example 228, and the solution was stirred at room temperature for 30 minutes. The stirred solution was poured into a saturated aqueous solution of NaHCO$_3$, and extraction was carried out with EtOAc. The extract was dried over Na$_2$SO$_4$, then, the drying agent was separated by filtration and the solvent was evaporated under reduced pressure. The obtained residue was purified by a preparative TLC plate (2 mm; mobile phase: CHCl$_3$/8M ammonia MeOH solution=8/1; v/v) to obtain 60 mg of the title compound (colorless amorphous).
[α]$_D^{25}$=-225° (c=0.032, CHCl$_3$)
MS (ESI pos.) m/z: 796 ([M+H]$^+$)
$^1$H-NMR (600 MHz, CDCl$_3$) δ (ppm); 1.37-4.89 (m, 27H), 3.91 (s, 3H), 6.66-6.75 (m, 1H), 6.86-6.93 (m, 1H), 6.92-6.99 (m, 1H), 7.05-7.20 (m, 2H), 7.20-7.28 (m, 1H), 7.50-7.79 (m, 1H), 7.90 (d, J=8.7 Hz, 1H), 8.27-8.46 (m, 1H)

Example 230

Synthesis of (4R)-1-(5-chloro-3-(5-isopropyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 230-1: Synthesis of 2-bromo-4-isopropyl-1-methoxy benzene

A solution of 20.0 g of 1-isopropyl-4-methoxy benzene, 1.07 g of ammonium nitrate, and 23.7 g of N-bromosuccinimide in MeCN (66.5 ml) was stirred at room temperature for one hour. To the reaction solution was added EtOAc and a saturated aqueous solution of NaHCO$_3$, liquid separation was performed, and the aqueous layer was extracted with EtOAc. The combined organic layer was washed with saturated brine and dried over MgSO$_4$, then, the drying agent was separated by filtration, and the filtrate was concentrated under reduced pressure. The residue was purified by column chromatography (silicagel 60; mobile phase: EtOAc/n-hexane=1/9, v/v) to obtain 30.4 g of the title compound.
MS (CI pos.) m/z: 228 ([M−1]$^+$), 230 ([M+1]$^+$)
$^1$H-NMR (600 MHz, CDCl$_3$) δ (ppm); 1.53 (s, 6H), 2.79-2.87 (m, 1H), 3.86 (s, 3H), 6.82 (d, J=8.7 Hz, 1H), 7.11 (dd, J=8.3, 2.3 Hz, 1H), 7.39 (d, J=2.3 Hz, 1H)

Step 230-2: Synthesis of 5-chloro-3-hydroxy-3-(5-isopropyl-2-methoxyphenyl)-1,3-dihydro-2H-indol-2-one With 20.0 g of the compound obtained in Step 230-1 and 10.6 g of 5-chloroisatin as starting materials, 16.2 g of the title compound (pale yellow solid) was obtained by a similar method to Step 21-1.

MS (ESI neg.) m/z: 330 ([M−H]$^−$)
$^1$H-NMR (600 MHz, DMSO-d$_6$) δ (ppm); 1.18 (d, J=6.9 Hz, 6H), 2.81-2.89 (m, 1H), 3.32 (s, 3H), 6.52 (s, 1H), 6.65 (d, J=1.8 Hz, 1H), 6.73 (d, J=8.3 Hz, 1H), 6.76 (d, J=8.3 Hz, 1H), 7.07 (dd, J=8.5, 2.5 Hz, 1H), 7.13 (dd, J=8.5, 2.1 Hz, 1H), 7.62 (d, J=2.3 Hz, 1H), 10.33 (s, 1H)

Step 230-3: Synthesis of (4R)-1-[5-chloro-3-(5-isopropyl-2-methoxyphenyl)-2-oxo-2,3-dihydro-1H-indol-3-yl]-4-hydroxy-N,N-dimethyl-L-prolinamide (levorotatory isomer and dextrorotatory isomer)

From 3.00 g of the compound obtained in Step 230-2 and (4R)-4-hydroxy-N,N-dimethyl-L-prolinamide trifluoroacetate (9.95 mmol), respectively 1.55 g (Isomer A, colorless amorphous) and 2.78 g (Isomer B, colorless amorphous) of two species of diastereoisomers of the title compound were obtained by a similar method to Step 21-2.
Isomer A: [α]$_D^{25}$=+207° (c=0.460, CHCl$_3$)
MS (ESI pos.) m/z: 494 ([M+Na]$^+$)
$^1$H-NMR (600 MHz, DMSO-d$_6$) δ (ppm); 1.23 (dd, J=6.9, 2.3 Hz, 6H), 1.60-1.66 (m, 1H), 1.75-1.83 (m, 1H), 2.43 (s, 3H), 2.53 (s, 3H), 2.86-2.94 (m, 1H), 3.08-3.12 (m, 1H), 3.17 (dd, J=9.6, 5.5 Hz, 1H), 3.41 (s, 3H), 3.63 (dd, J=8.7, 6.0 Hz, 1H), 4.18-4.24 (m, 1H), 4.54 (d, J=4.6 Hz, 1H), 6.44 (d, J=1.8 Hz, 1H), 6.76 (d, J=8.3 Hz, 1H), 6.79 (d, J=8.3 Hz, 1H), 7.09 (dd, J=8.5, 2.5 Hz, 1H), 7.13 (dd, J=8.3, 2.3 Hz, 1H), 7.90 (s, 1H), 10.51 (s, 1H)
Isomer B: [α]$_D^{25}$=-215° (c=0.642, CHCl$_3$)
MS (ESI pos.) m/z: 494 ([M+Na]$^+$)
$^1$H-NMR (600 MHz, DMSO-d$_6$) δ (ppm); 1.10-1.19 (m, 6H), 1.59-3.69 (m, 9H), 1.62 (dd, J=11.7, 6.2 Hz, 1H), 1.76-1.88 (m, 1H), 3.42 (s, 3H), 4.26-4.33 (m, 1H), 4.61-4.74 (m, 1H), 4.82 (d, J=4.6 Hz, 1H), 6.69 (d, J=1.8 Hz, 1H), 6.74 (d, J=8.3 Hz, 1H), 6.78 (d, J=8.3 Hz, 1H), 7.06 (dd, J=8.7, 2.3 Hz, 1H), 7.13 (dd, J=8.5, 2.1 Hz, 1H), 7.69 (s, 1H), 10.47 (s, 1H)

Step 230-4: Synthesis of (4R)-1-(5-chloro-3-(5-isopropyl-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 800 mg of the compound obtained in Step 230-3 (Isomer B) and 542 mg of 4-methoxy-2-(trifluoromethoxy) benzene sulfonyl chloride as starting materials, 750 mg of the title compound (colorless amorphous) was obtained by a similar method to Example 2.
[α]$_D^{25}$=-168° (c=0.450, CHCl$_3$)
MS (ESI pos.) m/z: 726 ([M+H]$^+$), 748 ([M+Na]$^+$)
$^1$H-NMR (600 MHz, CDCl$_3$) δ (ppm); 1.13-1.22 (m, 6H), 1.35-3.91 (m, 13H), 2.46 (s, 3H), 3.86 (s, 3H), 4.51-4.58 (m, 1H), 4.61-4.79 (m, 1H), 6.67 (d, J=8.3 Hz, 1H), 6.84 (s, 1H), 6.91 (dd, J=9.2, 2.3 Hz, 1H), 7.01-7.12 (m, 2H), 7.21 (dd, J=8.7, 2.3 Hz, 1H), 7.55-7.71 (m, 1H), 7.84 (d, J=8.7 Hz, 1H)

Example 231

Synthesis of (4R)-1-(3-(5-tert-butyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 231-1: Synthesis of 2-bromo-4-tert-butyl-1-methoxy benzene

From 20.0 g of 1-tert-butyl-4-methoxy benzene, 29.3 g of the title compound (pale brown oil) was obtained by a similar procedure to Step 230-1.

MS (ESI neg.) m/z: 344 ([M−H]⁻)
¹H-NMR (600 MHz, DMSO-d₆) δ (ppm); 1.26 (s, 9H), 3.33 (s, 3H), 6.54-6.55 (m, 1H), 6.64-6.65 (m, 1H), 6.74 (d, J=8.3 Hz, 1H), 6.77 (d, J=8.3 Hz, 1H), 7.12-7.15 (m, 1H), 7.22 (dd, J=8.5, 2.5 Hz, 1H), 7.79-7.81 (m, 1H), 10.33 (s, 1H)

Step 231-2: 3-(5-tert-butyl-2-methoxyphenyl)-5-chloro-3-hydroxy-1,3-dihydro-2H-indol-2-one Synthesis of With 9.96 g of 5-chloroisatin and 20.0 g of the compound obtained in Step 231-1 as starting materials, 16.2 g of the title compound (yellow solid) was obtained by a similar procedure to Step 230-2.
MS (ESI neg.) m/z: 344 ([M−H]⁻)
¹H-NMR (600 MHz, DMSO-d₆) δ (ppm); 1.26 (s, 9H), 3.33 (s, 3H), 6.54-6.55 (m, 1H), 6.64-6.65 (m, 1H), 6.74 (d, J=8.3 Hz, 1H), 6.77 (d, J=8.3 Hz, 1H), 7.12-7.15 (m, 1H), 7.22 (dd, J=8.5, 2.5 Hz, 1H), 7.79-7.81 (m, 1H), 10.33 (s, 1H)

Step 231-3: Synthesis of (4R)-1-[3-(5-tert-butyl-2-methoxyphenyl)-5-chloro-2-oxo-2,3-dihydro-1H-indol-3-yl]-4-hydroxy-N,N-dimethyl-L-prolinamide (levorotatory isomer and dextrorotatory isomer)

From 3.00 g of the compound obtained in Step 231-2 and (4R)-4-hydroxy-N,N-dimethyl-L-prolinamide trifluoroacetate (9.54 mmol), respectively 1.71 g (Isomer A, colorless amorphous) and 2.58 g (Isomer B, colorless amorphous) of two species of diastereoisomers of the title compound were obtained by a similar procedure to Step 21-2.
Isomer A: $[\alpha]_D^{25}$=+198° (c=0.243, CHCl₃)
MS (ESI pos.) m/z: 508 ([M+Na]⁺)
¹H-NMR (600 MHz, DMSO-d₆) δ (ppm); 1.31 (s, 9H), 1.62-1.67 (m, 1H), 1.76-1.83 (m, 1H), 2.44 (s, 3H), 2.55 (s, 3H), 3.06-3.11 (m, 1H), 3.12-3.17 (m, 1H), 3.41 (s, 3H), 3.59-3.65 (m, 1H), 4.19-4.25 (m, 1H), 4.57 (d, J=4.6 Hz, 1H), 6.42 (d, J=1.8 Hz, 1H), 6.74-6.79 (m, 2H), 7.13 (dd, J=8.3, 2.3 Hz, 1H), 7.21 (dd, J=8.7, 2.8 Hz, 1H), 8.15 (s, 1H), 10.50 (s, 1H)
Isomer B: $[\alpha]_D^{25}$=−206° (c=0.488, CHCl₃)
MS (ESI pos.) m/z: 508 ([M+Na]⁺)
¹H-NMR (600 MHz, DMSO-d₆) δ (ppm); 1.17-1.28 (m, 9H), 1.56-3.77 (m, 4H), 1.60-1.67 (m, 1H), 1.77-1.93 (m, 1H), 2.50-2.51 (m, 3H), 3.42 (s, 3H), 4.24-4.31 (m, 2H), 4.57-4.71 (m, 1H), 4.83 (d, J=4.1 Hz, 1H), 6.66 (s, 1H), 6.73 (d, J=8.3 Hz, 1H), 6.77 (d, J=8.7 Hz, 1H), 7.13 (dd, J=8.5, 2.1 Hz, 1H), 7.19 (dd, J=8.7, 2.8 Hz, 1H), 7.70-8.01 (m, 1H), 10.45 (s, 1H)

Step 231-4: Synthesis of (4R)-1-(3-(5-tert-butyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 800 mg of the compound obtained in Step 231-3 (Isomer B) and 526 mg of 4-methoxy-2-(trifluoromethoxy) benzene sulfonyl chloride as starting materials, 600 mg of the title compound (colorless amorphous) was obtained by a similar method to Example 2.
$[\alpha]_D^{25}$=−175° (c=0.531, CHCl₃)
MS (ESI pos.) m/z: 740 ([M+H]⁺), 762 ([M+Na]⁺), (ESI neg.) m/z: 738 ([M−H]⁻)
¹H-NMR (600 MHz, CDCl₃) δ (ppm); 1.21-1.31 (m, 9H), 1.42-3.92 (m, 11H), 2.53 (s, 3H), 3.88 (s, 3H), 4.50-4.57 (m, 1H), 4.60-4.79 (m, 1H), 6.68 (d, J=8.3 Hz, 1H), 6.86 (s, 1H), 6.93 (dd, J=8.9, 2.5 Hz, 1H), 6.98-7.14 (m, 1H), 7.20-7.29 (m, 2H), 7.72-7.89 (m, 1H), 7.86 (d, J=8.7 Hz, 1H), 8.29-8.42 (m, 1H)

Example 232

Synthesis of (4R)-1-(3-(5-sec-butyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 232-1: Synthesis of 2-bromo-4-sec-butyl-1-methoxy benzene

From 26.0 g of 1-sec-butyl-4-methoxy benzene, 36.6 g of the title compound (pale brown oil) was obtained by a similar procedure to Step 230-1.
MS (CI pos.) m/z: 243 ([M−1]⁺), 245 ([M+1]⁺)
¹H-NMR (600 MHz, CDCl₃) δ (ppm); 0.80 (t, J=7.3 Hz, 3H), 1.19 (d, J=6.9 Hz, 3H), 1.49-1.58 (m, 2H), 2.48-2.55 (m, 1H), 3.86 (s, 3H), 6.82 (d, J=8.3 Hz, 1H), 7.06 (dd, J=8.3, 2.3 Hz, 1H), 7.35 (d, J=2.3 Hz, 1H)

Step 232-2: Synthesis of 3-(5-sec-butyl-2-methoxyphenyl)-5-chloro-3-hydroxy-1,3-dihydro-2H-indol-2-one From 9.96 g of 5-chloroisatin and 20.0 g of the compound obtained in Step 232-1, 16.5 g of the title compound (yellow solid) was obtained by a similar procedure to Step 230-2.
MS (ESI pos.) m/z: 368 ([M+Na]⁺)
¹H-NMR (600 MHz, DMSO-d₆) δ ppm; 0.83 (t, J=7.3 Hz, 3H), 1.23 (t, J=6.6 Hz, 3H), 1.52-1.66 (m, 2H), 2.57-2.67 (m, J=6.4 Hz, 1H), 3.39 (s, 3H), 6.60 (s, 1H), 6.69 (s, 1H), 6.79-6.85 (m, 2H), 7.08-7.13 (m, 1H), 7.21 (dd, J=8.3, 2.3 Hz, 1H), 7.63-7.67 (m, 1H), 10.41 (s, 1H)

Step 232-3: Synthesis of 3-(5-sec-butyl-2-methoxyphenyl)-3,5-dichloro-1,3-dihydro-2H-indol-2-one From 3.00 g of the compound obtained in Step 232-2, 5.16 g of the title compound (crude form) was obtained by a similar procedure to Step 230-3. The resultant compound was subjected to the next step without purification.
MS (ESI pos.) m/z: 386 ([M+Na]⁺)
¹H-NMR (600 MHz, CDCl₃) δ (ppm); 0.88 (t, J=7.3 Hz, 3H), 1.28 (d, J=6.9 Hz, 3H), 1.59-1.69 (m, 2H), 2.63-2.70 (m, 1H), 3.51 (s, 3H), 4.30-4.40 (m, 1H), 6.74 (dd, J=8.3, 2.8 Hz, 1H), 6.84 (d, J=8.3 Hz, 1H), 6.93 (s, 1H), 7.14-7.22 (m, 2H), 7.82 (s, 1H), 7.88 (s, 1H)

Step 232-4: Synthesis of (4R)-1-[3-(5-sec-butyl-2-methoxyphenyl)-5-chloro-2-oxo-2,3-dihydro-1H-indol-3-yl]-4-hydroxy-N,N-dimethyl-L-prolinamide With 5.10 g of the compound obtained in Step 232-3 and (4R)-4-hydroxy-N,N-dimethyl-L-prolinamide trifluoroacetate (9.54 mmol) as starting material, respectively, 1.27 g (Isomer A: colorless amorphous) and 2.49 g (Isomer B: colorless amorphous) of two species of diastereoisomers of the title compound were obtained by a similar procedure to Step 230-4.
Isomer A: MS (ESI pos.) m/z: 508 ([M+Na]⁺)
¹H-NMR (600 MHz, CDCl₃) δ (ppm); 0.82-0.89 (m, 3H) 1.27 (d, J=6.88 Hz, 3H) 1.61-1.67 (m, 1H) 1.82-1.90 (m, 1H) 2.08-2.15 (m, 1H) 2.62-2.72 (m, 4H) 2.74-2.86 (m, 3H) 3.36

(d, J=22.47 Hz, 1H) 3.51-3.56 (m, 1H) 3.57 (s, 3H) 3.69 (d, J=12.38 Hz, 1H) 3.93-3.99 (m, 1H) 4.34 (d, J=3.67 Hz, 1H) 6.74 (dd, J=8.25, 4.13 Hz, 1H) 6.78 (d, J=8.25 Hz, 1H) 6.85 (d, J=12.38 Hz, 1H) 7.05-7.10 (m, 1H) 7.12 (dd, J=8.25, 1.83 Hz, 1H) 7.77-7.98 (m, 1H) 8.50-8.71 (m, 1H)

Isomer B: MS (ESI pos.) m/z: 508 ([M+Na]$^+$)
$^1$H-NMR (600 MHz, CDCl$_3$) δ (ppm); 0.81-0.87 (m, 3H) 1.17-1.25 (m, 3H) 1.45-1.65 (m, 2H) 1.86-1.97 (m, 1H) 2.05-2.19 (m, 1H) 2.51-2.67 (m, 5H) 2.68-2.87 (m, 3H) 3.31-3.54 (m, 1H) 3.58 (d, J=2.75 Hz, 3H) 4.55-4.65 (m, 1H) 4.75-5.01 (m, 1H) 6.70-6.79 (m, 2H) 6.95-7.01 (m, 1H) 7.02-7.06 (m, 1H) 7.07 (dd, J=8.25, 1.83 Hz, 1H) 7.72 (d, J=11.00 Hz, 1H) 8.98 (s, 1H)

Step 232-5: Synthesis of (4R)-1-(3-(5-sec-butyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 630 mg of the compound obtained in Step 232-4 (Isomer B) as starting material, 472 mg of the title compound (colorless amorphous) was obtained by a similar method to Example 2.

$[\alpha]_D^{30}$=−173° (c=0.135, CHCl$_3$)
MS (ESI pos.) m/z: 740 ([M+H]$^+$), 762 ([M+Na]$^+$), (ESI neg.) m/z: 738 ([M−H]$^-$)
$^1$H-NMR (600 MHz, CDCl$_3$) δ (ppm); 0.71-0.82 (m, 3H) 1.05-1.20 (m, 3H) 1.31-2.10 (m, 6H) 2.40-2.57 (m, 4H) 2.64-2.84 (m, 3H) 3.02-3.30 (m, 1H) 3.31-3.64 (m, 3H) 3.79-3.88 (m, 3H) 4.44-4.57 (m, 1H) 4.57-4.79 (m, 1H) 6.64 (t, J=8.7 Hz, 1H) 6.84 (s, 1H) 6.90 (dd, J=8.7, 2.3 Hz, 1H) 6.94-7.11 (m, 2H) 7.19 (d, J=9.2 Hz, 1H) 7.44-7.70 (m, 1H) 7.82 (d, J=9.2 Hz, 1H) 8.24-8.35 (m, 1H)

Example 233

Synthesis of (4R)-1-{5-chloro-1-{[4-methoxy-2-(trifluoromethoxy)phenyl]sulfonyl}-3-[2-(methylthio) phenyl]-2-oxo-2,3-dihydro-1H-indol-3-yl}-4-hydroxy-N,N-dimethyl-L-prolinamide (levorotatory isomer and dextrorotatory isomer)

Step 233-1: Synthesis of 5-chloro-3-hydroxy-3-[2-(methylthio) phenyl]-1,3-dihydro-2H-indol-2-one With 15.0 g of 1-bromo-2-(methylthio) benzene and 10.3 g of 5-chloroisatin as starting materials, 11.5 g of the title compound (orange red solid) was obtained by a similar method to Step 21-1.

MS (ESI pos.) m/z: 306 ([M+H]$^+$), (ESI neg.) m/z: 304 ([M−H]$^-$)
$^1$H-NMR (600 MHz, DMSO-d$_6$) δ (ppm); 2.10 (s, 3H) 6.67 (d, J=2.3 Hz, 1H) 6.78 (s, 1H) 6.83 (d, J=8.7 Hz, 1H) 7.23 (dd, J=8.3, 2.3 Hz, 1H) 7.32 (d, J=3.2 Hz, 2H) 7.86-7.95 (m, 1H) 10.57 (s, 1H)

Step 233-2: Synthesis of (4R)-1-{5-chloro-3-[2-(methylthio) phenyl]-2-oxo-2,3-dihydro-1H-indol-3-yl}-4-hydroxy-N,N-dimethyl-L-prolinamide From 5.00 g of the compound obtained in Step 233-1 and (4R)-4-hydroxy-N,N-dimethyl-L-prolinamide trifluoroacetate (21.3 mmol), 5.59 g of a diastereoisomer mixture of the title compound (brown amorphous) was obtained by a similar method to Step 28-2.

MS (ESI pos.) m/z: 446 ([M+H]$^+$), 468 ([M+Na]$^+$), (ESI neg.) m/z: 444 ([M−H]$^-$)
$^1$H-NMR (600 MHz, CDCl$_3$) δ (ppm); 1.72-2.80 (m, 11H) 3.44-4.69 (m, 4H) 6.67-6.82 (m, 1H) 6.96-7.46 (m, 5H) 8.25 (s, 0.6H) 8.41 (d, J=7.8 Hz, 0.4H) 8.78 (s, 0.6H) 9.15 (s, 0.4H)

Step 233-3: Synthesis of (4R)-1-{5-chloro-1-{[4-methoxy-2-(trifluoromethoxy)phenyl]sulfonyl}-3-[2-(methylthio) phenyl]-2-oxo-2,3-dihydro-1H-indol-3-yl}-4-hydroxy-N,N-dimethyl-L-prolinamide (levorotatory isomer and dextrorotatory isomer)

To a solution of 2.10 g of the compound obtained in Step 233-2 in DMF (20 ml) was added 198 mg of NaH under ice cooling and the reaction mixture was stirred for one hour. Thereafter, a solution of 1.44 g of 4-methoxy-2-(trifluoromethoxy)benzene sulfonyl chloride in DMF (4 ml) was added and the solution was stirred for 12 hours. After the end of the reaction, water was added under ice cooling and the solution was extracted with CHCl$_3$. The organic layer was washed with saturated brine and dried over MgSO$_4$, then, the drying agent was separated by filtration and the solvent was evaporated under reduced pressure. The obtained residue was purified by column chromatography (Chromatorex NH; mobile phase: MeCN/EtOAc=1/1; v/v), then, recrystallization from CHCl$_3$-EtOAc was carried out to obtain 849 mg of one of two species of diastereoisomers of the title compound (Isomer A: colorless solid). The filtrate was concentrated under reduced pressure, the obtained residue was purified by column chromatography (silicagel 60; mobile phase: MeOH/CHCl$_3$=2/98; v/v) to obtain 827 mg (Isomer B: colorless amorphous).

Isomer A: $[\alpha]_D^{30}$=+149° (c=0.118, CHCl$_3$)
MS (ESI pos.) m/z: 700 ([M+H]$^+$), 722 ([M+Na]$^+$), (ESI neg.) m/z: 698 ([M−H]$^-$)
$^1$H-NMR (600 MHz, CDCl$_3$) δ (ppm); 1.71-1.78 (m, 1H) 2.03 (s, 3H) 2.04-2.08 (m, 1H) 2.48 (s, 3H) 2.72 (s, 3H) 3.30-3.35 (m, 1H) 3.37-3.44 (m, 1H) 3.89 (s, 3H) 4.03-4.08 (m, 1H) 4.28-4.33 (m, 1H) 6.79 (d, J=1.8 Hz, 1H) 6.85 (d, J=1.8 Hz, 1H) 6.91 (dd, J=8.7, 2.3 Hz, 1H) 7.23-7.30 (m, 2H) 7.33 (d, J=7.8 Hz, 1H) 7.44 (t, J=7.6 Hz, 1H) 7.95 (d, J=8.7 Hz, 1H) 8.27-8.32 (m, 1H) 8.44 (d, J=7.8 Hz, 1H)

Isomer B: $[\alpha]_D^{30}$=−208° (c=0.106, CHCl$_3$)
MS (ESI pos.) m/z: 700 ([M+H]$^+$), 722 ([M+Na]$^+$), (ESI neg.) m/z: 698 ([M−H]$^-$)
$^1$H-NMR (600 MHz, CDCl$_3$) δ (ppm); 1.32-4.68 (m, 19H) 6.71-8.48 (m, 10H)

Example 234

Synthesis of (4R)-1-(5-chloro-3-(2-methoxybenzyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide

Step 234-1: Synthesis of 5-chloro-3-hydroxy-3-(2-methoxybenzyl)-1,3-dihydro-2H-indol-2-one With 4.50 g of 2-methoxybenzyl chloride and 4.34 g of 5-chloroisatin as starting materials, 2.19 g of the title compound (orange red solid) was obtained by a similar method to Step 21-1.

MS (ESI pos.) m/z: 304 ([M+H]$^+$), 326 ([M+Na]$^+$), (ESI neg.) m/z: 302 ([M−H]$^-$)
$^1$H-NMR (600 MHz, DMSO-d$_6$) δ (ppm); 2.86-3.25 (m, 2H) 3.43 (s, 3H) 6.11-7.10 (m, 7H) 10.19 (s, 1H)

Step 234-2: Synthesis of (4R)-1-[5-chloro-3-(2-methoxybenzyl)-2-oxo-2,3-dihydro-1H-indol-3-yl]-4-hydroxy-N,N-dimethyl-L-prolinamide From 4.57 g of the compound obtained in Step 234-1 and (4R)-4-hydroxy-N,N-dimethyl-L-prolinamide trifluoroacetate (18.1 mmol), 4.26 g of a diastereo mixture of the title compound (brown solid) was obtained by a similar method to Step 28-2.

MS (ESI pos.) m/z: 434 ([M+H]$^+$), 466 ([M+Na]$^+$), (ESI neg.) m/z: 442 ([M−H]$^−$)

$^1$H-NMR (600 MHz, DMSO-d$_6$) δ (ppm); 1.57-5.26 (m, 18H) 6.39-7.15 (m, 7H) 10.26 (s, 0.5H) 10.36 (s, 0.5H)

Step 234-3: Synthesis of (4R)-1-(5-chloro-3-(2-methoxybenzyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 800 mg of the compound obtained in Step 234-2 and 550 mg of 4-methoxy-2-(trifluoromethoxy)benzene sulfonyl chloride as starting materials, respectively 64.4 mg (Isomer A: colorless amorphous) and 64.2 mg (Isomer B: colorless amorphous) of two species of diastereoisomers of the title compound were obtained by a similar method to Example 2.

Isomer A: [α]$_D^{30}$=−58.3° (c=0.106, CHCl$_3$)

MS (ESI pos.) m/z: 698 ([M+H]$^+$), 720 ([M+Na]$^+$), (ESI neg.) m/z: 696 ([M−H]$^−$)

$^1$H-NMR (600 MHz, CDCl$_3$) δ (ppm); 1.84-1.90 (m, 1H) 2.04-2.10 (m, 1H) 2.57 (d, J=10.6 Hz, 1H) 2.75-2.81 (m, 3H) 2.89 (s, 3H) 2.95 (d, J=12.8 Hz, 1H) 3.34-3.39 (m, 1H) 3.45 (dd, J=10.3, 4.4 Hz, 1H) 3.49 (s, 3H) 3.89 (s, 3H) 4.24-4.30 (m, 1H) 4.76 (t, J=7.6 Hz, 1H) 6.50-6.59 (m, 2H) 6.65 (d, J=7.8 Hz, 1H) 6.76 (s, 1H) 6.91 (dd, J=8.7, 2.3 Hz, 1H) 7.05 (t, J=7.8 Hz, 1H) 7.15 (dd, J=8.7, 2.3 Hz, 1H) 7.30 (s, 1H) 7.58 (d, J=8.7 Hz, 1H) 8.25 (d, J=9.2 Hz, 1H)

Isomer B: MS (ESI pos.) m/z: 698 ([M+H]$^+$), 720 ([M+Na]$^+$), (ESI neg.) m/z: 696 ([M−H]$^−$)

$^1$H-NMR (600 MHz, CDCl$_3$) δ (ppm); 1.83-1.89 (m, 2H) 2.39 (s, 3H) 2.64 (s, 3H) 3.25 (d, J=12.8 Hz, 1H) 3.49 (s, 3H) 3.58-3.64 (m, 2H) 3.74 (dd, J=11.0, 4.6 Hz, 1H) 3.85 (dd, J=11.2, 3.0 Hz, 1H) 3.93 (s, 3H) 4.45-4.50 (m, 1H) 6.44-6.49 (m, 2H) 6.55-6.59 (m, 1H) 6.79 (brs, 1H) 6.95 (dd, J=9.2, 2.3 Hz, 1H) 6.98-7.02 (m, 1H) 7.13 (dd, J=8.7, 2.3 Hz, 1H) 7.41 (d, J=2.3 Hz, 1H) 7.54 (d, J=8.7 Hz, 1H) 8.24 (d, J=9.2 Hz, 1H)

Example 235

Synthesis of (4R)-1-[5-chloro-1-{[4-methoxy-2-(trifluoromethoxy)phenyl]sulfonyl}-3-(1-naphthyl)-2-oxo-2,3-dihydro-1H-indol-3-yl]-4-hydroxy-N,N-dimethyl-L-prolinamide (levorotatory isomer)

Step 235-1: Synthesis of 5-chloro-3-hydroxy-3-(1-naphthyl)-1,3-dihydro-2H-indol-2-one With 2.81 g of 1-naphthyl bromide 4.34 g, 5-chloroisatin as starting material, 4.30 g of the title compound (yellow solid) was obtained by a similar method to Step 21-1.

MS (ESI pos.) m/z: 322 ([M+Na]$^+$), (ESI neg.) m/z: 308 ([M−H]$^−$)

$^1$H-NMR (300 MHz, DMSO-d$_6$) δ (ppm); 6.89 (d, J=2.0 Hz, 1H), 6.99-7.09 (m, 2H), 7.29-7.50 (m, 3H), 7.52-7.64 (m, 2H), 7.94 (dd, J=7.6, 4.0 Hz, 3H), 10.87 (s, 1H)

Step 235-2: Synthesis of (4R)-1-[5-chloro-3-(1-naphthyl)-2-oxo-2,3-dihydro-1H-indol-3-yl]-4-hydroxy-N,N-dimethyl-L-prolinamide (levorotatory isomer and dextrorotatory isomer)

From 1.00 g of the compound obtained in Step 235-1 and 628 mg of (4R)-4-hydroxy-N,N-dimethyl-L-prolinamide hydrochloride, respectively 203 mg (Isomer A: orange color amorphous) and 221 mg (Isomer B: orange color amorphous) of two species of diastereoisomers of the title compound were obtained by a similar method to Step 21-2.

Isomer A: [α]$_D^{25}$=+565° (c=0.046, CHCl$_3$)

MS (ESI neg.) m/z: 448 ([M−H]$^−$)

$^1$H-NMR (300 MHz, DMSO-d$_6$) δ (ppm); 1.56-4.95 (m, 13H), 6.68-8.11 (m, 10H), 10.41 (s, 1H)

Isomer B: [α]$_D^{25}$=−423° (c=0.105, CHCl$_3$)

MS (ESI pos.) m/z: 472 ([M+Na]$^+$), (ESI neg.) m/z: 448 ([M−H]$^−$)

$^1$H-NMR (300 MHz, DMSO-d$_6$) δ (ppm); 1.58-2.81 (m, 9H), 3.09-3.29 (m, 2H), 4.45-4.96 (m, 2H), 6.90 (d, J=8.2 Hz, 2H), 7.26 (dd, J=8.3, 2.1 Hz, 2H), 7.32-8.12 (m, 6H), 10.99 (s, 1H)

Step 235-3: Synthesis of (4R)-1-[5-chloro-1-{[4-methoxy-2-(trifluoromethoxy)phenyl]sulfonyl}-3-(1-naphthyl)-2-oxo-2,3-dihydro-1H-indol-3-yl]-4-hydroxy-N,N-dimethyl-L-prolinamide (levorotatory isomer)

With 150 mg of the compound obtained in Step 235-2 (Isomer B) and 135 mg of 4-methoxy-2-(trifluoromethoxy)benzene sulfonyl chloride as starting materials, 148 mg of the title compound (colorless amorphous) was obtained by a similar method to Example 2.

[α]$_D^{25}$=285° (c=0.534, CHCl$_3$)

MS (ESI pos.) m/z: 704 ([M+H]$^+$), 726 ([M+Na]$^+$), (ESI neg.) m/z: 702 ([M−H]$^−$)

$^1$H-NMR (300 MHz, CDCl$_3$) δ (ppm); 1.74-2.89 (m, 9H), 3.53 (dd, J=9.7, 5.2 Hz, 2H), 3.92 (s, 3H), 4.56-4.90 (m, 2H), 6.95 (d, J=8.5 Hz, 2H), 7.09-7.84 (m, 8H), 7.97 (d, J=8.7 Hz, 1H), 8.38 (d, J=8.2 Hz, 1H), 8.84 (s, 1H)

Example 236

Synthesis of (4R)-1-(5-chloro-3-[5-(cyanomethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

To a solution of 350 mg of compound obtained in Example 203 (Isomer B) and 87 mg of Py in CHCl$_3$ (3 ml) was added dropwise a solution of 87 mg of thionyl chloride in CHCl$_3$ (1 ml) under ice cooling. The solution was stirred at the same temperature for one hour, then a saturated aqueous solution of NaHCO$_3$ was added to the reaction mixture and the resulting mixture was extracted with EtOAc; the organic layer was washed with saturated brine and dried over Na$_2$SO$_4$, then, the drying agent was separated by filtration, the solvent was evaporated under reduced pressure to obtain 328 mg of residue. To a solution of the obtained residue in MeCN (8 ml) was added 319 mg of potassium cyanide and 13 mg of 18-crown-6-ether, and the reaction mixture was refluxed for one hour. To the solution was added water and the resulting mixture was extracted with EtOAc, the organic layer was washed with saturated brine, dried over Na$_2$SO$_4$, then, the drying agent was separated by filtration and the solvent was evaporated under reduced pressure. The obtained residue was purified by column chromatography (silicagel 60N; mobile phase: CHCl₃MeOH=20/1 to 9/1; v/v) to obtain 276 mg of the title compound.

$[\alpha]_D^{25}$=−150° (c=0.226, CHCl₃)

MS (ESI pos.) m/z: 723 ([M+H]⁺), 745 ([M+Na]⁺), (ESI neg.) m/z: 721 ([M−H]⁻)

¹H-NMR (600 MHz, CDCl₃) δ (ppm); 1.63-1.92 (m, 2H), 2.17-2.32 (m, 3H), 2.67-2.80 (m, 3H), 2.82-2.92 (m, 3H), 2.97-3.04 (m, 1H), 3.23-3.52 (m, 3H), 3.76-3.84 (m, 3H), 4.09-4.18 (m, 1H), 4.24-4.34 (m, 1H), 4.63-4.73 (m, 1H), 6.54 (d, J=8.25 Hz, 1H), 6.76 (s, 1H), 6.83 (dd, J=8.94, 2.52 Hz, 1H), 6.92 (dd, J=8.25, 1.83 Hz, 1H), 6.97-7.06 (m, 1H), 7.13 (dd, J=8.71, 2.29 Hz, 1H), 7.41-7.57 (m, 1H), 7.75 (d, J=9.17 Hz, 1H), 8.18-8.28 (m, 1H)

Example 237

Synthesis of (4R)-1-(5-chloro-3-[4-(hydroxymethyl)-2-methoxyphenyl]-1-{[4-methoxy-2-(trifluoromethoxy) phenyl]sulfonyl}-2-oxo-2,3-dihydro-1H-indol-3-yl)-4-hydroxy-N,N-dimethyl-L-prolinamide Step 237-1: Synthesis of (4-bromo-3-methoxyphenyl)methanol To a solution of 5.00 g of 3-methoxybenzyl alcohol in MeCN-water (180 ml, 1:1) was added 8.60 g sodium hydrogen sulfite and 8.19 g of sodium bromate and the reaction mixture was stirred at room temperature for two hours. After the reaction, an aqueous solution of 10% sodium thiosulfate and Et₂O were added, and liquid separation was performed. After the organic layer was sequentially washed with 5% K₂CO₃, water and saturated brine, and dried over MgSO₄, the drying agent was separated by filtration and the solvent was evaporated under reduced pressure. The obtained residue was purified by column chromatography (silicagel 60; mobile phase: EtOAc/n-hexane=1/4; v/v) to obtain 5.02 g of the title compound (colorless solid).

MS (EI pos.) m/z: 216 ([M]⁺)

¹H-NMR (600 MHz, CDCl₃) δ (ppm); 3.80 (s, 3H) 4.70 (s, 2H) 6.71 (dd, J=8.7, 3.2 Hz, 1H) 7.05 (d, J=3.2 Hz, 1H) 7.40 (d, J=8.7 Hz, 1H)

Step 237-2: Synthesis of [(4-bromo-3-methoxybenzyl)oxy](tert-butyl) dimethyl silane With 5.02 g of the compound obtained in Step 237-1 as starting material, 6.99 g of the title compound (colorless oil) was obtained by a similar method to Step 216-3.

MS (ESI pos.) m/z: 357 ([M+Na]⁺)

¹H-NMR (600 MHz, CDCl₃) δ (ppm); 0.07 (s, 6H) 0.91 (s, 9H) 3.74 (s, 3H) 4.63 (s, 2H) 6.61 (dd, J=8.7, 3.2 Hz, 1H) 7.10 (d, J=3.2 Hz, 1H) 7.30 (d, J=8.7 Hz, 1H)

Step 237-3: Synthesis of 3-[4-({[tert-butyl(dimethyl) silyl]oxy}methyl)-2-methoxyphenyl]-5-chloro-3-hydroxy-1,3-dihydro-2H-indol-2-one With 6.99 g of the compound obtained in Step 237-2 and 3.21 g of 5-chloroisatin as starting materials, 1.66 g of the title compound (colorless solid) was obtained by a similar method to Step 21-1.

MS (ESI pos.) m/z: 434 ([M+H]⁺), 456 ([M+Na]⁺), (ESI neg.) m/z: 432 ([M−H]⁻)

¹H-NMR (600 MHz, DMSO-d₆) δ (ppm); −0.12 (d, J=11.0 Hz, 6H) 0.80 (s, 9H) 3.29 (s, 2H) 3.70 (s, 3H) 4.24-4.33 (m, 1H) 6.71-6.74 (m, 1H) 6.79 (dd, J=8.71, 2.8 Hz, 1H) 6.87-6.90 (m, 1H) 7.05 (d, J=2.8 Hz, 1H) 7.29 (dd, J=8.5, 2.1 Hz, 1H) 7.37-7.45 (m, 1H) 10.62 (s, 1H)

Step 237-4: Synthesis of (4R)-1-{3-[4-({[tert-butyl (dimethyl)silyl]oxy}methyl)-2-methoxyphenyl]-5-chloro-2-oxo-2,3-dihydro-1H-indol-3-yl}-4-hydroxy-N,N-dimethyl-L-prolinamide With 1.64 g of the compound obtained in Step 237-3 and (4R)-4-hydroxy-N,N-dimethyl-L-prolinamide trifluoroacetate (5.67 mmol) as starting materials, respectively 901 mg (Isomer A: colorless solid) and 288 mg (Isomer B: colorless amorphous) of two species of diastereoisomers of the title compound were obtained by a similar method to Step 28-2.

Isomer A: $[\alpha]_D^{29}$=+153° (c=0.117, CHCl₃)

MS (ESI pos.) m/z: 574 ([M+H]⁺), 596 ([M+Na]⁺), (ESI neg.) m/z: 572 ([M−H]⁻)

¹H-NMR (600 MHz, CDCl₃) δ (ppm); −0.16 (d, J=9.6 Hz, 6H) 0.19-4.72 (m, 18H) 0.80 (m, 9H) 6.77-9.02 (m, 7H)

Isomer B: MS (ESI pos.) m/z: 574 ([M+H]⁺), 596 ([M+Na]⁺), (ESI neg.) m/z: 572 ([M−H]⁻)

¹H-NMR (600 MHz, CDCl₃) δ (ppm); −0.12 (d, J=3.2 Hz, 6H) 0.82 (s, 9H) 0.90-0.94 (m, 1H) 1.91-2.00 (m, 1H) 2.33-2.61 (m, 4H) 2.64-2.78 (m, 3H) 2.87-3.24 (m, 2H) 3.80 (s, 3H) 4.02-4.29 (m, 1H) 4.63-4.73 (m, 1H) 4.71-4.91 (m, 2H) 6.66 (d, J=8.7 Hz, 1H) 6.80 (dd, J=8.7, 2.3 Hz, 1H) 6.94-7.00 (m, 1H) 7.08-7.13 (m, 1H) 7.18 (brs, 1H) 7.72-7.86 (m, 1H)

Step 237-5: Synthesis of (4R)-1-(5-chloro-3-[4-(hydroxymethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 278 mg of the compound obtained in Step 237-4 (Isomer B) as starting material, 168 mg of the title compound (colorless amorphous) was obtained by a similar method to Example 2.

MS (ESI pos.) m/z: 714 ([M+H]⁺), 736 ([M+Na]⁺), (ESI neg.) m/z: 712 ([M−H]⁻)

¹H-NMR (600 MHz, CDCl₃) δ (ppm); 2.08-2.14 (m, 1H) 2.32-2.42 (m, 1H) 2.44-2.52 (m, 1H) 2.65 (s, 3H) 2.93 (s, 3H) 3.06-3.14 (m, 1H) 3.20-3.30 (m, 1H) 3.43-3.65 (m, 1H) 3.75 (s, 3H) 3.87 (s, 3H) 3.95-4.02 (m, 1H) 4.55-4.64 (m, 1H) 5.16-5.38 (m, 2H) 6.61 (d, J=2.8 Hz, 1H) 6.69 (dd, J=9.2, 2.8 Hz, 1H) 6.80-6.82 (m, 1H) 6.86 (dd, J=8.7, 2.3 Hz, 1H) 7.12-7.22 (m, 2H) 7.30 (d, J=8.7 Hz, 1H) 7.44-7.62 (m, 1H) 7.98-8.08 (m, 1H)

Example 238

Synthesis of (4R)-1-(5-chloro-3-(5-cyano-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide Step 238-1: Synthesis of 3-(5-chloro-3-hydroxy-2-oxo-2,3-dihydro-1H-indol-3-yl)-4-methoxy benzo nitrile Under nitrogen atmosphere, to a solution of 5.0 g of 3-bromo-4-methoxy benzonitrile in THF (40 ml), under a temperature condition of −78° C., was added 8.83 ml of a solution of 2.67 mol/L n-butyl lithium in n-hexane over one hour, and the reaction mixture was further stirred for one hour under the same temperature condition.

Under nitrogen atmosphere, to a suspension of 3.57 g of 5-chloroisatin in THF (100 ml) was added 865 mg of NaH under ice cooling and the reaction mixture was stirred for one hour. Thereafter, the solution prepared beforehand was added dropwise. The solution was stirred at the same temperature for two hours, then, a saturated aqueous solution of $NH_4Cl$ and EtOAc were added and liquid separation was performed; the organic layer was washed with saturated brine and dried over $MgSO_4$, then, the drying agent was separated by filtration and the solvent was evaporated under reduced pressure. The obtained residue was purified by column chromatography (silicagel 60; mobile phase: EtOAc/n-hexane=1/1 to MeOH/$CHCl_3$=1/9; v/v) to obtain 460 mg of the title compound (colorless solid).

MS (ESI pos.) m/z: (ESI neg.) m/z: 313 ([M–H]$^-$)
$^1$H-NMR (600 MHz, DMSO-$d_6$) δ (ppm); 3.52 (s, 3H) 6.83 (d, J=8.3 Hz, 1H) 6.85 (d, J=2.3 Hz, 1H) 6.89 (s, 1H) 7.07 (d, J=8.7 Hz, 1H) 7.21 (dd, J=8.3, 1.8 Hz, 1H) 7.80 (dd, J=8.5, 2.1 Hz, 1H) 8.09 (d, J=2.3 Hz, 1H)

Step 238-2: Synthesis of (4R)-1-[5-chloro-3-(5-cyano-2-methoxyphenyl)-2-oxo-2,3-dihydro-1H-indol-3-yl]-4-hydroxy-N, N-dimethyl-L-prolinamide From 459 mg of the compound obtained in Step 238-1 and 341 mg of (4R)-4-hydroxy-N,N-dimethyl-L-prolinamide hydrochloride, 453 mg of a mixture of two species of diastereoisomers of the title compound (brown amorphous) was obtained by a similar method to Step 28-2.

MS (ESI pos.) m/z: 455 ([M+H]$^+$), 477 ([M+Na]$^+$), (ESI neg.) m/z: 453 ([M–H]$^-$)
$^1$H-NMR (600 MHz, $CDCl_3$) δ (ppm); 1.81-3.12 (m, 10H) 3.52-4.03 (m, 5H) 4.34-4.76 (m, 1H) 6.74-6.99 (m, 3H) 7.11-7.21 (m, 1H) 7.55-7.69 (m, 1H) 8.38-8.75 (m, 2H)

Step 238-3: Synthesis of (4R)-1-(5-chloro-3-(5-cyano-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 451 mg of the compound obtained in Step 238-2 and 303 mg of 4-methoxy-2-(trifluoromethoxy)benzene sulfonyl chloride as starting materials, respectively 139 mg (Isomer A: colorless amorphous) and 260 mg (Isomer B: colorless amorphous) of two species of diastereoisomers of the title compound were obtained by a similar method to Example 2.

Isomer A: $[α]_D^{29}$=+180° (c=0.118, $CHCl_3$)
MS (ESI pos.) m/z: 709 ([M+H]$^+$), 731 ([M+Na]$^+$), (ESI neg.) m/z: 707 ([M–H]$^-$)
$^1$H-NMR (600 MHz, $CDCl_3$) δ (ppm); 1.66-1.73 (m, 1H), 1.85-1.91 (m, 1H), 2.42 (s, 3H), 2.77 (s, 3H), 3.30-3.41 (m, 2H), 3.63 (s, 3H), 3.84 (dd, J=9.4, 7.1 Hz, 1H), 3.91 (s, 3H), 4.17-4.22 (m, 1H), 6.81 (d, J=8.3 Hz, 1H), 6.90 (d, J=2.3 Hz, 2H), 6.92 (dd, J=8.7, 2.3 Hz, 1H), 7.31 (dd, J=8.7, 2.3 Hz, 1H), 7.59 (dd, J=8.5, 2.1 Hz, 1H), 7.94 (d, J=8.7 Hz, 1H), 8.24 (d, J=9.2 Hz, 1H), 8.58 (d, J=2.3 Hz, 1H), Isomer B: MS (ESI pos.) m/z: 709 ([M+H]$^+$), 731 ([M+Na]$^+$), (ESI neg.) m/z: 707 ([M–H]$^-$)
$^1$H-NMR (600 MHz, $CDCl_3$) δ (ppm); 1.77-1.88 (m, 1H), 2.42-2.56 (m, 3H), 2.71-3.07 (m, 3H), 3.13-3.38 (m, 2H), 3.52-3.80 (m, 3H), 3.87-3.90 (m, 3H), 4.43-4.80 (m, 2H), 6.78-6.84 (m, 1H), 6.85-6.90 (m, 1H), 6.91-6.96 (m, 1H), 6.96-7.13 (m, 1H), 7.22-7.30 (m, 1H), 7.24-7.30 (m, 1H), 7.53-7.61 (m, 1H), 7.81-7.93 (m, 1H), 8.15-8.64 (m, 2H)

Example 239

Synthesis of (4R)-1-(5-chloro-3-(2,6-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 239-1; Synthesis of 5-chloro-3-(2,6-dimethoxyphenyl)-3-hydroxy-1,3-dihydro-2H-indol-2-one Under nitrogen atmosphere, to a solution of 22.8 g of 1,3-dimethoxy benzene in THF (150 ml) was added dropwise a solution of 1.59 mol/L n-butyl lithium in an n-hexane solution (104 ml) over 30 minutes under ice cooling, and the reaction mixture was stirred at room temperature for one hour. The solution was cooled by ice again, 10.0 g of 5-chloroisatin and was added, and the reaction mixture was stirred at room temperature for two hours. An aqueous solution of saturated $NH_4Cl$ was added to the solution and the resulting mixture was extracted with EtOAc; the organic layer was washed with saturated brine and dried over $Na_2SO_4$, then, the drying agent was separated by filtration and the solvent was evaporated under reduced pressure. The obtained residue was purified by column chromatography (silicagel 60N; mobile phase: $CHCl_3$/MeOH=50/1 to 10/1; v/v) to obtain 14.2 g of the title compound.

MS (ESI pos.) m/z: 342 ([M+H]$^+$)
$^1$H-NMR (600 MHz, $CDCl_3$) δ (ppm); 1.58-1.66 (m, 1H), 3.59-4.08 (m, 6H), 6.52-6.69 (m, 2H), 6.71 (s, 1H), 6.79 (d, J=8.25 Hz, 1H), 7.09-7.18 (m, 1H), 7.20-7.28 (m, 1H), 8.52 (s, 1H)

Step 239-2 Synthesis of (4R)-1-[5-chloro-3-(2,6-dimethoxyphenyl)-2-oxo-2,3-dihydro-1H-indol-3-yl]-4-hydroxy-N,N-dimethyl-L-prolinamide From 14.0 g of the compound obtained in Step 239-1 and 18.2 g of (4R)-4-hydroxy-N,N-dimethyl-L-prolinamide trifluoroacetate, respectively 2.61 g (Isomer A: amorphous) and 4.5 μg (Isomer B: amorphous) of two species of diastereoisomers of the title compound were obtained by a similar procedure to Step 21-2.

Isomer A: MS (ESI pos.) m/z: 460 ([M+H]$^+$), 482 ([M+Na]$^+$), (ESI neg.) m/z: 458 ([M–H]$^-$)
$^1$H-NMR (200 MHz, DMSO-$d_6$) δ (ppm); 1.64-1.93 (m, 3H), 2.95-3.26 (m, 6H), 3.44-3.93 (m, 8H), 4.10-4.29 (m, 1H), 4.30-4.59 (m, 1H), 6.62-6.90 (m, 3H), 7.01-7.34 (m, 3H), 10.45-10.57 (m, 1H)

Isomer B: MS (ESI pos.) m/z: 460 ([M+H]$^+$), 482 ([M+Na]$^+$), (ESI neg.) m/z: 458 ([M–H]$^-$)
$^1$H-NMR (200 MHz, DMSO-$d_6$) δ (ppm); 1.49-1.67 (m, 1H), 1.81-2.05 (m, 1H), 2.24 (t, J=7.69 Hz, 1H), 2.36 (s, 3H), 2.76 (s, 3H), 3.42-3.62 (m, 4H), 3.88-4.23 (m, 4H), 4.49-4.62 (m, 1H), 4.76 (d, J=5.27 Hz, 1H), 6.54-6.70 (m, 2H), 6.81 (d, J=7.91 Hz, 1H), 6.94 (d, J=2.20 Hz, 1H), 7.08 (dd, J=8.35, 2.20 Hz, 1H), 7.24 (t, J=8.13 Hz, 1H), 9.97 (s, 1H)

Step 239-3 Synthesis of (4R)-1-(5-chloro-3-(2,6-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 1.00 g of the compound obtained in Step 239-2 (Isomer B) and 759 mg of 4-methoxy-2-(trifluoromethoxy)benzene sulfonyl chloride as starting materials, 1.05 g of the title compound (amorphous) was obtained by a similar procedure to Example 2.

$[\alpha]_D^{25}$=193° (c=0.733, CHCl$_3$)

MS (ESI pos.) m/z: 714 ([M+H]$^+$), 736 ([M+Na]$^+$), (ESI neg.) m/z: 712 ([M−H]$^-$)

$^1$H-NMR (600 MHz, CDCl$_3$) δ (ppm); 1.67-1.78 (m, 1H), 1.86-2.00 (m, 1H), 2.51 (s, 5H), 2.64 (s, 3H), 3.39-3.61 (m, 4H), 3.87 (s, 3H), 3.96 (s, 3H), 4.32 (s, 1H), 4.49-4.62 (m, 1H), 6.51 (d, J=8.71 Hz, 1H), 6.65 (d, J=8.25 Hz, 1H), 6.87 (s, 1H), 6.90 (dd, J=8.71, 2.29 Hz, 1H), 7.15-7.23 (m, 2H), 7.35 (s, 1H), 7.82 (d, J=8.71 Hz, 1H), 8.45 (d, J=8.71 Hz, 1H)

Example 240

Synthesis of (4R)-1-(5-chloro-3-(2,3-dimethoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 50 mg of the compound (Isomer B) described in Preparation 3.26 of the brochure Publication No. WO01/055130 and 55 mg of 4-methoxy-2-(trifluoromethoxy)benzene sulfonyl chloride as starting materials, 26 mg of the title compound (colorless amorphous) was obtained by a similar method to Example 2.

$[\alpha]_D^{25}$=−159° (c=0.224, CHCl$_3$)

MS (ESI pos.) m/z: 714 ([M+H]$^+$), 736 ([M+Na]$^+$), (ESI neg.) m/z: 712 ([M−H]$^-$)

$^1$H-NMR (600 MHz, DMSO-d$_6$) δ (ppm); 1.50-1.64 (m, 2H), 1.80-1.91 (m, 1H), 2.38 (s, 3H), 2.75 (d, J=5.5 Hz, 3H), 3.06-3.64 (m, 5H), 3.76 (s, 3H), 3.89 (s, 3H), 4.57-4.87 (m, 2H), 6.82 (dd, J=8.3, 1.4 Hz, 1H), 6.87 (d, J=1.4 Hz, 1H), 6.94 (dd, J=9.2, 2.3 Hz, 1H), 6.99-7.08 (m, 2H), 7.24 (dd, J=9.2, 2.3 Hz, 1H), 7.38 (s, 1H), 7.90 (d, J=9.2 Hz, 1H), 8.35 (d, J=9.2 Hz, 1H)

Example 241

Synthesis of (4R)-1-(5-chloro-3-(2-fluorophenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 241-1: Synthesis of 5-chloro-3-(2-fluorophenyl)-3-hydroxy-1,3-dihydro-2H-indol-2-one With 5.00 g of 5-chloroisatin and 6.92 g of 1-bromo-2-fluorobenzene as starting materials, 5.41 g of the title compound (yellow solid) was obtained by a similar method to Step 21-1.

MS (ESI neg.) m/z: 276 ([M−H]$^-$)

$^1$H-NMR (300 MHz, DMSO-d$_6$) δ (ppm); 6.86-6.93 (m, 2H), 6.97-7.12 (m, 2H), 7.24-7.44 (m, 3H), 7.85-7.97 (m, 1H), 10.67 (s, 1H)

Step 241-2: Synthesis of (4R)-1-[5-chloro-3-(2-fluorophenyl)-2-oxo-2,3-dihydro-1H-indol-3-yl]-4-hydroxy-N,N-dimethyl-L-prolinamide (levorotatory isomer and dextrorotatory isomer)

From 2.00 g of the compound obtained in Step 241-1 and 1.40 g of (4R)-4-hydroxy-N,N-dimethyl-L-prolinamide hydrochloride, respectively 637 mg (Isomer A: yellow amorphous) and 789 mg (Isomer B: brown amorphous) of two species of diastereoisomers of the title compound were obtained by a similar method to Step 21-2.

Isomer A: $[\alpha]_D^{25}$=+286° (c=0.051, CHCl$_3$)

MS (ESI pos.) m/z: 418 ([M+H]$^+$), 440 ([M+Na]$^+$), (ESI neg.) m/z: 416 ([M−H]$^-$)

$^1$H-NMR (300 MHz, DMSO-d$_6$) δ (ppm); 1.61-1.93 (m, 2H), 2.46 (s, 3H), 2.58 (s, 3H), 3.11 (dd, J=9.2, 5.4 Hz, 1H), 3.21-3.31 (m, 1H), 3.70 (dd, J=8.9, 6.1 Hz, 1H), 4.19-4.30 (m, 1H), 4.68 (d, J=4.4 Hz, 1H), 6.61 (d, J=2.0 Hz, 1H), 6.86 (d, J=8.4 Hz, 1H), 7.02-7.13 (m, 1H), 7.24 (dd, J=8.2, 2.3 Hz, 1H), 7.31-7.42 (m, 2H), 8.05-8.23 (m, 1H), 10.82 (s, 1H)

Isomer B: $[\alpha]_D^{25}$=−256° (c=0.342, CHCl$_3$)

MS (ESI pos.) m/z: 418 ([M+H]$^+$), 440 ([M+Na]$^+$), (ESI neg.) m/z: 416 ([M−H]$^-$)

$^1$H-NMR (300 MHz, DMSO-d$_6$) δ (ppm); 1.64-2.00 (m, 2H), 2.38-2.60 (m, 7H), 3.20 (dd, J=9.0, 5.4 Hz, 1H), 4.32-4.44 (m, 1H), 4.73 (dd, J=8.9, 2.8 Hz, 1H), 4.89 (d, J=4.7 Hz, 1H), 6.82 (d, J=8.4 Hz, 1H), 6.97 (d, J=2.2 Hz, 1H), 7.06 (dd, J=11.3, 8.4 Hz, 1H), 7.17-7.28 (m, 2H), 7.29-7.41 (m, 1H), 7.91-8.08 (m, 1H), 10.70 (s, 1H)

Step 241-3: Synthesis of (4R)-1-(5-chloro-3-(2-fluorophenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 400 mg of the compound obtained in Step 241-2 (Isomer B) and 340 mg of 4-methoxy-2-(trifluoromethoxy) benzene sulfonyl chloride as starting materials, 271 mg of the title compound (yellow amorphous) was obtained by a similar method to Example 2.

$[\alpha]_D^{25}$=−229° (c=0.636, CHCl$_3$)

MS (ESI pos.) m/z: 672 ([M+H]$^+$), 694 ([M+Na]$^+$), (ESI neg.) m/z: 670 ([M−H]$^-$)

$^1$H-NMR (600 MHz, CDCl$_3$) δ (ppm); 1.95-2.08 (m, 3H), 2.44 (s, 3H), 2.64 (d, J=9.6 Hz, 1H), 2.72 (s, 3H), 3.55 (dd, J=10.3, 3.9 Hz, 1H), 3.91 (s, 3H), 4.51-4.78 (m, 2H), 6.73-6.96 (m, 3H), 7.03-7.41 (m, 4H), 7.86-8.04 (m, 2H), 8.35 (d, J=8.7 Hz, 1H)

Example 242

Synthesis of (4R)-1-{5-chloro-1-{[4-methoxy-2-(trifluoromethoxy)phenyl]sulfonyl}-2-oxo-3-[2-(trifluoromethoxy)phenyl]-2,3-dihydro-1H-indol-3-yl}-4-hydroxy-N,N-dimethyl-L-prolinamide (levorotatory isomer)

With 400 mg of the compound described in Preparation 3.35 of the brochure Publication No. WO01/055130 and 290 mg of 4-methoxy-2-(trifluoromethoxy)benzene sulfonyl chloride as starting materials, 304 mg of the title compound (brown amorphous) was obtained by a similar method to Example 2.

$[\alpha]_D^{25}$=159° (c=0.281, CHCl$_3$)

MS (ESI pos.) m/z: 738 ([M+H]$^+$), 760 ([M+Na]$^+$), (ESI neg.) m/z: 736 ([M−H]$^-$)

$^1$H-NMR (600 MHz, CDCl$_3$) δ (ppm); 1.49-1.70 (m, 3H), 1.83-1.91 (m, 1H), 2.20-2.48 (m, 4H), 2.71 (s, 3H), 3.21-3.31 (m, 1H), 3.89 (s, 3H), 4.58-4.73 (m, 2H), 6.84-6.91 (m, 1H), 6.94 (dd, J=9.2, 2.3 Hz, 1H), 7.00 (d, J=2.3 Hz, 1H), 7.11-7.17

(m, 1H), 7.22-7.45 (m, 3H), 7.91 (d, J=8.7 Hz, 1H), 8.09 (d, J=7.3 Hz, 1H), 8.35 (d, J=9.2 Hz, 1H)

Example 243

Synthesis of (4R)-1-(5-chloro-3-(2,5-dimethylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 243-1: Synthesis of 5-chloro-3-(2,5-dimethylphenyl)-3-hydroxy-1,3-dihydro-2H-indol-2-one With 8.00 g of 1-bromo-2,5-dimethyl benzene and 5.79 g of 5-chloroisatin as starting materials, 8.15 g of the title compound (colorless amorphous) was obtained by a similar method to Step 21-1.
MS (ESI neg.) m/z: 286 ([M−H]⁻)
¹H-NMR (200 MHz, DMSO-d₆) δ (ppm); 1.74 (s, 3H), 2.33 (s, 3H), 6.74 (s, 1H), 6.80 (d, J=2.2 Hz, 1H), 6.86-7.07 (m, 3H), 7.30 (dd, J=8.4, 2.2 Hz, 1H), 7.68 (s, 1H), 10.68 (s, 1H)

Step 243-2: Synthesis of (4R)-1-[5-chloro-3-(2,5-dimethylphenyl)-2-oxo-2,3-dihydro-1H-indol-3-yl]-4-hydroxy-N,N-dimethyl-L-prolinamide (levorotatory isomer and dextrorotatory isomer)

From 864 mg of the compound obtained in Step 243-1 and 585 mg of (4R)-4-hydroxy-N,N-dimethyl-L-prolinamide hydrochloride, respectively 481 mg (Isomer A: yellow amorphous) and 263 mg (Isomer B: orange color amorphous) of two species of diastereoisomers of the title compound were obtained by a similar method to Step 21-2.
Isomer A: $[\alpha]_D^{25}$=+277° (c=0.202, CHCl₃)
MS (ESI pos.) m/z: 428 ([M+H]⁺), 450 ([M+Na]⁺), (ESI neg.) m/z: 426 ([M−H]⁻)
¹H-NMR (300 MHz, DMSO-d₆) δ (ppm); 1.56-1.95 (m, 5H), 2.22-2.65 (m, 8H), 3.00-3.25 (m, 2H), 3.67 (dd, J=9.1, 5.8 Hz, 1H), 4.17-4.31 (m, 1H), 4.64 (d, J=2.8 Hz, 1H), 6.39-6.64 (m, 1H), 6.82-7.06 (m, 4H), 7.23 (dd, J=8.4, 2.2 Hz, 1H), 7.88-8.29 (m, 1H), 10.86 (s, 1H)
Isomer B: $[\alpha]_D^{25}$=−265° (c=0.272, CHCl₃)
MS (ESI pos.) m/z: 428 ([M+H]⁺), 450 ([M+Na]⁺), (ESI neg.) m/z: 426 ([M−H]⁻)
¹H-NMR (300 MHz, DMSO-d₆) δ (ppm); 1.40-2.99 (m, 15H), 4.18-5.06 (m, 3H), 6.71-7.09 (m, 5H), 7.25 (dd, J=8.1, 1.9 Hz, 1H), 7.80 (s, 1H), 10.13-11.43 (m, 1H)

Step 243-3: Synthesis of (4R)-1-(5-chloro-3-(2,5-dimethylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 215 mg of the compound obtained in Step 243-2 (Isomer B) and 190 mg of 4-methoxy-2-(trifluoromethoxy) benzene sulfonyl chloride as starting materials, 171 mg of the title compound (colorless amorphous) was obtained by a similar method to Example 2.
$[\alpha]_D^{25}$=−198° (c=0.391, CHCl₃)
MS (ESI pos.) m/z: 682 ([M+H]⁺), 704 ([M+Na]⁺), (ESI neg.) m/z: 680 ([M−H]⁻)
¹H-NMR (600 MHz, CDCl₃) δ (ppm); 1.32-4.12 (m, 20H), 4.60-4.78 (m, 2H), 6.78-7.13 (m, 5H), 7.29 (d, J=8.7 Hz, 1H), 7.68-8.04 (m, 2H), 8.25-8.49 (m, 1H)

Example 244

Synthesis of (4R)-1-(5-chloro-3-[2-methoxy-5-(1H-tetrazol-5-ylmethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

To a solution of 200 mg of the compound obtained in Example 236 in xylene (2 ml) was added 500 mg of tributyltin azide and the reaction mixture was stirred at 100° C. for one hour. A saturated aqueous solution of NH₄Cl was added, the resulting mixture was extracted with CHCl₃; the organic layer was washed with water and with saturated brine, then, the solution was dried over MgSO₄, the drying agent was separated by filtration, and then the solvent was evaporated under reduced pressure. The obtained residue was purified by column chromatography (silicagel 60N; mobile phase: CHCl₃/MeOH=20/1 to 10/1; v/v) to obtain 11 mg of the title compound.
$[\alpha]_D^{25}$=−204° (c=0.150, CHCl₃)
MS (ESI pos.) m/z: 766 ([M+H]⁺), 788 ([M+Na]⁺), (ESI neg.) m/z: 764 ([M−H]⁻)
¹H-NMR (600 MHz, CDCl₃) δ (ppm); 1.04-2.40 (m, 3H), 2.42-2.82 (m, 6H), 3.04-3.34 (m, 3H), 3.37-3.58 (m, 2H), 3.87 (s, 3H), 4.20-4.45 (m, 2H), 4.47-4.99 (m, 2H), 6.54-6.72 (m, 1H), 6.87 (s, 1H), 6.88-6.94 (m, 1H), 6.96-6.99 (m, 1H), 7.16 (dd, J=8.48, 2.06 Hz, 1H), 7.23 (dd, J=8.94, 2.06 Hz, 1H), 7.86 (d, J=8.71 Hz, 1H), 8.04-8.50 (m, 3H)

Example 245

Synthesis of (4R)-1-(5-chloro-3-(2-methoxy-3-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 245-1: Synthesis of 5-chloro-3-hydroxy-3-(2-methoxy-3-methylphenyl)-1,3-dihydro-2H-indol-2-one Under nitrogen atmosphere, to a solution of 11.9 g of 2-methoxy toluene 12.5 g and TMEDA in THF (65 ml) was added dropwise a solution of 2.60 mol/L n-butyl lithium n-hexane solution (39.4 ml) over 30 minutes under ice cooling and the reaction mixture was stirred at room temperature for one hour.
Under nitrogen atmosphere, to a solution of 6.00 g of NaH in THF (130 ml) was added 12.4 g of 5-chloroisatin and the reaction mixture was stirred for one hour. The solution prepared beforehand was added dropwise over 10 minutes at the same temperature. A saturated aqueous solution of NH₄Cl was added, the solution was extracted with EtOAc; the organic layer was washed with saturated brine and dried over Na₂SO₄, then, the drying agent was separated by filtration and the solvent was evaporated under reduced pressure. The obtained residue was purified by column chromatography (silicagel 60N; mobile phase: CHCl₃/MeOH=100/1 to 20/1; v/v), the obtained solid was further washed by stirring in EtOAc (30 ml), then, the solid was collected by filtration to obtain 2.45 g of the title compound.
MS (ESI pos.) m/z: 304 ([M+H]⁺), 326 ([M+Na]⁺), (ESI neg.) m/z: 302 ([M−H]⁻)
¹H-NMR (200 MHz, CDCl₃) δ (ppm); 2.15 (s, 3H), 3.09 (s, 3H), 6.64 (s, 1H), 6.79 (d, J=2.20 Hz, 1H), 6.88 (d, J=8.35 Hz, 1H), 7.05-7.20 (m, 2H), 7.24 (dd, J=8.35, 2.20 Hz, 1H), 7.68 (dd, J=7.25, 2.42 Hz, 1H), 10.47 (s, 1H)

Step 245-2: Synthesis of (4R)-1-[5-chloro-3-(2-methoxy-3-methylphenyl)-2-oxo-2,3-dihydro-1H-indol-3-yl]-4-hydroxy-N,N-dimethyl-L-prolinamide From 2.40 g of the compound obtained in Step 245-1 and 3.05 g of (4R)-4-hydroxy-N,N-dimethyl-L-prolinamide trifluoroacetate, 796 mg of the title compound was obtained by a similar procedure to Step 21-2.

$[\alpha]_D^{25}$=−160° (c=0.364, CHCl$_3$)

MS (ESI pos.) m/z: 444 ([M+H]$^+$), 466 ([M+Na]$^+$), (ESI neg.) m/z: 442 ([M−H]$^-$)

$^1$H-NMR (600 MHz, CDCl$_3$) δ (ppm); 1.66-1.78 (m, 1H), 1.91-2.08 (m, 2H), 2.19-2.23 (m, 3H), 2.42-2.59 (m, 3H), 2.74 (s, 3H), 2.93-3.15 (m, 2H), 3.23-3.30 (m, 3H), 4.64-4.71 (m, 1H), 4.84-5.04 (m, 1H), 6.73 (d, J=8.25 Hz, 1H), 6.98 (s, 1H), 7.01-7.12 (m, 3H), 7.76 (d, J=7.79 Hz, 1H), 9.33 (s, 1H)

Step 245-3: Synthesis of (4R)-1-(5-chloro-3-(2-methoxy-3-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 786 mg of the compound obtained in Step 245-2 and 587 mg of 4-methoxy-2-(trifluoromethoxy)benzene sulfonyl chloride as starting materials, 720 mg of the title compound (amorphous) was obtained by a similar procedure to Example 2.

$[\alpha]_D^{25}$=152° (c=0.685, CHCl$_3$)

MS (ESI pos.) m/z: 698 ([M+H]$^+$), 720 ([M+Na]$^+$), (ESI neg.) m/z: 696 ([M−H]$^-$)

$^1$H-NMR (600 MHz, CDCl$_3$) δ (ppm); 1.09-1.47 (m, 2H), 1.73-1.97 (m, 2H), 2.11-2.18 (m, 3H), 2.21-2.31 (m, 3H), 2.64-2.77 (m, 3H), 2.95-3.38 (m, 4H), 3.78-3.87 (m, 3H), 4.52-4.63 (m, 1H), 4.64-4.80 (m, 1H), 6.81 (s, 1H), 6.88 (dd, J=8.71, 2.29 Hz, 1H), 6.91-6.98 (m, 1H), 6.99-7.09 (m, 2H), 7.16-7.24 (m, 1H), 7.52-7.65 (m, 1H), 7.87 (d, J=8.71 Hz, 1H), 8.31 (d, J=9.17 Hz, 1H

Example 246

Synthesis of (4R)-1-(5-chloro-3-(4-methoxybiphenyl-3-yl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 246-1: Synthesis of 5-chloro-3-hydroxy-3-(4-methoxybiphenyl-3-yl)-1,3-dihydro-2H-indol-2-one With 18.4 g of 4-methoxybiphenyl and 15.1 g of 5-chloroisatin as starting materials, 15.2 g of the title compound (yellow solid) was obtained by a similar method to Step 245-1.

MS (ESI pos.) m/z: 388 ([M+Na]$^+$)

$^1$H-NMR (600 MHz, DMSO-d$_6$) δ (ppm); 3.45 (s, 3H), 6.70 (s, 1H), 6.82 (d, J=6.4 Hz, 1H), 6.83 (s, 1H), 6.96 (d, J=8.3 Hz, 1H), 7.19 (dd, J=8.3, 2.3 Hz, 1H), 7.31 (t, J=7.3 Hz, 1H), 7.45 (t, J=7.8 Hz, 2H), 7.56 (dd, J=8.5, 2.5 Hz, 1H), 7.66 (d, J=6.9 Hz, 2H), 8.07 (d, J=2.3 Hz, 1H), 10.44 (s, 1H)

Step 246-2: Synthesis of (4R)-1-[5-chloro-3-(4-methoxybiphenyl-3-yl)-2-oxo-2,3-dihydro-1H-indol-3-yl]-4-hydroxy-N,N-dimethyl-L-prolinamide (levorotatory isomer and dextrorotatory isomer)

From 2.93 g of the compound obtained in Step 246-1 and (4R)-4-hydroxy-N,N-dimethyl-L-prolinamide trifluoroacetate (8.00 mmol), respectively 0.84 g (Isomer A, pale yellow solid) and 1.73 g (Isomer B, pale yellow solid) of two species of diastereoisomers of the title compound were obtained by a similar procedure to Step 21-2.

Isomer A: $[\alpha]_D^{25}$=+262° (c=0.34, CHCl$_3$)

MS (ESI pos.) m/z: 528 ([M+Na]$^+$)

$^1$H-NMR (600 MHz, CDCl$_3$) δ (ppm); 1.87-1.95 (m, 1H), 2.13 (dd, J=13.3, 6.0 Hz, 1H), 2.69 (s, 3H), 2.87 (s, 3H), 3.58-3.71 (m, 5H), 3.81 (d, J=12.8 Hz, 1H), 4.04 (dd, J=11.0, 6.9 Hz, 1H), 4.39 (s, 1H), 6.83 (d, J=8.3 Hz, 1H), 6.88 (s, 1H), 6.90 (d, J=8.3 Hz, 1H), 7.13 (dd, J=8.5, 2.1 Hz, 1H), 7.34 (t, J=7.3 Hz, 1H), 7.46 (t, J=7.8 Hz, 2H), 7.52 (dd, J=8.3, 2.3 Hz, 1H), 7.65 (d, J=6.9 Hz, 2H), 8.29 (s, 1H), 9.89 (s, 1H)

Isomer B: $[\alpha]_D^{25}$=−277° (c=0.24, CHCl$_3$)

MS (ESI pos.) m/z: 528 ([M+Na]$^+$)

$^1$H-NMR (600 MHz, CDCl$_3$) δ (ppm); 1.73-3.61 (m, 11H), 3.63 (s, 3H), 4.63-5.10 (m, 2H), 6.73 (d, J=8.3 Hz, 1H), 6.88 (d, J=8.7 Hz, 1H), 7.07 (dd, J=8.3, 1.8 Hz, 2H), 7.29 (t, J=7.3 Hz, 1H), 7.43 (t, 2H), 7.54 (dd, J=8.5, 2.5 Hz, 1H), 7.69 (d, J=6.9 Hz, 2H), 8.20 (s, 1H), 9.44 (s, 1H)

Step 246-3: Synthesis of (4R)-1-(5-chloro-3-(4-methoxybiphenyl-3-yl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 304 mg of the compound obtained in Step 246-2 (Isomer B) and 210 mg of 4-methoxy-2-(trifluoromethoxy) benzene sulfonyl chloride as starting materials, 260 mg of the title compound (pale yellow amorphous) were obtained by a similar method to Example 2.

$[\alpha]_D^{25}$=−203° (c=0.25, CHCl$_3$)

MS (ESI pos.) m/z: 782 ([M+Na]$^+$)

$^1$H-NMR (600 MHz, CDCl$_3$) δ (ppm); 1.25-3.77 (m, 14H), 3.87 (s, 3H), 4.59-4.85 (m, 2H), 6.84 (d, J=8.3 Hz, 1H), 6.87 (s, 1H), 6.93 (dd, J=9.2, 2.3 Hz, 1H), 7.17 (s, 1H), 7.22-7.31 (m, 2H), 7.41 (t, J=7.8 Hz, 2H), 7.54 (d, J=7.8 Hz, 1H), 7.65 (d, J=7.3 Hz, 2H), 7.89 (d, J=8.7 Hz, 1H), 8.06 (s, 1H), 8.32 (s, 1H)

Example 247

Synthesis of (4R)-1-(5-chloro-3-(5-fluoro-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 247-1: Synthesis of 5-chloro-3-(5-fluoro-2-methoxyphenyl)-3-hydroxy-1,3-dihydro-2H-indol-2-one With 16.9 g of 2-bromo-4-fluoroanisol and 10.0 g of 5-chloroisatin as starting materials, 15.7 g of the title compound (yellow solid) was obtained by a similar method to Step 21-1.

MS (ESI pos.) m/z: 330 ([M+Na]$^+$)
$^1$H-NMR (600 MHz, DMSO-d$_6$) δ (ppm); 3.38 (s, 3H), 6.76 (s, 1H), 6.79 (d, J=2.3 Hz, 1H), 6.81 (d, J=8.3 Hz, 1H), 6.88 (dd, J=8.9, 4.4 Hz, 1H), 7.06-7.12 (m, 1H), 7.19 (dd, J=8.3, 1.8 Hz, 1H), 7.53 (dd, J=10.1, 3.2 Hz, 1H), 10.46 (s, 1H)

Step 247-2: Synthesis of (4R)-1-[5-chloro-3-(5-fluoro-2-methoxyphenyl)-2-oxo-2,3-dihydro-1H-indol-3-yl]-4-hydroxy-N,N-dimethyl-L-prolinamide (levorotatory isomer and dextrorotatory isomer)

From 2.00 g of the compound obtained in Step 247-1 and (4R)-4-hydroxy-N,N-dimethyl-L-prolinamide trifluoroacetate (4.00 mmol), respectively 295 mg (Isomer A, white solid) and 702 mg (Isomer B, white solid) of two species of diastereoisomers of the title compound were obtained by a similar procedure to Step 21-2.

Isomer A: [α]$_D^{25}$=+165° (c=0.23, CHCl$_3$)
MS (ESI pos.) m/z: 470 ([M+Na]$^+$)
$^1$H-NMR (600 MHz, DMSO-d$_6$) δ (ppm); 1.57-1.63 (m, 1H), 1.75-1.83 (m, 1H), 2.45-2.48 (m, 3H), 2.57 (s, 3H), 3.03 (dd, J=9.6, 5.0 Hz, 1H), 3.15 (dd, J=9.9, 5.7 Hz, 1H), 3.42 (s, 3H), 3.60 (dd, J=9.2, 5.5 Hz, 1H), 4.17-4.23 (m, 1H), 4.64 (d, J=4.6 Hz, 1H), 6.45 (d, J=2.3 Hz, 1H), 6.78 (d, J=8.3 Hz, 1H), 6.91 (dd, J=9.2, 4.6 Hz, 1H), 7.06-7.11 (m, 1H), 7.17 (dd, J=8.3, 2.3 Hz, 1H), 7.87 (dd, J=9.6, 3.2 Hz, 1H), 10.57 (s, 1H)

Isomer B: [α]$_D^{25}$=-208° (c=0.20, CHCl$_3$)
MS (ESI pos.) m/z: 470 ([M+Na]$^+$)
$^1$H-NMR (600 MHz, DMSO-d$_6$) d ppm 1.59-3.50 (m, 10H), 4.32 (s, 1H), 4.68 (s, 1H), 4.88 (s, 1H), 6.73 (d, J=8.3 Hz, 1H), 6.83 (d, J=2.3 Hz, 1H), 6.89 (dd, J=8.7, 4.6 Hz, 1H), 7.02-7.07 (m, 1H), 7.14 (dd, J=8.3, 1.8 Hz, 1H), 7.73 (s, 1H), 10.46 (s, 1H)

Step 247-3: Synthesis of (4R)-1-(5-chloro-3-(5-fluoro-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 300 mg of the compound obtained in Step 247-2 (Isomer B) and 235 mg of 4-methoxy-2-(trifluoromethoxy) benzene sulfonyl chloride as starting materials, 497 mg of the title compound (pale yellow amorphous) was obtained by a similar method to Example 2.

[α]$_D^{25}$=-240° (c=0.27, CHCl$_3$)
MS (ESI pos.) m/z: 724 ([M+Na]$^+$)
$^1$H-NMR (600 MHz, CDCl$_3$) δ (ppm); 1.64-3.63 (m, 14H), 3.82 (s, 3H), 4.38-4.85 (m, 2H), 6.63 (dd, J=8.5, 3.9 Hz, 1H), 6.82 (s, 1H), 6.84-6.90 (m, 2H), 7.00 (s, 1H), 7.19 (dd, J=9.2, 2.3 Hz, 1H), 7.52 (s, 1H), 7.82 (d, J=8.7 Hz, 1H), 8.26 (d, J=5.0 Hz, 1H)

Example 248

Synthesis of (4R)-1-(5-chloro-3-(5-chloro-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 248-1: Synthesis of 5-chloro-3-(5-chloro-2-methoxyphenyl)-3-hydroxy-1,3-dihydro-2H-indol-2-one With 14.6 g of 2-bromo-4-chloro anisole and 8.00 g of 5-chloroisatin as starting materials, 13.3 g of the title compound (yellow solid) was obtained by a similar method to Step 21-1.

MS (ESI pos.) m/z: 346 ([M+Na]$^+$)
$^1$H-NMR (600 MHz, DMSO-d$_6$) δ (ppm); 3.40 (s, 3H), 6.78 (s, 1H), 6.80 (d, J=2.3 Hz, 1H), 6.81 (d, J=8.3 Hz, 1H), 6.90 (d, J=8.7 Hz, 1H), 7.20 (dd, J=8.5, 2.1 Hz, 1H), 7.32 (dd, J=8.7, 2.8 Hz, 1H), 7.74 (d, J=2.8 Hz, 1H), 10.47 (s, 1H)

Step 248-2: Synthesis of (4R)-1-[5-chloro-3-(5-chloro-2-methoxyphenyl)-2-oxo-2,3-dihydro-1H-indol-3-yl]-4-hydroxy-N,N-dimethyl-L-prolinamide (levorotatory isomer and dextrorotatory isomer)

From 2.00 g of the compound obtained in Step 248-1 and (4R)-4-hydroxy-N,N-dimethyl-L-prolinamide trifluoroacetate (3.80 mmol), respectively, 327 mg (Isomer A, pale yellow solid) and 814 mg (Isomer B, pale yellow solid) of two species of diastereoisomers of the title compound were obtained by a similar procedure to Step 21-2.

Isomer A: [α]$_D^{25}$=+206° (c=0.36, CHCl$_3$)
MS (ESI pos.) m/z: 486 ([M+Na]$^+$)
$^1$H-NMR (600 MHz, CDCl$_3$) δ (ppm); 1.82-1.88 (m, 1H), 2.08 (dd, J=13.1, 5.7 Hz, 1H), 2.69 (s, 3H), 2.79 (s, 3H), 3.35 (s, 1H), 3.55 (dd, J=12.4, 3.7 Hz, 1H), 3.58 (s, 3H), 3.68-3.73 (m, 1H), 3.96 (dd, J=11.0, 6.4 Hz, 1H), 4.36 (s, 1H), 6.74 (d, J=8.7 Hz, 1H), 6.80 (d, J=8.3 Hz, 1H), 6.85 (s, 1H), 7.14 (dd, J=8.3, 2.3 Hz, 1H), 7.23 (dd, J=8.7, 2.8 Hz, 1H), 8.02 (s, 1H), 9.39 (s, 1H)

Isomer B: [α]$_D^{25}$=-221° (c=0.24, CHCl$_3$)
MS (ESI pos.) m/z: 486 ([M+Na]$^+$)
$^1$H-NMR (600 MHz, CDCl$_3$) δ (ppm); 1.64-3.64 (m, 11H), 3.56 (s, 3H), 4.59-4.98 (m, 2H), 6.70 (d, J=8.7 Hz, 1H), 6.72 (d, J=8.3 Hz, 1H), 6.95 (s, 1H), 7.08 (dd, J=8.3, 1.8 Hz, 1H), 7.18 (dd, J=8.7, 2.8 Hz, 1H), 7.91 (s, 1H), 9.24 (s, 1H)

Step 248-3: Synthesis of (4R)-1-(5-chloro-3-(5-chloro-2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 300 mg of the compound obtained in Step 248-2 (Isomer B) and 235 mg of 4-methoxy-2-(trifluoromethoxy) benzene sulfonyl chloride as starting materials, 497 mg of the title compound (pale yellow amorphous) was obtained by a similar method to Example 2.

[α]$_D^{25}$=-150° (c=0.26, CHCl$_3$)
MS (ESI pos.) m/z: 740 ([M+Na]$^+$)
$^1$H-NMR (600 MHz, CDCl$_3$) δ (ppm); 1.26-3.71 (m, 14H), 3.81-3.89 (m, 3H), 4.52-4.77 (m, 2H), 6.66 (d, J=8.3 Hz, 1H), 6.86 (s, 1H), 6.91 (dd, J=9.2, 2.3 Hz, 1H), 7.06 (s, 1H), 7.17 (dd, J=8.7, 2.8 Hz, 1H), 7.23 (dd, J=8.9, 2.1 Hz, 1H), 7.75-7.78 (m, 1H), 7.85 (d, J=8.7 Hz, 1H), 8.28 (s, 1H)

Example 249

Synthesis of (4R)-1-(5-chloro-3-{5-[hydroxy(phenyl)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide To a solution of 132 mg of the compound obtained in Step 185-1 in THF (1.8 ml), under a temperature condition of -78° C., was added dropwise a solution of 1.0 mol/L phenyl magnesium bromide in THF (0.46 ml) over 15 minutes and the reaction mixture was stirred under the same temperature condition for two hours. The solution was further stirred for one hour on ice, a saturated aqueous solution of NH$_4$Cl and CHCl₃ were added and liquid separation was performed. The organic layer was washed with water and with saturated brine, dried over MgSO₄, then, the drying agent was separated by filtration and the solvent was evaporated under reduced pressure. The obtained residue was purified by column chromatography (silicagel 60; mobile phase: MeOH/CHCl₃=2/98; v/v) to obtain 62.4 mg of the title compound (colorless amorphous).

MS (ESI pos.) m/z: 790 ([M+H]⁺), 812 ([M+Na]⁺), (ESI neg.) m/z: 788 ([M−H]⁻)

¹H-NMR (600 MHz, CDCl₃) δ (ppm); 1.13-4.90 (m, 20H) 5.79 (s, 1H) 6.54-6.66 (m, 1H) 6.78-6.84 (m, 1H) 6.84-6.91 (m, 1H) 6.94-7.05 (m, 2H) 7.13-7.23 (m, 2H) 7.23-7.37 (m, 4H) 7.80 (d, J=8.71 Hz, 1H) 7.85-8.06 (m, 1H) 8.18-8.37 (m, 1H)

Example 250

Synthesis of (4R)-1-(3-(5-benzyl-2-methoxyphenyl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

A solution of 5 mg of NaBH₄ in TFA (1 ml) was stirred for 15 minutes at room temperature, then, a solution of 28.1 mg of the compound obtained in Example 249 in TFA (3 ml) was added dropwise over 10 minutes. Two hours later, the solution was diluted with water, neutralized with NaOH, and the resulting mixture was extracted with CHCl₃. The organic layer was washed with water and with saturated brine and dried over MgSO₄, then, the drying agent was separated by filtration and the solvent was evaporated under reduced pressure. The obtained residue was purified by column chromatography (silicagel 60; mobile phase: MeOH/CHCl₃=2/98; v/v) to obtain 25.3 mg of the title compound (colorless amorphous).

[α]$_D^{30}$=−81.9° (c=0.052, CHCl₃)

MS (ESI pos.) m/z: 774 ([M+H]⁺), 796 ([M+Na]⁺), (ESI neg.) m/z: 772 ([M−H]⁻)

¹H-NMR (600 MHz, CDCl₃) δ (ppm); 1.47-1.66 (m, 1H) 1.69-1.76 (m, 1H) 2.38-2.45 (m, 3H) 2.45-2.75 (m, 3H) 3.01-3.95 (m, 11H) 4.36-4.86 (m, 2H) 6.62 (d, J=8.25 Hz, 1H) 6.78-7.31 (m, 10H) 7.64-7.77 (m, 1H) 7.81 (d, J=8.71 Hz, 1H) 8.25-8.42 (m, 1H)

Example 251

Synthesis of (4R)-1-(5-chloro-3-(2-methoxy-4-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 251-1: Synthesis of 5-chloro-3-hydroxy-3-(2-methoxy-4-methylphenyl)-1,3-dihydro-2H-indol-2-one With 22.3 g of 3-methoxy toluene and 33.1 g of 5-chloroisatin as starting materials, 6.98 g of the title compound (colorless solid) was obtained by a similar method to Step 239-1.

MS (ESI pos.) m/z: 304 ([M+H]⁺), (ESI neg.) m/z: 302 ([M−H]⁻)

¹H-NMR (600 MHz, DMSO-d₆) δ (ppm); 3.29 (s, 3H) 3.37 (s, 3H) 6.51 (s, 1H) 6.66-6.69 (m, 2H) 6.79 (d, J=8.25 Hz, 1H) 6.82 (d, J=7.79 Hz, 1H) 7.16 (dd, J=8.25, 2.29 Hz, 1H) 7.63 (d, J=7.79 Hz, 1H) 10.35 (s, 1H)

Step 251-2: Synthesis of (4R)-1-[5-chloro-3-(2-methoxy-4-methylphenyl)-2-oxo-2,3-dihydro-1H-indol-3-yl]-4-hydroxy-N,N-dimethyl-L-prolinamide From 2.0 g of the compound obtained in Step 251-1 and 1.41 g of (4R)-4-hydroxy-N,N-dimethyl-L-prolinamide hydrochloride, respectively 1.03 g (Isomer A: colorless amorphous) and 1.24 g (Isomer B: colorless amorphous) of two species of diastereoisomers of the title compound were obtained by a similar method to Step 28-2.

Isomer A; MS (ESI pos.) m/z: 444 ([M+H]⁺), 466 ([M+Na]⁺), (ESI neg.) m/z: 442 ([M−H]⁻)

¹H-NMR (600 MHz, CDCl₃) δ (ppm); 1.79-1.89 (m, 1H) 2.06-2.14 (m, 1H) 2.33 (s, 3H) 2.65 (s, 3H) 2.69 (s, 3H) 3.05-3.14 (m, 1H) 3.53-3.62 (m, 1H) 3.58 (s, 3H) 3.68 (dd, J=13.07, 2.06 Hz, 1H) 3.92 (dd, J=10.78, 6.65 Hz, 1H) 4.29-4.38 (m, 1H) 6.62 (s, 1H) 6.77 (d, J=8.25 Hz, 1H) 6.88-6.97 (m, 2H) 7.12 (dd, J=8.25, 2.29 Hz, 1H) 7.99 (d, J=7.34 Hz, 2H)

Isomer B; MS (ESI pos.) m/z: 444 ([M+H]⁺), 466 ([M+Na]⁺), (ESI neg.) m/z: 442 ([M−H]⁻)

¹H-NMR (600 MHz, CDCl₃) δ (ppm); 1.92-1.99 (m, 1H) 2.00-2.10 (m, 1H) 2.31 (s, 3H) 2.52 (s, 3H) 2.59-2.69 (m, 1H) 2.73 (s, 3H) 3.30-3.51 (m, 1H) 3.60 (s, 3H) 4.60-4.69 (m, 1H) 4.82-5.00 (m, 1H) 6.62 (s, 1H) 6.65-6.69 (m, 1H) 6.80 (d, J=7.79 Hz, 1H) 6.97-7.02 (m, 1H) 7.03-7.09 (m, 1H) 7.65-7.77 (m, 1H) 8.49-9.07 (m, 1H)

Step 251-3: Synthesis of (4R)-1-(5-chloro-3-(2-methoxy-4-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 443 mg of the compound obtained in Step 251-2 (Isomer B) and 305 mg of 4-methoxy-2-(trifluoromethoxy) benzene sulfonyl chloride as starting materials, 113 mg of the title compound (colorless amorphous) was obtained by a similar method to Example 2.

[α]$_D^{30}$=−147° (c=0.092, CHCl₃)

MS (ESI pos.) m/z: 698 ([M+H]⁺), 720 ([M+Na]⁺), (ESI neg.) m/z: 696 ([M−H]⁻)

¹H-NMR (600 MHz, CDCl₃) δ (ppm); 1.55-1.64 (m, 1H) 1.55-3.89 (m, 1H) 1.76-1.82 (m, 1H) 2.25 (s, 3H) 2.31 (s, 3H) 2.63-2.75 (m, 3H) 3.05-3.29 (m, 1H) 3.45-3.62 (m, 3H) 3.84 (s, 3H) 4.48-4.62 (m, 1H) 4.62-4.86 (m, 1H) 6.52 (s, 1H) 6.72 (d, J=7.79 Hz, 1H) 6.82-6.84 (m, 1H) 6.89 (dd, J=9.17, 2.29 Hz, 1H) 7.01-7.09 (m, 1H) 7.18 (dd, J=8.71, 2.29 Hz, 1H) 7.54-7.67 (m, 1H) 7.83 (d, J=8.71 Hz, 1H) 8.23-8.38 (m, 1H)

Example 252

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-methoxy-N,N-dimethyl-L-prolinamide (levorotatory isomer)

To a solution of 698 mg of the compound obtained in Step 103-3 in-methylene chloride (4 ml) was added a 48% aqueous solution of fluoroboric acid (260 ul), followed by the addition of a solution of trimethylsilyl diazo methane in 2 mol/L Et₂O (2 ml) under ice cooling. Thereafter, the solution was stirred at room temperature for one hour, water and Et₃N were added, the resulting mixture was extracted with CHCl₃ and the solvent was evaporated under reduced pressure. The obtained residue was purified by column chromatography (silicagel 60; mobile phase: MeOH/CHCl₃=1/20; v/v) to obtain 430 mg of the title compound (amorphous).

[α]$_D^{25}$=−150° (c=0.200, CHCl₃)

MS (ESI pos.) m/z: 712 ([M+H]⁺), 734 ([M+Na]⁺)

¹H-NMR (600 MHz, CDCl₃) δ (ppm); 1.14-3.40 (m, 17H), 3.60 (s, 2H), 3.85 (s, 3H), 4.23 (s, 1H), 4.71 (s, 1H), 6.63 (d, J=7.3 Hz, 1H), 6.83 (s, 1H), 6.89 (dd, J=8.9, 2.5 Hz, 1H), 6.99 (dd, J=8.5, 2.1 Hz, 1H), 7.10 (s, 1H), 7.20 (d, J=6.9 Hz, 1H), 7.54 (s, 1H), 7.84 (d, J=9.2 Hz, 1H), 8.27 (s, 1H)

Example 253

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(pyridin-2-ylmethyl)amino]-N,N-dimethylpropanamide (levorotatory isomer)

Step 253-1: Synthesis of [(1S)-2-(dimethylamino)-1-methyl-2-oxo ethyl](pyridin-2-ylmethyl) carbamic acid Under nitrogen atmosphere, to a solution of 2.00 g of benzyl[(1S)-2-(dimethylamino)-1-methyl-2-oxo ethyl]carbamate in DMF was added 0.33 g of NaH under ice cooling and the reaction mixture was stirred at room temperature for 10 minutes. Therein, a solution of 3.25 g of 2-(bromo methyl) pyridine in DMF (15 ml) was added, and the solution was stirred at room temperature for 3 hours. A saturated aqueous solution of NaHCO₃ was added to the reaction solution, and the resulting mixture was extracted with EtOAc. The combined organic layer was washed with water and with saturated brine and dried over MgSO₄, then, the drying agent was separated by filtration and the solvent was evaporated under reduced pressure. The obtained residue was purified by column chromatography (silicagel 60N, moving bed: CHCl₃/EtOAc=1/1; v/v) to obtain 1.04 g of the title compound (colorless oil).

MS (ESI pos.) m/z: 364 ([M+Na]⁺)

¹H-NMR (300 MHz, CDCl₃) δ (ppm); 1.33 (d, J=6.8 Hz, 3H), 2.68 & 2.82 (each-s, 3H), 2.79 & 3.08 (each-s, 3H), 4.59-4.75 (m, 2H), 5.01-5.40 (m, 3H), 7.03-7.65 (m, 8H), 8.45-8.57 (m, 1H)

Step 253-2: Synthesis of (2S)—N,N-dimethyl-2-[(pyridin-2-ylmethyl)amino]propanamide With 0.97 g of the compound obtained in Step 253-1 as starting material, 0.60 g of the title compound (crude form) was obtained by a similar procedure to Step 11-4.

MS (ESI pos.) m/z: 208 ([M+H]⁺)

¹H-NMR (300 MHz, CDCl₃) δ (ppm); 1.26 (d, J=6.8 Hz, 3H), 2.50 (br.s, 1H), 2.98 (s, 3H), 3.01 (s, 3H), 3.63-3.76 (m, 2H), 3.88-3.95 (m, 1H), 7.11-7.18 (m, 1H), 7.38 (d, J=7.8 Hz, 1H), 7.60-7.70 (m, 1H), 8.50-8.59 (m, 1H)

Step 253-3: Synthesis of (2S)-2-{[5-chloro-3-(2-methoxyphenyl)-2-oxo-2,3-dihydro-1H-indol-3-yl](pyridin-2-ylmethyl)amino}-N,N-dimethylpropanamide (levorotatory isomer and dextrorotatory isomer)

With 789 mg of 3,5-dichloro-3-(2-methoxyphenyl)-1,3-dihydro-2H-indol-2-one and the compound obtained in Step 253-2 (2.56 mmol, crude form) as starting materials, respectively 821 mg (Isomer A, colorless amorphous) and 406 mg (Isomer B, colorless amorphous) of two species of diastereoisomers of the title compound were obtained by a similar method to Step 4-2.

Isomer A: [α]$_D^{25}$=−106° (c=0.200, CHCl₃)

MS (ESI pos.) m/z: 479 ([M+H]⁺)

¹H-NMR (300 MHz, CDCl₃) δ (ppm); 1.37 (d, J=6.8 Hz, 3H), 2.62 (s, 3H), 3.01 (s, 3H), 3.56 (s, 3H), 3.76-3.95 (m, 1H), 4.61-4.71 (m, 2H), 5.93 (m, 1H), 6.66 (d, J=8.2 Hz, 1H), 6.77-6.91 (m, 2H), 6.93-7.11 (m, 2H), 7.19-7.35 (m, 1H), 7.57-7.71 (m, 1H), 7.91 (dd, J=7.8, 1.7 Hz, 1H), 7.98-8.06 (m, 1H), 8.24-8.36 (m, 1H), 8.39-8.55 (m, 1H)

Isomer B: [α]$_D^{25}$=+156° (c=0.187, CHCl₃)

MS (ESI pos.) m/z: 479 ([M+H]⁺)

¹H-NMR (300 MHz, CDCl₃) δ (ppm); 1.52-1.62 (m, 3H), 2.86 (m, 6H), 3.50 (s, 3H), 3.95-4.11 (m, 1H), 4.34 (m, 1H), 4.87-5.06 (m, 1H), 5.76 (m, 1H), 6.76-6.83 (m, 2H), 6.95 (dd, J=8.2, 2.2 Hz, 1H), 7.01-7.09 (m, 1H), 7.09-7.20 (m, 1H), 7.24-7.33 (m, 2H), 7.52-7.66 (m, 1H), 8.24-8.34 (m, 2H), 8.39 (dd, J=4.5, 1.2 Hz, 1H)

Step 253-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)(pyridin-2-ylmethyl)amino]-N,N-dimethylpropanamide (levorotatory isomer)

With 507 mg of the compound obtained in Step 253-3 (Isomer A) and 191 mg of 4-methoxy-2-(trifluoromethoxy) benzene sulfonyl chloride as starting materials, 455 mg of the title compound (pink amorphous) was obtained by a similar procedure to Example 2.

[α]$_D^{26}$=−124° (c=0.205, CHCl₃)

MS (ESI pos.) m/z: 733 ([M+Na]⁺)

¹H-NMR (300 MHz, CDCl₃) δ (ppm); 1.16 (d, J=6.8 Hz, 3H), 2.55 (s, 3H), 2.96 (s, 3H), 3.25 (s, 3H), 3.85-3.96 (m, 4H), 4.44-4.60 (m, 2H), 5.98-6.05 (m, 1H), 6.71 (dd, J=8.3, 1.0 Hz, 1H), 6.91-7.07 (m, 5H), 7.20-7.29 (m, 1H), 7.53-7.61 (m, 1H), 7.77 (d, J=8.7 Hz, 1H), 7.82-7.88 (m, 1H), 7.98-8.05 (m, 1H), 8.07-8.15 (m, 1H), 8.38 (d, J=9.2 Hz, 1H)

Example 254

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N-methoxy-N-methyl propanamide (levorotatory isomer)

Step 254-1: Synthesis of tert-butyl{(1S)-2-[methoxy(methyl)amino]-1-methyl-2-oxo ethyl}carbamate With 2.00 g of N-(tert-butoxy carbonyl)-L-alanine and 1.55 g of N,O-dimethyl hydroxylamine hydrochloride as starting materials, 1.29 g of the title compound (colorless solid) was obtained by a similar procedure to Step 10-1.

MS (ESI pos.) m/z: 255 ([M+Na]⁺)

¹H-NMR (300 MHz, CDCl₃) δ (ppm); 1.31 (d, J=7.0 Hz, 3H), 1.44 (s, 9H), 3.21 (s, 3H), 3.77 (s, 3H), 4.61-4.74 (m, 1H), 5.16-5.31 (m, 1H)

Step 254-2: Synthesis of (2S)-2-amino-N-methoxy-N-methyl propanamide trifluoroacetate With 1.00 g of the compound obtained in Step 254-1 as starting material, 2.09 g of the title compound (crude form) was obtained by a similar procedure to Step 4-2.

MS (ESI pos.) m/z: 133 ([M+H]$^+$)
$^1$H-NMR (300 MHz, CDCl$_3$) δ (ppm); 1.34 (d, J=7.0 Hz, 3H), 3.18 (s, 3H), 3.74 (s, 3H), 4.14-4.28 (m, 1H), 8.14 (brs, 3H)

Step 254-3: Synthesis of (2S)-2-{[5-chloro-3-(2-methoxyphenyl)-2-oxo-2,3-dihydro-1H-indol-3-yl]amino}-N-methoxy-N-methyl propanamide (levorotatory isomer and dextrorotatory isomer)

With 1.21 g of 3,5-dichloro-3-(2-methoxyphenyl)-1,3-dihydro-2H-indol-2-one and the compound obtained in Step 254-2 (4.31 mmol, crude form) as starting materials, respectively 946 mg (Isomer A, colorless amorphous) and 686 mg (Isomer B, colorless amorphous) of two species of diastereoisomers of the title compound were obtained by a similar method to Step 4-2.

Isomer A: [α]$_D^{26}$=+85.0° (c=0.202, CHCl$_3$)
MS (ESI pos.) m/z: 404 ([M+H]$^+$)
$^1$H-NMR (300 MHz, CDCl$_3$) δ (ppm); 1.35 (d, J=7.0 Hz, 3H), 2.78-2.87 (m, 1H), 3.54 (s, 3H), 3.67 (s, 3H), 3.67 (s, 3H), 4.01-4.18 (m, 1H), 6.69-6.76 (m, 1H), 6.81 (dd, J=8.2, 0.9 Hz, 1H), 6.91 (d, J=2.2 Hz, 1H), 7.06-7.18 (m, 2H), 7.27-7.38 (m, 1H), 7.44-7.53 (m, 1H), 8.02 (dd, J=7.8, 1.7 Hz, 1H)

Isomer B: [α]$_D^{26}$=−112° (c=0.211, CHCl$_3$)
MS (ESI pos.) m/z: 404 ([M+H]$^+$)
$^1$H-NMR (300 MHz, CDCl$_3$) δ (ppm); 1.22 (d, J=6.8 Hz, 3H), 3.09 (s, 3H), 3.13-3.22 (m, 1H), 3.43 (s, 3H), 3.52 (s, 3H), 3.63-3.72 (m, 1H), 6.76-6.82 (m, 2H), 6.94 (d, J=2.3 Hz, 1H), 7.01-7.10 (m, 1H), 7.15 (dd, J=8.2, 2.2 Hz, 1H), 7.23-7.33 (m, 1H), 8.00 (dd, J=7.8, 1.7 Hz, 1H), 8.24-8.31 (m, 1H)

Step 254-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N-methoxy-N-methyl propanamide (levorotatory isomer)

With 305 mg of the compound obtained in Step 254-3 (Isomer B) and 225 mg of 4-methoxy-2-(trifluoromethoxy)benzene sulfonyl chloride as starting materials, 317 mg of the title compound (pale yellow amorphous) was obtained by a similar procedure to Example 1.

[α]$_D^{25}$=−135° (c=0.211, CHCl$_3$)
MS (ESI pos.) m/z: 680 ([M+Na]$^+$)
$^1$H-NMR (300 MHz, CDCl$_3$) δ (ppm); 0.94 (d, J=6.8 Hz, 3H), 3.13 (s, 3H), 3.35 (s, 6H), 3.62-3.75 (m, 1H), 3.88 (s, 3H), 6.67-6.74 (m, 1H), 6.84-6.95 (m, 3H), 6.97-7.06 (m, 1H), 7.20-7.33 (m, 2H), 7.83 (dd, J=7.8, 1.7 Hz, 1H), 7.91 (d, J=8.9 Hz, 1H), 8.35 (d, J=8.9 Hz, 1H)

Example 255

Synthesis of 2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N,2-trimethyl propanamide

Step 255-1: Synthesis of N-(tert-butoxy carbonyl)-2-methyl alanine 3.00 g of 2-methyl alanine was dissolved in 2 mol/L NaOH aqueous solution (30 ml), and THF (10 ml) and (Boc)$_2$O (25 ml) were added sequentially and the reaction mixture was stirred at room temperature for 15 hours. EtOAc was added, liquid separation was performed, the aqueous layer was adjusted to pH=2 with 1 mol/L hydrochloric acid, then, this was extracted with EtOAc. The organic layers were combined, washed sequentially with water and saturated brine and dried over MgSO$_4$, then, the drying agent was separated by filtration and the solvent was evaporated under reduced pressure to obtain 1.30 g of residue. The present compound was used in the next reaction without purification.

MS (ESI pos.) m/z: 226 ([M+Na]$^+$)
$^1$H-NMR (300 MHz, CDCl$_3$) δ (ppm); 1.44 (s, 9H), 1.53 (s, 6H)

Step 255-2: Synthesis of tert-butyl[2-(dimethylamino)-1,1-dimethyl-2-oxo ethyl]carbamate With 0.92 g of the compound obtained in Step 255-1 as starting material, 0.82 g of the title compound (colorless solid) was obtained by a similar procedure to Step 6-1a.

MS (ESI pos.) m/z: 253 ([M+Na]$^+$)
$^1$H-NMR (300 MHz, CDCl$_3$) δ (ppm); 1.43 (s, 9H), 1.52 (s, 6H), 3.07 (s, 6H)

Step 255-3: Synthesis of 2-amino-N,N,2-trimethyl propanamide trifluoroacetate With 0.72 g of the compound obtained in Step 255-2 as starting material, 1.49 g of the title compound (crude form) was obtained by a similar procedure to Step 4-1.

MS (ESI pos.) m/z: 131 ([M+H]$^+$)
$^1$H-NMR (300 MHz, DMSO-d$_6$) δ (ppm); 1.55 (s, 6H), 3.01 (s, 6H), 8.12 (brs, 3H)

Step 255-4: Synthesis of 2-{[5-chloro-3-(2-methoxyphenyl)-2-oxo-2,3-dihydro-1H-indol-3-yl]amino}-N,N,2-trimethyl propanamide With 868 mg of 3,5-dichloro-3-(2-methoxyphenyl)-1,3-dihydro-2H-indol-2-one and the compound obtained in Step 255-3 (3.10 mmol, crude form) as starting materials, 1.02 g of the title compound (colorless amorphous) was obtained by a similar method to Step 4-2.

MS (ESI pos.) m/z: 424 ([M+Na]$^+$)
$^1$H-NMR (300 MHz, CDCl$_3$) δ (ppm); 1.19 (s, 3H), 1.37 (s, 3H), 3.32 (s, 3H), 3.39 (s, 3H), 3.45-3.68 (brs, 3H), 6.55 (d, J=2.2 Hz, 1H), 6.77 (d, J=8.2 Hz, 1H), 6.86 (dd, J=8.2, 1.1 Hz, 1H), 6.99-7.08 (m, 1H), 7.17 (dd, J=8.2, 2.2 Hz, 1H), 7.23-7.31 (m, 1H), 8.05 (dd, J=7.9, 1.7 Hz, 1H), 10.53 (s, 1H)

Step 255-5: Synthesis of 2-[(5-chloro-3-(2-methoxyphenyl)-1-{[4-methoxy-2-(trifluoromethoxy)phenyl]sulfonyl}-2-oxo-2,3-dihydro-1H-indol-3-yl) amino]-N,N,2-trimethyl propanamide With 0.51 g of the compound obtained in Step 255-4 and 378 mg of 4-methoxy-2-(trifluoromethoxy)benzene sulfonyl chloride as starting materials, 0.38 g of the title compound (colorless solid) was obtained by a similar procedure to Example 2.

MS (ESI pos.) m/z: 656 ([M+H]$^+$)
$^1$H-NMR (300 MHz, CDCl$_3$) δ (ppm); 0.74 (s, 3H), 1.27 (s, 3H), 3.36 (s, 3H), 3.38 (s, 1H), 3.93 (s, 3H), 6.65 (d, J=2.3 Hz, 1H), 6.87 (dd, J=8.3, 1.0 Hz, 1H), 7.02-7.12 (m, 2H), 7.21-

7.35 (m, 3H), 7.42 (dd, J=8.9, 2.3 Hz, 1H), 7.75 (d, J=8.7 Hz, 1H), 8.10 (dd, J=8.0, 1.5 Hz, 1H), 8.22 (d, J=9.0 Hz, 1H)

7.03-7.13 (m, 1H), 7.24 (dd, J=8.2, 2.2 Hz, 1H), 7.26-7.35 (m, 1H), 8.03 (dd, J=7.7, 1.6 Hz, 1H), 10.49 (s, 1H)

Example 256

Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-2-cyclohexyl-N,N-dimethylacetamide (levorotatory isomer)

Step 256-1: Synthesis of tert-butyl[(1S)-1-cyclohexyl-2-(dimethylamino)-2-oxo ethyl]carbamate With 2.00 g of (2S)-[(tert-butoxy carbonyl)amino] (cyclohexyl)acetic acid as starting material, 2.19 g of the title compound (colorless solid) was obtained by a similar procedure to Step 6-1a.

MS (ESI pos.) m/z: 307 ([M+Na]$^+$)

$^1$H-NMR (300 MHz, CDCl$_3$) δ (ppm); 0.95-1.30 (m, 5H), 1.43 (s, 9H), 1.51-1.80 (m, 6H), 2.97 (s, 3H), 3.10 (s, 3H), 4.46 (dd, J=9.2, 6.4 Hz, 1H), 5.28 (d, J=8.9 Hz, 1H)

Step 256-2: Synthesis of (2S)-2-amino-2-cyclohexyl-N,N-dimethylacetamide trifluoroacetate With 1.57 g of the compound obtained in Step 256-1 as starting material, 3.61 g of the title compound (crude form) was obtained by a similar procedure to Step 4-1.

MS (ESI pos.) m/z: 185 ([M+H]$^+$)

$^1$H-NMR (300 MHz, CDCl$_3$) δ (ppm); 1.03-1.32 (m, 5H), 1.64-1.91 (m, 6H), 3.02 (s, 3H), 3.09 (s, 3H), 4.26-4.38 (m, 1H), 7.58 (brs, 3H)

Step 256-3: Synthesis of (2S)-2-{[5-chloro-3-(2-methoxyphenyl)-2-oxo-2,3-dihydro-1H-indol-3-yl]amino}-2-cyclohexyl-N,N-dimethylacetamide (levorotatory isomer and dextrorotatory isomer)

With 1.54 g of 3,5-dichloro-3-(2-methoxyphenyl)-1,3-dihydro-2H-indol-2-one and the compound obtained in Step 256-2 (5.50 mmol, crude form) as starting materials, respectively 0.97 g (Isomer A, colorless powder) and 1.44 g (Isomer B, colorless amorphous) of two species of diastereoisomers of the title compound were obtained by a similar method to Step 4-2.

Isomer A: [α]$_D^{26}$=+141° (c=0.210, CHCl$_3$)

MS (ESI pos.) m/z: 456 ([M+H]$^+$)

$^1$H-NMR (300 MHz, DMSO-d$_6$) δ (ppm); 0.87-1.23 (m, 5H), 1.34 (m, 2H), 1.50-1.74 (m, 3H), 1.80-1.93 (m, 1H), 2.53 (s, 3H), 2.57 (s, 3H), 3.08 (dd, J=9.2, 5.4 Hz, 1H), 3.28 (d, J=9.6 Hz, 1H), 3.49 (s, 3H), 6.70 (d, J=2.2 Hz, 1H), 6.82 (d, J=8.2 Hz, 1H), 6.93 (dd, J=8.2, 1.0 Hz, 1H), 7.00-7.08 (m, 1H), 7.17 (dd, J=8.2, 2.2 Hz, 1H), 7.25-7.35 (m, 1H), 7.76 (dd, J=7.8, 1.6 Hz, 1H), 10.57 (s, 1H)

Isomer B: [α]$_D^{26}$=−127° (c=0.198, CHCl$_3$)

MS (ESI pos.) m/z: 478 ([M+Na]$^+$)

$^1$H-NMR (300 MHz, DMSO-d$_6$) δ (ppm); 0.69-1.36 (m, 7H), 1.50-1.74 (m, 3H), 1.94-2.05 (m, 1H), 2.62 (s, 3H), 2.74 (s, 3H), 2.90-2.97 (m, 2H), 3.43 (s, 3H), 6.72 (d, J=2.2 Hz, 1H), 6.84 (d, J=8.4 Hz, 1H), 6.90 (dd, J=8.2, 1.0 Hz, 1H), Step 256-4: Synthesis of (2S)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-2-cyclohexyl-N,N-dimethylacetamide (levorotatory isomer)

With 0.85 g of Isomer B obtained in Step 256-3 and 595 mg of 4-methoxy-2-(trifluoromethoxy)benzene sulfonyl chloride as starting materials, 1.10 g of the title compound (colorless powder) was obtained by a similar procedure to Example 2.

[α]$_D^{25}$=−116° (c=0.195, CHCl$_3$)

MS (ESI pos.) m/z: 732 ([M+Na]$^+$)

$^1$H-NMR (300 MHz, CDCl$_3$) δ (ppm); 0.68-1.41 (m, 7H), 1.54-1.73 (m, 2H), 1.79-1.93 (m, 1H), 2.68 (s, 3H), 2.96 (s, 3H), 3.09 (s, 3H), 3.11-3.19 (m, 1H), 3.20-3.31 (m, 1H), 3.89 (s, 3H), 6.64 (dd, J=8.2, 1.0 Hz, 1H), 6.85-6.95 (m, 3H), 6.99-7.08 (m, 1H), 7.19-7.32 (m, 2H), 7.92 (d, J=8.7 Hz, 1H), 8.02 (dd, J=7.8, 1.7 Hz, 1H), 8.37 (d, J=9.2 Hz, 1H)

Example 257

Synthesis of (2R)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (dextrorotatory isomer)

Step 257-1: Synthesis of tert-butyl[(1R)-2-(dimethylamino)-1-methyl-2-oxo ethyl]carbamate With 2.00 g of N-(tert-butoxy carbonyl)-D-alanine as starting material, 1.97 g of the title compound (colorless oil) was obtained by a similar procedure to Step 6-1a.

MS (ESI pos.) m/z: 239 ([M+Na]$^+$)

$^1$H-NMR (300 MHz, CDCl$_3$) δ ppm; 1.30 (d, J=6.8 Hz, 3H), 1.44 (s, 9H), 2.97 (s, 3H), 3.06 (s, 3H), 4.56-4.71 (m, 1H), 5.43-5.57 (m, 1H)

Step 257-2: Synthesis of (2R)-2-amino-N,N-dimethylpropanamide trifluoroacetate

With 1.20 g of the compound obtained in Step 257-1 as starting material, 3.07 g of the title compound (crude form) was obtained by a similar procedure to Step 4-1.

MS (ESI pos.) m/z: 117 ([M+H]$^+$)

$^1$H-NMR (300 MHz, DMSO-d$_6$) δ (ppm); 1.30 (d, J=6.8 Hz, 3H), 2.89 (s, 3H), 3.02 (s, 3H), 4.27-4.40 (m, 1H), 8.07 (br.s, 3H)

Step 257-3: Synthesis of (2R)-2-{[5-chloro-3-(2-methoxyphenyl)-2-oxo-2,3-dihydro-1H-indol-3-yl]amino}-N,N-dimethyl propanamide (levorotatory isomer and dextrorotatory isomer)

With 1.54 g of 3,5-dichloro-3-(2-methoxyphenyl)-1,3-dihydro-2H-indol-2-one and the compound obtained in Step 257-2 (5.50 mmol, crude form) as starting materials, respectively 0.76 g (Isomer A, colorless powder) and 0.60 g (Isomer B, colorless powder) of two species of diastereoisomers of the title compound were obtained by a similar method to Step 4-2.

Isomer A: [α]$_D^{26}$=−148° (c=0.204, CHCl$_3$)

MS (ESI pos.) m/z: 410 ([M+Na]$^+$)

¹H-NMR (300 MHz, DMSO-d₆) δ (ppm); 1.15 (d, J=7.0 Hz, 3H), 2.72 (s, 3H), 2.78 (s, 3H), 2.92 (d, J=9.5 Hz, 1H), 3.45 (s, 3H), 3.71-3.87 (m, 1H), 6.69 (d, J=2.2 Hz, 1H), 6.82 (d, J=8.2 Hz, 1H), 6.92 (dd, J=8.2, 0.9 Hz, 1H), 7.06-7.14 (m, 1H), 7.20 (dd, J=8.3, 2.3 Hz, 1H), 7.27-7.37 (m, 1H), 7.92 (dd, J=7.8, 1.7 Hz, 1H), 10.41 (s, 1H)

Isomer B: $[\alpha]_D^{26}$=+111, (c=0.212, CHCl₃)

MS (ESI pos.) m/z: 410 ([M+Na]⁺)

¹H-NMR (300 MHz, DMSO-d₆) δ (ppm); 1.01 (d, J=6.7 Hz, 3H), 2.70 (s, 6H), 3.15 (d, J=8.2 Hz, 1H), 3.40-3.52 (m, 4H), 6.76-6.86 (m, 2H), 6.90 (d, J=7.5 Hz, 1H), 7.01-7.10 (m, 1H), 7.22 (dd, J=8.3, 2.3 Hz, 1H), 7.26-7.35 (m, 1H), 7.88 (dd, J=7.8, 1.7 Hz, 1H), 10.52 (s, 1H)

Step 257-4: Synthesis of (2R)-2-[(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (dextrorotatory isomer)

With 0.37 g of Isomer B obtained in Step 257-3 and 304 mg of 4-methoxy-2-(trifluoromethoxy)benzene sulfonyl chloride as starting materials, 504 mg of the title compound (colorless amorphous) was obtained by a similar procedure to Example 2.

$[\alpha]_D^{25}$=+150° (c=0.216, CHCl₃)

MS (ESI pos.) m/z: 664 ([M+Na]⁺)

¹H-NMR (300 MHz, CDCl₃) δ (ppm); 0.92 (d, J=6.7 Hz, 3H), 2.72 (s, 3H), 2.94 (s, 3H), 3.28 (m, 4H), 3.50-3.60 (m, 1H), 3.88 (s, 3H), 6.70 (dd, J=8.2, 1.0 Hz, 1H), 6.84-6.95 (m, 3H), 6.96-7.06 (m, 1H), 7.21-7.33 (m, 2H), 7.80 (dd, J=7.8, 1.7 Hz, 1H), 7.91 (d, J=8.7 Hz, 1H), 8.34 (d, J=8.9 Hz, 1H)

Example 258

Synthesis of (2S)-2-[benzyl(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer)

Step 258-1: Synthesis of benzyl[(1S)-2-(dimethylamino)-1-methyl-2-oxo ethyl]benzyl carbamate Under nitrogen atmosphere, a solution of 2.00 g of benzyl [(1S)-2-(dimethylamino)-1-methyl-2-oxo ethyl]carbamate in DMF was cooled by ice, and 0.33 g of NaH was added and the reaction mixture was stirred at room temperature for one hour. Therein, bromide benzyl (1.4 ml) was added and the solution was stirred at room temperature for 4 hours. A saturated aqueous solution of NaHCO₃ was added to the reaction solution and the resulting mixture was extracted with EtOAc. The combined organic layer was washed with water and with saturated brine and dried over MgSO₄; the drying agent was separated by filtration and the solvent was evaporated under reduced pressure. The obtained residue was separated and purified by column chromatography (silica gel, moving bed: hexane/EtOAc=1/1; v/v) to obtain 2.68 g of the title compound (colorless oil).

MS (ESI pos.) m/z: 363 ([M+Na]⁺)

¹H-NMR (300 MHz, CDCl₃) δ (ppm); 1.23-1.33 (m, 3H), 2.52 & 2.65 (each-s, 3H), 2.58 & 2.87 (each-s, 3H), 4.23-4.46 (m, 1H), 4.58-4.79 (m, 1H), 5.13-5.32 (m, 3H), 7.13-7.43 (m, 10H)

Step 258-2: Synthesis of (2S)-2-(benzyl amino)-N,N-dimethylpropanamide

With 2.00 g of the compound obtained in Step 258-1 as starting material, 0.77 g of the title compound (crude form) was obtained by a similar procedure to Step 11-4.

MS (ESI pos.) m/z: 207 ([M+H]⁺)

¹H-NMR (300 MHz, CDCl₃) δ (ppm); 1.22 (d, J=6.8 Hz, 3H), 2.95 (s, 3H), 2.99 (s, 3H), 3.50-3.62 (m, 2H), 3.78 (d, J=12.7 Hz, 1H), 7.19-7.38 (m, 5H)

Step 258-3: Synthesis of (2S)-2-{benzyl[5-chloro-3-(2-methoxyphenyl)-2-oxo-2,3-dihydro-1H-indol-3-yl]amino}-N,N-dimethylpropanamide (levorotatory isomer and dextrorotatory isomer)

With 0.95 g of 3,5-dichloro-3-(2-methoxyphenyl)-1,3-dihydro-2H-indol-2-one and the compound obtained in Step 258-2 (3.39 mmol, crude form) as starting materials, respectively 966 mg (Isomer A, colorless amorphous) and 501 mg (Isomer B, colorless amorphous) of two species of diastereoisomers of the title compound were obtained by a similar method to Step 4-2.

Isomer A: $[\alpha]_D^{25}$=−177° (c=0.224, CHCl₃)

MS (ESI pos.) m/z: 478 ([M+H]⁺)

¹H-NMR (300 MHz, DMSO-d₆) δ (ppm); 1.13-1.21 (m, 3H), 2.49 (s, 3H), 2.81 (s, 3H), 3.47 (s, 3H), 3.56-3.78 (m, 1H), 4.35-4.56 (m, 2H), 6.67 (d, J=8.2 Hz, 1H), 6.89-6.96 (m, 2H), 6.97-7.18 (m, 7H), 7.25-7.33 (m, 1H), 7.76 (dd, J=7.7, 1.6 Hz, 1H), 10.60 (s, 1H)

Isomer B: $[\alpha]_D^{25}$=+117° (c=0.164, CHCl₃)

MS (ESI pos.) m/z: 478 ([M+H]⁺)

¹H-NMR (300 MHz, DMSO-d₆) δ (ppm); 1.32-1.41 (m, 3H), 2.66 (s, 3H), 2.69 (s, 3H), 3.44 (s, 3H), 3.56-3.70 (m, 1H), 4.05-4.21 (m, 1H), 4.62-4.82 (m, 1H), 6.73 (d, J=8.2 Hz, 1H), 6.93 (dd, J=8.2, 1.0 Hz, 1H), 6.96-7.23 (m, 8H), 7.25-7.34 (m, 1H), 8.06 (dd, J=7.8, 1.7 Hz, 1H), 10.51 (s, 1H)

Step 258-4: Synthesis of (2S)-2-[benzyl(5-chloro-3-(2-methoxyphenyl)-1-{[4-methoxy-2-(trifluoromethoxy)phenyl]sulfonyl}-2-oxo-2,3-dihydro-1H-indol-3-yl)amino]-N,N-dimethylpropanamide (levorotatory isomer)

With 555 mg of isomer A obtained in Step 258-3 and 345 mg of 4-methoxy-2-(trifluoromethoxy)benzene sulfonyl chloride as starting materials, 668 mg of the title compound (colorless amorphous) was obtained by a similar procedure to Example 2.

$[\alpha]_D^{25}$=−133° (c=0.255, CHCl₃)

MS (ESI pos.) m/z: 732 ([M+H]⁺)

¹H-NMR (300 MHz, CDCl₃) δ (ppm); 0.97 (d, J=6.8 Hz, 3H), 2.49 (s, 3H), 2.97 (s, 3H), 3.39 (s, 3H), 3.49-3.59 (m, 1H), 3.91 (s, 3H), 4.38-4.51 (m, 2H), 5.91-5.99 (m, 1H), 6.73 (dd, J=8.3, 1.0 Hz, 1H), 6.90-7.12 (m, 7H), 7.13-7.29 (m, 3H), 7.74 (d, J=8.9 Hz, 1H), 7.82 (dd, J=7.7, 1.6 Hz, 1H), 8.38 (d, J=9.2 Hz, 1H)

Example 259

Synthesis of N2-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethyl-L-lysinamide A solution of 4 mol/L hydrochloric acid in EtOAc (5 ml) was added to 250 mg of compound obtained in Example 78, which was stirred for 50 minutes under ice cooling. Saturated K$_2$CO$_3$ was added, and the solution was extracted with EtOAc. The combined organic layer was washed with saturated brine and dried over Na$_2$SO$_4$, then, the drying agent was separated by filtration and the solvent was evaporated under reduced pressure. The obtained residue was separated and purified by column chromatography (silicagel 60, mobile phase: CHCl$_3$/MeOH/NH$_4$OH=4/1/0.05; v/v/v) to obtain 157 mg of the title compound (colorless amorphous).

MS (ESI pos.) m/z: 699 ([M+H]$^+$)

$^1$H-NMR (300 MHz, CDCl$_3$) δ (ppm); 1.09-1.50 (m, 6H), 2.59-2.65 (m, 1H), 2.73 (s, 3H), 2.96 & 2.96 (each-s, 3H), 3.10 & 3.11 (each-s, 3H), 3.27-3.38 (m, 2H), 3.89 & 3.89 (each-s, 3H), 6.62-6.70 (m, 1H), 6.84-6.96 (m, 3H), 6.99-7.07 (m, 1H), 7.19-7.35 (m, 2H), 7.87-8.05 (m, 2H), 8.37 (d, J=9.2 Hz, 1H)

Example 260

Synthesis of (4R)-1-(5-chloro-3-[5-(2-cyanoethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 260-1: Synthesis of 2-[3-(5-chloro-3-{(2S,4R)-2-[(dimethylamino)carbonyl]-4-hydroxypyrrolidin-1-yl}-1-{[4-methoxy-2-(trifluoromethoxy)phenyl]sulfonyl}-2-oxo-2,3-dihydro-1H-indol-3-yl)-4-methoxyphenyl]ethyl) 4-methyl benzene sulfonate To a solution of 1.00 g of compound obtained in Example 219 in Py (10 ml) was added 393 mg of p-toluene sulfonyl chloride and the reaction mixture was stirred at room temperature for two hours. 1 mol/L hydrochloric acid was added to the solution and the resulting mixture was extracted with EtOAc; the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=100/1 to 50/1; v/v) to obtain 597 mg of the title compound.

MS (ESI pos.) m/z: 882 ([M+H]$^+$), 904 ([M+Na]$^+$), (ESI neg.) m/z: 880 ([M−H]$^-$)

$^1$H-NMR (600 MHz, CDCl$_3$) δ (ppm); 1.11-1.52 (m, 2H), 1.66-2.28 (m, 3H), 2.34-3.20 (m, 11H), 3.22-3.70 (m, 3H), 3.84-3.92 (m, 3H), 4.04-4.33 (m, 2H), 4.38-4.83 (m, 2H), 6.62 (d, J=5.96 Hz, 1H), 6.81-7.08 (m, 3H), 7.18-7.32 (m, 3H), 7.50-7.76 (m, 2H), 7.85 (d, J=8.71 Hz, 1H), 8.01-8.54 (m, 3H)

Step 260-2: Synthesis of (4R)-1-(5-chloro-3-[5-(2-cyanoethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 290 mg of the compound obtained in Step 260-1 as starting material, 198 mg of the title compound was obtained by a similar method to Step 143-3.

[α]$_D^{25}$=−166° (c=0.170, CHCl$_3$)

MS (ESI pos.) m/z: 737 ([M+H]$^+$), 759 ([M+Na]$^+$), (ESI neg.) m/z: 735 ([M−H]$^-$)

$^1$H-NMR (600 MHz, CDCl$_3$) δ (ppm); 1.11-1.26 (m, 1H), 1.77-1.83 (m, 1H), 1.98-2.13 (m, 1H), 2.41-2.97 (m, 10H), 2.99-3.68 (m, 4H), 3.88 (s, 3H), 4.45-4.54 (m, 1H), 4.66-4.86 (m, 1H), 6.71 (d, J=8.25 Hz, 1H), 6.87 (s, 1H), 6.93 (dd, J=9.17, 2.29 Hz, 1H), 7.01-7.14 (m, 2H), 7.23 (d, J=9.17 Hz, 1H), 7.69-7.83 (m, 1H), 7.87 (d, J=8.71 Hz, 1H), 8.25-8.42 (m, 1H)

Example 261

Synthesis of (4R)-1-(5-chloro-3-{2-methoxy-5-[2-(1H-tetrazol-5-yl)ethyl]phenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 190 mg of the compound obtained in Step 260-2 as starting material, 108 mg of the title compound was obtained by a similar method to Example 244.

MS (ESI pos.) m/z: 780 ([M+H]$^+$), 802 ([M+Na]$^+$), (ESI neg.) m/z: 778 ([M−H]$^-$) [α]$_D^{25}$=−182° (c=0.330, CHCl$_3$)

$^1$H-NMR (600 MHz, CDCl$_3$) δ (ppm); 1.74-1.84 (m, 1H), 2.13-2.35 (m, 2H), 2.45-2.77 (m, 10H), 2.87-3.05 (m, 1H), 3.07-3.63 (m, 5H), 3.71-3.86 (m, 3H), 4.31-4.86 (m, 2H), 6.53-6.65 (m, 1H), 6.68-6.94 (m, 3H), 7.05 (d, J=7.79 Hz, 1H), 7.19 (dd, J=8.71, 1.83 Hz, 1H), 7.77-8.37 (m, 3H)

Example 262

Synthesis of (4R)-1-(5-chloro-3-{5-[5-hydroxypenta-2-en-1-yl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide Under nitrogen atmosphere, to a suspension of 497 mg of (3-hydroxy propyl)(triphenyl) phosphonium bromide in THF (5 ml) was added dropwise a solution of 1 mol/L lithium bis-(trimethylsilyl) amide in THF (1.43 ml) under ice cooling. After stirring at room temperature for one hour, the solution was cooled by ice, 300 mg of compound obtained in Example 219 in THF (5 ml) was added to a solution and the reaction mixture was stirred at room temperature for one hour. A saturated aqueous solution of NH$_4$Cl was added to the solution and the resulting mixture was extracted with EtOAc; the organic layer was washed with saturated brine and dried over Na$_2$SO$_4$, then, the drying agent was separated by filtration and the solvent was evaporated under reduced pressure. The obtained residue was purified by column chromatography (silicagel 60N; mobile phase: CHCl$_3$/MeOH=20/1 to 10/1; v/v) to obtain 206 mg of the title compound.

MS (ESI pos.) m/z: 768 ([M+H]$^+$), 790 ([M+Na]$^+$), (ESI neg.) m/z: 766 ([M−H]$^-$)

$^1$H-NMR (600 MHz, CDCl$_3$) δ (ppm); 1.70-1.79 (m, 1H), 1.83-1.95 (m, 1H), 2.22-2.53 (m, 5H), 2.71-2.85 (m, 3H), 2.99-3.16 (m, 1H), 3.19-3.73 (m, 10H), 3.79-3.88 (m, 3H), 4.40-4.55 (m, 1H), 4.68-4.83 (m, 1H), 5.39-5.64 (m, 2H), 6.58-6.65 (m, 1H), 6.78-6.85 (m, 1H), 6.84-6.89 (m, 1H), 6.95-7.02 (m, 1H), 7.14-7.19 (m, 1H), 7.40-7.52 (m, 1H), 7.66-7.85 (m, 2H), 8.23-8.35 (m, 1H)

Example 263

Synthesis of (4R)-1-(5-chloro-3-[5-(5-hydroxypentyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Under hydrogen atmosphere, suspension of 200 mg of the compound obtained in Example 262 and 20 mg of 5% palladium-carbon in MeOH (2 ml) was stirred at room temperature for one hour. The insoluble matter was separated by filtration with celite and the filtrate was concentrated under reduced pressure. The residue was purified by column chromatography (silicagel 60N; mobile phase: $CHCl_3/MeOH=30/1$ to 15/1; v/v) to obtain 86 mg of the title compound (amorphous).
$[\alpha]_D^{25}=188°$ (c=0.051, $CHCl_3$)
MS (ESI pos.) m/z: 770 ([M+H]$^+$), 792 ([M+Na]$^+$), (ESI neg.) m/z: 768 ([M−H]$^−$)
$^1$H-NMR (600 MHz, $CDCl_3$) δ (ppm); 1.50-1.65 (m, 6H), 1.73-1.93 (m, 2H), 2.40-2.48 (m, 3H), 2.52-2.60 (m, 3H), 2.73-2.85 (m, 3H), 3.12-3.25 (m, 1H), 3.39-3.71 (m, 7H), 3.87 (s, 3H), 4.52-4.61 (m, 1H), 4.70-4.83 (m, 1H), 6.66 (d, J=7.79 Hz, 1H), 6.86 (s, 1H), 6.90-6.94 (m, 1H), 7.02 (dd, J=8.25, 2.29 Hz, 1H), 7.07-7.16 (m, 1H), 7.22 (dd, J=8.71, 2.29 Hz, 1H), 7.56-7.69 (m, 1H), 7.84-7.89 (m, 1H), 8.29-8.39 (m, 1H)

Example 264

Synthesis of (4R)-1-(5-chloro-3-[2-methoxy-5-(5-oxo pentyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 80 mg of the compound obtained in Example 263 as starting material, 38 mg of the title compound (amorphous) was obtained by a similar method to Example 218.
MS (ESI pos.) m/z: 768 ([M+H]$^+$), (ESI neg.) m/z: 766 ([M−H]$^−$)
$^1$H-NMR (600 MHz, $CDCl_3$) δ (ppm); 1.51-1.70 (m, 5H), 1.74-1.86 (m, 1H), 2.35-2.59 (m, 5H), 2.66-2.88 (m, 3H), 3.08-3.25 (m, 1H), 3.26-3.42 (m, 2H), 3.50-3.64 (m, 5H), 3.86-3.89 (m, 3H), 4.53-4.64 (m, 1H), 4.70-4.83 (m, 1H), 6.66 (d, J=7.34 Hz, 1H), 6.86 (s, 1H), 6.90-6.95 (m, 1H), 7.01 (dd, J=8.25, 1.83 Hz, 1H), 7.05-7.13 (m, 1H), 7.22 (dd, J=8.94, 2.06 Hz, 1H), 7.49-7.68 (m, 1H), 7.81-7.89 (m, 1H), 8.29-8.38 (m, 1H), 9.75 (s, 1H)

Example 265

Synthesis of (4R)-1-(5-chloro-3-[2-methoxy-5-(5-piperidin-1-ylpentyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 20 mg of the compound obtained in Example 264 as starting material, 2 mg of the title compound (amorphous) was obtained by a similar method to Example 207.
MS (ESI pos.) m/z: 837 ([M+H]$^+$), (ESI neg.) m/z: 835 ([M−H]$^−$)
$^1$H-NMR (600 MHz, $CDCl_3$) δ (ppm); 1.45-1.85 (m, 10H), 2.19-2.93 (m, 16H), 3.05-3.73 (m, 8H), 3.83-3.86 (m, 3H), 4.33-4.73 (m, 2H), 6.59-6.66 (m, 1H), 6.84 (s, 1H), 6.87-6.91 (m, 1H), 6.96-7.01 (m, 1H), 7.04 (s, 1H), 7.15-7.20 (m, 1H), 7.80-7.85 (m, 1H), 7.92-8.00 (m, 1H), 8.38-8.48 (m, 1H)

Example 266

Synthesis of (4R)-1-(5-chloro-3-{5-[5-(dimethylamino)pentyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 10 mg of the compound obtained in Example 264 as starting material, 3 mg of the title compound (amorphous) was obtained by a similar method to Example 207.

MS (ESI pos.) m/z: 797 ([M+H]$^+$), (ESI neg.) m/z: 795 ([M−H]$^−$)
$^1$H-NMR (600 MHz, $CDCl_3$) δ (ppm); 1.45-1.68 (m, 8H), 2.12-2.37 (m, 10H), 2.37-2.62 (m, 6H), 3.17-3.24 (m, 1H), 3.49-3.65 (m, 5H), 3.83-3.90 (m, 3H), 4.37-4.50 (m, 1H), 4.59-4.75 (m, 1H), 6.61-6.67 (m, 1H), 6.83-6.94 (m, 3H), 6.96-7.03 (m, 1H), 7.17-7.23 (m, 1H), 7.81-7.88 (m, 1H), 7.91-8.04 (m, 1H), 8.36-8.50 (m, 1H)

Example 267

Synthesis of (2S)-1-(3-(3-methoxyphenyl)-1-{[4-methoxy-2-(trifluoromethoxy)phenyl]sulfonyl}-5-methyl-2-oxo-2,3-dihydro-1H-indol-3-yl)-N,N-dimethylpiperidine-2-carboxamide (levorotatory isomer)

Step 267-1: Synthesis of 3-hydroxy-3-(3-methoxyphenyl)-5-methyl-1,3-dihydro-2H-indol-2-one With 5.61 g of 3-methoxy bromobenzene and 3.23 g of 5-methyl isatin as starting materials, 5.09 g of the title compound was obtained by a similar method to Step 21-1.
MS (ESI neg.) m/z: 268 ([M−H]$^−$)
$^1$H-NMR (300 MHz, DMSO-$d_6$) δ (ppm); 2.21 (s, 3H), 3.73 (s, 3H), 6.57 (s, 1H), 6.66-6.71 (m, 1H), 6.78 (d, J=7.93 Hz, 1H), 6.80-6.85 (m, 1H), 6.88-6.91 (m, 1H), 6.93-6.96 (m, 1H), 7.01-7.08 (m, 1H), 7.19 (t, J=7.93 Hz, 1H), 10.29 (s, 1H)

Step 267-2: Synthesis of (2S)-1-[3-(3-methoxyphenyl)-5-methyl-2-oxo-2,3-dihydro-1H-indol-3-yl]-N,N-dimethylpiperidine-2-carboxamide From 808 mg of the compound obtained in Step 267-1 and 580 mg of (2S)—N,N-dimethylpiperidine-2-carboxamide hydrochloride, respectively 768 mg (Isomer A) and 124 mg (Isomer B) of two species of diastereoisomers of the title compound were obtained by a similar method to Step 21-2.
Isomer A: MS (ESI neg.) m/z: 406 ([M−H]$^−$)
$^1$H-NMR (300 MHz, DMSO-$d_6$) δ (ppm); 1.34-1.83 (m, 6H), 2.25 (s, 3H), 2.30 (s, 3H), 2.52-2.60 (m, 1H), 2.70 (s, 3H), 3.71 (s, 3H), 3.78-3.90 (m, 1H), 3.98-4.02 (m, 1H), 6.71 (d, J=8.24 Hz, 1H), 6.75-6.80 (m, 1H), 6.81-6.87 (m, 1H), 6.97-7.03 (m, 1H), 7.03-7.08 (m, 1H), 7.19 (t, J=8.00 Hz, 1H), 10.39 (brs, 1H)
Isomer B: MS (ESI neg.) m/z: 406 ([M−H]$^−$)
$^1$H-NMR (300 MHz, DMSO-$d_6$) δ (ppm); 1.38-1.64 (m, 5H), 1.76-1.97 (m, 1H), 2.11 (brs, 3H), 2.16 (s, 3H), 2.41-2.49 (m, 1H), 2.55-2.65 (m, 3H), 3.74 (s, 3H), 3.84-3.94 (m, 1H), 4.03-4.08 (m, 1H), 6.69 (d, J=7.93 Hz, 1H), 6.78-6.85 (m, 2H), 6.87-6.97 (m, 2H), 7.09-7.14 (m, 1H), 7.21 (t, J=8.00 Hz, 1H), 10.27 (brs, 1H)

Step 267-3: Synthesis of (2S)-1-(3-(3-methoxyphenyl)-1-{[4-methoxy-2-(trifluoromethoxy)phenyl]sulfonyl}-5-methyl-2-oxo-2,3-dihydro-1H-indol-3-yl)-N,N-dimethylpiperidine-2-carboxamide (levorotatory isomer)

With 100 mg of the compound obtained in Step 0249-2 (Isomer B) and 80 mg of 4-methoxy-2-(trifluoromethoxy) benzene sulfonyl chloride as starting materials, 115 mg of the title compound (amorphous) was obtained by a similar method to Example 2.
$[\alpha]_D^{30}=-241°$ (c=1.55, $CHCl_3$)
MS (ESI pos.) m/z: 662 ([M+H]$^+$)
$^1$H-NMR (300 MHz, $CDCl_3$) δ (ppm); 1.37-1.69 (m, 5H), 1.73-1.97 (m, 1H), 2.15-2.23 (m, 3H), 2.26 (s, 3H), 2.68 (s, 1H), 2.85 (s, 3H), 3.67 (s, 3H), 3.90 (s, 3H), 3.93-4.03 (m, 2H), 6.57-6.66 (m, 1H), 6.68-6.75 (m, 1H), 6.77-6.82 (m, 1H), 6.82-6.87 (m, 1H), 6.89 (s, 1H), 6.95 (dd, J=8.94, 2.25 Hz, 1H), 7.02-7.12 (m, 2H), 7.85 (d, J=8.39 Hz, 1H), 8.44 (d, J=9.02 Hz, 1H)

Example 268

Synthesis of (4R)-1-(3-(1,3-benzodioxol-5-yl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide Step 268-1: Synthesis of 3-(1,3-benzodioxol-5-yl)-5-chloro-3-hydroxy-1,3-dihydro-2H-indol-2-one With 3.00 g of 5-bromo-1,3-benzodioxol and 1.86 g of 5-chloroisatin as starting materials, 2.32 g of the title compound was obtained by a similar method to Step 21-1.

MS (ESI neg.) m/z: 302 ([M−H]⁻)

¹H-NMR (300 MHz, DMSO-d₆) δ (ppm); 5.96-6.03 (m, 2H), 6.59 (dd, J=8.08, 1.87 Hz, 1H), 6.74 (s, 1H), 6.80-6.94 (m, 2H), 7.14 (d, J=2.18 Hz, 1H), 7.31 (dd, J=8.24, 2.18 Hz, 1H), 10.52 (brs, 1H)

Step 268-2: Synthesis of (4R)-1-[3-(1,3-benzodioxol-5-yl)-5-chloro-2-oxo-2,3-dihydro-1H-indol-3-yl]-4-hydroxy-N,N-dimethyl-L-prolinamide From 911 mg of the compound obtained in Step 268-1 and 590 mg of (4R)-4-hydroxy-N,N-dimethyl-L-prolinamide hydrochloride, 488 mg of a diastereoisomer mixture of the title compound (Isomer A:Isomer B=1:4) was obtained by a similar method to Step 21-2.

Isomer A:Isomer B=1:4 compound:

MS (ESI neg.) m/z: 442 ([M−H]⁻)

¹H-NMR (300 MHz, DMSO-d₆) δ (ppm); 1.68-1.88 (m, 1H), 2.18-2.29 (m, 1H), 2.44 (s, 3H), 2.58 (s, 3H), 2.99-3.13 (m, 1H), 4.30-4.42 (m, 1H), 4.61-4.69 (m, 1H), 4.77-4.85 (m, 1H), 5.97-6.05 (m, 2H), 6.73-6.88 (m, 3H), 7.06-7.30 (m, 3H), 10.85 (brs, 1H)

Step 268-3: Synthesis of (4R)-1-(3-(1,3-benzodioxol-5-yl)-5-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide With 200 mg of the compound obtained in Step 268-2 (Isomer A:Isomer B=1:4) and 150 mg of 4-methoxy-2-(trifluoromethoxy)benzene sulfonyl chloride as starting materials, 155 mg of the title compound (Isomer A:Isomer B=1:4, amorphous) was obtained by a similar method to Example 2.

MS (ESI pos.) m/z: 720 ([M+Na]⁺), (ESI neg.) m/z: 696 ([M−H]⁻)

¹H-NMR (300 MHz, DMSO-d₆) δ (ppm); 1.60-4.83 (m, 17H), 5.97-8.30 (m, 9H)

Example 269

Synthesis of (4R)-1-(5-chloro-3-(4-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

5-chloro-3-hydroxy-3-(4-methoxyphenyl)-1,3-dihydro-2H-indol-2-one

Step 269-1: Synthesis of (4R)-1-[5-chloro-3-(4-methoxyphenyl)-2-oxo-2,3-dihydro-1H-indol-3-yl]-4-hydroxy-N,N-dimethyl-L-prolinamide From 807 mg of 5-chloro-3-hydroxy-3-(4-methoxyphenyl)-1,3-dihydro-2H-indol-2-one, which is the compound described in preparation 1.4A of Publication No. WO2001098295, and 593 mg of (4R)-4-hydroxy-N,N-dimethyl-L-prolinamide hydrochloride, respectively 174 mg (Isomer A) and 222 mg (Isomer B) of two species of diastereoisomers of the title compound were obtained by a similar method to Step 21-2.

Isomer A: MS (ESI neg.) m/z: 428 ([M−H]⁻)

¹H-NMR (300 MHz, DMSO-d₆) δ (ppm); 1.64-1.89 (m, 2H), 2.47 (s, 3H), 2.54 (s, 3H), 2.91-3.05 (m, 2H), 3.73 (s, 3H), 3.73-3.79 (m, 1H), 4.19-4.35 (m, 1H), 4.67 (d, J=4.82 Hz, 1H), 6.84 (d, J=8.24 Hz, 1H), 6.92 (d, J=9.02 Hz, 2H), 7.09 (d, J=2.02 Hz, 1H), 7.21 (dd, J=8.24, 2.18 Hz, 1H), 7.39 (d, J=9.01 Hz, 2H), 10.85 (brs, 1H)

Isomer B: MS (ESI neg.) m/z: 428 ([M−H]⁻)

¹H-NMR (300 MHz, DMSO-d₆) δ (ppm); 1.62-1.86 (m, 2H), 2.22 (dd, J=8.55, 6.68 Hz, 1H), 2.35 (s, 3H), 2.55 (s, 3H), 3.03 (dd, J=8.47, 5.83 Hz, 1H), 3.72 (s, 3H), 4.31-4.44 (m, 1H), 4.64 (dd, J=8.94, 3.50 Hz, 1H), 4.79 (d, J=4.97 Hz, 1H), 6.81-6.91 (m, 3H), 7.18-7.26 (m, 2H), 7.34-7.38 (m, 2H), 10.84 (brs, 1H)

Step 269-2: Synthesis of (4R)-1-(5-chloro-3-(4-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 100 mg of the compound obtained in Step 269-1 (Isomer B) and 80 mg of 4-methoxy-2-(trifluoromethoxy)benzene sulfonyl chloride as starting materials, 48 mg of the title compound (amorphous) was obtained by a similar method to Example 2.

$[\alpha]_D^{30}$=−156° (c=0.658, CHCl₃)

MS (ESI pos.) m/z: 706 ([M+Na]⁺), (ESI neg.) m/z: 682 ([M−H]⁻)

¹H-NMR (300 MHz, CDCl₃) δ (ppm); 1.86-1.95 (m, 2H), 2.26 (dd, J=10.34, 4.12 Hz, 1H), 2.35 (s, 3H), 2.62 (s, 3H), 3.38 (dd, J=10.18, 4.90 Hz, 1H), 3.75 (s, 3H), 3.92 (s, 3H), 4.38-4.53 (m, 1H), 4.69 (t, J=7.07 Hz, 1H), 6.72-6.80 (m, 2H), 6.82-6.90 (m, 1H), 6.97 (dd, J=8.94, 2.41 Hz, 1H), 7.19-7.33 (m, 3H), 7.52 (d, J=2.18 Hz, 1H), 7.85 (d, J=8.70 Hz, 1H), 8.33 (d, J=9.01 Hz, 1H)

Example 270

Synthesis of (4R)-1-(5-chloro-3-(3-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 270-1: Synthesis of (4R)-1-[5-chloro-3-(3-methoxyphenyl)-2-oxo-2,3-dihydro-1H-indol-3-yl]-4-hydroxy-N,N-dimethyl-L-prolinamide From 870 mg of 5-chloro-3-hydroxy-3-(3-methoxyphenyl)-1,3-dihydro-2H-indol-2-one, which is the compound described in preparation 1.3A of Publication No. WO2001098295, and 595 mg of (4R)-4-hydroxy-N,N-dimethyl-L-prolinamide hydrochloride, respectively 246 mg (Isomer A) and 80 mg (Isomer B) of two species of diastereoisomers of the title compound were obtained by a similar method to Step 21-2.

Isomer A: MS (ESI neg.) m/z: 428 ([M−H]⁻)
$^1$H-NMR (300 MHz, DMSO-$d_6$) δ (ppm); 1.73 (s, 2H), 2.47 (s, 3H), 2.55 (s, 3H), 3.14-3.21 (m, 1H), 3.74 (s, 3H), 3.74-3.83 (m, 1H), 4.19-4.37 (m, 1H), 4.63-4.79 (m, 1H), 6.80-6.98 (m, 3H), 7.06-7.16 (m, 2H), 7.19-7.31 (m, 2H), 10.88 (brs, 1H)

Isomer B: MS (ESI neg.) m/z: 428 ([M−H]⁻)
$^1$H-NMR (300 MHz, DMSO-$d_6$) δ (ppm); 1.62-1.92 (m, 2H), 2.18-2.29 (m, 1H), 2.34 (s, 3H), 2.56 (s, 3H), 3.00-3.13 (m, 1H), 3.75 (s, 3H), 4.29-4.47 (m, 1H), 4.65-4.73 (m, 1H), 4.82 (d, J=5.13 Hz, 1H), 6.85 (dd, J=8.16, 1.48 Hz, 3H), 7.12-7.31 (m, 4H), 10.89 (s, 1H)

Step 270-2: Synthesis of (4R)-1-(5-chloro-3-(3-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 70 mg of the compound obtained in Step 270-1 (Isomer B) and 56 mg of 4-methoxy-2-(trifluoromethoxy)benzene sulfonyl chloride as starting materials, 36 mg of the title compound (amorphous) was obtained by a similar method to Example 2.

$[α]_D^{30}$=−170° (c=0.556, CHCl$_3$)
MS (ESI pos.) m/z: 706 ([M+Na]⁺), (ESI neg.) m/z: 682 ([M−H]⁻)
$^1$H-NMR (300 MHz, CDCl$_3$) δ (ppm); 1.87-1.97 (m, 2H), 2.26-2.33 (m, 1H), 2.34 (s, 3H), 2.65 (s, 3H), 3.40 (dd, J=10.10, 4.97 Hz, 1H), 3.78 (s, 3H), 3.92 (s, 3H), 4.43-4.56 (m, 1H), 4.70 (t, J=6.76 Hz, 1H), 6.71-6.82 (m, 2H), 6.84-6.89 (m, 1H), 6.97 (dd, J=9.01, 2.33 Hz, 1H), 7.03-7.15 (m, 2H), 7.21-7.30 (m, 1H), 7.49 (d, J=2.33 Hz, 1H), 7.86 (d, J=8.70 Hz, 1H), 8.34 (d, J=8.86 Hz, 1H)

Example 271

Synthesis of (4R)-1-(3-(1,3-benzodioxol-4-yl)-4-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

Step 271-1: Synthesis of 3-(1,3-benzodioxol-4-yl)-4-chloro-3-hydroxy-1,3-dihydro-2H-indol-2-one With 9.00 g of 4-bromo-1,3-benzodioxol and 1.81 g of 4-chloroisatin as starting materials, 1.33 g of the title compound was obtained by a similar method to Step 21-1.

MS (ESI neg.) m/z: 302 ([M−H]⁻)
$^1$H NMR (300 MHz, DMSO-$d_6$) δ (ppm); 5.74 (dd, J=6.84, 0.78 Hz, 2H), 6.73-6.93 (m, 4H), 7.18-7.28 (m, 1H), 7.35 (dd, J=7.54, 1.79 Hz, 1H), 10.66 (brs, 1H)

Step 271-2: Synthesis of (4R)-1-[3-(1,3-benzodioxol-4-yl)-4-chloro-2-oxo-2,3-dihydro-1H-indol-3-yl]-4-hydroxy-N,N-dimethyl-L-prolinamide From 800 mg of the compound obtained in Step 271-1 and 1.03 g of (4R)-4-hydroxy-N,N-dimethyl-L-prolinamide hydrochloride, 395 mg of one of the diastereoisomers (Isomer B) of the title compound was obtained by a similar method to Step 21-2.

Isomer B: MS (ESI pos.) m/z: 466 ([M+Na]⁺)
$^1$H-NMR (300 MHz, DMSO-$d_6$) δ (ppm); 1.69-1.81 (m, 1H), 1.89-2.04 (m, 1H), 2.43 (s, 3H), 2.54 (s, 3H), 3.37-3.47 (m, 1H), 4.38 (s, 1H), 4.67 (s, 1H), 4.84 (d, J=4.20 Hz, 1H), 5.77 (dd, J=10.34, 0.85 Hz, 2H), 6.72-6.85 (m, 4H), 7.15-7.24 (m, 1H), 7.58 (dd, J=5.28, 4.20 Hz, 1H), 10.64 (brs, 1H)

Step 271-3: Synthesis of (4R)-1-(3-(1,3-benzodioxol-4-yl)-4-chloro-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer)

With 132 mg of the compound obtained in Step 271-2 (Isomer B) and 105 mg of 4-methoxy-2-(trifluoromethoxy) benzene sulfonyl chloride as starting materials, 101 mg of the title compound (amorphous) was obtained by a similar method to Example 2.

$[α]_D^{30}$=−59° (c=1.54, CHCl$_3$)
MS (ESI pos.) m/z: 720 ([M+Na]⁺)
$^1$H-NMR (300 MHz, CDCl$_3$) δ (ppm); 1.93-2.07 (m, 1H), 2.10-2.24 (m, 1H), 2.48 (s, 3H), 2.68 (s, 3H), 3.07 (d, J=10.41 Hz, 1H), 3.75 (dd, J=10.49, 4.27 Hz, 1H), 3.90 (s, 3H), 4.45-4.62 (m, 1H), 4.47-4.61 (m, 1H), 5.16 (d, J=1.55 Hz, 1H), 5.47 (d, J=1.55 Hz, 1H), 6.60-6.69 (m, 1H), 6.75 (t, J=7.93 Hz, 1H), 6.84-6.96 (m, 2H), 7.02 (dd, J=8.24, 0.78 Hz, 1H), 7.27 (t, J=8.24 Hz, 1H), 7.32-7.42 (m, 1H), 7.99 (d, J=8.08 Hz, 1H), 8.41 (d, J=8.86 Hz, 1H)

Example 272

Synthesis of (4R)-1-[3-(1,3-benzodioxol-4-yl)-1-{[4-methoxy-2-(trifluoromethoxy)phenyl]sulfonyl}-2-oxo-5-(trifluoromethoxy)-2,3-dihydro-1H-indol-3-yl]-4-hydroxy-N,N-dimethyl-L-prolinamide

Step 272-1: Synthesis of 3-(1,3-benzodioxol-4-yl)-3-hydroxy-5-(trifluoromethoxy)-1,3-dihydro-2H-indol-2-one With 7.80 g of 4-bromo-1,3-benzodioxol and 2.30 g of 5-trifluoromethoxyisatin as starting materials, 1.65 g of the title compound was obtained by a similar method to Step 21-1.

MS (ESI pos.) m/z: 376 ([M+Na]⁺), (ESI neg.) m/z: 352 ([M−H]⁻)
$^1$H-NMR (300 MHz, DMSO-$d_6$) δ (ppm); 5.78 (dd, J=18.19, 0.93 Hz, 2H), 6.78-7.05 (m, 4H), 7.15-7.32 (m, 2H), 10.64 (s, 1H)

Step 272-2: Synthesis of (4R)-1-[3-(1,3-benzodioxol-4-yl)-2-oxo-5-(trifluoromethoxy)-2,3-dihydro-1H-indol-3-yl]-4-hydroxy-N,N-dimethyl-L-prolinamide From 800 mg of the compound obtained in Step 272-1 and 528 mg of (4R)-4-hydroxy-N,N-dimethyl-L-prolinamide hydrochloride, 1.13 g of a mixture of two species of diastereoisomers of the title compound was obtained by a similar method to Step 21-2.

MS (ESI pos.) m/z: 494 ([M+H]$^+$), (ESI neg.) m/z: 492 ([M–H]$^-$)

$^1$H-NMR (300 MHz, CDCl$_3$) δ (ppm); 1.90-2.05 (m, 1H), 2.14-2.31 (m, 1H), 2.54-2.95 (m, 6H), 3.10 (d, J=8.55 Hz, 0.7H), 3.56-3.62 (m, 0.7H), 3.64 (d, J=4.20 Hz, 0.3H), 3.79-3.89 (m, 0.3H), 3.89-4.00 (m, 0.3H), 4.28-4.39 (m, 0.3H), 4.38-4.51 (m, 0.7H), 4.85 (dd, J=8.16, 6.45 Hz, 0.7H), 5.89 (dd, J=7.85, 1.48 Hz, 0.6H), 6.00 (dd, J=9.56, 1.32 Hz, 1.4H), 6.73-7.59 (m, 6H), 8.85 (s, 0.7H), 9.70 (s, 0.3H)

Step 272-3: Synthesis of (4R)-1-[3-(1,3-benzodioxol-4-yl)-1-{[4-methoxy-2-(trifluoromethoxy)phenyl]sulfonyl}-2-oxo-5-(trifluoromethoxy)-2,3-dihydro-1H-indol-3-yl]-4-hydroxy-N,N-dimethyl-L-prolinamide With 373 mg of the compound obtained in Step 272-2 and 263 mg of 4-methoxy-2-(trifluoromethoxy)benzene sulfonyl chloride as starting materials, respectively 213 mg (Isomer A, amorphous) and 134 mg (Isomer B, amorphous) of isomers of the title compound were obtained by a similar method to Example 2.

Isomer A: MS (ESI pos.) m/z: 748 ([M+H]$^+$)

$^1$H-NMR (300 MHz, CDCl$_3$) δ (ppm); 1.78-1.91 (m, 1H), 1.97-2.13 (m, 1H), 2.56 (s, 3H), 2.66 (s, 3H), 3.39-3.48 (m, 1H), 3.51-3.62 (m, 1H), 3.90-4.01 (m, 4H), 4.30-4.39 (m, 1H), 5.40 (d, J=1.71 Hz, 1H), 5.52 (d, J=1.71 Hz, 1H), 6.71 (dd, J=7.69, 1.17 Hz, 1H), 6.85-6.93 (m, 2H), 6.96 (dd, J=9.01, 2.33 Hz, 1H), 7.04 (d, J=2.64 Hz, 1H), 7.13-7.22 (m, 1H), 7.54 (dd, J=8.24, 1.09 Hz, 1H), 8.00 (d, J=9.01 Hz, 1H), 8.32 (d, J=8.86 Hz, 1H)

Isomer B: $[α]_D^{30}$=–168° (c=0.933, CHCl$_3$)

MS (ESI pos.) m/z: 748 ([M+H]$^+$)

$^1$H-NMR (300 MHz, CDCl$_3$) δ (ppm); 1.82-1.95 (m, 1H), 2.05-2.18 (m, 1H), 2.46-2.72 (m, 2H), 2.50 (s, 3H), 2.64 (s, 3H), 3.57 (dd, J=10.18, 3.96 Hz, 1H), 3.91 (s, 3H), 4.33-4.45 (m, 1H), 4.58 (dd, J=8.55, 5.44 Hz, 1H), 5.64 (d, J=1.40 Hz, 1H), 5.77 (d, J=1.40 Hz, 1H), 6.72 (d, J=4.82 Hz, 2H), 6.79-6.90 (m, 2H), 6.97 (dd, J=9.01, 2.33 Hz, 1H), 7.11-7.20 (m, 1H), 7.34-7.41 (m, 1H), 7.97 (d, J=9.01 Hz, 1H), 8.41 (d, J=9.01 Hz, 1H)

Example 273

Synthesis of (2S)-1-[5-chloro-1-{[4-methoxy-2-(trifluoromethoxy)phenyl]sulfonyl}-3-(2-naphthyl)-2-oxo-2,3-dihydro-1H-indol-3-yl]-N,N-dimethylpiperidine-2-carboxamide (levorotatory isomer)

Step 273-1: Synthesis of 5-chloro-3-hydroxy-3-(2-naphthyl)-1,3-dihydro-2H-indol-2-one With 11.1 g of 2-bromonaphthalene and 5.00 g of 5-chloroisatin as starting materials, 7.81 g of the title compound was obtained by a similar method to Step 21-1.

MS (ESI neg.) m/z: 308 ([M–H]$^-$)

$^1$H-NMR (300 MHz, DMSO-d$_6$) δ (ppm); 6.89-7.02 (m, 2H), 7.14 (d, J=2.33 Hz, 1H), 7.27-7.38 (m, 2H), 7.45-7.58 (m, 2H), 7.79-7.98 (m, 4H), 10.64 (s, 1H)

Step 273-2: Synthesis of (2S)-1-[5-chloro-3-(2-naphthyl)-2-oxo-2,3-dihydro-1H-indol-3-yl]-N,N-dimethylpiperidine-2-carboxamide From 2.02 g of the compound obtained in Step 273-1 and (2S)—N,N-dimethylpiperidine-2-carboxamide trifluoroacetate (6.51 mmol), respectively 1.77 g (Isomer A), 476 mg (Isomer B) of two species of diastereoisomers of the title compound were obtained by a similar method to Step 21-2.

Isomer A: MS (ESI neg.) m/z: 446 ([M–H]$^-$)

$^1$H-NMR (300 MHz, DMSO-d$_6$) δ (ppm); 1.37-1.94 (m, 7H), 2.34 (s, 3H), 2.76 (s, 3H), 3.79-3.94 (m, 1H), 4.05-4.12 (m, 1H), 6.86-6.93 (m, 1H), 7.29-7.38 (m, 2H), 7.40-7.61 (m, 3H), 7.75-8.00 (m, 4H), 10.73 (s, 1H)

Isomer B: MS (ESI neg.) m/z: 446 ([M–H]$^-$)

$^1$H-NMR (300 MHz, DMSO-d$_6$) δ (ppm); 1.49 (s, 6H), 1.84-1.98 (m, 1H), 2.19 (s, 3H), 2.64 (s, 3H), 3.86-3.99 (m, 1H), 4.06-4.15 (m, 1H), 6.85 (d, J=8.39 Hz, 1H), 7.14 (d, J=2.18 Hz, 1H), 7.22 (dd, J=8.32, 2.25 Hz, 1H), 7.44-7.55 (m, 2H), 7.76-7.99 (m, 5H), 10.62 (s, 1H)

Step 273-3: Synthesis of (2S)-1-[5-chloro-1-{[4-methoxy-2-(trifluoromethoxy)phenyl]sulfonyl}-3-(2-naphthyl)-2-oxo-2,3-dihydro-1H-indol-3-yl]-N,N-dimethylpiperidine-2-carboxamide (levorotatory isomer)

With 200 mg of the compound obtained in Step 273-2 (Isomer B) and 154 mg of 4-methoxy-2-(trifluoromethoxy) benzene sulfonyl chloride as starting materials, 198 mg of the title compound (amorphous) was obtained by a similar method to Example 2.

$[α]_D^{30}$=–239° (c=0.297, CHCl$_3$)

MS (ESI pos.) m/z: 724 ([M+Na]$^+$)

$^1$H-NMR (300 MHz, DMSO-d$_6$) δ (ppm); 1.60 (m, 5H), 1.86-2.02 (m, 1H), 2.24 (s, 3H), 2.41-2.48 (m, 1H) 2.67 (s, 3H) 3.71-3.85 (m, 1H) 3.99 (s, 3H) 4.01-4.06 (m, 1H) 7.08-7.15 (m, 1H) 7.16-7.21 (m, 1H) 7.32-7.41 (m, 2H) 7.44-7.62 (m, 5H) 7.79 (d, J=8.86 Hz, 1H) 7.85-7.94 (m, 2H) 8.30 (d, J=9.01 Hz, 1H)

Synthesis Example 2

Synthesis of (4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer; identical compound to Example 103)

A solution of 152 g of the compound obtained in Step 138-4 and 2.78 g of K$_2$CO$_3$ in MeOH (1.5 L) was stirred at room temperature for 10 hours. The solution was neutralized with 1 mol/L hydrochloric acid under ice cooling, then, the resulting mixture was concentrated under reduced pressure. The obtained crude form was purified by column chromatography (silicagel 60N, CHCl$_3$/MeOH/NH$_4$OH=100/2/0.2 to 100/7/0.7; v/v/v) to obtain 132.5 g of the title compound (pale yellow amorphous). The obtained amorphous was dissolved in EtOH (1.46 L), water (1.13 L) was added dropwise into the solution at room temperature over 45 minute, then the solution was stirred for 17.5 hours. After stirring for 2.5 hours under ice cooling, the precipitation was collected by filtration to obtain 130.1 g of the title compound (colorless crystal).

m.p.: 192-193° C. (EtOH—H$_2$O)

Test Example 1

1) V1b, V1a and V2 receptor binding assay

Preparation of each crude membrane sample prepared from Human V1b, V1a and V2 receptor expressing cells and receptor binding assay using these, were carried out according to the methods of Br. J. Pharmacol. (1998) 125, 1463-1470. A summary of the methods is given below.

CHO cells expressing human V1b receptor, and 293F T cells expressing human V1a and V2 receptors were homogenized respectively in 50 mmol/L Tris hydrochloric acid buffer solution (pH7.4, containing 10 mmol/L magnesium chloride). Each obtained homogenate was centrifuged for 20 minutes at 50,000×g and 4° C., the sediment was resuspended in a 50 mmol/L Tris hydrochloric acid buffer solution (pH7.4, containing 10 mmol/L magnesium chloride and 0.1% bovine serum albumin), which served as a crude membrane preparation. This crude membrane preparation was added with [$^3$H] (Arg$^8$) vasopressin (final concentration: 0.1 nmol/L to 0.4 nmol/L), and each test drug (final concentration: 0.1 nmol/L to 1μmol/L or 0.01 nmol/L to 0.1 μmol/L) to 22° C. for 90 minutes. After the end of the reaction, the reaction solution was filtrated using a GF/C glass fiber filter, which had been presoaked in 0.3% polyethyleneimine for two hours. After the GF/C glass fiber filter was dried sufficiently, scintillator was added, and the radioactivity on the filter was measured using a liquid scintillation counter. Binding of [$^3$H] (Arg$^8$)-vasopressin in the presence of (Arg$^8$)-vasopressin, in the amounts of 0.1 μmol/L in the V1b receptor binding assay and 5 μmol/L in the V1a and V2 receptor binding assay, were taken as non-specific binding, and the value obtained by subtracting non-specific binding from the total binding in the absence (Arg$^8$)-vasopressin served as specific binding. Based on the inhibition curve at each compound concentration, the 50% inhibition concentration (IC$_{50}$ value) of the test drug was calculated. The results are shown in Table 1.

In addition, regarding the V1b receptor binding assay, the value obtained by, subtracting the amount of binding in the presence of 0.1 μmol/L test drug from the total amount of binding, divided by the amount of specific binding, served as the rate of inhibition (% of inhibition) of the test drug at the concentration tested. The results of measurement of the rate of inhibition are shown in Table 2.

In addition, structural formulae of the compounds obtained in each example are shown in Table 3.

TABLE 1

Result of receptor binding test (IC$_{50}$ value)

| Example No. | Isomer | IC50 value (nmol/L) V1b | V1a | V2 |
|---|---|---|---|---|
| SSR149415 (Subject Compound) | | 1.2 | 42 | 595 |
| 2 | | 2.6 | 743 | 4014 |
| 5 | | 16 | 2180 | >10000 |
| 31 | | 5.2 | 953 | >10000 |
| 38 | A | 31 | >10000 | >10000 |
| 41 | | 7.1 | 3763 | >10000 |
| 61 | | 15 | 1470 | >10000 |
| 71 | | 6.3 | 4050 | >10000 |
| 81 | | 18 | 677 | >10000 |
| 103 | | 2.3 | 504 | 3370 |
| 116 | | 2.9 | 653 | >10000 |
| 120 | | 11 | 6790 | >10000 |
| 126 | | 15 | 8240 | >10000 |
| 140 | | 1.1 | 355 | 3190 |
| 147 | | 1.2 | 1110 | 5650 |
| 170 | | 0.56 | 65.1 | 4050 |
| 191 | | 1.8 | 293 | 3340 |
| 192 | | 4.3 | 792 | >10000 |
| 195 | A | 0.56 | 573 | >10000 |
| 217 | | 0.96 | 404 | 3100 |
| 225 | | 0.32 | 101 | 5050 |

TABLE 2

Rate of inhibition (V1b: % of inhibition)

| Example No. | Rate of inhibition (%) |
|---|---|
| 4 | 102 |
| 7 | 96 |
| 40 | 66 |
| 43 | 92 |
| 58 | 77 |
| 80 | 69 |
| 83 | 72 |
| 86 | 86 |
| 89 | 104 |
| 90 | 97 |
| 92 | 102 |
| 96 | 73 |
| 102 | 102 |
| 104 | 94 |
| 105 | 95 |
| 107 | 102 |
| 112 | 55 |
| 117 | 95 |
| 118 | 67 |
| 121 | 47 |
| 135 | 92 |
| 137 | 96 |
| 139 | 103 |
| 144 | 95 |
| 146 | 94 |
| 148 | 85 |
| 150 | 89 |
| 152 | 107 |
| 154 | 100 |
| 161 | 78 |
| 169 | 93 |
| 171 | 95 |
| 173 | 104 |
| 176 | 97 |
| 190 | 93 |
| 199 | 98 |
| 201 | 53 |
| 203 | 87 |
| 206 | 105 |
| 221 | 102 |
| 230 | 101 |
| 236 | 93 |
| 238 | 89 |
| 240 | 85 |

TABLE 3
Structure of compounds obtained in each example
| Example | Structure |
|---|---|
| 1 | 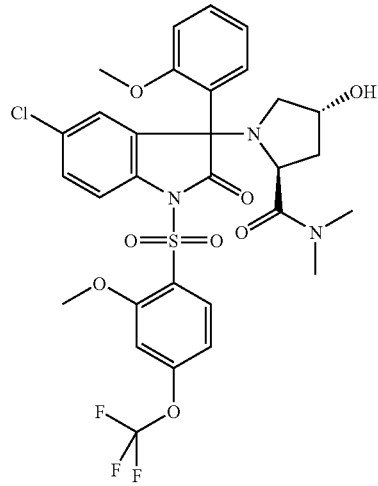 |
| 2 | 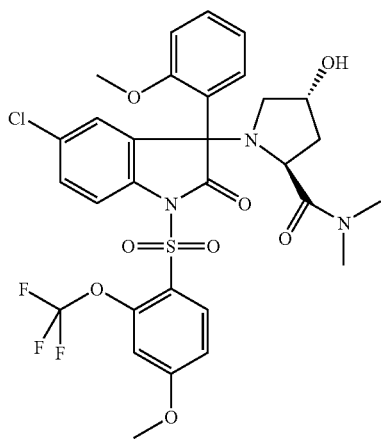 |
| 3 | 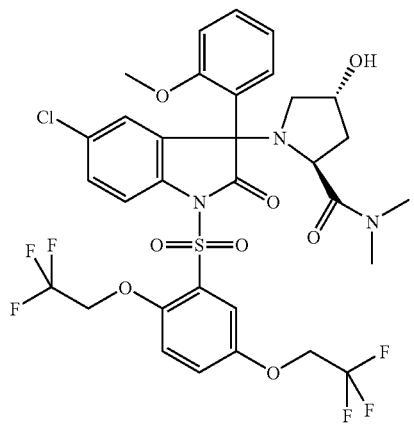 |

TABLE 3-continued
Structure of compounds obtained in each example
| Example | Structure |
|---|---|
| 4 | 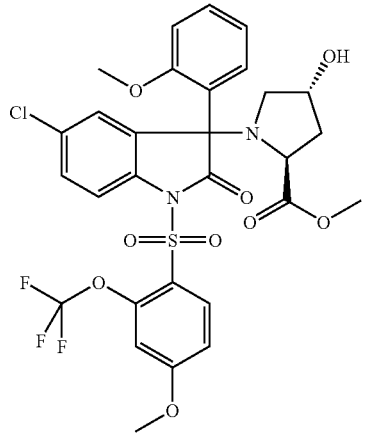 |
| 5 | 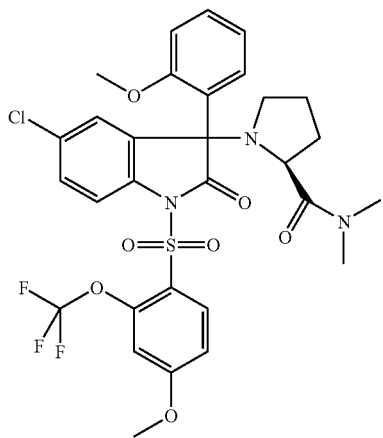 |
| 6 | 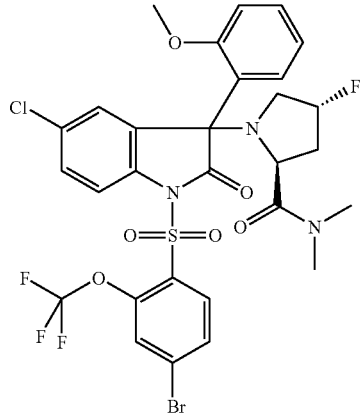 |

TABLE 3-continued

Structure of compounds obtained in each example

| Example | Structure |
|---------|-----------|
| 7 | 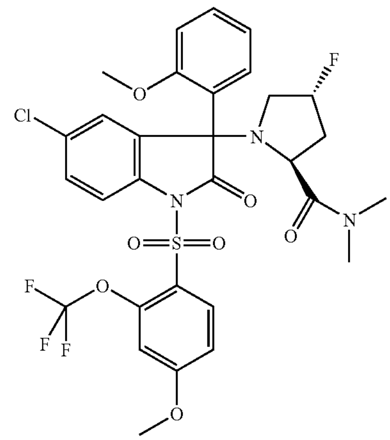 |
| 8 | 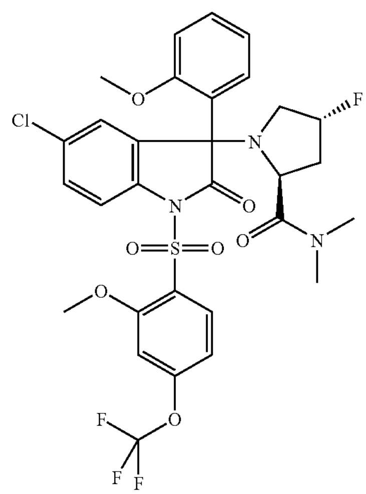 |
| 9 | 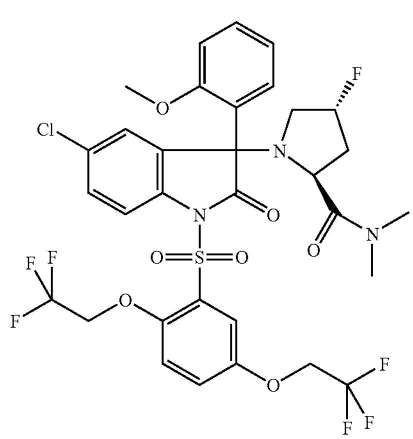 |

TABLE 3-continued
Structure of compounds obtained in each example
| Example | Structure |
|---|---|
| 10 | 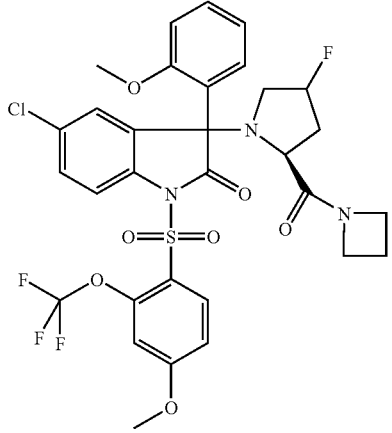 |
| 11 | 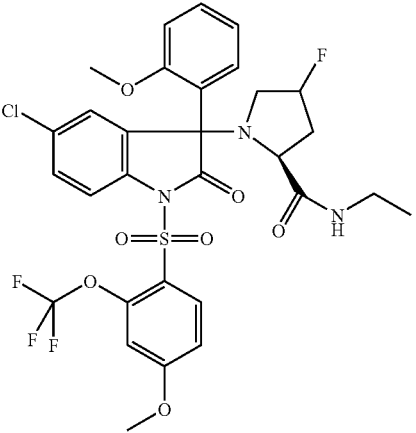 |
| 12 | 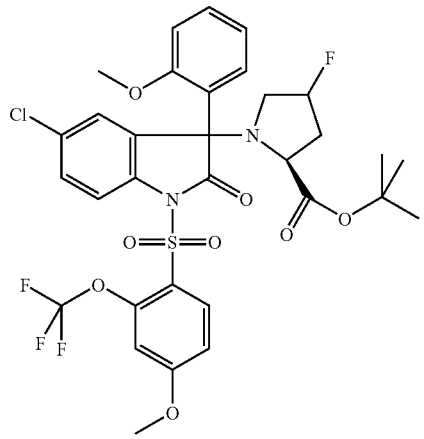 |

TABLE 3-continued
Structure of compounds obtained in each example
| Example | Structure |
|---|---|
| 13 | 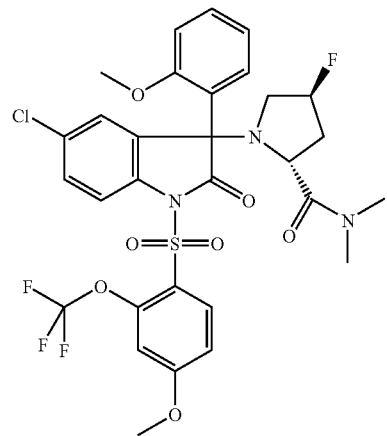 |
| 14 | 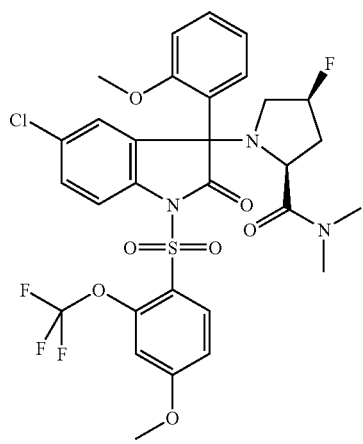 |
| 15 | 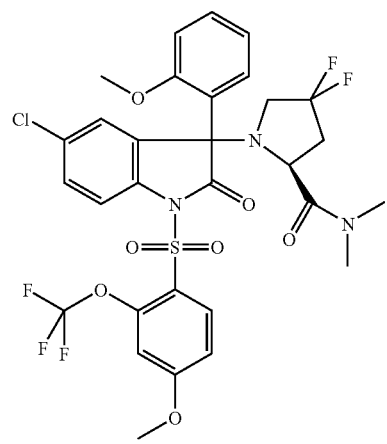 |

TABLE 3-continued

Structure of compounds obtained in each example

| Example | Structure |
|---|---|
| 16 | 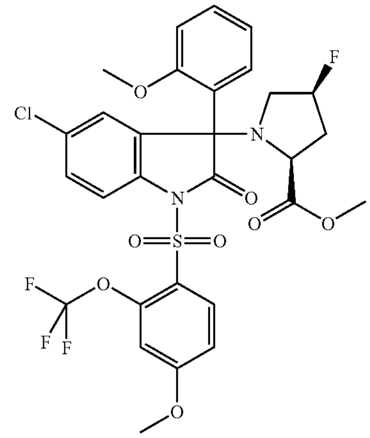 |
| 17 | 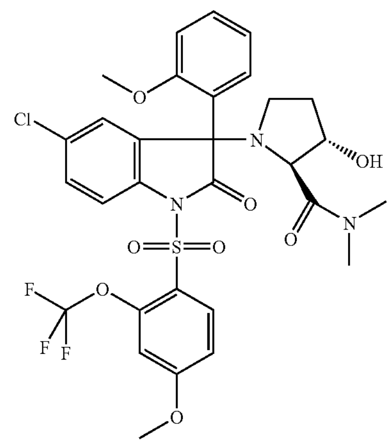 |
| 18 | 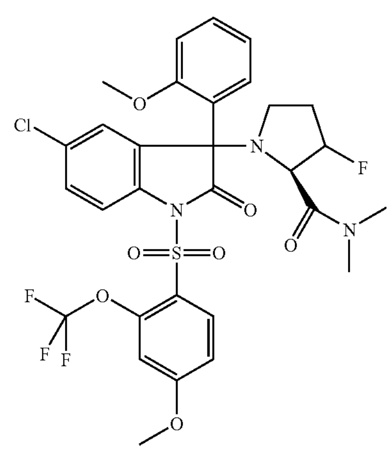 |

TABLE 3-continued
| Example | Structure |
| --- | --- |
| 19 | 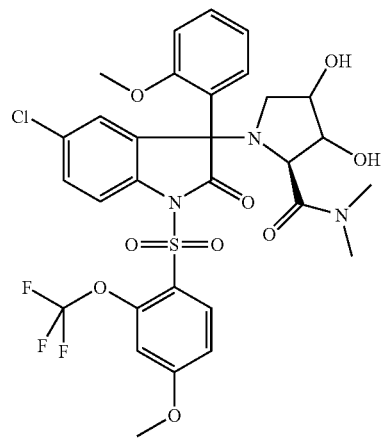 |
| 20 | 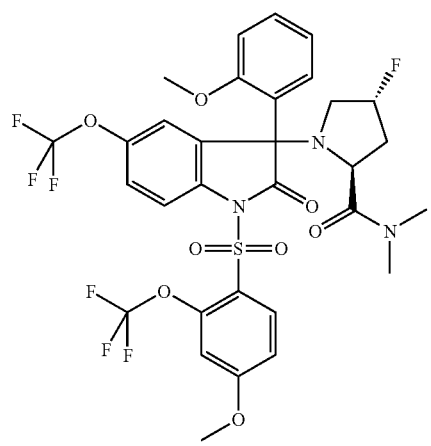 |
| 21 | 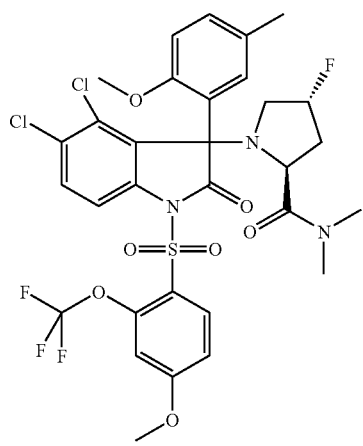 |

TABLE 3-continued
Structure of compounds obtained in each example
| Example | Structure |
|---|---|
| 22 | 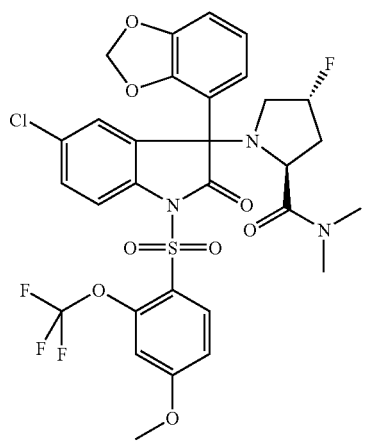 |
| 23 | 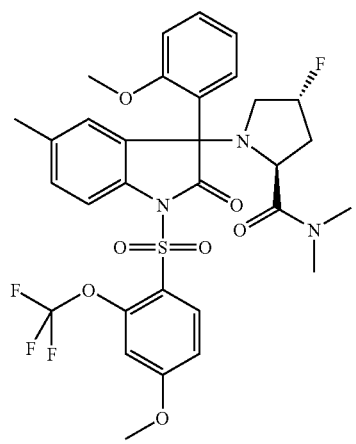 |
| 24 | 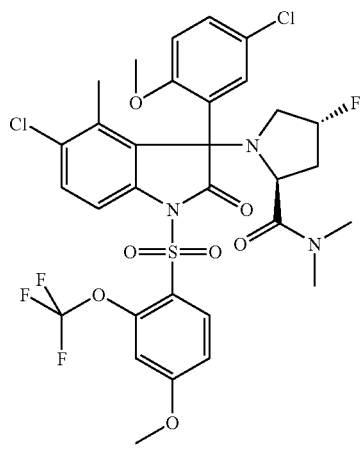 |

TABLE 3-continued

Structure of compounds obtained in each example

| Example | Structure |
|---------|-----------|
| 25 | 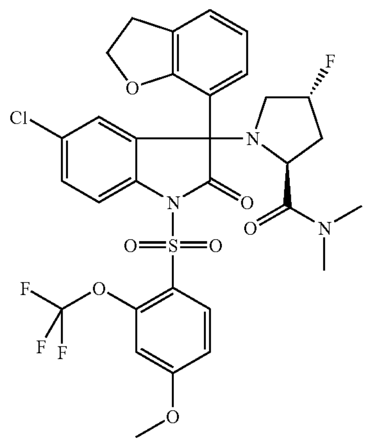 |
| 26 | 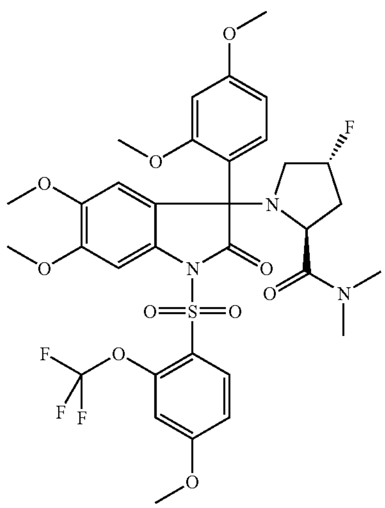 |
| 27 | 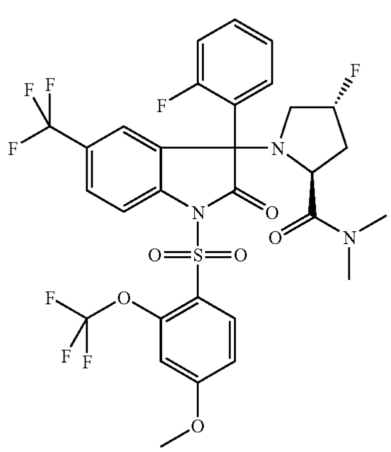 |

TABLE 3-continued

Structure of compounds obtained in each example

| Example | Structure |
|---|---|
| 28 | 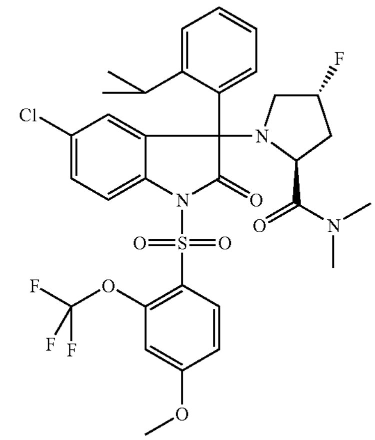 |
| 29 | 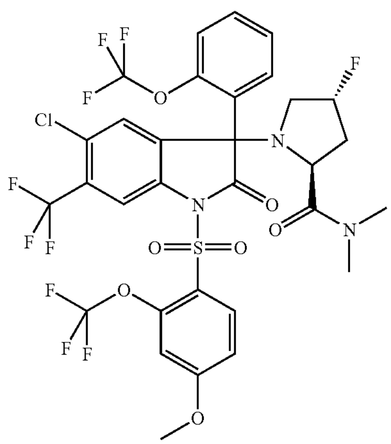 |
| 30 | 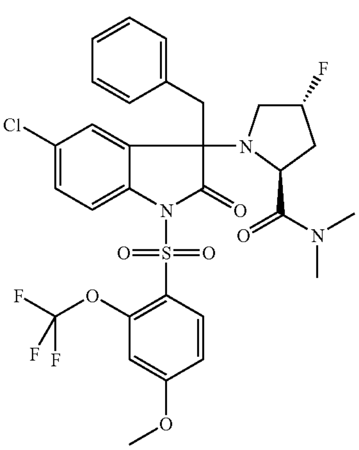 |

TABLE 3-continued
Structure of compounds obtained in each example
| Example | Structure |
|---------|-----------|
| 31 | 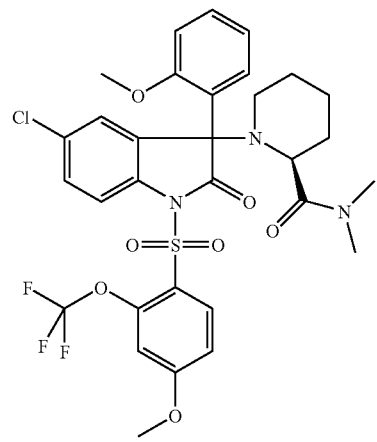 |
| 32 | 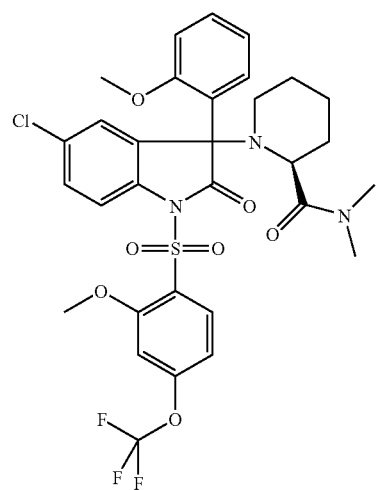 |
| 33 | 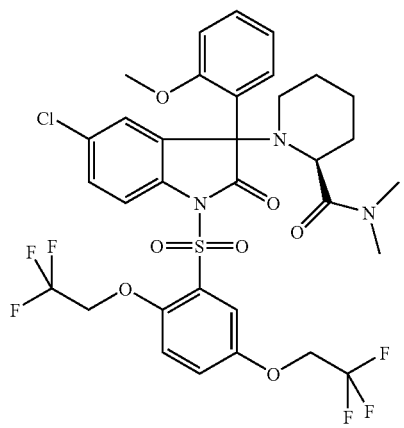 |

TABLE 3-continued

Structure of compounds obtained in each example

| Example | Structure |
|---|---|
| 34 | 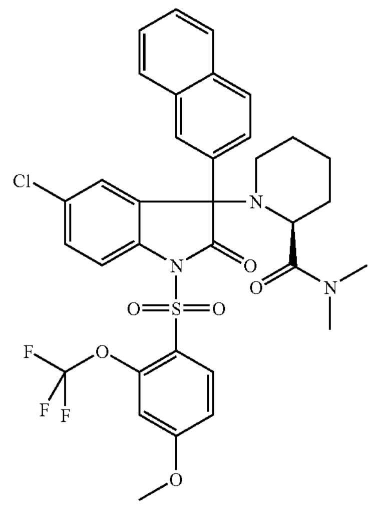 |
| 35 | 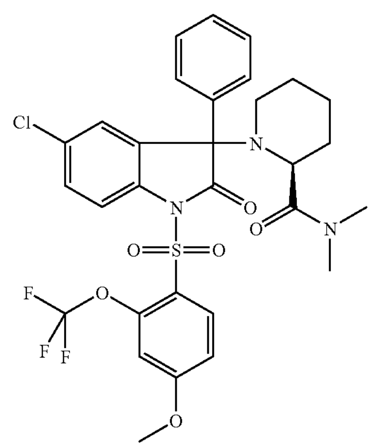 |
| 36 | 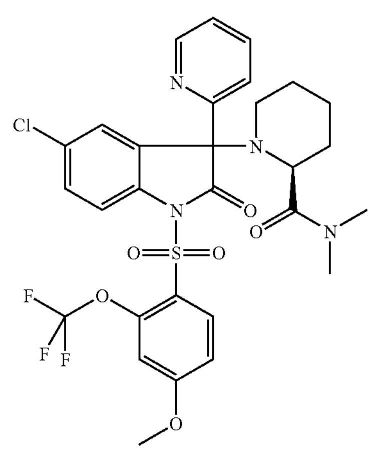 |

TABLE 3-continued

Structure of compounds obtained in each example

| Example | Structure |
|---------|-----------|
| 37 | 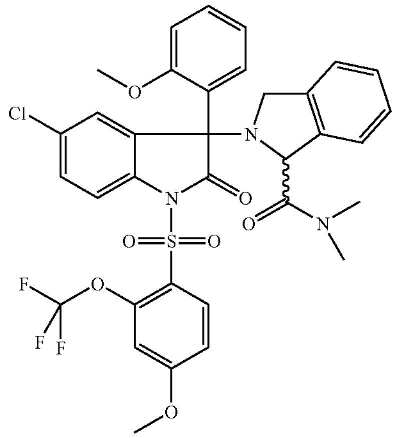 |
| 38 | 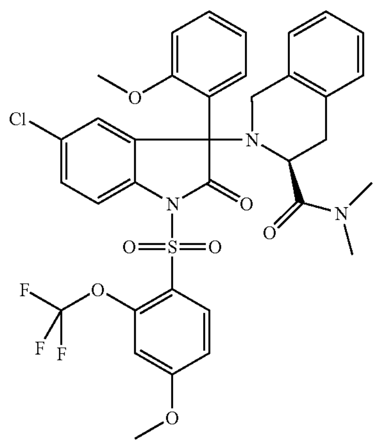 |
| 39 | 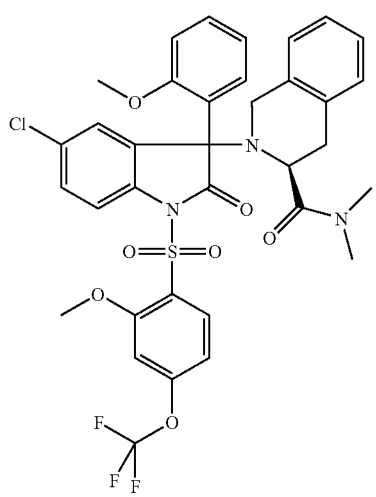 |

TABLE 3-continued

Structure of compounds obtained in each example

| Example | Structure |
|---|---|
| 40 | 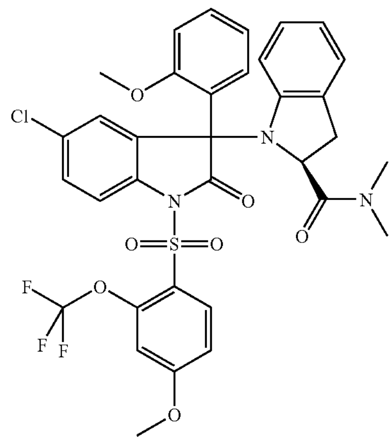 |
| 41 | 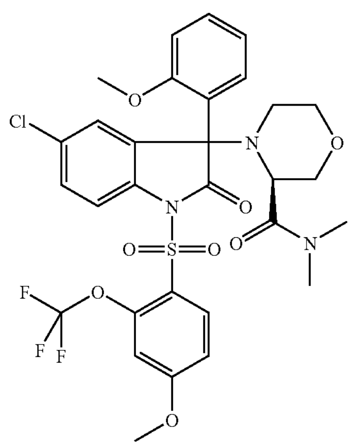 |
| 42 | 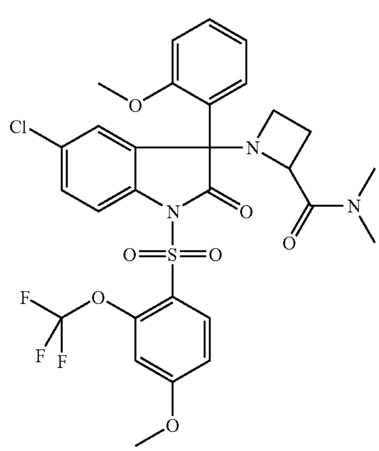 |

TABLE 3-continued
Structure of compounds obtained in each example
| Example | Structure |
|---|---|
| 43 | 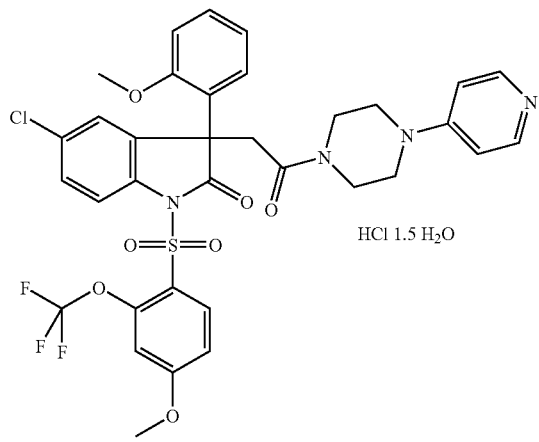 HCl 1.5 H₂O |
| 44 | 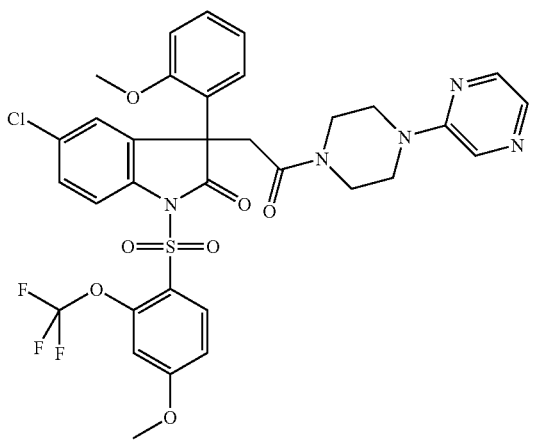 |
| 45 | 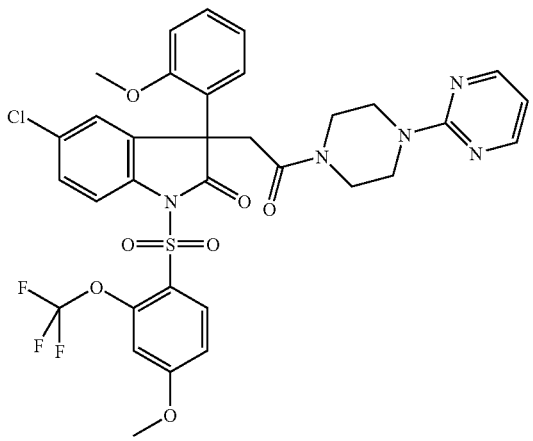 |

TABLE 3-continued
Structure of compounds obtained in each example
| Example | Structure |
|---|---|
| 46 | 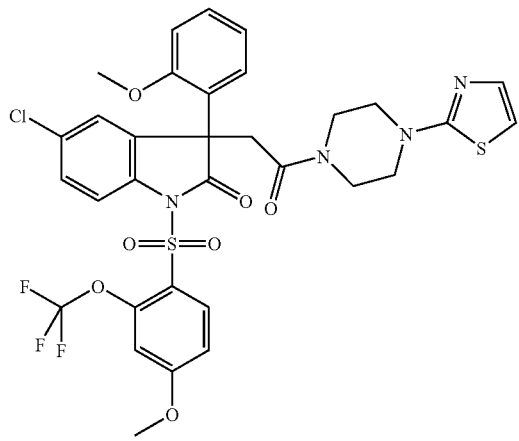 |
| 47 | 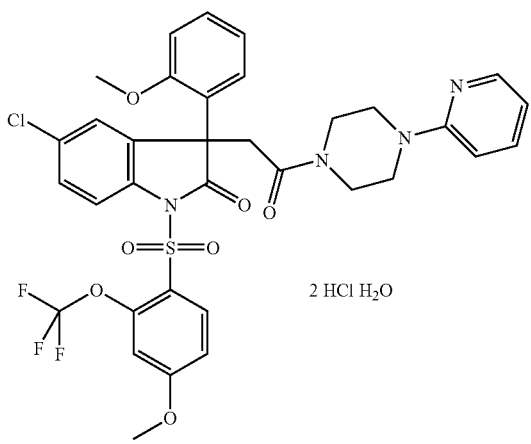 2 HCl H₂O |
| 48 | 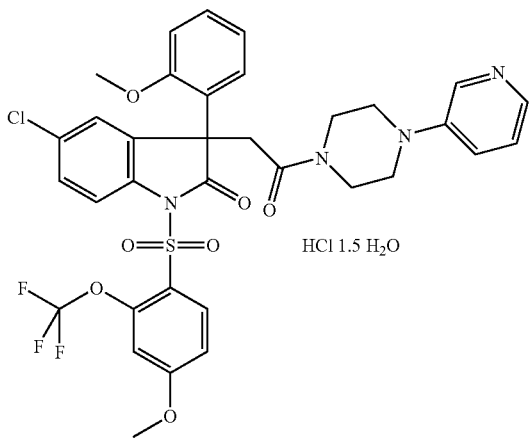 HCl 1.5 H₂O |

TABLE 3-continued

Structure of compounds obtained in each example

| Example | Structure |
|---------|-----------|
| 49 | 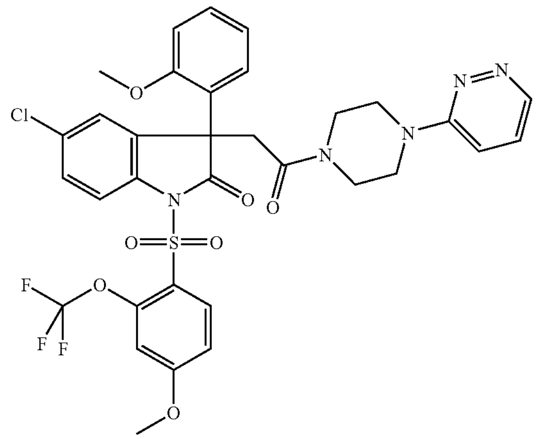 |
| 50 | 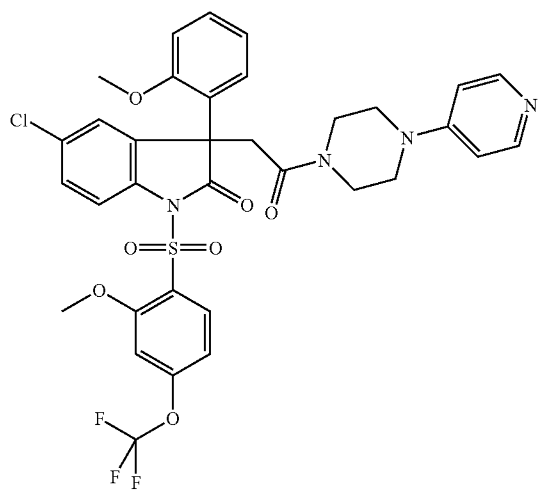 |
| 51 | 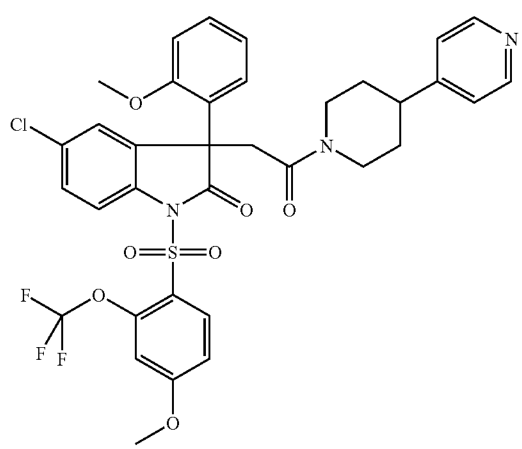 |

TABLE 3-continued

Structure of compounds obtained in each example

| Example | Structure |
|---------|-----------|
| 52 | 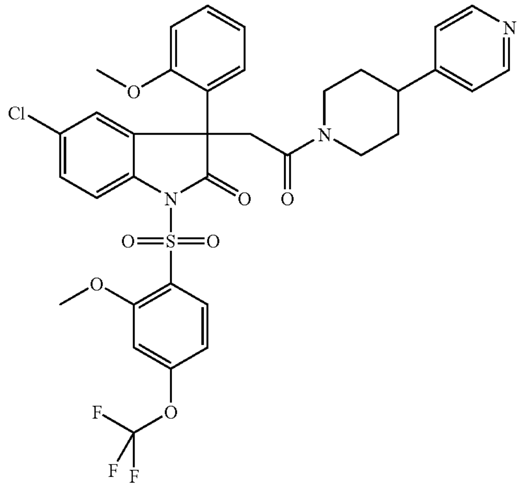 |
| 53 | 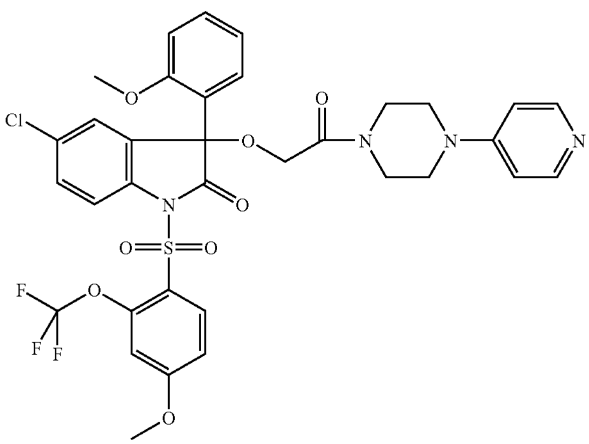 |
| 54 | HCl H₂O |

TABLE 3-continued

Structure of compounds obtained in each example

| Example | Structure |
|---|---|
| 55 | 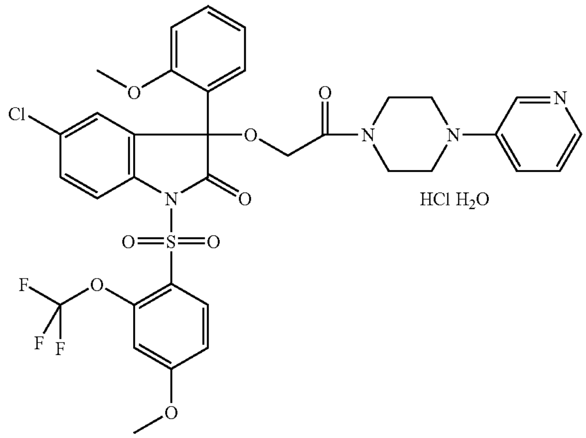 |
| 56 | 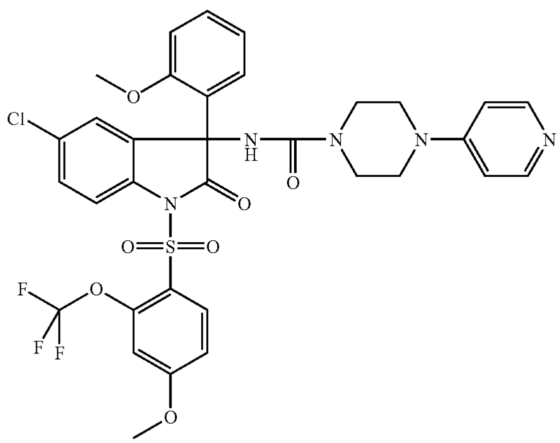 |
| 57 | 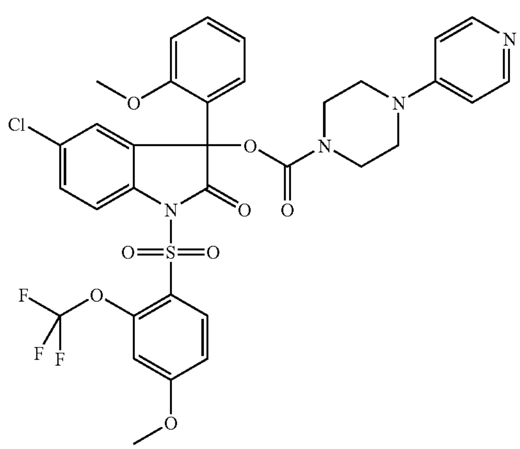 |

TABLE 3-continued

Structure of compounds obtained in each example

| Example | Structure |
|---------|-----------|
| 58 | 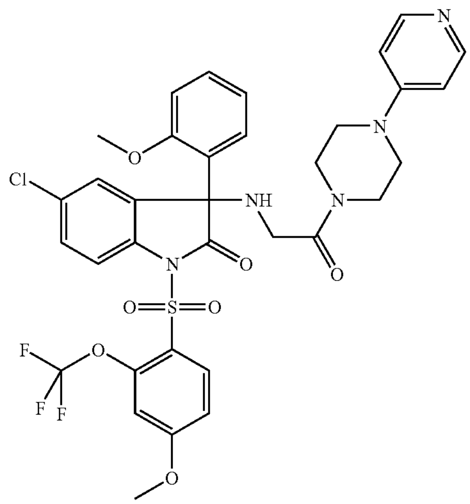 |
| 59 | 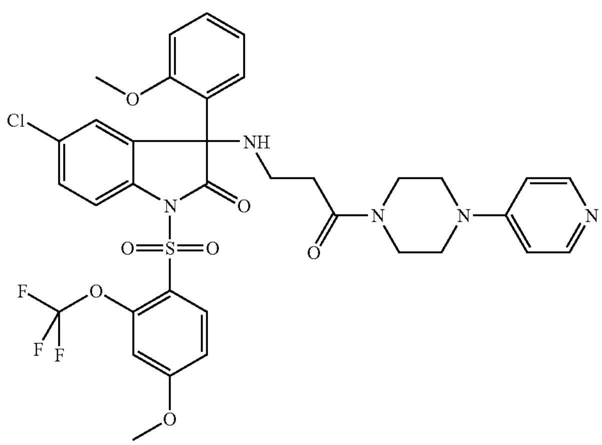 |
| 60 | 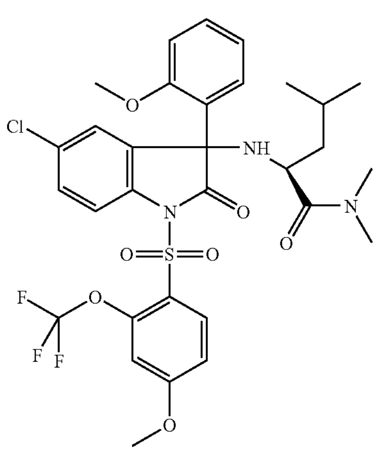 |

TABLE 3-continued
Structure of compounds obtained in each example
| Example | Structure |
|---------|-----------|
| 61 | 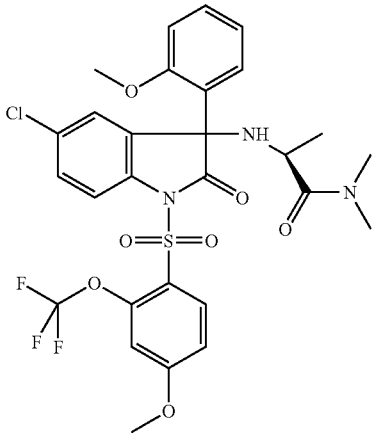 |
| 62 | 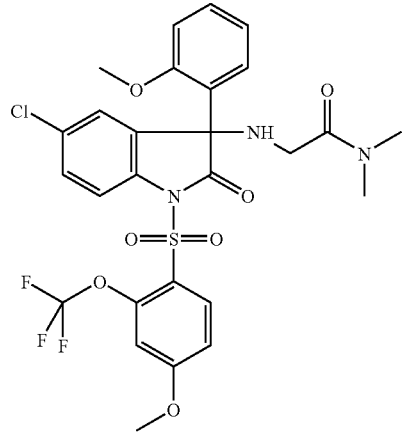 |
| 63 | 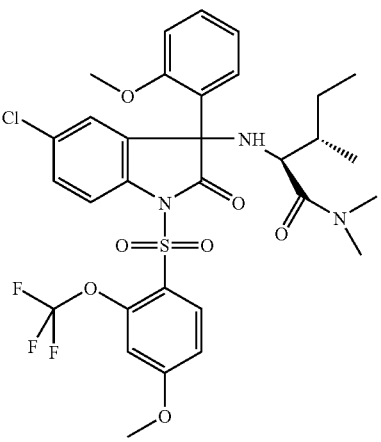 |

TABLE 3-continued

Structure of compounds obtained in each example

| Example | Structure |
|---------|-----------|
| 64 | 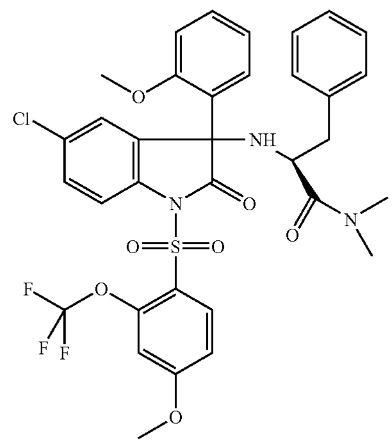 |
| 65 | 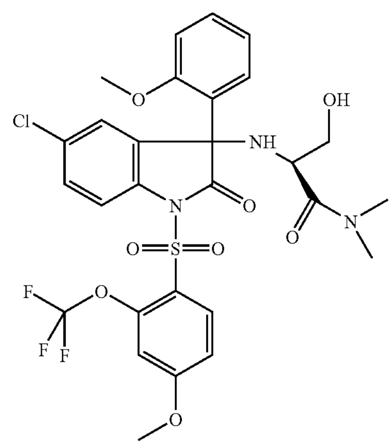 |
| 66 | 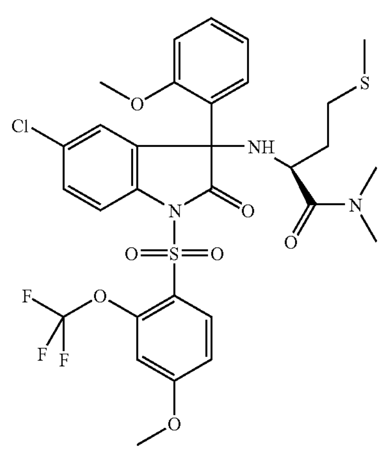 |

TABLE 3-continued

Structure of compounds obtained in each example

| Example | Structure |
|---------|-----------|
| 67 | 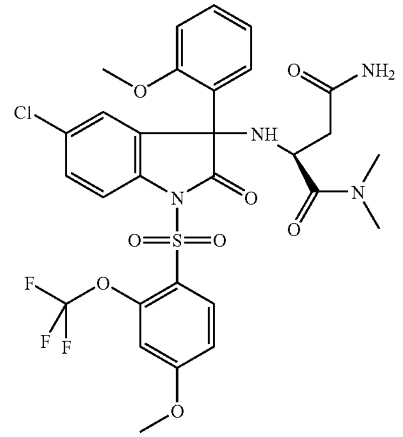 |
| 68 | 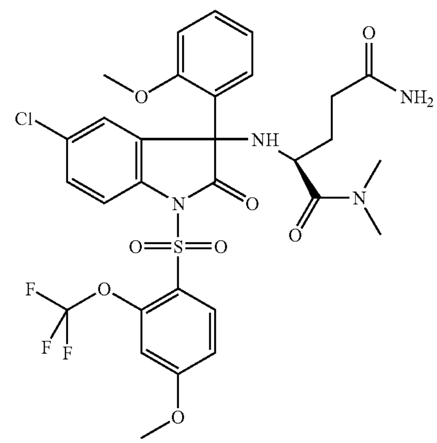 |
| 69 | 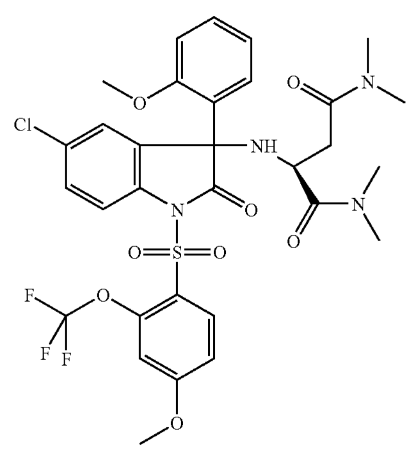 |

TABLE 3-continued
Structure of compounds obtained in each example
| Example | Structure |
|---|---|
| 70 | 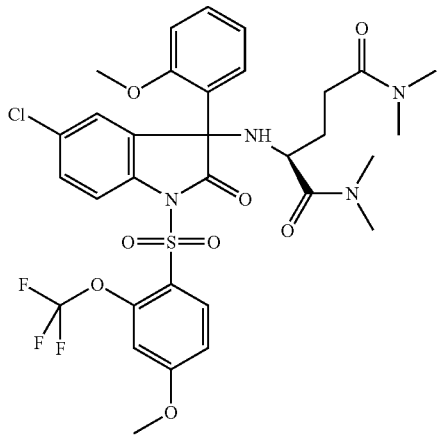 |
| 71 | 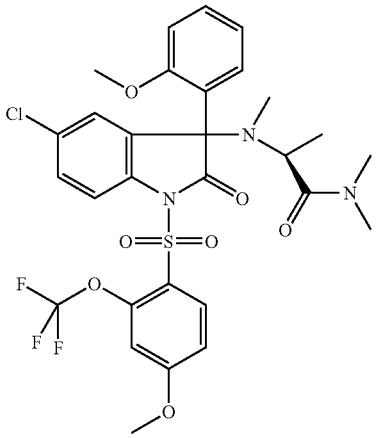 |
| 72 | 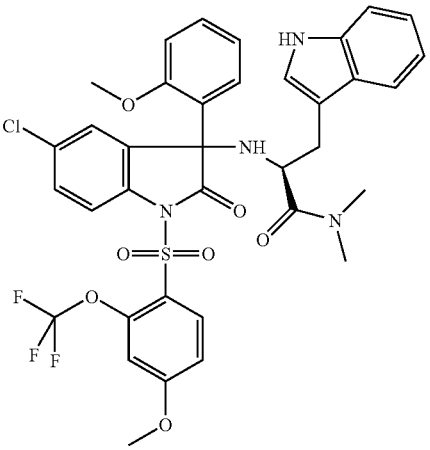 |

TABLE 3-continued
Structure of compounds obtained in each example
| Example | Structure |
|---------|-----------|
| 73 | 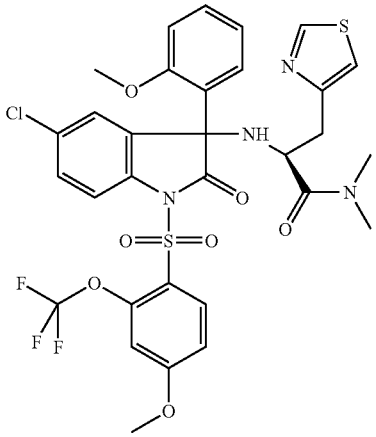 |
| 74 | 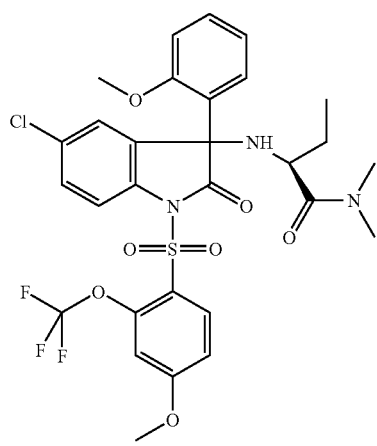 |
| 75 | 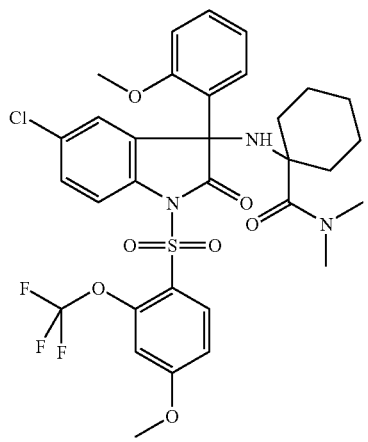 |

TABLE 3-continued
Structure of compounds obtained in each example
| Example | Structure |
|---|---|
| 76 | 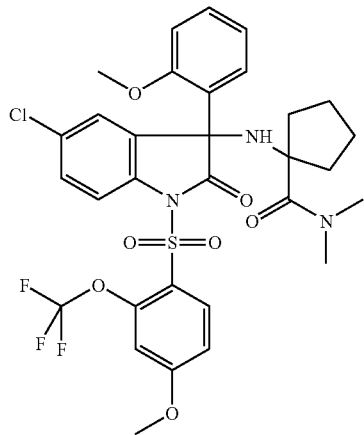 |
| 77 | 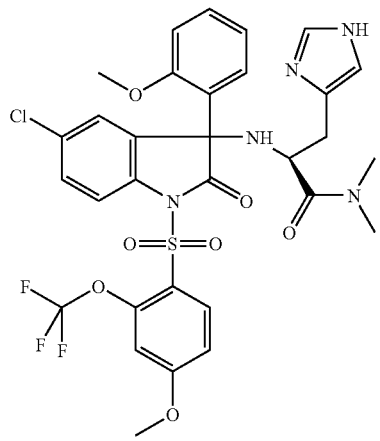 |
| 78 | 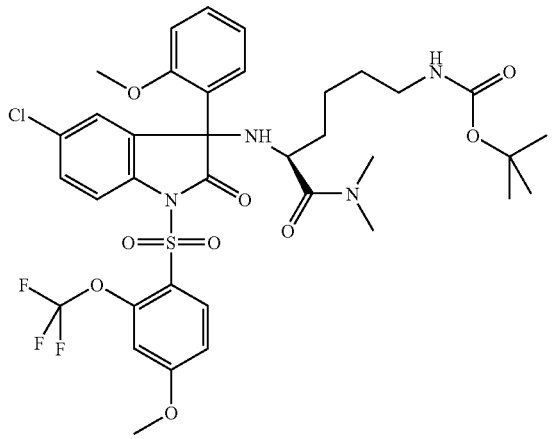 |

TABLE 3-continued
Structure of compounds obtained in each example
| Example | Structure |
|---|---|
| 79 | 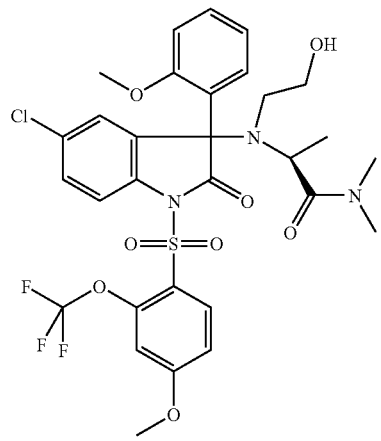 |
| 80 | 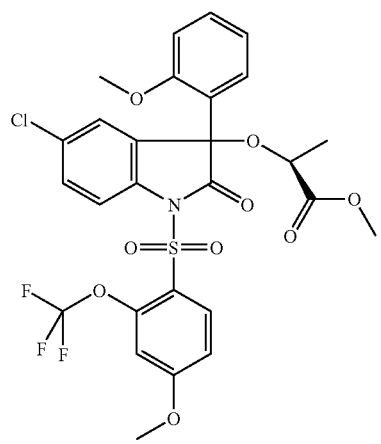 |
| 81 | 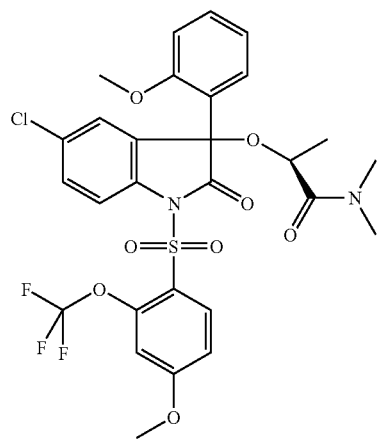 |

TABLE 3-continued
Structure of compounds obtained in each example
| Example | Structure |
|---------|-----------|
| 82 | 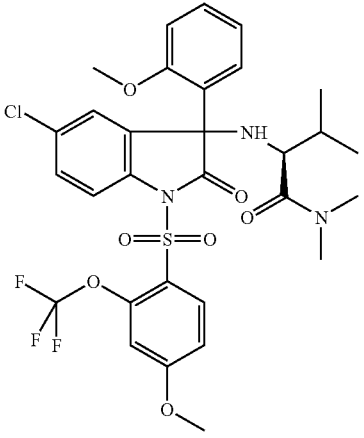 |
| 83 | 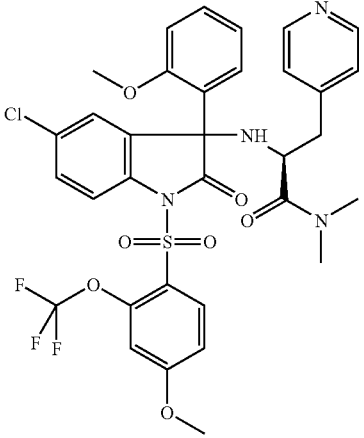 |
| 84 | 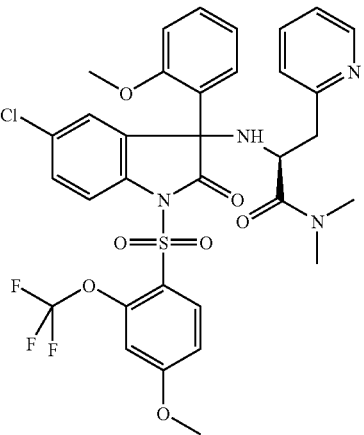 |

TABLE 3-continued

Structure of compounds obtained in each example

| Example | Structure |
|---------|-----------|
| 85 | 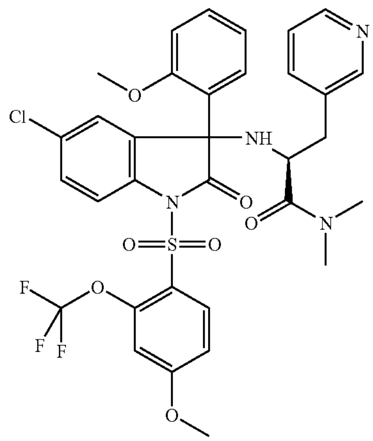 |
| 86 | 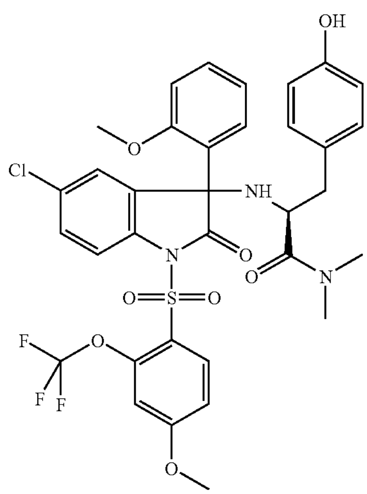 |
| 87 | 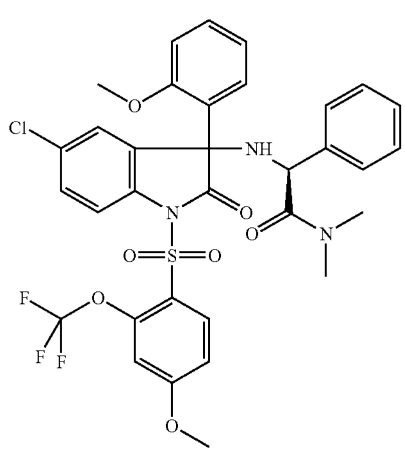 |

TABLE 3-continued
Structure of compounds obtained in each example
| Example | Structure |
|---|---|
| 88 | 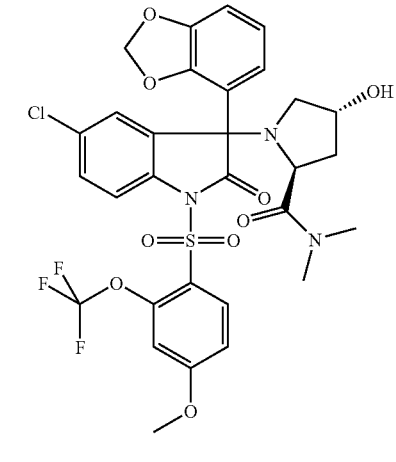 |
| 89 | 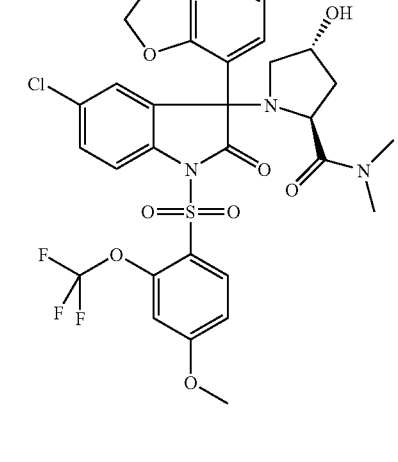 |
| 90 | 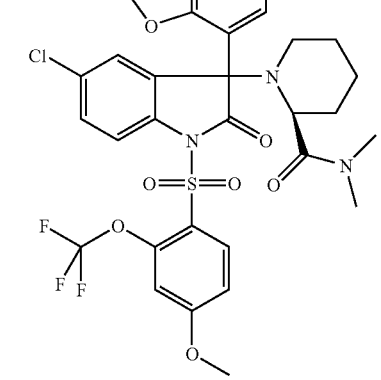 |

TABLE 3-continued
Structure of compounds obtained in each example
| Example | Structure |
|---|---|
| 91 | 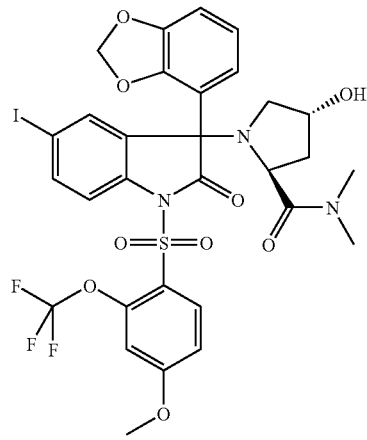 |
| 92 | 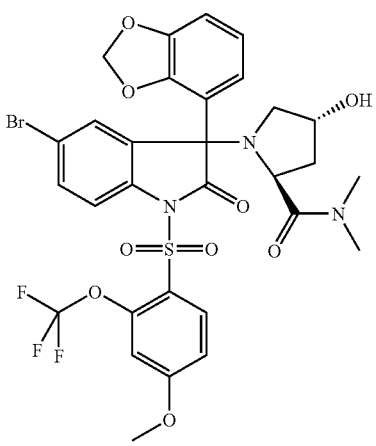 |
| 93 | 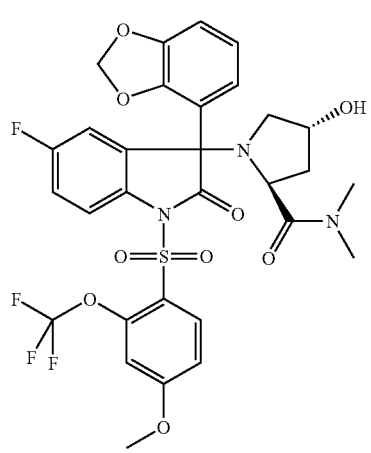 |

TABLE 3-continued
Structure of compounds obtained in each example
| Example | Structure |
|---|---|
| 94 | 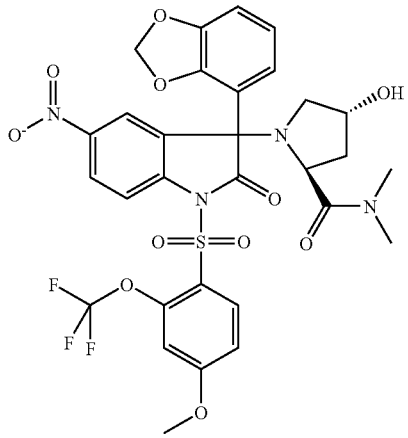 |
| 95 | 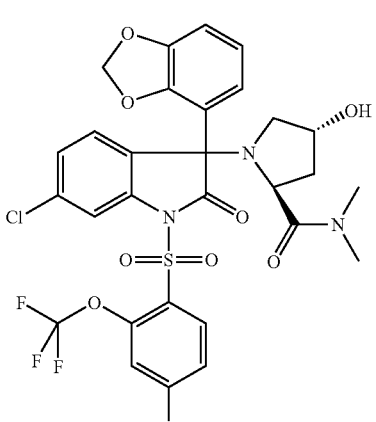 |
| 96 | 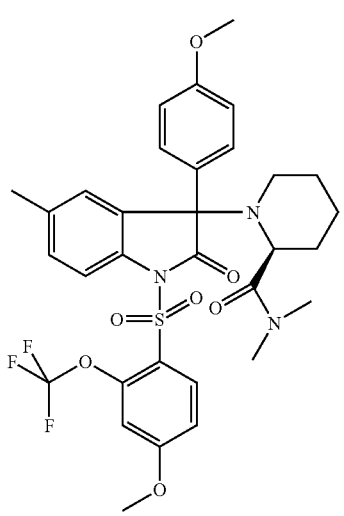 |

TABLE 3-continued

Structure of compounds obtained in each example

| Example | Structure |
|---|---|
| 97 | 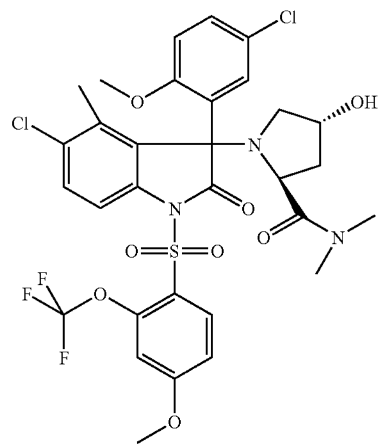 |
| 98 | 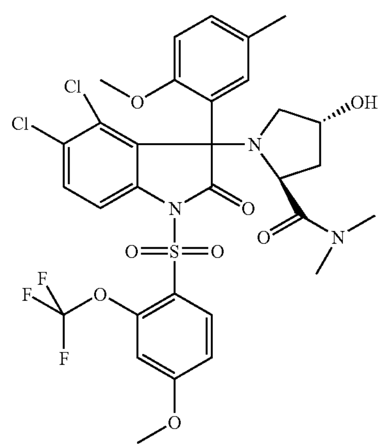 |
| 99 | 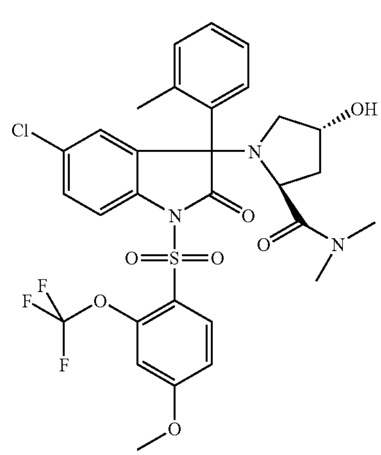 |

TABLE 3-continued

Structure of compounds obtained in each example

| Example | Structure |
|---------|-----------|
| 100 | 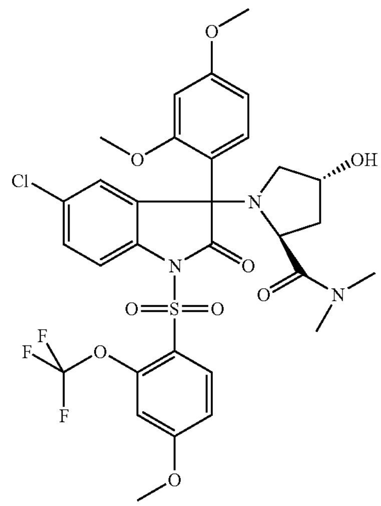 |
| 101 | 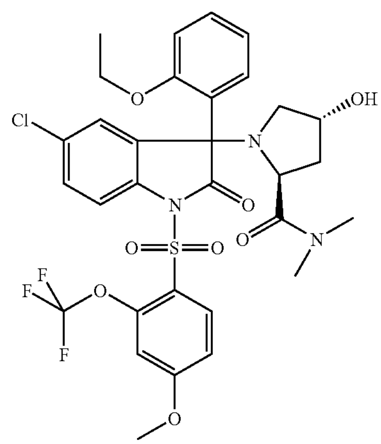 |
| 102 | 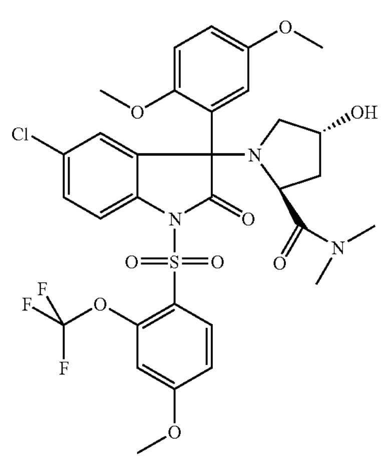 |

TABLE 3-continued
Structure of compounds obtained in each example
| Example | Structure |
|---------|-----------|
| 103 | 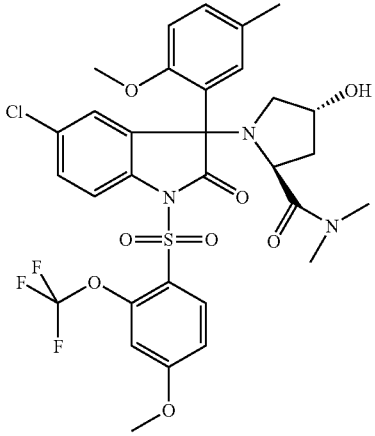 |
| 104 | 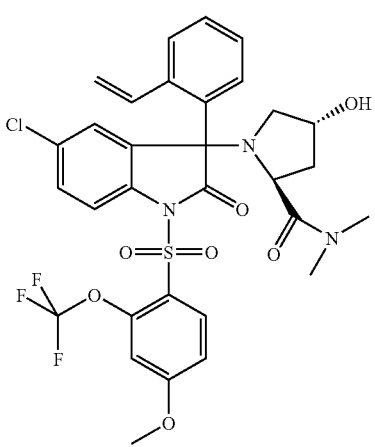 |
| 105 | 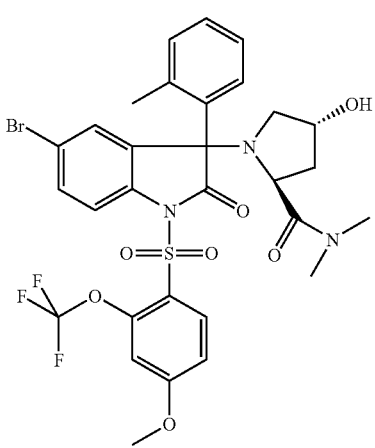 |

TABLE 3-continued
Structure of compounds obtained in each example
| Example | Structure |
|---|---|
| 106 | 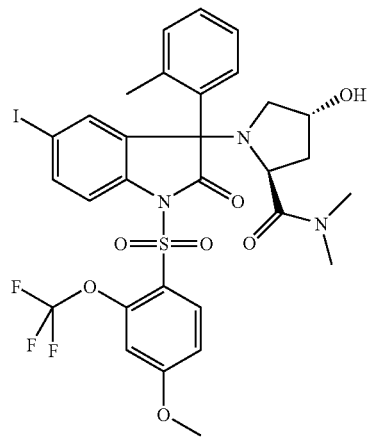 |
| 107 | 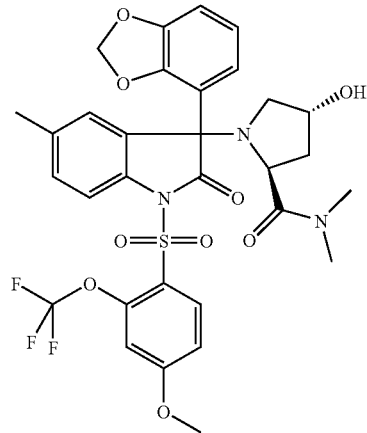 |
| 108 | 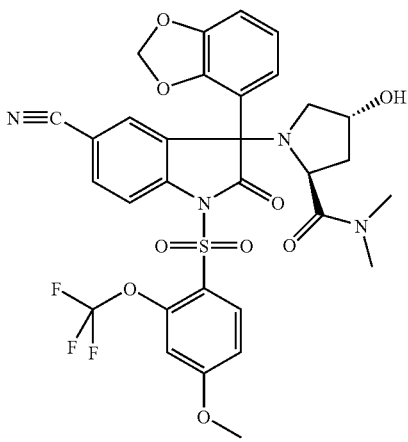 |

TABLE 3-continued

Structure of compounds obtained in each example

| Example | Structure |
|---------|-----------|
| 109 | 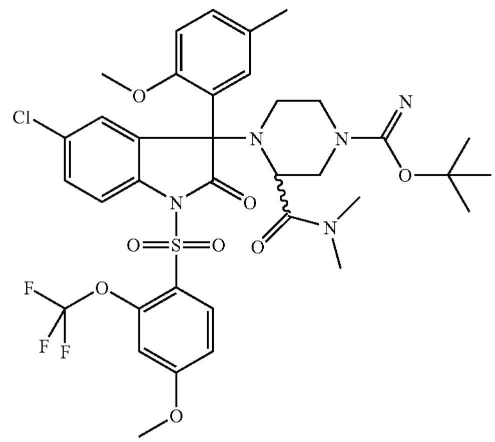 |
| 110 | 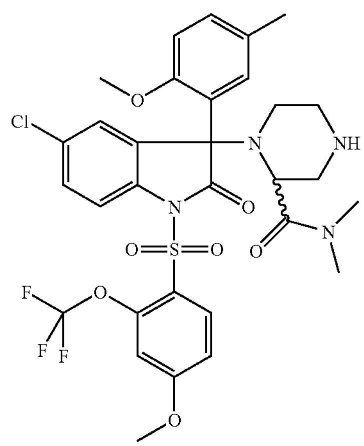 |
| 111 | 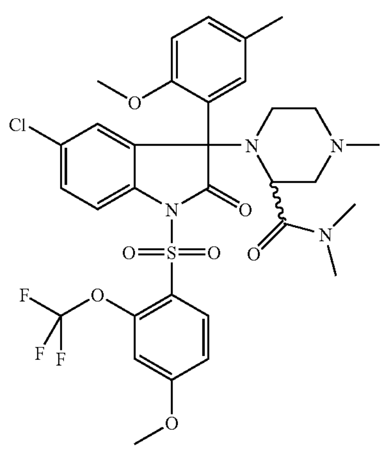 |

TABLE 3-continued
Structure of compounds obtained in each example
| Example | Structure |
|---|---|
| 112 | 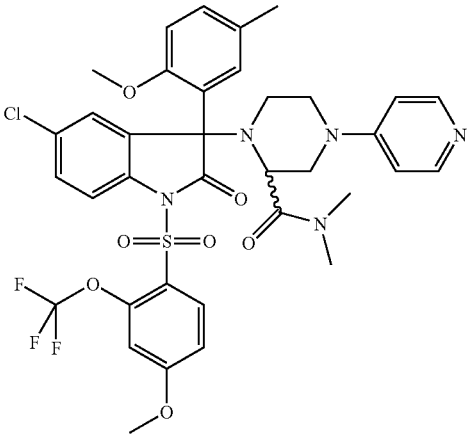 |
| 113 | 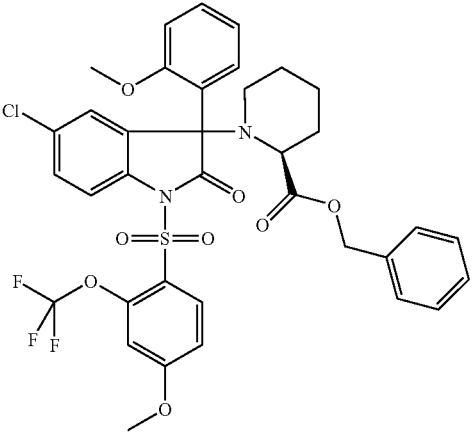 |
| 114 | 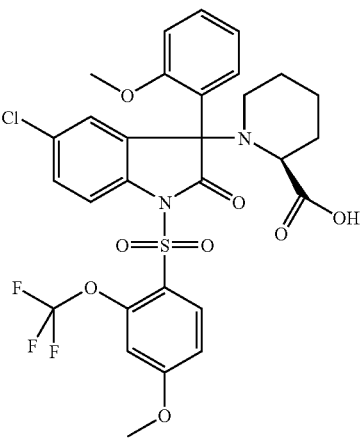 |

TABLE 3-continued
Structure of compounds obtained in each example
| Example | Structure |
|---|---|
| 115 | 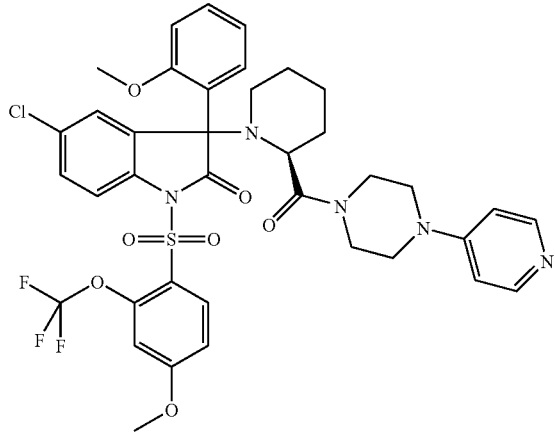 |
| 116 | 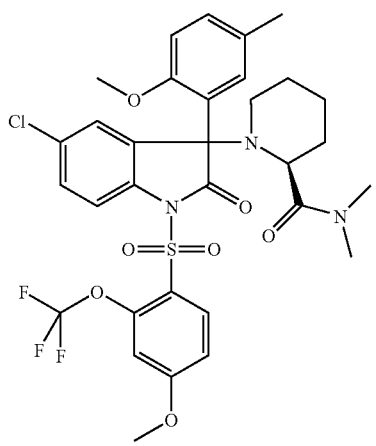 |
| 117 | 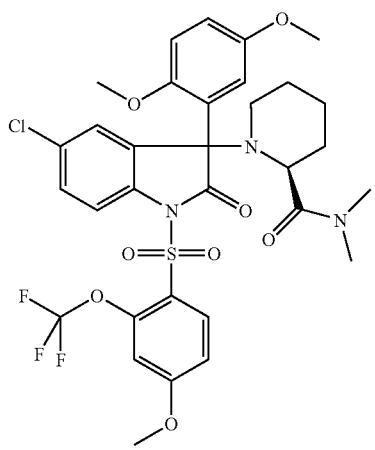 |

TABLE 3-continued

Structure of compounds obtained in each example

| Example | Structure |
|---|---|
| 118 | 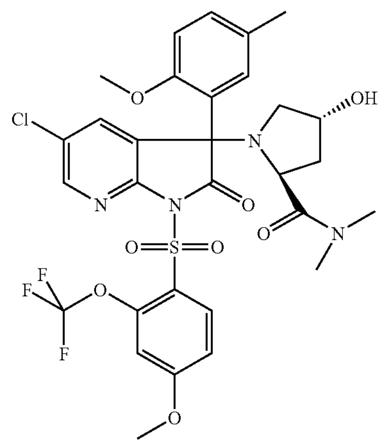 |
| 119 | 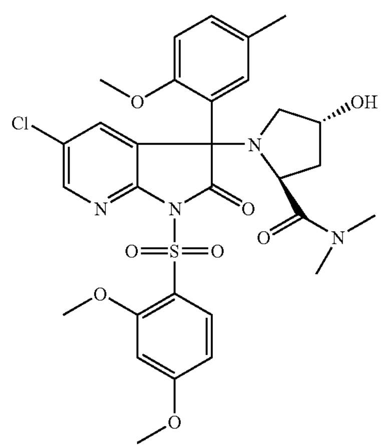 |
| 120 | 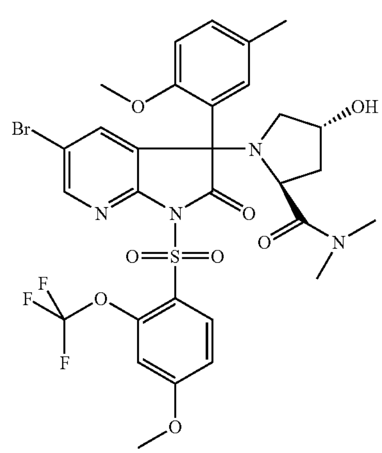 |

TABLE 3-continued

Structure of compounds obtained in each example

| Example | Structure |
|---------|-----------|
| 121 | 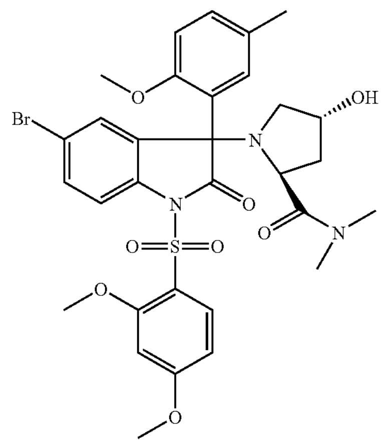 |
| 122 | 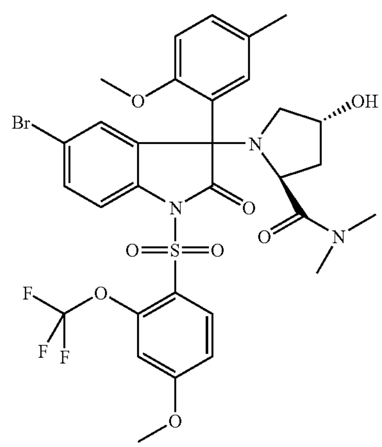 |
| 123 | 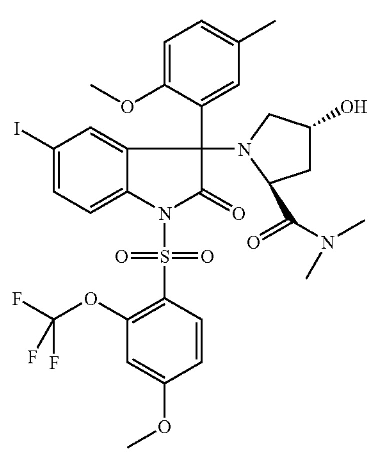 |

TABLE 3-continued

Structure of compounds obtained in each example

| Example | Structure |
|---------|-----------|
| 124 | 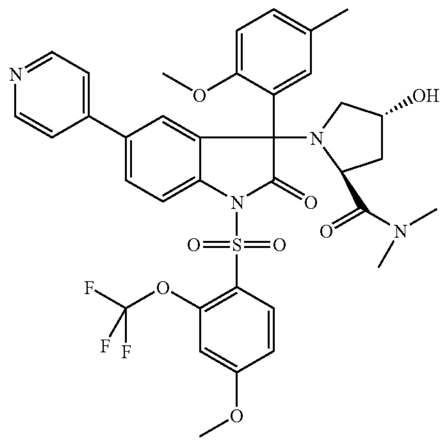 |
| 125 | 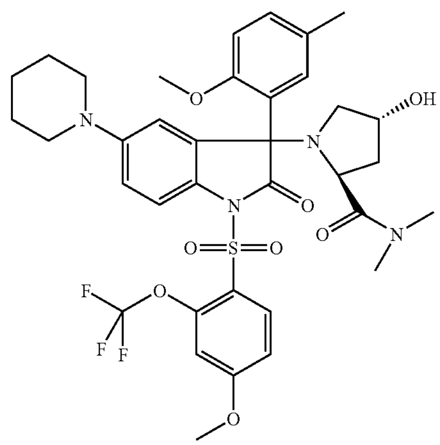 |
| 126 | 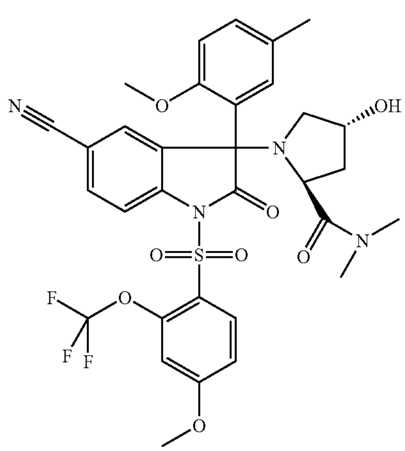 |

TABLE 3-continued

Structure of compounds obtained in each example

| Example | Structure |
|---|---|
| 127 | 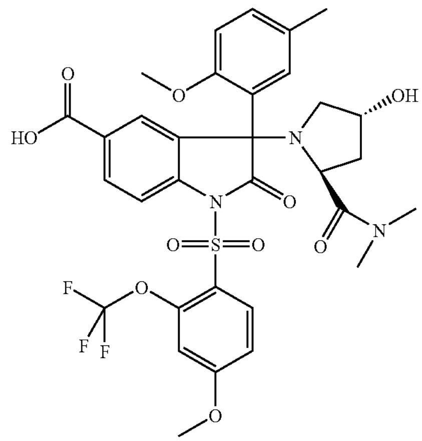 |
| 128 | 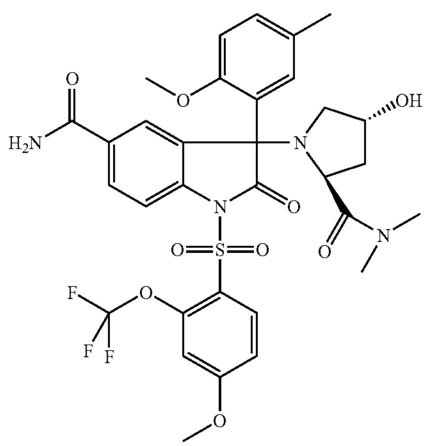 |
| 129 | 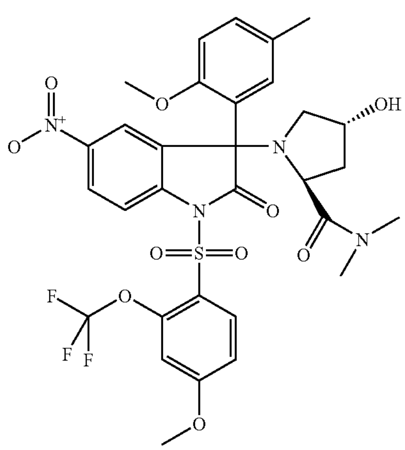 |

TABLE 3-continued

| Structure of compounds obtained in each example | |
|---|---|
| Example | Structure |
| 130 | |
| 131 | |
| 132 | |

TABLE 3-continued
Structure of compounds obtained in each example
| Example | Structure |
|---|---|
| 133 | 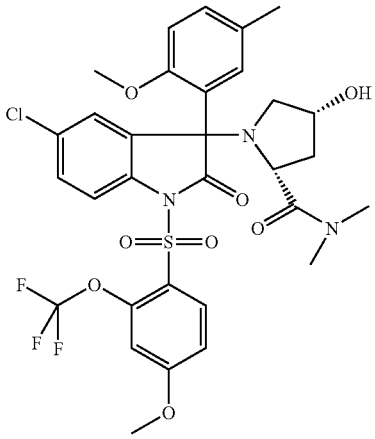 |
| 134 | 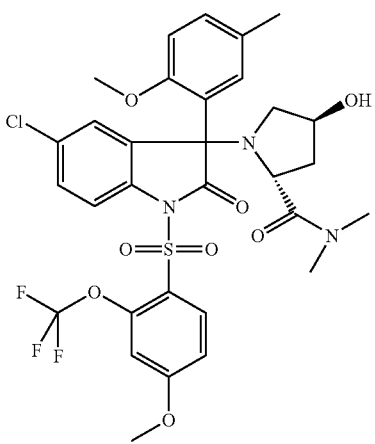 |
| 135 | 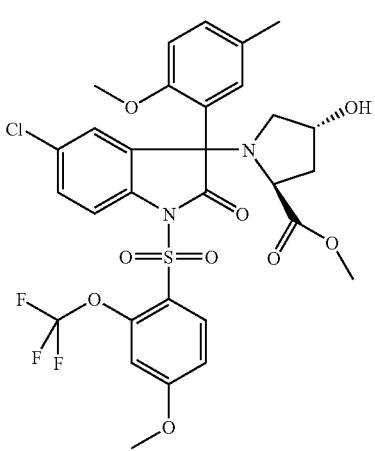 |

TABLE 3-continued

Structure of compounds obtained in each example

| Example | Structure |
|---|---|
| 136 | 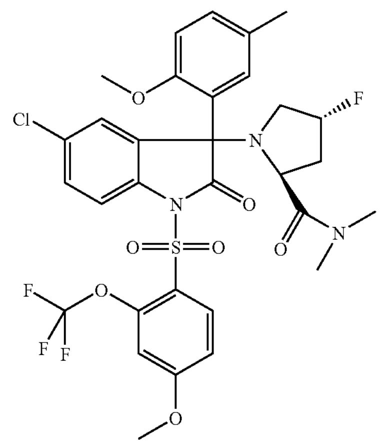 |
| 137 | 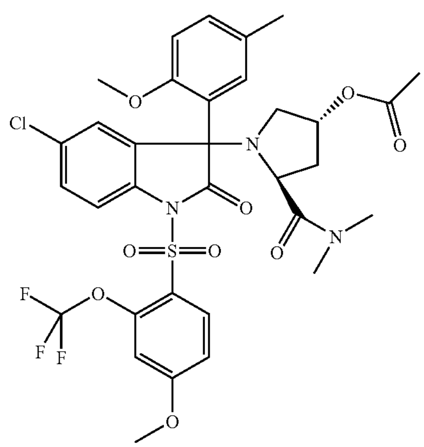 |
| 138 | 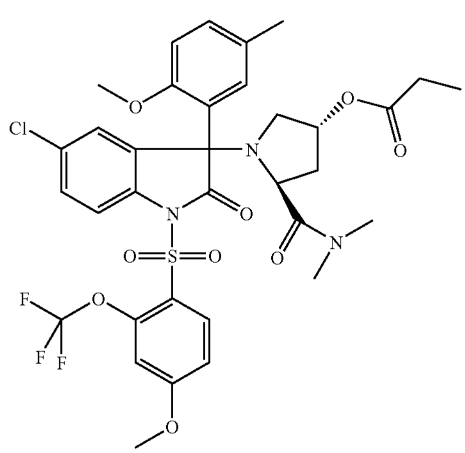 |

TABLE 3-continued

Structure of compounds obtained in each example

| Example | Structure |
|---|---|
| 139 | 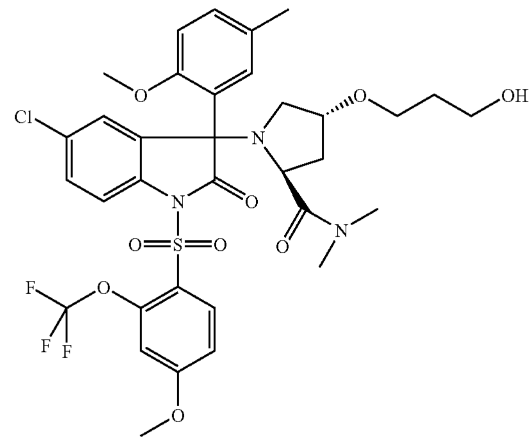 |
| 140 | 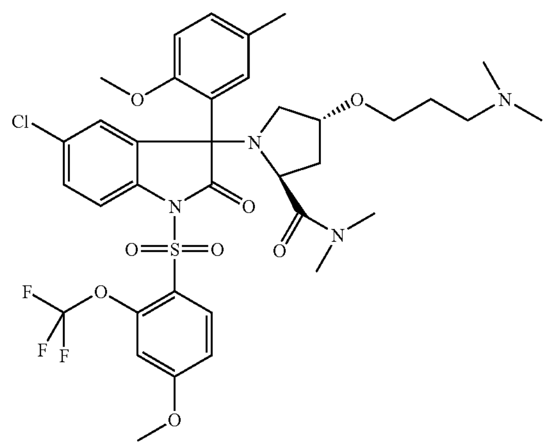 |
| 141 | 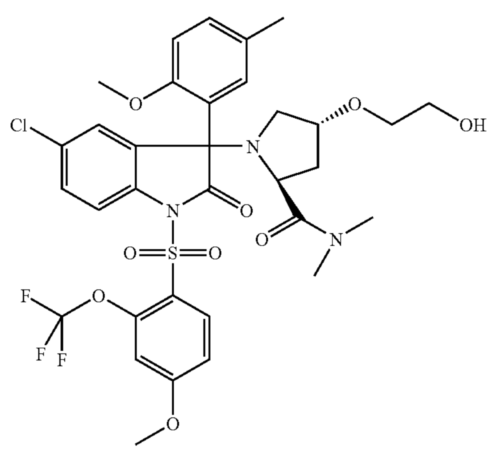 |

TABLE 3-continued

Structure of compounds obtained in each example

| Example | Structure |
|---------|-----------|
| 142 | 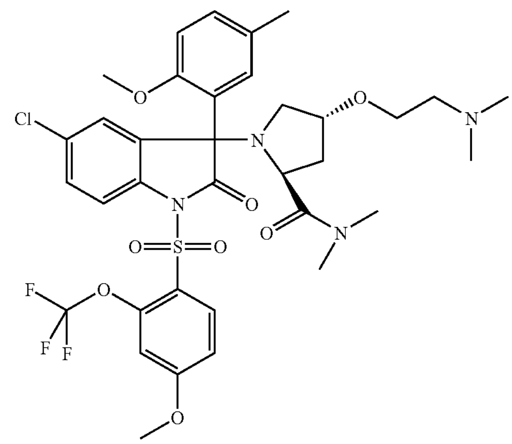 |
| 143 | 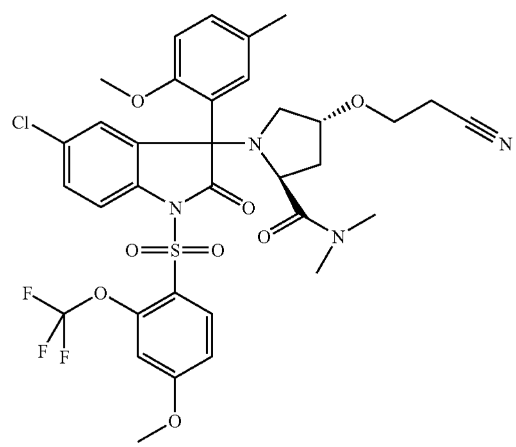 |
| 144 | 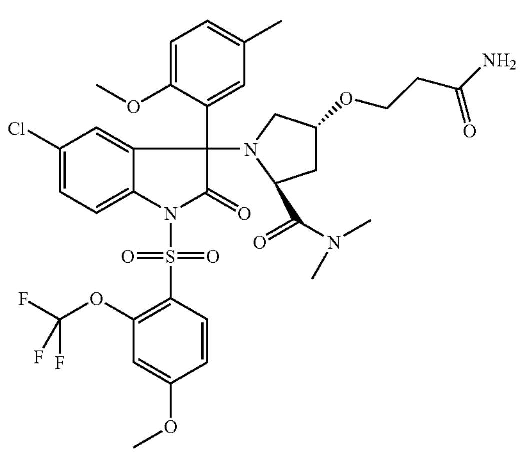 |

TABLE 3-continued

Structure of compounds obtained in each example

| Example | Structure |
|---------|-----------|
| 145 | 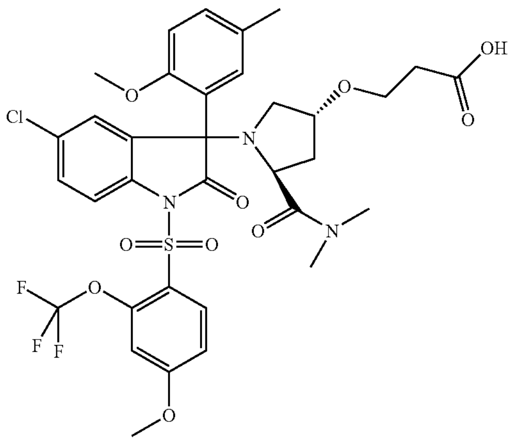 |
| 146 | 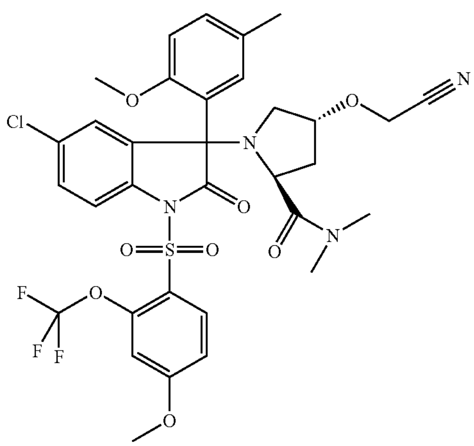 |
| 147 | 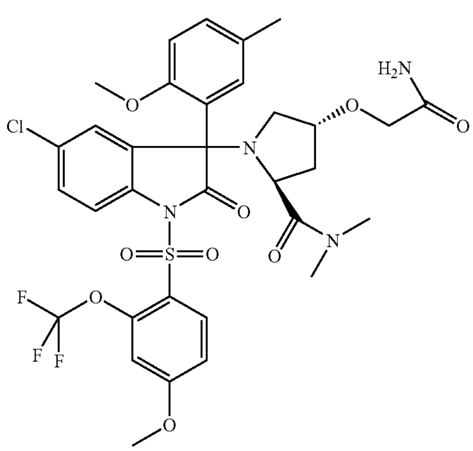 |

TABLE 3-continued

Structure of compounds obtained in each example

| Example | Structure |
|---|---|
| 148 | 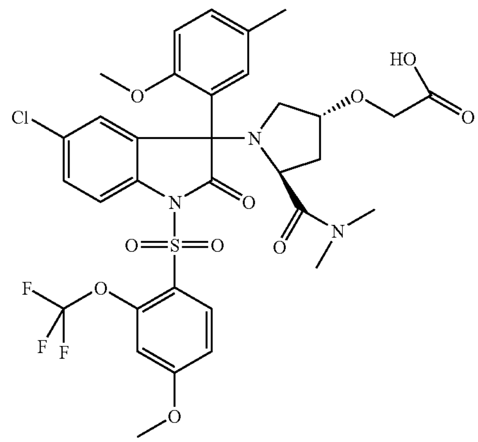 |
| 149 | 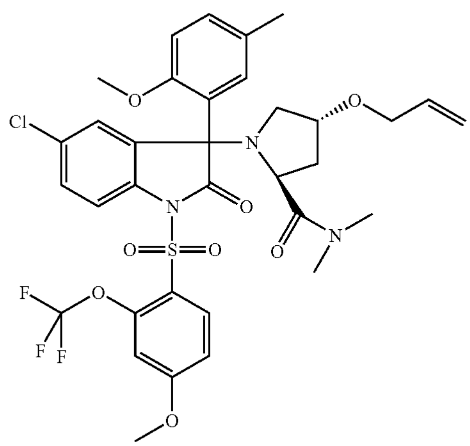 |
| 150 | 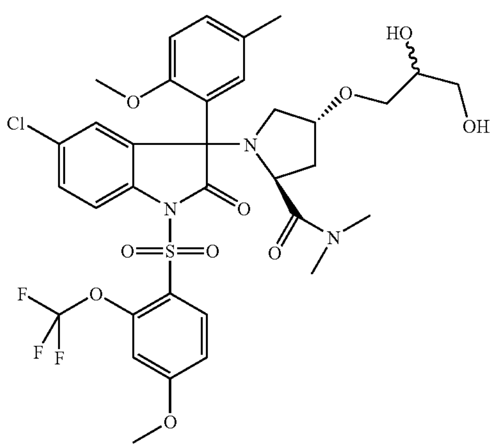 |

TABLE 3-continued

Structure of compounds obtained in each example

| Example | Structure |
|---|---|
| 151 | 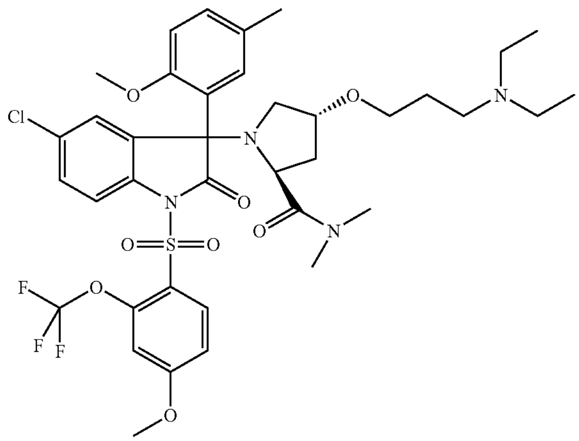 |
| 152 | 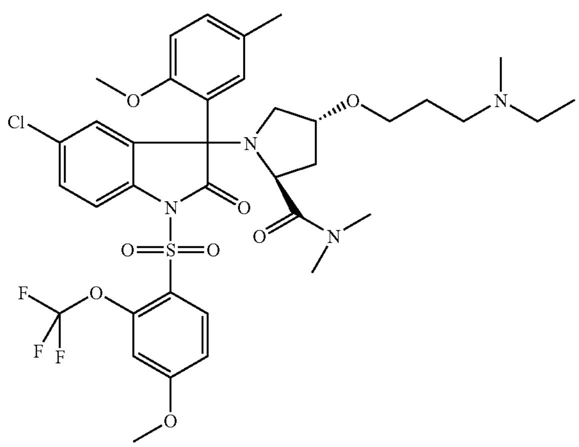 |
| 153 | 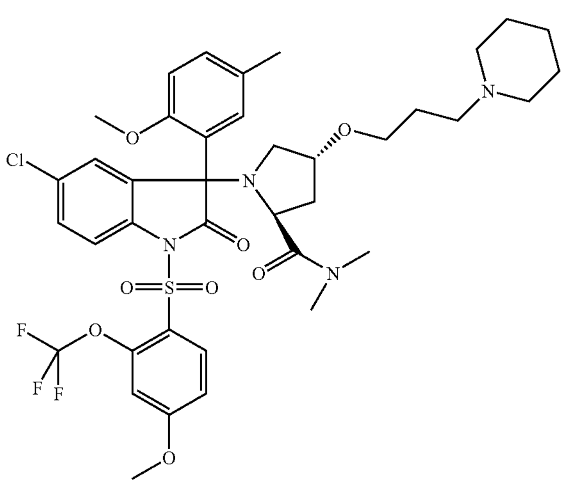 |

TABLE 3-continued

Structure of compounds obtained in each example

| Example | Structure |
|---|---|
| 154 | 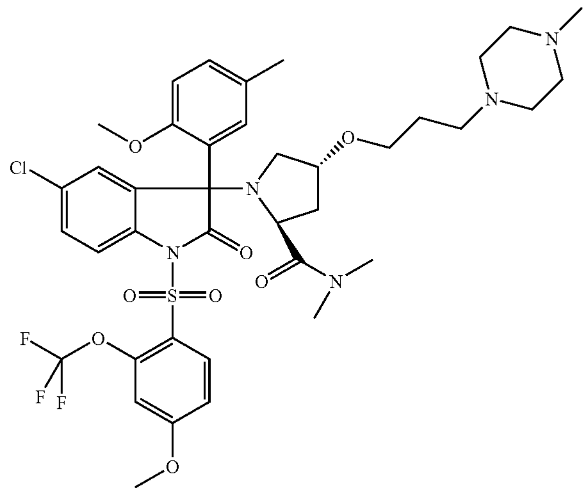 |
| 155 | 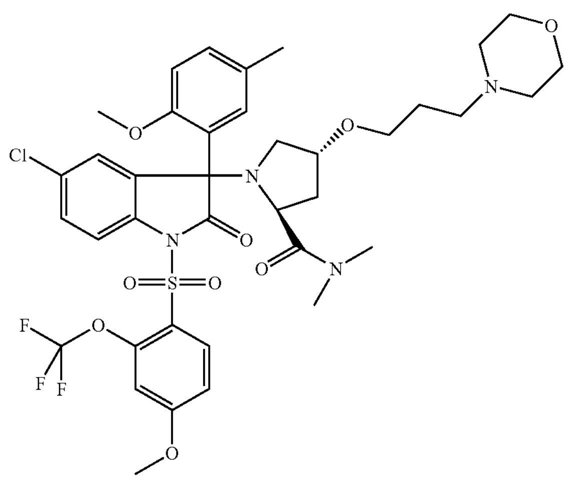 |
| 156 | 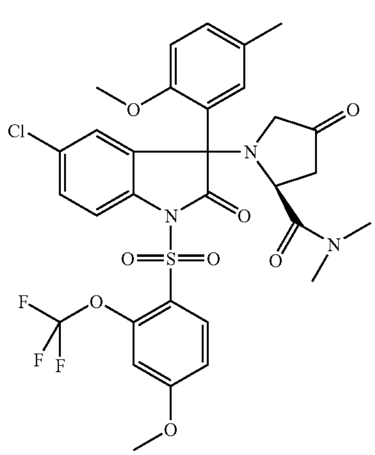 |

TABLE 3-continued
Structure of compounds obtained in each example
| Example | Structure |
|---------|-----------|
| 157 | 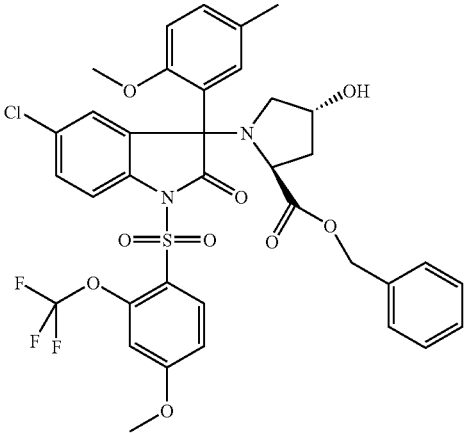 |
| 158 | 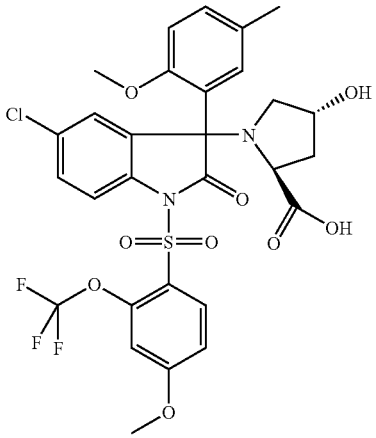 |
| 159 | 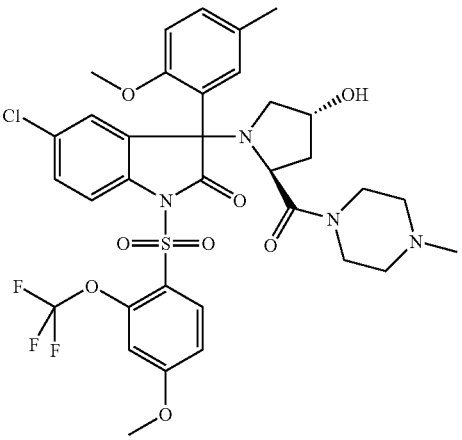 |

TABLE 3-continued
Structure of compounds obtained in each example
| Example | Structure |
|---|---|
| 160 | 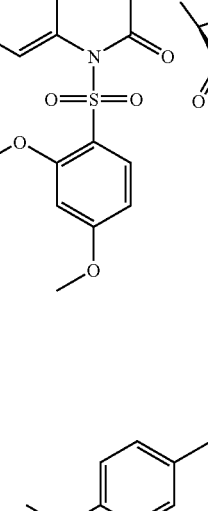 |
| 161 | 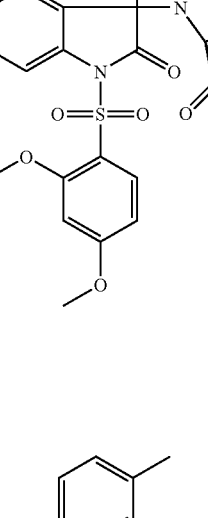 |
| 162 | 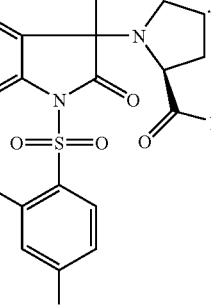 |

447

TABLE 3-continued

Structure of compounds obtained in each example

| Example | Structure |
|---------|-----------|
| 163 | 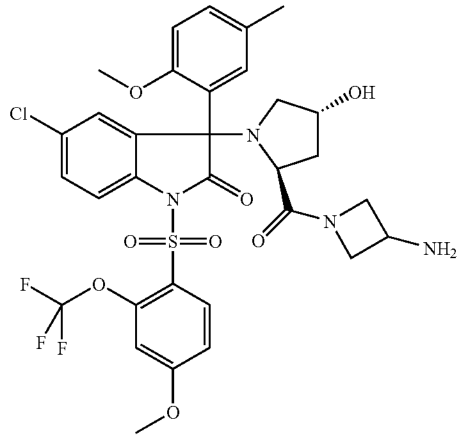 |
| 164 | 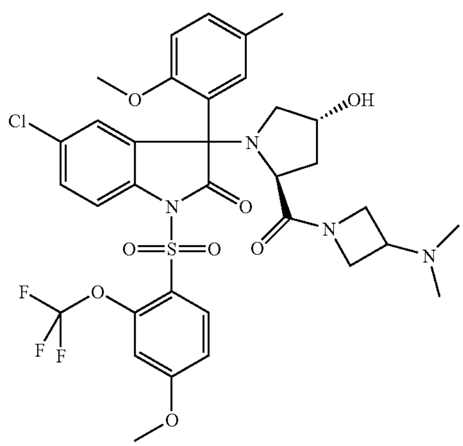 |
| 165 | 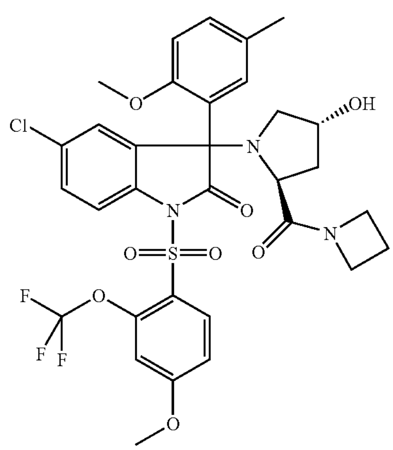 |

448

TABLE 3-continued

Structure of compounds obtained in each example

| Example | Structure |
|---|---|
| 166 | 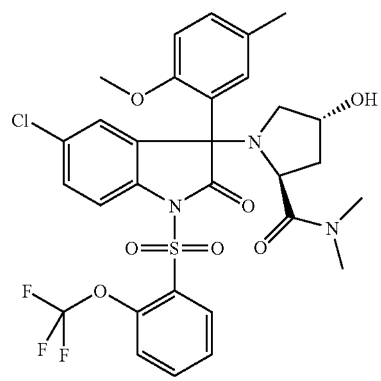 |
| 167 | 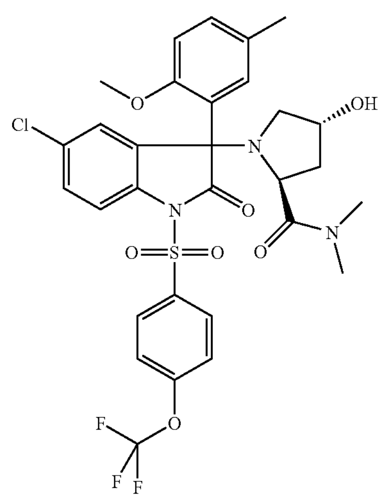 |
| 168 | 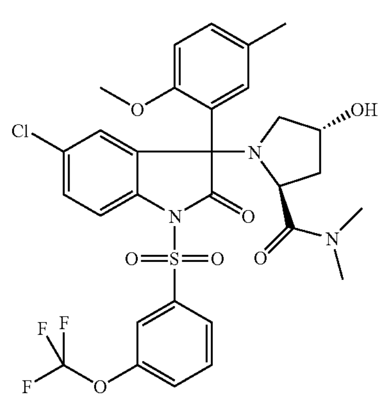 |

TABLE 3-continued

Structure of compounds obtained in each example

| Example | Structure |
|---------|-----------|
| 169 | 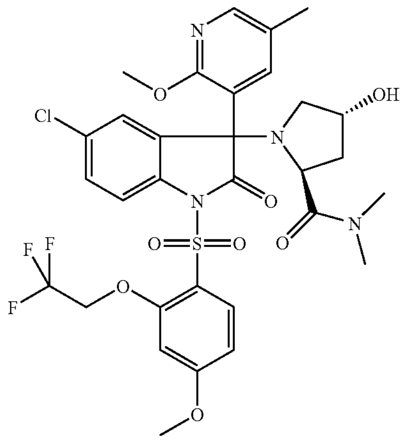 |
| 170 | 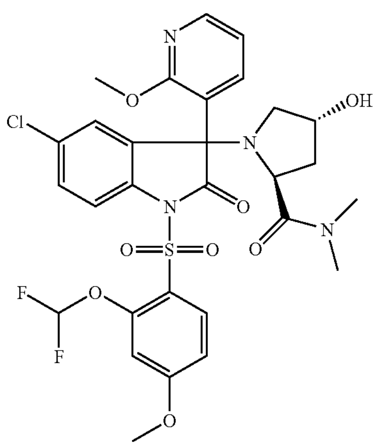 |
| 171 | 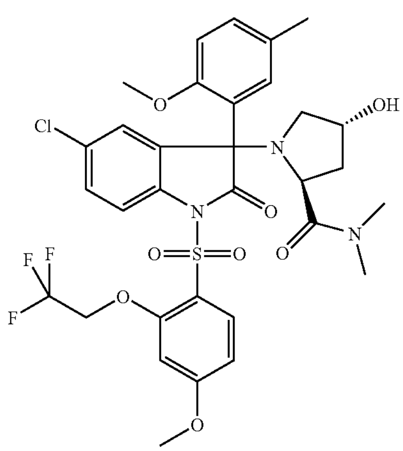 |

TABLE 3-continued
Structure of compounds obtained in each example
| Example | Structure |
|---|---|
| 172 | 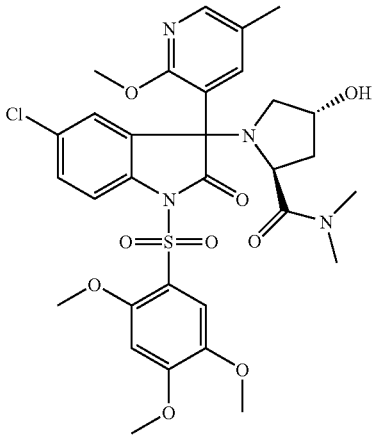 |
| 173 | 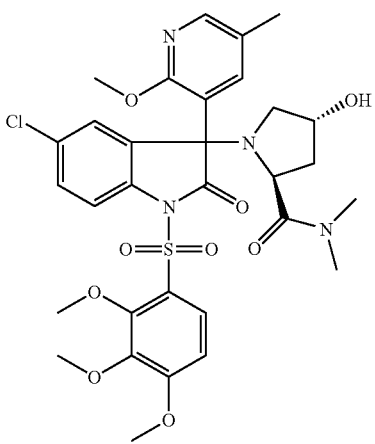 |
| 174 | 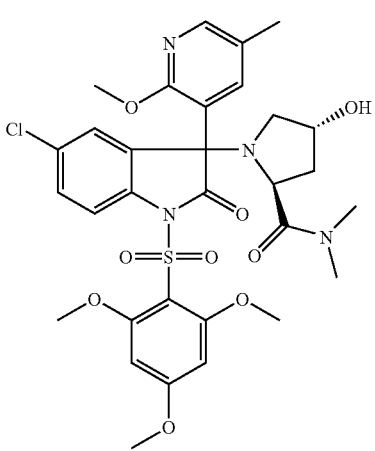 |

TABLE 3-continued

Structure of compounds obtained in each example

| Example | Structure |
|---------|-----------|
| 175 | 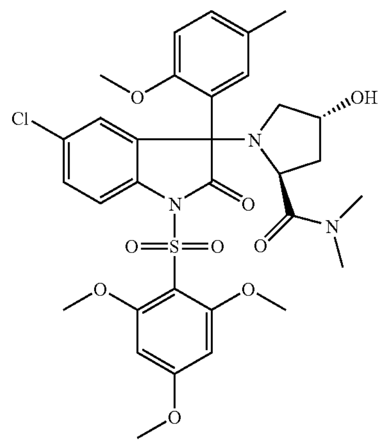 |
| 176 | 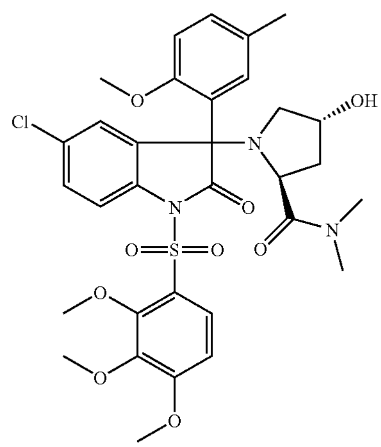 |
| 177 | 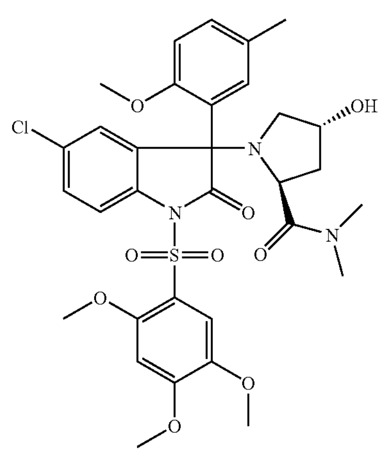 |

TABLE 3-continued
Structure of compounds obtained in each example
| Example | Structure |
|---|---|
| 178 | 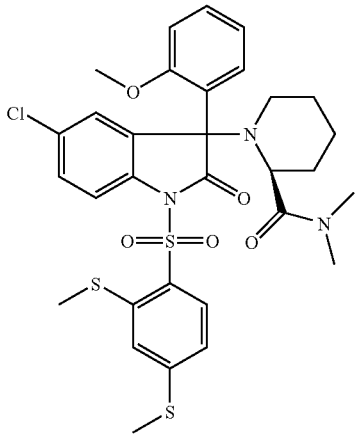 |
| 179 | 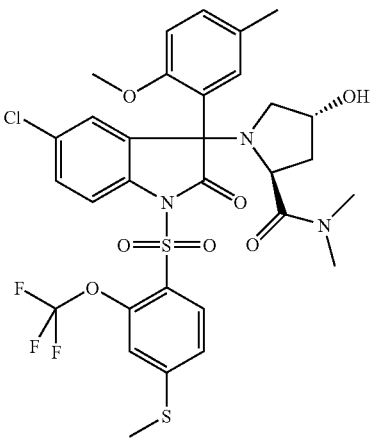 |
| 180 | 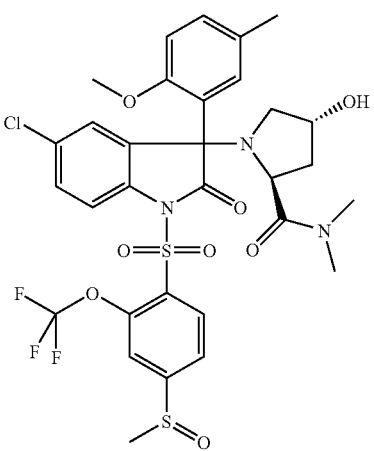 |

TABLE 3-continued
Structure of compounds obtained in each example
| Example | Structure |
|---------|-----------|
| 180 | 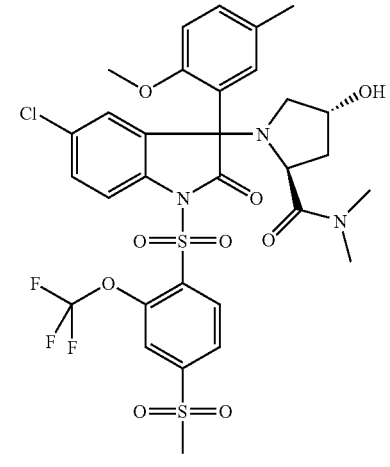 |
| 181 | 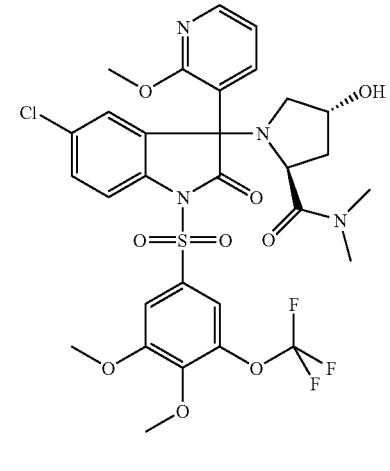 |
| 182 | 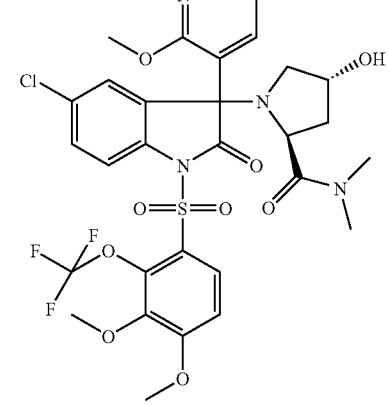 |

TABLE 3-continued
Structure of compounds obtained in each example
| Example | Structure |
|---|---|
| 183 | 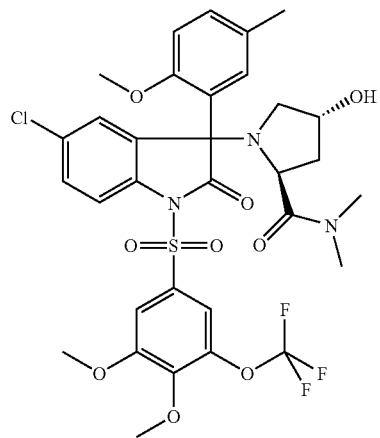 |
| 184 | 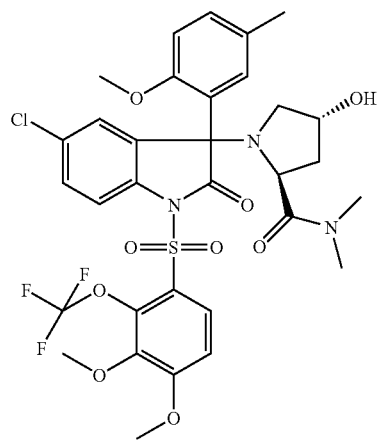 |
| 185 | 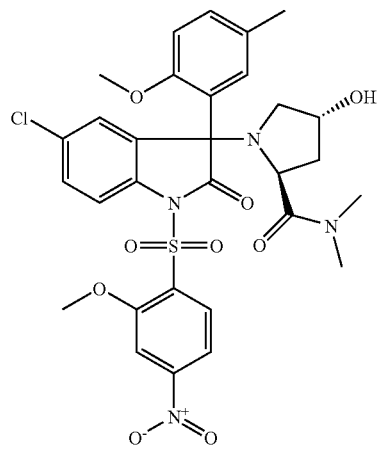 |

TABLE 3-continued
Structure of compounds obtained in each example
| Example | Structure |
|---|---|
| 186 | 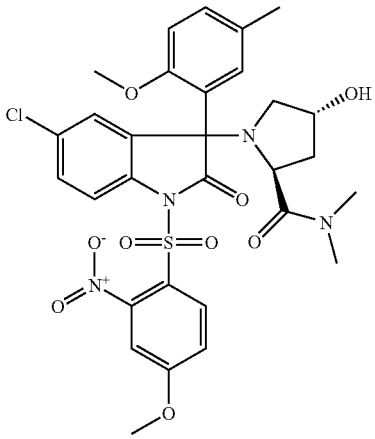 |
| 187 | 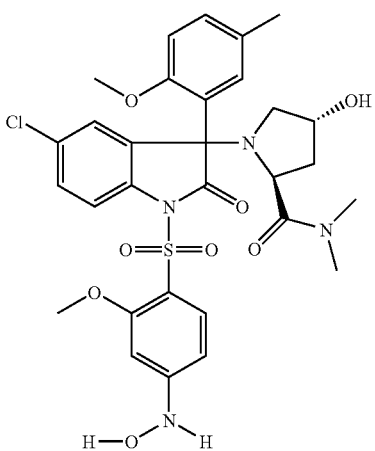 |
| 188 | 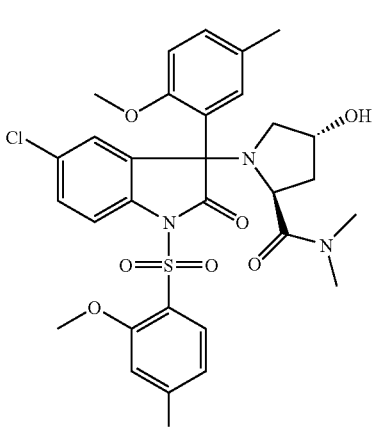 |

TABLE 3-continued

Structure of compounds obtained in each example

| Example | Structure |
|---|---|
| 189 | 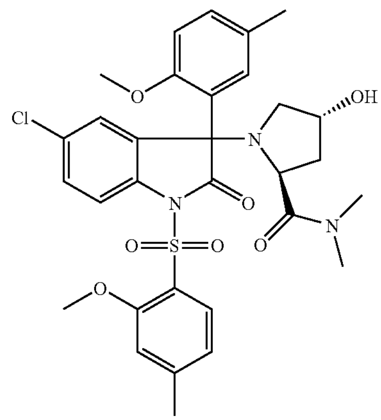 |
| 190 | 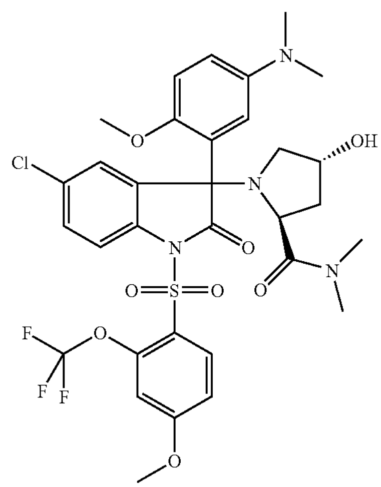 |
| 191 | 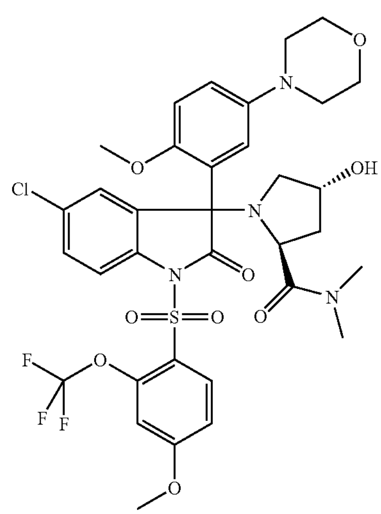 |

TABLE 3-continued

| Structure of compounds obtained in each example | |
|---|---|
| Example | Structure |
| 192 | |
| 193 | |
| 194 | |

TABLE 3-continued
Structure of compounds obtained in each example
| Example | Structure |
|---|---|
| 195 | 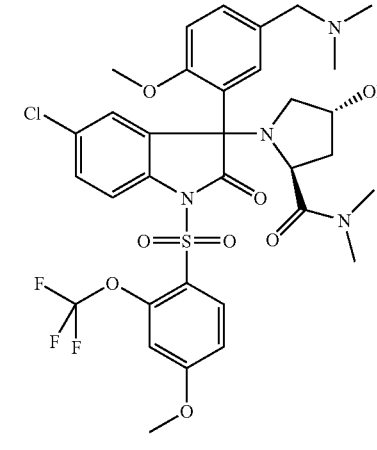 |
| 196 | 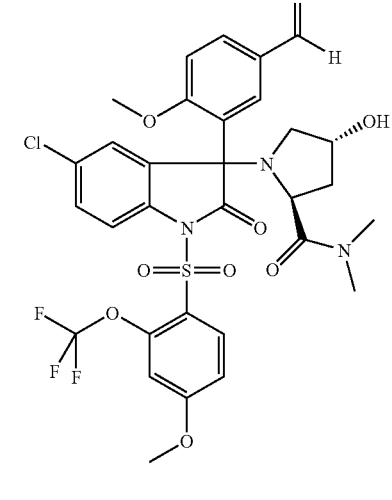 |
| 197 | 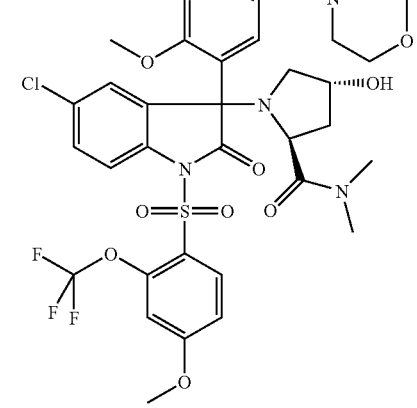 |

TABLE 3-continued

Structure of compounds obtained in each example

| Example | Structure |
|---------|-----------|
| 198 | 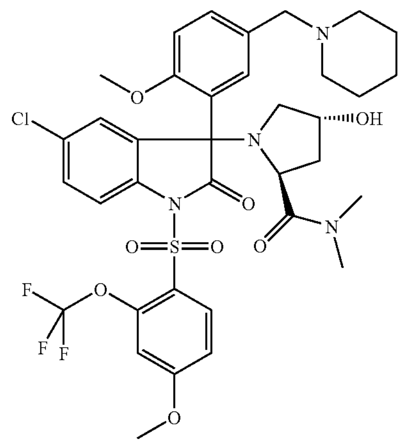 |
| 199 | 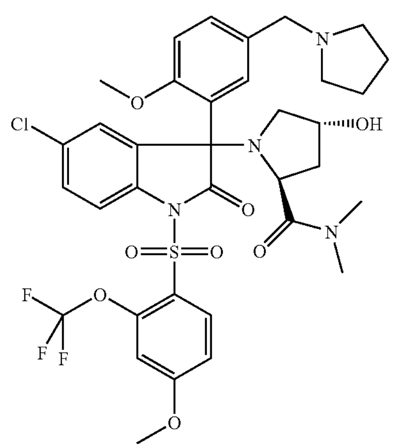 |
| 200 | 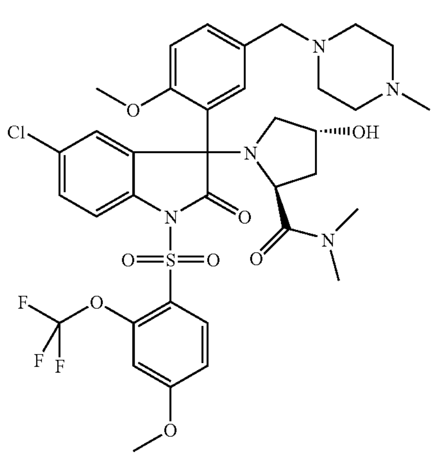 |

TABLE 3-continued

Structure of compounds obtained in each example

| Example | Structure |
|---|---|
| 201 | 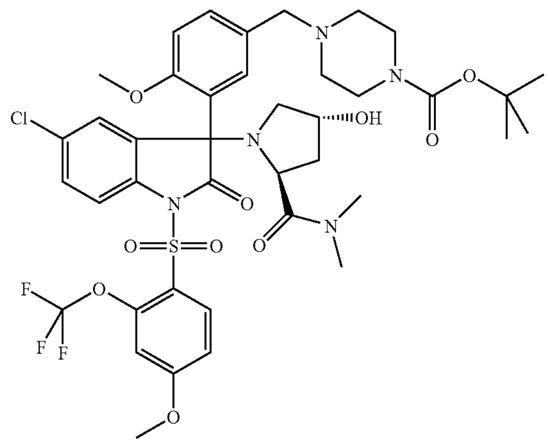 |
| 202 | 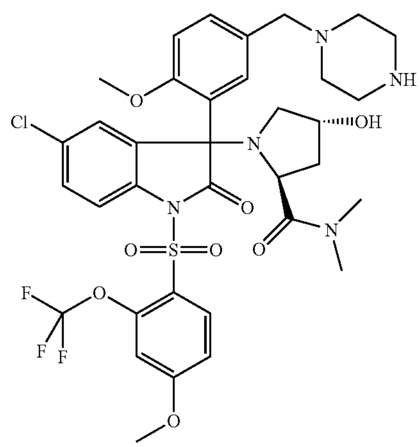 |
| 203 | 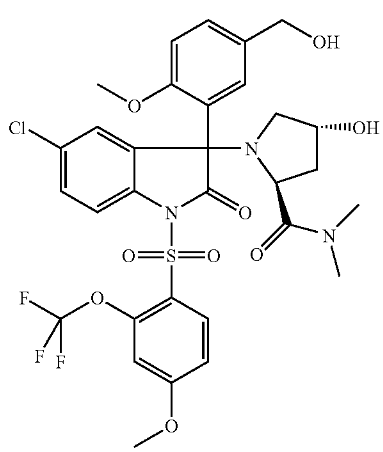 |

TABLE 3-continued

Structure of compounds obtained in each example

| Example | Structure |
|---|---|
| 204 | 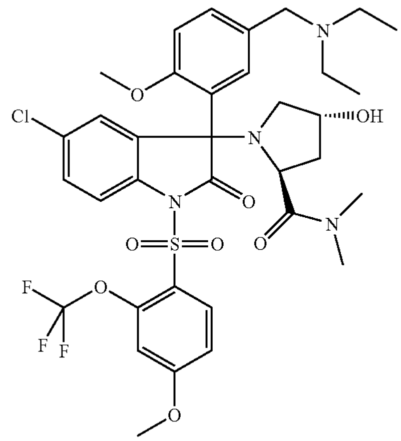 |
| 205 | 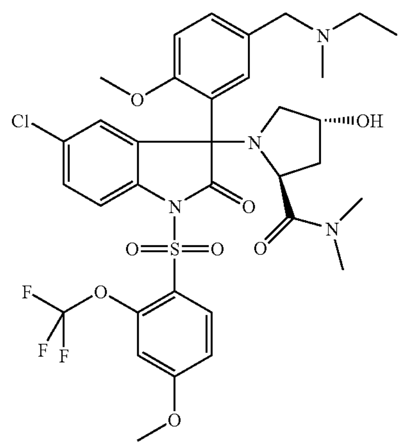 |
| 206 | 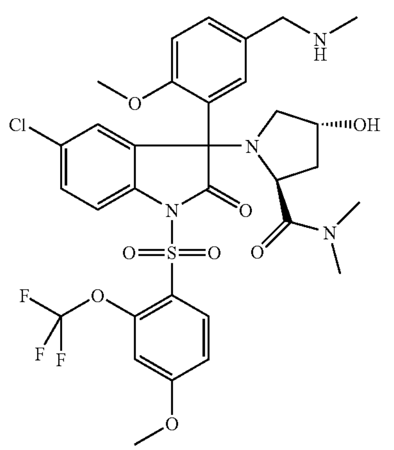 |

TABLE 3-continued

Structure of compounds obtained in each example

| Example | Structure |
|---------|-----------|
| 207 | 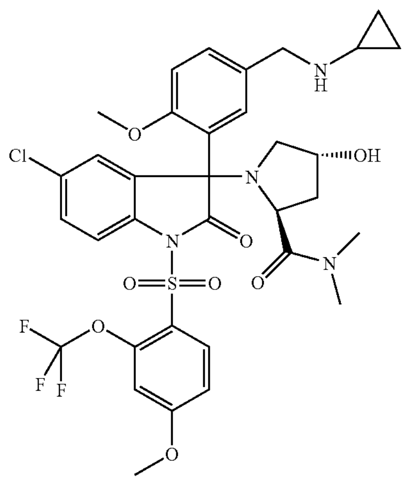 |
| 208 | 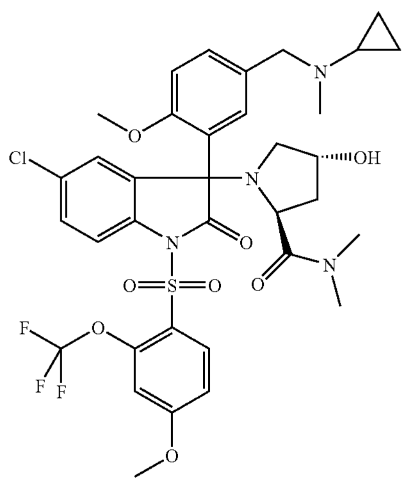 |
| 209 | 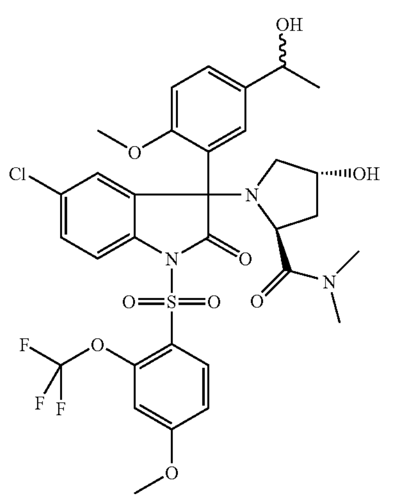 |

TABLE 3-continued
Structure of compounds obtained in each example
| Example | Structure |
|---|---|
| 210 | 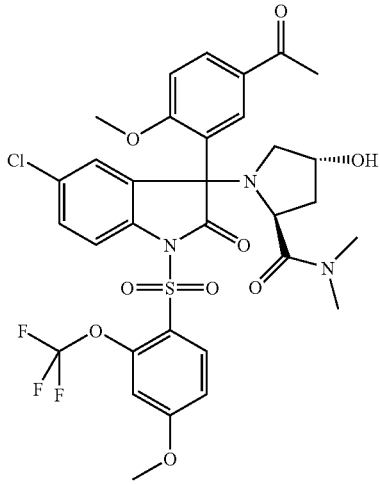 |
| 211 | 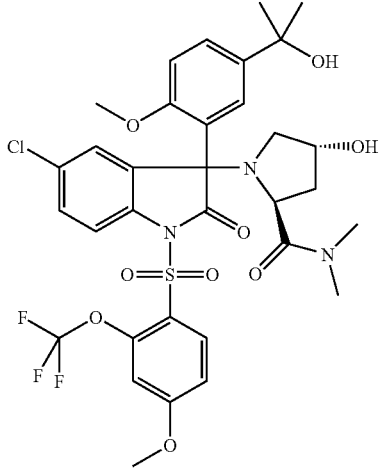 |
| 212 | 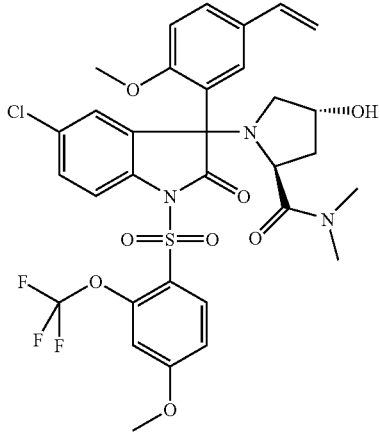 |

481
TABLE 3-continued
Structure of compounds obtained in each example
| Example | Structure |
|---|---|
| 213 | 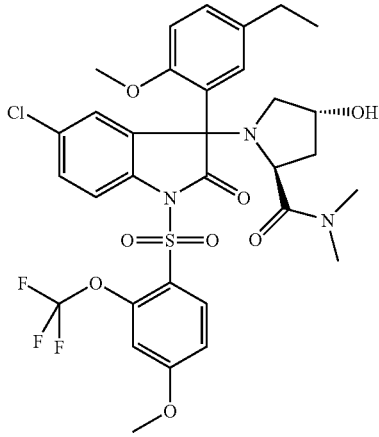 |
| 214 | 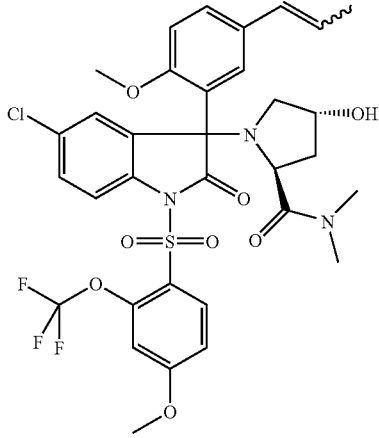 |
| 215 | 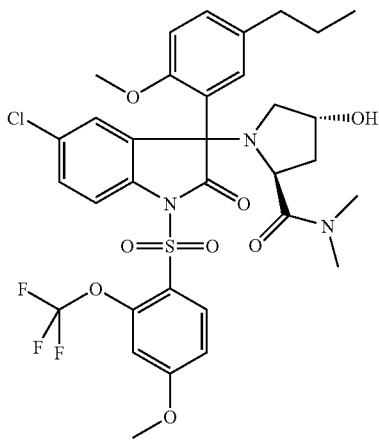 |

TABLE 3-continued
Structure of compounds obtained in each example
| Example | Structure |
|---------|-----------|
| 216 | 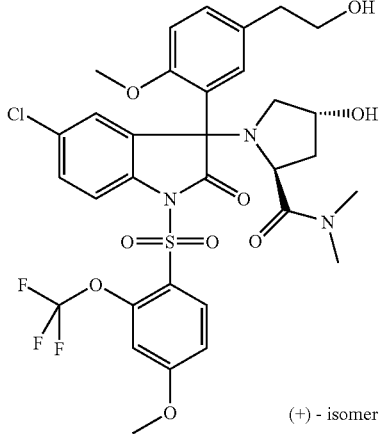 (+)-isomer |
| 217 | 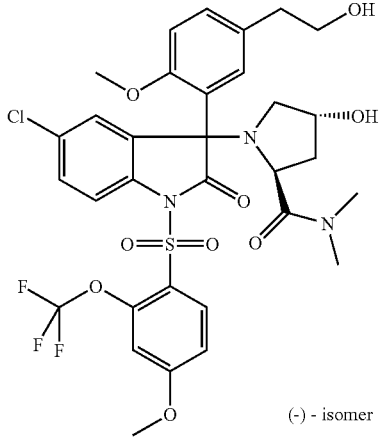 (−)-isomer |
| 218 | 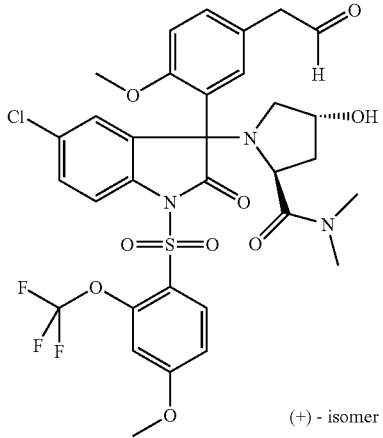 (+)-isomer |

TABLE 3-continued
Structure of compounds obtained in each example
| Example | Structure |
|---|---|
| 219 | 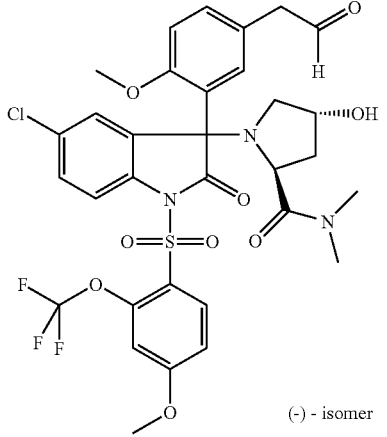 (−)-isomer |
| 220 | 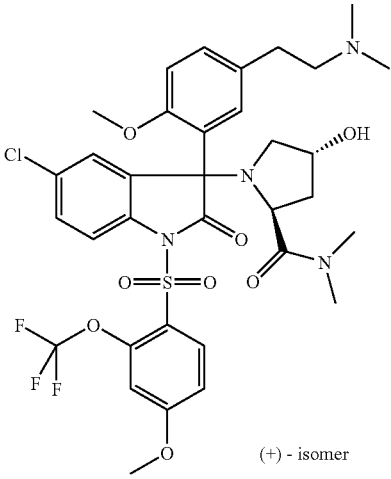 (+)-isomer |
| 221 | 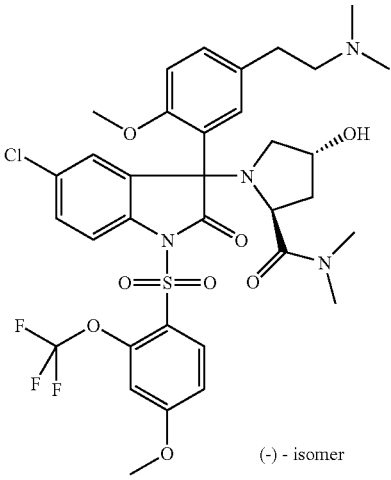 (−)-isomer |

TABLE 3-continued

Structure of compounds obtained in each example

| Example | Structure |
|---|---|
| 222 | 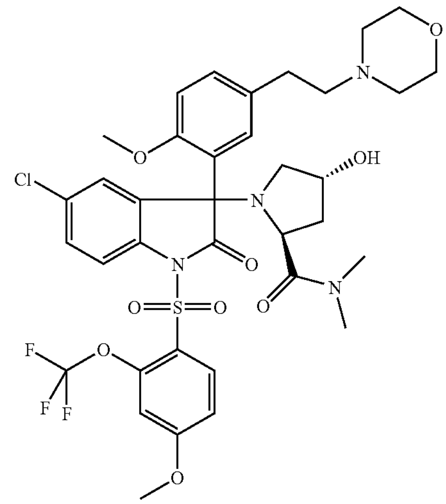 |
| 223 | 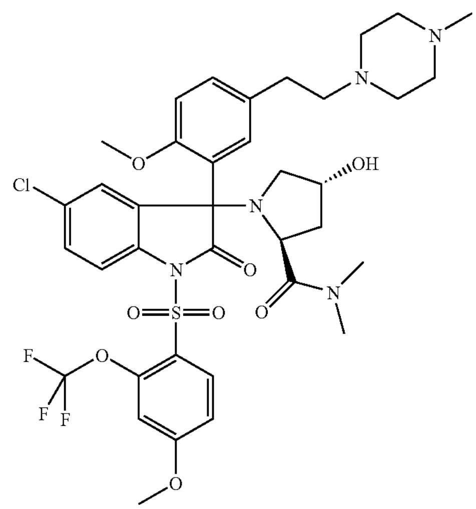 |
| 224 | 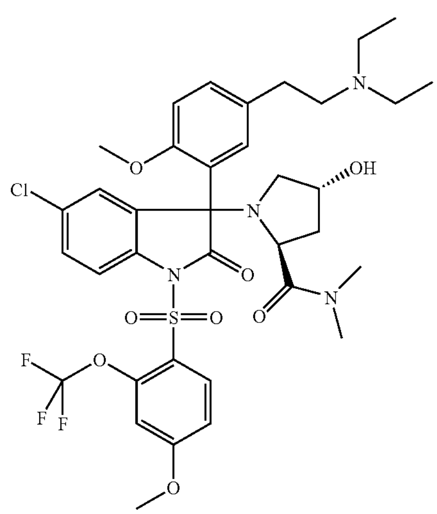 |

TABLE 3-continued
Structure of compounds obtained in each example
| Example | Structure |
|---------|-----------|
| 225 | 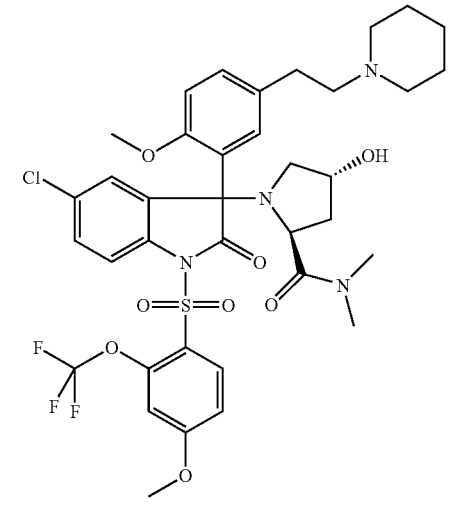 |
| 226 | 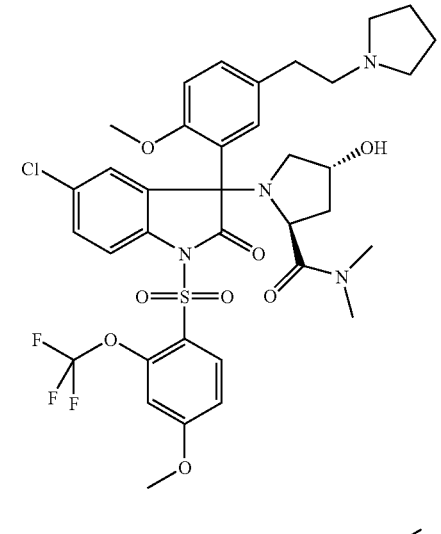 |
| 227 | 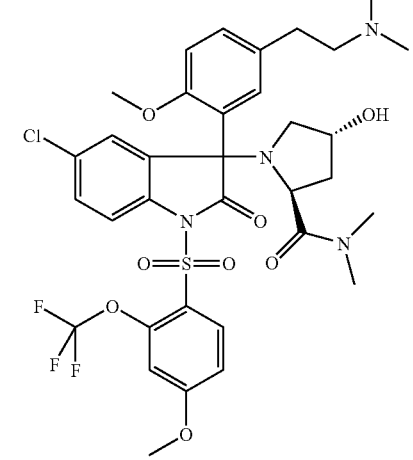 |

TABLE 3-continued
Structure of compounds obtained in each example
| Example | Structure |
|---|---|
| 228 | 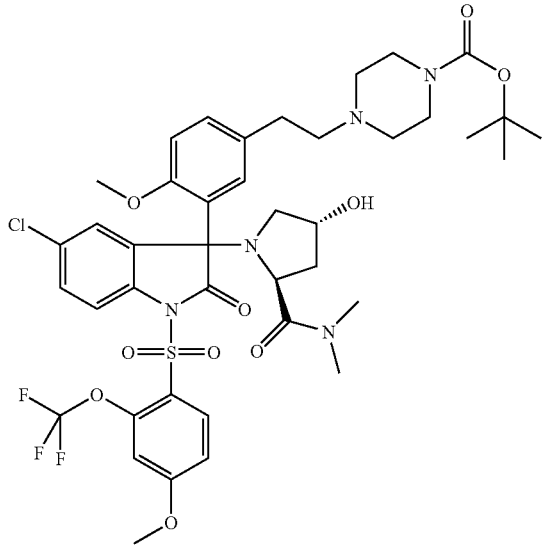 |
| 229 | 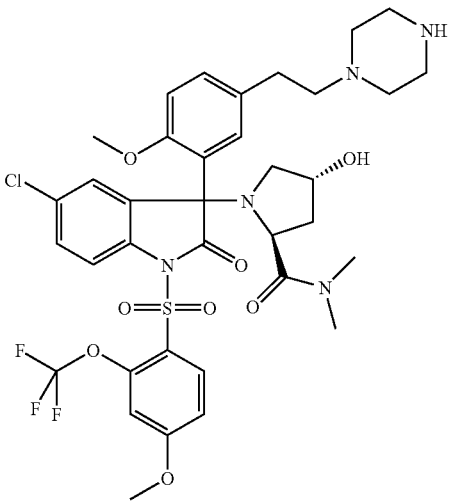 |
| 230 | 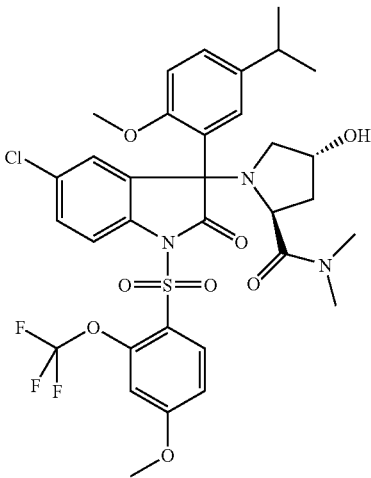 |

TABLE 3-continued

| Example | Structure |
|---|---|
| 231 | 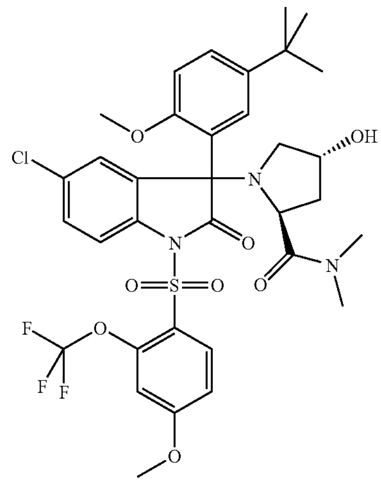 |
| 232 | 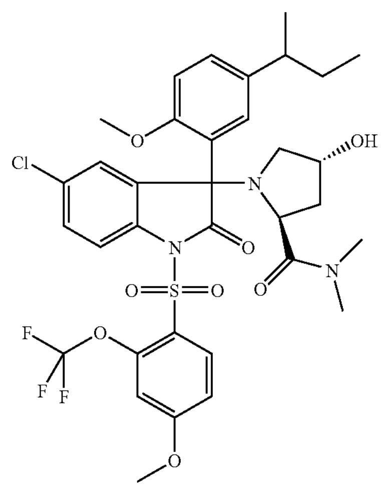 |
| 233 | 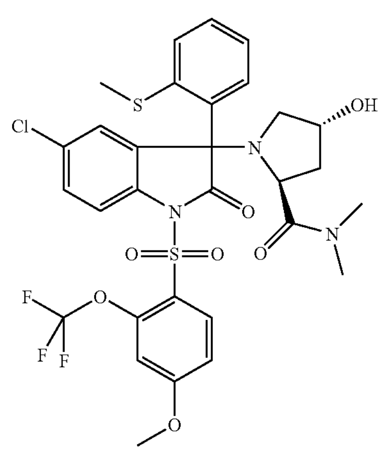 |

TABLE 3-continued

| Example | Structure |
|---|---|
| 234 | 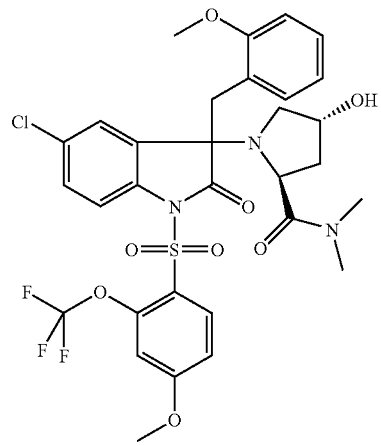 |
| 235 | 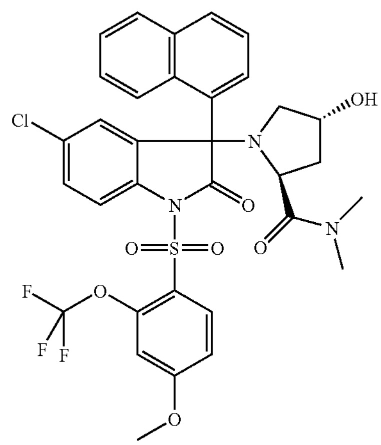 |
| 236 | 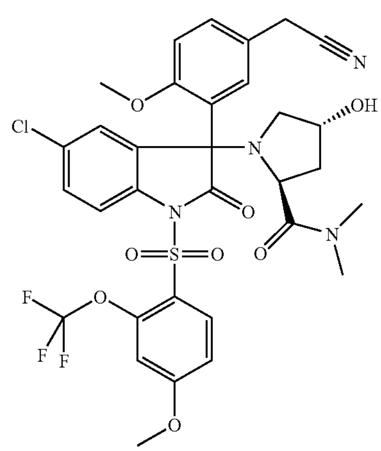 |

TABLE 3-continued
Structure of compounds obtained in each example
| Example | Structure |
|---------|-----------|
| 237 | 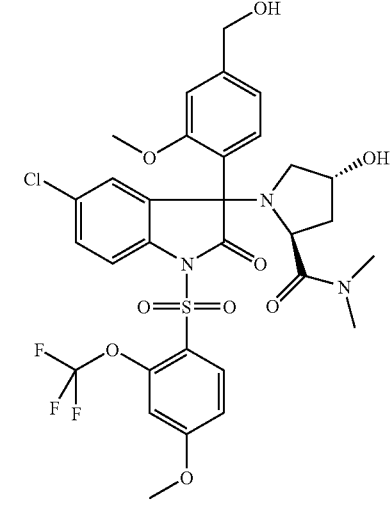 |
| 238 | 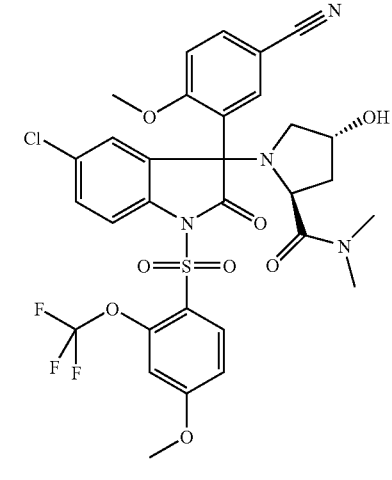 |
| 239 | 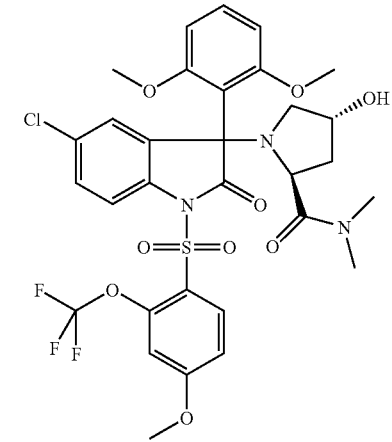 |

TABLE 3-continued
Structure of compounds obtained in each example
| Example | Structure |
|---------|-----------|
| 240 | 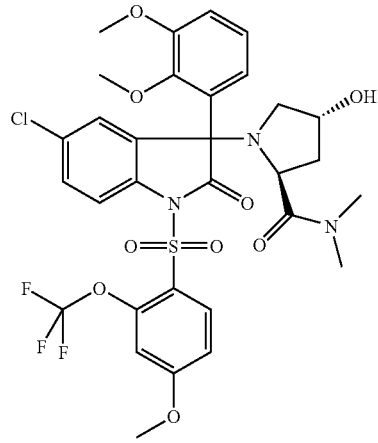 |
| 241 | 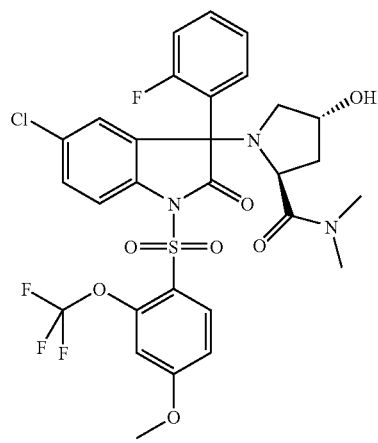 |
| 242 | 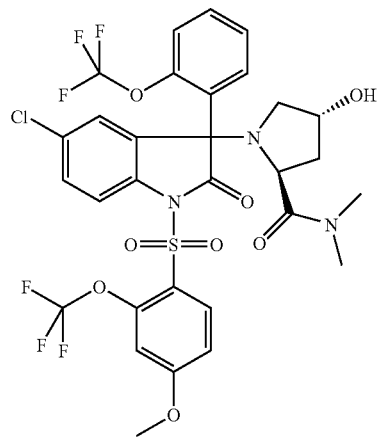 |

TABLE 3-continued
Structure of compounds obtained in each example
| Example | Structure |
|---------|-----------|
| 243 | 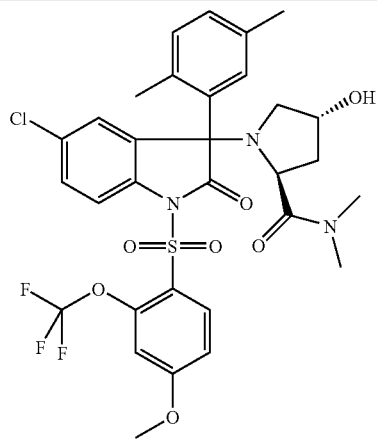 |
| 244 | 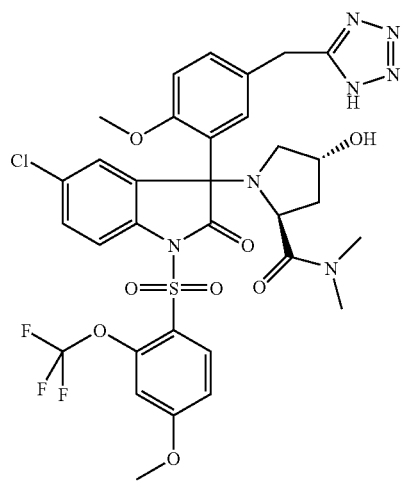 |
| 245 | 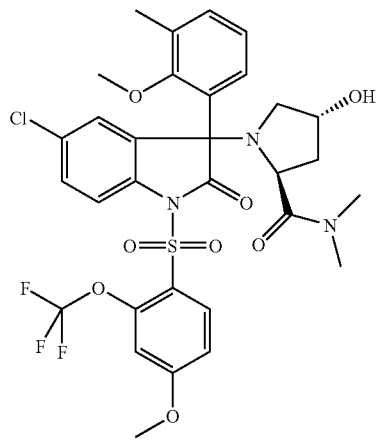 |

503
504
TABLE 3-continued
Structure of compounds obtained in each example
| Example | Structure |
|---|---|
| 246 | 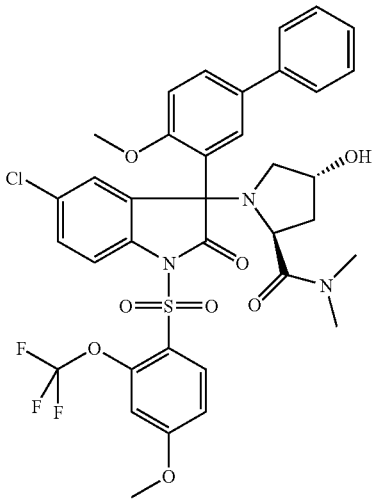 |
| 247 | 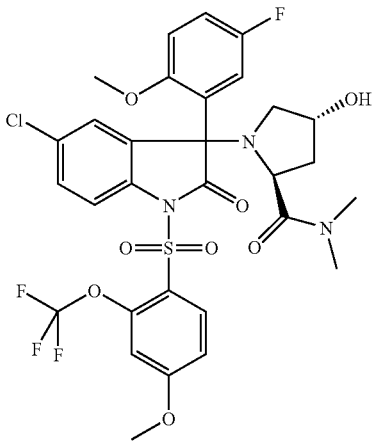 |
| 248 | 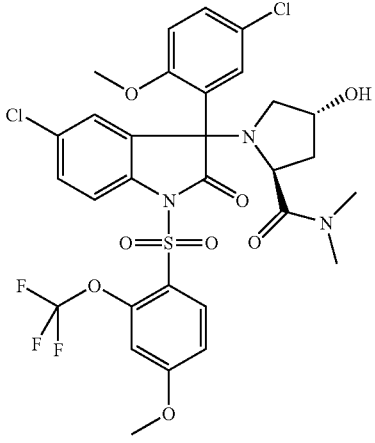 |

TABLE 3-continued

Structure of compounds obtained in each example

| Example | Structure |
|---------|-----------|
| 249 | 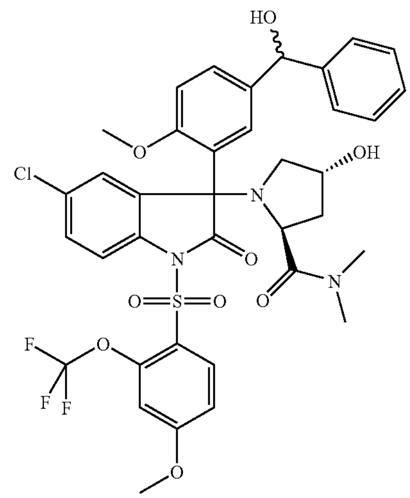 |
| 250 | 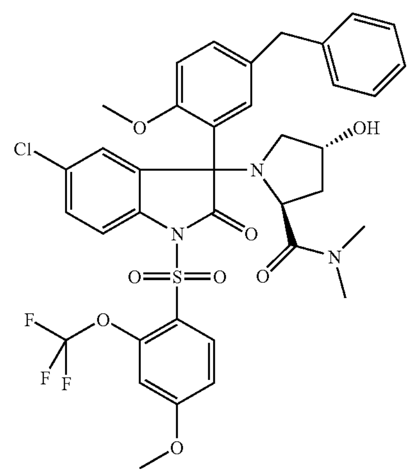 |
| 251 | 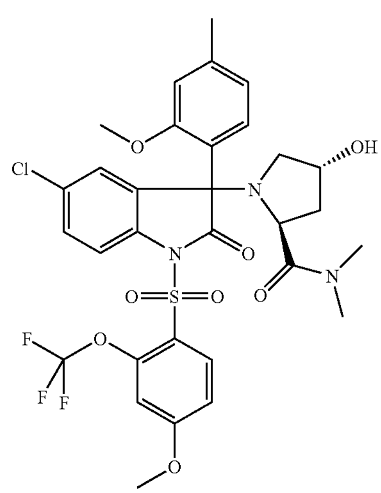 |

TABLE 3-continued
Structure of compounds obtained in each example
| Example | Structure |
|---|---|
| 252 | 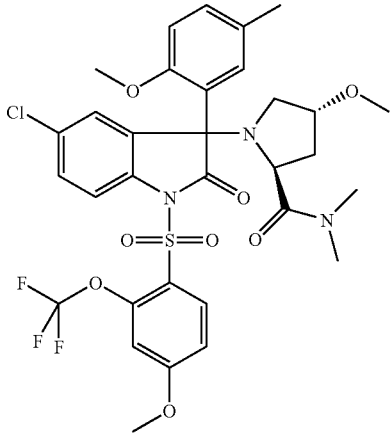 |
| 253 | 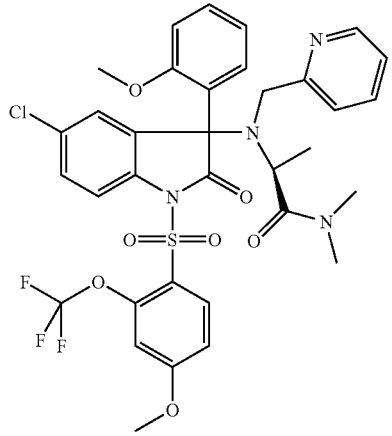 |
| 254 | 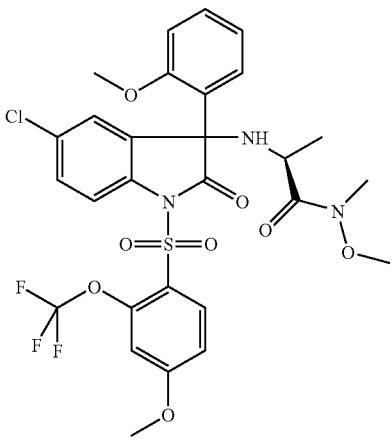 |

TABLE 3-continued
Structure of compounds obtained in each example
| Example | Structure |
|---|---|
| 255 | 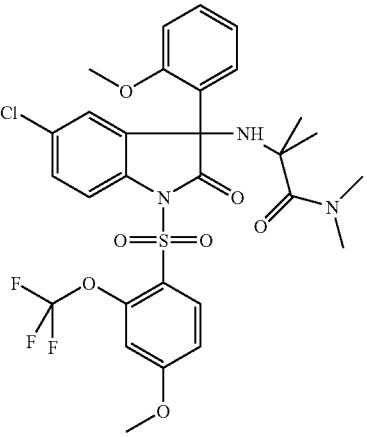 |
| 256 | 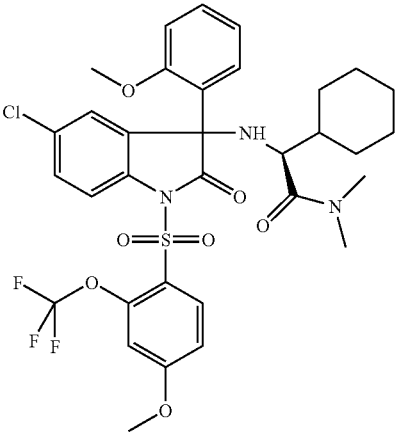 |
| 257 | 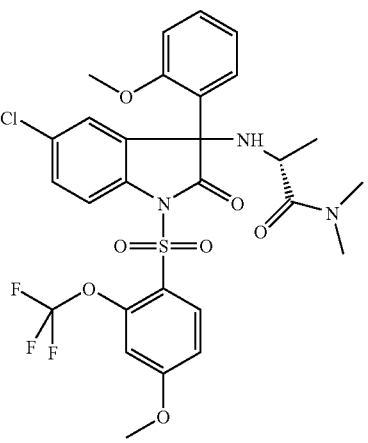 |

TABLE 3-continued

Structure of compounds obtained in each example

| Example | Structure |
|---------|-----------|
| 258 | 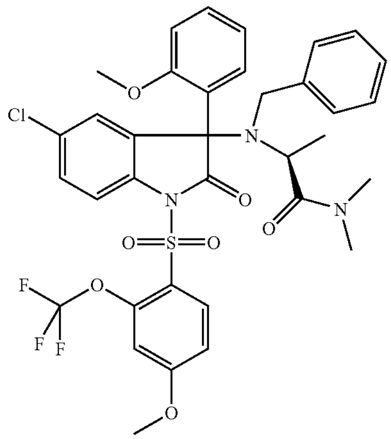 |
| 259 | 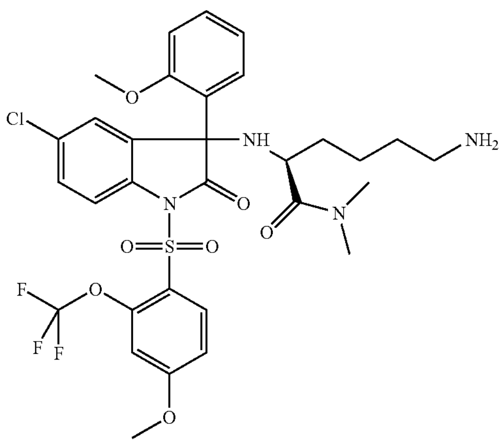 |
| 260 | 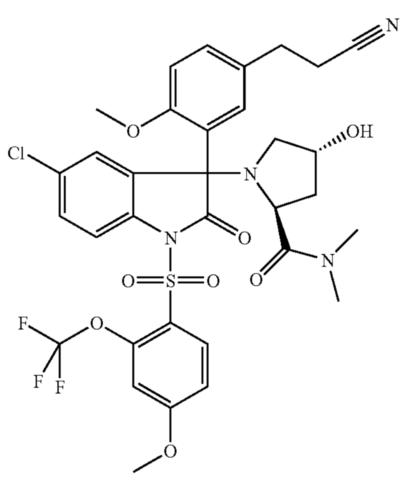 |

TABLE 3-continued

Structure of compounds obtained in each example

| Example | Structure |
|---------|-----------|
| 261 | 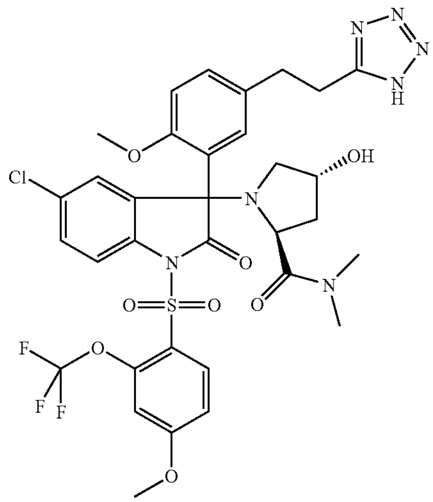 |
| 262 | 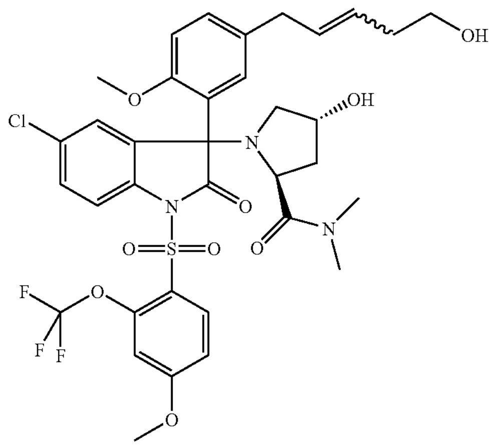 |
| 263 | 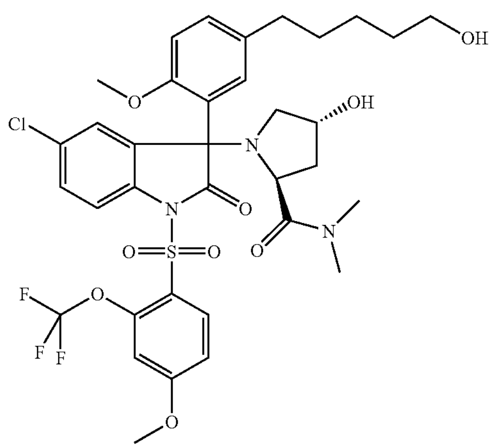 |

TABLE 3-continued
Structure of compounds obtained in each example
| Example | Structure |
|---|---|
| 264 | 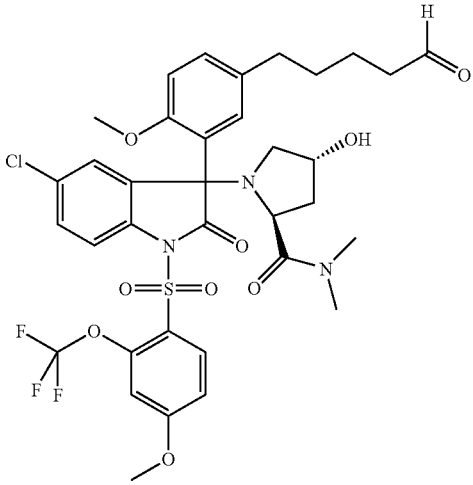 |
| 265 | 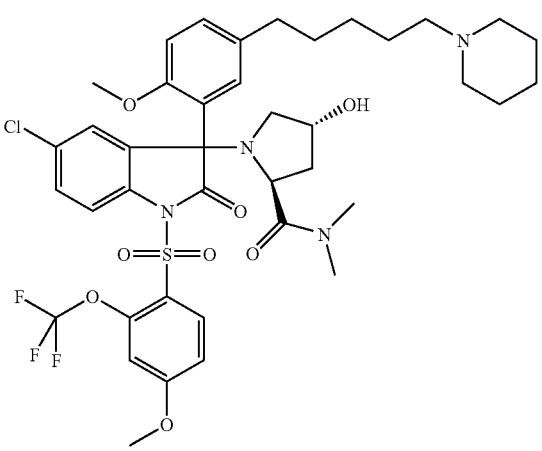 |
| 266 | 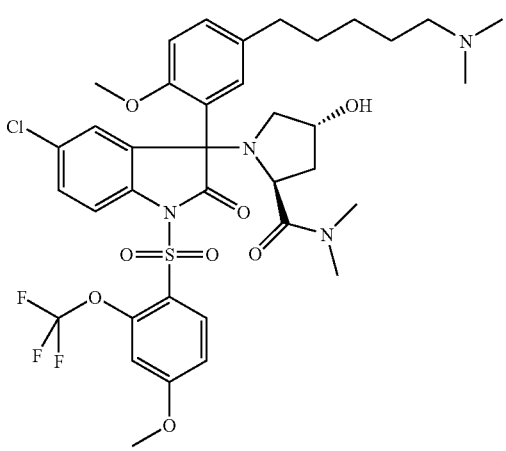 |

TABLE 3-continued

Structure of compounds obtained in each example

| Example | Structure |
|---|---|
| 267 | 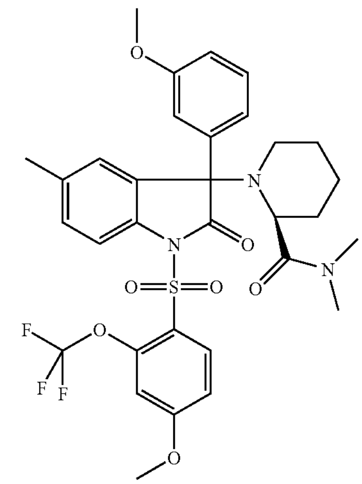 |
| 268 | 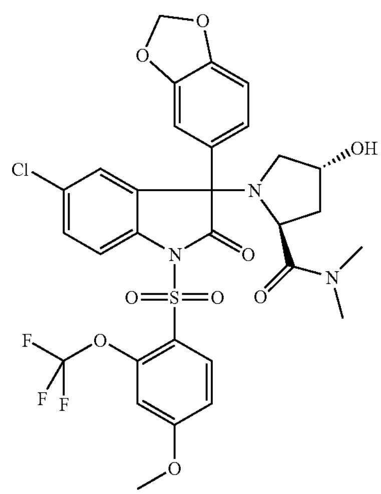 |
| 269 | 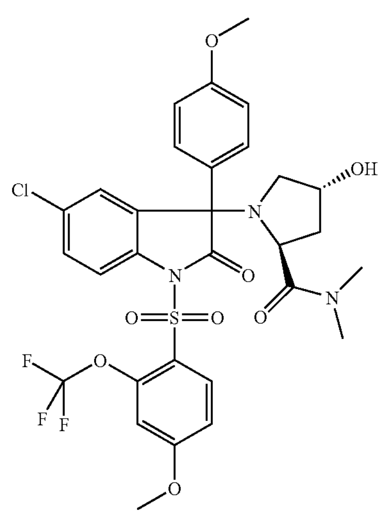 |

TABLE 3-continued

Structure of compounds obtained in each example

| Example | Structure |
|---|---|
| 270 | 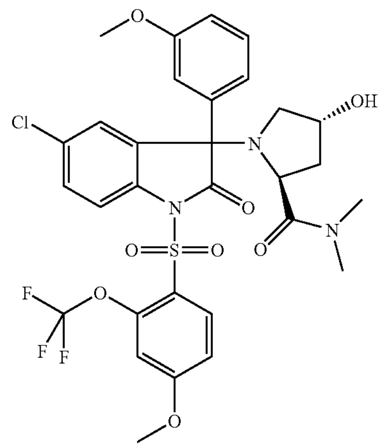 |
| 271 | 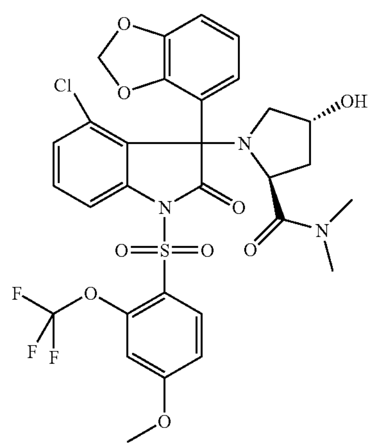 |
| 272 | 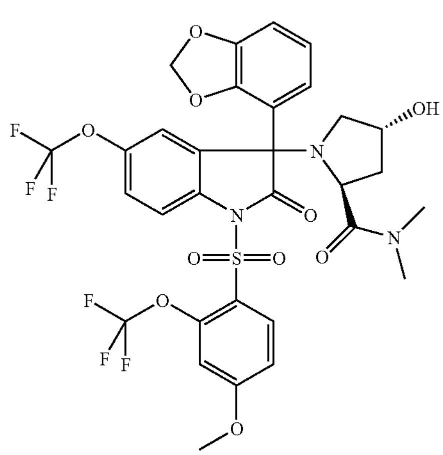 |

TABLE 3-continued

Structure of compounds obtained in each example

| Example | Structure |
|---------|-----------|
| 273 | 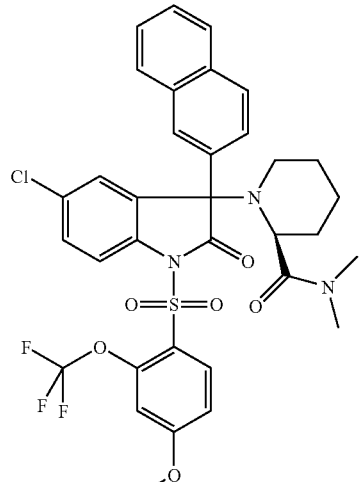 |

The invention claimed is:

1. A 1,3-dihydro-2H-indol-2-one compound represented by Formula (I), or pharmaceutically acceptable salts thereof:

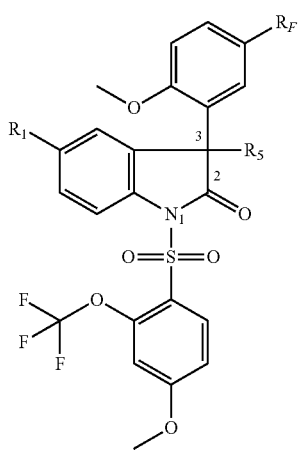

(1)

(wherein, $R_1$ represents a halogen atom or a cyano group; $R_5$ represents a group represented by Formula (3)

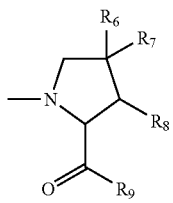

(3)

(wherein, $R_6$ represents a group represented by the formula —$OR_{10}$,
$R_7$ represents a hydrogen atom,
$R_8$ represents a hydrogen atom, $R_9$ represents a group represented by the formula —$NR_{14}R_{15}$,
$R_{10}$ represents a hydrogen atom, or an alkyl group having 1 to 3 carbon atoms substituted by a group selected from the Substituent G group described below,
$R_{14}$ represents a methyl group,
$R_{15}$ represents a methyl group, a group represented by Formula (4)

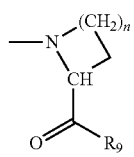

(4)

(wherein, n represents an integer from 2 to 3, and $R_9$ has the same meaning as above), a group represented by Formula (5)

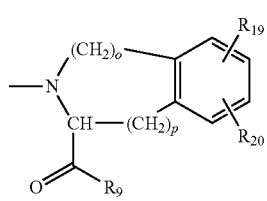

(5)

(wherein, o and p both represent an integer 1,
$R_{19}$ represents a hydrogen atom, and
$R_{20}$ represents a hydrogen atom,
$R_9$ has the same meaning as above), a group represented by Formula (6)

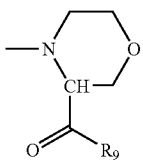

(6)

(wherein, $R_9$ has the same meaning as above),
a group represented by Formula (8)

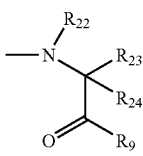

(8)

(wherein, $R_{22}$ represents a hydrogen atom or a methyl group,
$R_{23}$ represents a methyl group,
$R_{24}$ represents a hydrogen atom, and
$R_9$ has the same meaning as above),
or a group represented by Formula (9)

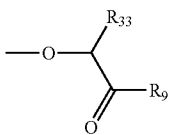

(9)

(wherein, $R_{33}$ represents a methyl group, and
$R_9$ has the same meaning as above);
$R_F$ represents a hydrogen atom, a methyl group, an alkyl group having 1 to 2 carbon atoms substituted by a group selected from the Substituent F group described below, a 4-pyridyl group, or a 4-morpholinyl group,
the Substituent F group represents a hydroxyl group, a dimethyl amino group, or a 1-pyperidynyl group,
the Substituent G group represents a carbamoyl group or a dimethyl amino group.

2. The 1,3-dihydro-2H-indol-2-one compound, or a pharmaceutically acceptable salt thereof as recited in claim 1, wherein $R_5$ represents Formula (3).

3. The 1,3-dihydro-2H-indol-2-one compound, or a pharmaceutically acceptable salt thereof as recited in claim 1, wherein $R_5$ represents Formula (4).

4. The 1,3-dihydro-2H-indol-2-one compound, or a pharmaceutically acceptable salt thereof as recited in claim 1, wherein $R_5$ represents Formula (5).

5. The 1,3-dihydro-2H-indol-2-one compound, or a pharmaceutically acceptable salt thereof as recited in claim 1, wherein $R_5$ represents Formula (6).

6. The 1,3-dihydro-2H-indol-2-one compound, or a pharmaceutically acceptable salt thereof as recited in claim 1, wherein $R_5$ represents Formula (8).

7. The 1,3-dihydro-2H-indol-2-one compound, or a pharmaceutically acceptable salt thereof as recited in claim 1, wherein $R_5$ represents Formula (9).

8. A mixture of any one species or two or more species selected from the following compound group, or pharmaceutically acceptable salts thereof of claim 1:
(4R)-1-(5-chloro-3-(2-methoxyphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
1-(5-chloro-3-(2-methoxyphenyl)-1-[([4-methoxy-2-(trifluoromethoxy)phenyl]sulfonyl}-2-oxo-2,3-dihydro-1H-indol-3-yl)-N,N-dimethyl-L-prolinamide (levorotatory isomer),
(2S)-1-(5-chloro-3-(2-methoxyphenyl)-1-{[4-methoxy-2-[(trifluoromethoxy)phenyl]sulfonyl}-2-oxo-2,3-dihydro-1H-indol-3-yl)-N,N-dimethylpiperidine-2-carboxamide (levorotatory isomer),
(3S)-2-(5-chloro-3-(2-methoxyphenyl)-1-[4-methoxy-2-(trifluoromethoxy)phenyl]sulfonyl}-2-oxo-2,3-dihydro-1H-indol-3-yl)-N,N-dimethyl-1,2,3,4-tetrahydroisoquinoline-3-carboxamide (levorotatory isomer),
(3S)-4-(5-chloro-3-(2-methoxyphenyl)-1-{[4-methoxy-2-(trifluoromethoxy)phenyl]sulfonyl}-2-oxo-2,3-dihydro-1H-indol-3-yl)-N,N-dimethylmorpholine-3-carboxamide (levorotatory isomer),
(2S)-2-[(5-chloro-3-(2-methoxyphenyl)-1-[4-methoxy-2-(trifluoromethoxy)phenyl]sulfonyl}-2-oxo-2,3-dihydro-1H-indol-3-yl)amino]-N,N-dimethylpropanamide (levorotatory isomer),
(2S)-2-[(5-chloro-3-(2-methoxyphenyl)-1-{([4-methoxy-2-(trifluoromethoxy)phenyl]sulfonyl}-2-oxo-2,3-dihydro-1H-indol-3-yl)(methyl)amino]-N,N-dimethylpropanamide (levorotatory isomer),
(2S)-2-[(5-chloro-3-(2-methoxyphenyl)-1-{([4-methoxy-2-(trifluoromethoxy)phenyl]sulfonyl}-2-oxo-2,3-dihydro-1H-indol-3-yl)oxy]-N,N-dimethylpropanamide (levorotatory isomer),
(4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(2S)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-N,N-dimethylpiperidine-2-carboxamide (levorotatory isomer),
(4R)-1-(5-cyano-3-(2-methoxy-5-methylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(5-chloro-3-(2-methoxy-5-methylphenyl)-1-{[4-methoxy-2-(trifluoromethoxy)phenyl]sulfonyl}-2-oxo-2,3-dihydro-1H-indol-3-yl)-4-[3-(dimethylamino)propoxy]-N,N-dimethyl-L-prolinamide (levorotatory isomer),
(4R)-4-(2-amino-2-oxoethoxy)-1-(5-chloro-3-(2-methoxy-5-methylphenyl)-1-([4-methoxy-2-(trifluoromethoxy)phenyl]sulfonyl}-2-oxo-2,3-dihydro-1H-indol-3-yl)-N,N-dimethyl-L-prolinamide (levorotatory isomer),
(4R)-1-(5-chloro-3-(2-methoxy-5-morpholin-4-ylphenyl)-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer),
(4R)-1-(5-chloro-3-(2-methoxy-5-pyridin-4-ylphenyl)-1-{[4-methoxy-2-(trifluoromethoxy)phenyl]sulfonyl)-2-oxo-2,3-dihydro-1H-indol-3-yl)-4-hydroxy-N,N-dimethyl-L-prolinamide (levorotatory isomer),
(4R)-1-(5-chloro-3-{5-[(dimethylamino)methyl]-2-methoxyphenyl}-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer or dextrorotatory isomer), (4R)-1-(5-chloro-3-(2-hydroxyethyl)-2-methoxyphenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer), and (4R)-1-(5-chloro-3-[2-methoxy-5-(2-piperidin-1-ylethyl)phenyl]-1-{[4-methoxy-2-(trifluoromethoxy)phenyl]sulfonyl}-2-oxo-2,3-dihydro-1H-indol-3-yl)-4-hydroxy-N,N-dimethyl-L-prolinamide (levorotatory isomer).

9. A pharmaceutical composition comprising as an active ingredient said 1,3-dihydro-2H-indol-2-one compound or pharmaceutically acceptable salts thereof as recited in claim 1, and a pharmaceutically acceptable carrier.

* * * * *